USO12252537B2

(12) United States Patent
Tuna et al.

(10) Patent No.: US 12,252,537 B2
(45) Date of Patent: Mar. 18, 2025

(54) ANTIBODY MOLECULES THAT BIND CD137 AND OX40

(71) Applicant: F-star Beta Limited, Cambridge (GB)

(72) Inventors: Mihriban Tuna, Cambridge (GB);
Miguel Gaspar, Cambridge (GB);
Michelle Morrow, Cambridge (GB);
Edmund Poon, Cambridge (GB)

(73) Assignee: INVOX PHARMA LIMITED, London (GB)

( * ) Notice: Subject to any disclaimer, the term of this patent is extended or adjusted under 35 U.S.C. 154(b) by 954 days.

(21) Appl. No.: 17/259,796

(22) PCT Filed: Jul. 12, 2019

(86) PCT No.: PCT/EP2019/068796
§ 371 (c)(1),
(2) Date: Jan. 12, 2021

(87) PCT Pub. No.: WO2020/011966
PCT Pub. Date: Jan. 16, 2020

(65) Prior Publication Data
US 2022/0048996 A1 Feb. 17, 2022

(30) Foreign Application Priority Data

Jul. 12, 2018 (GB) ..................................... 1811407
Nov. 9, 2018 (GB) ..................................... 1818281
Feb. 26, 2019 (GB) ..................................... 1902598

(51) Int. Cl.
*C07K 16/28* (2006.01)
*A61K 39/00* (2006.01)
(Continued)

(52) U.S. Cl.
CPC .......... *C07K 16/2818* (2013.01); *A61P 35/02* (2018.01); *C07K 16/2827* (2013.01);
(Continued)

(58) Field of Classification Search
CPC ............ C07K 16/2818; C07K 16/2827; C07K 16/2878; C07K 16/468; C07K 2317/565;
(Continued)

(56) References Cited

U.S. PATENT DOCUMENTS 3,909,459 A 9/1975 Friese et al.
3,967,230 A 6/1976 Kamigaito et al.
(Continued)

FOREIGN PATENT DOCUMENTS

CN 101802006 A 8/2010
CN 104955845 A 9/2015
(Continued)

OTHER PUBLICATIONS

Chen et al., Enhancement and destruction of antibody function by somatic mutation: unequal occurrence is controlled by V gene combinatorial associations. EMBO J. Jun. 15, 1995;14(12):2784-94. (Year: 1995).*

(Continued)

*Primary Examiner* — Aurora M Fontainhas
*Assistant Examiner* — Selam Berhane
(74) *Attorney, Agent, or Firm* — Wolf, Greenfield & Sacks, P.C.

(57) ABSTRACT

The present application relates to antibody molecules that bind and am able to agonise both CD137 and OX40. The antibody molecules comprise a CDR-based binding site for CD137, and an OX40 antigen-binding site that is located in a constant domain of the antibody molecule. The antibody molecules of the invention find application, for example, in the treatment of diseases, such as cancer and infectious diseases.

22 Claims, 28 Drawing Sheets

Specification includes a Sequence Listing.

(51) Int. Cl.
*A61P 35/02* (2006.01)
*C07K 16/46* (2006.01)
(52) U.S. Cl.
CPC ........ *C07K 16/2878* (2013.01); *C07K 16/468* (2013.01); *A61K 2039/505* (2013.01); *C07K 2317/32* (2013.01); *C07K 2317/565* (2013.01); *C07K 2317/64* (2013.01); *C07K 2317/75* (2013.01); *C07K 2317/92* (2013.01)
(58) Field of Classification Search
CPC ............ C07K 2317/64; C07K 2317/75; C07K 2317/92; A61P 35/02; A61K 2039/505
See application file for complete search history.

(56) References Cited

U.S. PATENT DOCUMENTS

| | | | |
|---|---|---|---|
| 4,004,183 | A | 1/1977 | Oki et al. |
| 5,595,756 | A | 1/1997 | Bally et al. |
| 6,380,664 | B1 | 4/2002 | Pollner |
| 7,288,638 | B2 | 10/2007 | Jure-Kunkel et al. |
| 7,592,426 | B2 | 9/2009 | Ebel et al. |
| 8,217,149 | B2 | 7/2012 | Irving et al. |
| 8,383,796 | B2 | 2/2013 | Korman et al. |
| 8,911,732 | B2 | 12/2014 | Dennis et al. |
| 9,567,399 | B1 | 2/2017 | Campbell et al. |
| 9,617,338 | B1 | 4/2017 | Campbell et al. |
| 10,090,646 | B2 | 10/2018 | Takaoka et al. |
| 10,205,305 | B2 | 2/2019 | Uegaki et al. |
| 10,233,258 | B2 | 3/2019 | Akamatsu et al. |
| 10,604,576 | B2 | 3/2020 | Campbell et al. |
| 11,214,618 | B2 | 1/2022 | Tuna et al. |
| 11,214,620 | B2 | 1/2022 | Campbell et al. |
| 11,548,948 | B2 | 1/2023 | Tuna et al. |
| 11,629,193 | B2 | 4/2023 | Tuna et al. |
| 2003/0030355 | A1 | 2/2003 | Honda |
| 2009/0055944 | A1 | 2/2009 | Korman et al. |
| 2012/0237498 | A1 | 9/2012 | Ahrens et al. |
| 2012/0276104 | A1 | 11/2012 | Woisetschlager |
| 2013/0034559 | A1 | 2/2013 | Queva et al. |
| 2014/0004121 | A1 | 1/2014 | Fanslow, III et al. |
| 2014/0341917 | A1 | 11/2014 | Nastri et al. |
| 2015/0214697 | A1 | 7/2015 | Yoshida et al. |
| 2015/0259420 | A1 | 9/2015 | Triebel et al. |
| 2016/0043531 | A1 | 2/2016 | Firstenberg et al. |
| 2016/0137740 | A1 | 5/2016 | Hammond et al. |
| 2016/0244528 | A1 | 8/2016 | Gray et al. |
| 2017/0198050 | A1 | 7/2017 | Eckelman et al. |
| 2017/0355756 | A1* | 12/2017 | Julien .................... C07K 16/18 |
| 2017/0362321 | A1 | 12/2017 | Campbell et al. |
| 2018/0118841 | A1 | 5/2018 | Ellmark et al. |
| 2018/0175592 | A1 | 6/2018 | Uegaki et al. |
| 2018/0194862 | A1 | 7/2018 | Akamatsu et al. |
| 2018/0339031 | A1 | 11/2018 | Masternak et al. |
| 2019/0106494 | A1 | 4/2019 | Wang et al. |
| 2019/0202920 | A1 | 7/2019 | Tuna et al. |
| 2019/0256602 | A1 | 8/2019 | Campbell et al. |
| 2019/0330344 | A1 | 10/2019 | Tuna et al. |
| 2019/0330351 | A1 | 10/2019 | Campbell et al. |
| 2019/0338032 | A1 | 11/2019 | Campbell et al. |
| 2019/0338049 | A1 | 11/2019 | Tuna et al. |
| 2020/0407446 | A1 | 12/2020 | McCourt et al. |
| 2021/0139590 | A1 | 5/2021 | Tuna et al. |
| 2021/0237498 | A1 | 8/2021 | Yoda et al. |
| 2021/0238299 | A1 | 8/2021 | Pechouckova et al. |
| 2021/0277134 | A1 | 9/2021 | Lakins et al. |
| 2021/0301022 | A1 | 9/2021 | Wollerton et al. |
| 2021/0309753 | A1 | 10/2021 | Tuna et al. |
| 2021/0355228 | A1 | 11/2021 | Lakins et al. |
| 2022/0049007 | A1 | 2/2022 | Lakins et al. |
| 2022/0185890 | A1 | 6/2022 | Tuna et al. |
| 2022/0185894 | A1 | 6/2022 | Campbell et al. |
| 2022/0267421 | A1 | 8/2022 | Munoz-Olaya et al. |
| 2022/0275092 | A1 | 9/2022 | Morrow et al. |
| 2023/0357413 | A1 | 11/2023 | Tuna et al. |
| 2023/0406935 | A1 | 12/2023 | Tuna et al. |

FOREIGN PATENT DOCUMENTS

| | | | | |
|---|---|---|---|---|
| CN | 104968364 | A | 10/2015 | |
| CN | 107523546 | A | 12/2017 | |
| EP | 1025230 | B1 | 2/2006 | |
| EP | 1180123 | B1 | 7/2008 | |
| EP | 2407487 | A1 | 1/2012 | |
| EP | 2546268 | A1 | 1/2013 | |
| EP | 2242771 | B1 | 7/2013 | |
| EP | 2905030 | A1 | 8/2015 | |
| EP | 2215121 | B1 | 2/2016 | |
| EP | 3354661 | A1 | 8/2018 | |
| EP | 3470426 | A1 | 4/2019 | |
| JP | S51-046628 | A | 4/1976 | |
| JP | 2003-022886 | A | 1/2003 | |
| JP | 2011-521905 | A | 7/2011 | |
| JP | 2012-500006 | A | 1/2012 | |
| JP | 2016-513467 | A | 5/2016 | |
| JP | 2016-533395 | A | 10/2016 | |
| JP | 2017-010741 | A | 1/2017 | |
| JP | 2018-508475 | A | 3/2018 | |
| RU | 2017112379 | | 10/2018 | |
| TW | 201642897 | A | 12/2016 | |
| WO | WO 2005/035584 | A1 | 4/2005 | |
| WO | WO 2006/072620 | A1 | 7/2006 | |
| WO | WO 2006/088447 | A1 | 8/2006 | |
| WO | WO 2006/099141 | A2 | 9/2006 | |
| WO | WO 2008/003103 | A2 | 1/2008 | |
| WO | WO-2008068048 | A2 * | 6/2008 | .............. A61P 31/10 |
| WO | WO 2009/000006 | A1 | 12/2008 | |
| WO | WO 2009/068204 | A1 | 6/2009 | |
| WO | WO 2009/126944 | A1 | 10/2009 | |
| WO | WO 2009/132876 | A1 | 11/2009 | |
| WO | WO 2010/019570 | A2 | 2/2010 | |
| WO | WO 2010/057047 | A1 | 5/2010 | |
| WO | WO 2010/111282 | A1 | 9/2010 | |
| WO | WO 2010/124797 | A1 | 11/2010 | |
| WO | WO 2012/130831 | A1 | 10/2012 | |
| WO | WO 2013/181634 | A2 | 12/2013 | |
| WO | WO 2014/004549 | A2 | 1/2014 | |
| WO | WO 2014/008218 | A1 | 1/2014 | |
| WO | WO 2014/052064 | A1 | 4/2014 | |
| WO | WO 2014/089113 | A1 | 6/2014 | |
| WO | WO 2014/140180 | A1 | 9/2014 | |
| WO | WO 2014/151910 | A1 | 9/2014 | |
| WO | WO 2015/048312 | A1 | 4/2015 | |
| WO | WO 2015/049537 | A1 | 4/2015 | |
| WO | WO 2015/119923 | A1 | 8/2015 | |
| WO | WO 2015/138920 | A1 | 9/2015 | |
| WO | WO 2015/198312 | A1 | 12/2015 | |
| WO | WO 2015/200119 | A1 | 12/2015 | |
| WO | WO 2016/028672 | A1 | 2/2016 | |
| WO | WO 2016/040880 | A1 | 3/2016 | |
| WO | WO 2016/111645 | A1 | 7/2016 | |
| WO | WO 2016/162505 | A1 | 10/2016 | |
| WO | WO 2016/177802 | A1 | 11/2016 | |
| WO | WO 2016/185016 | A1 | 11/2016 | |
| WO | WO 2016/200782 | A1 | 12/2016 | |
| WO | WO 2017/009456 | A1 | 1/2017 | |
| WO | WO 2017/015560 | A2 | 1/2017 | |
| WO | WO 2017/019846 | A8 | 2/2017 | |
| WO | WO 2017/025498 | A1 | 2/2017 | |
| WO | WO 2017/049452 | A1 | 3/2017 | |
| WO | WO 2017/052241 | A1 | 3/2017 | |
| WO | WO 2017/055398 | A2 | 4/2017 | |
| WO | WO 2017/062888 | A1 | 4/2017 | |
| WO | WO 2017/077085 | A2 | 5/2017 | |
| WO | WO 2017/087589 | A2 | 5/2017 | |
| WO | WO 2017/087901 | A2 | 5/2017 | |
| WO | WO 2017/123650 | A2 | 7/2017 | |
| WO | WO 2017/182672 | A1 | 10/2017 | |
| WO | WO 2017/193032 | A1 | 11/2017 | |
| WO | WO 2017/205738 | A1 | 11/2017 | |
| WO | WO 2017/220555 | A1 | 12/2017 | |
| WO | WO 2017/220569 | A1 | 12/2017 | |
| WO | WO 2017/220990 | A9 | 12/2017 | |
| WO | WO 2018/017673 | A1 | 1/2018 | |
| WO | WO 2018/056821 | A1 | 3/2018 | |
| WO | WO 2018/060480 | A1 | 4/2018 | |

(56) References Cited

FOREIGN PATENT DOCUMENTS

| WO | WO 2018/091740 A2 | 5/2018 |
|---|---|---|
| WO | WO 2018/115859 A1 | 6/2018 |
| WO | WO 2018/127610 A1 | 7/2018 |
| WO | WO 2018/222711 A2 | 12/2018 |
| WO | WO 2019/025545 A1 | 2/2019 |

OTHER PUBLICATIONS

Edwards et al., The remarkable flexibility of the human antibody repertoire; isolation of over one thousand different antibodies to a single protein, BLyS. J Mol Biol. Nov. 14, 2003;334(1):103-18. (Year: 2003).*
Koenig et al., Mutational landscape of antibody variable domains reveals a switch modulating the interdomain conformational dynamics and antigen binding. PNAS Jan. 24, 2017 114 (4) E486-E495; first published Jan. 5, 2017; (Year: 2017).*
Kussie, Paul H., "A Single Engineered Amino Acid Substitution Changes Antibody Fine Specificity", 1994, Journal of Immunology 152(1): pp. 146-152. (Year: 1994).*
Otano, et al. CD137 (4-1BB) costimulation of CD8+ T cells is more potent when provided in cis than in trans with respect to CD3-TCR stimulation. Nat Commun 12, 7296 (2021). https://doi.org/10.1038/s41467-021-27613-w (Year: 2021).*
Shepherd et al. T Cell Immunity to Bacterial Pathogens: Mechanisms of Immune Control and Bacterial Evasion. Int J Mol Sci. Aug. 26, 2020;21(17):6144. doi: 10.3390/ijms21176144. (Year: 2020).*
[No Author Listed] Abstract for CHI Immuno-Oncology Summit Europe. Mar. 18-22, 2019. 1 page. PDR303.
[No Author Listed] First-in-Class bispecific antibodies for cancer immunotherapy. Presentation at Takeda. Dec. 13, 2016. 24 pages. PDR160.
[No Author Listed] F-Star Modular Bispecific Antibodies. Summary for ATLAS deck. Presented at JP Morgan. Jan. 2017. 1 page. PDR159.
[No Author Listed], Pipeline Overview: F-star is developing a pipeline of bispecific antibodies focused on oncology and immuno-oncology. F-Start website update. Sep. 2016. 2 pages. PDR126.
Ascierto et al., Initial efficacy of anti-lymphocyte activation gene-3 (anti-LAG-3:BMS-986016) in combination with nivolumab (nivo) in pts with melanoma (MEL) previously treated with anti-PD-1/PD-L1 therapy. J Clin Oncology. May 20, 2017;35(15):9520-9520. Abstract only. doi: 10.1200/JCO.2017.35.15_suppl.9520. EPub May 30, 2017.
Berg et al., Biochemistry. 5th ed. New York. 2002. Accessible at https://www.ncbi.nlm.nih.gov/books/NBK22358/section5.5. Accessed Jun. 9, 2021. 4 pages.
Bernett et al., Abstract P122: Multiple bispecific checkpoint combinations enhance T cell activity. J Immunother Cancer. 2016;4(Suppl 1):P122. 2 pages.
Bernett et al., Multiple bispecific checkpoint combinations enhance T cell activity. Xencor Poster Presentation. 2016. 1 page.
Bodhankar et al., PD-L1 Monoclonal Antibody Treats Ischemic Stroke by Controlling Central Nervous System Inflammation. Stroke. Oct. 2015;46(10):2926-34. doi: 10.1161/STROKEAHA.115.010592. Epub Aug. 25, 2015.
Borlak et al., Immune-mediated liver injury of the cancer therapeutic antibody catumaxomab targeting EpCAM, CD3 and Fcγ receptors. Oncotarget. May 10, 2016;7(19):28059-74. doi: 10.18632/oncotarget.8574.
Brewis, Development of an anti-PD-L1 Fcab. Presentation. Human Antibodies and Hybrodomas Conference. Oct. 2018. 22. PDR 312.
Brewis, Identification of a PD-L1 binding Fcab: a potent inhibitor of immunosuppressive signals. Abstract. Huamn Antibodies and Hybridomas 2018. Jun. 11, 2018. 1 page. PDR282.
Brewis, The use of bispecific antibodies to modulate anti-tumour immune responses. Oral Presentation at ELRIG-Research and Innovation. Mar. 29, 2017. 33 pages. PDR177.
Brewis, The use of bispecific antibodies to modulate anti-tumour immune responses. Oral Presentation at PEPtalk. Jan. 12, 2017. 26 pages. PDR163.
Burova et al., Abstract 1484: Combined treatment with anti-LAG-3 and anti-PD-1 fully human monoclonal antibodies inhibits tumor growth in immunocompetent double-humanized LAG-3/PD-1 mice. Proceedings: AACR 107th Annual Meeting 2016. Apr. 16-20, 2016. New Orleans, LA. doi: 10.1158/1538-7445.AM2016-1484. Published Jul. 2016. 8 pages.
Burova et al., Abstract P195: A novel anti-human LAG-3 antibody in combination with anti-human PD-1 (REGN2810) shows enhanced anti-tumor activity in PD-1 x LAG-3 dual-humanized mice and favorable pharmacokinetic and safety profiles in cynomolgus monkey. J Immunother Cancer. 2016;4(Suppl 1):P195. 2 pages.
Camisaschi et al., LAG-3 expression defines a subset of CD4(+)CD25(high)Foxp3(+) regulatory T cells that are expanded at tumor sites. J Immunol. Jun. 1, 2010;184(11):6545-51. doi: 10.4049/jimmunol.0903879. Epub Apr. 26, 2010.
Cemerski et al., T cell activation and anti-tumor efficacy of anti-LAG-3 antibodies is independent of LAG-3-MHCII blocking capacity. Poster Presentation. 30th Annual Meeting and Associated Programs of the Society for Immunotherapy of Cancer (SITC 2015). National Harbor, MD. Nov. 4-8, 2015. 1 page.
Chen et al., Molecular mechanisms of T cell co-stimulation and co-inhibition. Nat Rev Immunol. Apr. 2013;13(4):227-42. doi: 10.1038/nri3405. Epub Mar. 8, 2013. Erratum in: Nat Rev Immunol. Jul. 2013;13(7):542.
Chiu et al., Antibody Structure and Function: The Basis for Engineering Therapeutics. Antibodies (Basel). Dec. 3, 2019;8(4):55. doi: 10.3390/antib8040055.
Curran et al., PD-1 and CTLA-4 combination blockade expands infiltrating T cells and reduces regulatory T and myeloid cells within B16 melanoma tumors. Proc Natl Acad Sci U S A. Mar. 2, 2010;107(9):4275-80. doi: 10.1073/pnas.0915174107. Epub Feb. 16, 2010.
Davies, Analytical challenges for next generation biologics. Oral Presentation at Waters Biopharma Mini-Seminar. May 24, 2017. 20 pages. PDR191.
Davies, Bispecific Antibodies: New Opportunities for Novel Therapies. Oral Presentation at Bioprocess UK 2016. Nov. 26, 2016. 14 pages. PDR 135.
Davies, Overcoming the Manufacturing Challenges for Bisepcific mAbs. Oral Presentation at 5th Annual Cell Culture and Bioprocessing Congress. Nov. 6, 2016. 16 pages. PDR142.
Davies, Overcoming the Manufacturing Challenges for Bisepcific mAbs. Oral Presentation at Biopronet 3rd Annual Scientific Symposium. Oct. 20, 2016. 16 pages. PDR136.
Daxini et al., Vasculitis associated with immune checkpoint inhibitors-a systematic review. Clin Rheumatol. Sep. 2018;37(9):2579-2584. doi: 10.1007/s10067-018-4177-0. Epub Jun. 19, 2018.
Demeure et al., T Lymphocytes infiltrating various tumour types express the MHC class II ligand lymphocyte activation gene-3 (LAG-3): role of LAG-3/MHC class II interactions in cell-cell contacts. Eur J Cancer. Sep. 2001;37(13):1709-18. doi: 10.1016/s0959-8049(01)00184-8.
Deng et al., LAG-3 confers poor prognosis and its blockade reshapes antitumor response in head and neck squamous cell carcinoma. Oncoimmunology. Oct. 7, 2016;5(11):e1239005. doi: 10.1080/2162402X.2016.1239005.
Doody et al., Abstract B091: a LAG-3/PD-L1 bispecific antibody inhibits tumor growth in two syngeneic colon carcinoma models. Second CRI-CIMT-EATI-AACR International Cancer Immunotherapy Conference: Translating Science into Survival. Sep. 25-28, 2016. New York, NY. doi: 10.1158/23/26-6066.IMM2016-B091. Published Nov. 2016. 8 pages.
Doody, An anti-murine LAG-3/PD-L1 bispecific antibody which modulates T cell activity and inhibits tumour growth. Oral Presentation at 2nd Annual Advances in Immuno-Oncology Congress. May 16, 2017. 17 pages. PDR188.
Doody, In vivo Efficacy of bispecific antibodies targeting two immmune-modulatory receptors. Oral Presentation at PEGS Europe. Nov. 4, 2016. 16 pages. PDR144.

(56) References Cited

OTHER PUBLICATIONS

Everett et al., A LAG-3/PD-L1 bispecific antibody inhibits tumour growth in two syngeneic colon carcinoma models. Poster Presentation. AACR Tumor Immunology and Immunotherapy. Oct. 21, 2016. 1 page. PDR137.

Everett et al., Abstract PR06: a LAG-3/PD-L1 bispecific antibody inhibits tumour growth in two syngeneic colon carcinoma models. AACR Special Conference on Tumor Immunology and Immunotherapy. Oct. 20-23, 2016. Boston, MA. Doi: 10.1158/2326-6074.TUMIMM16-PR06. Published Mar. 2017. 8 pages.

Everett, a LAG-3/PD-L1 Bispecific Antibody Inhibits Tumour Growth in Two Syngeneic Colon Carcinoma Models. Oral Presentation at AACR Tumor Immunology and Immunotherapy. Boston, MA. Oct. 20-23, 2016. 5 pages. PDR141.

Fiehler, Development of an anti-PD-L1 Fcab. Presentation. European Antibody Congress. Oct. 29, 2018. 26 pages. PDR312.

Foy et al., Poxvirus-Based Active Immunotherapy with PD-1 and LAG-3 Dual Immune Checkpoint Inhibition Overcomes Compensatory Immune Regulation, Yielding Complete Tumor Regression in Mice. PLoS One. Feb. 24, 2016;11(2):e0150084. doi: 10.1371/journal.pone.0150084.

F-STAR, First-in-Class Bispecific Antibodies for Cance Immunotherapy. Jul. 2016. Presentation. 14 pages. PDR119.

Gandhi et al., Expression of LAG-3 by tumor-infiltrating lymphocytes is coincident with the suppression of latent membrane antigen-specific CD8+ T-cell function in Hodgkin lymphoma patients. Blood. Oct. 1, 2006;108(7):2280-9. doi: 10.1182/blood-2006-04-015164. Epub Jun. 6, 2006.

Gliddon, Pushing all the buttons: innovating in immuno-oncology with mAb. Oral Presentation at Phacilitate Immunotherapy World 2017. Jan. 18, 2017. 11 pages. PDR165.

Grosso et al., Programmed death-ligand 1 (PD-L1) expression in various tumor types. J Immunother Cancer. 2013;1(Suppl 1):P53. http://www.immunotherapyofcancer.org/content/1/S1/P53. 1 page.

Haines et al., Abstract 4714: Blockade of LAG-3 amplifies immune activation signatures and augments curative antitumor responses to anti-PD-1 therapy in immune competent mouse models of cancer. Proceedings: AACR Annual Meeting 2017. Apr. 1-5, 2017. Washington, DC. doi: 10.1158/1538-7445.AM2017-4714. Published Jul. 2017. 8 pages.

Herbst et al., Predictive correlates of response to the anti-PD-L1 antibody MPDL3280A in cancer patients. Nature. Nov. 27, 2014;515(7528):563-7. doi: 10.1038/nature14011. Author Manuscript.

Hid Cadena et al., Checks and Balances in Autoimmune Vasculitis. Front Immunol. Feb. 22, 2018;9:315. doi: 10.3389/fimmu.2018.00315.

Horn et al., CD3xPDL1 bi-specific T cell engager (BiTE) simultaneously activates T cells and NKT cells, kills PDL1+ tumor cells, and extends the survival of tumor-bearing humanized mice. Oncotarget. Aug. 3, 2017;8(35):57964-57980. doi: 10.18632/oncotarget.19865.

Huang et al., Abstract PR03: Combinatorial blockade of PD-1, CTLA-4, and LAG-3 pathways inhibits murine ovarian tumor growth. Abstracts: AACR Special Conference: Advances in Ovarian Cancer Research: Exploiting Vulnerabilites. Oct. 17-20, 2015. Orlando, FL. doi: 10.1158/1557-3265.OVCA15-PR03. Published Jan. 2016. 8 pages.

Iwai et al., Involvement of PD-L1 on tumor cells in the escape from host immune system and tumor immunotherapy by PD-L1 blockade. Proc Natl Acad Sci U S A. Sep. 17, 2002;99(19):12293-7. doi: 10.1073/pnas.192461099. Epub Sep. 6, 2002.

Jochems et al., Analyses of functions of an anti-PD-L1/TGF?R2 bispecific fusion protein (M7824). Oncotarget. Sep. 8, 2017;8(43):75217-75231. doi: 10.18632/oncotarget.20680.

Kehry et al., Abstract 271: Targeting PD-1, TIM-3 and LAG-3 in combination for improved immunotherapy combinations. AACR 106th Annual Meeting. Apr. 18-22, 2015. Philadelphia, PA. doi: 10.1158/1538-7445.AM2015-271. 8 pages.

Klooster et al., Abstract B088: Generation of immuno-modulatory receptor binding bispecific antibodies to modulate tumor immunity. Second CRI-CIMT-EATI-AACR International Cancer Immunotherapy Conference: Translating Science into Survival. Sep. 25-28, 2016. New York, NY. doi: 10.1158/2326-6066.IMM2016-B088. 4 pages.

Koopmans et al., A novel bispecific antibody for EGFR-directed blockade of the PD-1/PD-L1 immune checkpoint. Oncoimmunology. May 31, 2018;7(8):e1466016. doi: 10.1080/2162402X.2018.1466016.

Kraman et al., A LAG-3/PD-L1 bispecific antibody inhibits tmour growth in two syngeneic colon carcinoma models. Poster Presentation. BSI/NVVI Congress. Dec. 6, 2016. 1 page. PDR153.

Kraman et al., A LAG-3/PD-L1 bispecific antibody inhibits tumour growth in two syngeneic colon carcinoma models. Abstract B091. Poster Presentation. CRI-CIMT-EATI-AACR Cancer Immunotherapy Conference. Sep. 26, 2016. 1 page. PDR129.

Kraman et al., A LAG-3/PD-L1 bispecific antibody inhibits tumour growth in two syngeneic colon carcinoma models. Poster 003. Poster Presentation. 2nd Annual Advances in Immuno-Oncology Congress. May 15, 2017. 1 page. PDR185.

Kraman et al., A LAG-3/PD-L1 bispecific antibody inhibits tumour growth in two syngeneic colon carcinoma models. Poster 1103. Poster Presentation. Keystone Symposium—Cancer Immunology and Immunotherapy. Mar. 19, 2017. 1 page. PDR174.

Kraman et al., A LAG-3/PD-L1 bispecific antibody inhibits tumour growth in two syngeneic colon carcinoma models. Poster 128. Poster Presentation at SITC. Nov. 9, 2016. 1 page. PDR143.

Kraman et al., A LAG-3/PD-L1 bispecific antibody inhibits tumour growth in two syngeneic colon carcinoma models. Poster 5651. Poster Presentation. AACR Annual Meeting. Apr. 1, 2017. 1 page. PDR176.

Kraman et al., A Lag-3/PD-L1 bispecific antibody inhibits tumour growth in two syngeneic colon carcinoma models. Poster Presentation. International Conference on Human & Translational Immunology. Sep. 16, 2016. 1 page. PDR123.

Kraman et al., A LAG-3/PD-L1 bispecific antibody inhibits tumour growth in two syngeneic colon carcinoma models. Poster 3005. Poster Presentation. Keystome Symposium—Biobetters and Next-Generation Biologics. Jan. 22-26, 2017. 1 page. PDR164.

Kraman et al., Abstract 5651:A LAG-3/PD/L1 bispecific antibody inhibits tumor growth in two syngeneic colon carcinoma models. AACR Annual Meeting 2017. Apr. 1-5, 2017. Washington, DC. Doi: 10.1158/1538-7445.AM2017-5651. 8 pages.

La Motte-Mohs et al., Abstract 3217: MGD013, a bispecific PD-1 x LAG-3 Dual-Affinity Re-Targeting (DART®) protein with T-cell immunomodulatory activity for cancer treatment. AACR 107th Annual Meeting. Apr. 16-20, 2016. New Orleans, LA. Doi: 10.1158/1538-7445.AM2016-3217. 8 pages.

La Motte-Mohs et al., MGD013, a bispecific PD-1 x LAG-3 Dual-Affinity Re-Targeting (DART®) protein with T-cell immunomodulatory activity for cancer treatment. Poster Presentation. 2016. http://ir.macrogenics.com/events.cfm. 1 page.

Larkin et al., Combined Nivolumab and Ipilimumab or Monotherapy in Untreated Melanoma. N Engl J Med. Jul. 2, 2015;373(1):23-34. doi: 10.1056/NEJMoa1504030. Epub May 31, 2015. Erratum in: N Engl J Med. Nov. 29, 2018;379(22):2185.

Levitan, Amgen Halts Rilotumumab Development Due to Increased Death Signal. Cancer Network. Nov. 26, 2014. Retrieved from www.cancernetwork.com/view/amgen-halts-rilotumumab-development-due-increased-death-signal. 3 pages.

Liu et al., Dual Targeting of Innate and Adaptive Checkpoints on Tumor Cells Limits Immune Evasion. Cell Rep. Aug. 21, 2018;24(8):2101-2111. doi: 10.1016/j.celrep.2018.07.062.

Mccourt et al., KY1055; a novel ICOS/PD-L1 bispecific antibody, enhance T cell activation and delivers potent monotherapy antitumour response in vivo. Abstract. CIMT 2018. Feb. 28, 2018. 1 page. PDR245.

Mccourt et al., KY1055; a novel ICOS/PD-L1 bispecific antibody, enhance T cell activation and delivers potent monotherapy antitumour response in vivo. Poster Presentation. CIMT Conference. May 9, 2018. 1 page. PDR 264.

Mccourt et al., KY1055; a novel ICOS/PD-L1 bispecific antibody, enhance T cell activation and delivers potent monotherapy antitumour response in vivo. Presentation. CIMT Conference. May 9, 2018. 13 pages. PDR265.

(56) References Cited

OTHER PUBLICATIONS

Michaelson et al., Anti-tumor activity of stability-engineered IgG-like bispecific antibodies targeting TRAIL-R2 and LTbetaR. MAbs. Mar. 2009-Apr;1(2):128-41. doi: 10.4161/mabs.1.2.7631. Epub Mar. 11, 2009.
Munoz-Olaya, Development of an anti-PD-L1Fcab. Presentation. PEGS Lisbon. Nov. 16, 2018. 24 pages. PDR321.
Nalivaiko et al., A Recombinant Bispecific CD20xCD95 Antibody With Superior Activity Against Normal and Malignant B-cells. Mol Ther. Feb. 2016;24(2):298-305. doi: 10.1038/mt.2015.209. Epub Nov. 19, 2015.
Pavlidou et al., Simultaneous costimulatory T-cell engagement and checkpoint inhibition by PRS-344/ONC0055, a 4-1BB/PD-L1 bispecific compound for tumor localized activation of the immune system. SITC 2018. Poster Presentation. 2018. 1 page.
Powles et al., MPDL3280A (anti-PD-L1) treatment leads to clinical activity in metastatic bladder cancer. Nature. Nov. 27, 2014;515(7528):558-62. doi: 10.1038/nature13904.
Sainson et al., KY1055, a novel ICOS/PD-L1 bispecific antibody, efficiently enhances T cell activation and delivers a potent anti-tumour response in vivo. Abstract. AACR. Jan. 22, 2018. 1 page. PDR236.
Sainson et al., KY1055, a novel ICOS/PD-L1 bispecific antibody, efficiently enhances T cell activation and delivers a potent anti-tumour response in vivo. Poster Presentation. AACR 2018. Apr. 4, 2018. 1 page. PDR254.
Strauss et al., Phase I Trial of M7824 (MSB0011359C), a Bifunctional Fusion Protein Targeting PD-L1 and TGF?, in Advanced Solid Tumors. Clin Cancer Res. Mar. 15, 2018;24(6):1287-1295. doi: 10.1158/1078-0432.CCR-17-2653. Epub Jan. 3, 2018.
Tuna, Identification of a PD-L1 binding FCAB: a potent inhibitor of immunosuppressive signals. Abstract. European Antibody Congress. May 3, 2018. 1 page. PDR270.
Tuna, The use of bispecific antibodies to modulate anti-tumour immune responses. Oral Presentation at 10th Annual Proteins and Antibodies Congress. Apr. 24, 2017. 26 pages. PDR183.
Vanamee et al., Structural principles of tumor necrosis factor superfamily signaling. Sci Signal. Jan. 2, 2018;11(511):eaao4910. doi: 10.1126/scisignal.aao4910. 12 pages.
Weismann, a LAG-3/PD-L1 Bispecific Antibody Inhibits Tumour Growth In Two Syngeneic Colon Carcinoma Models. International Conference on Human and Translational Immunology. Rhodes, Greece. Sep. 16-21, 2016 Presentation. 6 pages. PDR128.
Wherry, T cell exhaustion. Nat Immunol. Jun. 2011;12(6):492-9. doi: 10.1038/ni.2035.
Wilton, KY1055, a bispecific mAb2 targeting ICOS and PD-L1. Presentation. Feb. 21, 2018. 17 pages. PDR238.
Wolchok et al., Nivolumab plus ipilimumab in advanced melanoma. N Engl J Med. Jul. 11, 2013;369(2):122-33. doi: 10.1056/NEJMoa1302369. Epub Jun. 2, 2013. Erratum in: N Engl J Med. Nov. 29, 2018;379(22):2185. Author Manuscript.
Woo et al., Immune inhibitory molecules LAG-3 and PD-1 synergistically regulate T-cell function to promote tumoral immune escape. Cancer Res. Feb. 1, 2012;72(4):917-27. doi: 10.1158/0008-5472.CAN-11-1620. Epub Dec. 20, 2011.
Workman et al., Negative regulation of T cell homeostasis by lymphocyte activation gene-3 (CD223). J Immunol. Jan. 15, 2005;174(2):688-95. doi: 10.4049/jimmunol.174.2.688.
Workman et al., The CD4-related molecule, LAG-3 (CD223), regulates the expansion of activated T cells. Eur J Immunol. Apr. 2003;33(4):970-9. doi: 10.1002/eji.200323382.
Wydro, Bispecific antibodies: new opportunities for novel therapies. Oral Presentation at 7th Annual Biologics Symposium. Mar. 1, 2017. 24 pages. PDR172.
Wykes et al., Immune checkpoint blockade in infectious diseases. Nat Rev Immunol. Feb. 2018;18(2):91-104. doi: 10.1038/nri.2017.112. Epub Oct. 9, 2017.
Zhang et al., Structural basis of a novel PD-L1 nanobody for immune checkpoint blockade. Cell Discov. Mar. 7, 2017;3:17004. doi: 10.1038/celldisc.2017.4.

International Search Report and Written Opinion for Application No. PCT/EP2019/068796, mailed Oct. 2, 2019.
International Preliminary Report on Patentability for Application No. PCT/EP2019/068796, mailed Jan. 21, 2021.
[No Author Listed] F-star Alpha: A new asset centric company. Retrieved from http://www.onenucleus.com/media/Events/LSLS/11%20feb%202014/Jane%20Dancer.pdf on Jan. 8, 2015. 15 pages.
Asgarov et al., A new anti-mesothelin antibody targets selectively the membrane-associated form. MAbs. Apr. 2017;9(3):567-577. doi: 10.1080/19420862.2017.1288770.
Bacac et al., Abstract 1494: CEA TCB: A novel head-to-tail 2:1 T cell bispecific antibody for treatment of CEA-positive solid tumors. Oncoimmunology. Aug. 2016; 5(Abstract): e1203498. Epub Jun. 24, 2016. doi: 10.1080/2162402X.2016.1203498.
Chester et al., 4-1BB agonism: adding the accelerator to cancer immunotherapy. Cancer Immunol Immunother. Oct. 2016;65(10):1243-8. doi: 10.1007/s00262-016-1829-2. Epub Mar. 31, 2016.
Chester et al., Dual antibody therapy to harness the innate anti-tumor immune response to enhance antibody targeting of tumors. Curr Opin Immunol. Apr. 2015;33:1-8. doi: 10.1016/j.coi.2014.12.010. Epub Jan. 7, 2015.
Goding et al., Combination of adoptive cell transfer, anti-PD-L1 and anti-LAG-3 antibodies for the treatment of recurrent tumors: better with more. OncoImmunology. Oct. 22, 2013;2(8):e25050-1-e25050-3.
Hasenhindl et al., Creating stable stem regions for loop elongation in Fcabs—insights from combining yeast surface display, in silico loop reconstruction and molecular dynamics simulations. Biochim Biophys Acta. 2014;1844(9):1530-1540. doi:10.1016/j.bbapap.2014.04.020.
Hasenhindl et al., Stability assessment on a library scale: a rapid method for the evaluation of the commutability and insertion of residues in C-terminal loops of the CH3 domains of IgG1-Fc. Protein Eng Des Sel. 2013;26(10):675-682.
Jing et al., Combined immune checkpoint protein blockade and low dose whole body irradiation as immunotherapy for myeloma. Journal of Immunotherapy of Cancer. doi: 10.1186/S40425-014-0043-Z. Jan. 20, 2015. 15 pages.
Kraman et al., A LAG-3/PD-L1 bispecific antibody inhibits tumor growth in two syngeneic colon carcinoma models. Journal of ImmunoTherapy of Cancer. 2016;4(Suppl 1):82(abstract P124).
Kraman et al., A LAG-3/PD-L1 bispecific antibody inhibits tumor growth in two syngeneic colon carcinoma models. Retrieved from http://www.f-star.com/media/73722/A-LAG-3-PD-L1-bispecific-antibody-inhibits-tumour-growth-in-two-syngeneic-colon-carcinoma-models.pdf. Nov. 9-13, 2016. 1 page.
Lakins et al., A Novel CD137/PD-L1 Bispecific Antibody Modulates the Tumour Microenvironmentby Activating CD8+ T cells and Results in Tumour Growth Inhibition. F-Star Poster. Nov. 7, 2018. 1 page. Retrieved from https://www.f-star.com/media/87488/201811-SITC-2018-F-star-FS222-Poster-ONLINE.pdf.
Lee et al., 4-1BB and OX40 dual costimulation synergistically stimulate primary specific CD8 T cells for robust effector function. J Immunol. Sep. 1, 2004;173(5):3002-12. doi: 10.4049/jimmunol.173.5.3002.
Leung et al., A HER2-specific Modified Fc Fragment (Fcab) Induces Antitumor Effects Through Degradation of HER2 and Apoptosis. Mol Ther. Nov. 2015;23(11):1722-1733. doi: 10.1038/mt.2015.127. Epub Aug. 3, 2015. Erratum in: Mol Ther. Nov. 2015;23(11):1794.
Lobner et al., Engineered IgG1-Fc—one fragment to bind them all. Immunol Rev. Mar. 2016;270(1):113-31. doi: 10.1111/imr.12385.
Lobner et al., Two-faced Fcab prevents polymerization with VEGF and reveals thermodynamics and the 2.15 A crystal structure of the complex. MAbs. Oct. 2017;9(7):1088-1104. doi: 10.1080/19420862.2017.1364825. Epub Aug. 17, 2017.
Lundqvist et al., 31st Annual Meeting and Associated Programs of the Society for Immunotherapy of Cancer (SITC 2016): Part One. Journal for Immunotherapy of Cancer. Nov. 16, 2016;4(1):74(abstract P124).
Qui et al., CD134 plus CD137 dual costimulation induces Eomesodermin in CD4 T cells to program cytotoxic Th1 differentiation. J Immunol. Oct. 1, 2011;187(7):3555-64. doi: 10.4049/jimmunol.1101244. Epub Aug. 31, 2011.

(56) References Cited

OTHER PUBLICATIONS

Ramelet et al., Beneficial outcome of combination therapy with 4-1BB targeting antibody. Eur J Cancer. Nov. 29, 2016;69(Suppl 1):S96-S97.
Sallin et al., The anti-lymphoma activities of anti-CD137 monoclonal antibodies are enhanced in FcγRIII(-/-) mice. Cancer Immunol Immunother. Sep. 2014;63(9):947-58. doi: 10.1007/s00262-014-1567-2. Epub Jun. 14, 2014.
Schlothauer et al., Novel human IgG1 and IgG4 Fc-engineered antibodies with completely abolished immune effector functions. Protein Eng Des Sel. Oct. 2016;29(10):457-466. doi: 10.1093/protein/gzw040. Epub Aug. 29, 2016.
Shindo et al., Combination immunotherapy with 4-1BB activation and PD-1 blockade enhances antitumor efficacy in a mouse model of subcutaneous tumor. Anticancer Res. Jan. 2015;35(1):129-36.
Vilgelm et al., Combinatorial approach to cancer immunotherapy: strength in numbers Journal of Leukocyte Biology. 2016;100(2):275-90. Epub Jun. 2, 2016.
Wozniak-Knopp et al., Designing Fcabs: well-expressed and stable high affinity antigen-binding Fc fragments. Protein Eng Des Sel. Sep. 1, 2017;30(9):657-671. doi: 10.1093/protein/gzx042.
Wozniak-Knopp et al., Introducing antigen-binding sites in structural loops of immunoglobulin constant domains: Fc fragments with engineered HER2/neu-binding sites and antibody properties. Protein Eng Des Sel. 2010;23(4):289-297. doi:10.1093/protein/gzq005.
Xu et al., In vitro characterization of five humanized OKT3 effector function variant antibodies. Cell Immunol. Feb. 25, 2000;200(1):16-26.
[No Author Listed], FS118 First in Human Study in Patients With Advanced Malignancies. Sponsored by F-star Therapeutics Limited. Clinical Trial. Retreived from https://clinicaltrials.gov/ct2/show/NCT03440437. Feb. 22, 2018. 7 pages.
Asgarov et al., A new anti-mesothelin antibody targets selectively the membrane-associated form. MAbs. Apr. 2017;9(3):Supplementary Data. doi: 10.1080/19420862.2017.1288770. 6 pages.
Awuah et al., Reduced Shedding of Surface Mesothelin Improves Efficacy of Mesothelin-Targeting Recombinant Immunotoxins. Mol Cancer Ther. Jul. 2016;15(7):1648-55. doi: 10.1158/1535-7163.MCT-15-0863. Epub May 18, 2016.
Callahan et al., Targeting T Cell Co-receptors for Cancer Therapy. Immunity. May 1, 20167;44(5):1069-78. doi: 10.1016/j.immuni.2016.04.023.
Chatterjee et al., Noninvasive Imaging of Immune Checkpoint Ligand PD-L1 in Tumors and Metastases for Guiding Immunotherapy. Mol Imaging. Jan. 2017-Dec. 16:1536012117718459. doi: 10.1177/1536012117718459. 5 pages.
Chu et al., An Update on Anti-CD137 Antibodies in Immunotherapies for Cancer. Int J Mol Sci. Apr. 12, 2019;20(8):1822. doi: 10.3390/ijms20081822. 17 pages.
Dahlén et al., Bispecific antibodies in cancer immunotherapy. Ther Adv Vaccines Immunother. Feb. 2018;6(1):3-17. doi: 10.1177/2515135518763280. Epub Mar. 28, 2018.
Del Bano et al., A Bispecific Antibody-Based Approach for Targeting Mesothelin in Triple Negative Breast Cancer. Front Immunol. Jul. 10, 2019;10:1593. doi: 10.3389/fimmu.2019.01593.
El-Khoueiry et al., The relationship of pharmacodynamics (PD) and pharmacokinetics (PK) to clinical outcomes in a phase I study of OX40 agonistic monoclonal antibody (mAb) PF-04518600 (PF-8600). J Clin Oncol. May 20, 2017. 35(15_suppl):3027-3027. Meeting Abstract. 2017 ASCO Annual Meeting I. doi: 10.1200/JCO.2017.35.15_suppl.3027. 4 pages.
Faroudi et al., Abstract 2399: LAG-3/PD-L1 mAb2 can overcome PD-L1-mediated compensatory upregulation of LAG-3 induced by single-agent checkpoint blockade. Proceedings: AACR Annual Meeting 2019; Mar. 29-Apr. 3, 2019. Atlanta, GA. Doi: 10.1158/1538-7445.AM2019-2399. Published Jul. 2019. 4 pages.
Faroudi et al., Abstract B009: FS118, a LAG-3/PD-L1 bispecific antibody, capable of driving potent anti-tumour immune responses and overcome PD-(L)1-mediated compensatory. Sep. 25-28, 2019. Fifth CRI-CIMT-EATI-AACR International Cancer Immunotherapy Conference (2019): Translating Science into Survival. Paris. 1 page.
Faroudi et al., FS118, a LAG-3/PD-L1 bispecific antibody, capable of driving potent anti-tumour immune responses and overcome PD-(L)1-mediated compensatory. Sep. 25-28, 2019. Poster. Fifth CRI-CIMT-EATI-AACR International Cancer Immunotherapy Conference (2019): Translating Science into Survival. Paris. 1 page.
Frenzel et al., Phage display-derived human antibodies in clinical development and therapy. MAbs. Oct. 2016;8(7):1177-1194. doi: 10.1080/19420862.2016.1212149. Epub Jul. 14, 2016.
F-STAR, Next-Generation Bispecifics for Cancer Immunotherapy. Feb. 2020. Presented on Mar. 11, 2020 at Immuno-Oncology Summit Europe 2020. London. 46 pages.
F-STAR, Redirecting T Cells. Overcoming Cancer. Improving Lives. Oct. 2019 Presentation in Investor Meeting. 36 pages.
F-STAR, Redirecting T Cells. Overcoming Cancer. Improving Lives. Apr. 2020 Presentation in Investor Meeting. 43 pages.
F-STAR, Redirecting T Cells. Overcoming Cancer. Improving Lives. Jan. 2020 Presentation in Investor Meeting. 41 pages.
Gaspar et al., FS120 mAb2, a dual agonist bispecific antibody targeting OX40 and CD137, activates T cells in vitro and induces FcγR-independent anti-tumour activity. SITC 2018. Nov. 7, 2018. Poster. 10 pages.
Gaspar, FS120 mAb2, a dual agonist bispecific antibody targeting OX40 and CD137. Sitc 2018. Nov. 11, 2018. Presentation. 12 pages.
Geuijen et al., Abstract 541: An unbiased screen identifies a CD137xPD-L1 bispecific IgG1 antibody with unique T cell activation and binding properties. Cancer Res. 2019;79(13_Supplement):541. Poster Presentation AACR Conference 2019. Jul. 1, 2019. doi: 10.1158/1538-7445.AM2019-541. 4 pages.
Glisson et al., Phase 1 study of MEDI0562, a humanized OX40 agonist monoclonal antibody (mAb), in adult patients (pts) with advanced solid tumors. Annals Onocol. Oct. 1, 2016;27(6):vi361. doi: 10.1093/annonc/mdw378.07.
Gunde et al., Abstract 1532: A novel, monovalent tri-specific antibody-based molecule that simultaneously modulates PD-L1 and 4-1BB exhibits potent anti-tumoral activity in vivo. Cancer Res. 2019;79(13_Supplement): 1532. AACR Conference 2019. Jul. 1, 2019. doi: 10.1158/1538-7445.AM2019-1532. 4 pages.
Hassan et al., Mesothelin Immunotherapy for Cancer: Ready for Prime Time? J Clin Oncol. Dec. 2016;34(34):4171-4179. doi: 10.1200/JCO.2016.68.3672. Epub Oct. 31, 2016.
Hassan et al., Phase II clinical trial of amatuximab, a chimeric antimesothelin antibody with pemetrexed and cisplatin in advanced unresectable pleural mesothelioma. Clin Cancer Res. Dec. 1, 2014;20(23):5927-36. doi: 10.1158/1078-0432.CCR-14-0804. Epub Sep. 17, 2014.
Hebb et al., Administration of low-dose combination anti-CTLA4, anti-CD137, and anti-OX40 into murine tumor or proximal to the tumor draining lymph node induces systemic tumor regression. Cancer Immunol Immunother. Jan. 2018;67(1):47-60. doi: 10.1007/s00262-017-2059-y. Epub Sep. 13, 2017. Author Manuscript. 20 pages.
Ho et al., A novel high-affinity human monoclonal antibody to mesothelin. Int J Cancer. May 1, 2011;128(9):2020-30. doi: 10.1002/ijc.25557.
Kraman et al., Dual blockade of PD-L1 and LAG-3 with FS118, a unique bispecific antibody, induces CD8+ T-cell activation and modulates the tumour microenvironment to promote anti-tumour immune responses. Apr. 14-18, 2018. Poster 2719. Proceedings of the American Association for Cancer Research Annual Meeting 2018. Chicago, IL. 2 pages.
Kraman et al., Dual blockade of PD-L1 and LAG-3 with FS118, a unique bispecific antibody, induces T-cell activation with the potential to drive potent anti-tumour immune responses. Nov. 7, 2017;5 Suppl 2 (87):Abstract P348. 32nd Annual Meeting and Pre-Conference Programs of the Society for Immunotherapy of Cancer (SITC). Part II. Nov. 8-12, 2017. National Harbor, MD. 2 pages.
Kraman et al., Dual blockade of PD-L1 and LAG-3 with FS118, a unique bispecific antibody, induces T-cell activation with the potential to drive potent anti-tumour immune responses. Apr. 14-18,

(56) References Cited

OTHER PUBLICATIONS

2018;78(13 Suppl);Abstract 2719. Proceedings of the American Association for Cancer Research Annual Meeting 2018. Chicago, IL. 5 pages.

Kraman et al., Dual blockade of PD-L1 and LAG-3 with FS118, a unique bispecific antibody, induces T-cell activation with the potential to drive potent anti-tumour immune responses. Poster P348. 32nd Annual Meeting and Pre-Conference Programs of the Society for Immunotherapy of Cancer (SITC). Part II. Nov. 8-12, 2017. National Harbor, MD. 1 page.

Kraman et al., FS118, a Bispecific Antibody Targeting LAG-3 and PD-L1, Enhances T-Cell Activation Resulting in Potent Antitumor Activity. Clin Cancer Res. Jul. 1, 2020;26(13):3333-3344. doi: 10.1158/1078-0432.CCR-19-3548. Epub Apr. 16, 2020.

Kunik et al., Structural consensus among antibodies defines the antigen binding site. PLoS Comput Biol. 2012;8(2):e1002388. doi: 10.1371/journal.pcbi.1002388. Epub Feb. 23, 2012. 12 pages.

Kvarnhammar et al., The CTLA-4 x OX40 bispecific antibody ATOR-1015 induces anti-tumor effects through tumor-directed immune activation. J Immunother Cancer. Apr. 11, 2019;7(1):103. doi: 10.1186/s40425-019-0570-8.

Lakins et al., FS222 mAb2, a bispecific conditional agonist antibody targeting CD137 and PD-L1, induces potent lymphocyte activation and has a favourable safety profile. F-star, Cambridge, UK. Poster Presentation. AACR Annual Meeting Mar. 29-Apr 3, 2019 Atlanta, GA. Poster No. 1540. 1 page.

Lakins et al., Optimising TNFRSF agonism and checkpoint blockade with a novel CD137/PD-L1 bispecific antibody. Abstracts Therapeutic Development. Dec. 1, 2018;29(Supplement 10):X30. doi: 10.1093/annonc/mdy487.014. 1 page.

Lamberts et al., ImmunoPET with Anti-Mesothelin Antibody in Patients with Pancreatic and Ovarian Cancer before Anti-Mesothelin Antibody-Drug Conjugate Treatment. Clin Cancer Res. Apr. 1, 2016;22(7):1642-52. doi: 10.1158/1078-0432.CCR-15-1272. Epub Nov. 20, 2015.

Li et al., Discovery and preclinical characterization of the antagonist anti-PD-L1 monoclonal antibody LY3300054. J Immunother Cancer. Apr. 30, 2018;6(1):31. doi: 10.1186/s40425-018-0329-7. Erratum in: J Immunother Cancer. Jun. 4, 2018;6(1):45.

Ma et al., Recognition of mesothelin by the therapeutic antibody MORAb-009: structural and mechanistic insights. J Biol Chem. Sep. 28, 2012;287(40):33123-31. doi: 10.1074/jbc.M112.381756. Epub Jul. 11, 2012.

Mayes et al., Abstract 539: A bispecific Fc-silenced IgG1 antibody (MCLA-145) requires PD-L1 binding to activate CD137. Cancer Res. 2019;79(13_Supplement):539. AACR Presentation 2019. Jul. 1, 2019. doi: 10.1158/1538-7445.AM2019-539. 4 pages.

Mccourt, Development of an ICOS/PD-L1 Bispecific, Mar. 18-22, 2019. Abstract. Cambridge Healthtech Institute's 4th Annual Immuno-Oncology Summit Europe 2019 (London).

Melero et al., Clinical development of immunostimulatory monoclonal antibodies and opportunities for combination. Clin Cancer Res. Mar. 1, 2013;19(5):997-1008. doi: 10.1158/1078-0432.CCR-12-2214.

Perez-Ruiz et al., Anti-CD137 and PD-1/PD-L1 Antibodies En Route toward Clinical Synergy. Clin Cancer Res. Sep. 15, 2017;23(18):5326-5328. doi: 10.1158/1078-0432.CCR-17-1799. Epub Aug. 8, 2017.

Poon et al., Dual agonist bispecific antibody targeting OX40 and DC137 mediates anti-tumour immunity and synergises with PD-1/PD-L1 blockade to improve survival in a syngeneic mouse model. AACR 2019. Mar. 29, 2019. Poster. 9 pages.

Ryan et al., A novel biologic platform elicits profound T cell costimulatory activity and antitumor immunity in mice. Cancer Immunol Immunother. Apr. 2018;67(4):605-613. doi: 10.1007/s00262-018-2116-1. Epub Jan. 11, 2018.

Schroeder, Chapter 13: Immunoglobulins and Their Genes. From Arthritis and Allied Conditions: A Textbook of Rheumatology. 15th Ed. vol 1. Eds Koopman et al.Lippincot Williams & Wilkins. pp. 289-304. Supplied by the British Library Jul. 31, 2023.

Tang et al., A human single-domain antibody elicits potent antitumor activity by targeting an epitope in mesothelin close to the cancer cell surface. Mol Cancer Ther. Apr. 2013;12(4):416-26. doi: 10.1158/1535-7163.MCT-12-0731. Epub Jan. 31, 2013.

Tuna, Delivering the next immuno-oncology breakthrough. PEGS Europe 2018. Nov. 11, 2018. Presentation. 24 pages.

Yap et al., A first-in-human phase I study of FS118, an anti-LAG-3/PD-L1 bispecific antibody in patients with solid tumors that have progressed on prior PD-1/PD-L1 therapy. Journal of Clinical Oncology. Jun. 1, 2019. Poster TPS2652. 2019 ASCO Annual Meeting Proceedings. 20 pages.

Yap et al., Abstract TPS2652: A first-in-human phase I study of FS118, an anti-LAG-3/PD-L1 bispecific antibody in patients with solid tumors that have progressed on prior PD-1/PD-L1 therapy. Journal of Clinical Oncology. May 15, 2019;37(15_suppl). 2019 ASCO Annual Meeting Proceedings. 4 pages.

Yap et al., A first-in-human phase I study of FS118, an anti-LAG-3/PD-L1 bispecific antibody in patients with solid tumors that have progressed on prior PD-1/PD-L1 therapy. Journal of Clinical Oncology. May 26, 2019;37(15_suppl). 3 pages.

Yonezawa et al., Boosting Cancer Immunotherapy with Anti-CD137 Antibody Therapy. Clin Cancer Res. Jul. 15, 2015;21(14):3113-20. doi: 10.1158/1078-0432.CCR-15-0263. Epub Apr. 23, 2015.

Zhao et al., Novel Antibody Therapeutics Targeting Mesothelin In Solid Tumors. Clin Cancer Drugs. Oct. 2016;3(2):76-86. doi: 10.2174/2212697X036661602YAP et al., A first-in-human phase I study of FS118, an anti-LAG-3/PD-L1 bispecific antibody in patients with solid tumors that have progressed on prior PD-1/PD-L1 therapy. Journal of Clinical Oncology. May 26, 2019;37(15_suppl). 3 pages. 18215744.

[No Author Listed], Molecular biological basis of immunotherapy. New and Orphan Drugs for Leukemia Therapeutics. Sep. 30, 2016. 387-390. Retrieved on Dec. 18, 2023. 7 pages.

Brinkmann et al., The making of bispecific antibodies. MAbs. Feb. 2017/Mar.;9(2):182-212. doi: 10.1080/19420862.2016.1268307.

Cooper, The Development and Causes of Cancer. From The Cell: Molecular Approach. 2nd Ed. Sunderland, MA. Sinauer Associates. 2000. 9 pages.

Golfier et al., Anetumab ravtansine: a novel mesothelin-targeting antibody-drug conjugate cures tumors with heterogeneous target expression favored by bystander effect. Mol Cancer Ther. Jun. 2014;13(6):1537-48. doi: 10.1158/1535-7163.MCT-13-0926. Epub Apr. 8, 2014.

Han et al., Bispecific anti-CD3 x anti-HER2 antibody mediates T cell cytolytic activity to HER2-positive colorectal cancer in vitro and in vivo. Int J Oncol. Dec. 2014;45(6):2446-54. doi: 10.3892/ijo.2014.2663. Epub Sep. 18, 2014.

Heppner et al., Tumor heterogeneity: biological implications and therapeutic consequences. Cancer Metastasis Rev. 1983;2(1):5-23. doi: 10.1007/BF00046903.

Lin et al., Fc-dependent expression of CD137 on human NK cells: insights into "agonistic" effects of anti-CD137 monoclonal antibodies. Blood. Aug. 1, 2008;112(3):699-707. doi: 10.1182/blood-2007-11-122465. Epub Jun. 2, 2008.

Link et al., Abstract 3752: Preclinical pharmacology of MP0310: a 4-1BB/FAP bispecific DARPin drug candidate promoting tumor-restricted T-cell costimulation. Cancer Res. Jul. 1, 2018;78(13_Supplement):3752.

Liu et al., Abstract 3642: Tumor-antigen expression-dependent activation of the CD137 costimulatory pathway by bispecific DART® proteins. Cancer Res. Jul. 1, 2017;77(13_Supplement):3642.

Lo et al., Effector-attenuating Substitutions That Maintain Antibody Stability and Reduce Toxicity in Mice. J Biol Chem. Mar. 3, 2017;292(9):3900-3908. doi: 10.1074/jbc.M116.767749. Epub Jan. 11, 2017.

Reichen et al., Abstract 3029: FAP-mediated tumor accumulation of a T-cell agonistic FAP/4-1BB DARPin drug candidate analyzed by SPECT/CT and quantitative biodistribution. Cancer Res. Jul. 1, 2018;78(13_Supplement):3029.

Seckinger et al., Development and characterization of NILK-2301, a novel CEACAM5xCD3 κλ bispecific antibody for immunotherapy of CEACAM5-expressing cancers. J Hematol Oncol. Dec. 12, 2023;16(1):117. doi: 10.1186/s13045-023-01516-3.

(56) References Cited

OTHER PUBLICATIONS

Segal et al., Results from an Integrated Safety Analysis of Urelumab, an Agonist Anti-CD137 Monoclonal Antibody. Clin Cancer Res. Apr. 15, 2017;23(8):1929-1936. doi: 10.1158/1078-0432.CCR-16-1272. Epub Oct. 18, 2016.
Wang et al., Retargeting T cells for HER2-positive tumor killing by a bispecific Fv-Fc antibody. PLoS One. Sep. 23, 2013;8(9):e75589. doi: 10.1371/journal.pone.0075589. eCollection 2013.
U.S. Appl. No. 16/955,450, filed Jun. 18, 2020, Tuna et al.
U.S. Appl. No. 17/259,634, filed Jan. 12, 2021, Munoz-Olaya et al.
U.S. Appl. No. 17/259,680, filed Jan. 12, 2021, Pechouckova et al.
U.S. Appl. No. 17/259,677, filed Jan. 12, 2021, Munoz-Olaya et al.
U.S. Appl. No. 17/259,754, filed Jan. 12, 2021, Lakins et al.
U.S. Appl. No. 17/259,642, filed Jan. 12, 2021, Wollerton et al.
U.S. Appl. No. 17/259,714, filed Jan. 12, 2021, Tuna et al.
U.S. Appl. No. 17/259,791, filed Jan. 12, 2021, Lakins et al.
PCT/EP2019/068796, Oct. 2, 2019, International Search Report and Written Opinion.
PCT/EP2019/068796, Jan. 21, 2021, International Preliminary Report on Patentability.

\* cited by examiner

| IMGT | IMGT exon numbering | EU numbering | Kabat numbering | Wt Fcab | FS20-22-38 | FS20-22-41 | FS20-22-47 | FS20-22-49 | FS20-22-85 | FS20-31-58 | FS20-31-66 | FS20-31-94 | FS20-31-102 | FS20-31-108 | FS20-31-115 |
|---|---|---|---|---|---|---|---|---|---|---|---|---|---|---|---|
| 1.4 | 1 | 341 | 361 | G | | | | | | | | | | | |
| 1.3 | 2 | 342 | 363 | Q | | | | | | | | | | | |
| 1.2 | 3 | 343 | 364 | P | | | | | | | | | | | |
| 1.1 | 4 | 344 | 365 | R | | | | | | | | | | | |
| 1 | 5 | 345 | 366 | E | | | | | | | | | | | |
| 2 | 6 | 346 | 367 | P | | | | | | | | | | | |
| 3 | 7 | 347 | 368 | Q | | | | | | | | | | | |
| 4 | 8 | 348 | 369 | V | | | | | | | | | | | |
| 5 | 9 | 349 | 370 | Y | | | | | | | | | | | |
| 6 | 10 | 350 | 371 | T | | | | | | | | | | | |
| 7 | 11 | 351 | 372 | L | | | | | | | | | | | |
| 8 | 12 | 352 | 373 | P | | | | | | | | | | | |
| 9 | 13 | 353 | 374 | P | | | | | | | | | | | |
| 10 | 14 | 354 | 375 | S | | | | | | | | | | | |
| 11 | 15 | 355 | 376 | R | | | | | | | | | | | |
| 12 | 16 | 356 | 377 | D | | | | | | | | | | | |
| 13 | 17 | 357 | 378 | E | | | | | | | | | | | |
| 14 | 18 | 358 | 381 | L | Y | Y | Y | Y | Y | Y | W | W | | | |
| 15 | 19 | 359 | 382 | T | W | W | W | W | W | Y | Y | A | A | W | W |
| 16 | 20 | 360 | 383 | K | D | D | D | D | S | H | S | S | | | |
| 17 | 21 | 361 | 384 | N | Q | Q | Q | Q | G | G | G | G | | | |
| 18 | 22 | 362 | 385 | Q | E | E | E | E | E | E | E | E | | | |
| 19 | 23 | 363 | 386 | V | | | | | | | | | | | |
| 20 | 24 | 364 | 387 | S | | | | | | | | | | | |
| 21 | 25 | 365 | 388 | L | | | | | | | | | | | |
| 22 | 26 | 366 | 389 | T | | | | | | | | | | | |
| 23 | 27 | 367 | 390 | C | | | | | | | | | | | |
| 24 | 28 | 368 | 391 | L | | | | | | | | | | | |
| 25 | 29 | 369 | 392 | V | | | | | | | | | | | |
| 26 | 30 | 370 | 393 | K | | | | | | | | | | | |
| 27 | 31 | 371 | 394 | G | | | | | | | | | | | |
| 28 | 32 | 372 | 395 | F | | | | | | | | | | | |
| 29 | 33 | 373 | 396 | Y | | | | | | | | | | | |
| 30 | 34 | 374 | 397 | P | | | | | | | | | | | |
| 35 | 35 | 375 | 398 | S | | | | | | | | | | | |
| 36 | 36 | 376 | 399 | D | | | | | | | | | | | |
| 37 | 37 | 377 | 400 | I | | | | | | | | | | | |
| 38 | 38 | 378 | 401 | A | | | | | | | | | | | |
| 39 | 39 | 379 | 402 | V | | | | | | | | | | | |
| 40 | 40 | 380 | 405 | E | | | | | | | | | | | |
| 41 | 41 | 381 | 406 | W | | | | | | | | | | | |
| 42 | 42 | 382 | 407 | E | | | | | | | | | | | |

(Top-Bottom) SEQ ID NOs: 47, 61, 63, 66, 54, 69, 84, 77, 82, 86, 90, 93

Figure 1

| IMGT | | 43 | 44 | 45 | 45.1 | 45.2 | 45.3 | 45.4 | 77 | 78 | 79 | 80 | 81 | 82 | 83 | 84 | 84.1 | 84.2 | 84.3 | 84.4 | 85.4 | 85.3 | 85.2 | 85.1 | 85 | 86 | 87 | 88 | 89 | 90 | 91 |
|---|---|---|---|---|---|---|---|---|---|---|---|---|---|---|---|---|---|---|---|---|---|---|---|---|---|---|---|---|---|---|---|
| IMGT exon numbering | | 43 | 44 | 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 |
| EU numbering | | 408 | 410 | 411 | 414 | 415 | 416 | 417 | 418 | 419 | 420 | 421 | 422 | 423 | 424 | 425 | 426 | 427 | 428 | 430 | 433 | 434 | 435 | 436 | 437 | 438 | 439 | 440 | 441 | 442 | 443 |
| Kabat numbering | | 383 | 384 | 385 | 386 | 387 | 388 | 389 | 390 | 391 | 392 | 393 | 394 | 395 | 396 | 397 | 398 | 399 | 400 | 401 | 402 | 403 | 404 | 405 | 406 | 407 | 408 | 409 | 410 | 411 | 412 |
| Wt Fcab | | S | N | G | Q | P | E | N | N | Y | K | T | T | P | P | V | L | D | S | D | G | S | F | F | L | Y | S | K | L | T | V |
| FS20-22-38 | | | | | A | E | E | Y | D | | | | | | | | | | | | | | | | | | | | | | |
| FS20-22-41 | | | | | D | E | Q | F | A | | | | | | | | | | | | | | | | | | | | | | |
| FS20-22-47 | | | | | D | E | Q | F | A | | | | | | | | | | | | | | | | | | | | | | |
| FS20-22-49 | | | | | D | E | Q | F | A | | | | | | | | | | | | | | | | | | | | | | |
| FS20-22-85 | | | | | D | E | Q | F | A | | | | | | | | | | | | | | | | | | | | | | |
| FS20-31-58 | | | | | | | | | D | | | | | | | | | | | | | | | | | | | | | | |
| FS20-31-66 | | | | | | R | | H | D | | | | | | | | | | | | | | | | | | | | | | |
| FS20-31-94 | | | | | | | | V | D | | | | | | | | | | | | | | | | | | | | | | |
| FS20-31-102 | | | | | | | | I | D | | | | | | | | | | E | | | | | | | | | | | | |
| FS20-31-108 | | | | | E | Q | K | | D | | | | | | | | | | E | | | | | | | | | | | | |
| FS20-31-115 | | | | | | | | F | D | | | | | | | | L | | | | | | | | | | | | | | |

(Top-Bottom) SEQ ID NOs: 47, 61, 63, 66, 54, 69, 84, 77, 82, 86, 90, 93

Figure 1 continued

| IMGT | IMGT exon numbering | EU numbering | Kabat numbering | Wt Fcab | FS20-22-38 | FS20-22-41 | FS20-22-47 | FS20-22-49 | FS20-22-85 | FS20-31-58 | FS20-31-66 | FS20-31-94 | FS20-31-102 | FS20-31-108 | FS20-31-115 |
|---|---|---|---|---|---|---|---|---|---|---|---|---|---|---|---|
| 92 | 73 | 413 | 444 | D |  |  |  |  |  | P | P | P | P | P | P |
| 93 | 74 | 414 | 445 | K | Q | Q | Q | Q | Q | Y | Y | Y | Y | Y | Y |
| 94 | 75 | 415 | 446 | S | Y | Y | Y | Y | W | W | W | W | W | W | W |
| 95 | 76 | 416 | 447 | R |  |  |  |  |  |  |  |  |  |  |  |
| 96 | 77 | 417 | 448 | W |  |  |  |  |  |  |  |  |  |  |  |
| 97 | 78 | 418 | 449 | Q | N | N | S | N | N | G | G | G | G | G | G |
| 98 | 79 | 419 | 450 | Q | P | P | P | P | P | S | V | G | V | A | A |
| 99 | 80 | 420 | 451 | G |  |  | A |  | F | P | P | P | P | K | K |
| 100 | 81 | 421 | 452 | N | D | D | D | D | D | R | R | G | R | R | R |
| 101 | 82 | 422 | 453 | V | Y | Y | Y | Y | D | T | T | T | T | T | T |
| 101.1 |  |  |  |  |  |  |  |  |  |  |  |  |  |  |  |
| 101.2 |  |  |  |  |  |  |  |  |  |  |  |  |  |  |  |
| 101.3 |  |  |  |  |  |  |  |  |  |  |  |  |  |  |  |
| 101.4 |  |  |  |  |  |  |  |  |  |  |  |  |  |  |  |
| 102 | 83 | 423 | 454 | F |  |  |  |  |  |  |  |  |  |  |  |
| 103 | 84 | 424 | 455 | S |  |  |  |  |  |  |  |  |  |  |  |
| 104 | 85 | 425 | 456 | C |  |  |  |  |  |  |  |  |  |  |  |
| 105 | 86 | 426 | 457 | S |  |  |  |  |  |  |  |  |  |  |  |
| 106 | 87 | 427 | 458 | V |  |  |  |  |  |  |  |  |  |  |  |
| 107 | 88 | 428 | 459 | M |  |  |  |  |  |  |  |  |  |  |  |
| 108 | 89 | 429 | 460 | H |  |  |  |  |  |  |  |  |  |  |  |
| 109 | 90 | 430 | 461 | E |  |  |  |  |  |  |  |  |  |  |  |
| 110 | 91 | 431 | 462 | A |  |  |  |  |  |  |  |  |  |  |  |
| 112 | 92 | 432 | 463 | L |  |  |  |  |  |  |  |  |  |  |  |
| 113 | 93 | 433 | 464 | H |  |  |  |  |  |  |  |  |  |  |  |
| 114 | 94 | 434 | 465 | N |  |  |  |  |  |  |  |  |  |  |  |
| 115 | 95 | 435 | 466 | H |  |  |  |  |  |  |  |  |  |  |  |
| 116 | 96 | 436 | 467 | Y |  |  |  |  |  |  |  |  |  |  |  |
| 117 | 97 | 437 | 468 | T |  |  |  |  |  |  |  |  |  |  |  |
| 118 | 98 | 438 | 469 | Q |  |  |  |  |  |  |  |  |  |  |  |
| 119 | 99 | 439 | 470 | K |  |  |  |  |  |  |  |  |  |  |  |
| 120 | 100 | 440 | 471 | S |  |  |  |  |  |  |  |  |  |  |  |
| 121 | 101 | 441 | 472 | L |  |  |  |  |  |  |  |  |  |  |  |
| 122 | 102 | 442 | 473 | S |  |  |  |  |  |  |  |  |  |  |  |
| 123 | 103 | 443 | 474 | L |  |  |  |  |  |  |  |  |  |  |  |
| 124 | 104 | 444 | 475 | S |  |  |  |  |  |  |  |  |  |  |  |
| 125 | 105 | 445 | 476 | P |  |  |  |  |  |  |  |  |  |  |  |
| 129 | 106 CH3 | 446 | 477 | G |  |  |  |  |  |  |  |  |  |  |  |

(Top-Bottom) SEQ ID NOs: 47, 61, 63, 66, 54, 69, 84, 77, 82, 86, 90, 93

- G1/4420
- G1AA/Lob12.3
- G1AA/3H3

D

A

B

A

ANTIBODY MOLECULES THAT BIND CD137 AND OX40

RELATED APPLICATION

This Application is a national stage filing under 35 U.S.C. § 371 of International Patent Application Serial No. PCT/EP2019/068796, filed Jul. 12, 2019, the entire contents of which is incorporated herein by reference in its entirety.

Reference to a Sequence Listing Submitted as a Text File via EFS-WEB

The instant application contains a Sequence Listing which has been submitted in ASCII format via EFS-Web and is hereby incorporated by reference in its entirety. Said ASCII copy, created on Sep. 20, 2021, is named F083170012US00-SUBSEQ-ZGE and is 251,534 bytes in size.

The present invention relates to antibody molecules that bind and are able to agonise both CD137 and OX40. The antibody molecules comprise a CDR-based binding site for CD137, and an OX40 antigen-binding site that is located in a constant domain of the antibody molecule. The antibody molecules of the invention find application, for example, in the treatment of diseases, such as cancer and infectious diseases.

BACKGROUND TO THE INVENTION

The mammalian immune system is a finely balanced system which is sometimes disrupted by diseases such as cancers. Checkpoint receptors play an instrumental role in the immune system's response to disease by exerting either co-stimulatory or co-inhibitory effects, the balance of which determines the fate of the immune response (Pardall, 2012). Co-inhibitors inhibit T cell proliferation and induce the release of anti-inflammatory cytokines. They dampen inflammation and avoid organ/tissue damage from excessive immune reaction. Co-stimulators, on the other hand, promote T cell clonal expansion, effector differentiation and survival in order to facilitate the development of a protective immune response.

One proven cancer immunotherapy approach triggers the immune system to recognize and kill tumour cells by targeting these checkpoint receptors with antibodies that either block the function of co-inhibitory receptors or induce the activity of co-stimulatory receptors (Pardall, 2012). Antibodies that block the activity of co-inhibitory receptors have shown good clinical activity and are currently approved for the treatment of cancer (Larkin et al. 2015). Antibodies that induce the activity of co-stimulatory receptors have demonstrated great potential in preclinical model systems (Moran et al., 2013; Schaer et al., 2014) and several agents are currently in clinical trials (Mayes of al., 2018, Melero et al, 2013). These antibodies are also termed agonist antibodies as they aim to mimic the ligands of these co-stimulatory receptors Several T cell co-stimulatory receptors are members of the TNF superfamily of receptors, a large family of proteins involved in both immune and non-immune cell functions expressed at the cell surface (Bremer, 2013). Structural analysis of the complexes formed between TNF family receptors and their cognate ligands indicates that in the majority of the cases there is a trimer to trimer stoichiometry and TNFR family ligands are typically expressed at the cell surface as trimers (Wajant, 2015). The proposed model for TNFR activation is that interaction with a trimeric ligand induces the trimerization of monomeric receptors and Initiates signal transduction. This presupposes that TNFR family members are expressed as monomers and only ligand interaction induces the formation of receptor trimers. This model has recently been questioned (Vanamee & Faustman, 2018) and the association of these monomers into higher order structures in the absence of ligand Interaction is still a matter of debate. The existence of pre-assembled receptor dimers or even inactive trimers that require additional clustering of multiple receptor complexes would explain the lower activity of some soluble, trimer-only, TNF ligands as compared to their membrane bound forms that can form ligand superclusters and induce TNF receptor superclusters thereby inducing higher levels of receptor activation (Müller et al., 2008). This theory is also in line with the observation that TNFR-specific antibodies typically have no or low agonistic activity and require secondary crosslinking of antibody-TNF receptor complexes in order to Induce sufficient receptor clustering and activation, thereby mimicking the TNF ligand superclusters (Wajant, 2015).

The secondary crosslinking of antibody-TNF receptor complexes can be achieved in vitro by crosslinking agents, such as protein A or G or secondary antibodies targeting the constant domains of TNF receptor-specific agonist antibodies (Vanamee & Faustman. 2018; Wajant, 2015). However, in vivo, this secondary crosslinking requires the interaction with Fc gamma receptors present on the surface of immune cells such as macrophages, NK cells or B cells. The interaction of antibodies with Fc gamma receptors is complex as there are 6 Fc gamma receptors in humans with different expression patterns and affinities for the 4 human IgG isotypes (Bruhns et al., 2009). Fc gamma receptors have been shown to be required for optimal anti-tumour activity of agonist antibodies targeting TNF receptor superfamily targets in vivo (Bulliard et al., 2013; Bulliard et al., 2014). However, the dependency of TNFR agonist antibodies on Fc gamma receptor mediated crosslinking to induce strong activation of the receptors is likely to limit their overall activity in vivo due to several reasons: 1) antibody bound cells will need to interact with Fc gamma receptor expressing cells in trans and the frequency of this interaction will limit the activation of the TNFR-expressing cells; 2) the affinity of Fc gamma receptors for human IgG is typically far lower compared to the affinity of a typical therapeutic antibody for its target (micromolar range versus nanomolar range respectively); and 3) Fc gamma receptors mediate the effector functions of antibodies such as ADCC (antibody-dependent cell-mediated cytotoxicity) and ADCP (antibody-dependent cellular phagocytosis) and therefore have the potential to eliminate the very cells that the agonist antibodies are intended to activate (Mayes et al., 2018).

Bivalent bispecific antibodies that use one of the cognate antigens to crosslink a TNF receptor agonist represent an alternative to Fc gamma receptor meditated crosslinking. The antibody crosslinking effect would result from binding to a TNF receptor family member and another cell surface expressed receptor either on the same cell, in cis, or another cell. In trans. This mechanism of antibody crosslinking would then result in superclustering of the TNF receptor provided the second target is expressed at high levels, mimicking the TNF ligand superclusters. The bispecific antibody approach to TNFR agonist antibody development has several theoretical advantages to monospecific agonist antibodies: 1) the TNFR agonism can be directed to particular immune cells in the tumour microenvironment and periphery by targeting a second antigen, such as a checkpoint receptor or tumour associated antigen, as the second specificity of the bispecific antibody; 2) the affinity of the crosslinking binding domains of the bispecific antibody can be designed to be higher than the affinity of the antibody for Fc gamma receptors, thereby making the crosslinking more effective; 3) antibody effector functions can be selectively disabled using mutations, thereby ensuring there is no depletion of the cells intended to be activated; 4) agonism of two separate TNF receptors can be achieved in a single dual agonist molecule, combining the activation of different immune cells into a stronger stimulation of the immune response; 5) targeting co-expressed receptors can result in the activation of a single cell in cis without the requirement of two cells interacting together.

Several of the TNF receptor family members have overlapping expression patterns in immune cells. Specifically, OX40, CD137, GITR and CD27 are expressed on activated T cells and co-expression of OX40 and CD137 has been verified experimentally (Ma et al., 2005).

OX40 is predominantly expressed on activated T cells, including CD4+ T cells, CD8+ T cells, type 1 and type 2 T helper (Th1 and Th2) cells and regulatory T (Treg) cells, and is also expressed on activated natural killer (NK) cells. Interaction of OX40 with its ligand OX40 ligand (OX40L). expressed on antigen presenting cells (APCs), increases T cell clonal expansion, differentiation and survival, and enhances the generation of memory T cells (Croft et al., 2009). OX40 stimulation can have a direct effect on T cells, promoting their proliferation and survival, or an indirect effect via the enhanced production of inflammatory cytokines, such as IL2 and IFNγ. OX40 signalling can also modulate the function of Tregs, although on these cells it abrogates their suppressive activity (Takeda et al., 2004). In cancer OX40 was found to be expressed on tumour infiltrating T cells from patients with head and neck, melanoma and colorectal cancers, where high levels of OX40 positive lymphocytes correlate with better survival (Petty et al., 2002; Vetto et al., 1997). Pre-clinical studies of OX40 agonist antibodies in mice have demonstrated therapeutic efficacy in several syngeneic tumour models but the effectiveness of targeting OX40 as a monotherapy has been variable and seems to correlate with the immunogenicity of the tumour (Kjærgaard et al., 2000). This Is consistent with the view that OX40 expression on tumour-specific T cells would require sufficient priming likely not provided by poorly immunogenic tumours. In certain syngeneic models the anti-tumour activity of the OX40 antibody OX86 has been determined to result from its ability to deplete Intratumoural Tregs that express high levels of OX40, in a Fc gamma receptor dependent manner (Bulliard et al., 2014).

Agonist antibodies to OX40 are currently in clinical trials for cancer with most showing good safety profiles, but limited clinical activity (Curti et al., 2013). The isotype chosen for these antibodies is varied but several investigational drugs are Fc gamma receptor enabled human IgG1 antibodies, aiming possibly to deplete Tregs as the mechanism of action. The lack of clear clinical activity of these antibodies has prompted combination trials of OX40 agonist antibodies with several other therapies including PD1/PD-L1 or CTLA4 inhibition, anti-VEGF therapy and the tyrosine kinase inhibitor axitinib.

This Treg depletion mechanism of action has been demonstrated to be very effective in pre-clinical models and several receptors can be targeted to eliminate Tregs such as GITR (Bulliard et al., 2014) and CTLA4 (Simpson et al., 2013). However, antibodies targeting the equivalent receptors in humans have not been shown to have the same levels of anti-tumour efficacy in the clinic (Glisson et al., 2016; Tran et al., 2017). The reasons for this are unclear but lower levels of Fc gamma receptor expressing cells such as macrophages in human tumours as compared to mouse syngeneic tumour models (Milas et al., 1987) could be part of the explanation for the lack of clinical translatability of the mechanism of action of these antibodies. Other reasons could be the different levels of expression of these markers in human Tregs as compared to mouse Tregs (Aspeslagh et al., 2016).

CD137 is also expressed on activated T cells, including CD4+, CD8+. Th1, Th2 and Tregs, but Its expression profile also includes B cells, natural killer (NK) cells, natural killer T (NKT) cells and dendritic cells (DCs) (Bartkowiak & Curran, 2015). Like in the case of OX40, interaction of CD137 with its ligand triggers the activation of intracellular signalling pathways that result in T cell survival, proliferation and Induction of cytotoxic activity. CD137 stimulation preferentially stimulates CD8+ T cells when compared to CD4+ T cells and leads to their proliferation, survival and cytotoxic effector function via the production of Inflammatory cytokines, and also contributes to the differentiation and maintenance of memory CD8+ T cells. CD137 has also been demonstrated to be expressed specifically on tumour-reactive subsets of tumour-infiltrating lymphocytes (TILs) (Weigelin et al., 2016), which provides part of the rationale behind its agonistic engagement in vivo and its use in TIL selection for adoptive transfer. CD137 monotherapy is efficacious in several preclinical Immunogenic tumour models such as M C38, CT26 and B cell lymphomas. However, for even more effective treatment of established tumours, CD137 engagement in combination with other agents such as chemotherapy, cytokines and other checkpoint regulators have shown enhanced beneficial effects in tumour growth reduction (Bartkowiak & Curran, 2015). Targeting CD137 in pre-clinical models with agonist antibodies is also associated with liver inflammation and transaminitis that results from increased CD8+ T cell accumulation dependent on IL27 production by myeloid cells (Bartkowiak et al., 2018).

Agonist antibodies to CD137 are currently in clinical trials for cancer, however clinical progress has been slowed by dose-limiting high-grade liver inflammation, likely resembling the observations made in mice (Sanchez-Paulete et al., 2016). Urelumab (BMS-663513) was the first CD137 agonist antibody to enter clinical trials and showed signs of clinical activity before trials were stopped due to fatal hepatotoxicity at doses above 1 mg/kg (Segal et al., 2017). It is a human IgG4 antibody that is able to activate CD137 in the absence of crosslinking (U.S. Pat. No. 8,137,667 B2), though activity is increased upon crosslinking as expected per the theory of superdustering-mediated full receptor activation. In contrast, no dose-limiting toxicities have been observed with utomilumab (PF-05082566) when tested up to 10 mg/kg (Toicher et al., 2017). It is a human IgG2 antibody, and is only able to activate CD137 upon crosslinking (U.S. Pat. No. 8,337,850 B2). Additional clinical trials are underway with both antibodies, testing both monotherapies and combination with radiotherapy and chemotherapy as well as existing targeted and immuno-oncology therapies. Due to the hepatotoxicity seen with urelumab, this antibody has had to be dosed at very low levels and the early signs of clinical activity have not yet been observed at these levels.

Several bispecific molecules targeting either CD137 or OX40 are in early stage development by a number of companies. Tumour targeting of CD137 stimulation is being tested by Macrogenics using HER2- and EphA2-targeted CD137 agonist DART molecules, by Roche using FAPalpha- or CD20-targeted CD137 ligand fusion proteins, and by Pieris Pharmaceuticals using HER2-targeted CD137 agonist anticalin molecules. OX40 and CTLA4 dual targeting is being tested by Aligator Biosciences to specifically deplete intratumoral Tregs expected to express high levels of both targets.

Co-stimulation of OX40 and CD137 in vivo has been shown to stimulate both CD4+ and CD8+ T cells and to induce the cytotoxic function of both antigen experienced and antigen-inexperienced bystander CD4+ T cells. (Qui et a)., 2011). Interestingly, dual co-stimulation was able to induce transplanted CD4+ T cells to reduce tumour growth in immune deficient mice inoculated with a melanoma syngeneic tumour model (B16-F10), highlighting the ability of this therapy to Induce tumoricidal activity of CD4+ T cells (Qui of al., 2011). A phase dose escalation clinical trial studying the effect of combining an OX40 agonist (PF-04518600) with a CD137 agonist (utomilumab-PF-05082566) is currently underway (NCT02315066) to evaluate the safety of this combination, and a phase Ib/II clinical trial combining the same TNFR agonists with PD-1 blockade via avelumab is also currently underway (NCT02554812). These studies will look at the combination of simple monospecific agonist antibodies that will require Fc gamma receptor crosslinking for their agonism and may therefore underestimate the clinical activity of targeting these receptors in combination.

The dual co-stimulation of OX40 and CD137 has also recently been tested in mice using a bispecific antibody approach by chemically conjugating two existing antibodies against OX40 and CD137 (Ryan et al., 2018). The molecule, termed OrthomAb, was able to induce the proliferation of CD4+ and CD8+ T cells as well as the production of inflammatory cytokines IL-2 and IFN 7 in vitro. In vivo. OrthomAb was also able to reduce tumour growth of a melanoma syngeneic tumour model (B16-F10). The bivalent bispecific nature of OrthomAb is predicted to allow for efficient crosslinking of the molecules when engaged to both targets, leading to the clustering of OX40 and CD137 receptors and consequently T cell activation.

These results validate the bispecific antibody approach to targeting OX40 and CD137 in a single molecule. The process of manufacture of the OrthomAb molecule generates multiple higher order species as well as the desired antibody dimers that need to be further purified by several rounds of size exclusion steps. This manufacturing process is unlikely to make this approach viable for anything other than a research tool to validate specific combinations of targets. Furthermore, the structure of this bispecific antibody, where two large macromolecules are held together by a small chemical linker, is likely to be unstable in vivo and no pharmacokinetic data to address this was shown. Unfortunately, the in vivo anti-tumour effect of OrthomAb was only compared to the activity of either OX40 or CD137 agonist antibodies and not to their combination, making it unclear whether the molecule was having an effect due to its bispecificity or due to OrthomAb behaving as a combination of single-agent agonist antibodies against OX40 and CD137.

The rationale for combining the agonism of TNF receptor family members OX40 and CD137 in a single bivalent, bispecific and stable molecule is therefore established and has the potential to perform Fc gamma receptor-independent superdustering of OX40 and CD137, thereby activating both CD4+ and CD8+ T cells to mount an effective anti-tumour immune response. Based on the preclinical combination data generated with monoclonal antibodies targeting either the OX40 or CD137 pathways, this molecule also has potential as a combination partner to enhance the effect of standard of care cancer therapies to provide patient benefit.

Statements of Invention

The present inventors have recognised that antibody molecules which bind to both CD137 and OX40 and which are capable of inducing clustering and signalling of OX40 and/or CD137 when bound to both targets, are highly effective in activating immune cells, for example in a tumour microenvironment. In addition, the present inventors recognised that restricting the activation of CD137 to locations where CD137 and OX40 are co-expressed would be highly effective in activating immune cells without eliciting toxicities associated with known anti-CD137 agonist molecules. This is expected to be useful, for example, in immunotherapy for the treatment of cancer and other diseases.

As described in the background section above, it is thought that initial ligation of OX40 ligand or CD137 ligand to OX40 or CD137, respectively, initiates a chain of events that leads to receptor trimerisation, followed by receptor clustering, activation and subsequent initiation of potent anti-tumour T cell activity. For a therapeutic agent to efficiently achieve activation of OX40 or CD137. it is therefore expected that several receptor monomers need to be bridged together in a way that mimics bridging by the trimeric ligand.

The present inventors have isolated antibody molecules which comprise a complementarity determining region (CDR)-based antigen-binding site for CD137 and an OX40 antigen-binding site located in a constant domain of the antibody molecule. The inventors have shown that such antibody molecules are capable of binding both targets concurrently when both targets are co-expressed. Co-expression in this sense encompasses situations where CD137 and OX40 are expressed on the same cell, for example an Immune cell, and situations where CD137 and OX40 are expressed on different cells, for example two different immune cells located adjacent to each other in the tumour microenvironment. Thus, the antibody molecules of the invention are believed to be capable of binding in cis to both targets expressed on a single cell, as well as being capable of binding in trans to the two targets expressed on different cells.

The present inventors have further shown that an antibody molecule which comprises a CDR-based antigen-binding site for CD137 and an OX40 antigen-binding site located in a constant domain of the antibody molecule, was capable of binding bivalently to both targets. Specifically, the present inventors showed that when such an antibody molecule was allowed to bind to OX40 and CD137, and the resulting complexes were crosslinked and subjected to mass spectrometry analysis, 19% of the complexes were shown to comprise two OX40 moieties and two CD137 moieties, demonstrating that the antibody molecule was bound bivalently to both targets.

Further, the inventors have shown that when these antibody molecules are bound to both targets they are capable of inducing clustering and signalling of OX40 and CD137 in vitro. By acting in this way, such antibody molecules are termed "dual agonists", i.e. the antibody molecules are capable of inducing signalling via the receptors as a result of crosslinking by dual binding to both OX40 and CD137.

As demonstrated in the examples, OX40 Is preferentially expressed on CD4+ T cells and CD137 is preferentially expressed on CD8+ T cells. The present inventors have demonstrated that the antibody molecules are able to induce agonism of OX40 on CD4+ T cells. In these cases, it is believed that the antibody molecule is binding to CD137 via its CDR-based antigen-binding domain to crosslink the antibody molecule and the OX40 antigen-binding domain is, at the same time, able to bind to, cluster and activate OX40 expressed on the CD4+ T cells. Similarly, the present inventors have demonstrated that the antibody molecules are able to induce agonism of CD137 on CD8+ T cells. In these cases, it is believed that the antibody molecule is binding to OX40 via its OX40 antigen-binding domain to crosslink the antibody molecule and the OX40 antigen-binding domain Is, at the same time, able to bind to, cluster and activate CD137 expressed on the CD8+ T cells.

Furthermore, the inventors have shown that antibody molecules comprising the two antigen-binding sites as detailed above and which had been modified to reduce or abrogate binding to Fcγ receptors were able to induce signalling via the receptors when CD137 and OX40 were co-expressed, showing agonism occurred without requiring crosslinking by Fcγ receptors. Since Fcγ receptor-mediated crosslinking is not required for activity of the antibody molecule of the invention, signalling via the OX40 or CD137 receptors is expected to be localised to sites where both targets are present, such as in the tumour microenvironment. Thus, the antibody molecule Is capable of driving agonism autonomously, based on the expression of both specific targets and without the need for additional crosslinking agents.

Further, since Fcγ receptor-binding is needed for ADCC, it is expected that this reduction in binding to Fcγ receptors will also result in reduced ADCC such that the target immune cells will not be depleted by the antibody molecules of the invention. The present inventors considered this to be Important as the antibody molecules were designed to activate immune cells expressing CD137 and/or OX40 in order to promote an immune response. Depletion of these immune cells is therefore not desired. The inventors demonstrated that antibody molecules having the properties defined herein were able to activate and Induce the proliferation of immune cells, in particular T cells that express CD137 and/or OX40.

The present inventors have further shown that antibody molecules comprising CD137 and OX40 antigen-binding sites as detailed above were capable of suppressing tumour growth in vivo in mice. Furthermore, more effective tumour growth suppression was observed with the bispecific antibody molecules as compared to a combination of two monospecific antibody molecules where one of the antibody molecules comprised a CDR-based antigen-binding site for CD137 and the other molecule comprised a CDR-based antigen-binding site for OX40, demonstrating that concurrent engagement and agonism of OX40 and CD137 results in improved anti-tumour efficacy. In addition, the antibody molecules were shown to be able to induce complete tumour regression and establishment of protective immunological memory against re-challenge with tumour cells in a CT26 mouse tumour model. It is therefore expected that the antibody molecules of the Invention will show efficacy in the treatment of cancer in human patients. Since these antibody molecules have abrogated ADCC activity, it is expected that they are therefore suppressing tumour growth by agonizing the target Immune cells without significantly depleting these beneficial T cells (memory and effector cells).

As observed in the in vivo studies in mice, the activation and proliferation of T cells induced by the antibody molecules described herein was a systemic, rather than a tumour-localised, effect. Furthermore, an increase in proliferation and activation of peripheral central memory and effector memory CD4+ and CD8+ T cells was observed in a preliminary dose range finding study in cynomolgus monkeys administered with an antibody molecule of the invention. Thus, as well as targeting of T cells in the tumour microenvironment, peripheral memory T cells expressing OX40 and CD137 are expected to be targeted by the antibody molecule to drive an expansion of tumour-reactive T cells that will then provide their anti-tumour effect.

Therefore, in addition to the site of the actual tumour itself, the anatomical location affected by the tumour can also be considered to include locations elsewhere in the body, e.g. lymph nodes in the periphery, at which tumour-specific immune responses are generated.

As explained in the background section above, clinical development of CD137 agonist molecules has been held back at least in part due to treatment being either associated with dose-limiting high-grade liver inflammation (urelumab) or low clinical efficacy (utomilumab).

Without wishing to be bound by theory, it Is thought that T cells present in the liver may have the potential to be activated by anti-CD137 agonist molecules, leading to liver inflammation. CD8+ T cells have been shown to promote liver inflammation and apoptosis after sepsis/viral infection (Wesche-Soldato et al., 2007). Anti-CD137 agonist antibody therapy in mice has been shown to result in CD137-dependent T cell infiltration into the liver (Dubrot J et al., 2010). The results from these studies, when taken together, indicate that anti-CD137 agonist antibodies with high activity, such as urelumab, may cause infiltration of activated CD8+ T cells Into the liver, thereby leading to liver Inflammation. The activity of utomilumab may have been too low for this effect to be observed. Alternatively, the dose-limiting liver toxicity observed with urelumab treatment may be due to the particular epitope bound by this antibody.

The present inventors conducted an extensive selection program to isolate antibody molecules that bind dimeric human CD137 with high affinity, i.e. are expected to bind CD137 with high avidity. In view of the selection protocol used, the antibody molecules are expected to bind to monomeric CD137 with a lower affinity than the affinity observed for dimeric CD137. 'Affinity' as referred to herein may refer to the strength of the binding interaction between an antibody molecule and its cognate antigen as measured by K D. As would be readily apparent to the skilled person, where the antibody molecule is capable of forming multiple binding interactions with an antigen (e.g. where the antibody molecule is capable of binding the antigen bivalently and, optionally, the antigen is dimeric) the affinity, as measured by $K_D$, may also be influenced by avidity, whereby avidity refers to the overall strength of an antibody-antigen complex.

Expression of CD137 by Immune cells, such as T cells, is upregulated on activation. Without wishing to be bound by theory, it is thought that due to the high expression of CD137 on activated immune cells, CD137 will be in the form of dimers, trimers and higher-order multimers on the surface of such cells. In contrast, naïve immune cells, such as naïve T cells, express low or negligible levels of CD137 on their cell surface and any CD137 present is therefore likely to be in monomeric form. It is therefore expected that antibody molecules which bind to CD137 with high avidity, will preferentially bind to activated immune cells, such as activated T cells, as opposed to naïve Immune cells.

In light of the above, it is therefore expected that antibody molecules of the invention will be largely unable to activate CD137 in the absence of crosslinking via engagement with OX40. Further, as described above, the present inventors developed antibody molecules in which Fcγf receptor mediated crosslinking had been reduced or abrogated with the expectation that this would avoid activation of CD137 at locations where there is little or no co-expression of OX40. Disablement of Fcγ receptor binding was shown not to affect the anti-tumour activity of the antibody molecule. Without wishing to be bound by theory, it Is believed that such antibody molecules will show reduced toxicity when administered to patients. This is thought to be because CD137 activation will be largely restricted to locations where OX40 and CD137 are co-expressed at levels sufficient to drive clustering and activation of CD137. The present inventors have shown that in a preliminary dose range finding study in cynomolgus monkeys, doses of an antibody molecule of the invention were well tolerated up to 30 mg/kg.

The present inventors have shown that the antibody molecules of the invention are capable of inducing low levels of OX40 clustering and activation even in the absence of crosslinking. Unlike CD137 agonist antibodies, OX40 agonist antibodies have not shown any dose-limiting toxicities (DLTs) In the clinic and OX40 agonist activity in the absence of crosslinking is therefore not expected to represent a problem for clinical treatment. To the contrary, depending on the condition to be treated, a low level of OX40 agonist activity by the antibody molecules in the absence of crosslinking may be advantageous. Without wishing to be bound by theory, it is thought that antibody molecules comprising an OX40 antigen-binding site with this property may be useful in the context of cancer treatment by inducing limited activation and expansion of tumour-reactive T cells in the absence of crosslinking, leading to a larger pool of tumour-reactive T cells which can then be further activated by crosslinked Fcab molecules in the tumour microenvironment.

A further advantage of the antibody molecules of the invention that have been modified to reduce or abrogate binding to Fcγ receptors may be that these antibody molecules have anti-tumour activity that is not reliant on the depletion of OX40-expressing regulatory T cells (Tregs). Tregs are located in the periphery, which are potentially protective and may reduce the impact of autoimmunity that may be caused by over-stimulating the immune system (Vignali D A et al., 2008). Thus, it has been postulated that Treg depletion may have a significant effect on reducing tumour growth in mouse models (Bulliard et al., 2014. Simpson et at, 2013). However, there is limited evidence that Treg depletion in human tumours can be achieved by ADCC and, if Treg depletion does occur in humans, this does not seem to result in such dramatic anti-tumour activity as has been observed in mouse models (Powell et at, 2007; Nizar S et al., 2009; Glisson B S et al., 2016; Tran B et at, 2017). Thus, if the antibody molecule does not significantly deplete Tregs but still has anti-tumour activity, this may Indicate that the antibody molecule has anti-tumour activity that is Independent of Fcγ receptor-mediated Treg depletion.

The antibody molecules have further been shown to be capable of binding with high affinity both to human and cynomolgus CD137 and to human and cynomolgus OX40. This cross-reactivity is advantageous, as it allows dosing and safety testing of the antibody molecules to be performed in cynomolgus monkeys during preclinical development.

A further feature of the antibody molecules identified by the inventors is that the antigen-binding site for CD137 and the antigen-binding site for OX40 are both contained within the antibody structure itself. In particular, the antibody molecules do not require other proteins to be fused to the antibody molecule via linkers or other means to result in molecule which can bind bivalently to both of its targets. This has a number of advantages. Specifically, the antibody molecules identified by the Inventors can be produced using methods similar to those employed for the production of standard antibodies, as they do not comprise any additional fused portions. The structure is also expected to result in improved antibody stability, as linkers may degrade over time, resulting in a heterogeneous population of antibody molecules. Those antibodies in the population having only one protein fused may not be able to act as a dual agonist and signal via the receptors as a result of crosslinking by binding to both OX40 and CD137. Cleavage or degradation of the linker could take place prior to administration or after administration of the therapeutic to the individual (e.g. through enzymatic cleavage or the in vivo pH of the individual), thereby resulting in a reduction of its effectiveness whilst circulating in the individual. As there are no linkers in the antibody molecules identified by the inventors, the antibody molecules are expected to retain the same number of binding sites both before and after administration. Furthermore, the structure of the antibody molecules identified by the inventors is also preferred from the perspective of immunogenicity of the molecules, as the introduction of fused proteins or linkers or both may induce immunogenicity when the molecules are administered to an individual, resulting in reduced effectiveness of the therapeutic.

Thus, the present invention provides:

[1] An antibody molecule that binds to CD137 and OX40, comprising
 (a) a complementarity determining region (CDR)-based antigen-binding site for CD137; and
 (b) an OX40 antigen-binding site located in a CH3 domain of the antibody molecule;
 wherein the CDR-based antigen-binding site comprises CDRs 1-6 set forth in:
 (i) SEQ ID NOs 1, 2, 3, 4, 5 and 6, respectively [FS30-10-16];
 (ii) SEQ ID NOs 1, 2, 16, 4, 5 and 6, respectively [FS30-10-3];
 (iii) SEQ ID NOs 1, 2, 21, 4, 5 and 6, respectively [FS30-10-12];
 (iv) SEQ ID NOs 25, 26, 27, 4, 5 and 28, respectively [FS30-35-14]; or
 (v) SEQ ID NOs 33, 34, 35, 4, 5 and 36, respectively [FS30-5-37]; and
 wherein the OX40 antigen-binding site comprises a first sequence, a second sequence, and a third sequence located in the AB, CD and EF structural loops of the CH3 domain, respectively, wherein the first, second and third sequence have the sequence set forth in SEQ ID NOs 51, 52 and 53, respectively [FS20-22.49].

[2] An antibody molecule that binds to CD137 and OX40, comprising
 (a) a complementarity determining region (CDR)-based antigen-binding site for CD137; and
 (b) an OX40 antigen-binding site located in a CH3 domain of the antibody molecule;
 wherein the CDR-based antigen-binding site comprises CDRs 1-6 set forth in:
 (i) SEQ ID NOs 7, 8, 9, 10, 11 and 6. respectively [FS30-10-16];
 (ii) SEQ ID NOs 7, 8, 17, 10, 11 and 6, respectively [FS30-10-3];
 (iii) SEQ ID NOs 7, 8, 22, 10, 11 and 6, respectively [FS30-10-12];

(iv) SEQ ID NOs 29, 30, 31, 10, 11 and 28, respectively [FS30-35-14]; or
(v) SEQ ID NOs 37, 38, 39, 10, 11 and 36, respectively [FS30-5-37]; and
wherein the OX40 antigen-binding site comprises a first sequence, a second sequence, and a third sequence located in the AB, CD and EF structural loops of the CH3 domain, respectively, wherein the first, second and third sequence have the sequence set forth in SEQ ID NOs 51, 52 and 53, respectively [FS20-22.49].

[3] The antibody molecule according to [1] or [2], wherein:
(i) the first sequence is located at positions 14 to 18 of the CH3 domain of the antibody molecule;
(ii) the second sequence is located at positions 45.1 to 77 of the CH3 domain of the antibody molecule; and/or
(iii) the third sequence is located at positions 93 to 101 of the CH3 domain of the antibody molecule; and
wherein the amino acid residue numbering is according to the IMGT numbering scheme.

[4] The antibody molecule according to any one of [1] to [3], wherein the antibody molecule comprises the CH3 domain sequence set forth in SEQ ID NO: 54 [FS20-22.49].

[5] The antibody molecule according to any one of [1] to [4], wherein the antibody molecule comprises CDRs 1-6 set out in any one of (i) to (iv) of [1] or [2].

[6] The antibody molecule according to any one of [1] to [5], wherein the antibody molecule comprises CDRs 1-6 set out in any one of (i) to (iii) of [1] or [2].

[7] The antibody molecule according to any one of [1] to [6], wherein the antibody molecule comprises CDRs 1-6 set out in (i) of [1] or [2].

[8] The antibody molecule according to any one of [1] to [7], wherein the antibody molecule comprises a heavy chain variable (VH) domain and/or light chain variable (VL) domain, preferably a VH domain and a VL domain.

[9] The antibody molecule according to any one of [1] to [8], wherein the antibody molecule comprises an immunoglobulin heavy chain and/or an immunoglobulin light chain, preferably an immunoglobulin heavy chain and an immunoglobulin light chain.

[10] The antibody molecule according to [8] or [9], wherein the antibody molecule comprises the VH domain and/or VL domain, preferably the VH domain and the VL domain set forth in:
(i) SEQ ID NOs 12 and 14, respectively [FS30-10-16];
(ii) SEQ ID NOs 18 and 14, respectively [FS30-10-3];
(iii) SEQ ID NOs 23 and 14, respectively [FS30-10-12];
(iv) SEQ ID NOs 170 and 172, respectively [FS30-35-14]; or
(v) SEQ ID NOs 40 and 42, respectively [FS30-5-37];

[11] The antibody molecule according to [10], wherein the antibody molecule comprises the VH domain and VL domain set out in any one of (i) to (Iv) of [10].

[12] The antibody molecule according to [10] or [11], wherein the antibody molecule comprises the VH and VL domain set out in any one of (i) to (iii) of [10].

[13] The antibody molecule according to any one of [10] to [12], wherein the antibody molecule comprises the VH domain and VL domain set out in (i) of [10].

[14] An antibody molecule according to any one of [1] to [13], wherein the antibody molecule is a human IgG1 molecule.

[15] The antibody molecule according to any one of [1] to [14], wherein the antibody molecule comprises the heavy chain and light chain of antibody:
(i) FS20-22-49AA/FS30-10-16 set forth in SEQ ID NOs 95 and 97, respectively;
(ii) FS20-22-49AA/FS30-10-3 set forth in SEQ ID NOs 99 and 97, respectively;
(iii) FS20-22-49AA/FS30-10-12 set forth in SEQ ID NOs 103 and 97, respectively;
(iv) FS20-22-49AA/FS30-35-14 set forth in SEQ ID NOs 105 and 107, respectively; or
(v) FS20-22-49AA/FS30-5-37 set forth in SEQ ID NOs 109 and 111, respectively.

[16] The antibody molecule according to [15], wherein the antibody molecule comprises the light chain and heavy chain set out in any one of (1) to (iv) of [15].

[17] The antibody molecule according to [15], wherein the antibody molecule comprises the light chain and heavy chain set out in any one of (i) to (iii) of [15].

[18] The antibody molecule according to [15], wherein the antibody molecule comprises the light chain and heavy chain set out in (i) of [15].

[19] The antibody molecule according to any one of [1] to [18], wherein the antibody molecule binds human CD137 and human OX40.

[20] The antibody molecule according to [19], wherein the human CD137 consists of or comprises the sequence set forth in SEQ ID NO: 127.

[21] The antibody molecule according to [19] or [20], wherein the human OX40 consists of or comprises the sequence set forth in SEQ ID NO:130.

[22] The antibody molecule according to any one of [1] to [21], wherein the antibody molecule binds cynomolgus CD137 and cynomolgus OX40.

[23] The antibody molecule according to [22], wherein the cynomolgus CD137 consists of or comprises the sequence set forth in SEQ ID NO: 129.

[24] The antibody molecule according to [23] or [24], wherein the cynomolgus OX40 consists of or comprises the sequence set forth in SEQ ID NO:131.

[25] The antibody molecule according to any one of [5] to [7], [11] to [13] and [16] to [18], wherein the antibody molecule binds human CD137 and human OX40, and the affinity ($K_D$) by which the antibody molecule binds human CD137 is within 2-fold of the affinity ($K_D$) by which the antibody molecule binds human OX40.

[26] The antibody molecule according to any one of [19] to [25], wherein the antibody molecule is capable of binding to human CD137 and human OX40 concurrently.

[27] The antibody molecule according to any one of [1] to [26], wherein the antibody molecule is capable of activating OX40 on an immune cell in the presence of cell-surface expressed CD137.

[28] The antibody molecule according to any one of [1] to [27], wherein binding of the antibody molecule to OX40 on an immune cell and to CD137 causes clustering of OX40 on the Immune cell.

[29] The antibody molecule according to any one of [1] to [28], wherein the antibody molecule Is capable of activating CD137 on an Immune cell in the presence of cell-surface expressed OX40.

[30] The antibody molecule according to any one of [1] to [29], wherein binding of the antibody molecule to CD137 on an immune cell and to OX40 causes clustering of CD137 on the immune cell, and wherein OX40 is expressed on the same immune cell or on a separate cell.

[31] The antibody molecule according to any once of claims [27] to [30], wherein the immune cell is a T cell.

[32] The antibody molecule according to any one of [1] to [31], wherein the antibody molecule has been modified to reduce or abrogate binding of the CH2 domain of the antibody molecule to one or more Fcγ receptors.

[33] The antibody molecule according to any one of [1] to [32], wherein the antibody molecule does not bind to one or more Fcγ receptors.

[34] The antibody molecule according to [32] or [33], wherein the Fcγ receptor is selected from the group consisting of. FcγRI, FcγfRIIa, FcγRIIb and FcγRIII.

[35] The antibody molecule according to any one of [1] to [34], wherein the antibody molecule is capable of inducing proliferation of T cells.

[36] A conjugate comprising the antibody molecule according to any one of [1] to [35] and a bioactive molecule.

[37] A conjugate comprising the antibody molecule according to any one of [1] to [36] and a detectable label.

[38] A nucleic acid molecule or molecules encoding the antibody molecule according to any one of [1] to [35].

[39] A nucleic acid molecule or molecules encoding the antibody molecule according to any one of [1] to [4], [8] to [10], [14] to [15], and [19] to [35], wherein the nucleic acid molecule(s) comprise(s) the heavy chain nucleic acid sequence and/or light chain nucleic acid sequence of:
(i) FS20-22-49AA/FS30-10-16 set forth in SEQ ID NOs 96 and 98, respectively;
(ii) FS20-22-49AA/FS30-10-3 set forth in SEQ ID NOs 100 and 102, respectively;
(iii) FS20-22.49AA/FS30-10-12 set forth in SEQ ID NOs 104 and 102, respectively;
(iv) FS20-22-49AA/FS30-35-14 set forth in SEQ ID NOs 106 and 108, respectively, or
(v) FS20-22-49AA/FS30-5.37 set forth in SEQ ID NOs 110 and 112, respectively.

[40] A vector or vectors comprising the nucleic acid molecule or molecules according to any one of [38] to [39].

[41] A recombinant host cell comprising the nucleic acid molecule(s) according to any one of [38] to [39], or the vector(s) according to [40].

[42] A method of producing the antibody molecule according to any one of [1] to [35] comprising culturing the recombinant host cell of [41] under conditions for production of the antibody molecule.

[43] The method according to [42] further comprising isolating and/or purifying the antibody molecule.

[44] A pharmaceutical composition comprising the antibody molecule or conjugate according to any one of [1] to [37] and a pharmaceutically acceptable excipient.

[45] The antibody molecule or conjugate according to any one of [1] to [37] for use in a method for treatment of the human or animal body by therapy.

[46] A method of treating a disease or disorder in an individual comprising administering to the Individual a therapeutically effective amount of the antibody molecule or conjugate according to any one of [1] to [37].

[47] The antibody molecule or conjugate for use according to [45]. wherein the antibody molecule or conjugate is for use in treating a cancer or an infection disease in an individual.

[48] The method of [46], wherein the disease or disorder is a cancer or an infectious disease in an Individual.

[49] The use of the antibody molecule or conjugate according to any one of [1] to [37] in the preparation of a medicament for the treatment of cancer or an infectious disease.

[50] The antibody molecule or conjugate for use according to [47], method of [48], or use of the antibody molecule or conjugate according to [49], wherein the cancer is a solid cancer, optionally wherein the solid cancer is selected from the group consisting of melanoma, bladder cancer, brain cancer, breast cancer, ovarian cancer, lung cancer, colorectal cancer. cervical cancer, liver cancer, head and neck cancer, pancreatic cancer, renal cancer and stomach cancer.

[51] The antibody molecule or conjugate for use according to [47], method of [48], or use of the antibody molecule or conjugate according to [49]. wherein the infectious disease is a persistent viral infection, optionally wherein the persistent viral infection is selected from the group consisting of human immunodeficiency virus (HIV), Epstein-Barr virus, Cytomegalovirus, Hepatitis B virus, Hepatitis C virus, Varicella Zoster virus.

[52] The antibody molecule or conjugate for use according to [47], method of [48], or use of the antibody molecule or conjugate according to [49], wherein the infectious disease is a persistent bacterial infection, optionally wherein the persistent bacterial infection is a persistent infection of *Staphylococcus aureus, Hemophilus influenza, Mycobacterium tuberculosis, Mycobacterium leprae, Helicobacter pylori, Treponema pallidum, Enterococcus faecalis*, or *Streptococcus pneumoniae*.

[53] The antibody molecule or conjugate for use according to [47], method of [48], or use of the antibody molecule or conjugate according to [49], wherein the infectious disease is a persistent fungal infection, optionally wherein the persistent fungal injection is a persistent infection of *Candida*, e.g. *Candida albicans, Cryptococcus (gattii* and *neoformans), Talaromyces (Penicillium) marneffe, Microsporum*, e.g. *Microsporum audouinii*, and *Trichophyton tonsurans*.

[54] The antibody molecule or conjugate for use according to [47], method of [48], or use of the antibody molecule or conjugate according to [49]. wherein the infectious disease is a persistent parasitic infection, optionally wherein the persistent parasitic injection is a persistent infection of *Plasmodium*, such as *Plasmodium falciparum*. or *Leishmania*, such as *Leishmania donovani*.

[55] The antibody molecule or conjugate for use according to any one of [45], [47] and [50] to [54], where the treatment comprises administering the antibody molecule or conjugate to the individual in combination with a second therapeutic.

[56] The method according to [46], [48] and [50] to [54], wherein the method further comprises administering a therapeutically effective amount of a second therapeutic to the individual.

[57] The antibody molecule or conjugate for use in a method of treating a cancer in an Individual according to [47] or [50], wherein the method comprises administering the antibody molecule or conjugate to the individual in combination with an antibody that binds PD-1 or PD-L1.

BRIEF DESCRIPTION OF THE FIGURES

FIG. 1 shows an alignment of the sequences of the CH3 domains of Fcabs FS20-22-38. FS20-22-41, FS20-22-47, FS20-22-49, FS20-22-85, FS20-31-58, FS20-31.66, FS20-31-94, FS20-31-102, FS20-31-108, and FS20-31-115, as well as the wild-type (WT) Fcab. The positions of the AB. CD and EF structural loops, as well as any amino acid substitutions, deletions (denoted by a tilde "~") or insertions present in the CH3 domains of the Fcabs compared with the WT sequence are indicated. The numbers of the residues according to the IMGT, IMGT exon (consecutive numbering), EU and Kabat numbering systems are shown.

FIGS. 2A and B show IL2 release in the presence of increasing concentrations of anti-CD137mAb and in the presence (FIG. 2A) or absence (FIG. 2B) of a crosslinking antibody. G1A/20H4.9 showed activity in the presence and absence of the crosslinking antibody, whereas activity of the G1AA/MOR7480.1 and G1AA/FS30-10-16 antibodies was observed only in the presence of the crosslinking antibody. FIGS. 2C and D show IL-2 release in the presence of increasing concentrations of anti-CD137 FS30 mAb in mAb$^2$ format comprising an anti-human OX40 Fcab (FS20-22-49AA/FS30-5-37, FS20-22-49AA/FS30-10-3, FS20-22-49AA/FS30-10-12, FS20-22-49AA/FS30-10-16 and FS20-22-49AA/FS30-35-14) in the presence (FIG. 2C) or absence (FIG. 2D) of a crosslinking agent. Controls were included as follows: anti-CD137 antibody G21MOR7480.1 (positive control); anti-OX40 mAb G1/11D4 and mAb$^2$ FS20-22-49AA/4420 (negative controls); anti-FITC mAb G114420 (isotype negative control). FIG. 2C shows that there was a concentration dependent increase in the activation of DO11.10-hCD137 cells, as evidenced by an increase in mouse IL-2 release, in the presence of the crosslinked positive control mAb (G2/MOR7480.1) and the anti-CD137 FS30 mAb$^2$ (FS20-22-49AA/FS30-5-37, FS20-22-49AA/FS30-10-3, FS20-22-49AA/FS30-10-12, FS20-22-49AA/FS30-10-16 and FS20-22-49AA/FS30-35-14), but not in the presence of the negative control mAbs and mAb$^2$ (G1/4420, FS20-22-49AA/4420 and G1/11 D4). FIG. 2D shows that in the absence of crosslinking, the positive control G2/MOR7480.1, the mAb$^2$ FS20-22-49AA/FS30-5-37. FS20-22-49AA/FS30-10-3, FS20-22-49AA/FS30-10-12, FS20-22-49AA/FS30-10-16 and FS20-22-49AA/FS30-35-14, and the negative controls G1/4420, FS20-22-49AA/4420 and G1/11D4 showed no to weak T cell activation, as evidenced by the low basal levels of IL-2 measured.

FIG. 3A shows IL-2 release in the presence of mAbs G1/4420 (anti-FITC; isotype control), G1AA/MOR7480.1 (anti-CD137), G1AA/FS30-10-16 (anti-CD137), G1AA/20H4.9 (anti-CD137), G1AA/11D4 (anti-OX40), FS20-22-49AA/4420 (OX40/FITC mock mAb$^2$) and FS20-22-49AA/4420 plus G1AA/FS30-10-16 in combination, as well as mAb$^2$ FS20-22-49AA/FS30-10-16, at a concentration of 3.7 nM. The results show that only the OX40/CD137 mAb$^2$ increased activation of T cells in the absence of artificial crosslinking agents compared to the isotype control, whereas the OX40-targeting antibodies G1AA/11D4 and FS20-22-49AA/4420 and the anti-CD137 antibody G1AA/20H4.9 only showed increased T cell activation in the presence of artificial crosslinking agents compared to the isotype control, and the anti-CD137 antibodies G1AA/MOR7480.1 and G1AA/FS30-10-16 showed no statistically significant activity even in the presence of artificial crosslinking agent. FIG. 3B shows IL-2 release in the presence of OX40/CD137 mAb$^2$ FS20-22-49AA/FS30-10-16 at increasing concentrations in the presence and absence of an artificial crosslinking agent (anti-human CH2 antibody). The results show that the activation of T cells induced by the OX40/CD137 mAb$^2$ in the absence of the anti-human CH2 antibody was comparable to when it was tested in the presence of this artificial crosslinking agent. FIGS. 3C and D show IL-2 release in the presence of increasing concentrations of mAb and mAb$^2$ in the presence (FIG. 3D) and absence (FIG. 3C) of an artificial crosslinking agent (FITC-dextran for the anti-FITC mAb and OX40/FITC mock mAb$^2$ controls, and anti-human CH2 antibody for all other molecules tested). The controls were as follows: G1/4420 (anti-FITC), Gill 1D4 (anti-OX40), G2/MOR7480.1 (anti-CD137), G1/11 D4 plus G2/MOR7480.1 in combination, and FS20-22-49AA/4420 (OX40/FITC mock mAb$^2$). The results show that there was a concentration dependent Increase in the activation of T cells when OX40 was bound by the controls G1/11 D4, both alone and when dosed in combination with anti-CD137 mAb G2/MOR7480.1, and FS20-22-49A/4420 when they were crosslinked. The OX40/CD137 mAb$^2$ had comparable activity in the presence and absence of artificial crosslinking agent, and activity was similar to that of the crosslinked OX40 Fcab (FS20-22-49AA/4420 Xlink). Little activity was seen with only the anti-CD137 control antibody (G2/MOR7480.1) both with and without crosslinking.

FIG. 4A shows IL-2 release in the presence of mAb and mAb$^2$ at a concentration of 3.7 nM. The results show that only the OX40/CD137 mAb$^2$ increased activation of T cells in the absence of artificial crosslinking agents. The OX40-targeting antibodies G1AA/11D4 and FS20-22-49AA/4420 and the anti-CD137 antibody G1AA/20H4.9 only showed increased T cell activation in the presence of crosslinking agents. No activity was detected for the anti-CD137 antibodies G1AA/MOR7480.1 and G1AA/FS30-10-16 even in the presence of artificial crosslinking agent, confirming the results of the SEA assay as reported in FIG. 3A. FIG. 4B shows IL-2 release induced by increasing concentrations of OX40/CD137 mAb$^2$ FS20-22-49AA/FS30-10-16 in the presence and absence of an artificial crosslinking agent (anti-human CH2 antibody). The OX40/CD137 mAb$^2$ had comparable activity in the presence and absence of the artificial crosslinking agent. FIG. 4C shows IL-2 release in the presence of increasing concentrations of OX40/CD137 mAb$^2$ and controls in the absence of artificial crosslinking agents, while FIG. 4D shows IL-2 release in the presence of increasing concentrations of the single-agent controls G114420, G1/11 D4, G2/MOR7480.1 and FS20-22-49AA/4420 in the presence of an artificial crosslinking agent (FITC-dextran or anti-human CH2 antibody as appropriate). The results show that the OX40/CD137 mAb$^2$ had sub-nanomolar or single-digit nanomolar activity in the absence of artificial crosslinking agent. As expected, the G1/4420 control had no activity regardless of the presence of crosslinking agent. Without the presence of a crosslinking agent, the controls G1/11 D4, FS20-22-49AA/4420, G2/MOR7480.1, and the combination of G1/1104 and G2/MOR7480.1 had little or no activity. When crosslinked by anti-human CH2 antibody or FITC-dextran. the single-agent anti-OX40 and anti-CD137 controls exhibited a concentration dependent Increase in the activation of T cells, thus demonstrating that the assay was able to detect signalling via either OX40 or CD137 receptors on T cells.

FIGS. 5A and B show IL-2 release in a CD4+ T cell activation assay in the presence of Increasing concentrations of mAb and mAb$^2$. as indicated. mAb and mAb$^2$ were tested in the presence (FIG. 5B) or absence (FIG. 5A) of artificial crosslinking agents (FITC-dextran for the anti-FITC mAb and OX40/FITC mock mAb$^2$ controls, and anti human CH2 antibody for all other molecules tested). The results show that the OX40/CD137 mAb$^2$ was able to activate CD4+ T cells in the absence of an artificial crosslinking agent. CD4' T cells were activated by the crosslinked anti-OX40 controls G1 AA/11 D4 and FS20-22-49AA/4420 (alone and in combination with G1AA/FS30-10-16) but not by the single-agent anti-CD137 controls G1AA/MOR7480.1 and G1AA/FS30-10-16. The anti-OX40 control FS20-22-49AA/4420 also showed a low level of activity in the presence of CD4+ T cells when not crosslinked, which was greatly increased upon crosslinking of the antibody. The anti-OX40 Fcab shared by both the FS20-22-49AA/4420 mock mAb$^2$ and the FS20-22-49AA/FS30-10-16 mAb$^2$ was therefore shown to be able to activate CD4+ T cells via agonism of OX40 when the antibodies were crosslinked by artificial crosslinking agent or Fab-binding to CD137. FIGS. 5C and D show IL-2 release in a CD8+ T cell activation assay in the presence of increasing concentrations of mAb and mAb$^2$, as indicated. mAb and mAb$^2$ were tested in the presence (FIG. 5D) or absence (FIG. 5C) of artificial crosslinking agents (see legend to FIGS. 5A and B for details). The results show that the OX40/CD137 mAb$^2$ was able to activate CD8+ T cells in the absence of an artificial crosslinking agent. Activation of CD8+ T cells was observed for both anti-CD137 controls G1AA/MOR7480.1 and G1AA/FS30-10-16 (alone and in combination with FS20-22-49AA/4420), as well as by the anti-OX40 controls FS20-22-49AA/4420 and, to a lesser extent, G1AA/11D4, In the presence of artificial crosslinking agent. The anti-CD137 Fab arms common to both the G1AA/FS30-10-16 control mAb and the FS20-22-49AA/FS30-10-16 mAb$^2$ were therefore shown to be able to agonise CD137 expressed on CD8+ T cells when the antibodies were crosslinked either by artificial crosslinking agent or Fcab-binding to OX40. while the anti-OX40 Fcab shared by both the FS20-22-49AA/4420 mock mAb$^2$ and the FS20-22-49AA/FS30-10-16 mAb$^2$ was able to activate CD8+ T cells via agonism of OX40 when the antibodies were crosslinked by artificial crosslinking agent or Fab-binding to CD137. FIGS. 5E and F show IL-2 release in a CD4+ and a CD8+ T cell activation assay, respectively, in the presence of mAb/mAb$^2$ at a concentration of 3.7 nM and in the presence or absence of an artificial crosslinking agent (see legend to FIGS. 5A and B for details).

FIG. 5E shows that the OX40/CD137 mAb$^2$ was able to activate CD4+ T cells in the absence of an artificial crosslinking agent CD4+ T cells were activated by the crosslinked anti-OX40 controls G1AA/11 D4 and FS20-22-49AA/4420 but not by the single-agent anti-CD137 controls G1AA/MOR7480.1 and G1AA/FS30-10-16. The anti-OX40 control FS20-22-49AA/4420 also showed a low level of activity when not crosslinked, which was greatly increased upon crosslinking of the antibody. The anti-OX40 Fcab shared by both the FS20-22-49AA/4420 mock mAb$^2$ and the FS20-22-49AA/FS30-10-16 mAb$^2$ was therefore shown to be able to activate CD4+ T cells via agonism of OX40 when the antibodies were crosslinked by artificial crosslinking agent or Fab-binding to CD137. FIG. 5F shows that the OX40/CD137 mAb$^2$ was able to activate CD8+ T cells in the absence of an artificial crosslinking agent. Activation of CD8+ T cells was observed for anti-CD137 controls G1AA/20H4.9 and G1AA/FS30-10-16 (alone and in combination with FS20-22-49AA/4420) in the presence of artificial crosslinking agent, but not for the anti-CD137 control G1AA/MOR7480.1 or for the crosslinked anti-OX40 controls G1AA/11D4 and FS20-22-49AA/4420. Activation of CD8+ T cells was also observed for anti-CD137 control G1AA/20H4.9 in the absence of artificial crosslinking agent. The anti-CD137 Fab arms common to both the G1AA/FS30-10-16 control mAb and the FS20-22-49AA/FS30-10-16 mAb$^2$ were therefore shown to be able to agonise CD137 expressed on CD8+ T cells when the antibodies were crosslinked either by artificial crosslinking agent or Fcab-binding to OX40.

FIGS. 7A and B show IL-2 release in the presence of increasing concentrations of a mAb$^2$ which binds mouse OX40 and mouse CD137 receptors (FS20m-232-91AA/Lob12.3), and control antibodies, in the absence (FIG. 7A) and presence (FIG. 7B) of an artificial crosslinking agent (anti-human CH2 antibody or FITC-dextran as appropriate). Controls were antibodies G1/4420 (anti-FITC), G1AA/OX86 (anti-mOX40), G1AA/Lob12.3 (anti-mCD137), G1AA/OX86 plus G1AA/Lob12.3 in combination, and FS20m-232-91AA/4420 (mOX40/FITC mock mAb$^2$). The results show that in the absence of a crosslinking agent, the controls G1AA/OX86, FS20m-232-91AA/4420, G1AA/Lob12.3, and the combination of G1AA/OX86 and G1AA/Lob12.3 had no activity. When crosslinked by anti-human CH2 antibody or FITC-dextran, the G1AA/OX86, FS20m-232-91AA/4420, and G1AA/OX86 plus G1AA/Lob12.3 controls exhibited a concentration dependent increase in the activation of T cells. A marginal increase in activity was observed for the G1AA/Lob12.3 control when crosslinked. The OX40/CD137 mAb$^2$ showed good activity regardless of the presence of an artificial crosslinking agent. FIGS. 7C and D show the activity of different anti-mouse CD137 antibodies (G1AA/Lob12.3 and G1AA/3H3) in the absence (FIG. 7C) or presence (FIG. 7D) of a crosslinking antibody (clone MK1A6) In CD3-stimulated DO11.10-mCD137 cells. Activity of G1AA/3H3 was observed in the presence and absence of the crosslinking antibody whereas the activity of the G1AA/Lob12.3 antibody was observed only in the presence of the crosslinking antibody. Therefore, the G1AA/3H3 antibody is termed 'crosslink-Independent' and the G1AA/Lob12.3 antibody is termed 'crosslink-dependent'.

In FIG. 10A, the mean CT26 tumour volumes (plus or minus the standard error of the mean) of Balb/c mice treated with G1/OX86 (anti-OX40 positive control without the LALA mutation), G1/Lob12.3 (anti-CD137 positive control without the LALA mutation), G1/4420 (IgG control), the combination of G1/OX86 and G1/Lob12.3, the combination of the anti-OX40 mAb G1AA/OX86 and the anti-CD137 mAb G1AA/Lob12.3 (both with the LALA mutation), FS20m-232-91/Lob12.3 (OX40/CD137 mAb$^2$ without the LALA mutation) and FS20m-232-91AA/Lob12.3 (OX40/CD137 mAb$^2$ with the LALA mutation) are shown. The results show that treatment with the OX40/CD137 mAb$^2$ both with and without the LALA mutation (FS20m-232-91AA/Lob12.3 and FS20m-232-91/Lob12.3, respectively) resulted in a reduction in tumour growth compared to treatment with the anti-OX40 antibody G1/OX86, the anti-CD137 antibody G1/Lob12.3, the combination of these two antibodies (G1/OX86 plus G1/Lob12.3), and the combination of the LALA-containing anti-OX40 and anti-CD137 antibodies (G1AA/OX86 plus G1AA/Lob12.3). FIG. 10B shows the tumour volumes (over time) of individual CT26 tumour-bearing mice treated via Intraperitoneal injection with 3 mg/kg of either isotype control (clone G1AA/4420), mOX40/FITC mock mAb$^2$ (clone FS20m-232-91AA/4420), anti-mCD137 mAb (done G1AA/Lob12.3), the combination of mOX40/FITC mock mAb$^2$ and anti-mCD137 mAb, or mOX40/CD137 mAb$^2$ (clone FS20m-232-91AA/Lob12.3). The horizontal dashed lines indicate where 0 mm$^3$ lies on the y-axis. Qualitatively, mOX40/CD137 mAb$^2$ and the combination of mOX40/FITC mock mAb$^2$ and anti-mCD137 mAb inhibited CT26 tumour growth in a subset of animals. FIG/ 10C shows the mean tumour volumes (plus or minus the standard error of the mean) of the CT26-tumour bearing mice individually represented in FIG. 10B. The group treated with the mOX40/CD137 mAb$^2$ had a delayed early tumour growth phase (days 10-22) compared to the isotype control group. The anti-mCD137 mAb and the mOX40/FITC mock mAb$^2$ had no effect on early tumour growth rates either as single agents or in combination. FIG. 10D shows a Kaplan-Meier survival plot of the same CT26 tumour-bearing mice represented in FIGS. 10B and 10C. Survival analysis shows that treatment with the mOX40/CD137 mAb$^2$, but not with the anti-mCD137 mAb and the mOX40/FITC mock mAb$^2$ either as single agents or in combination, resulted in statistically significant increases in survival compared to isotype control. (Pairwise comparison was performed using log-rank (Mantel-Cox) test; **** p≤0.0001, ns=not statistically significant.)

FIG. 12A), G1AA/5C4 (anti-PD-1; FIG. 12B), tested either in the presence or absence of the FS20-22-49AA/FS30-10-16 mAb$^2$. The results show a concentration-dependent increase in the activation of T cells when the FS20-22-49AA/FS30-10-16 was present and that the addition of G1AA/S1 or G1AA/5C4 to FS20-22-49AA/FS30-10-16 mAb$^2$ increased the IL-2 release (maximum response) as compared to T cells treated with the mAb$^2$ alone. No activity was seen when T cells were treated with the control antibodies alone. Statistical testing between groups G1/4420 plus FS20-22-49AA/FS30-10-16 and G1AA/S1 plus FS20-22-49AA/FS30-10-16 (FIG. 12A) or G1/4420 plus FS20-22-49AA/FS30-10-16 and G1AA/5C4 plus FS20-22-49AA/FS30-10-16 (FIG. 12B) was performed using two-way ANOVA and Tukey's multiple comparison test with asterisks indicating the p-value (* p<0.032,  p<0.0021, * p<0.0002, **** p<0.0001).

(FIG. 13B) an anti-mouse PD-1 antibody, (FIG. 13C) an anti-mouse OX40/CD137 mAb$^2$ (FS20m-232-91AA/Lob12.3 mAb$^2$), or (FIG. 13D) a combination of an anti-mouse PD-1 antibody and the anti-mouse OX40/CD137 mAb² FS20m-232-91AA/Lob12.3 mAb² are shown. The proportion of mice with regressed tumours (defined as a tumour volume of less than or equal to 62.5 mm³) at the termination of study, 60 days following cell inoculation, are shown for each treatment group. The results show that the combination of an anti-PD-1 antagonist antibody and FS20m-232-91AA/Lob12.3 led to the highest proportion of animals, 7 out of 15 (47%). with complete tumour regression response (FIG. 13D). Mice subjected to single agent treatment with anti-PD-1 antibody (FIG. 13B) or FS20m-232-91AA/Lob12.3 (FIG. 13C) showed 0% and 7% tumour regression at the end of the study, respectively. FIG. 13E shows a Kaplan-Meier survival plot of CT26-tumour bearing mice treated as described for FIGS. 13A-D. Survival analysis showed that the combination of FS20m-232-91AA/Lob12.3 and the anti PD-1 antibody, resulted in a statistically significant survival benefit compared to isotype control antibodies (log-rank (Mantel Cox) test, $p<0.0001$). No significant survival differences were observed for single agent treatments compared to isotype control antibodies.

FIG. 14A shows tumour volumes of CT26-tumour bearing mice treated via intraperitoneal (i.p.) injection with either 10 mg/kg isotype control antibody (G1AA/4420), or 0.1, 0.3, 1, 3 or 10 mg/kg of FS20m-232-91AA/Lob12.3. The proportion of mice with regressed tumours (defined as a tumour volume of less than or equal to 62.5 mm³) at the termination of study, 67 days following cell inoculation, is shown for each treatment group (see top right of each graph). The results show that 0.3, 1, 3 or 10 mg/kg of FS20m-232-91AA/Lob12.3 resulted in tumour regression in 4% (1/25), 4% (1/25), 8% (2/25) and 4% (1/25) of animals at the end of the study, respectively. None of the animals in the isotype control and 0.1 mg/kg FS20m-232-91AA/Lob12.3 groups showed tumour regression. FIG. 14B shows a Kaplan-Meier survival plot of CT26-tumour bearing mice treated as described for FIG. 14A. Survival analysis showed that FS20m-232-91AA/Lob12.3 at all dose levels tested resulted in statistically significant survival benefit compared to isotype control. Comparison of 1 and 3 mg/kg groups, and 3 and 10 mg/kg groups, showed no statistical difference in survival. Pairwise comparison was performed between each group and 10 mg/kg isotype control, unless indicated, using log-rank (Mantel-Cox) test * $p \le 0.05$, * $p \le 0.0005$, ** $p \le 0.0001$, ns=not statistically significant.

FIG. 15A shows the mean CT26 tumour volumes in BALB/c mice treated with G1/4420 (IgG control), FS20m-232-91AA/Lob12.3 (OX40/CD137 mAb² with crosslink-dependent CD137 agonist clone Lob12.3) and FS20m-232-91AA/3H3 (OX40/CD137 mAb² with crosslink-independent CD137 agonist clone 3H3). Mean tumour volumes plus or minus the standard error of the mean are shown. The results show that treatment with either of the OX40/CD137 mAb² antibodies (FS20m-232-91AA/Lob12.3 or FS20m-232-91AA/3H3) resulted in a reduction in tumour growth compared to treatment with the isotype control antibody (G1/4420) and that no difference in the level of reduction was observed in mice treated with FS20m-232-91AA/Lob12.3 or FS20m-232-91AA/3H3. FIG. 15B shows a Kaplan-Meier survival plot of CT26-tumour bearing mice treated as described for FIG. 15A. Survival analysis showed that treatment with either of the OX40/CD137 mAb² (FS20m-232-91AA/Lob12.3 or FS20m-232-91AA/3H3) resulted in a statistically significant survival benefit compared to treatment with the isotype control antibody (log-rank (Mantel Cox) test $p<0.05$) but that no difference was observed between mice treated with either of the OX40/CD137 mAb².

DETAILED DESCRIPTION

Figure 2:
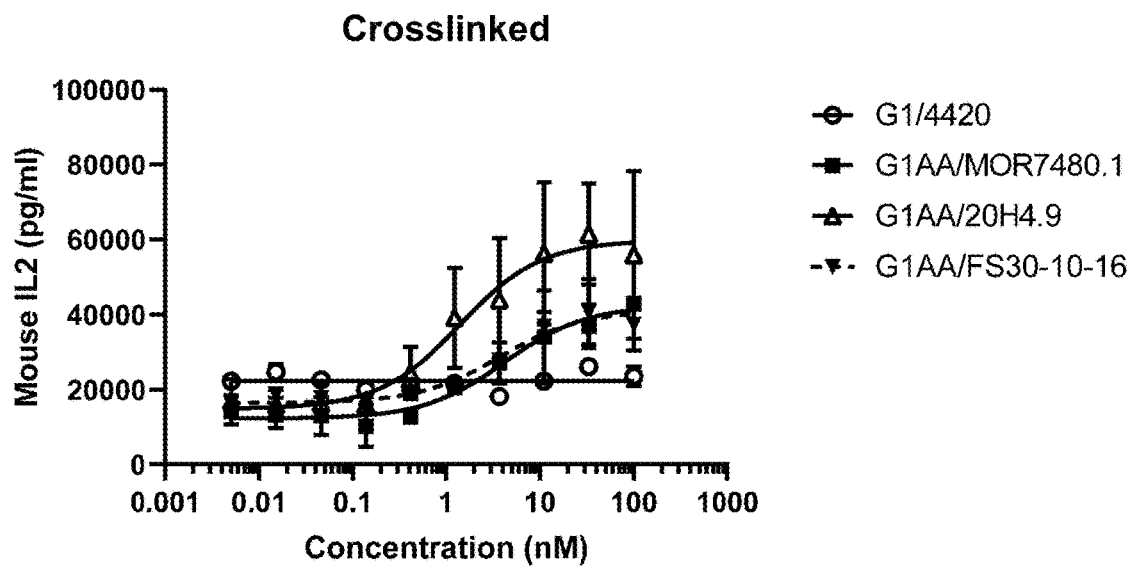
FIG. 2 shows the activity of CD137 mAb and OX40/CD137 mAb$^2$ in a human CD137 T cell activation assay in the presence and absence of crosslinking.
Figure 2:
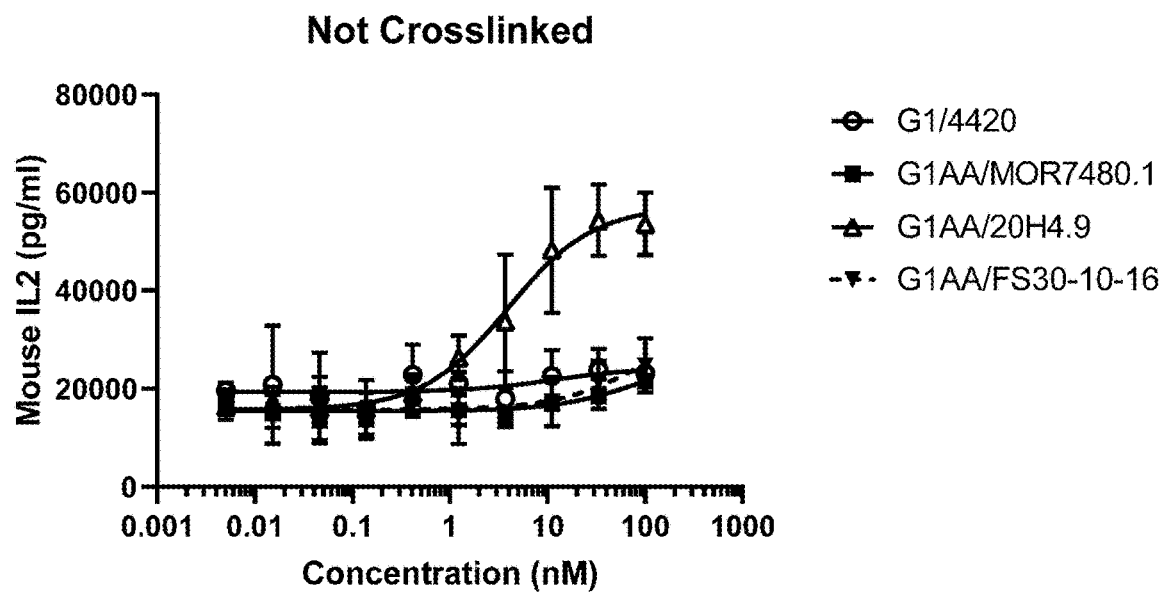
Figure 2:
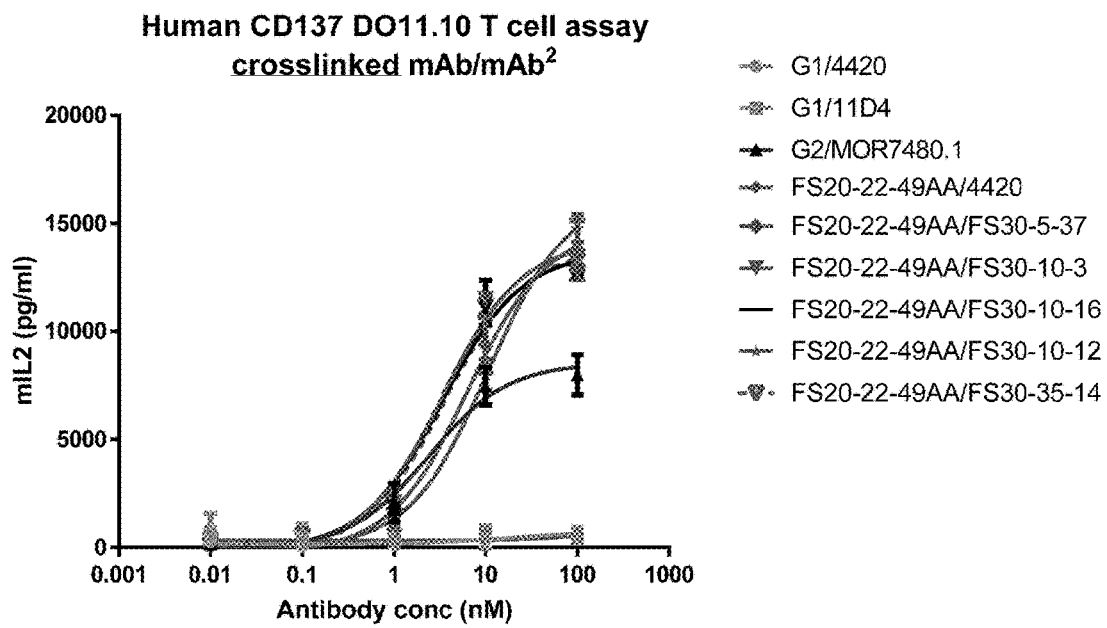
Figure 2:
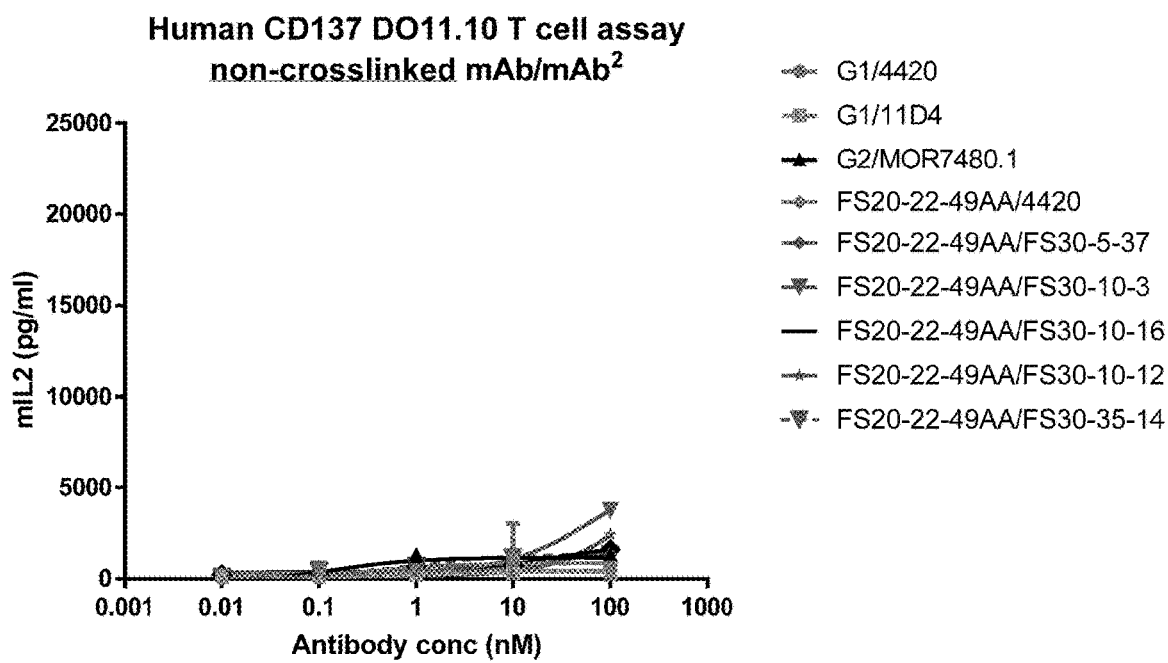

Aspects and embodiments of the present invention will now be discussed with reference to the accompanying figures. Further aspects and embodiments will be apparent to those skilled in the art. All documents mentioned in this text are incorporated herein by reference.

The present invention relates to antibody molecules which bind both to CD137 and OX40. Specifically, the antibody molecules of the present invention comprise a CDR-based antigen binding site for CD137 and an OX40 antigen binding site located in a constant domain of the antibody molecule. The terms "CD137" and "OX40" may refer to human CD137 and human OX40, murine CD137 and murine OX40, and/or cynomolgus monkey CD137 and cynomolgus monkey OX40, unless the context requires otherwise. Preferably the terms "CD137" and "OX40" refer to human CD137 and human OX40, unless the context requires otherwise.

The term "antibody molecule" describes an immunoglobulin whether natural or partly or wholly synthetically produced. The antibody molecule may be human or humanised, preferably human. The antibody molecule is preferably a monoclonal antibody molecule. Examples of antibodies are the immunoglobulin isotypes, such as immunoglobulin G, and their isotypic subclasses, such as IgG1, IgG2, IgG3 and IgG4, as well as fragments thereof.

The antibody molecule may be isolated, in the sense of being free from contaminants, such as antibodies able to bind other polypeptides and/or serum components.

The term "antibody molecule", as used herein, thus includes antibody fragments, provided said fragments comprise a CDR-based antigen binding site for CD137 and an OX40 antigen binding site located in a constant domain. Unless the context requires otherwise, the term "antibody molecule", as used herein, is thus equivalent to "antibody molecule or fragment thereof".

It is possible to take monoclonal and other antibodies and use techniques of recombinant DNA technology to produce other antibodies or chimeric molecules which retain the specificity of the original antibody. Such techniques may involve introducing the CDRs, or variable regions, and/or the constant domain sequences providing the OX40 antigen binding site, into a different immunoglobulin. Introduction of the CDRs of one immunoglobulin into another immunoglobulin is described for example in EP-A-184187, GB 2188638A or EP-A-239400. Similar techniques could be employed for the relevant constant domain sequences. Alternatively, a hybridoma or other cell producing an antibody molecule may be subject to genetic mutation or other changes, which may or may not alter the binding specificity of antibodies produced.

As antibodies can be modified in a number of ways, the term "antibody molecule" should be construed as covering antibody fragments, derivatives, functional equivalents and homologues of antibodies, including any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in EP-A-0120694 and EP-A-0125023.

An example of an antibody fragment comprising both CDR sequences and CH3 domain Is a minibody, which comprises an scFv joined to a CH3 domain (Hu et al., 1996).

The antibody molecule of the present invention binds to CD137 and OX40. Binding in this context may refer to specific binding. The term "specific" may refer to the situation in which the antibody molecule will not show any significant binding to molecules other than its specific binding partner(s), here CD137 and OX40. The term "specific" is also applicable where the antibody molecule is specific for particular epitopes, such as epitopes on CD137 and OX40, that are carried by a number of antigens in which case the antibody molecule will be able to bind to the various antigens carrying the epitope. In a preferred embodiment, the antibody molecule of the present invention does not bind, or does not show any significant binding to, to TNFRSF1A, TNFRSF1B, GITR, NGFR, CD40 and/or DR6.

Antibodies and methods for their construction and use are well-known in the art and are described in, for example, Holliger and Hudson 2005. It is possible to take monoclonal and other antibodies and use techniques of recombinant DNA technology to produce other antibodies or chimeric molecules which retain the specificity of the original antibody. Such techniques may involve introducing CDRs or variable regions of one antibody molecule into a different antibody molecule (EP-A-184187, GB 2188638A and EP-A-239400).

A CDR-based antigen-binding site is an antigen-binding site in an antibody variable region. A CDR-based antigen-binding site, may be formed by three CDRs, such as the three light chain variable domain (VL) CDRs or three heavy chain variable domain (VH) CDRs. Preferably the CDR-based antigen-binding site is formed by six CDRs, three VL CDRs and three VH CDRs. The contributions of the different CDRs to the binding of the antigen may vary in different antigen binding sites.

The three VH domain CDRs of the antigen-binding site may be located within an immunoglobulin VH domain and the three VL domain CDRs may be located within an immunoglobulin VL domain. For example, the CDR-based antigen-binding site may be located in an antibody variable region.

The antibody molecule may have one or preferably more than one, for example two, CDR-based antigen binding sites for the first antigen. The antibody molecule thus may comprise one VH and one VL domain but preferably comprises two VH and two VL domains, i.e. two VH/VL domain pairs, as is the case in naturally-occurring IgG molecules, for example.

The CDR-based antigen-binding site may comprise the three VH CDRs or three VL CDRs. preferably the three VH CDRs and the three VL CDRs, of antibody FS30-10-16, FS30-10.3, FS30-10-12, or FS30-35-14, or FS30-5-37, preferably antibody FS30-10-16.

The VH and VL domain sequences of these antibodies are set forth as follows: (i) the VH and VL domain sequences for SEQ ID NOs FS30-10-16 are shown in SEQ ID NOs 12 and 14, respectively;
  (ii) the VH and VL domain sequences for SEQ ID NOs FS30-10-3 are shown in SEQ ID NOs 18 and 14, respectively;
  (iii) the VH and VL domain sequences for SEQ ID NOs FS30-10-12 are shown in SEQ ID NOs 23 and 14, respectively;
  (iv) the VH and VL domain sequences for SEQ ID NOs FS30-35-14 are shown in SEQ ID NOs 170 and 172, respectively; and
  (v) the VH and VL domain sequences for SEQ ID NOs FS30-5-37 are shown in SEQ ID NOs 40 and 42, respectively.

The skilled person would have no difficulty in determining the sequences of the CDRs from the VH and VL domain sequences of the antibodies set out above. The CDR sequences may, for example, be determined according to Kabat (Kabat et al., 1991) or the international ImMunoGeneTics Information system (IMGT) (Lefranc et al., 2015).

The VH domain CDR1, CDR2 and CDR3 sequences of the antibody molecule according to IMGT numbering may be the sequences located at positions 27-38, 56-65, and 105-117, of the VH domain of the antibody molecule, respectively.

The VH domain CDR1, CDR2 and CDR3 sequences of the antibody molecule according to Kabat numbering may be the sequences at located positions 31-35, 50-65, and 95-102 of the VH domain, respectively.

The VL domain CDR1, CDR2 and CDR3 sequences of the antibody molecule according to IMGT numbering may be the sequences located at positions 27-38, 56-65, and 105-117, of the VL domain, respectively.

The VL domain CDR1, CDR2 and CDR3 sequences of the antibody molecule according to Kabat numbering may be the sequences at located positions 24-34, 50-56, and 89-97 of the VL domain, respectively.

For example, the antibody molecule may comprise the sequence of the VH domain CDR1, CDR2 and CDR3 of:
  (i) SEQ ID NOs 1, 2 and 3, respectively [FS30-10-16];
  (ii) SEQ ID NOs 1, 2 and 16, respectively [FS30-10-3];
  (iii) SEQ ID NOs 1, 2 and 21, respectively [FS30-10-12]:
  (iv) SEQ ID NOs 25, 26 and 27, respectively [FS30.35-14]; or
  (v) SEQ ID NOs 33, 34 and 35, respectively [FS30-5-37],
  wherein the CDR sequences are defined according to the ImMunoGeneTics (IMGT) numbering scheme.

The antibody molecule may comprise the sequence of the VH domain CDR1, CDR2 and CDR3 of:
  (i) SEQ ID NOs 7, 8 and 9, respectively [FS30-10-16];
  (ii) SEQ ID NOs 7, 8 and 17, respectively [FS30-10-3];
  (iii) SEQ ID NOs 7, 8 and 22, respectively [FS30-10-12]:
  (iv) SEQ ID NOs 29, 30 and 31, respectively [FS30.35-14]; or
  (v) SEQ ID NOs 37, 38 and 39, respectively [FS30-5-37],
  wherein the CDR sequences are defined according to the Kabat numbering scheme.

For example, the antibody molecule may comprise the sequence of the VL domain CDR1, CDR2 and CDR3 of:
  (i) SEQ ID NOs 4, 5 and 6, respectively [FS30-10-16];
  (ii) SEQ ID NOs 4, 5 and 6, respectively [FS30-10.3];
  (iii) SEQ ID NOs 4, 5 and 6, respectively [FS30-10-12];
  (iv) SEQ ID NOs 4, 5 and 28, respectively [FS30-35-14]; or
  (v) SEQ ID NOs 4, 5 and 36, respectively [FS30-5-37],
  wherein the CDR sequences are defined according to the ImMunoGeneTics (IMGT) numbering scheme.

For example, the antibody molecule may comprise the sequence of the VL domain CDR1, CDR2 and CDR3 of:
  (i) SEQ ID NOs 10, 11 and 6. respectively [FS30-10-16];
  (ii) SEQ ID NOs 10, 11 and 6, respectively [FS30-10.3];
  (iii) SEQ ID NOs 10, 11 and 6, respectively [FS30-10-12];
  (iv) SEQ ID NOs 10, 11 and 28, respectively [FS30-35-14]; or (v) SEQ ID NOs 10, 11 and 36, respectively [FS30-5-37], wherein the CDR sequences are defined according to the Kabat numbering scheme.

The VH and VL sequences of antibodies FS30-10-16, FS30-10-3, and FS30-10-12 are identical with the exception of the residue at position 109 of the VH according to the IMGT numbering scheme (residue 97 of the VH according to the Kabat numbering scheme). Thus, the antibody molecule may comprise the VH domain CDR1, CDR2 and CDR3 sequences and/or VL domain CDR1, CDR2 and CDR3 sequences, VH domain sequence and/or VL domain sequence, of antibody FS30-10-16, wherein the antibody molecule optionally comprises an amino acid substitution at position 109 of the heavy chain according to the IMGT numbering scheme (residue 97 of the heavy chain according to the Kabat numbering scheme), wherein the residue at said position is preferably selected from the group consisting of asparagine (N), threonine (T) and leucine (L).

The CDR-based antigen-binding site may comprise the VH or VL domains, preferably the VH and VL domains, of antibody FS30-10-16, FS30-10-3, FS30-10-12, FS30-35-14, or FS30-5-37, preferably antibody FS30-10-16, FS30-10-3, FS30-10-12, or FS30-35-14, more preferably antibody FS30-10-16, FS30-10-3, or FS30-10-12, most preferably antibody FS30-10-16.

The VH domain of antibodies FS30-10-16, FS30-10-3, FS30-10-12, FS30-35-14, and FS30-5-37 may have the sequence set forth in SEQ ID NOs 12, 18, 23, 170, and 40, respectively. The VL domain of antibodies FS30-10-16, FS30-10-3, FS30-10-12, FS30-35-14, and FS30-5-37 may have the sequence set forth in SEQ ID NOs 14, 14, 14, 172, and 42, respectively.

The antibody molecule of the invention comprises an OX40 antigen-binding site located in the constant domain of the antibody molecule. The constant domain may be a CL, CH1, CH2, CH3, or CH4 domain, preferably the constant domain is a CH1, CH2, or CH3 domain, more preferably a CH2 or CH3 domain, most preferably a CH3 domain.

Amino acid residue positions of the constant domain are numbered herein according to the ImMunoGeneTics (IMGT) numbering scheme, unless otherwise indicated. The IMGT numbering scheme is described in Lefranc et al., Dev. Comp. Immunol., 29, 185-203 (2005).

The OX40 antigen-binding site may comprise a first, second, and third sequence, located in a first, second, and third structural loop of the constant domain, respectively. Engineering of antibody constant domain structural loops to create antigen-binding sites for target antigens is known in the art and is described, for example, Wozniak-Knapp et al., 2010, and patent publication nos. WO2006/072620 and WO2009/132876. Preferably, the first, second, and third structural loops are the AB, CD, and EF structural loops of the CH3 domain of the antibody molecule, respectively. In the CH3 domain, the AB, CD, and EF structural loops are located at residues 11-18, 43-78 and 92-101 of the CH3 domain, respectively. Modification of the structural loop sequences of antibody constant domains to create new antigen-binding sites is described, for example, in WO2006/072620 and WO2009/132876.

In a preferred embodiment, the OX40 antigen-binding site of the antibody molecule comprises the first, second, and third sequence of:
  (i) FS20-22-49 set forth in SEQ ID NOs 51, 52 and 53, respectively;
  (ii) FS20-22-38 set forth in SEQ ID NOs 51, 59 and 60, respectively;
  (iii) FS20-22-41 set forth in SEQ ID NOs 51, 52 and 60, respectively;
  (iv) FS20-22-47 set forth in SEQ ID NOs 51, 52 and 65, respectively, or
  (v) FS20-22-85 set forth in SEQ ID NOs 51, 52 and 68, respectively.

The OX40 antigen-binding site may comprise the AB, CD and EF structural loop sequences of FS20-22-49, FS20-22.38, FS20-22.41, FS20-22-47, or FS20-22-85, wherein the AB, CD and EF structural loops are the sequences located at residues 11-18, 43-78 and 92-101 of the CH3 domain, respectively and the CH3 domain of FS20-22.49, FS20-22-38, FS20-22.41, FS20-22-47, or FS20-22-85 Is set forth in SEQ ID NO: 54, 61, 63, 66, and 69, respectively.

In a more preferred embodiment, the OX40 antigen-binding site of the antibody molecule comprises the first, second, and third sequence of FS20-22-49 set forth in SEQ ID NOs 51, 52 and 53, respectively. For example, the OX40 antigen-binding site may comprise the AB, CD and EF structural loop sequences of FS20-22-49 set forth in SEQ ID NOs 56, 57 and 58, respectively.

Where the OX40 antigen-binding site of the antibody molecule comprises the first, second, and third sequence of FS20-22-38, FS20-22-41, FS20-22-47, FS20-22-49, or FS20-22-85, the first, second and third sequence are preferably located at positions 14 to 18, 45.1 to 77, and 93 to 101 of the CH3 domain of the antibody molecule. respectively.

Where the OX40 antigen-binding site comprises the AB, CD and EF structural loop sequences of FS20-22-38, FS20-22.41, FS20-22-47, FS20-22-49, or FS20-22-85, the AB, CD and EF structural loop sequences are preferably located at positions 11 to 18, 43 to 78, and 92 to 101 of the CH3 domain of the antibody molecule, respectively.

The antibody molecule may further comprise a leucine (L) at position 91 of the CH3 domain of the antibody molecule. In particular, an antibody molecule comprising an OX40 antigen-binding site comprising the first, second, and third sequence of FS20-22-85 may comprise a leucine at position 91 of the CH3 domain of the antibody molecule.

In an alternative embodiment, the OX40 antigen-binding site of the antibody molecule comprises the first, second, and third sequence of:
  (i) FS20-31-58 set forth in SEQ ID NOs 71, 72 and 73, respectively:
  (ii) FS20-31-66 set forth in SEQ ID NOs 71, 72 and 76, respectively;
  (iii) FS20-31-94 set forth in SEQ ID NOs 79, 80 and 81, respectively;
  (iv) FS20-31-102 set forth in SEQ ID NOs 84, 85 and 76, respectively;
  (v) FS20-31-108 set forth in SEQ ID NOs 84, 88 and 89, respectively; or
  (vi) FS20-31-115 set forth in SEQ ID NOs 84, 92 and 89, respectively.

The OX40 antigen-binding site may comprise the AB, CD and EF structural loop sequences of FS20-31-58, FS20-31-66, FS20-31-94, FS20-31-102, FS20-31-108, or FS20-31-115, wherein the AB, CD and EF structural loops are the sequences located at residues 11-18, 43-78 and 92-101 of the CH3 domain, respectively and the CH3 domain of FS20-31-58, FS20-31-66, FS20-31-94, FS20-31-102, FS20-31-108, or FS20-31-115 is set forth in SEQ ID NO: 54, 61, 63, 66, and 69, respectively.

Where the OX40 antigen-binding site of the antibody molecule comprises the first, second, and third sequence of FS20-31-58. FS20-31-66, FS20-31-94. FS20-31-102, FS20-31-108, or FS20-31-115, the first, second and third sequence are preferably located at positions 14 to 18, 45.1 to 77, and 92 to 101 of the CH3 domain of the antibody molecule, respectively.

Where the OX40 antigen-binding site comprises the AB, CD and EF structural loop sequences of FS20-31-58, FS20-31-66, FS20-31-94, FS20-31-102, FS20-31-108, or FS20-31-115, the AB, CD and EF structural loop sequences are preferably located at positions 11 to 18, 43 to 78, and 92 to 101 of the CH3 domain of the antibody molecule, respectively.

As an alternative to IMGT numbering, amino acid residue positions in the constant domain, including the position of amino acid sequences, substitutions, deletions and insertions as described herein, may be numbered according to IMGT exon numbering (also referred to as consecutive numbering), EU numbering, or Kabat numbering. The concordance between IMGT numbering, IMGT exon numbering, EU numbering, and Kabat numbering of the residue positions of the CH3 domain are shown in FIG. 1.

Thus, for example, where the present application refers to the first, second and third sequence being located at positions 14 to 18, 45.1 to 77, and 93 to 101 of the CH3 domain of the antibody molecule, respectively, where the residue positions are numbered in accordance with the IMGT numbering scheme, the first, second and third sequence are located at positions 18 to 22, 46 to 50, and 74 to 82 of the CH3 domain, where the residue positions are numbered. In accordance with the IMGT axon numbering scheme, as shown in FIG. 1.

In one embodiment, the antibody molecule comprises a CH3 domain which comprises, has, or consists of the CH3 domain sequence of FS20-22-38, FS20-22-41, FS20-22-47, FS20-22-49, FS20-22-85, FS20-31-58, FS20-31-66, FS20-31-94, FS20-31-102, FS20-31-108, or FS20-31-115, wherein the CH3 domain sequence of FS20-22-38, FS20-22-41, FS20-22-47, FS20-22-49, FS20-22-85, FS20-31-58, FS20-31.66, FS20-31-94, FS20-31-102, FS20-31-108, and FS20-31-115 is set forth in SEQ ID NOs 54, 61, 63, 66, 69, 74, 77, 82, 86, 90, and 93, respectively.

In a preferred embodiment, the antibody molecule comprises a CH3 domain which comprises, has, or consists of the CH3 domain sequence of FS20-22-49, set forth in SEQ ID NO 54.

The CH3 domain of the antibody molecule may optionally comprise an additional lysine residue (K) at the immediate C-terminus of the CH3 domain sequence.

In addition, the antibody molecule of the invention may comprise a CH2 domain of an immunoglobulin G molecule, such as a CH2 domain of an IgG1, IgG2, IgG3, or IgG4 molecule. Preferably the antibody molecule of the invention comprises a CH2 domain of an IgG1 molecule. The CH2 domain may have the sequence set forth in SEQ ID NO: 48.

The CH2 domain of the antibody molecule may comprise one or more mutations that reduce or abrogate binding of the CH2 domain to one or more Fcγ receptors, such as FcγRI, FcγRIIa, FcγRIIb, FcγRIII. and/or to complement. The inventors postulate that reducing or abrogating binding to Fcγ receptors will decrease or eliminate ADCC mediated by the antibody molecule. Similarly, reducing or abrogating binding to complement is expected to reduce or eliminate CDC mediated by the antibody molecule. Mutations to decrease or abrogate binding of the CH2 domain to one or more Fcγ receptors and/or complement are known in the art (Wang et al., 2018). These mutations include the "LALA mutation" described in Bruhns et al., 2009 and Hezareh et al., 2001, which involves substitution of the leucine residues at IMGT positions 1.3 and 1.2 of the CH2 domain with alanine (L1.3A and L1.2A). Alternatively, the generation of a-glycosyl antibodies through mutation of the conserved N-linked glycosylation site by mutating the aparagine (N) at IMGT position 84.4 of the CH2 domain to alanine, glycine or glutamine (N84.4A, N84.4G or N84.4Q) is also known to decrease IgG1 effector function (Wang et al., 2018). As a further alternative, complement activation (C1q binding) and ADCC are known to be reduced through mutation of the proline at IMGT position 114 of the CH2 domain to alanine or glycine (P114A or P114G) (Idusogie et al., 2000; Klein et al., 2016). These mutations may also be combined in order to generate antibody molecules with further reduced or no ADCC or CDC activity.

Thus, the antibody molecule may comprise a CH2 domain, wherein the CH2 domain comprises:
  (1) alanine residues at positions 1.3 and 1.2; and/or
  (ii) an alanine or glycine at position 114; and/or
  (iii) an alanine, glutamine or glycine at position 84.4;
  wherein the amino acid residue numbering is according to the IMGT numbering scheme.

In a preferred embodiment, the antibody molecule comprises a CH2 domain, wherein the CH2 domain comprises:
  (i) an alanine residue at position 1.3; and
  (ii) an alanine residue at position 1.2;
  wherein the amino acid residue numbering Is according to the IMGT numbering scheme.

For example, the CH2 domain may have the sequence set forth in SEQ ID NO: 49.

In an alternative preferred embodiment, the antibody molecule comprises a CH2 domain, wherein the CH2 domain comprises:
  (1) an alanine residue at position 1.3;
  (ii) an alanine residue at position 1.2; and
  (iii) an alanine at position 114;
  wherein the amino acid residue numbering Is according to the IMGT numbering scheme.

For example, the CH2 domain may have the sequence set forth in SEQ ID NO: 50.

In a preferred embodiment, the antibody molecule that binds to CD137 and OX40 comprises
  (a) a CDR-based antigen-binding site for CD137; and
  (b) an OX40 antigen-binding site located in a CH3 domain of the antibody molecule;
  wherein the CDR-based antigen-binding site comprises the three VH CDRs and three VL CDRs (CDRs 1-6) of antibody FS30-10-16, FS30-10-3, FS30-10-12, FS30-35-14, or FS30-5-37, preferably FS30-10-16, FS30-10-3, or FS30-10-12, more preferably FS30-10-16 or FS30-10.3, most preferably FS30-10-16; and
  wherein the OX40 antigen-binding site comprises a first sequence, a second sequence and a third sequence located in the AB, CD and EF structural loops of the CH3 domain, respectively, wherein the first second and third sequences have the sequence of FS20-22-49 set forth in SEQ ID NOs 51, 52 and 53, respectively.

In a further preferred embodiment, the antibody molecule that binds to CD137 and OX40 comprises
  (a) a CDR-based antigen-binding site for CD137; and
  (b) a CH3 domain which comprises, has, or consists of the sequence set forth in SEQ ID NO: 54 [FS20-22-49];
  wherein the CDR-based antigen-binding site comprises the three VH CDRs and three VL CDRs (CDRs 1-6) of antibody FS30-10-16, FS30-10-3, FS30-10-12, FS30-35-14, or FS30-5-37, preferably FS30-10-16, FS30-10-3, or FS30-10-12. more preferably FS30-10-16 or FS30-10-3, most preferably FS30-10-16.

In a yet further preferred embodiment, the antibody molecule that binds to CD137 and OX40 comprises
  (a) a VH domain and a VL domain comprising the CDR-based antigen binding site for CD137; and
  (b) a CH3 domain which comprises, has, or consists of the sequence set forth in SEQ ID NO: 54 [FS20-22-49]:
    wherein the VH and VL domain comprises, has, or consists of the VH and VL of antibody FS30-10-16, FS30-10-3, FS30-10-12, FS30-35-14, or FS30-5-37, preferably FS30-10-16, FS30-10-3, or FS30-10-12, more preferably FS30-10-16 or FS30-10-3, most preferably FS30-10-16.

In a further preferred embodiment, the antibody molecule that binds to CD137 and OX40 comprises a heavy chain which comprises, has, or consists of the heavy chain and light chain of antibody.
  (i) FS20-22.49AA/FS30-10-16 set forth in SEQ ID NOs 95 and 97, respectively;
  (ii) FS20-2249AA/FS30-10-3 set forth in SEQ ID NOs 99 and 97, respectively;
  (iii) FS20-22.49AA/FS30-10-12 set forth in SEQ ID NOs 103 and 97, respectively;
  (iv) FS20-22.49AA/FS30-35-14 set forth in SEQ ID NOs 105 and 107, respectively, or
  (v) FS20-22.49AA/FS30-5.37 set forth in SEQ ID NOs 109 and 111, respectively;
    wherein the antibody molecule preferably comprises the light chain and heavy chain set out in (i) to (iv), more preferably comprises the light chain and heavy chain set out in (i) to (iii), most preferably comprises the light chain and heavy chain set out in (i).

The antibody molecules of the present invention may also comprise variants a first, second or third sequence, AB, CD or EF structural loop sequence, CH3 domain, CH2 domain, CH2 and CH3 domain, CDR, VH domain, VL domain, light chain and/or heavy chain sequences disclosed herein. Suitable variants can be obtained by means of methods of sequence alteration, or mutation, and screening. In a preferred embodiment, an antibody molecule comprising one or more variant sequences retains one or more of the functional characteristics of the parent antibody molecule, such as binding specificity and/or binding affinity for CD137 and OX40. For example, an antibody molecule comprising one or more variant sequences preferably binds to CD137 and/or OX40 with the same affinity, or a higher affinity, than the (parent) antibody molecule. The parent antibody molecule is an antibody molecule which does not comprise the amino acid substitution(s), deletion(s), and/or insertion(s) which have been incorporated into the variant antibody molecule.

For example, an antibody molecule of the invention may comprise a first, second or third sequence, AB, CD or EF structural loop sequence, CH3 domain, CH2 domain, CH2 and CH3 domain, CDR, VH domain, VL domain, light chain and/or heavy chain sequence which has at least 70%, at least 75%, at least 80%, at least 85%, at least 90%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity to a structural loop, CH3 domain, CH2 domain. CH2 and CH3 domain, CDR, VH domain, VL domain, light chain or heavy chain sequence disclosed herein.

In a preferred embodiment, the antibody molecule of the invention comprises a CH3 domain sequence which has at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity to the CH3 domain sequence set forth in SEQ ID NO: 54 [FS20-22-49].

In a further preferred embodiment, the antibody molecule has or comprises a CH2 domain sequence, which has at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity to the CH2 domain sequence set forth in SEQ ID NO: 48 or 49.

Sequence identity is commonly defined with reference to the algorithm GAP (Wisconsin GCG package. Accelerys Inc, San Diego USA). GAP uses the Needleman and Wunsch algorithm to align two complete sequences, maximising the number of matches and minimising the number of gaps. Generally, default parameters are used, with a gap creation penalty equaling 12 and a gap extension penalty equaling 4. Use of GAP may be preferred but other algorithms may be used, e.g. BLAST (which uses the method of Altschul et al, 1990), FASTA (which uses the method of Pearson and Lipman, 1988), or the Smith-Waterman algorithm (Smith and Waterman, 1981), or the TBLASTN program, of Altschul et al., 1990 supra, generally employing default parameters. In particular, the psi-Blast algorithm (Altschul et al., 1997) may be used.

An antibody molecule of the invention may also comprise a first, second or third sequence, AB, CD or EF structural loop sequence, CH3 domain, CH2 domain, CH2 and CH3 domain, CDR, VH domain, VL domain, light chain and/or heavy chain which has one or more amino acid sequence alterations (addition, deletion, substitution and/or insertion of an amino acid residue), preferably 20 alterations or fewer, 15 alterations or fewer, 10 alterations or fewer, 5 alterations or fewer, 4 alterations or fewer, 3 alterations or fewer, 2 alterations or fewer, or 1 alteration compared with a first, second or third sequence, AB, CD or EF structural loop sequence, CH3 domain. CH2 domain, CH2 and CH3 domain, Fcab, CDR, VH domain, VL domain, light chain or heavy chain sequence disclosed herein. In particular, alterations may be made in one or more framework regions of the antibody molecule outside the VH and VL domain sequences and/or in one or more framework regions of the CH3 domain. For example, the alterations may be in the CH3 domain outside of the sequences described herein as a first, second and third sequences, or as AB, CD or EF structural loop sequences.

In a preferred embodiment, the antibody molecule of the invention may comprise a CH3 domain sequence with one or more amino acid sequence alterations (addition, deletion, substitution and/or insertion of an amino acid residue), preferably 20 alterations or fewer, 15 alterations or fewer, 10 alterations or fewer, 5 alterations or fewer, 4 alterations or fewer, 3 alterations or fewer, 2 alterations or fewer, or 1 alteration compared with the CH3 domain sequence set forth in SEQ ID NO: 54, 61, 63, 66, 69, 74, 77, 82, 86, 90, or 93.

In a further preferred embodiment, the antibody molecule comprises a CH2 domain sequence, with one or more amino acid sequence alterations (addition, deletion, substitution and/or insertion of an amino acid residue), preferably 20 alterations or fewer, 15 alterations or fewer, 10 alterations or fewer, 5 alterations or fewer, 4 alterations or fewer, 3 alterations or fewer, 2 alterations or fewer, or 1 alteration compared with the CH2 domain sequence set forth in SEQ ID NO: 48 or 49.

In preferred embodiments in which one or more amino acids are substituted with another amino acid, the substitutions may be conservative substitutions, for example according to the following Table. In some embodiments, amino acids in the same category in the middle column are substituted for one another, i.e. a non-polar amino acid is substituted with another non-polar amino acid for example. In some embodiments, amino acids in the same line in the rightmost column are substituted for one another.

| ALIPHATIC | Non-polar | G A P |
| | | I L V |
| | Polar-uncharged | C S T M |
| | | N Q |
| | Polar-charged | D E |
| | | K R |
| AROMATIC | | H F WY |

In some embodiments, substitution(s) may be functionally conservative. That is, in some embodiments the substitution may not affect (or may not substantially affect) one or more functional properties (e.g. binding affinity) of the antibody molecule comprising the substitution as compared to the equivalent unsubstituted antibody molecule.

The antibody molecule preferably binds to human CD137 and human OX40. Preferably, the antibody molecule is capable of simultaneously binding to human CD137 and human OX40, wherein human CD137 and human OX40 are co-expressed. Co-expression in this sense encompasses situations where CD137 and OX40 are expressed on the same cell, for example an immune cell such as a T cell, and situations where CD137 and OX40 are expressed on different cells, for example two different immune cells located adjacent to each other in the tumour microenvironment. Thus, the antibody molecules of the Invention are believed to be capable of binding to both targets on a single cell in cis as well as being capable of binding to the two targets expressed on different cells in trans.

The antibody molecule preferably binds to dimeric human CD137 with an affinity ($K_D$) of 8 nM, 7 nM, 6 nM, 5 nM, 4 nM, 3 nM, 2 nM, 1 nM, 0.5 nM, 0.4 nM, or 0.3 nM or with a higher affinity. Preferably, the antibody molecule binds to human CD137, with an affinity ($K_D$) of 0.3 nM, or with a higher affinity. The antibody molecule may bind dimeric CD137 with a higher affinity than monomeric CD137. The human CD137 may, for example, have the sequence set forth in SEQ ID NO: 127.

The antibody molecule preferably binds to dimeric human OX40 with an affinity ($K_D$) of 8 nM, 7 nM, 6 nM, 5 nM, 4 nM, 3 nM, 2 nM, 1 nM, 0.5 nM, 0.4 nM, or 0.3 nM or with a higher affinity. Preferably, the antibody molecule binds to human OX40, with an affinity ($K_D$) of 0.3 nM, or with a higher affinity. The antibody molecule may bind dimeric OX40 with a higher affinity than monomeric OX40. The human OX40 may, for example, have the sequence set forth in SEQ ID NO: 130.

The antibody molecule preferably binds to cynomolgus CD137 and cynomolgus OX40. Binding to cynomolgus CD137 and OX40 as well as human CD137 and OX40 Is beneficial as it permits testing of the antibody molecule in cynomolgus monkeys for efficacy and toxicity prior to administration to humans. Preferably, the antibody molecule is capable of simultaneously binding to cynomolgus CD137 and cynomolgus OX40, wherein cynomolgus CD137 and cynomolgus OX40 are co-expressed.

The antibody molecule preferably binds to dimeric cynomolgus CD137 with an affinity ($K_D$) of 10 nM, 9 nM, 8 nM, 7 nM, 6 nM, 5 nM, 4 nM, 3 nM, 2 nM, 1 nM, 0.5 nM, 0.4 nM. or 0.3 nM or with a higher affinity. Preferably, the antibody molecule binds to dimeric cynomolgus CD137, with an affinity ($K_D$) of 0.3 nM, or with a higher affinity. The cynomolgus CD137 may, for example, have the sequence set forth in SEQ ID NO: 129.

The antibody molecule preferably binds to dimeric cynomolgus OX40 with an affinity ($K_D$) of 8 nM, 7 nM, 6 nM, 5 nM, 4 nM, 3 nM, 2.5 nM, 2 nM, 1.5 nM, or 1 nM or with a higher affinity. Preferably, the antibody molecule binds to cynomolgus OX40, with an affinity ($K_D$) of 1 nM, or with a higher affinity. The cynomolgus OX40 may, for example, have the sequence set forth in SEQ ID NO: 131.

The antibody molecule preferably binds to dimeric cynomolgus OX40 with an affinity ($K_D$) that is within 10-fold, 9-fold, 8-fold, 7-fold, 6-fold, or 5-fold of the affinity ($K_D$) that the antibody molecule binds to dimeric human OX40. Preferably, the antibody molecule preferably binds to dimeric cynomolgus OX40 with an affinity ($K_D$) that is within 5-fold of the affinity ($K_D$) that the antibody molecule binds to dimeric human OX40.

The antibody molecule preferably binds to dimeric cynomolgus CD137 with an affinity ($K_D$) that is within 30-fold, 20-fold, 10-fold, 5-fold, 4-fold, 3-fold, or 2-fold of the affinity ($K_D$) that the antibody molecule binds to dimeric human CD137. Preferably, the antibody molecule binds to dimeric cynomolgus CD137 with an affinity ($K_D$) that is within 2-fold of the affinity ($K_D$) that the antibody molecule binds to dimeric human CD137.

As described in the present Examples, it is thought that the similarity in binding to human and cynomolgus antigens may be advantageous as it would be hoped that the behaviour of the mAb$^2$ in cynomolgus monkey studies could be extrapolated to humans. This is thought to be beneficial for carrying out efficacy and toxicity studies carried out with the antibody molecule in cynomolgus monkeys, which may be predictive of the efficacy and toxicity of the antibody molecule in humans.

The antibody molecule preferably binds to dimeric human CD137 with an affinity ($K_D$) that is within 10-fold, 9-fold, 8-fold, 7-fold, 6-fold, or 5-fold of the affinity ($K_D$) that the antibody molecule binds to dimeric human OX40. Preferably, the antibody molecule preferably binds to dimeric human CD137 with an affinity ($K_D$) that is within 2-fold of the affinity ($K_D$) that the antibody molecule binds to dimeric human OX40.

The antibody molecule preferably binds to dimeric cynomolgus CD137 with an affinity ($K_D$) that is within 10-fold, 9-fold, 8-fold, 7-fold, 6-fold, or 5-fold of the affinity ($K_D$) that the antibody molecule binds to dimeric cynomolgus OX40.

As described in the present Examples, it Is thought that an antibody molecule having similar affinity for binding to both targets, i.e. CD137 and OX40 may be advantageous because the antibody molecule would be more likely to bind to cells which express both targets.

The binding affinity of an antibody molecule to a cognate antigen, such as human OX40. human CD137, cynomolgus OX40, or cynomolgus CD137 can be determined by surface plasmon resonance (SPR), such as Biacore, for example. The binding affinity of an antibody molecule to OX40 or CD137 expressed on a cell surface can be determined by flow cytometry.

The antibody molecules have been shown to have range of activities on ligand binding. For example the antibody molecule may be capable of blocking, may not be capable of blocking, or may be capable of partially blocking binding of CD137L to CD137.

Preferably, the antibody molecule may be capable of blocking, may not be capable of blocking, or may be capable of partially blocking binding of CD137L to CD137. More preferably, the antibody molecule Is capable of partially blocking binding of CD137L to CD137.

Preferably, the antibody molecule is capable of inducing signalling of OX40 and/or CD137 as a result of crosslinking by dual binding to both OX40 and CD137 when the two targets are co-expressed. By acting in this way, such antibody molecules are termed "dual agonists", i.e. the antibody molecules are capable of inducing signalling via the receptors as a result of crosslinking by dual binding to both OX40 and CD137. Thus, preferably the antibody molecule is capable of eliciting dual agonism when both OX40 and CD137 are co-expressed. As described herein, such dual agonists are expected to be advantageous. For example, it is believed that such a dual agonist may be able to elicit a stronger stimulation of the immune response, as it could combine the activation of different immune cells, e.g. combine the activity of CD8+ and CD4+ T cells by binding to both targets on different cells in trans. As a further example, it is believed that such a dual agonist may be able to result in the activation of a single cell co-expressing both targets without the requirement of two cells interacting together, by binding to both targets in cis.

More preferably, the dual agonist should be able to drive agonism autonomously by simultaneous engagement with its specific targets (OX40 and CD137) and without the need for additional crosslinking, e.g. crosslinking agents or Fcγ receptors. As described herein, such autonomous activity is expected to be advantageous as it will be restricted to locations where both targets are co-expressed and therefore is expected to reduce toxicity potentially associated with activation of CD137 at locations where there is little or no co-expression of OX40.

The ability of an antibody molecule to activate T cells can be measured using a T cell activation assay. T cells release IL-2 on activation. A T cell activation assay may therefore measure IL-2 release to determine the level of T cell activation induced by the antibody molecule.

For example, the ability of the antibody molecule to activate T cells is determined by measuring the concentration of the antibody molecule required to achieve half-maximal release of IL-2 by the T cells in a T cells activation assay. This is referred to as the $EC_{50}$ below.

In a preferred embodiment, the antibody molecule has an $EC_{50}$ in a T cell activation assay which is within 50-fold, 40-fold, 30-fold, 20-fold, 10-fold, or 5-fold of the $EC_{50}$ of FS20-22-49AA/FS30-10-16 in the same assay, wherein FS20-22-49AA/FS30-10-16 consists of the heavy chain of SEQ ID NO: 95 and the light chain of SEQ ID NO: 97.

For example, the antibody molecule may have an $EC_{50}$ in a T cell activation assay of 30 nM or less, 25 nM or less, 20 nM or less, 14 nM or less, 10 nM or less, 5 nM or less, 4 nM or less, 3 nM or less, 2 nM or less, 1.5 nM, 1 nM or 0.5 nM or less, preferably 1.5 nM or less. more preferably 1 nM or less when crosslinked.

In addition, or alternatively, the ability of an antibody molecule to activate T cells may be determined by measuring the maximum concentration of IL-2 released by the T cells in a T cell activation assay in the presence of the antibody molecule.

In a preferred embodiment, the maximum concentration of IL-2 released by the T cells in a T cell activation assay in the presence of the antibody molecule is within 20%, or 10% of the maximum concentration of IL-2 released by the T cells in the presence of FS20-22.49AA/FS30-10-16 in the same assay, wherein FS20-22.49AA/FS30-10-16 consists of the heavy chain of SEQ ID NO: 95 and the light chain of SEQ ID NO: 97.

The T cell activation assay preferably comprises T cells co-expressing OX40 and CD137. In a preferred embodiment, the T cell activation assay does not comprise any agents capable of crosslinking the antibody molecules other than CD137 and OX40.

The T cell activation assay may be a T cell assay as described herein, such as a pan-T cell assay, a CD4+ T cell assay, or a CD8+ T cell assay as described in the present Examples.

For example, a T cell activation assay may be an IL-2 release assay based on T cells isolated from human Peripheral Blood Mononuclear Cells (PBMCs). A CD4+ T cell activation assay or a CD8+ T cell activation assay may be an IL-2 release assay based on CD4+ T cells or CD8+ T cells Isolated from human PBMCs, respectively. As explained in the present Examples, an antibody molecule which is capable of activating T cells in both a CD4+ and a CD8+ T cell assay, is capable of activating both OX40 and CD137 (also referred to as a 'dual agonist'). For example, the T cell activation assay may comprise isolating human PBMCs from leucocyte depletion cones. Methods for isolating PBMCs are known in the art and described in the present examples. The T cells may then be isolated from the PBMCs. Methods for isolating T cells (all T cells, CD4+ T cells, or CD8+ T cells) from PBMCs are again known in the art and described in the present Examples.

The activation assay may involve preparing the required number of T cells for example in experimental media, such as a T cell medium. The required number of T cells may be prepared at a concentration of $1.0 \times 10^6$ cells/mi. T cells may then be stimulated using a suitable T cell activation reagent that provides the signals required for T cell activation. For example, the T cell activation reagent may be a reagent comprising CD3 and CD28, such as beads comprising CD3 and CD28. Isolated T cells may be incubated overnight with the T cell activation reagent to activate the T cells. Following this, the activated T cells may be washed to separate the T cells from the T cell activation reagent and resuspended in T cell medium at a suitable concentration, such as $2.0 \times 10^8$ cells/mi. Activated T cells may then be added to plates coated with anti-human CD3 antibody.

A suitable dilution of each test antibody molecule may be prepared and added to the wells. The T cells may then be incubated at 37° C. 5% $CO_2$ for 24 hours with the test antibody. Supernatants may be collected and assayed to determine the concentration of IL-2 in the supernatant. Methods for determining the concentration of IL-2 in a solution are known in the art and described in the present examples. The concentration of human IL-2 may be plotted versus the log concentration of the antibody molecule. The resulting curves may be fitted using the log (agonist) versus response equation.

The antibody molecule may be conjugated to a bioactive molecule or a detectable label. In this case, the antibody molecule may be referred to as a conjugate. Such conjugates find application in the treatment of diseases as described herein.

For example, the bioactive molecule may be an immune system modulator, such as a cytokine, preferably a human cytokine. For example, the cytokine may be a cytokine which stimulates T cell activation and/or proliferation. Examples of cytokines for conjugation to the antibody molecule include IL-2, IL-10, IL-12, IL-15, IL-21, GM-CSF and IFN-gamma.

Alternatively, the bioactive molecule may be a ligand trap, such as a ligand trap of a cytokine, e.g. of TGF-beta or IL-6.

Alternatively, the bioactive molecule may be a therapeutic radioisotope.

Radioimmunotherapy is used in cancer treatment, for example. Therapeutic radioisotopes suitable for radioimmunotherapy are known in the art and include yttrium-90, iodine-131, bismuth-213, astatine-211, lutetium 177, rhenium-188, copper-67, actinium-225, and iodine-125 and terbium-161.

Suitable detectable labels which may be conjugated to antibody molecules are known in the art and include radioisotopes such as iodine-125, iodine-131, yttrium-90, indium-111 and technetium-99; fluorochromes, such as fluorescein, rhodamine, phycoerythrin, Texas Red and cyanine dye derivatives for example,Cy7 and Alexa750; chromogenic dyes, such as diaminobenzidine; latex beads; enzyme labels such as horseradish peroxidase; phosphor or laser dyes with spectrally isolated absorption or emission characteristics; and chemical moieties, such as biotin, which may be detected via binding to a specific cognate detectable moiety, e.g. labelled avidin.

The antibody molecule may be conjugated to the bioactive molecule or detectable label by means of any suitable covalent or non-covalent linkage, such as a disulphide or peptide bond. Where the bioactive molecule is a cytokine, the cytokine may be joined to the antibody molecule by means of a peptide linker. Suitable peptide linkers are known in the art and may be 5 to 25, 5 to 20, 5 to 15, 10 to 25, 10 to 20. or 10 to 15 amino acids in length.

In some embodiments, the bioactive molecule may be conjugated to the antibody molecule by a cleavable linker. The linker may allow release of the bioactive molecule from the antibody molecule at a site of therapy. Linkers may include amide bonds (e.g, peptidic linkers), disulphide bonds or hydrazones. Peptide linkers for example may be cleaved by site specific proteases, disulphide bonds may be cleaved by the reducing environment of the cytosol and hydrazones may be cleaved by add-mediated hydrolysis.

The invention also provides an isolated nucleic acid molecule or molecules encoding an antibody molecule of the invention. The skilled person would have no difficulty in preparing such nucleic acid molecules using methods well-known in the art.

The nucleic add molecule or molecules may, for example, comprise the sequence set forth in SEQ ID NO: 55 or 113, 62, 64, 67, 70, 75, 78, 83, 87, 91, or 94, which encode the CH3 domains of FS20-22-49. FS20-22-38, FS20-22-41, FS20-22-47, FS20-22-85, FS20-31-58, FS20-31-66, FS20-31-94, FS20-31-102, FS20-31-108 and FS20-31-115, respectively. For example, the nucleic acid molecule or molecules may comprise the sequence set forth in SEQ ID NO: 55 or 113, both of which encode the CH3 domain of FS20-22-49. In some embodiments, the nucleic acid molecule or molecules comprise the sequence set forth in SEQ ID NO: 113, which encodes the CH3 domain of FS20-22-49. Preferably, the nucleic acid molecule or molecules comprise the sequence set forth in SEQ ID NO: 55, which encodes the CH3 domain of FS20-22-49.

The nucleic acid molecule or molecules may encode the VH domain and/or VL domain, preferably the VH domain and VL domain of antibody FS30-10-16, FS30-10-3, FS30-10-12, FS30-35-14, or FS30-5-37, preferably antibody FS30-10-16, FS30-10-3, FS30-10-12, or FS30-10-12, most preferably antibody FS30-10-16. The VH and VL domain sequences of these antibodies are described herein.

For example, the nucleic acid molecule(s) may comprise:
(i) the VH domain nucleic add sequence of antibody FS30-10-16 set forth in SEQ ID NO: 13, and/or the VL domain nucleic acid sequence of antibody FS30-10-16 set forth in SEQ ID NO: 15; or
(ii) the VH domain nucleic add sequence of antibody FS30-10-3 set forth in SEQ ID NO: 19, and/or the VL domain nucleic acid sequence of antibody FS30-10.3 set forth in SEQ ID NO: 20:
(iii) the VH domain nucleic acid sequence of antibody FS30-10-12 set forth in SEQ ID NO: 24, and/or the VL domain nucleic add sequence of antibody FS30-10-12 set forth in SEQ ID NO: 20;
(iv) the VH domain nucleic acid sequence of antibody FS30-35-14 set forth in SEQ ID NO: 171, and/or the VL domain nucleic acid sequence of antibody FS30-35-14 set forth in SEQ ID NO: 32; or
(v) the VH domain nucleic acid sequence of antibody FS30-5-37 set forth in SEQ ID NO: 41, and/or the VL domain nucleic acid sequence of antibody FS30-5.37 set forth in SEQ ID NO: 43.

The nucleic acid molecule or molecules may encode the heavy chain and/or light chain, preferably the heavy chain and light chain of antibody FS20-22-49AA/FS30-10-16, FS20-22-49AA/FS30-10-3, FS20-22-49AA/FS30-10-12, FS20-22-49AA/FS30.35-14, or FS20-22-49AA/FS30-5-37, preferably antibody FS20-22-49AA/FS30-10-16, FS20-22-49AA/FS30-10-3, FS20-22-49AA/FS30-10-12, or FS20-22-49AA/FS30-35-14, more preferably antibody FS20-22.49AA/FS30-10-16, FS20-22.49AA/FS30-10-3 or FS20-22.49AA/FS30-10-12, most preferably FS20-22-49AA/FS30-10-16. The VH and VL domain sequences of these antibodies are described herein.

For example, the nucleic acid molecule(s) may comprise:
(1) the heavy chain nucleic acid sequence of antibody FS20-22-49AA/FS30-10-16 set forth in SEQ ID NO: 96, and/or the light chain nucleic acid sequence of antibody FS20-22.49AA/FS30-10-16 set forth in SEQ ID NO: 98; or
(ii) the heavy chain nucleic acid sequence of antibody FS20-22-49AA/FS30-10-3 set forth in SEQ ID NO: 100, and/or the light chain nucleic acid sequence of antibody FS20-22.49AA/FS30-10-3 set forth in SEQ ID NO: 102;
(iii) the heavy chain nucleic acid sequence of antibody FS20-22-49AA/FS30-10-12 set forth in SEQ ID NO: 104, and/or the light chain nucleic acid sequence of antibody FS20-22.49AA/FS30-10-12 set forth in SEQ ID NO: 102;
(iv) the heavy chain nucleic acid sequence of antibody FS20-22-49AA/FS30.35-14 set forth in SEQ ID NO: 106, and/or the light chain nucleic acid sequence of antibody FS20-22-49AA/FS30-35-14 set forth in SEQ ID NO: 108; or
(v) the heavy chain nucleic acid sequence of antibody FS20-22-49AA/FS30-5-37 set forth in SEQ ID NO: 110, and/or the light chain nucleic acid sequence of antibody FS20-22-49AA/FS30-5-37 set forth in SEQ ID NO: 112.

Where the nucleic acid encodes the VH and VL domain, or heavy and light chain, of an antibody molecule of the invention, the two domains or chains may be encoded on two separate nucleic acid molecules.

An isolated nucleic acid molecule may be used to express an antibody molecule of the invention. The nucleic acid will generally be provided in the form of a recombinant vector for expression. Another aspect of the invention thus provides a vector comprising a nucleic acid as described above.

Suitable vectors can be chosen or constructed, containing appropriate regulatory sequences, including promoter sequences, terminator fragments, polyadenylation sequences, enhancer sequences, marker genes and other sequences as appropriate. Preferably, the vector contains appropriate regulatory sequences to drive the expression of the nucleic acid in a host cell. Vectors may be plasmids. viral e.g, phage, or phagemid, as appropriate.

A nucleic acid molecule or vector as described herein may be introduced into a host cell. Techniques for the introduction of nucleic acid or vectors into host cells are well established in the art and any suitable technique may be employed. A range of host cells suitable for the production of recombinant antibody molecules are known in the art, and include bacterial, yeast, insect or mammalian host cells. A preferred host cell is a mammalian cell, such as a CHO, NS0, or HEK cell, for example a HEK293 cell.

Another aspect of the invention provides a method of producing an antibody molecule of the invention comprising expressing a nucleic acid encoding the antibody molecule in a host cell and optionally isolating and/or purifying the antibody molecule thus produced. Methods for culturing host cells are well-known in the art. The method may further comprise isolating and/or purifying the antibody molecule. Techniques for the purification of recombinant antibody molecules are well-known in the art and include, for example HPLC, FPLC or affinity chromatography, e.g. using Protein A or Protein L. In some embodiments, purification may be performed using an affinity tag on antibody molecule. The method may also comprise formulating the antibody molecule into a pharmaceutical composition, optionally with a pharmaceutically acceptable excipient or other substance as described below. As explained above, CD137 and OX40 are both expressed on cells of the immune system, including T cells. For example, OX40 is expressed on cells of the immune system, including activated T cells, in particular CD4+ T cells, CD8+ T cells, type 1 T helper (Th1) cells, type 2 T helper (Th2) cells and regulatory T (Treg) cells, and tumour-infiltrating T cells, as well as activated natural killer (NK) cells. CD137 is expressed on cells of the immune system, including T cells, in particular CDB+ T cells, B cells, NK cells and tumour-infiltrating lymphocytes (TILs). CD137 is expressed at a lower level on CD4+ T cells than CD8+ T cells (see Example 14 and FIG. 6) but has also been shown to be Involved in inducing proliferation and activation of some subsets of CD4+ T cells (Wen et al., 2002).

OX40 activation has been shown to play a role in enhancing T cell activation. T cell clonal expansion, T cell differentiation and survival, and the generation of memory T cells. CD137 activation has been shown to play a role in enhancing proliferation, survival and the cytotoxic effector function of CD8+ T cells, as well as CD8+ T cell differentiation and maintenance of memory CD8+ T cells. Activation of CD137 has also been demonstrated to enhance NK cell-mediated ADCC, as well as B cell proliferation, survival and cytokine production.

In light of the immune response enhancing activity of OX40 and CD137, OX40 and CD137 agonist molecules have been investigated in the context of cancer treatment, and are also expected to find application in the treatment of infectious diseases.

The antibody molecules as described herein may thus be useful for therapeutic applications, in particular in the treatment of cancer and infectious diseases.

An antibody molecule as described herein may be used in a method of treatment of the human or animal body. Related aspects of the invention provide;
(i) an antibody molecule described herein for use as a medicament,
(ii) an antibody molecule described herein for use in a method of treatment of a disease or disorder,
(iii) the use of an antibody molecule described herein in the manufacture of a medicament for use in the treatment of a disease or disorder, and,
(iv) a method of treating a disease or disorder in an individual, wherein the method comprises administering to the individual a therapeutically effective amount of an antibody molecule as described herein.

The individual may be a patient, preferably a human patient.

Treatment may be any treatment or therapy in which some desired therapeutic effect is achieved, for example, the inhibition or delay of the progress of the condition, and includes a reduction in the rate of progress, a halt in the rate of progress, amelioration of the condition, cure or remission (whether partial or total) of the condition, preventing, ameliorating, delaying, abating or arresting one or more symptoms and/or signs of the condition or prolonging survival of an individual or patient beyond that expected in the absence of treatment.

Treatment as a prophylactic measure (i.e, prophylaxis) is also included. For example, an individual susceptible to or at risk of the occurrence or re-occurrence of a disease such as cancer may be treated as described herein. Such treatment may prevent or delay the occurrence or re-occurrence of the disease in the individual.

A method of treatment as described may be comprise administering at least one further treatment to the individual in addition to the antibody molecule. The antibody molecule described herein may thus be administered to an individual alone or in combination with one or more other treatments. Where the antibody molecule Is administered to the Individual in combination with another treatment, the additional treatment may be administered to the individual concurrently with, sequentially to, or separately from the administration of the antibody molecule. Where the additional treatment is administered concurrently with the antibody molecule, the antibody molecule and additional treatment may be administered to the individual as a combined preparation. For example, the additional therapy may be a known therapy or therapeutic agent for the disease to be treated.

Whilst an antibody molecule may be administered alone, antibody molecules will usually be administered in the form of a pharmaceutical composition, which may comprise at least one component in addition to the antibody molecule. Another aspect of the invention therefore provides a pharmaceutical composition comprising an antibody molecule as described herein. A method comprising formulating an antibody molecule into a pharmaceutical composition is also provided.

Pharmaceutical compositions may comprise, in addition to the antibody molecule, a pharmaceutically acceptable excipient, carrier, buffer, stabilizer or other materials well known to those skilled in the art. The term "pharmaceutically acceptable" as used herein pertains to compounds, materials, compositions, and/or dosage forms which are, within the scope of sound medical judgement, suitable for use in contact with the tissues of a subject (e.g., human) without excessive toxicity, irritation, allergic response, or other problem or complication, commensurate with a reasonable benefit/risk ratio. Each carrier, excipient, etc. must also be "acceptable" in the sense of being compatible with the other Ingredients of the formulation. The precise nature of the carrier or other material will depend on the route of administration, which may be by infusion, injection or any other suitable route, as discussed below.

For parenteral, for example subcutaneous or intravenous administration, e.g. by injection, the pharmaceutical composition comprising the antibody molecule may be in the form of a parenterally acceptable aqueous solution which is pyrogen-free and has suitable pH, isotonicity and stability. Those of relevant skill in the art are well able to prepare suitable solutions using, for example, isotonic vehicles, such as Sodium Chloride Injection, Ringer's Injection, Lactated Ringer's Injection. Preservatives, stabilizers, buffers, antioxidants and/or other additives may be employed as required including buffers such as phosphate, citrate and other organic acids; antioxidants, such as ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens, such as methyl or propyl paraben; catechol; resorcinol; cyclohexanol: 3'-pentanol; and m-cresol); low molecular weight polypeptides: proteins, such as serum albumin, gelatin or immunoglobulins; hydrophilic polymers, such as polyvinylpyrrolidone: amino acids, such as glycine, glutamine, asparagines, histidine, arginine, or lysine; monosaccharides, disaccharides and other carbohydrates including glucose, mannose or dextrins; chelating agents, such as EDTA; sugars, such as sucrose, mannitol, trehalose or sorbitol: salt-forming counter-ions, such as sodium; metal complexes (e.g. Zn-protein complexes); and/ or non ionic surfactants, such as TWEEN™, PLURONICS™ or polyethylene glycol (PEG).

In some embodiments, antibody molecules may be provided in a lyophilised form for reconstitution prior to administration. For example, lyophilised antibody molecules may be re-constituted in sterile water and mixed with saline prior to administration to an individual.

Administration may be in a "therapeutically effective amount", this being sufficient to show benefit to an individual. The actual amount administered, and rate and time-course of administration, will depend on the nature and severity of what is being treated, the particular individual being treated, the clinical condition of the individual, the cause of the disorder, the site of delivery of the composition, the type of antibody molecule, the method of administration, the scheduling of administration and other factors known to medical practitioners. Prescription of treatment, e.g. decisions on dosage etc., Is within the responsibility of general practitioners and other medical doctors, and may depend on the severity of the symptoms and/or progression of a disease being treated. Appropriate doses of antibody molecules are well known in the art (Ledermann et al., 1991; Bagshawe et al., 1991). Specific dosages indicated herein, or in the Physician's Desk Reference (2003) as appropriate for an antibody molecule being administered, may be used. A therapeutically effective amount or suitable dose of an antibody molecule can be determined by comparing in vitro activity and in vivo activity in an animal model. Methods for extrapolation of effective dosages in mice and other test animals to humans are known. The precise dose will depend upon a number of factors, including whether the size and location of the area to be treated, and the precise nature of the antibody molecule.

A typical antibody dose is in the range 100 µg to 1 g for systemic applications, and 1 µg to 1 mg for topical applications. An initial higher loading dose, followed by one or more lower doses, may be administered. This is a dose for a single treatment of an adult individual, which may be proportionally adjusted for children and infants, and also adjusted for other antibody formats in proportion to molecular weight.

Treatments may be repeated at daily, twice-weekly, weekly or monthly Intervals, at the discretion of the physician. The treatment schedule for an individual may be dependent on the pharmacokinetic and pharmacodynamic properties of the antibody composition, the route of administration and the nature of the condition being treated.

Treatment may be periodic, and the period between administrations may be about two weeks or more, e.g. about three weeks or more, about four weeks or more, about once a month or more, about five weeks or more, or about six weeks or more. For example, treatment may be every two to four weeks or every four to eight weeks. Suitable formulations and routes of administration are described above.

In a preferred embodiment, an antibody molecule as described herein may be for use in a method of treating cancer.

Cancer may be characterised by the abnormal proliferation of malignant cancer cells. Where a particular type of cancer, such as breast cancer, is referred to, this refers to an abnormal proliferation of malignant cells of the relevant tissue, such as breast tissue. A secondary cancer which is located in the breast but is the result of abnormal proliferation of malignant cells of another tissue, such as ovarian tissue, is not a breast cancer as referred to herein but an ovarian cancer.

The cancer may be a primary or a secondary cancer. Thus, an antibody molecule as described herein may be for use in a method of treating cancer in an individual, wherein the cancer is a primary tumour and/or a tumour metastasis.

A tumour of a cancer to be treated using an antibody molecule as described herein may comprise TILs that express OX40 and/or CD137, e.g. on their cell surface. In one embodiment, the tumour may have been determined to comprise TILs that express one or both of OX40 and CD137. Methods for determining the expression of an antigen on a cell surface are known in the art and include, for example, flow cytometry.

For example, the cancer to be treated using an antibody molecule as described herein may be selected from the group consisting of leukaemias, such as acute myeloid leukaemia (AML), chronic myeloid leukaemia (CML), acute lymphoblastic leukaemia (ALL) and chronic lymphocytic leukaemia (CLL); lymphomas, such as Hodgkin lymphoma, non-Hodgkin lymphoma and multiple myeloma; and solid cancers, such as sarcomas (e.g, soft tissue sarcomas), skin cancer (e.g. Merkel cell carcinoma), melanoma, bladder cancer (e.g. bladder urothelial carcinoma), brain cancer (e.g. glioblastoma multiforme), breast cancer, uterine/endometrial cancer, ovarian cancer (e.g. ovarian serous cystadenoma), prostate cancer, lung cancer (e.g. non-small cell lung carcinoma (NSCLC), such as lung squamous cell carcinoma, and small cell lung cancer (SCLC)), colorectal cancer (e.g. colorectal adenocarcinoma), cervical cancer (e.g. cervical squamous cell cancer and endocervical adenocarcinoma), liver cancer (e.g. hepatocellular carcinoma), head and neck cancer (e.g. head and neck squamous-cell carcinoma), oesophageal cancer (e.g. oesophageal carcinoma), pancreatic cancer, renal cancer (e.g. renal cell cancer), adrenal cancer, stomach cancer (e.g, stomach adenocarcinoma), testicular cancer (e.g. testicular germ cell tumours), cancer of the gall bladder and biliary tracts (e.g. cholangiocarcinoma), thyroid cancer, thymus cancer, bone cancer, and cerebral cancer.

In a preferred embodiment, the cancer to be treated using an antibody molecule as described herein is a solid cancer.

More preferably, the cancer to be treated using an antibody molecule as described herein Is a solid cancer selected from the group consisting of melanoma, bladder cancer, brain cancer, breast cancer, ovarian cancer, lung cancer, colorectal cancer, cervical cancer, liver cancer, head and neck cancer, pancreatic cancer, renal cancer and stomach cancer.

In a further preferred embodiment, the cancer to be treated using an antibody molecule as described herein may be a cancer which is responsive to treatment with one or more check-point inhibitors, such as an antibody which binds PD-1, PD-L1 or CTLA4. Such tumours are thought to have higher TIL levels and/or higher tumour mutational burden than tumours which are not responsive to check-point inhibitor therapy. Such tumours are also referred to as warm or hot tumours.

Examples of such tumours include head and neck squamous-cell carcinoma (HNSCC), melanoma, lung cancer (such as squamous lung cancer, lung adenocarcinoma, non-small cell lung carcinoma [NSCLC], or small-cell lung carcinoma [SCLC]), prostate cancer, cervical cancer, bladder cancer, breast cancer, thyroid cancer, kidney cancer, colorectal cancer (MSI or MSS; e.g. colorectal adenocarcinoma), oesophageal cancer, non-Hodgkin's lymphoma (NHL), gastric cancer, endometrial cancer, pancreatic cancer, ovarian cancer, hepatocellular carcinoma, mesothelioma, and urothelial cancer. In a preferred embodiment, the cancer is gastric cancer. The cancer may further be a cancer which has not previously been treated with a chemotherapeutic or radiotherapeutic agent, i.e. the Individual to be treated may be a cancer patient which has not received treatment with a chemotherapeutic or radiotherapeutic agent for the cancer in question. In a preferred embodiment, the antibody molecule as described herein is for use in a method of treating a cancer which is responsive to one or more immune-checkpoint inhibitors in an individual, wherein the method comprises treating the patient with the antibody molecule in combination with an agent which inhibits the interaction between PD-1 and PD-L1.

Alternatively, the cancer to be treated using an antibody molecule as described herein may be a cancer, such as pancreatic cancer or prostate cancer which is not responsive to treatment with one or more check-point inhibitors, such as an antibody which binds PD-1. PD-L1 or CTLA4. Such tumours are also referred to as cold tumours.

The present inventors have shown that tumours which did not respond to treatment with an anti-PD-1 or anti-PD-L1 antibody alone, were responsive to treatment with the anti-PD-1 or anti-PD-L1 antibody in combination with an antibody molecule as described herein. Thus, the antibody molecule of the Invention may be for use in a method of treating cancer in an individual, wherein the cancer is not responsive, or is refractory, to treatment with one or more check-point inhibitors alone, and wherein the method comprises administering the antibody molecule to the Individual in combination with an agent which Inhibits the Interaction between PD-1 and PD-L1. A method of treating a cancer in an individual, wherein the cancer is not responsive, or is refractory, to treatment with one or more check-point inhibitors alone, and wherein the method comprises administering the antibody molecule to the individual in combination with an agent which inhibits the interaction between PD-1 and PD-L1 is also contemplated.

Without wishing to be bound by theory, it is thought that treatment of a cancer which is not responsive to treatment with one or more check-point inhibitors alone, with chemotherapy, radiotherapy, an immunotherapeutic agent, such as an immunostimulatory agent, or an anti-tumour vaccine will result in cancer cell death which in turn will result in an increase in TILs in the tumour and higher expression of immunosuppressive receptors, which in turn will make the cancer responsive to treatment with check-point inhibitors, i.e. turn a cold tumour into a warm tumour. Thus, the antibody molecule of the invention may be for use in a method of treating cancer in an individual, wherein the cancer is not responsive, or is refractory, to treatment with one or more check-point inhibitors alone, and wherein the method comprises administering the antibody molecule to the individual in combination with a chemotherapeutic, radiotherapeutic, or immunostimulatory agent, or an anti-cancer vaccine and optionally an agent which Inhibits the Interaction between PD-1 and PD-L1. A method of treating a cancer in an individual, wherein the cancer is not responsive, or is refractory, to treatment with one or more check-point inhibitors alone, and wherein the method comprises administering the antibody molecule to the individual in combination with a chemotherapeutic, radiotherapeutic, or immunostimulatory agent, or an anti-cancer vaccine and optionally an agent which inhibits the interaction between PD-1 and PD-L1 is also contemplated. In a preferred embodiment, the agent which Inhibits the Interaction between PD-1 and PD-L1 is an antibody which binds PD-1 or PD-L1.

In the context of cancer, treatment may Include Inhibiting cancer growth, including complete cancer remission, and/or inhibiting cancer metastasis, as well as inhibiting cancer recurrence. Cancer growth generally refers to any one of a number of indices that indicate change within the cancer to a more developed form. Thus, indices for measuring an inhibition of cancer growth include a decrease in cancer cell survival, a decrease in tumour volume or morphology (for example, as determined using computed tomographic (CT), sonography, or other imaging method). a delayed tumour growth, a destruction of tumour vasculature, improved performance in delayed hypersensitivity skin test, an increase in the activity of anti-cancer immune cells or other anti-cancer immune responses, and a decrease in levels of tumour-specific antigens. Activating or enhancing immune responses to cancerous tumours in an individual may Improve the capacity of the Individual to resist cancer growth, in particular growth of a cancer already present in the subject, and/or decrease the propensity for cancer growth in the individual.

In the context of cancer treatment, an antibody molecule as described herein may be administered to an individual in combination with another anti-cancer therapy or therapeutic agent, such as an anti-cancer therapy or therapeutic agent which has been shown to be suitable, or potentially suitable, for the treatment of the cancer in question. For example, the antibody molecule may be administered to the individual in combination with a chemotherapeutic agent, radiotherapy, a radionuclide, an immunotherapeutic agent, an anti-tumour vaccine, an oncolytic virus, an adoptive cell transfer (ACT) therapy, such as adoptive NK cell therapy or therapy with chimeric antigen receptor (CAR) T-cells, autologous TILs or gamma/delta T cells, or an agent for hormone therapy. An antibody molecule as described herein may also be administered to an individual in combination with an adjuvant or neoadjuvant, such as a neoadjuvant hormone therapy, an anti-angiogenic agent, such as an anti-VEGF or anti-VEGFR2 antibody, or a cytotoxic agent.

Without wishing to be bound by theory, it is thought that the antibody molecule described herein may act as an adjuvant in anti-cancer therapy. Specifically, it is thought that administration of the antibody molecule to an in individual in combination with chemotherapy or radiotherapy, for example, will trigger a greater immune response against the cancer than is achieved with chemotherapy or radiotherapy alone.

One or more chemotherapeutic agents for administration in combination with an antibody molecule as described herein may be selected from the group consisting of: taxanes, cytotoxic antibiotics, tyrosine kinase inhibitors, PARP inhibitors, B-Raf enzyme inhibitors, MEK inhibitors, c-MET inhibitors, VEGFR inhibitors, PDGFR inhibitors, alkylating agents, platinum analogues, nucleoside analogues, antifolates, thalidomide derivatives, antineoplastic chemotherapeutic agents and others. Taxanes include docetaxel, paclitaxel and nab-paclitaxel; cytotoxic antibiotics include actinomycin, bleomycin, and anthracyclines such as doxorubicin, mitoxantrone and valrubicin; tyrosine kinase inhibitors include erlotinib, gefitinib, axitinib, PLX3397, imatinib, cobemitinib and trametinib; PARP inhibitors include piraparib; B-Raf enzyme inhibitors include vemurafenib and dabrafenib; alkylating agents include dacarbazine, cyclophosphamide and temozolomide; platinum analogues include carboplatin, cisplatin and oxaliplatin; nucleoside analogues include azacitidine, capecitabine, fludarabine, fluorouracil and gemcitabine and; antifolates include methotrexate and pemetrexed. Other chemotherapeutic agents suitable for use in the present invention include defactinib, entinostat, eribulin, Irinotecan and vinblastine. A chemotherapeutic agent for administration in combination with an antibody molecule as described herein may be a fluoropyrimidine. For example, where the cancer to be treated is HER2 negative, such as HER2 negative gastric cancer, the antibody molecule as described herein may be administered in combination with platinum a platinum analogue and a fluoropyrimidine. Where the cancer to be treated is HER2 positive, such as HER2 positive gastric cancer, the antibody molecule as described herein may be administered in combination with platinum or a platinum analogue, a fluoropyrimidine and trastuzumab.

Preferred therapeutic agents for administration with an antibody molecule as described herein are doxorubicin, mitoxantrone, cyclophosphamide, cisplatin, and oxaliplatin.

A radiotherapy for administration in combination with an antibody molecule as described herein may be external beam radiotherapy or brachytherapy.

Radionuclides for administration with an antibody molecule as described herein may be selected from the group consisting of: yttrium-90, iodine-131, bismuth-213, astatine-211, lutetium 177, rhenium-188, copper-67. actinium-225. Iodine-125 and terbium-161.

An immunotherapeutic agent for administration in combination with an antibody molecule as described herein may be a therapeutic antibody molecule, nucleotide, cytokine, or cytokine-based therapy. For example, the therapeutic antibody molecule may bind to an immune regulatory molecule, e.g. an inhibitory checkpoint molecule or an immune costimulatory molecule, a receptor of the Innate Immune system, or a tumour antigen, e.g. a cell surface tumour antigen or a soluble tumour antigen. Examples of immune regulatory molecules to which the therapeutic antibody molecule may bind include CTLA-4, LAG-3, TIGIT, TIM-3, VISTA, programmed death-ligand 1 (PD-L1), programmed cell death protein 1 (PD-1), CD47, CD73, CSF-1R, KIR, CD40, HVEM, IL-10 and CSF-1. Examples of receptors of the innate immune system to which the therapeutic antibody molecule may bind include TLR1, TLR2, TLR4, TLR5, TLR7, TLR9, RIG-I-like receptors (e.g. RIG-I and MDA-5), and STING. Examples of tumour antigens to which the therapeutic antibody molecule may bind include HER2, EGFR, CD20 and TGF-beta.

The present Inventors have shown that administration of an antibody molecule of the invention in combination with an anti-PD-1 or anti-PD-L1 antibody resulted in enhanced T cell activation and tumour regression in a mouse tumour model compared with treatment with either the antibody molecule of the Invention or an anti-PD-1 or anti-PD-L1 antibody alone. Without wishing to be bound by theory, these results suggest that administration of the antibody molecule of the invention in combination with an agent capable of inhibiting the Interaction between PD-1 and PD-L1 results in enhanced anti-tumour effects, as well as that such a combined administration may be suitable for the treatment of tumours which are refractory or resistant or have relapsed following PD-1 or PD-L1 antibody monotherapy.

Thus, the antibody molecule of the invention may be for use in a method of treating cancer in an Individual, wherein the method comprises administering the antibody molecule in combination with an agent which is capable of inhibiting the interaction between PD-1 and PD-L1. Also provided is an agent capable of inhibiting the interaction between PD1 and PD-L1, such as an antibody molecule which binds PD-1 or PD-L1, for use in a method of treating cancer in an individual, wherein the method comprises administering the agent which is capable of inhibiting the interaction between PD-1 and PD-L1 in combination with an antibody of the invention. A method of treating cancer in an individual comprising administering to the individual a therapeutically effective amount of the antibody molecule of the invention and a therapeutically effective amount of an agent which is capable of inhibiting the interaction between PD-1 and PD-L1.

In a preferred embodiment, the agent which is capable of inhibiting the interaction of PD-1 and PD-L1 is an antibody molecule which binds PD-1 or PD-L1. Antibodies which bind to PD-1 are known in the art and include nivolumab (5C4) and pembrolizumab. Known antibodies which bind to PD-L1 include YW243.55.S1, durvalumab, atezolizumab and avelumab. The antibody molecule of the invention may be for administration with one of these known anti-PD-1 or PD-L1 antibodies, or with another anti-PD-1 or PD-L1 antibody. The preparation of alternative antibodies which bind to PD-1 or PD-L1 is within the capabilities of the skilled person using routine methods.

The nucleic acid for administration in combination with an antibody molecule as described herein may be an siRNA.

The cytokines or cytokine-based therapy may be selected from the group consisting of: IL-2, prodrug of conjugated IL2, GM-CSF, IL-7, IL-12, IL-9, IL-15, IL-18, IL-21, and type interferon.

Anti-tumour vaccines for the treatment of cancer have both been implemented in the clinic and discussed in detail within scientific literature (such as Rosenberg, 2000). This mainly Involves strategies to prompt the Immune system to respond to various cellular markers expressed by autologous or allogenic cancer cells by using those cells as a vaccination method, both with or without granulocyte-macrophage colony-stimulating factor (GM-CSF). GM-CSF provokes a strong response in antigen presentation and works particularly well when employed with said strategies.

An antibody molecule as described herein may also be administered to an individual with cancer, in particular an Individual with gastric cancer, in combination with ramucirumab and/or paclitaxel; irinotecan and docetaxel or paclitaxel; or pembrolizumab. Treatment with an antibody molecule as described herein in combination with pembrolizumab is preferred in the treatment of MSI-H and/or dMM R gastric cancer.

In light of the immune response enhancing activity of OX40 and CD137, OX40 and CD137 dual agonist molecules are expected to find application in the treatment of infectious diseases. Thus, in another preferred embodiment, the antibody molecule as described herein may be for use in a method of treating an infectious disease, such as an acute or a persistent infectious disease.

Without wishing to be bound by theory, it is thought that OX40 and CD137 agonist molecules may be able to enhance the immune response against an acute infectious disease caused by a pathogen by inducing rapid infiltration and activation of innate immune cells, such as neutrophils and monocytes, thereby facilitating the clearance of the pathogen responsible for the acute infectious disease. Therefore, in a further embodiment, the antibody molecule as described herein may be for use in a method of treating an acute infectious disease, such as an acute bacterial disease. In a preferred embodiment, the acute infectious disease is an acute bacterial disease caused by an infection by a gram-positive bacterium, such as a bacterium of the genus *Listeria*, *Streptococcus pneumoniae* or *Staphylococcus aureus*.

Infectious diseases are normally cleared by the immune system but some infections persist for long periods of time, such as months or years, and are ineffectively combatted by the immune system. Such infections are also referred to as persistent or chronic infections.

Preferably, the antibody molecule as described herein is used to treat a persistent infectious disease, such as a persistent viral, bacterial, fungal or parasitic infection, preferably a persistent viral or bacterial infection.

In a preferred embodiment, the persistent viral Infection to be treated using an antibody molecule as described herein is a persistent infection of: human immunodeficiency virus (HIV), Epstein-Barr virus, Cytomegalovirus, Hepatitis B virus, Hepatitis C virus, Varicella Zoster virus.

In a preferred embodiment, the persistent bacterial infection to be treated using an antibody molecule as described herein is a persistent infection of: *Staphylococcus aureus*, *Hemophilus influenza*, *Mycobacterium tuberculosis*, *Mycobacterium leprae*. *Helicobacter pylori*, *Treponema pallidum*, *Enterococcus faecalis*, or *Streptococcus pneumoniae*.

CD137 agonism has been described to be beneficial in the context of treatment of infections by gram positive bacteria. Thus, in a preferred embodiment, the persistent bacterial Infection to be treated using an antibody molecule as described herein is a persistent infection by a gram-positive bacterium. In a more preferred embodiment, the persistent bacterial infection is a persistent infection by a gram-positive bacterium selected from the group consisting of: *Staphylococcus aureus*, *Mycobacterium leprae*. *Enterococcus faecalis*, and *Streptococcus pneumoniae*.

In a preferred embodiment, the persistent fungal infection to be treated using an antibody molecule as described herein is a persistent infection of: *Candida*, e.g. *Candida albicans*, *Cryptococcus* (*gattii* and *neoformans*), *Talaromyces* (*Penicillium*) *marneffe*, *Microsporum*, e.g. *Microsporum audouinii*, and *Trichophyton tonsurans*.

In a preferred embodiment, the persistent parasitic infection to be treated using an antibody molecule as described herein is a persistent infection of: *Plasmodium*, such as *Plasmodium falciparum*, or *Leishmania*, such as *Leishmania donovani*.

In the context of treatment of a persistent Infectious disease, the antibody molecule may be administered to an individual in combination with a second therapy or therapeutic agent which has been shown to be suitable, or is expected to be suitable, for treatment of the pathogen in question. For example, the antibody molecule may be administered to the individual in combination with an immunotherapeutic agent. An immunotherapeutic agent for administration in combination with an antibody molecule as described herein may be a therapeutic antibody molecule. For example, the therapeutic antibody molecule may bind to a receptor of the innate immune system. Examples of receptors of the innate immune system to which the therapeutic antibody molecule may bind include TLR1, TLR2, TLR4, TLR5, TLR7, TLR9, RIG-I-like receptors (e.g. RIG-I and MDA-5), and STING.

Where the antibody molecule is used to prevent an infectious disease, the antibody molecule may be administered in combination with a vaccine for the pathogen in question. Without wishing to be bound by theory, it is thought that the antibody molecule described herein may act as an adjuvant in vaccination. Specifically, it is thought that administration of the antibody molecule to an in individual in combination with vaccine, will trigger a greater immune response against the pathogen than is achieved with the vaccine alone.

In the context of the treatment of a persistent infectious disease, treatment may Include eliminating the infection, reducing the pathogenic load of the individual, and preventing recurrence of the infection. For example, the treatment may comprise preventing, ameliorating, delaying, abating or arresting one or more symptoms and/or signs of the persistent infection. Alternatively, the treatment may include preventing an infectious disease.

The features disclosed in the foregoing description, or in the following claims, or in the accompanying drawings, expressed in their specific forms or in terms of a means for performing the disclosed function, or a method or process for obtaining the disclosed results, as appropriate, may, separately, or In any combination of such features, be utilised for realising the invention in diverse forms thereof.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

For the avoidance of any doubt, any theoretical explanations provided herein are provided for the purposes of improving the understanding of a reader. The inventors do not wish to be bound by any of these theoretical explanations.

Any section headings used herein are for organizational purposes only and are not to be construed as limiting the subject matter described.

Throughout this specification, including the claims which follow, unless the context requires otherwise, the word "comprise" and "include", and variations such as "comprises", "comprising", and "Including" will be understood to Imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment Includes from the one particular value and/or to the other particular value. Similarly, when values are expressed as approximations, by the use of the antecedent "about," it will be understood that the particular value forms another embodiment. The term "about" in relation to a numerical value is optional and means for example +/−10%.

EXAMPLES

The present inventors aimed to generate mAb$^2$ that were capable of agonising both OX40 and CD137 in the absence of artificial crosslinking agents or Fcγ receptor-mediated crosslinking and that were capable of producing an enhanced immune response against diseases such as cancer. In this context, a mAb$^2$ is an antibody molecule that comprises a CDR-based antigen-binding site that binds CD137 and an OX40 antigen-binding site located in the CH3 domain of the antibody molecule.

In order to achieve this aim, the present inventors firstly used selection and affinity maturation methods to identify Fcabs that were able to bind OX40 and induce T cell activation in humans and mouse, respectively (see Examples 2 and 3). The inventors subsequently introduced the OX40 antigen-binding site from these Fcabs into a mAb$^2$ format and show that several of these anti-human OX40 "mock" mAb$^2$ were able to bind human and cynomolgus OX40 with a high affinity and activate T cells when cross linked (see Example 4). Out of these, clone FS20-22-49 showed the highest increase in agonistic activity upon crosslinking and also had the lowest EC$_{50}$ for its agonistic activity in the presence of crosslinking and was therefore taken forward as the OX40 antigen-binding site for development of the subject mAb$^2$.

In order to develop the CDR-based antigen binding site that binds and is capable of agonising CD137, the present inventors used selection methods to identify monoclonal antibodies (mAbs) that could bind human CD137 and were only capable of activating T cells when cross linked (see Example 5). The CDRs from these identified mAbs were subsequently cloned into mAb$^2$ that comprised the FS20-22-49 OX40 antigen binding site. The CDRs of these mAb$^2$ were sequence optimised in order to produce the following mAb$^2$-FS20-22-49AA/FS30-10-3, FS20-22-49AA/FS30-10-12, FS20-22-49AA/FS30-10-16, FS20-22-49AA/FS30-35-14 and FS20-22-49AA/FS30-5-37 (see Example 6). All of these mAb$^2$ were demonstrated to have a high level of specificity to human CD137 and were able to activate CD137 when crosslinked in a T cell activation assay (see Example 7). None of the mAb$^1$ showed any significant ability to activate CD137 in the absence of crosslinking.

Having established that the FS20-22-49AA OX40 antigen-binding site in the selected mAb$^2$ was capable of binding and activating OX40 when crosslinked and that, separately, the FS30-10-3, FS30-10-12, FS30-10-16, FS30-35-14 and FS30-5-37 CD137 CDR-based antigen-binding sites were capable of binding and activating CD137 when crosslinked, the present Inventors sought to demonstrate that the mAb$^2$ containing these antigen-binding domains were capable of activating both OX40 and CD137 (also referred to as 'dual agonism'). Such a dual agonist would be able to i) bind to OX40 to crosslink the mAb$^2$ and bind to, cluster and activate (agonise) CD137, and ii) bind to CD137 to crosslink the mAb$^2$ and bind to, cluster and activate (agonise) OX40. Importantly, the dual agonist should be able to drive agonism autonomously, based on the expression of the specific targets (OX40 and CD137) and without the need for additional crosslinking agents.

The present inventors demonstrated that the tested mAb$^2$ molecules were able to bind human CD137, human OX40, cynomolgus CD137 and cynomolgus OX40 (see Example 8) and that the tested mAb$^2$ molecules were capable of binding to human CD137 and human OX40 simultaneously (see Example 9). The present inventors showed that the 'LALA' mutation in the CH2 domain of the mAb$^2$ reduced their binding to Fcγ receptors and that mAb$^2$ clone FS20-22-49AA/FS30-10-16 was unable to induce ADCC activation in an ADCC bioassay (see Example 10).

The present inventors also showed that the tested OX40/CD137 mAb$^2$ molecules bound to cell-expressed human and cynomolgus OX40 and CD137, with no non-specific binding observed (see Example 11).

The present inventors then demonstrated that the tested mAb$^2$ molecules containing this LALA mutation were able to induce T-cell activation in the absence of artificial crosslinking agents in a T cell activation assay using staphylococcal enterotoxin A (SEA; see Example 12). The present inventors also demonstrated that the tested mAb$^2$ molecules could induce T-cell activation in the absence of artificial crosslinking agents in a pan-T cell activation assay and that this activity is dependent on the mAb$^2$ engaging both OX40 and CD137 at the same time (see Example 13 and 16). The inventors additionally confirmed that the FS20-22-49AA/FS30-10-16 mAb$^2$ was able to activate these receptors in CD4+ and CD8+ T cells, respectively, in the absence of crosslinking (see Example 14).

As the anti-human OX40/CD137 mAb$^2$ did not bind to mouse proteins, in order to test the potential of an OX40/CD137 mAb$^2$ to illicit a T-cell mediated anti-tumour response a parallel mAb$^2$ was made targeting mouse OX40 and mouse CD137, both with and without the LALA mutation (labelled FS20m-232-91 AA/Lob12.3 and FS20m-232-91/Lob12.3, respectively).

The inventors showed that the FS20m-232-91AA/Lob12.3 mAb$^2$ can induce T cell activation without any additional crosslinking agents and that this activity is dependent on the mAb$^2$ engaging both OX40 and CD137 at the same time (see Examples 15 and 16).

The present Inventors demonstrate that the FS20m-232-91AA/Lob12.3 and FS20m-232-91/Lob12.3 mAb$^2$ have anti-tumour efficacy in vivo in a CT26 syngeneic tumour model (see Example 17). The inventors additionally demonstrate that the FS20m-232-91AA/Lob12.3 mAb$^2$ has an effect on circulating T cells, increasing the frequency of activated and proliferating T cells (see Examples 18 and 19). The inventors demonstrated that the FS20m-232-91AA/Lob12.3 mAb$^2$ has anti-tumour efficacy in vivo in a B16-F10 syngeneic tumour model (see Example 20).

The inventors carried out an analytical characterisation and preliminary stability assessment of the mAb$^2$ (see Example 21). All five mAb$^2$ tested showed favourable analytical characterisation and favourable stability.

The present inventors have demonstrated that the combination of the FS20-22-49AA/FS30-10-16 mAb$^2$ with an anti-PD-L1 or anti-PD-1 antibody in a T cell activation assay using SEA can result in an increase in the maximal activity of T cells in vitro above that seen with the OX40/CD137 mAb$^2$ alone. The present inventors have further shown that treatment with the combination of the FS20m-232-91AA/Lob12.3 mAb$^2$ and an anti-PD-1 antibody in vivo in a CT26 mouse tumour model was able to result in an increase in anti-tumour activity, to provide a survival benefit, and to enhance pharmacodynamic modulation of proliferating T cells and NK cells compared to treatment with either single agent (see Example 22). The present inventors have demonstrated that the FS20m-232-91AA/Lob12.3 mAb$^2$ has dose-dependent anti-tumour activity in vivo in a CT26 syngeneic tumour model up to a certain dose level and that this activity was maintained at higher dose levels. The inventors have also shown that the FS20m-232-91AA/Lob12.3 mAb$^2$ can induce establishment of protective immunological memory in "complete responder" mice and protect against re-inoculation with CT26 cells (see Example 23). The inventors have demonstrated that the FS20m-232-91AA/Lob12.3 mAb$^2$ has an effect on circulating T cells, significantly increasing the frequency of proliferating (Ki67+) CD4+ and CD8+ T cells at varying dose levels (see Example 24). The Inventors have further shown that the FS20m-232-91AA/Lob12.3 mAb$^2$ Is able to increase the frequency of activated (CD69+) and proliferating (Ki67+) CD8 T cells, and that CD4 T-cell depletion has a detrimental effect on this peripheral pharmacodynamic response mediated by the FS20m-232-91AA/Lob12.3 mAb$^2$ (see Example 25). The inventors have shown that the FS20-22-49AA/FS30-10-16 mAb$^2$ had similar functional activity in a primary cynomolgus monkey PBMC assay compared to an equivalent human assay, that the mAb$^2$ was well tolerated in cynomolgus monkeys at doses up to 30 mg/kg, and that it was able to induce a drug-related increase in proliferation and activation of central memory and effector memory CD4+ and CD8+ T cells and NK cells in cynomolgus monkeys (see Example 26).

The inventors have also shown that when studied in BALB/c mice, the FS20m-232-91AA/Lob12.3 mAb$^2$ induced a moderate and transient increase in levels of T cell infiltration and proliferation in the liver compared to a crosslink-independent CD137 agonist, which induced elevated and sustained liver T cell infiltration, proliferation and activation (see Example 27). Lastly, in a CT26 syngeneic mouse tumour model, the Inventors have shown that between mice treated with either the FS20m-232-91AA/Lob12.3 mAb$^2$ or an OX40/CD137 mAb$^2$ comprising the same OX40 Fcab paired with a crosslink-independent anti-CD137 Fab clone, there were no differences in tumour growth or survival, despite the ability of the crosslink-independent Fab clone to induce increased T cell levels and proliferation as compared to the crosslink-dependent anti-CD137 Lob12.3 clone of the FS20m-232-91AA/Lob12.3 mAb$^2$ (see Example 28).

These experiments are described in more detail in the following Examples.

Example 1—Antigen Selection and Characterisation

The selection and screening methods used to identify mAb$^2$ that are capable of binding and agonising both OX40 and CD137 required the use of various OX40 and CD137 antigens. The production of these antigens is described in more detail below.

1.1 OX40 Antigens

OX40 antigens used for the selection of Fcabs specific for human and mouse OX40 and for testing cross-reactivity of selected Fcabs with cynomolgus OX40 were either prepared in-house or obtained from commercial sources as described below.

1.1.1 Preparation of Recombinant, Soluble Human, Cynomolgus and Mouse OX40 Antigens To prepare recombinant, soluble, dimeric OX40 antigens, the extracellular domain of OX40 was fused to mouse Fc, which improved the solubility and stability of the antigen. Specifically, the extracellular domain of the relevant OX40 (human, cynomolgus or mouse) was cloned into the pFUSE-mIgG2aFc2 vector (Invivogen cat no pfuse-mg2afc2) using EcoRI-HF and BglII restriction enzymes to produce antigens with a mouse IgG2a Fc domain at the C terminus. The recombinant OX40 antigens were then produced by transient expression in HEK293-6E cells (National Research Council of Canada) and purified using mAb Select SuRe protein A columns (GE Healthcare, 11003494), followed by size-exclusion chromatography (SEC) to ensure that the resulting antigen was a single species and did not contain aggregates.

To prepare biotinylated versions of the recombinant OX40 antigens, the antigens were biotinylated using EZ-LINK™ Sulfo-NHS—SS-Biotin kit (Thermo Fisher Scientific, cat no 21331) following the manufacturers protocol. Biotinylated OX40 antigen was used for the selection experiments described below but not for binding affinity measurements. Purification of the biotinylated OX40 antigens was performed in two steps, using a PD-10 desalting column (GE Healthcare. 17-0851-01) followed by an Amicon 30k spin column Millipore, UFC903024) according to manufacturers instructions. Biophysical properties of the recombinant antigens were characterized by SE-HPLC analysis to ensure that no aggregates were present and by PAGE to verify the size of the molecules. Size determination by PAGE indicated that the soluble antigens were dimeric, as their estimated molecular weight was double that of the predicted molecular weight of a monomer. The recombinant antigens were also analysed by gel-shift analysis which showed that the extent of biotinylation was above 90%. ELISA and surface plasmon resonance (SPR) were used to confirm that the biotinylated, recombinant human (hOX40-mFc), mouse (mOX40-mFc) and cynomolgus (cOX40-mFc) OX40 antigens could be bound by OX40-specific antibodies (antibody 11D4 [European Patent No. 2242771] for human and cynomolgus OX40; polyclonal sheep anti-human OX40 antibody for cynomolgus OX40 [R&D Systems cat no AF3388]; antibody ACT35 for human OX40 [Biolegend cat no 35002] and antibody OX86 for mouse OX40 [Biolegend cat no 119408]). These antigens are listed in Table 2 below.

1.1.2 Preparation of Cell Lines Expressing Human, Cynomolgus and Mouse OX40

Human, cynomolgus and mouse OX40 (see Table 1 for sequences) were cloned into vector pLVX-EF1a-IRES-puro (Clontech, Cat. No 631253) using SpeI-HF and NotI-HF restriction enzymes. The vectors were then transformed into the Lenti-X 293T cell line (Clontech, Cat. No 632180) together with a Lenti-X HTX packaging mix (Clontech cat no. 631249) to generate lentivirus. The lentivirus were then used to transduce DO11.10 cells (National Jewish Health). Cells overexpressing OX40 were selected by incubation of the cells with 5 μg/ml puromycin (Life Technologies cat no A11113803) for approximately 2 weeks, followed by cell line Boning by serial dilution. Expression of OX40 by the cell fines was tested by flow cytometry using fluorescently-labelled OX40-specific antibodies (OX86; ACT35; and polyclonal sheep anti-human OX40, as described in Example 1.1.1 and Table 2). Cell lines expressing human (DO11.10-hOX40), mouse (DO11.10-mOX40) or cynomolgus (DO11.10-cOX40) OX40, in which all cells showed at least 10-fold higher fluorescence values than non-transduced cells in the flow cytometry analysis, were selected. These cell lines are listed in Table 2 below.

TABLE 1

OX40 sequences

| Gene of interest | Species | Source | Clone ID (catalogue no) | Gen bank accession number | SEQ ID NO |
|---|---|---|---|---|---|
| OX40 | Human | Thermo Fisher Scientific | MHS6278-202858046 | BC105070 | 132 |
| OX40 | Cynomolgus | Gene synthesis | N/A | XP_005545179 | 134 |
| OX40 | Mouse | Gene synthesis | N/A | NM_011659.2 | 133 |

1.1.3 Commercially Available OX40 Antigens

Several commercially available OX40 antigens were tested.

Recombinant His-tagged human OX40 extracellular domain was obtained from SinoBiologicals (Cat #10481-H08H-50). However, SE-HPLC analysis of this antigen showed that less than 50% of the antigen was in a monomeric, non-aggregated form. This antigen was therefore not used in subsequent analysis.

Recombinant human OX40/human Fc (hOX40-hFc) and recombinant mouse OX40/human Fc (mOX40-hFc), which comprised the human IgG1 Fc domain at the C-terminus, were obtained from R&D Systems (hOX40-hFc: Cat #3388-OX-050; mOX40-hFc: Cat #1256-OX-050) and biotinylated in-house. The biophysical properties of these soluble antigens were characterised by SE-HPLC analysis to ensure that no aggregates were present and by PAGE to verify the size of the molecules. Size determination by PAGE indicated that the soluble antigens were dimeric, as their estimated molecular weight was twice that expected for the monomeric antigen. The soluble antigens were also analysed by gel-shift analysis which showed that the extent of biotinylation was above 909/0. ELISA and SPR were used to confirm that the biotinylated, recombinant human (hOX40-hFc) and mouse (mOX40-hFc) OX40 antigens could be bound by OX40-specific antibodies (11D4; ACT35; and OX86 as described in Example 1.1.1 and Table 2 below.

TABLE 2

OX40 antigens

| Antigen name | Source (commercial/ prepared in-house) | Biotinylated version prepared? | Species | Soluble/ cell-expressed antigen | Antigen format | SEQ ID NO/ Source of antigen |
|---|---|---|---|---|---|---|
| hOX40-mFc | in-house | yes | human | soluble | dimeric | 135 |
| mOX40-mFc | in-house | yes | mouse | soluble | dimeric | 136 |
| cOX40-mFc | in-house | yes | cynomolgus | soluble | dimeric | 137 |
| DO11.10-hOX40 | in-house | no | human | cell-expressed | natural conformation | 132 |
| DO11.10-mOX40- | in-house | no | mouse | cell-expressed | natural conformation | 133 |
| DO11.10-cOX40 | in-house | no | cynomolgus | cell-expressed | natural conformation | 134 |
| hOX40-hFc | commercial | yes | human | soluble | dimeric | Cat no 3388-OX-050 (R&D Systems) |
| mOX40-hFc | commercial | yes | mouse | soluble | dimeric | Cat no 1256-OX-050 (R&D Systems) |

1.2 CD137 Antigens

CD137 antigens used for the selection of mAbs specific for human CD137 and for testing cross-reactivity of selected Fcabs with cynomolgus OX40 were either prepared in-house or obtained from commercial sources as described below.

1.2.1 Preparation of Recombinant, Soluble Human and Cynomolgus CD137 Antigens

As several commercially available recombinant antigens were found to be unsuitable for use, e.g. due to unacceptable levels of aggregates being present when tested, the following recombinant dimeric and monomeric antigens (Table 3) were produced in-house for use in selections, screening and further characterisation of the anti-CD137 mAbs.

TABLE 3

Recombinant human and cynomolgus CD137 antigens

| Type | Designation | Species | Soluble or cell-expressed | Biotinylated version prepared? | Antigen Format | SEQ ID NOs |
|---|---|---|---|---|---|---|
| Recombinant | hCD137-mFc-Avi | Human | Soluble | Yes | Dimer | 138 & 141 |
| Recombinant | hCD137-Avi-His | Human | Soluble | Yes | Monomer | 158 |
| Recombinant | cCD137-mFc-Avi | Cynomolgus monkey | Soluble | Yes | Dimer | 140 & 141 |

The monomeric antigen was produced by cloning DNA encoding the extracellular domain of human CD137 along with an Avi sequence and six C-terminal histidine residues into modified pFUSE vectors (Invivogen cat no pfuse-mg2afc2) using EcoRI-HF and BamHI-HF restriction enzymes. The vectors were transfected into HEK293-6E cells, and expressed CD137 was purified using a HisTrap™ excel nickel column (GE Healthcare, 17-3712-06) and size-exclusion chromatography (SEC) to ensure that the antigen was a single species and did not contain aggregates.

To produce the dimeric antigens, DNA constructs encoding the extracellular domain of the human or cynomolgus (cyno) CD137 fused with the mIgG2a Fc domain along with an Avi sequence were Boned into modified pFUSE vectors and transfected into HEK293-6E cells. Recombinant CD137 was purified using MabSelect SuRe™ protein A column (GE Healthcare, 11003494) and size-exclusion chromatography (SEC) to ensure antigen was a single species and did not contain aggregates.

Biotinylated versions of the dimeric and monomeric CD137 antigens were prepared using a BirA biotin-biotin protein ligase reaction kit (Avidity LLC, BirA500) to produce monomeric CD137 antigen labelled with a single biotin molecule and dimeric CD137 antigens labelled with two biotin molecules, one per each of the two monomers. Specifically, 3 mg of the CD137 antigen was mixed with 7.8 μl BirA enzyme mix to a molar ratio of enzyme to substrate of 1:50. Additives were then added in accordance with the manufacturer's recommendations (142 μl Biomix A, 142 μl Biomix B, 142 μl Biotin) and the reaction mix was incubated for two hours at room temperature. To maintain the integrity of the biotinylated antigens, the reaction mix was immediately buffer exchanged to DPBS using Amicon 30 μm filters.

The CD137 antigens were further purified by SEC to ensure removal of the BirA enzyme and produce a final high quality monodispersed protein preparation with no high molecular weight aggregates. Specifically, antigens from the same production lot were mixed together and analysed for stability and purity by size-exclusion high-performance liquid chromatography (SE-HPLC), SDS polyacrylamide gel electrophoresis (SDS-PAGE), and size-exclusion chromatography with multi-angle light scattering (SEC-MALS). Complete biotinylation of the proteins was confirmed by a streptavidin-shifting SDS-PAGE gel. The recombinant human CD137 antigens were confirmed to bind an anti-human CD137 positive control antibody, 20H4.9 (U.S. Pat. No. 7,288,638). in vitro by surface-plasmon resonance (SPR) and to DO11.10 cells expressing human CD137 ligand by flow cytometry. The recombinant cyno CD137 antigen was confirmed to bind to DO11.10 cells expressing cyno CD137 ligand by flow cytometry. To ensure as high a purity as possible for the CD137 antigens used in the selection protocols, thorough protein characterisation of the antigens was performed to ensure that the percentage of protein aggregates present did not exceed 2%.

1.2.2 Preparation of Cell Lines Expressing Human, Cynomolgus and Mouse CD137

DO11.10 cells (National Jewish Health) expressing full-length human or cyno CD137, designated 'DO11.10-hCD137' and 'DO11.10-cCD137' respectively (see Table 4), were produced in order to present the antigen in its most natural confirmation during selection and further characterisation of the selected anti-CD137 mAbs. DO11.10 cells expressing full-length mouse CD137, designated 'DO11.10-mCD137', were also generated in order to determine the binding of an anti-mouse OX40/CD137 mAb$^2$ to bind cell-expressed mouse CD137 (see Example 11.2).

Lentiviral transduction was used to generate DO11.10 cells over-expressing human, cyno or mouse CD137 receptors using the Lenti-X HTX Packaging System (Clontech, 631249). Lenti-X expression vector (pLVX) (Clontech, 631253) containing cDNA encoding the human CD137 (SEQ ID NO: 126), cyno CD137 (SEQ ID NO:128) or mouse CD137 (SEQ ID NO: 164) was co-transfected with a Lenti-X HTX Packaging Mix into the Lenti-X 293T Cell Line (Clontech, 632180) to generate virus. The DO11.10 cell line was then transduced with these lentiviral vectors.

Expression of human, cyno or mouse CD137 on these cells was confirmed by binding of anti-CD137 positive control antibodies (20H4.9. MOR7480.1 (Patent Publication No. US 2012/0237498 A1) and Lob12.3 (University of Southampton), respectively) to the cells using flow cytometry.

TABLE 4

Cell surface-expressed human and cynomolgus CD137 antigens

| Type | Designation | Species | Presentation | SEQ ID |
|---|---|---|---|---|
| Cell | DO11.10-hCD137 | Human | Cell surface-expressed | 126 |

TABLE 4-continued

Cell surface-expressed human and cynomolgus CD137 antigens

| Type | Designation | Species | Presentation | SEQ ID |
|------|-------------|---------|--------------|--------|
| Cell | DO11.10-cCD137 | Cynomolgus monkey | Cell surface-expressed | 128 |
| Cell | DO11.10-mCD137 | Mouse | Cell surface-expressed | 164 |

2.1 Naïve Selection of Anti-Human OX40 Fcabs

In order to select Fcabs specific for human OX40 from naïve phage libraries both recombinant biotinylated soluble, dimeric human OX40 (hOX40-mFc; see Table 2) and cell-expressed human OX40 (DO11.10-hOX40) were used as antigens. Cells expressing human OX40 were used in addition to recombinant biotinylated soluble, dimeric human OX40 in some of the selection protocols to ensure that the selected Fcabs were capable of binding to OX40 in its natural conformation on the cell surface.

Six naïve phage libraries displaying the CH3 domain (IMGT numbering 1.4-130) comprising partially randomised AB loops (residues 14 to 18 according to the IMGT numbering scheme) and EF loops (residues 92 to 101 according to the IMGT numbering scheme) in the CH3 domain were constructed. One of the six libraries additionally comprised clones with an Insertion of either two or four amino acids (encoded by two or four NNK colons) at position 101 in the EF loop of the CH3 domain (inserted residues are numbered 101.1 to 101.4 according to the IMGT numbering scheme).

All six libraries were subjected to three rounds of selection using recombinant biotinylated soluble, dimeric human OX40 (hOX40-mFc; see Table 2). All six libraries were also subjected to a further selection campaign using hOX40-mFc in a first round of selection followed by cell-expressed human OX40 (DO11.10-hOX40 in two further selection rounds: see Table 2).

2133 clones identified following the third round of selection from the six libraries were screened by ELISA for binding to human OX40. This resulted in 32 unique positive binders being identified. which were sub-cloned and expressed as soluble Fcabs (consisting of a truncated hinge [SEQ ID NO: 101], CH2 and CH3 domain) in HEK Expi293 cells (Fcabs cloned into pTT5 vector [National Research Council of Canada] transfected using ExpiFectamine 293 Transfection kit [Life Technologies, A14524] Into Expi293F cells [Life technologies, A14527]).

The 32 unique Fcabs were tested for their ability to bind cell-expressed human OX40 (DO11.10-hOX40). 15 of the 32 Fcabs screened showed cell binding to DO11.10-hOX40 and the $EC_{50}$ for these interactions ranged from 0.1 to 62 nM. The 15 Fcabs that showed binding to DO11.10-hOX40 were tested using an in-house human NF-κB reporter assay that tests for activation of the NF-κB signalling pathway. Six of the 15 Fcabs showed an increase in activity when crosslinked with an anti-human Fc antibody in the human NF-κB reporter assay, suggesting that these Fcabs would be able to activate OX40 signalling. Fcabs designated FS20-22 and FS20-31 showed high levels of activity in this assay, and their activity increased when the Fcab was crosslinked with an anti-human CH2 mAb (done MK1A6 (Jefferis et al., 1985 and Jefferis et al., 1992), produced in-house). These were selected for affinity maturation.

2.2 Affinity Maturation of Anti-Human OX40 Fcabs

Affinity maturation libraries for FS20-22 and FS20-31 were created by randomizing five residues in the AB loop (residues 14 to 18) or five residues in the CD loop (residues 45.1 to 77) of the CH3 domain using randomized primers from ELLA Biotech using an equimolar distribution of amino acids excluding cysteines, or by randomizing portions of the EF loop (residues 92 to 94 and 97 to 101 of the CH3 domain (all residue numbering according to the IMGT numbering scheme).

1410 Fcabs from the outputs of the affinity maturation were screened by ELISA for binding to human OX40 and 204 unique positive binders were identified, sub-cloned and expressed as soluble Fcabs in HEK Expi293 cells as described in Example 2.1 above.

The off-rates of the soluble Fcabs when bound to hOX40-mFc were measured using a Biacore 3000 (GE Healthcare) in the absence and presence of anti-CH2 crosslinking using anti-human CH2 mAb clone MK1A6 (see Example 2.1). Fcabs with improved off-rates as compared to the relevant parental Fcab were further screened for binding to cell-expressed human OX40 and for activity in the in-house human T cell activation assay. All of the Fcabs bound cell-expressed human OX40, 10 Fcabs from the FS20-22 lineage and 18 Fcabs from the FS20-31 lineage showed high levels of activity in the human T cell activation assay were selected for loop shuffling as described below.

For the FS20-22 lineage, two loop-shuffled libraries were generated by shuffling three CD loops, six EF loops and either the parental AB loop or an affinity matured AB loop. For the FS20-31 lineage, one loop-shuffled library was generated containing four AB loops, seven CD loops and seven EF loops.

Shuffled sequences were expressed as soluble Fcabs in HEK Expi293 cells as described in Example 2.1 above and screened for binding to biotinylated hOX40-mFc antigen using Dip and Read™ Streptavidin Biosensors (Pall FortêBio, 18-5050) on an Octet $QK^e$ System (Pall FortêBio). Fcabs with an improved off-rate when bound to hOX40-mFc as compared to the parental Fcab were sequenced, resulting in 35 unique Fcab from the FS20-22 lineage and 62 from the FS20-31 lineage. The unique Fcabs identified were tested for binding to hOX40-mFc antigen in the presence and absence of CH2 crosslinking using anti-human CH2 mAb clone MK1A6 using a Biacore 3000 instrument (GE Healthcare).

For the FS20-22 lineage, 18 Fcabs were chosen for expression in mock (4420 LALA) $mAb^2$ format and further characterisation on the basis of the slowest off-rate with CH2 crosslinking when bound to hOX40-mFc, the greatest difference in the off-rate between non-crosslinked and CH2 crosslinked off-rates when bound to hOX40-mFc and the strength of binding to hOX40-mFc as above. For the FS20-31 lineage, the nine Fcabs with the slowest off-rate when bound to hOX40-mFc with CH2 crosslinking and the nine Fcabs with the slowest off-rate when bound to hOX40-mFc without CH2 crosslinking were chosen for expression and further characterisation in mock (4420 LALA) $mAb^2$ format. As a number of Fcabs were common to both these groups of nine Fcabs, additional Fcabs which showed slow of rates when bound to hOX40-mFc in the absence of CH2 crosslinking were chosen from the FS20-31 lineage to bring the total number of Fcabs from this lineage for expression and further characterisation in mock $mAb^2$ format to 18. Using the data from the T cell activation assay, a further six Fcabs from the FS20-22 lineage and eight Fcabs from the FS20-31 lineage were identified which showed high activity in this assay and which were therefore also expressed in mock (4420 LALA) $mAb^2$ format and further characterised (see Example 4).

3.1. Naïve Selection of Anti-Mouse OX40 Fcabs

A naïve yeast library displaying CH1 to CH3 domains of human IgG1, which contained randomisations in the AB loop (residues 11-18 according to the IMGT numbering scheme) and the EF loop (residues 92-101 according to the IMGT numbering scheme) of the CH3 domain and included a five-residue randomised insertion between residues 16 and 17 (according to the IMGT numbering scheme) of the AB loop, was used for selections. The yeast were incubated with biotinylated recombinant murine OX40 fused to a human IgG Fc domain (mOX40-hFc; Table 2) and sorted by MACS using streptavidin coated beads. Three rounds of FACS selections were then performed using decreasing concentrations of biotinylated mOX40-hFc in the presence of a fivefold molar excess of hFc. The cells were stained with streptavidin-allophycocyanin (APC) (BD Bioscience, 349024) or anti-Biotin-APC (Miltenyl Biotec, 130-090-856) and sorted using a FACSAria (BD Bioscience) cell sorter. 182 individual Fcabs from enriched populations were screened for antigen binding and two unique positive binders were subcloned and expressed as soluble Fcabs as previously described in Example 2.1. Fcabs were characterised for binding to mOX40-hFc by ELISA and for activity in an in-house mouse NF-κB reporter assay. Only one Fcab, FS20m-232, was active in the NF-κB reporter assay and showed binding to cells expressing mouse OX40 so this Fcab was selected for affinity maturation.

3.2 Affinity Maturation of mOX40 Fcab

Three phage display affinity maturation libraries were constructed by randomising seven residues in the AB loop (residues 15-16.5 according to the IMGT numbering scheme) (Library 1), six residues in the CD loop (residues 45.1-78 according to the IMGT numbering scheme) (library 2) or five residues in the EF loop (residues 92-94 and 97-98 according to the IMGT numbering scheme) (Library 3) of the FS20m-232 Fcab using randomized primers from ELLA Biotech using an equimolar distribution of amino acids excluding cysteine. Three selection rounds were performed on the affinity maturation libraries using recombinant biotinylated mOX40-mFc alternatingly captured on streptavidin-coated (ThermoFisher Scientific, 11205D) and neutravidin-coated (ThermoFisher Scientific, 14203 and A2666) Dynabeads. Decreasing antigen concentrations from 50 nM (Round 1) to 10 nM (Round 2), to 1 nM (Round 3) were used to identify high affinity binders. 1655 individual phage from the third selection round were screened by phage ELISA for binding to mOX40-mFc and 98 unique positive binders were Identified, subcloned and expressed as soluble Fcabs in HEK Expi293 cells as described in Example 2.1. The Fcabs were further screened for cell binding and activity in a mouse NF-κB reporter assay. The most active Fcabs were selected for loop shuffling.

A loop-shuffled library was generated containing 27 CD loops (all 26 unique sequences identified from the affinity maturation and the WT sequence) shuffled with 37 EF loops (those with the best binding to mouse OX40 in phage ELISA and WT sequence), with all shuffled clones containing the AB loop of the FS20m-232 Fcab. 750 shuffled sequences were expressed as soluble Fcabs (containing a truncated hinge) in HEK Expi293 cells as described above. HEK supernatants containing the Fcabs were screened for improved off-rates by measuring binding of the Fcabs to biotinylated mOX40-mFc (Table 2) using Dip and Read™ Streptavidin Biosensors (Pall FortëBio, 18-5050) on an Octet QK® System (Pall FortëBio). The 11 unique AB loop randomized Fcabs and 60 unique EF loop randomized Fcabs were subcloned and expressed as soluble Fcabs in HEK Expi293 cells as described above. These Fcabs were further screened alongside the 43 shuffled Fcabs with the slowest off-rates for cell binding and activity in a mouse T cell activation assay. The FS20m-232-91 Fcab had the slowest off-rate when bound to biotinylated mOX40-mFc and the highest activity in the mouse T cell activation assay when crosslinked by anti-human CH2 mAb clone MK1A6 and was therefore selected as the mouse (surrogate) Fcab for use in subsequent experiments.

Example 4—Construction, Expression and Characterization of Anti-OX40 Fcab in mAb² Format 4.1 Construction and Expression of Mock mAb²

"Mock" mAb² comprising the anti-human OX40 and anti-mouse OX40 Fcabs identified above were prepared in order to allow the characterization of these Fcabs in mAb² format. These mock mAb² were prepared from the anti-OX40 Fcabs and the variable regions of anti-FITC antibody 4420 (Bedzyk et al., 1989 and Bedzyk et al., 1990) in a human IgG1 backbone (see SEQ ID NO: 114, SEQ ID NO: 115, and SEQ ID NO: 116 for details) or the variable regions of anti-hen egg white lysozyme (HEL) antibody 01.3 (Braden et al., 1996) in a human IgG1 backbone (see SEQ ID NO: 117 and SEQ ID NO: 118 for details) by replacing the CH3 domains of the anti-FITC and anti-HEL antibodies with the CH3 domains of the anti-OX40 Fcabs within XhoI and BamHI sites present in the sequence of the unmodified CH3 domain of human IgG1. The mock mAb² comprised the light chain of the anti-FITC mAb 4420 (SEQ ID NO: 116) or of the anti-HEL mAb D1.3 (SEQ ID NO: 118), respectively, and also contained the LALA mutation in the CH2 domain of the heavy chain to reduce Fc-gamma receptor interaction and potential Fc-gamma receptor-induced crosslinking. The presence of the LALA mutation in mock mAb² and mAb² referred to in these examples is denoted by the suffix 'AA' at the end of the Fcab part of their clone names.

The mock mAb² were produced by transient expression in HEK293-6E cells and purified using mAb Select SuRe protein A columns.

4.2 Binding Affinity of Anti-Human OX40 Fcabs in Mock mAb² Format to Cell-Expressed Human and Cynomolgus OX40

The affinity of the anti-human OX40 Fcabs in mock (4420 LALA) mAb² format for binding to cell-expressed human or cynomolgus OX40 (DO11.10 cells expressing either human [DO11.10-hOX40] or cynomolgus OX40 [DO11.10-cOX40]; see Table 2) was measured using flow cytometry. Non-specific binding was also assessed by testing for binding to HEK cells not expressing OX40 by flow cytometry.

Mock (4420 LALA) mAb² and control mAb dilutions (2× final concentration) were prepared in triplicate in 1×DPBS (Gibco, 14190-094). DO11.10-hOX40 or DO11.10-cOX40 or HEK cell suspensions were prepared in PBS+2% BSA (Sigma, A7906) and seeded at $4 \times 10^6$ cell/ml with 50 µl/well in V-bottomed 96-well plates (Costar, 3897). 50 µl of the mock (4420 LALA) mAb² or control mAb (anti-human OX40 mAb, 11 D4) dilutions were added to the wells containing cells (final volume 100 µl) and incubated at 4° C. for 1 hour. The plates were washed and 100 µl/well of secondary antibody (anti-human Fc-488 antibody, Jackson ImmunoResearch, 109-546-098) diluted 1:1000 in PBS+2% BSA was then added and incubated for 30 mins at 4° C. in the dark. The plates were washed and resuspended in 100 µl of PBS containing DAPI (Biotium, cat no 40043) at 1 µg/ml.

The plates were read using a Canto II flow cytometer (BD Bioscience). Dead cells were excluded and the fluorescence in the FITC channel (488 nm/530/30) was measured. The data was fit using log (agonist) vs response in GraphPad Prism Software.

The Fcabs (all tested in mock [4420 LALA] mAb$^2$ format) and the positive-control anti-human OX40 mAb, 11D4, in a human IgG1 backbone and containing the LALA mutation in the CH2 domain of the heavy chain (G1AA/11 D4; SEQ ID NOs 173 and 175), bound to human OX40 with a range of affinities. Five clones from the FS20-22 lineage and six from the FS20-31 lineage were tested for their ability to bind cell-expressed human and cynomolgus OX40; the binding affinities of these clones are set out in Table 5.

TABLE 5

Binding affinity of anti-OX40 Fcabs in mock (4420 LALA) mAb$^2$ format to cell-expressed human or cynomolgus OX40

| mock (4420 LALA) mAb$^2$/mAb | Binding to DO11.10-hOX40 EC$_{50}$ (nM) | Binding to DO11.10-cOX40 EC$_{50}$ (nM) |
| --- | --- | --- |
| FS20-22-38AA/4420 | 0.8315 | 0.5925 |
| FS20-22-41AA/4420 | 0.2991 | 0.1821 |
| FS20-22-47AA/4420 | 0.7655 | 0.5809 |
| FS20-22-49AA/4420 | 0.7412 | 0.3197 |
| FS20-22-85AA/4420 | 0.4486 | 1.058 |
| FS20-31-58AA/4420 | 0.7466 | 1.454 |
| FS20-31-66AA/4420 | 0.2677 | 2.038 |
| FS20-31-94AA/4420 | 0.6132 | 3.52 |
| FS20-31-102AA/4420 | 0.5366 | 0.3948 |
| FS20-31-108AA/4420 | 0.6516 | 0.3716 |
| FS20-31-115AA/4420 | 0.7853 | 1.235 |
| G1AA/11D4 | 0.8143 | 0.2126 |

4.3 Activation of OX40 In Vitro by Anti-OX40 Fcabs in Mock mAb$^2$ Format

Activated T cells express OX40 on their cell surface. Binding of the trimeric OX40 ligand to OX40 results in trimerisation of the receptor. As the OX40 ligand is expressed as clusters on the cell surface of antigen-presenting cells, the interaction between the OX40 ligand and OX40 results in the clustering of OX40, which is known to be essential for OX40 signalling and further T cell activation. Antibodies that agonise OX40 must mimic this clustering activity of the OX40 ligand. In the case of monospecific anti-OX40 antibodies, Fc gamma receptors bind to the Fc domains of the antibodies and crosslink them, resulting in OX40 clustering.

The anti-human OX40 and anti-mouse OX40 Fcabs in LALA mutation-containing mock (4420) mAb$^2$ format described above were tested in T cell activation assays for their ability to activate OX40 expressed on T cells upon crosslinking of the Fcabs in the presence of a crosslinking agent. The human T cell activation assay for testing of the anti-human OX40 Fcabs in mock (4420 LALA) mAb$^2$ format involved the isolation of T cells from human peripheral blood mononuclear cells (PBMCs) and tested for the release of IL-2. which is a marker of T cell activation. The assays were carried out in a similar manner to that described later in Example 13 and involved the use of anti-human CH2 mAb clone MK1A6 or FITC-dextran (Sigma) in order to crosslink the positive-control antibody (11D4) or the Fcabs in mock (4420 LALA) mAb$^2$ format, respectively.

The anti-human OX40 Fcabs in mock (4420 LALA) mAb$^2$ format when crosslinked by the Fab target (FITC-dextran) showed a range of activities in the T cell activation assay. All of the Fcabs had the ability to co-stimulate T cells in the presence of an anti-CD3 antibody and Induce the production of human IL2. The Fcabs from the FS20-22 and FS20-31 lineages showed an activity both with and without crosslinking. Specifically, the Fcabs from these lineages had activity in the absence of a crosslinking agent which was significantly increased upon crosslinking. Since these Fcabs have high cross-reactivity to cynomolgus OX40 (comparable to binding human OX40). toxicology studies would be possible in this species. Of the cones in the FS20-22 lineage, clones FS20-22-41, FS20-22-47, FS20-22-49 and FS20-22-85 had the lowest EC$_{50}$ values for their agonistic activity when crosslinked and are therefore the preferred clones from this lineage. Of these, clone FS20-22-49 showed the highest increase in agonist activity upon crosslinking and also had the lowest EC$_{50}$ for it agonist activity in the presence of crosslinking and is therefore the preferred clone.

As described above, the present inventors aimed to generate mAb$^2$ that are capable of agonising both OX40 and CD137 in the absence of additional crosslinking agents. The above experiments demonstrate that the FS20-22-49 Fcab is able to activate OX40 In the presence of an additional crosslinking agent. In order to generate a dual agonist that does not require additional crosslinking agents, the inventors elected to generate anti-CD137 antibodies with the Intention of using the CDRs from these antibodies in the eventual OX40- and CD137-targeting mAb$^2$ molecule.

Example 5-Selection and Characterisation of Anti-Human CD137 Antibodies

Synthetic naive phagemid libraries displaying the Fab domain of human germlines with randomisation in the CDR1, CDR2 and CDR3 (MSM Technologies) were used for naïve selections of anti-human CD137 mAbs with the recombinant and cell surface-expressed CD137 antigens described in Example 1.2.

Fab libraries were selected in three rounds using Streptavidin Dynabeads (Thermo Fisher Scientific, 11205D) and Neutravidin-binding protein coupled to Dynabeads (Thermo Fisher Scientific, 31000) to isolate the phage bound to biotinylated human CD137-mFc-Avi or human CD137-Avi-His. To ensure Fab binding to cell surface-expressed CD137, first round outputs from the selections using recombinant CD137 antigen were also subjected to two further rounds of selections using DO11.10-hCD137 cells and a fourth round with DO11.10-cCD137 cells.

About 2200 clones from the round 3 and 4 outputs were screened by phage ELISA for binding to human and cyno CD137-mFc-Avi. Blotinylated mFc was included as a negative control. The variable regions of the positive clones (clones with a CD137 binding signal at least 4-fold higher than the binding signal to mFc) were sequenced which led to the Identification of 36 unique VH/VL sequence combinations. Sequences Identified originated from both selections using recombinant CD137 antigen and cell surface-expressed CD137 antigen with several clones isolated using both selection strategies. Based on the phage ELISA, 22 out of the 36 clones were cynomolgus monkey (cyno) crossreactive, but as the sensitivity of the phage ELISA might not have been sufficient to detect weak cyno crossreactive binders, all 36 clones were taken forward for reformatting into IgG1 molecules. For each clone the VH and VL domains were individually cloned into pTT5 expression vector (National Research Council of Canada) containing either CH1, CH2 (with a LALA mutation in the CH2 domain and CH3 domains, or CL domains, respectively. The resulting pTT5-FS30 VH with LALA mutation (AA) and pTT5-

FS30 VL vectors were transiently cotransfected into HEK293-6E cells. Twenty-eight clones expressed as soluble IgG1 molecules. These were purified by mAb Select SuRe Protein A columns and subjected to further testing.

The binding of the anti-CD137 mAbs was analysed in an ELISA using human and cyno CD137-mFc-Avi. Of the 28 clones tested, 10 showed dose-dependent binding to human CD137-mFc-Avi, and no binding to human OX40-mFc-Avi, mFc or streptavidin. Within this group, four clones, FS30-5, FS30-10, FS30-15 and FS30-16, were crossreactive to cyno CD137-mFc-Avi. Due to the low number of cyno crossreactive clones obtained, additional clones were screened and expressed as described above. This resulted in the isolation of one additional cyno crossreactive binder FS30-35.

The anti-human CD137 mAbs FS30-5, FS30-10, FS30-15 and FS30-16 were tested for binding to cells expressing human or cynomolgus CD137 (DO11.10-hCD137 or DO11.10-cCD137) using flow cytometry. Non-specific binding was also assessed by testing binding to DO11.10 cells and HEK293 cells lacking CD137 expression. Binding affinities were compared with those of two positive control mAbs, MOR7480.1 (US Patent No. 2012/0237498) and 20H4.9 (U.S. Pat. No. 7,288,638), the variable domains of which were cloned and expressed in human IgG1 format comprising the LAIR mutation in the CH2 domain (G1AA format).

The FS30-5, FS30-10, FS30-15 and FS30-16 clones were found to bind to cell surface-expressed human and cyno CD137 receptors with $EC_{50}$ values in the range of 0.15-0.57 nM, comparable to the positive control mAbs. No binding to parental DO11.10 or HEK293 cells was observed showing the specificity of the binding. No binding of the 20H4.9 positive control anti-CD137 antibody to cyno CD137 was observed in these cells. Published data (U.S. Pat. No. 7,288,638) show that 20H4.9 in IgG1 format does bind to cyno CD137 on PMA (Phorbol Myristate Acetate) induced cyno PMBCs. In the hands of the present inventors, the 20H4.9 In G1AA format bound to recombinant cyno CD137 but the affinity was much lower than for human CD137 (data not shown), which may explain the lack of binding observed with the antibody to DO11.10-cCD137 cells.

In order to determine the biophysical characteristics of the FS30 mAbs, they were subjected to Size Exclusion Chromatography (SEC) and the percentage of the monomeric fraction analysed. All four FS30 mAbs tested showed a single-peak profile and were >97% monomeric. This high level of monomeric protein allowed functional activity testing to proceed.

The functional activity of the anti-CD137 mAbs was then analysed in a primary T cell activation assay. In vivo, anti-CD137 mAbs induce agonism by recruitment of Fcγ receptors, thereby causing clustering of the mAbs and the CD137 receptor. To mimic the maximum ability of the mAbs to cluster surface CD137 receptor molecules, FS30 mAbs were crosslinked using an anti-human CH2 antibody (clone MK1A6, produced in-house) prior to the assay. T cell activation was compared to non-crosslinked mAbs. The anti-hen egg-white lysozyme (HEL) antibody 01.3 in a human IgG1 backbone with the LALA mutation (G1AA/HelD1.3) was included as a negative control.

When crosslinked, the FS30-5, FS30-10, FS30-15 and FS30-16 mAbs showed potent activity in the T cell activation assay, with $EC_{50}$ values of less than 10 nM and a maximum level of IL-2 (E) similar to the positive control anti-CD137 mAbs (anti-CD137 MOR7480.1 mAb, 5637 hIL-2 µg/ml; and anti-CD137 20H4.9 mAb, 10232 hIL-2 µg/ml). The $E_{max}$ of the FS30-6 mAb (1512 hIL-2 pg/ml) was significantly lower than that of the positive controls and the other FS30 mAbs, indicating a lower overall level of T cell activation. Unlike the positive control anti-CD137 20H4.9 mAb, which showed activity in the absence of crosslinking (hIL-2 production of 3174 pg/ml), the FS30 mAbs showed no activity (when not crosslinked as indicated by the background response levels of IL-2 measured).

Example 6—Construction and Expression of mAb$^2$ Targeting Human OX40 and Human CD137 mAb$^2$ comprising an anti-human OX40 Fcab paired with anti-human CD137 Fabs were prepared. The human OX40-targeting Fcab FS20-22-49 was selected for pairing with the CD137-targeting Fabs because of its higher activity in T cell assays (see Example 4.3).

6.1 Expression and Characterisation of mAbs in mAb$^2$ Format mAb$^2$ molecules were prepared which consisted of an IgG1 molecule, comprising the CDRs of either the FS30-5, FS30-10, FS30-15, FS30-16 or FS30-35 clone and including the LALA mutation in the CH2 domain, and the FS20-22-49 human OX40 receptor-binding site in the CH3 domain. These mAb$^2$ molecules were generated by replacing the VH domain of an anti-human OX40 mAb$^2$. FS20-22-49AA/HelD1.3, with the corresponding VH domains of the FS30 clones and cotransfecting the generated VH with the corresponding light chain of the FS30 mAbs. The LALA mutation in the CH2 domain of the IgG1 molecule was retained in the resulting mAb$^2$ molecules. These mAb$^2$ molecules were designated FS20-22-49AA/FS30-5, FS20-22-49AA/FS30-10, FS20-22-49AA/FS30-15, FS20-22-49AA/FS30-16 and FS20-22-49AA/FS30-35. The mAb$^2$ were produced by transient expression in HEK293-6E cells and purified using mAb Select SuRe protein A columns.

CD137 belongs to the tumour necrosis factor receptor superfamily (TNFRSF) of cytokine receptors (Moran et al., 2013). To analyse the specificity of the anti-CD137 Fab binding site of the five mAb$^2$ molecules, binding of the mAb$^2$ to human CD137 and five closely-related human TNFRSF members (TNFRSF1A, TNFRSF1B, GITR, NGFR and CD40) was tested using SPR. The aim was to demonstrate 1000-fold specificity by showing no binding of the mAb$^2$ to closely-related antigens at a concentration of 1 JM, but showing binding to CD137 receptors at a concentration of 1 nM.

Whereas the FS20-22-49AA/FS30-5, FS20-22-49AA/FS30-10, FS20-22-49AA/FS30-16 and FS20-22-49AA/FS30-35 mAb$^2$ showed a high level of specificity (close to 1000-fold), the FS20-22-49AA/FS30-15 mAb$^2$ showed non-specific binding to all five closely-related TNFRSF members tested. The non-specific binding exhibited by this clone was about 5-10 fold lower on average than the binding to CD137 receptors at the same concentration, and was concluded to be due to the Fab binding site of the mAb$^2$ molecule, as the FS30-15 mAb showed the same binding profile when tested for binding to the same five TNFRSF members closely related to CD137. Based on this data, the FS30-15 clone was omitted from further selection campaigns.

6.2 Sequence Optimisation of Anti-CD137 mAbs Whilst the FS30-5, FS30-10, FS30-16 and FS30-35 anti-CD137 mAbs showed high affinity and specificity for CD137, and activity in a T cell activation assay, they contained one or more potential post-translational modification (PTM) sites within the CDR loops. It was decided to further engineer these clones in an attempt to identify amino acid residues which could be substituted at these sites while retaining or improving binding and activity. The potential PTM sites Identified included methionine residues in the VH CDR3 (Kabat position M100D and M100H in FS30-5, M97 in FS30-10, M100A in FS30-16, and M100F in FS30-35). a potential aspartate isomerisation motif in the VH CDR2 (Kabat position D54G55 in FS30-16) and a potential deamidation site in the VL CDR3 (Kabat position Q90G91 in FS30-16).

Site-directed mutagenesis was carried out using the five FS20-22-49AA/FS30 mAb$^2$ clones as templates and primers that contained the degenerate codon NNK at the sites encoding methionine, aspartate or glycine residues to allow for all possible amino acid substitutions. Cysteine residues and amino acids capable of producing novel potential PTM motifs were excluded. Clones were expressed and screened for binding to DO11.10-hCD137 cells. Clones with similar (within two-fold) or improved binding at 10 nM compared to the parental mAb$^2$ clones were selected for expression at 30-50 ml scale, purified on Protein A columns and screened in a T cell activation assay using DO11.10-hCD137 cells and the anti-human CH2 antibody MK1A6 as crosslinking agent.

DO11.10-hCD137 cells were washed once in PBS and resuspended in DO11.10 cell medium (RPMI medium (Life Technologies) with 10% FBS (Life Technologies) and 5 µg/ml puromycin (Life Technologies, A11113803)) at a concentration of $1.0 \times 10^8$ cells/ml. 96-well flat-bottomed plates were coated with anti-mouse CD3 antibody (Thermo Fisher Scientific, clone 17A2) by incubation with 0.1 pg/ml anti-mouse CD3 antibody diluted in PBS for 2 hours at 37° C., 5% $CO_2$ and then washed twice with PBS. DO11.10-hCD137 cells were added to the plates at $1 \times 10^5$ cell/well. A 2 µM dilution of each test antibody was prepared in DPBS (Gibco) and further diluted 1:10 in DO1 1.10 cell medium (30 µl+270 µl) to obtain a 200 nM dilution. The MK1A6 crosslinking agent was added to the wells in a 1:1 molar ratio with the test antibody samples to be crosslinked. In a 96-well plate, serial dilutions of each antibody or antibody/crosslinking agent mixture were prepared. 100 µl of diluted antibody or antibody/crosslinking agent mixture was added to the DO11.10-hCD137 cells on the plate.

Cells were incubated at 37° C., 5% $CO_2$ for 72 hours. Supernatants were collected and assayed with a mouse IL-2 ELISA kit (eBioscience or R&D Systems) following the manufacturer's instructions. Plates were read at 450 nm using the plate reader with Gen5 Software, BioTek. Absorbance values of 630 nm were subtracted from those of 450 nm (Correction). The standard curve for calculation of cytokine concentration was based on a four-parameter logistic curve fit (Gen5 Software, BioTek). The concentration of mouse IL-2 (mIL-2) was plotted vs the log concentration of antibody and the resulting curves were fitted using the log (agonist) vs response equation in GraphPad Prism.

For each of the clones, a limited number of amino acids which retained or improved binding to cell-surface CD137 were identified for substitution of the methionine residue in the heavy chain CDR3. The FS20-22-49AA/FS30-16 mAb$^2$ clone contained three potential PTM sites and mutation of each of them led to a small reduction in binding affinity. When these were combined in one molecule the reduced binding was additive (data not shown) and, consequently, this clone was not pursued further. Few mutations were found that improved binding to CD137 and functional activity, compared with the relevant parent clone. Three mutant mAb$^2$ clones, all derived from the FS20-22-49AA/FS30-10 mAb$^2$ clone, were found to have improved binding affinity and functional activity. These mAb$^2$ contained either an asparagine, a threonine or a leucine residue substituted for the methionine residue at position 97 In the parent FS20-22-49AA/FS30-10 mAb$^2$ and were designated FS20-22-49AA/FS30-10-3, FS20-22-49AA/FS30-10-12 and FS20-22-49AA/FS30-10-16, respectively. Although the $EC_{50}$ values for mutant clones derived from the FS20-22-49AA/FS30-35 parent mAb$^2$ clone showed no improvement in functional activity compared to the parent clone, one mutant clone, designated FS20-22-49AA/FS30-35-14, which contained an alanine residue substituted for the methionine residue at position 100F in the parent clone, did however show improved binding. In the case of the FS20-22-49AA/FS30-5 parent mAb$^2$ clone, both the methionine residue at position 100D and the methionine residue at position 100H were changed, respectively, for an isoleucine residue and a leucine residue in the same molecule to result in a mutant mAb$^2$ clone, designated FS20-22-49AA/FS30-5-37. The FS20-22-49AA/FS30-10-3, FS20-22-49AA/FS30-10-12, FS20-22-49AA/FS30-10-16, FS20-22-49AA/FS30-35-14 and FS20-22-49AA/FS30-5-37 clones were selected for further characterisation.

6.3 Human CD137 Ligand Blocking Assays

The CD137-CD137L interaction is required for activation of the CD137 receptor. Agonistic anti-CD137 antibodies may drive activation of CD137 by mimicking the ligand interaction, thereby potentially blocking ligand binding, or driving clustering and activation of the receptors without interfering with ligand binding. Where the antibody potentially mimics the CD137L, it may block the interaction of the receptor and the ligand. It is known in the art that MOR7480.1 blocks the ligand/receptor interaction (US 2012/0237498), whereas the 20H4.9 antibody has previously been reported to not block the interaction between CD137 and its ligand (U.S. Pat. No. 7,288,638). The anti-human CD137 mAb$^2$ clones FS20-22-49AA/FS30-5-37, FS20-22-49AA/FS30-10-3, FS20-22-49AA/FS30-10-12, FS20-22-49ANFS30-10-16 and FS20-22-49AA/FS30-35-14 were tested for their ability to block the CD137-CD137L interaction using an ELISA-based method. Anti-OX40 mAb 11D4 (European Patent No. 2242771) in IgG1 format (G1/11 D4; SEQ ID NOs 174 and 175) was used as an isotype/negative control; the mAb$^2$ FS20-22-49AA/4420 comprising the anti-OX40 Fcab clone FS20-22-49AA and Fab region of the anti-FITC antibody 4420 was used as a negative control mAb$^2$ for OX40 binding; and anti-CD137 mAbs G1/MOR7480.1 (SEQ ID NOs 119 and 120) and G1/20H4.9 (SEQ ID NOs 121 and 122) as positive controls for CD137 binding and ligand blocking activity.

Specifically, recombinant human CD137-mFc-Avi antigen was coated overnight at 4° C. on Maxisorp 96-well plates at a concentration of 1 µg/ml in PBS. The following day, plates were washed with PBST (PBS+0.05% Tween20™) and blocked with PBS+1% BSA (Sigma, A3059-500G) for 1 hour at room temperature with agitation. After blocking, the plates were washed again with PBST. A 100 nM dilution of each test antibody was prepared in PBS+1% BSA and added to the CD137-coated plates and incubated for 1 hour at room temperature with agitation. After this Incubation, the plates were washed with PBST and then incubated with 20 ng/ml CD137L-His (R&D Systems, 2295-4L-025/CF) in PBS for 1 hour at room temperature with agitation. The plates were then washed with PBST and then incubated with anti-his secondary antibody (R&D Systems, MAB050H) at a 1 in 1000 dilution in PBS for 1 hour at room temperature with agitation. The plates were then washed with PBST and incubated with TMB detection reagent (Thermo Fisher Scientific, 002023) until the positive control wells turned blue and then the reaction was stopped with the addition of 2N $H_2SO_4$. Plates were read at 450 nm using the plate reader with Gen5 Software, BioTek. Absorbance values of 630 nm were subtracted from those of 450 nm (Correction). The subtracted absorbance values were plotted vs the log concentration of antibody and the resulting curves were fitted using the log (Inhibitor) vs response equation in GraphPad Prism. Values were normalised by setting the G1/11D4 and G1/MOR7480.1 control mAbs as 0 and 100% blocking values, respectively. The data was analysed using a one-way ANOVA test and Holm-Sidak's multiple comparisons test using GraphPad Prism.

A range of blocking activities was observed for the five anti-human CD137 $mAb^2$ clones tested. FS20-22-49AA/FS30-5-37 showed, like the positive control antibodies, complete inhibition of the receptor-ligand interaction. All $mAb^2$ clones containing the Fab regions of the anti-CD137 mAbs of the FS30-10 lineage (i.e., FS20-22-49AA/FS30-10-3, FS20-22-49AA/FS30-10-12 and FS20-22-49AA/FS30-10-16) inhibited the interaction between CD137 and CD137L by 49-54% and were therefore considered partial blockers. By only partially blocking the interaction between CD137 and CD137L, It Is possible that these mAbs may not completely inhibit the natural interaction of CD137L with its receptor such that some CD137 signalling may still occur via this mechanism, even if one of these antibodies is bound. The FS20-22-49AA/FS30-35-14 clone, like the negative control FS20-22-49AA/4420 $mAb^2$ molecule, lacked the ability to significantly inhibit the receptor-ligand interaction and was therefore considered to be a non-blocker.

In summary, the results of this ELISA-based assay showed that the panel of anti-CD137 mAbs tested showed a range of ligand blocking abilities, including complete, partial and no blocking activity. Clones FS20-22-49AA/FS30-10-3, FS20-22-49AA/FS30-10-12, FS20-22-49AA/FS30-10-16 and FS20-22-49AA/FS30-35-14 each showed a blocking activity that was different from that of the positive-control anti-CD137 mAbs. Since a range of ligand blocking activities was identified, the functional activity of each of the antibodies was tested.

Clones FS20-22-49AA/FS30-5-37, FS20-22-9AA/FS30-10-3, FS20-22-49AA/FS30-10-12 and FS20-22-49AA/FS30-10-16 were further tested for their ability to block the CD137-CD137L interaction using a cell-based method. A range of blocking activities was observed, with FS20-22-49AA/FS30-5-37 showing, like the positive control antibody (G1/MOR7480.1) used in this assay, complete inhibition of the receptor-ligand interaction. All three $mAb^2$ clones containing the Fab regions of the anti-CD137 mAbs of the FS30-10 lineage (i.e., FS20-22-49AA/FS30-10-3, FS20-22-49AA/FS30-10-12 and FS20-22-49AA/FS30-10-16) inhibited the interaction between CD137 and CD137L by 46-76% and were therefore considered partial blockers. The results of this assay were therefore similar to those of the ELISA-based blocking assay and showed that the panel of anti-CD137 mAbs tested exhibited a range of ligand blocking abilities from complete to partial blocking activity. Clones FS20-22-49AA/FS30-10-3, FS20-22-49AA/FS30-10-12 and FS20-22-49AA/FS30-10-16 each showed a blocking activity that was different from that of the positive-control antibody.

Example 7—Binding Specificity and Functional Activity of mAb and $mAb^2$ Clones in a Human CD137 T Cell Activation Assay 7.1 Binding Specificity of $mAb^2$ Clones CD137 and OX40 belongs to the tumour necrosis factor receptor superfamily (TNFRSF) of cytokine receptors (Moran et al., 2013). To analyse the specificity of the anti-CD137 Fab as well as the OX40 Fcab binding site of the five $mAb^2$ molecules, binding of the FS20-22-49AA/FS30-10-3, FS20-22-49AA/FS30-10-12, FS20-22-49AA/FS30-10-16, FS20-22-49AA/FS30-35-14 and FS20-22-49AA/FS30-5-37 $mAb^2$ to human CD137, human OX40 and six closely-related human TNFRSF members was tested using surface plasmon resonance (SPR). The aim was to demonstrate 1000-fold specificity by showing no binding of the $mAb^2$ to closely-related antigens at a concentration of 1 µM, but showing binding to CD137 and OX40 receptors at a concentration of 1 nM. The anti-CD137 mAb MOR7480.1 and anti-OX40 mAb 11D4 were used as positive controls.

Briefly, flow cells on CM5 chips were immobilised with approx. 1000 RU of either human CD137-mFc-Avi (Table 3), OX40-mFc (Table 2), recombinant human TNFRSF1A-Fc, recombinant human TNFRSF1B-Fc, recombinant human GITR-Fc, recombinant human NGFR-Fc, recombinant human CD40-Fc or recombinant human DR6-Fc. Flow cell 1 was left for blank immobilisation. The five $mAb^2$ were diluted to 1 µM and 1 nM in 1× HBS-EP buffer (GE Healthcare, product code BR100188), allowed to flow over the chip for 3 min and then allowed to dissociate for 4 minutes. A 30-second injection of 10 mM glycine pH 1.5 was used for regeneration. Positive control mAbs were injected at 50-100 nM to demonstrate the coating of each antigen. Binding levels were determined at the end of the association phase and compared.

All of the selected $mAb^2$ showed a high level of specificity for the human CD137 and OX40 receptors similar to or higher than the MOR7480.1 and 11 D4 positive controls, respectively.

7.2 Functional Activity of CD137 Agonist Antibodies in a Human CD137 T Cell Activation Assay To understand the activity of different anti-CD137 agonist antibodies, a T cell activation assay using DO11.10-hCD137 cells was used. The anti-CD137 agonist antibodies G1AA/MOR7480.1 (SEQ ID NOs: 125 and 120), G1AA/20H4.9 (SEQ ID NOs: 165 and 122) and G1AA/FS30-10-16 (SEQ ID NOs: 154 and 97) were tested, as well as the anti-FITC antibody 4420 In IgG1 format (G1/4420; SEQ ID NOs: 115 and 116) as an isotype negative control. The antibody molecules were tested both in the presence and absence of the crosslinking anti-human CH2 antibody MK1A6 (see Example 2.1). Mouse IL-2 production was used as a measure of T cell activation.

DO11.10-hCD137 cells were washed once in PBS and resuspended in DO11.10 cell media (RPMI medium (Life Technologies) with 10% FBS (Life Technologies) and 5 µg/ml puromycin (Life Technologies, A11113803) at a concentration of $1.0 \times 10^6$ cells/ml. 96-well flat-bottomed plates were coated with anti-mouse CD3 antibody (Thermo Fisher Scientific, clone 17A2) by incubation with 0.1 pg/ml anti-mouse CD3 antibody diluted in PBS for 2 hours at 37° C., 5% $CO_2$ and then washed twice with PBS. DO11.10-hCD137 cells were added to the plates at $1 \times 10^5$ cell/well. A 2 µM dilution of each test antibody was prepared in DPBS (Gibco) and further diluted 1:10 in DO11.10 cell medium (30 µl+270 µl) to obtain a 200 nM dilution. The MK1A6 crosslinking agent was added to the wells in a 1:1 molar ratio with the test antibodies where required. In a 96-well plate, serial dilutions of the antibody or antibody/crosslinking antibody mixture were prepared. 100 μl of the diluted antibody or antibody/crosslinking antibody mixture was added to the DO11.10-hCD137 cells on the plate. Cells were incubated at 37° C., 5% $CO_2$ for 72 hours. Supernatants were collected and assayed with mouse IL-2 ELISA kit (eBioscience or R&D Systems) following the manufacturer's instructions. Plates were read at 450 nm using the plate reader with the Gen5 Software, BioTek. Absorbance values of 630 nm were subtracted from those of 450 nm (Correction). The standard curve for calculation of cytokine concentration was based on a four parameter logistic curve fit (Gen5 Software, BioTek). The concentration of mouse IL-2 (mIL-2) was plotted vs the log concentration of antibody and the resulting curves were fitted using the log (agonist) vs response equation in GraphPad Prism.

The results of the assay are shown in FIGS. 2C and D. The anti-CD137 antibodies differed in their requirement for the crosslinking antibody for their activity, with all three anti-CD137 antibodies showing a concentration-dependent increase in IL-2 production in the presence of the crosslinking antibody, but only the G1AA/20H4.9 antibody showing activity in the absence of the crosslinking antibody. Therefore, G1AA/MOR7480.1 and G1AA/FS30-10-16 required the addition of the crosslinking antibody, i.e. their activity was 'crosslink-dependent', whereas G1AA/20H4.9 showed activity both in the presence and absence of the crosslinking antibody, i.e. its activity was 'crosslink-independent'.

7.3 Functional Activity of mAb² Clones in a Human CD137 T Cell Activation Assay

The functional activity of the selected FS20-22-49AA/FS30-5-37, FS20-22-49AA/FS30-10-3, FS20-22-49AA/FS30-10-12 and FS20-22-49AA/FS30-10-16 mAb² Bones was tested in a T cell activation assay using DO11.10-hCD137 cells. Anti-FITC antibody 4420 in IgG1 format (G1/4420: SEQ ID NOs 115 and 116) was used as an isotype negative control; anti-OX40 mAb G1/11 D4 (SEQ ID NOs 174 and 175) and mAb² clone FS20-22-49AA/4420 (SEQ ID NOs 123 and 116) were used as negative controls; and anti-CD137 antibody MOR7480.1 in both IgG1 (G1/MOR7480.1; SEQ ID NOs 119 and 120) and IgG2 (G2/MOR7480.1; SEQ ID NOs 124 and 120) formats, the IgG2 format being the format in which the antibody has been tested in clinical trials (Gopal et at, 2017; Tolcher et al., 2017), was used as a positive control. The mAb and mAb² molecules were crosslinked with the anti-human CH2 antibody, MK1A6 (see Example 2.1), and in one experiment the activity of non-crosslinked mAb and mAb² molecules was investigated. Mouse IL-2 production was used as a measure of T cell activation. The experiment was performed as described in Example 7.2.

When crosslinked, all five selected mAb² clones showed potent activity in the T cell activation assay, with average $EC_{50}$ values of less than 15 nM and average $E_{max}$ values in the range of about 16000-20000 pg/ml IL-2 (Table 6 and FIG. 2A). No activity of the tested mAb² clones was observed in the absence of crosslinking (FIG. 2B). The MOR7480.1 positive control antibody was observed to be active only when crosslinked ($EC_{50}$ of 3.3 nM and $E_{max}$ of 12575 pg/ml for G1/MOR7480.1, and $E_{50}$ of 2.4 nM and $E_{max}$ of 8547 pg/ml for G21MOR7480.1). The combination of a lack of activity of the crosslinked anti-OX40 mAb (G1/11 D4) and the low background signals observed for non-crosslinked anti-OX40 Fcab-containing mAb² molecules shows that the results of this assay are a read-out of CD137 activity only, most likely due to the high levels of CD137 receptor expression and non-detectable levels of OX40 receptor expression by the DO11.10 cells (data not shown).

TABLE 6

Activity of mAb2 in the human CD137 T cell activation assay

| mAb/mAb² | Activity of non-crosslinked mAbs/mAb² (n = 1) | | Activity of crosslinked mAbs/mAb² (Mean of n = 2) | |
|---|---|---|---|---|
| | $EC_{50}$ (nM) | $E_{max}$ (mIL-2 pg/ml) | $EC_{50}$ (nM) | $E_{max}$ (mIL-2 pg/ml) |
| G1/4420 | N/A | N/A | N/A | N/A |
| G1/11D4 | N/A | N/A | N/A | N/A |
| G1/MOR7480.1 | NM | NM | 3.3 | 12575 |
| G2/MOR7480.1 | N/A | N/A | 2.4 | 8547 |
| FS20-22-49AA/4420 | N/A | N/A | N/A | N/A |
| FS20-22-49AA/FS30-5-37 | N/A | N/A | 13.4 | 18129 |
| FS20-22-49AA/FS30-10-3 | N/A | N/A | 6.1 | 17049 |
| FS20-22-49AA/FS30-10-12 | N/A | N/A | 9.5 | 17183 |
| FS20-22-49AA/FS30-10-16 | N/A | N/A | 4.7 | 16310 |
| FS20-22-49AA/FS30-35-14 | N/A | N/A | 5.1 | 19837 |

Thus, mAb² comprising CDRs of the anti-human CD137 monoclonal antibodies FS30-5-37, FS30-10-3, FS30-10-12, FS30-10-16 and FS30-35-14 showed potent activity in being able to activate CD137 in the DO11.10-hCD137 T cell activation assay when cross-linked. No significant activity was observed in the absence of crosslinking. These mAb² contain the CH3 domain from the anti-human OX40 Fcab FS20-22-49, which also showed high activity when cross-linked in a T cell assay (see Example 4.3). The mAb² prepared with the LALA mutation were designated FS20-22-49AA/FS30-5-37, FS20-22-49AA/FS30-10-3. FS20-22-49AA/FS30-10-12, FS20-22-49AA/FS30-10-16.

These mAb² were selected for further analysis in order to determine if they were capable of acting as a dual agonist that can agonise both OX40 and CD137 autonomously, based on the expression of the specific targets and without the need for additional crosslinking agents.

Example 8-Binding Affinity of mAb² for Human and Cynomolgus OX40 and CD137

For CD137 affinity determination, a Biacore CM5 chip (GE Healthcare) was coated with anti human Fe using a Human Antibody Capture Kit (GE Healthcare) according to manufacturer's conditions, to a surface density of approximately 4000 RU. Samples of the test antibodies (mA& FS20-22-49AA/FS30-5-37, FS20-22-49AA/FS30-10-3, FS20-22-49AA/FS30-10-12 and FS20-22-49AA/FS30-10-16, anti-CD137 positive control G1/MOR7480.1 and anti-hOX40 negative control G1/11D4) were captured to approximately 80 RU. Human or cynomolgus CD137 (hCD137-mFc-Avi or cCD137-mFc-Avi) was flowed over at a range of concentrations in a three-fold dilution series starting at 200 nM, at a flow rate of 70 μl/min. The association time was 2 min and the dissociation time was 8 min. Running buffer was HBS-EP (GE Healthcare BR100188). Flow cells were regenerated by injecting 3M magnesium chloride at a flow rate of 30 μl/min for 30 seconds.

For OX40 affinity determination a Biacore CM5 chip was coated with anti-human Fab using a Human Fab Capture Kit (GE Healthcare 28958325) according to manufacturer's conditions. to a surface density of approximately 8000 RU.

Samples of the test antibodies (FS20-22-49AA/FS30-5-37, FS20-22-49AA/FS30-10-3. FS20-22-49AA/FS30-10-12 and FS20-22-49AA/FS30-10-16 mAb², G1/MOR7480.1 (negative control) and G1/11D4 (positive control)) were captured to approximately 80 RU and then human or cynomolgus OX40 antigen (hOX40-mFc or cOX40-mFc) was flowed over at a range of concentrations in a three-fold dilution series starting at 200 nM at a flow rate of 70 µl/min. The association time was 2 min and the dissociation time was 8 min. Running buffer was HBS-EP. Flow cells were regenerated by Injecting glycine-HCl at pH 2.1 at a flow rate of 30 µl/min for 30 seconds.

The data were analysed by double referencing against a flow cell which was intentionally left blank (no antibody binding). The binding kinetics were fit with a 1:1 Langmuir model to generate binding association ($k_a$) and dissociation ($k_d$) rates. Equilibrium binding constants ($K_D$) were calculated by dividing the dissociation rate by the association rate for each sample. Data analysis was performed with BiaEvaluation software version 3.2. The results are shown in Table 7.

TABLE 7

Binding affinity of mAb² to human and cynomolgus CD137 and OX40 as determined by SPR

| mAb/mAb² | CD137 Human $K_D$ (nM) | CD137 Cynomolgus $K_D$ (nM) | OX40 Human $K_D$ (nM) | OX40 Cynomolgus $K_D$ (nM) |
|---|---|---|---|---|
| G1/M0R7480.1 | 0.127 | NM | NB | NB |
| G1/11D4 | NB | NB | 0.0337 | NM |
| FS20-22-49AA/FS30-5-37 | 3.85 | 6.42 | 0.385 | 1.63 |
| FS20-22-49AA/FS30-10-3 | 0.342 | 0.318 | 0.285 | 1.11 |
| FS20-22-49AA/FS30-10-12 | 0.255 | 7.24 | 0.37 | 1.02 |
| FS20-22-49AA/FS30-10-16 | 0.17 | 0.15 | 0.214 | 0.861 |

NB ± No binding detected. NM ± Not measured.

The binding affinities for the OX40/CD137 mAb² show that these molecules bind with high affinity to both receptors. The affinity of these molecules for human OX40 is similar, which is to be expected as these molecules all share the OX40 Fcab. The affinity for cynomolgus OX40 is within 5-fold of human OX40. The affinity for human CD137 ranges from 4-0.2 nM and the cross-reactivity to cynomolgus CD137 Is also variable as the anti-CD137 Fabs are different in each molecule. FS20-22-49AA/FS30-10-16 has higher affinity for human CD137, as well as similar affinity for cynomolgus CD137. The similarity in binding to human and cyno antigens may be advantageous as it would be hoped that the behaviour of the mAb² in cynomolgus monkey studies could be extrapolated to humans.

Also, FS20-22-49AA/FS30-10-16 has similar affinity for human OX40 and human CD137 so it is expected that the mAb² should bind equally well to both targets when these are co-expressed.

A mAb² which binds to OX40 and CD137 and drives clustering and activation of both targets simultaneously, Is expected to act as a dual agonist. Both OX40 and CD137 are known to be present on T cells (Ma, et al., 2005). Without wishing to be bound by theory, it is thought that a mAb² having similar affinity for binding to both targets may be advantageous as a dual agonist because the mAb² would be more likely to bind to cells which express both targets. A mAb² which preferentially bound one target with significantly higher affinity than the other may not be able to act as a dual agonist as it may preferentially bind to cells which do not express both targets.

Example 9—Simultaneous Binding of mAb² to OX40 and CD137

9.1 Simultaneous Binding of mAb² to Human OX40 and Human CD137

The ability of the OX40/CD137 mAb² FS20-22-49AA/FS30-5-37, FS20-22-49AA/FS30-10-3 and FS20-22-49AA/FS30-10-16 to bind simultaneously to OX40 and CD137 was tested by SPR on a Biacore 3000. G1/MOR7480.1 was used as a control. In accordance with manufacturer's instructions, biotinylated human CD137 (hCD137-mFc-Avi-Bio) was diluted to 100 nM in HBS-EP buffer and immobilised on a Streptavidin (SA) chip (GE Healthcare BR100032) to a surface density of approximately 1000 RU, and a flow cell was activated and deactivated without any protein immobilised for background subtraction. The antibodies, diluted to 100 nM in HBS-EP buffer, were co-injected with either 100 nM of human OX40 (hOX40-mFc) or HBS-EP buffer at a flow rate of 30 µl/min. For each binding step, dissociation was followed for 3 minutes. The sensor chip was regenerated after each cycle with a 15 µl injection of Glycine 2.5 (GE Healthcare) at a flow rate of 30 µl/min. All mAb² tested were capable of simultaneously binding to OX40 and CD137. The control mAb, G1/MOR7480.1, only bound to CD137.

9.2 Simultaneous Binding of Murine Receptor-Targeting mAb² to Murine OX40 and Murine CD137

A mAb² comprising an anti-mouse OX40 Fcab with an anti-mouse CD137 Fab was prepared for testing of Its ability to bind simultaneously to murine OX40 and murine CD137. The mouse OX40-targeting Fcab FS20m-232-91 was selected because of its higher activity in T cell assays and the Fab of the anti-mouse CD137 antibody Lob12.3 (Taraban et al., 2002) in human IgG1 isotype format (G1/Lob12.3; University of Southampton) was selected for pairing with the FS20m-232-91 Fcab, as this showed good cell binding to mouse CD137-expressing cells and is widely used in the literature as an agonistic CD137 antibody with activity in vitro and in vivo. The mAb² containing the FS20m-232-91 CH3 domain and the Fab of the anti-mouse CD137 antibody Lob12.3 and the LALA mutation was designated 'FS20m-232-91AA/Lob12.3', whilst the mAb² containing the FS20m-232-91 CH3 domain and the Fab of the anti-mouse CD137 antibody Lob12.3 without the LALA mutation was designated 'FS20m-232-91/Lob12.3'.

The ability of FS20m-232-91AA/Lob12.3 mAb² to bind simultaneously to its two targets was tested by SPR on a BIAcore 3000 instrument (GE Healthcare). G1/Lob12.3 was used as a positive control. In accordance with manufacturer's instructions, recombinant mouse CD137 (mCD137-hFc; R&D Systems, cat. no. 937-4B-050) was diluted to 200 nM in Sodium Acetate pH 5.0 (GE Healthcare) and immobilised on a Biacore CM5 chip to a surface density of approximately 1000 RU, and a flow cell was activated and deactivated without any protein immobilised for background subtraction. The mAb² and positive control, diluted to 100 nM in HBS-EP buffer, were co-injected with either 100 nM of human OX40 (mOX40-mFc) or HBS-EP buffer at a flow rate of 30 µl/min. For each binding step dissociation was followed for 3 minutes. The sensor chip was regenerated after each cycle with a 30-second injection of aqueous glycine-HCl at pH 1.7 at a flow rate of 20 µl/min. The mAb² was capable of simultaneously binding to OX40 and CD137. The G1/Lob12.3 mAb only bound to CD137.

Example 10-Binding of mAb² to Fcγ Receptors

It is known from the literature that agonistic antibodies targeting TNFR family members require crosslinking via Fcγ receptors to drive clustering and activation of the target for in vivo activity (Wajant, 2015). However, this may not be desirable for an antibody which is intended to be a dual agonist. It was therefore decided to reduce the ability of the mAb² to bind to Fcγ receptors by insertion of the LALA mutation.

Human IgG1 isotype antibodies are capable of binding to Fcε receptors. This can result in them inducing effector function, such as Antibody Dependent Cellular Cytotoxicity (ADCC), of cells expressing the target, when they bind to Fcγ receptors, resulting in cell lysis. Since the intended mechanism of OX40/CD137 mAb² is to activate cells expressing OX40 and CD137 without killing them, reduction of ADCC induced by the mAb² is desirable. Also, since the OX40/CD137 mAb² are intended to function as dual agonists. their intended mechanism of action is to signal via the receptors as a result of crosslinking by dual binding to both OX40 and CD137 when either co-expressed on the same cell or expressed on different cells, and so the ability to crosslink via Fcγ receptors Is not a requirement for function.

Further, it is known that CD137-targeting antibodies have shown liver toxicity in the clinic (Segal et al., 2017) and, although the toxicity mechanism is not known, it is possible that it relies on FcγR-mediated crosslinking of anti-CD137 antibodies and activation of CD137-expressing cells in the liver or in the periphery. Preventing CD137 agonism via FcγR-mediated crosslinking may decrease any toxicity risk of the OX40/CD137 mAb² of the invention as these molecules will only crosslink via dual binding to OX40 and CD137.

Binding by SPR was used to confirm that the presence of the LALA mutation in the mAb² FS20-22-49AA/FS30-10-16 had reduced binding affinity for Fcγ receptors, specifically hFcγR1 (R&D Systems, cat. no. 1257-FC-050/CF), hFcγR2a (R&D Systems, cat. no. 1330-CD-050/CF), hFcγR2b (R&D Systems, cat. no. 1460-CD-050/CF) and hFcγR3a (R&D Systems, cat. no. 4325-FC-050/CF). Anti-hOX40 mAbs G1AA/11 D4 and G1/11 D4 (with and without the LALA mutation, respectively) and anti-CD137 mAbs G1AA/20H4.9 and G1/20H4.9 (with and without the LALA mutation, respectively), all in hIgG1 isotype format, and anti-hCD137 mAb G4120H4.9. in hIgG4 isotype format, were used as control antibodies. Binding was tested on a Biacore 3000 instrument (GE Healthcare). Human OX40 (BPS Bioscience cat no 71310) and human CD137 (produced in house) biotinylated his-tagged antigens were coated onto an S A chip (GE Healthcare cat no BR100398) at 2 µM concentration. Human OX40 and human CD137 were coated on separate flow cells, while another flow cell was left blank for background subtraction. Regeneration conditions were determined to be 12 µl aqueous 10 mM glycine-HCl at pH2.0 at 20 µl/min flow rate. Antibodies (see Table 8) and human FcγRs (see Table 8) were diluted to 100 nM (antibodies) or 500 nM (human FcγRs) in HBS-P (0.01 M HEPES pH 7.4, 0.15 M NaCl, 0.005% v/v Surfactant P20, GE Healthcare, BR-1003-68) and co-injected at 20 µl/min flow rate and the dissociation was followed for 5 min.

Data analysis was performed with BiaEvaluation software version 3.2 RC1 by referencing against the blank flow cell and aligning the curves after the association of the antibody. Values for binding response at the end of the association phase were generated by subtracting the absolute response at the end of the association phase of the FcγR from the absolute response at the end of the association phase of the antibody to normalize the effect of the antibody binding to the OX40 and CD137 receptors.

Measuring values for binding response at the end of the dissociation phase of FcγRI was done to demonstrate the effect of the LALA mutation in increasing the off-rate of FcγRI binding in the absence of the complete elimination of binding to this FcγR. These were generated by subtracting the absolute response at the end of the association phase of the FcγR from the absolute response at the end of the dissociation phase of the FcγR. Values for anti-CD137 antibodies were taken from the flow cell coated with CD137-his antigen, values for anti-OX40 antibodies were taken from the flow cell coated with OX40-his antigen, and for the OX40/CD137 mAb² from both the flow cell coated with OX40-his antigen and the flow cell coated with CD137-his antigen. The results are shown in Table 8.

TABLE 8

Binding response of antibodies to human Fcγreceptors by SPR

| mAb/mAb² | Antigen on chip | Binding response at end of association phase of FcγR (RU) (on rate) | | | | Decrease of binding response at end of dissociation phase of FcγR (RU) |
|---|---|---|---|---|---|---|
| | | FcγRIIa | FcγRIIb | FcγRIIIa | FcγRI | FcγRI |
| G1/11D4 | OX40-his | 123 | 89.7 | 142.7 | 370.3 | 46.4 |
| G1AA/1104 | OX40-his | 64.5 | 60.9 | 67.3 | 292.3 | 202.6 |
| G1/20H4.9 | CD137-his | 224.8 | 158.5 | 297.4 | 741 | −16.3 |
| G1AA/20H4.9 | CD137-his | 97.5 | 95.4 | 129.4 | 504.6 | 380.6 |
| G4/20H4.9 | CD137-his | 156 | 163.9 | 113.1 | 693.3 | 57.1 |
| FS20-22-49AA/FS30-10-16 | OX40-his | 37.4 | 34.3 | 31.4 | 237.5 | 234.8 |
| FS20-22-49AA/FS30-10-16 | CD137-his | 10.9 | 9 | 17.3 | 245.8 | 367.3 |

The mAb² and control antibodies without the LALA mutation all bound to each of the Fcγ receptors, as expected, in both IgG1 and IgG4 format. The mAb² and control antibodies in IgG1 format containing the LALA mutation showed significantly reduced binding at the end of the association phase (on-rate) to each of the tested Fcγ receptors, except for FcγRI, compared to the control antibodies in IgG1 format without the LALA mutation and the control antibody in IgG4 format. On rate binding of the high affinity Fcγ receptor, FcγRI, to hIgG1 LALA-containing antibodies decreased only marginally as compared to non-LALA-containing IgG1 antibodies, such that it was not significantly changed by Introduction of the mutation. However, the off-rate for FcγRI was faster for the antibodies containing the LALA mutation than those without LALA, as shown by a larger decrease of the binding response at the end of the dissociation phase of FcγRI (over 200 RU for each of the LALA containing antibodies compared to less than 60 RU for the non-LALA containing antibodies).

Overall, the OX40/CD137 mAb² containing the LALA mutation reduced binding to Fcγ receptors when compared to a wild type human IgG1, in a similar manner to other LALA-containing hIgG1 antibodies and at a lower level than the IgG4 control antibody. Since Fc-1 receptor-binding is needed for ADCC activity, it is expected that this reduction in binding to Fcγ receptors caused by the LALA mutation will also result in reduced ADCC such that the target cells will not be depleted by the mAb² binding. This is considered to be important since the OX40/CD137 mAb² are agonistic antibodies and therefore depletion of the target cells is not desired as these are the cells the mAb² aim to stimulate.

FcγRIIIa is expressed on immune effector cells, such as natural killer (NK) cells, and has been shown to be important in mediating ADCC (Chan et al., 2015). To determine whether the reduced binding of the FS20-22-49AA/FS30-10-16 mAb² to FcγRIIIa, as confirmed by the SPR data, translated into low or negligible activation of the ADCC pathway, an ADCC bioassay was performed using engineered Jurkat cells expressing FcγRIIIa as effector cells, and Raji cells overexpressing either human OX40 or human CD137 as target cells. The mAb² was observed not to induce ADCC activation in either the OX40-expressing or CD137-expressing Raji cells, as compared to the responses observed for the negative and positive control antibodies used in the assay.

It is known that other agonistic antibodies rely on Fcγ receptor-crosslinking of antibodies to create higher order structures (Stewart et al., 2014; Wajant, 2015), resulting in clustering and activation of receptors on the cell surface to exert their agonistic activity. Since Fcγ receptor-mediated crosslinking is not required for activity of the mAb² of the invention. agonism of cells will be localised to sites where both targets are present. As the LALA mutation in the OX40/CD137 mAb² results in reduced binding to Fcγ receptors, it is not expected that Fcy receptor crosslinking-driven activation via CD137-binding alone is possible. Consequently, the mAb² are unlikely to activate CD137-expressing cells in the absence of expression of OX40. Since there Is a known liver toxicity risk associated with targeting CD137 in humans (for example, as seen in treatment with urelumab (BMS-663513) (Segal et al., 2017) it is hoped that the reduction in likelihood of Fcy receptor-induced crosslinking of the mAb² containing the LALA mutation will reduce the chances of such liver toxicity occurring upon treatment with the mAb², as CD137 will only be activated where OX40 is also expressed. The current theory of CD137-induced liver toxicity indicates that myeloid cells expressing CD137 are the cell type responsible for the liver inflammation seen in mice treated with CD137 agonists (Bartkowiak, et al., 2018).

Macrophages are known to express FcγRI which could potentially mediate crosslinking of a CD137 targeting antibody, however, these cells are not known to express OX40. Therefore, the mAb² of the invention, containing the LALA mutation, should in theory not be able to activate liver macrophages which express CD137 but not also OX40. This is considered to reduce the liver toxicity risk of the OX40/CD137 mAb² of the invention when compared to either a CD137 agonist that requires Fcγ receptor crosslinking for activity or a CD137 agonist that does not require crosslinking for activity. In the case of OX40, while some residual activity of the Fcab has been observed in the absence of crosslinking which may lead to some activation of OX40 in the absence of CD137 binding, as dose-limiting toxicities have not been reported to date in clinical studies with OX40 agonists. this is not considered to be a risk.

Example 11—Binding of mAb² to Cells Expressing OX40 or CD137

11.1. Binding of mAb² to Cells Expressing Human or Cynomolgus OX40 or CD137

The binding affinity of the mAb² FS20-22-49AA/FS30-5-37, FS20-22-49AA/FS30-10-3, FS20-22-49AA/FS30-10-12 and FS20-22-49AA/FS30-10-16 for cell-expressed human or cynomolgus OX40 and CD137 was determined using flow cytometry. Dilutions (2× final concentration) of these mAb² antibodies and control antibodies G1/4420 (FITC), G1/11 D4 (OX40), G1/MOR7480.1 (CD137) and FS20-22-49AA/4420 (OX40/FITC mock mAb²) (all in IgG1 Isotype format) were prepared in 1×DPBS (Gibco, 14190-094). DO11.10-hOX40, DO11.10-cOX40, DO11.10-hCD137, DO11.10-cCD137 or HEK cell suspensions were prepared in PBS+2% BSA (Sigma, A7906) and seeded at $4×10^{11}$ cell/ml with 50 μl/well in V-bottomed 96-well plates (Costar, 3897). 50 μl of the antibody dilutions were added to the wells containing cells (final volume 100 μl) and incubated at 4° C. for 1 hour. The plates were washed and 100 μl/well of secondary antibody (anti-human Fc-488 antibody, Jackson ImmunoResearch, 109-546-098) diluted 1:1000 in PBS+2% BSA was then added and incubated for 30 mins at 4° C. in the dark. The plates were washed and resuspended in 100 μl of PBS containing DAPI (Biotium, cat no 40043) at 1 μg/ml. The plates were analysed using a Canto II flow cytometer (BD Bioscience) and the data analysed using FlowJo. Dead cells were identified by their higher fluorescence on the UV (405 nm/450/50) channel and excluded from analysis. The geometric mean fluorescence Intensity (GMFI) In the FITC channel (488 nm/530/30) was used as a measure of antibody binding. The GMFI data was fit using log (agonist) vs response (three parameters) in GraphPad Prism Software to generate $EC_{50}$ values.

TABLE 9

Binding affinity of anti-OX40/CD137 mAb² for 0011.10 cells expressing human or cynomolgus OX40 or CD137 as determined by flow cytometry.

| mAb | Human OX40 $EC_{50}$ (nM) | Cynomolgus OX40 $EC_{50}$ (nM) | Human CD137 $EC_{50}$ (nM) | Cynomolgus CD137 $EC_{50}$ (nM) | HEK $EC_{50}$ (nM) |
|---|---|---|---|---|---|
| G1/4420 | NB | NB | NB | NB | NB |
| G1/11D4 | 0.1248 | 0.09408 | NB | NB | NB |
| G1/M0R7480.1 | NB | NB | 0.07682 | 0.06119 | NB |
| FS20-22-49AA/4420 | 0.1619 | 0.3262 | NB | NB | NB |
| FS20-22-49AA/FS30-5-37 | 0.2007 | 0.3552 | 0.2578 | 0.1105 | NB |
| FS20-22-49AA/FS30-10-3 | 0.175 | 0.394 | 0.1197 | 0.0682 | NB |

TABLE 9-continued

Binding affinity of anti-OX40/CD137 mAb² for 0011.10 cells expressing human or cynomolgus OX40 or CD137 as determined by flow cytometry.

| mAb | Human OX40 $EC_{50}$ (nM) | Cynomolgus OX40 $EC_{50}$ (nM) | Human CD137 $EC_{50}$ (nM) | Cynomolgus CD137 $EC_{50}$ (nM) | HEK $EC_{50}$ (nM) |
|---|---|---|---|---|---|
| FS20-22-49AA/FS30-10-16 | 0.1566 | 0.3798 | 0.1291 | 0.08027 | NB |
| FS20-22-49AA/FS30-10-12 | 0.1517 | 0.3684 | 0.2899 | 0.1074 | NB |

NB: no binding observed.

The results confirm that the OX40/CD137 mAb² tested bind to human and cynomolgus OX40 and CD137 expressed on DO11.10 cells. The mAb² and the positive-controls (anti human OX40 mAb. G1/11D4, In a human IgG1 backbone; and anti-human CD137 mAb G1/MOR7480.1, in a human IgG1 backbone) bound to both human and cynomolgus OX40 and CD137 with a range of affinities (see Table 9). No cross-reactivity with other proteins expressed on the surface of the HEK cell line was observed as no binding could be detected with this cell line for any of the tested antibodies. Therefore, the OX40/CD137 mAb² bound specifically to human OX40 and human CD137, with no non-specific binding observed.

11.2 Binding of FS20-22-49AA/FS30-10-16 mAb² and Component Parts Thereof to Cells Expressing Human or Cynomolgus OX40 or CD137

To compare the affinity of the mAb² FS20-22-49AA/FS30-10-16 and its components parts, i.e. the OX40 Fcab (in OX40/FITC mock mAb² format FS20-22-49AA/4420) and the CD137 Fab (in IgG1 format FS30-010-016), for cell-expressed human or cynomolgus OX40 and CD137, the same method as described in Example 11.1 was used. However. in this experiment, instead of using HEK cells to analyse the non-specific binding, non-transduced DO11.10 cells were used. The G1/4420 anti-FITC antibody was used as a control. The experiment was repeated three times to Increase the reliability of the $EC_{50}$ values calculated. The mean average $EC_{50}$ values for the molecules tested are shown in Table 10.

The results confirm that the OX40/CD137 mAb² (FS20-22-49AA/FS30-10-16) binds to human and cynomolgus OX40 and CD137 expressed on DO11.10 cells with sub-nanomolar affinity, that the OX40 Fcab component of the mAb² binds to human and cynomolgus OX40 with comparable affinity to the OX40/CD137 mAb². and that the CD137 Fab component of the mAb² binds to human and cynomolgus CD137 with comparable affinity to the OX40/CD137 mAb². No non-specific binding to non-transduced DO11.10 cells was observed for the OX40/CD137 mAb², either of its component parts or the isotype control antibody (G114420). The results indicate that the affinity of the FS20-22-49AA/FS30-10-16 OX40/CD137 mAb² and the FS20-22-49AA OX40 Fcab for cell-expressed cynomolgus OX40 is greater (as shown by the lower $EC_{50}$ values) than previously observed (Example 11.1 and Table 9) and similar to the affinity results determined by SPR (Example 8 and Table 7). Since the mean $EC_{50}$ values detailed in Table 10 are the product of three independent experiments, these are a better representation of the affinity of the tested molecules for human and cynomolgus OX40 and CD137 expressed on DO11.10 cells.

11.3 Binding of mAb² to Cells Expressing Mouse OX40 or CD137

The binding affinity of the FS20m-232-91AA/Lob12.3 mAb² for cell-expressed mouse OX40 and CD137 was determined using flow cytometry. Dilutions (2×final concentration) of FS20m-232-91AA/Lob12.3 and control antibodies G1/4420 (FITC), G1/Lob12.3 (CD137), G1/OX86 (OX40) and FS20m-232-91AA/HEL D1.3 (OX40/HEL mock mAb²) were prepared in 1×DPBS (Gibco, 14190-094). DO11.10-mOX40, DO11.10-mCD137, or HEK cell suspensions were prepared in PBS+2% BSA (Sigma, A7906) and seeded at $4×10^8$ cell/ml with 50 μl/well in V-bottomed 96-well plates (Costar, 3897). 50 μl of the antibody dilutions were added to the wells containing cells (final volume 100 μl) and incubated at 4° C. for 1 hour. The plates were washed and 100 μl/well of secondary antibody (anti-human Fc-488 antibody. Jackson ImmunoResearch, 109-546-098) diluted 1:1000 in PBS+2% BSA was then added and incubated for 30 mans at 4C in the dark. The plates were washed and resuspended in 100 μl of PBS containing DAPI (Biotium, cat no 40043) at 1 μg/ml. The

TABLE 10

Binding affinity of anti-OX40/00137 mAb² FS20-22-49AA/FS30-10-16 and its component parts to DO11.10 cells expressing human or cynomolgus OX40 or CD137 as determined by flow cytometry.

| mAb | Human OX40 $EC_{50}$ Avg ± SD (nM) | Cynomolgus OX40 $EC_{50}$ Avg ± SD (nM) | Human CD137 $EC_{50}$ Avg ± SD (nM) | Cynomolgus CD137 $EC_{50}$ Avg ± SD (nM) | Non-transduced D011.10 $EC_{50}$ Avg ± SD (nM) |
|---|---|---|---|---|---|
| G1/4420 | NB | NB | NB | NB | NB |
| FS20-22-49AA/4420 | 0.23 ± 0.02 | 0.55 ± 0.14 | NB | NB | NB |
| G1/FS30-10-16 | NB | NB | 0.10 ± 0.05 | 0.09 ± 0.01 | NB |
| FS20-22-49AA/FS30-10-16 | 0.22 ± 0.01 | 0.71 ± 0.21 | 0.11 ± 0.02 | 0.12 ± 0.01 | NB |

Avg: Mean average;
SD: Standard deviation;
NB: no binding observed.

plates were analysed using a Canto II flow cytometer (BD Bioscience) and the data analysed using FlowJo. Dead cells were identified by their higher fluorescence on the UV (405 nm/450/50) channel and excluded from analysis. The geometric mean fluorescence intensity (GMFI) in the FITC channel (488 nm/530130) was used as a measure of antibody binding. The GMFI data was fit using log (agonist) vs response (three parameters) in GraphPad Prism Software to generate $EC_{50}$ values. The results are shown in Table 11.

TABLE 11

Binding affinity of anti-mouse OX40/CD137 $mAb^2$ for D011.10 cells expressing mouse OX40 or CD137 as determined by flow cytometry.

| mAb | Mouse OX40 EC50 (nM) | Mouse CD137 $EC_{50}$ (nM) |
|---|---|---|
| G1/4420 | NB | NB |
| G1/Lob12.3 | NB | 0.1206 |
| G1/OX86 | 0.5381 | NB |
| FS20m-232-91AA/HEL D1.3 | 0.2677 | NB |
| FS20m-232-91AA/Lob12.3 | 0.159 | 0.118 |

NB: no binding observed.

The results confirm that FS20m-232-91AA/Lob12.3 $mAb^2$ binds to mouse OX40 and CD137 expressed on DO11.10 cells. The $mAb^2$ and the positive-controls (anti-mouse OX40 mAb, OX86, in a human IgG1 backbone; and anti-mouse CD137 mAb Lob12.3, in a human IgG1 backbone) bound to mouse OX40 and/or CD137 with a range of affinities (see Table 11). No cross-reactivity with other proteins expressed on the surface of the HEK cell line was observed as no binding could be detected with this cell line for any of the tested antibodies.

Therefore, the anti-mouse OX40/CD137 $mAb^2$ bound specifically to mouse OX40 and mouse CD137, with no non-specific binding observed.

Example 12-Activity of OX40/CD137 $mAb^2$ Targeting Co-Expressed Receptors in a Staphylococcal Enterotoxin a (SEA) Assay OX40 expression on tumour infiltrating lymphocytes is likely to be accompanied by expression of CD137 as these two molecules are often co-expressed on activated T cells (Ma et al, 2005). Agonising OX40 and CD137 by a $mAb^2$ targeting these two co-expressed receptors can induce the proliferation and production of inflammatory cytokines by pre-activated T cells.

To become fully activated, T cells require two signals, a first signal which is antigen specific and is provided through the T-cell receptor which interacts with MHC (major histocompatibility complex) molecules displaying peptide antigen on the membrane of antigen presenting cells (APCs), and a second, antigen-nonspecific signal—the costimulatory signal—which is provided by the interaction between costimulatory molecules expressed on the membrane of the APC and the T cell.

To test the activity of the OX40/CD137 $mAb^2$, a T cell activation assay using staphylococcal enterotoxin A (SEA) superantigen as the first signal was established. SEA crosslinks MHC class II molecules on the surface of APCs and the TCR of T cells, thereby providing the first signal for T cell activation. For their full activation, the T cells must also receive the second, costimulatory signal, by the control molecules or $mAb^2$ crosslinked as appropriate. This assay is performed with isolated PBMCs from blood and should represent more closely what is expected to happen in vivo compared to an assay performed with isolated T cells.

The SEA-stimulation assay was used to establish the activity of different OX40 and CD137 agonist antibodies, and an OX40/CD137 $mAb^2$ antibody, in the presence or absence of artificial crosslinking agents, to compare different OX40/CD137 $mAb^2$ clones, and to establish a representative $EC_{50}$ value for the OX40/CD137 $mAb^2$ clone FS20-22-49AA/FS30-10-16 in a group of 10 PBMC donors.

12.1 Activity of OX40 and CD137 Agonist Antibodies on SEA-Stimulated PBMCs

To establish the sensitivity of the SEA assay to different OX40 and CD137 agonist antibodies, the $mAb^2$ antibody (FS22-20-49AA/FS30-10-16) and control antibodies listed in Table 12 were tested for their activity in the assay. G114420 (anti-FITC), G1AA/MOR7480.1 (anti-CD137), G1AA/FS30-10-16 (anti-CD137). G1AA/20H4.9 (anti-CD137), G1AA/11D4 (anti-OX40), and FS20-22-49AA/4420 (OX40/FITC mock $mAb^2$) were used as controls. IL-2 production was used as a measure of T cell activation.

TABLE 12

Details of antibodies and $mAb^2$ tested

| mAb/$mAb^2$ | Fab binding to | Fcab binding to | Isotype | LALA mutation | Crosslinker | Heavy chain SEQ ID | Light chain SEQ ID |
|---|---|---|---|---|---|---|---|
| G1/4420 | FITC | none | hIgG1 | No | FITC-dextran | 115 | 116 |
| G1AA/MOR7480.1 | hCD137 | none | hIgG1 | Yes | a-hCH2 | 125 | 120 |
| G1AA/FS30-10-16 | hCD137 | none | hIgG1 | Yes | a-hCH2 | 154 | 97 |
| G1AA/20H4.9 | hCD137 | none | hIgG1 | Yes | a-hCH2 | 165 | 122 |
| G1AA/11D4 | hOX40 | none | hIgG1 | No | a-hCH2 | 173 | 175 |
| FS20-22-49AA/4420 | FITC | hOX40 | hIgG1 | Yes | FITC-dextran | 123 | 116 |
| FS20-22-49AA/FS30-10-16 | hCD137 | hOX40 | hIgG1 | Yes | a-hCH2 | 95 | 97 |

Peripheral blood mononuclear cells (PBMCs) were isolated from leucocyte depletion cones (NHS Blood and Transplant service), a by-product of platelet donations. Briefly, leucocyte cone contents were flushed with PBS and overlaid on a Ficoll gradient (GE Lifesciences cat no 17144002). PBMCs were isolated by centrifugation and recovery of cells that did not cross the Ficoll gradient. PBMCs were further washed with PBS and remaining red blood cells were lysed through the addition of 10 ml red blood cell lysis buffer (eBioscience) according to the manufacturer's instructions. PBMCs were counted and resuspended to $2.0\times10^6$ cells/ml in T cell medium (RPMI medium (Life Technologies) with 10% FBS (Life Technologies), 1×

Penicillin Streptomycin (Life Technologies), Sodium Pyruvate (Gibco), 10 mM Hepes (Gibco), 2 mM L-Glutamine (Gibco) and 50 µM 2-mercaptoethanol (Gibco)). SEA (Sigma cat no S9399) was then added to PBMCs at 200 ng/ml and cells were added to the plates at 2×10$^5$ cell/well (100 µl/well). 2 µM dilutions of each test antibody (see Table 12 for details) were prepared in DPBS (Gibco) and further diluted 1:10 in T cell medium (30 µl+270 µl) to obtain 200 nM dilutions. The artificial crosslinking agents (anti-human CH2 antibody (clone MK1A6, produced in-house) or FITC-dextran (Sigma) (see Table 12) were added to the wells in a 1:1 molar ratio with the test antibodies where needed. In a 96-well plate, serial dilutions of the test antibodies were prepared and 100 µl of the diluted antibody mixture was added to the activated T cells on the plate.

Figure 3:
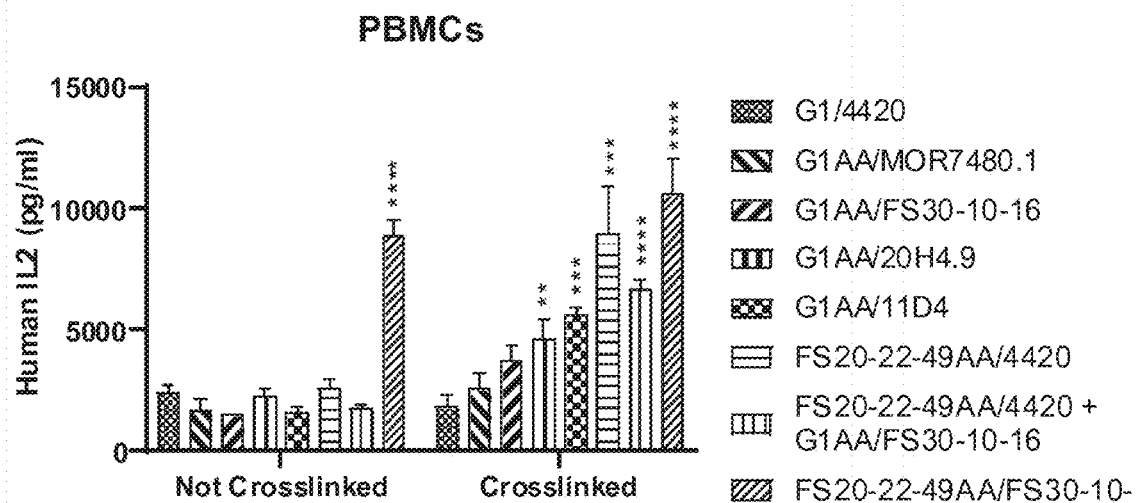
FIG. 3 shows the activity of CD137 mAb, OX40 Fcab and OX40/CD137 mAb$^2$ in staphylococcal enterotoxin A (SEA) assays. IL-2 release was measured in the presence of the mAb/mAb$^2$ indicated and in the presence and absence of crosslinking agents (FITC-dextran for the anti-FITC mAb and OX40/FITC mock mAb$^2$ controls, and anti-human CH2 antibody for all other molecules tested).
Figure 3:
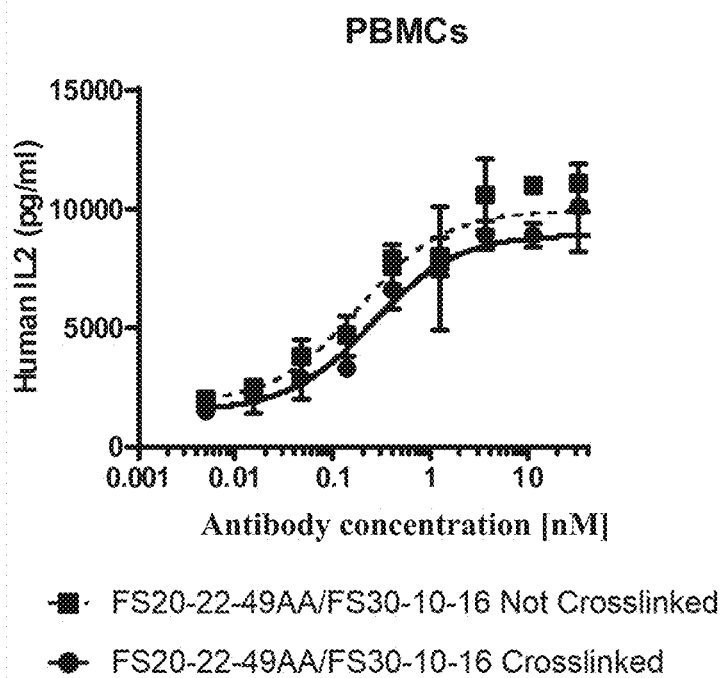
Figure 3:
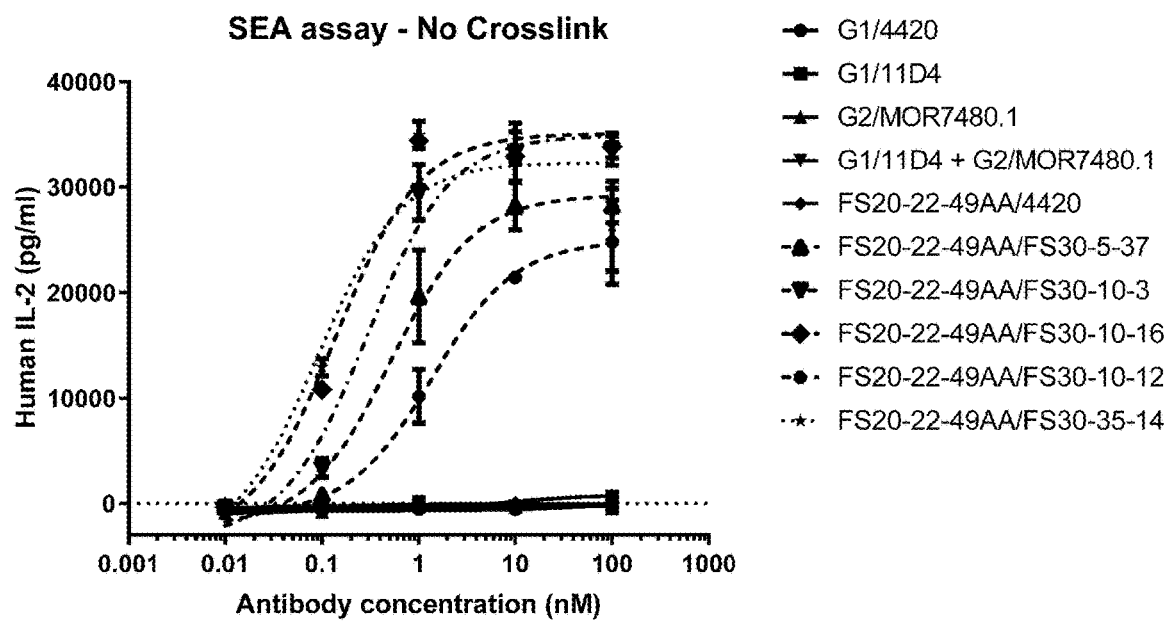
Figure 3:
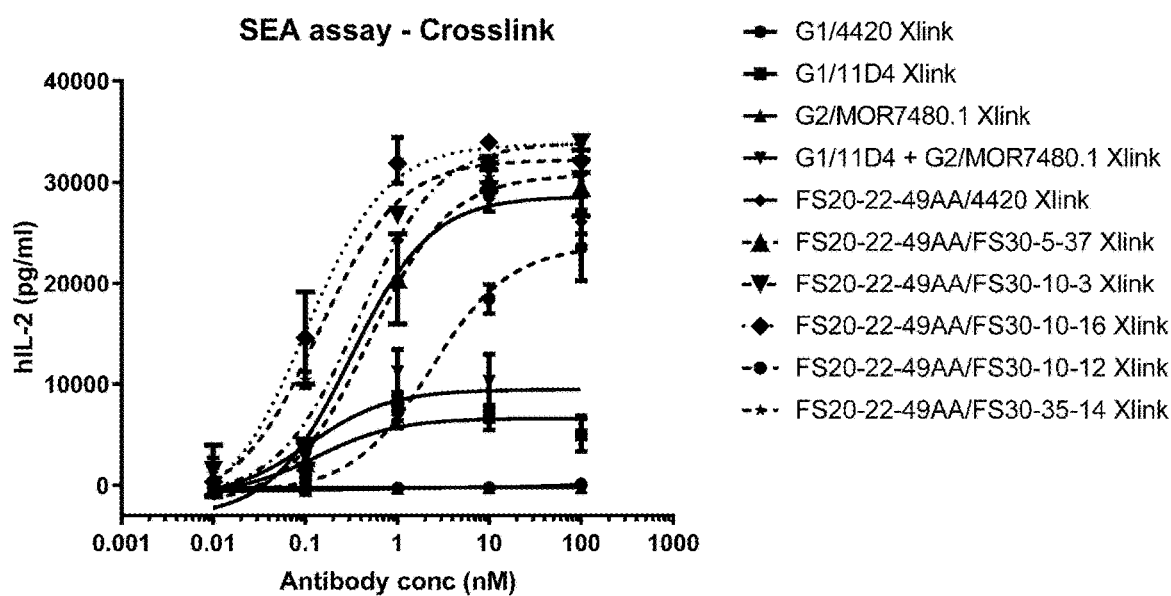

Cells were incubated at 37° C., 5% CO$_2$ for 120 hours. Supernatants were collected and IL-2 release was measured using a human IL-2 ELISA kit (eBioscience or R&D Systems) following the manufacturer's instructions. Plates were read at 450 nm using the plate reader with the Gen5 Software, BioTek. Absorbance values of 630 nm were subtracted from those of 450 nm (Correction). The standard curve for calculation of cytokine concentration was based on a four-parameter logistic curve fit (Gen5 Software, BioTek). The concentration of human IL-2 (hIL-2) was plotted vs the log concentration of the test antibodies and the resulting curves were fitted using the log (agonist) vs response equation in GraphPad Prism. Table 13 shows the EC$_{50}$ values and maximum response of the IL-2 release observed in the SEA assay in the presence or absence of crosslinking with artificial crosslinking agents. FIG. 3A shows the levels of IL-2 release induced by the tested antibodies at a single concentration (3.7 nM) in the SEA assay. The concentration at which these antibodies induced the highest levels of IL-2 production was chosen for this analysis. Statistical analysis was done by two-way ANOVA and Tukey's multiple comparison test. Asterisks above error bars represent the significant difference compared to isotype control (G1/4420)-treated samples (* $p<0.032$,  $p<0.0021$,  $p<0.0002$, ** $p<0.0001$). FIG. 3B shows plots of IL-2 release induced by the OX40/CD137 mAb$^2$ (FS20-22-49AA/FS30-10-16) in the presence or absence of artificial crosslinking agent in the SEA assay.

TABLE 13

SEA assay with OX40 and CD137 agonist antibodies and mAb2

| | No Crosslink | | | | Crosslink | | | |
|---|---|---|---|---|---|---|---|---|
| | EC$_{50}$ (nM) | | Max response | | EC$_{50}$ (nM) | | Max response | |
| mAbs/mAb$^2$ | (nM) | 95% Conf. Int. | (hIL-2 pg/ml) | 95% Conf. Int. | (nM) | 95% Conf. Int. | (hIL-2 pg/ml) | 95% Conf. Int. |
| G1/4420 | NAD | NAD | NAD | NAD | NAD | NAD | NAD | NAD |
| G1ANMOR7480.1 | NAD | NAD | NAD | NAD | NAD | NAD | NAD | NAD |
| G1ANFS30-10-16 | NAD | NAD | NAD | NAD | NAD | NAD | NAD | NAD |
| G1AA/20H4.9 | NAD | NAD | NAD | NAD | 0.3062 | 0.1224 to 0.7376 | 4324 | 3904 to 4762 |
| G1AA/11D4 | NAD | NAD | NAD | NAD | 0.07163 | 0.01113 to 0.2910 | 4269 | 3693 to 4864 |
| FS20-22-49AA/4420 | NAD | NAD | NAD | NAD | 0.3364 | 0.1377 to 0.7743 | 8719 | 7943 to 9532 |
| FS20-22-49AA/4420 + G1AA/FS30-10-16 | NAD | NAD | NAD | NAD | 0.3793 | 0.1665 to 0.8578 | 7644 | 6964 to 8358 |
| FS20-22-49AA/FS30-10-16 | 0.2548 | 0.1050 to 0.6082 | 8931 | 8028 to 9877 | 0.1877 | 0.06915 to 0.4945 | 9930 | 8920 to 10990 |

NAD = no activity detected.

The results show that only the OX40/CD137 mAb$^2$ (FS20-22-49AA/FS30-10-16) was able to increase IL-2 levels in the absence of artificial crosslinking agents and that the addition of artificial crosslinking agent did not increase the activity of the OX40/CD137 mAb$^2$, either in terms of EC$_{50}$ or maximum response. Activity of the OX40-targeting antibodies G1AA/11D4 and FS20-22-49AA/4420 and the anti-CD137 antibody G1AA/20H4.9 was observed only in the presence of artificial crosslinking agents, and no statistically significant activity was detected for the anti-CD137 antibodies G1AA/MOR7480.1 and G1AA/FS30-10-16, as compared to the isotype control, even in the presence of artificial crosslinking agent. The anti-OX40 antibody G1AA/11D4 induced higher IL-2 levels than the anti-CD137 antibodies G1AA/MOR7480.1 and G1AA/FS30-10-16, and a comparable IL-2 level to the anti-CD137 antibody G1AA/20H4.9, although the G1AA/11D4 antibody was observed to have greater potency than the G1 AA/20H4.9 antibody as indicated by its markedly lower EC$_{50}$ value. These results indicate that this SEA assay is more sensitive to OX40 agonism than to CD137 agonism. This is possibly related to OX40 being preferentially expressed on CD4+ T cells and CD137 being preferentially expressed on CD8+ T cells (Croft, 2014 and internal data shown in FIG. 6), and because there are typically more CD4+ T cells than CD8+ T cells in human PBMCs.

12.2 Activity of Different OX40/CD137 mAb$^2$ Clones on SEA-Stimulated PBMCs

Five different OX40/CD137 mAb$^2$ clones were tested for their activity in an SEA assay. Details of the mAb$^2$ and control antibodies used in the assay are provided in Table 14. G1/4420 (anti-FITC), Gill D4 (anti-OX40), G2/MOR7480.1 (anti-CD137), Gill D4 plus G21MOR7480.1 in combination, and FS20-22-49AA/4420 (OX40/FITC mock mAb$^2$) were used as controls. The assay was performed as described in Example 12.1.

TABLE 14

Details of antibodies and mAb2 tested

| mAb/mAb² | Fab binding to | Fcab binding to | Isotype | LALA mutation | Crosslinker | Heavy chain SEQ ID | Light chain SEQ ID |
|---|---|---|---|---|---|---|---|
| G1/4420 | FITC | none | hIgG1 | No | FITC-dextran | 115 | 116 |
| G1/11D4 | hOX40 | none | hIgG1 | No | a-hCH2 | 174 | 175 |
| G2/MOR7480.1 | hCD137 | none | hIgG2 | No | a-hCH2 | 124 | 120 |
| FS20-22-49AA/4420 | FITC | hOX40 | hIgG1 | Yes | FITC-dextran | 123 | 116 |
| FS20-22-49AA/FS30-5-37 | hCD137 | hOX40 | hIgG1 | Yes | a-hCH2 | 109 | 111 |
| FS20-22-49AA/FS30-10-3 | hCD137 | hOX40 | hIgG1 | Yes | a-hCH2 | 99 | 97 |
| FS20-22-49AA/FS30-10-12 | hCD137 | hOX40 | hIgG1 | Yes | a-hCH2 | 103 | 97 |
| FS20-22-49AA/FS30-10-16 | hCD137 | hOX40 | hIgG1 | Yes | a-hCH2 | 95 | 97 |
| FS20-22-49AA/FS30-35-14 | hCD137 | hOX40 | hIgG1 | Yes | a-hCH2 | 105 | 107 |

Table 15 shows the $EC_{50}$ values and maximum response of the IL-2 release observed in the SEA assay in the presence or absence of crosslinking with artificial crosslinking agents. FIGS. 3C and D shows plots of IL-2 release for the SEA assay.

G2/MOR7480.1). The OX40-targeting Fcab in mock mAb² format (4420 LALA) FS20-22-49AA/4420 showed some agonistic activity in the absence of crosslinking in this assay ($EC_{50}$ of 8.53 nM) but when crosslinked by binding of the Fab arms to FITC-dextran, had increased activity as dem-

TABLE 15

SEA assay with mAb² targeting OX40 and CD137

| | No Crosslink | | | | Crosslink | | | |
|---|---|---|---|---|---|---|---|---|
| | $EC_{50}$ (nM) | | Max response | | $EC_{50}$ (nM) | | Max response | |
| mAbs/mAb² | (nM) | 95% Conf. Int. | (hIL-2 pg/ml) | 95% Conf. Int. | (nM) | 95% Conf. Int. | (hIL-2 pg/ml) | 95% Conf. Int. |
| G1/4420 | NAD | NAD | NAD | NAD | NAD | NAD | NAD | NAD |
| G1/11D4 | NAD | NAD | NAD | NAD | 0.13 | 0.01 to 0.77 | 6614.00 | 4743 to 8561 |
| G2/MOR7480.1* | NAD | NAD | NAD | NAD | NAD | NAD | NAD | NAD |
| G1/11D4 + G2/MOR7480.1 | NAD | NAD | NAD | NAD | 0.11 | NAD | 9451.00 | 6633 to 12384 |
| FS20-22-49AA/4420 | 8.53 | 0.83 to 58.93 | 808.70 | 328.7 to 1602 | 0.31 | 0.15 to 0.68 | 28603.00 | 24885 to 32460 |
| FS20-22-49AA/FS30-5-37 | 0.51 | 0.26 to 0.97 | 29242.00 | 26131 to 32465 | 0.50 | 0.26 to 0.91 | 30748.00 | 27773 to 33822 |
| FS20-22-49AA/FS30-10-3 | 0.29 | 0.15 to 0.55 | 34945.00 | 31391 to 38616 | 0.38 | 0.20 to 0.69 | 33919.00 | 30775 to 37170 |
| FS20-22-49AA/FS30-10-12 | 1.36 | 0.73 to 2.65 | 24912.00 | 22201 to 27799 | 2.33 | 1.25 to 4.58 | 23721.00 | 21156 to 26587 |
| FS20-22-49AA/FS30-10-16 | 0.14 | 0.077 to 0.25 | 35115.00 | 32213 to 38074 | 0.10 | 0.06 to 0.18 | 33761.00 | 31415 to 36145 |
| FS20-22-49AA/FS30-35-14 | 0.09 | 0.021 to 0.30 | 32363.00 | 27164 to 37691 | 0.14 | 0.07 to 0.30 | 32212.00 | 28906 to 35597 |

NAD—no activity detected

FIGS. 3C and D and Table 15 show that no IL-2 production was observed with the non-crosslinked or crosslinked anti-FITC antibody G1/4420 or with the non-crosslinked anti-OX40 antibody (G1/11D4 alone or in combination with G2/MOR7480.1), as expected. IL-2 was produced by the T cells when OX40 was activated by binding of the anti-OX40 positive control antibody but only when artificial crosslinking agent was present ($EC_{50}$ of 0.13 nM for G1/11 D4 alone, and $EC_{50}$ of 0.11 nM when in combination with onstrated by the decrease in $EC_{50}$ (0.31 nM) and Increase in the maximum amount of IL-2 produced (max response), as shown by the increased production of IL-2.

No activity was observed with the crosslinked CD137-targeting antibody G2/MOR7480.1 alone, and the activity of the combination of the OX40-targeting antibody G1/11D4 and CD137-targeting antibody G2/MOR7480.1 when crosslinked was similar to that of the crosslinked OX40-targeting antibody G1/11 D4 alone.

In this SEAT cell activation assay, the activity of the five OX40/CD137 mAb$^2$ clones (see Table 15) was comparable regardless of the presence of artificial crosslinking agent. The activity of the OX40/CD137 mAb$^2$ in the presence of artificial crosslinking agent was also comparable to the crosslinked FS20-22-49AA/4420 mock mAb$^2$. These results of this SEA assay show that the OX40/CD137 mAb$^2$ are able to signal via OX40, without artificial crosslinking agents being required. as a result of crosslinking provided by the engagement of the anti-CD137 Fab arms of the mAb$^2$.

Although no activity was detected for the crosslinked CD137-targeting antibody G2/MOR7480.1 in this assay, it is expected that CD137 was expressed at a level on the T cells to allow crosslinking of the mAb$^2$ to occur. This expression is assumed to have been at a level at which each of the five mAb$^2$ clones, when bound to CD137, could also bind to OX40 and drive its activation to a much higher degree than the low level of activity induced by the non-crosslinked FS20-22-49AA/4420 mock mAb$^2$.

The T cell activation observed with the OX40/CD137 mAb$^2$ in the absence of artificial crosslinking agent also suggests that these molecules will be able to activate T cells where both OX40 and CD137 are expressed in vivo.

12.3 Activity of OX40/CD137 mAb$^2$ Clone FS20-22-49AA/FS30-10-16 on SEA-Stimulated PBMCs from 10 PBMC Donors The OX40/CD137 mAb$^2$ clone FS20-22-49AA/FS30-10-16 was tested in an SEA assay with PBMCs from 10 different donors to establish accurate $EC_{20}$, $EC_{30}$ and $EC_{50}$ values for its activity. The assay was performed as described in Example 12.1 in the absence of an artificial crosslinking agent. Mean values plus or minus standard deviation (SD) were calculated from the raw data for each donor. To calculate $EC_{50}$ values, the raw data was fit to a logistic function (4 parameters: Top, Bottom, Hill slope, and $EC_{50}$):

$$y(\log c) = \text{Bottom} + \frac{\text{Top} - \text{Bottom}}{1 + 10^{(\log EC_{50} - \log c) \cdot \text{HillSlope}}}$$

The y-axis shows the response measured (IL-2 levels), as a function of $\log_{10}(c)$, where c denotes the concentration of the test article.

$$y(\log c) = \text{Bottom} + \frac{\text{Top} - \text{Bottom}}{1 + 4 \cdot 10^{(\log EC_{20} - \log c) \cdot \text{HillSlope}}}$$

$$y(\log c) = \text{Bottom} + \frac{\text{Top} - \text{Bottom}}{1 + (7/3) \cdot 10^{(\log EC_{30} - \log c) \cdot \text{HillSlope}}}$$

Each parameter estimate from the fit has a standard error, which is indicative of the precision of that estimate. Since different donor and/or technical replicates for a given experiment will give different parameter estimates and different levels of precision (depending, for example, on the quality of the data in each case), the parameters from each donor and/or technical replicates were included into a weighted average. The weights were defined as the inverse of the square of the standard error of the parameter, under an assumption of parameter normality.

Additionally, the $\log_{10}(EC_{20})$ and $\log_{10}(EC_{30})$ values were calculated by fitting the data to similar equations:

$$\bar{x} = \frac{\Sigma w_i x_i}{\Sigma w_i}$$

$$SEM = SD \sqrt{\frac{\Sigma w_i^2}{(\Sigma w_i)^2}}$$

All logistic fits were performed using GraphPad Prism, and the weighted averaging was done using Microsoft Excel. The formulae used for the weighted average and the standard error of the weighted average are given below:

$$SD = \sqrt{\frac{N \Sigma w_i (x_i - \bar{x})^2}{(N-1) \Sigma w_i}}$$

wherein the weighted standard deviation has been estimated as:

The $EC_{20}$, $EC_{30}$ and $EC_{50}$ values for the IL-2 release observed for the OX40/CD137 mAb$^2$ in the SEA assay are shown in Table 16.

TABLE 16

$EC_{20}$, $EC_{30}$ and $EC_{50}$ values for the OX40/CD137 mAb$^2$ in the SEA assay

| | $EC_{50}$ (nM) | $EC_{30}$ (nM) | $EC_{20}$ (nM) |
|---|---|---|---|
| Donor 1 | 0.21 | 0.09 | 0.05 |
| Donor 2 | 0.38 | 0.14 | 0.08 |
| Donor 3 | 0.34 | 0.18 | 0.12 |
| Donor 4 | 0.36 | 0.18 | 0.11 |
| Donor 5 | 0.30 | 0.11 | 0.06 |
| Donor 6 | 0.41 | 0.17 | 0.10 |
| Donor 7 | 0.44 | 0.21 | 0.13 |
| Donor 8 | 0.29 | 0.15 | 0.10 |
| Donor 9 | 0.17 | 0.10 | 0.07 |
| Donor 10 | 0.04 | 0.02 | 0.02 |
| Weighted Average | 0.32 | 0.14 | 0.09 |
| 95% Conf. Int. | 0.25-0.41 | 0.11-0.18 | 0.07-0.12 |

These results show that the OX40/CD137 mAb$^2$ has comparable activity with PBMCs from different donors.

Example 13-Activity of Human OX40/CD137 mAb$^2$ in a Pan-T Cell Activation Assay The SEAT cell activation assay described in Example 12 used PBMCs and the superantigen SEA to stimulate T cells. To assess the effect of OX40 and CD137 agonists on isolated T cells, a T cell activation assay was established. In this assay, T cells were isolated and stimulated using an anti-CD3 antibody immobilised on a plastic surface. The immobilised anti-CD3 antibody is able to duster the TCR of T cells, providing the first signal required for T cell activation and the test molecules provided the second signal.

The T cell-stimulation assay was used to establish the activity of different OX40 and CD137 agonist antibodies and an OX40/CD137 mAb$^2$ antibody in the presence or absence of crosslinking agents, to compare different OX40/CD137 mAb$^2$ clones, and to establish a representative $EC_{50}$ value for the OX40/CD137 mAb$^2$ done FS20-22-49AA/FS30-10-16 in a group of nine PBMC donors.

13.1 Activity of OX40 and CD137 Agonist Antibodies in a Pan-T Cell Activation Assay To establish the sensitivity of the T cell activation assay to different OX40 and CD137 agonist antibodies, the mAb$^2$ antibody (FS20-22-49AA/FS30-10-16) and control antibodies listed in Table 17 were tested for their activity in the assay. G1/4420 (anti-FITC), G1AA/MOR7480.1 (anti- CD137), G1AA/FS30-10-16 (anti-CD137), G1AA/20H4.9 (anti-CD137), G1AA/11D4 (anti-OX40), and FS20-22-49AA/4420 (OX401FITC mock mAb[2]) were used as controls. IL-2 production was used as a measure of T cell activation.

TABLE 17

Details of antibodies and mAb[2] tested

| mAb/mAb[2] | Fab binding to | Fcab binding to | Isotype | LALA mutation | Crosslinker | Heavy chain SEQ ID | Light chain SEQ ID |
|---|---|---|---|---|---|---|---|
| G1/4420 | FITC | none | hIgG1 | No | FITC-dextran | 115 | 116 |
| G1AA/MOR7480.1 | hCD137 | none | hIgG1 | Yes | a-hCH2 | 125 | 120 |
| G1AA/FS30-10-16 | hCD137 | none | hIgG1 | Yes | a-hCH2 | 154 | 97 |
| G1AA/20H4.9 | hCD137 | none | hIgG1 | Yes | a-hCH2 | 165 | 122 |
| G1AA/11D4 | hOX40 | none | hIgG1 | No | a-hCH2 | 173 | 175 |
| FS20-22-49AA/4420 | FITC | hOX40 | hIgG1 | Yes | FITC-dextran | 123 | 116 |
| FS20-22-49AA/FS30-10-16 | hCD137 | hOX40 | hIgG1 | Yes | a-hCH2 | 95 | 97 |

Human PBMCs were isolated as described in Example 12.1. T cells were then isolated from the PBMCs using a Pan T Cell Isolation Kit II (Miltenyi Biotec Ltd) according to the manufacturer's instructions.

Human T-Activator CD3/CD28 Dynabeads (Life technologies) 1452D) were resuspended by vortexing. Beads were washed twice with T cell medium (RPMI medium (Life Technologies) with 109'6 FBS (Life Technologies), 1× Penicillin Streptomycin (Life Technologies), Sodium Pyruvate (Gibco), 10 mM Hopes (Gibco), 2 mM L-Glutamine (Gibco) and 50 μM 2-mercaptoethanol (Gibco)).

The required number of T cells at a concentration of $1.0 \times 10^6$ cells/ml in T cell medium were stimulated with the washed human T-Activator CD3/CD28 Dynabeads at a 2:1 cell to bead ratio in a T-25 flask (Sigma) and incubated overnight at 37° C., 5% $CO_2$ to activate the T cells. Activated T cells were washed from the Dynabeads and resuspended in T cell medium at a concentration of $2.0 \times 10^6$ cells/mi. 96-well flat-bottomed plates were coated with anti-human CD3 antibody through incubation with 2.5 μg/ml anti-human CD3 antibody (R&D Systems clone UHCT1) diluted in PBS for 2 hours at 37° C., 5% $CO_2$ and then washed twice with PBS. Activated T cells were added to the plates at $2 \times 10^0$ cell/well. 2 μM dilutions of each test antibody (see Table 17 for details) were prepared and added to the wells in a 1:1 molar ratio with crosslinking agent (anti-human CH2 antibody (clone MK1A6, produced in-house) or FITC-dextran (Sigma) (see Table 17)) where required, as described above in Example 12.1. In a 96-well plate, serial dilutions of the test antibodies were prepared and 100 μl of the diluted antibody mixture was added to the activated T cells on the plate.

Figure 4:
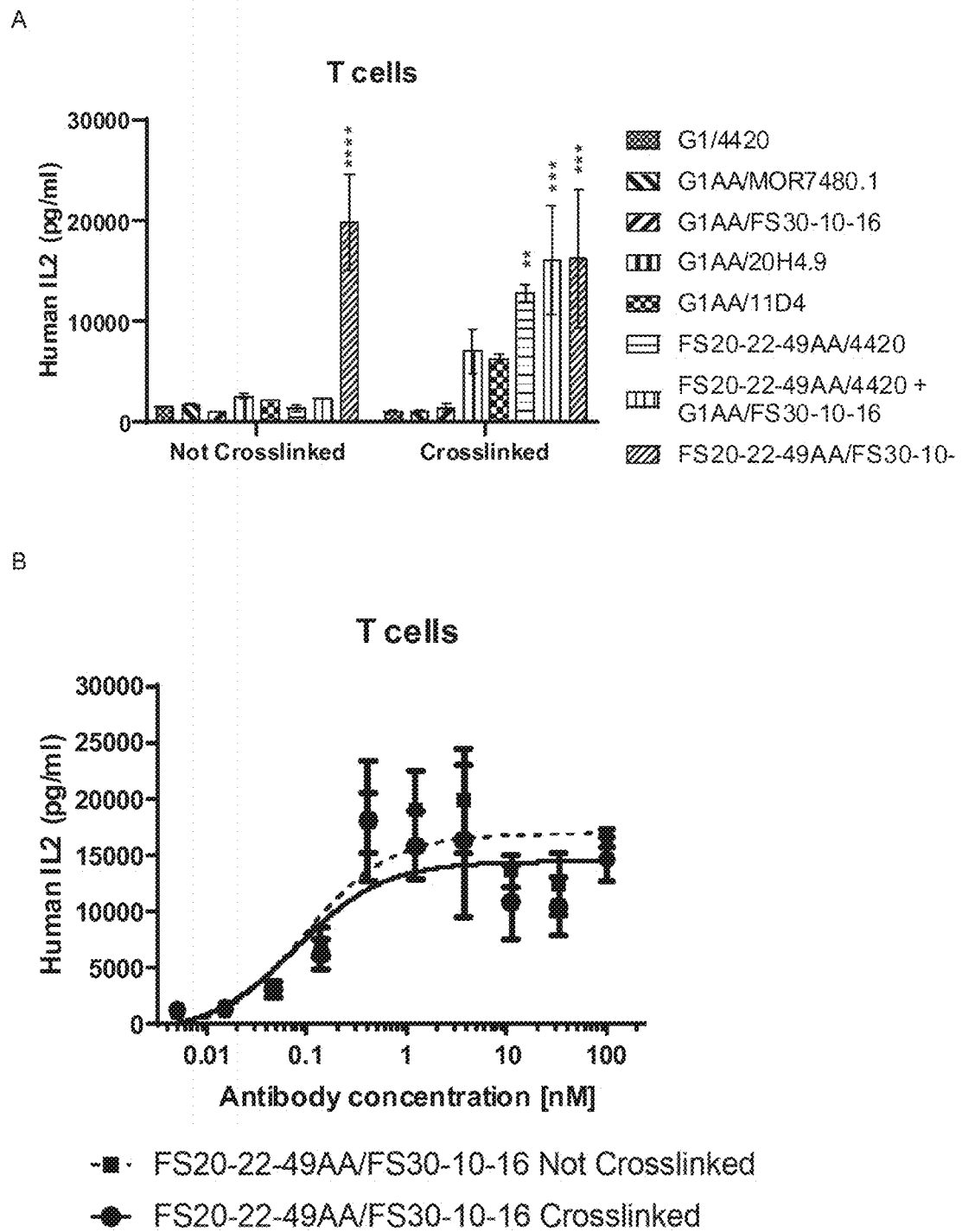
FIG. 4 shows the activity of CD137 mAb, OX40 Fcab and OX40/CD137 mAb$^2$ In human pan-T cell activation assays. IL-2 release was measured in the presence of the mAb/mAb$^2$ indicated and in the presence and absence of crosslinking agents (FITC-dextran for the anti-FITC mAb and OX401FITC mock mAb$^2$ controls, and anti-human CH2 antibody for all other molecules tested).
Figure 4:
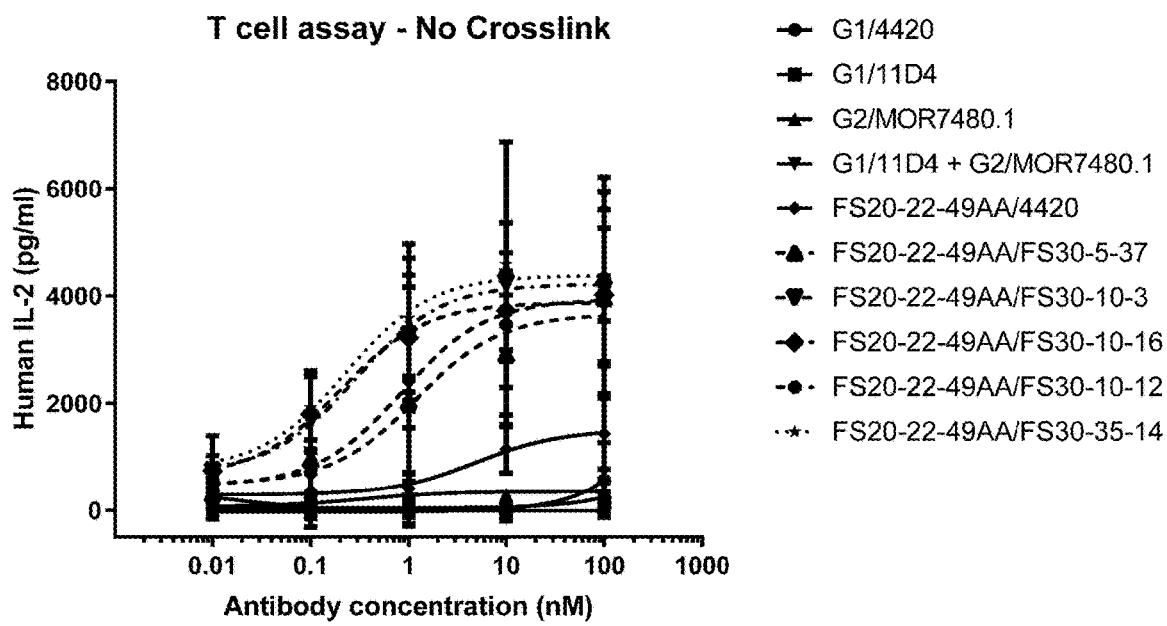
Figure 4:
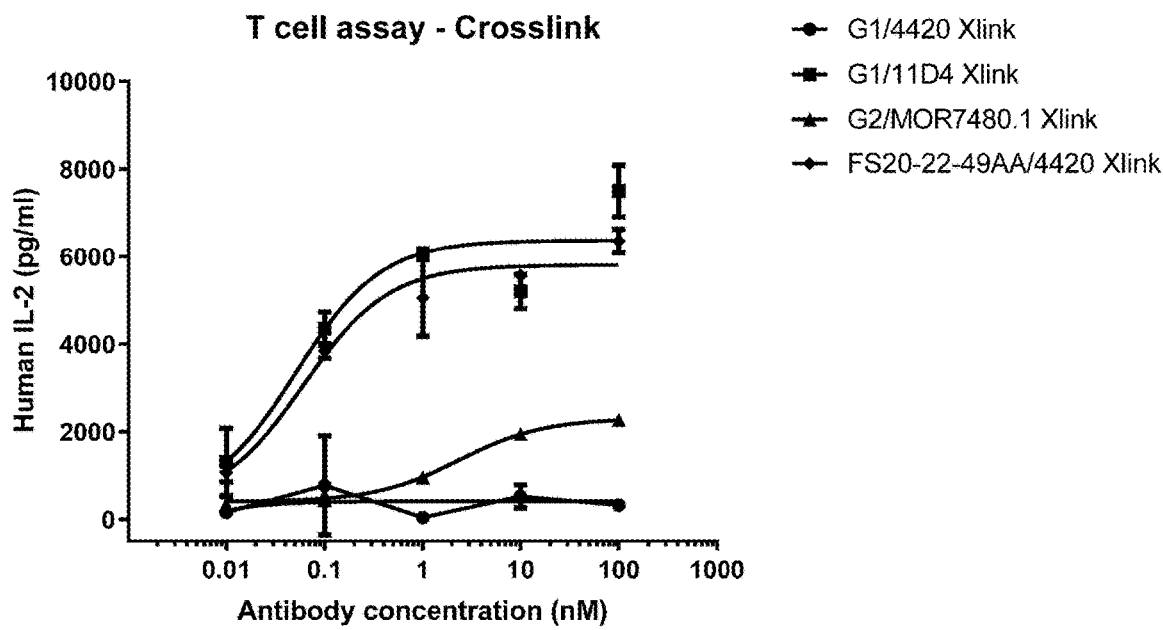

T cells were incubated at 37° C., 5% $CO_2$ for 72 hours. Supernatants were then collected, IL-2 release was measured and the data was prepared as described in Example 12.1. Table 18 shows the $EC_{50}$ values and maximum response of the IL-2 release observed in the T cell activation assay in the presence or absence of crosslinking with crosslinking agents. FIG. 4A shows the levels of IL-2 release induced by the tested antibodies at a single concentration (3.7 nM) in the T cell activation assay. The concentration at which these antibodies induced the highest levels of IL-2 production was chosen for this analysis.

Statistical analysis was done by two-way ANOVA and Tukey's multiple comparison test. Asterisks above error bars represent the significant difference compared to isotype control (G1/4420)-treated samples (* p<0.032,  p<0.0021,  p<0.0002, ** p<0.0001). FIG. 4B shows plots of IL-2 release induced by the OX40/CD137 mAb[2] (FS20-22-49AA/FS30-10-16) in the presence or absence of crosslinking agent in the T cell activation assay.

TABLE 18

T cell activation assay with OX40 and CD137 agonist antibodies and mAb[2]

| | No Crosslink | | | | Crosslink | | | |
|---|---|---|---|---|---|---|---|---|
| | $EC_{50}$ (nM) | | Max response | | $EC_{50}$ (nM) | | Max response | |
| mAbs/mAb[2] | (nM) | 95% Conf. Int. | (hIL-2 pg/ml) | 95% Conf. Int. | (nM) | 95% Conf. Int. | (hIL-2 pg/ml) | 95% Conf. Int. |
| G1/4420 | NAD | NAD | NAD | NAD | NAD | NAD | NAD | NAD |
| G1AA/MOR7480.1 | NAD | NAD | NAD | NAD | NAD | NAD | NAD | NAD |
| G1AA/FS30-10-16 | NAD | NAD | NAD | NAD | NAD | NAD | NAD | NAD |
| G1AA/20H4.9 | NAD | NAD | NAD | NAD | 0.234 | 0.04154 to 1.057 | 5303 | 4068 to 6620 |
| G1AA/11D4 | | | | | 0.1301 | 0.01642 to 0.6356 | 4130 | 3266 to 5037 |

TABLE 18-continued

T cell activation assay with OX40 and CD137 agonist antibodies and mAb²

| | No Crosslink | | | | Crosslink | | | |
|---|---|---|---|---|---|---|---|---|
| | EC$_{50}$ (nM) | | Max response | | EC$_{50}$ (nM) | | Max response | |
| mAbs/mAb² | (nM) | 95% Conf. Int. | (hIL-2 pg/ml) | 95% Conf. Int. | (nM) | 95% Conf. Int. | (hIL-2 pg/ml) | 95% Conf. Int. |
| FS20-22-49AA/4420 | NAD | NAD | NAD | NAD | 0.278 | 0.1611 to 0.4790 | 12450 | 11440 to 13488 |
| FS20-22-49AA/4420 + G1AA/FS30-10-16 | NAD | NAD | NAD | NAD | 0.1746 | 0.05500 to 0.5209 | 15001 | 12556 to 17552 |
| FS20-22-49AA/FS30-10-16 | 0.09306 | 0.03231 to 0.2430 | 16927 | 14533 to 19389 | 0.07916 | 0.01737 to 0.2851 | 14434 | 11757 to 17202 |

NAD—no activity detected.

The results show that only the OX40/CD137 mAb² (FS20-22-49AA/FS30-10-16) was able to increase IL-2 levels in the absence of artificial crosslinking agents and that the addition of artificial crosslinking agent did not increase the activity of the OX40/CD137 mAb², either in terms of EC$_{50}$ or maximum response. Activity of the OX40-targeting antibodies G1 AA/11 D4 and FS20-22-49AA/4420 and the anti-CD137 antibody G1AA/20H4.9 was observed only in the presence of artificial crosslinking agents, and no activity was detected for the anti-CD137 antibodies G1AA/MOR7480.1 and G1AA/FS30-10-16 even in the presence of artificial crosslinking agent. The OX40 agonist antibody FS20-22-49AA/4420 induced higher IL-2 levels than all three CD137 agonist antibodies. The anti-OX40 antibody G1AA/11 D4 induced higher IL-2 levels than the anti-CD137 antibodies G1AA/MOR7480.1 and G1AA/FS30-10-16, and a comparable IL-2 level to the anti-CD137 antibody G1AA/20H4.9, although the G1AA/11 D4 antibody was observed to have greater potency than the G1AA/20H4.9 antibody as indicated by its lower EC$_{50}$ value. These results indicate that this T cell activation assay is more sensitive to OX40 agonism than to CD137 agonism. As surmised in Example 12.1, this is possibly related to OX40 being preferentially expressed on CD4+ T cells and CD137 being preferentially expressed on CD8+ T cells (Croft, 2014 and internal data shown in FIG. 6), and because there are typically more CD4+ T cells than CD8+ T cells in human PBMCs.

13.2 Multiple Cytokine Analysis of the Activity of OX40 and CD137 Agonist Antibodies in a Pan-T Cell Activation Assay To better understand the effect of OX40 and CD137 stimulation on the T cell activation assay, the levels of multiple cytokines were analysed. The antibodies and mAb² antibody (FS20-22-49AA/FS30-10-16) and control antibodies listed in Table 19 were used. The control antibodies G1/4420 (anti-FITC), G1AA/FS30-10-16 (anti-CD137) and FS20-22-49AA/4420 (OX40/FITC mock mAb²) were tested in the presence of artificial crosslinking agents and the OX40/CD137 mAb² was tested in the absence of an artificial crosslinking agent. All antibodies were used at a single concentration (10 nM). The assay was performed as described in Example 13.1.

TABLE 19

Details of antibodies and mAb² tested

| mAb/mAb² | Fab binding to | Fcab binding to | Isotype | LALA mutation | Crosslinker | Heavy chain SEQ ID | Light chain SEQ ID |
|---|---|---|---|---|---|---|---|
| G1/4420 | FITC | none | hIgG1 | No | FITC-dextran | 115 | 116 |
| G1AA/FS30-10-16 | hCD137 | none | hIgG1 | Yes | a-hCH2 | 154 | 97 |
| FS20-22-49AA/4420 | FITC | hOX40 | hIgG1 | Yes | FITC-dextran | 123 | 116 |
| FS20-22-49AA/FS30-10-16 | hCD137 | hOX40 | hIgG1 | Yes | none | 95 | 97 |

The levels of the cytokines IL-2, IL-6, IL12p70, IL-13, TNFα, IFNγ and IL-10 in the supernatants collected after incubation were then determined using the Pro-inflammatory V-plex kit (MSD, K15049D-1) according to manufacturer's instructions. The results showed that the OX40/CD137 mAb² (FS20-22-49AA/FS30-10-16) and the crosslinked OX40-targeting antibody (FS20-22-49AA/4420) increased IL-2, IL-6, IL-12p70, IL-13 and TNFα cytokine release and decreased IL-10 release by T cells. No activity was detected for the anti-CD137 antibody (G1AA/FS30-10-16).

13.3 Activity of Different OX40/CD137 mAb² Bones in a Pan-T Cell Activation Assay Details of the molecules tested in this assay and their respective crosslinking agents, where applicable, are provided in Table 20 below. G1I4420 (anti-FITC). G1/11 D4 (anti-OX40), G2/MOR7480.1 (anti-CD137), G1/11 D4 plus G2/MOR7480.1 in combination, and FS20-22-49AA/4420 (OX40/FITC mock mAb²) were used as controls. All molecules were tested in the absence of an artificial crosslinking agent. The single-agent controls G1/4420, G1/11 D4, G2/MOR7480.1 and FS20-22-49AA/4420 were additionally tested in the presence of an artificial crosslinking agent. The assay was performed as described in Example 13.1.

TABLE 20

Details of antibodies and mAb² tested

| mAb/mAb² | Fab binding to | Fcab binding to | Isotype | LALA mutation | Crosslinker | Heavy chain SEQ ID | Light chain SEQ ID |
|---|---|---|---|---|---|---|---|
| G1/4420 | FITC | none | hIgG1 | No | FITC-dextran | 115 | 116 |
| G1/11D4 | hOX40 | none | hIgG1 | No | anti-hCH2 | 174 | 175 |
| G2/MOR7480.1 | hCD137 | none | hIgG2 | No | anti-hCH2 | 124 | 120 |
| FS20-22-49AA/4420 | FITC | hOX40 | hIgG1 | Yes | FITC-dextran | 123 | 116 |
| FS20-22-49AA/FS30-5-37 | hCD137 | hOX40 | hIgG1 | Yes | n/a | 109 | 111 |
| FS20-22-49AA/FS30-10-3 | hCD137 | hOX40 | hIgG1 | Yes | n/a | 99 | 97 |
| FS20-22-49AA/FS30-10-12 | hCD137 | hOX40 | hIgG1 | Yes | n/a | 103 | 97 |
| FS20-22-49AA/FS30-10-16 | hCD137 | hOX40 | hIgG1 | Yes | n/a | 95 | 97 |
| FS20-22-49AA/FS30-35-14 | hCD137 | hOX40 | hIgG1 | Yes | n/a | 105 | 107 |

Table 21 shows the $EC_{50}$ values and maximum response of the IL-2 release observed for all molecules tested in the T cell activation assay in the absence of crosslinking. Table 22 shows the $EC_{50}$ values and maximum response of the IL-2 release observed for the single-agent controls G1I4420, GiI1 1D4, G2/MOR7480.1 and FS20-22-49AA/4420 additionally tested in the presence of crosslinking agents. FIGS. 4C and D shows plots of IL-2 release for the T cell activation assay.

TABLE 21

T cell activation assay with mAb² targeting co-expressed receptors in the absence of crosslinking agent

| | No Crosslinking Agent | | | |
|---|---|---|---|---|
| | $EC_{50}$ (nM) | | Max response | |
| mAbs/mAb² | (nM) | 95% Conf. Int. | (hIL-2 pg/ml) | 95% Conf. Int. |
| G1/4420 | NAD | NAD | NAD | NAD |
| G1/11D4 | NAD | NAD | NAD | NAD |
| G2/M0R7480.1 | NAD | NAD | NAD | NAD |
| G1/11D4 + G2/M0R7480.1 | NAD | NAD | NAD | NAD |
| FS20-22-49AA/4420 | 5.02 | 0.2478 to 2583 | 1508 | 926.2 to 26580 |
| FS20-22-49AA/FS30-5-37 | 1.201 | 0.1358 to 15.06 | 3663 | 2817 to 4979 |
| FS20-22-49AA/FS30-10-3 | 0.2905 | 0.01754 to 3.867 | 4219 | 3204 to 5408 |
| FS20-22-49AA/FS30-10-12 | 0.845 | 0.01871 to 85.72 | 3939 | 2388 to 7001 |
| FS20-22-49AA/FS30-10-16 | 0.2019 | 0.0108 to 3.071 | 3873 | 3012 to 4897 |
| FS20-22-49AA/FS30-35-14 | 0.2285 | ND to 14.77 | 4379 | 2915 to 6181 |

NAD = no activity detected
ND = not determined

TABLE 22

Single-agent controls in the presence of crosslinking agent

| | With Crosslinking Agent | | | |
|---|---|---|---|---|
| | $EC_{50}$ (nM) | | Max response | |
| mAbs/mAb² | (nM) | 95% Cont. Int. | (hIL-2 pg/ml) | 95% Conf. Int. |
| G1/4420 | NAD | NAD | NAD | NAD |
| G1/11D4 | 0.05132 | ND to 0.3545 | 6375 | 5385 to 7400 |

TABLE 22-continued

Single-agent controls in the presence of crosslinking agent

| | With Crosslinking Agent | | | |
|---|---|---|---|---|
| | $EC_{50}$ (nM) | | Max response | |
| mAbs/mAb$^2$ | (nM) | 95% Cont. Int. | (hIL-2 pg/ml) | 95% Conf. Int. |
| G2/M0R7480.1 | 2.38 | 1.231 to 4.754 | 2306 | 2090 to 2545 |
| FS20-22-49AA/4420 | 0.06129 | 0.01408 to 0.1939 | 5806 | 5242 to 6386 |

NAD = no activity detected
ND = not determined

Table 21 and FIG. 4C show that the non-crosslinked OX40/CD137 mAb$^2$ had activity ($EC_{50}$ values ranging from 0.2019 to 1.201 nM) and were therefore capable of binding to both targets resulting in clustering of one or both of them to induce T cell activation. No IL-2 production was observed with the non-crosslinked or crosslinked anti-FITC antibody G1/4420, as expected, or with the non-crosslinked antl-OX40 antibody (Gill 1D4 alone or In combination with G2/MOR7480.1). IL-2 was produced by T cells when the OX40 receptor was targeted by the anti-OX40 positive control antibody in the presence of crosslinking agent ($EC_{50}$ of 0.05 nM for G1/11 D4 alone, and $EC_{50}$ of 0.02 nM when in combination with 15 G2/MOR7480.1).

The OX40-targeting Fcab in the mock mAb$^2$ format (4420 LALA) FS20-22-49AA/4420 had some agonistic activity in the absence of crosslinking (an $EC_{50}$ of 5.02 nM and a maximum response of 1508 μg/ml hIL-2), as seen in the SEA assay, and this activity was further enhanced when the mock mAb$^2$ was crosslinked by binding of Its Fab arms to FITC-dextran.

No activity was observed with the non-crosslinked anti-CD137 antibody G2/MOR7480.1 alone but, when crosslinked, it was capable of inducing T cell activation, indicating that, unlike the SEA T cell activation assay (Example 12), this assay is able to measure CD137 signalling by this anti-CD137 clone as well as the OX40 signalling confirmed above. The difference in activity observed for this crosslinked antibody compared to the same anti-CD137 done in IgG1 format (G1AA/MOR7480.1) in Example 13.1, for which no activity was detected in either the absence or presence of artificial crosslinking agent, may be explained by T-cell donor variability whereby some donors may respond better to CD137 stimulation than others.

In the human CD137 T cell activation assay using DO11.10-hCD137 cells described in Example 7.1, the test OX40/CD137 mAb$^2$ (FS20-22-49AA/FS30-5-37, FS20-22-49AA/FS30-10-3, FS20-22-49AA/FS30-10-12, FS20-22-49AA/FS30-10-16 and FS20-22-49AA/FS30-35-14) and the G2/MOR7480.1 control potently induced IL-2 production. It is therefore assumed that the anti-CD137 Fab arms of the OX40/CD137 mAb$^2$ are also capable of agonising T cell-expressed CD137 to produce a detectable IL-2 signal in the primary T cell activation assay of the present example.
13.4 Activity of OX40/CD137 mAb$^2$ Clone FS20-22-49AA/FS30-10-16 in a Pan-T Cell Activation Assay with T Cells from Nine PBMC Donors The OX40/CD137 mAb$^2$ clone FS20-22-49AA/FS30-10-16 was tested in a T cell activation assay with PBMCs from nine different donors to establish accurate $EC_{20}$, $EC_{50}$ and $EC_{50}$ values for its activity. The assay was performed as described in Example 13.1 in the absence of an artificial crosslinking agent.

Mean values plus or minus standard deviation (SD) were calculated from the raw data as described in Example 12.3 for each donor. $EC_{20}$, $EC_{30}$ and $EC_{50}$ values for the IL-2 release observed for the OX40/CD137 mAb$^2$ (FS20-22-49AA/FS30-10-16) in the T cell assay were also calculated as described in Example 12.3 and are shown in Table 23.

TABLE 23

$EC_{20}$, $EC_{30}$ and $EC_{50}$ values of the OX40/CD137 mAb$^2$ in a T cell activation assay

| | $EC_{50}$ (nM) | $EC_{30}$ (nM) | $EC_{20}$ (nM) |
|---|---|---|---|
| Donor 1 | 0.170 | 0.203 | 0.280 |
| Donor 2 | 0.067 | 0.103 | 0.153 |
| Donor 3 | 0.167 | 0.158 | 0.193 |
| Donor 4 | 0.251 | 0.226 | 0.223 |
| Donor 5 | 0.175 | 0.182 | 0.222 |
| Donor 6 | 0.116 | 0.177 | 0.264 |
| Donor 7 | 0.114 | 0.297 | 0.467 |
| Donor 8 | 0.121 | 0.283 | 0.448 |
| Donor 9 | 0.199 | 0.174 | 0.194 |
| Weighted Average | 0.179 | 0.067 | 0.040 |
| 95% Cont. Int. | 0.154-0.208 | 0.049-0.090 | 0.026-0.061 |

These results show that the OX40/CD137 mAb$^2$ has comparable activity on T cells from different donors.

Example 14—Activity of Human OX40/CD137 mAb$^2$ in CD4+ and CD8+ T Cell Activation Assays T cells can be subdivided into CD4+ and CD8+ T cells according to their function in the Immune system. CD4+ T cells are termed T helper cells and produce cytokines that modulate the immune response and CD8+ T cells are termed T killer cells and eliminate target cells directly. The expression of OX40 has been observed to be higher than CD137 expression on CD4+ T cells and, vice-versa, the expression of CD137 has been seen to be higher than OX40 expression on CD8+ T cells (Croft, 2014 and see FIG. 6). Despite this difference in expression levels, both CD4+ and CD8+ T cells co-express the two receptors (Ma et al., 2005).

To further explore the activity of the OX40/CD137 mAb$^2$ in these two populations of T cells, CD4+ and CD8+ T cells were Isolated for testing of the ability of the molecules listed in the Table 24 below to activate each T cell population in separate CD4+ and CD8+ T cell activation assays. In this assay, co-expression of OX40 and CD137 was utilised to determine crosslinking of the OX40/CD137 mAb$^2$ FS20-22-49AA/FS30-10-16. G1/4420 (anti-FITC), G1AA/11D4 (anti-OX40), G1AA/MOR7480.1 (anti-CD137) G1AA/FS30-10-16 (anti-CD137), FS20-22-49AA/4420 (OX40/FITC mock mAb$^2$), and FS20-22-49AA/4420 plus G1AA/FS30-10-16 in combination were used as controls. IL-2 production was used as a measure of T cell activation.

TABLE 24

Details of antibodies and mAb² tested

| mAb/mAb² | Fab binding to | Fcab binding to | Isotype | LALA mutation | Crosslinker | Heavy chain SEQ ID | Light chain SEQ ID |
|---|---|---|---|---|---|---|---|
| G1/4420 | FITC | none | hIgG1 | No | FITC-dextran | 115 | 116 |
| G1AA/11D4 | hOX40 | none | hIgG1 | Yes | anti-hCH2 | 173 | 175 |
| G1AA/MOR7480.1 | hCD137 | none | hIgG1 | Yes | anti-hCH2 | 125 | 120 |
| G1AA/FS30-10-16 | hCD137 | none | hIgG1 | Yes | anti-hCH2 | 154 | 97 |
| G1AA/20H4.9 | hCD137 | None | hIgG1 | Yes | anti-hCH2 | 165 | 122 |
| FS20-22-49AA/4420 | FITC | hOX40 | hIgG1 | Yes | FITC-dextran | 123 | 116 |
| FS20-22-49AA/FS30-10-16 | hCD137 | hOX40 | hIgG1 | Yes | anti-hCH2 | 95 | 97 |

To Isolate human CD4+ and CD8+ T cells, PBMCs were firstly Isolated as described in Example 13.1, CD4+ and CD8+ T cells were then separately isolated from the PBMCs using, respectively, a CD4+ T Cell Isolation Kit (human) (Miltenyi Biotec, 130-096-533) and a CD8+ T Cell Isolation Kit (human) (Miltenyi Biotec, 130-096-495) according to the manufacturer's instructions.

The CD4+ or CD8+ T cells were activated overnight in the required amount at a concentration of $1.0 \times 10^6$ cells/ml in T cell medium using Human T-Activator CD3/CD28 Dynabeads as described in Example 13.1.

The activated CD4+ or CD8+ T cells were washed from the Dynabeads and resuspended in T cell medium at a concentration of $2.0 \times 10^6$ cells/ml. 96-well flat-bottomed plates were coated with anti-human CD3 antibody through incubation with either 2.5 µg/ml (for the CD4+ T cell activation assay) or 10 pg/ml (for the CD8+ T cell activation assay) anti-human CD3 antibody (R&D Systems, clone UHCT1) diluted in PBS for 2 hours at 37° C., 5% $CO_2$ and then washed twice with PBS. Activated CD4+ or CD8+ T cells were then added to the respective plates at $2 \times 10^5$ cells/well. 2 µM dilutions of each test antibody (see Table 24 for details) were prepared and added to the wells in a 1:1 molar ratio with crosslinking agent (anti-human CH2 antibody or FITC-dextran (Sigma) (see Table 24)) where required, as described in Example 6. In a 96-well plate, serial dilutions of the test antibodies were prepared and 100 µl of the diluted antibody mixture was added to the activated CD4+ or CD8+ T cells on the respective plates.

Figure 5:
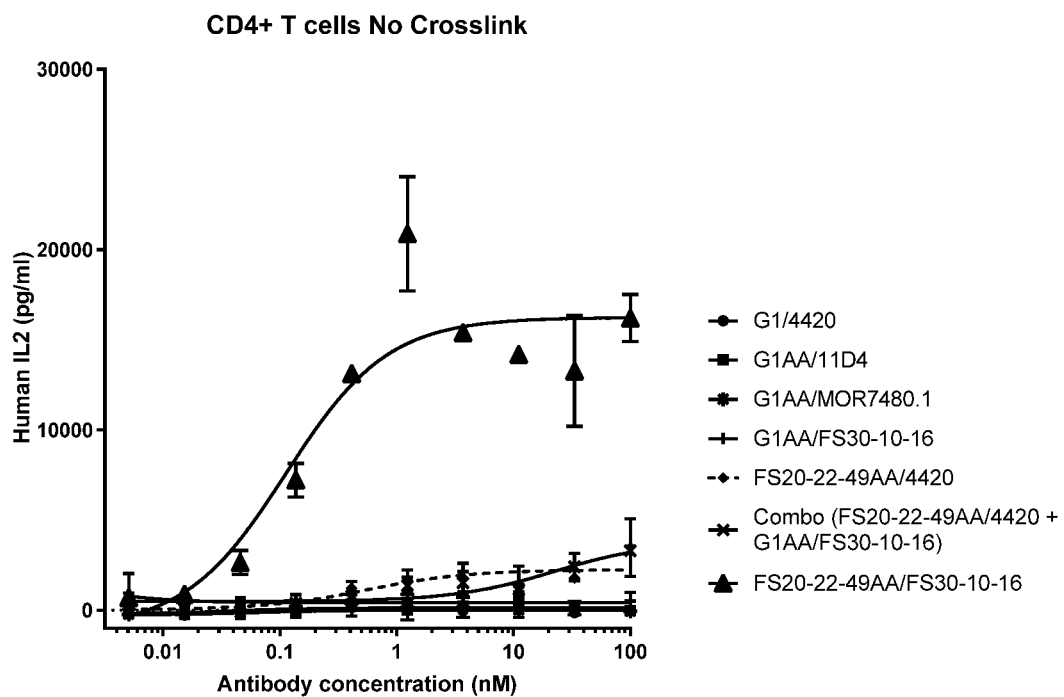
FIG. 5 shows the activity of human OX40/CD137 mAb$^2$ in CD4+ and CD8+ T cell activation assays.
Figure 5:
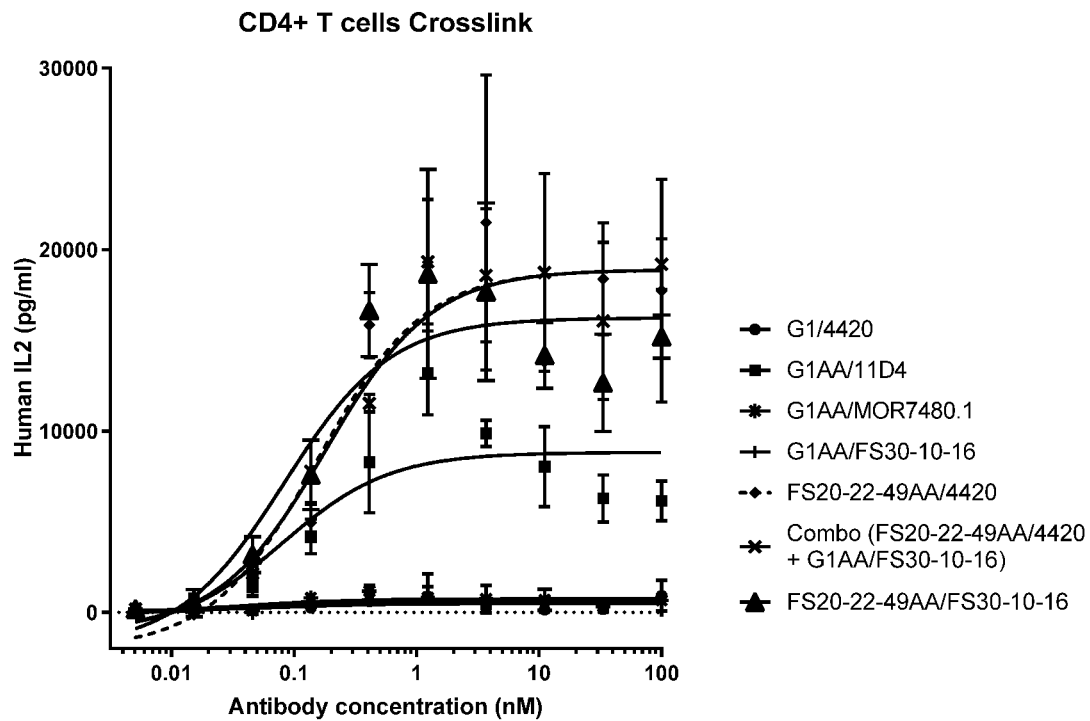
Figure 5:
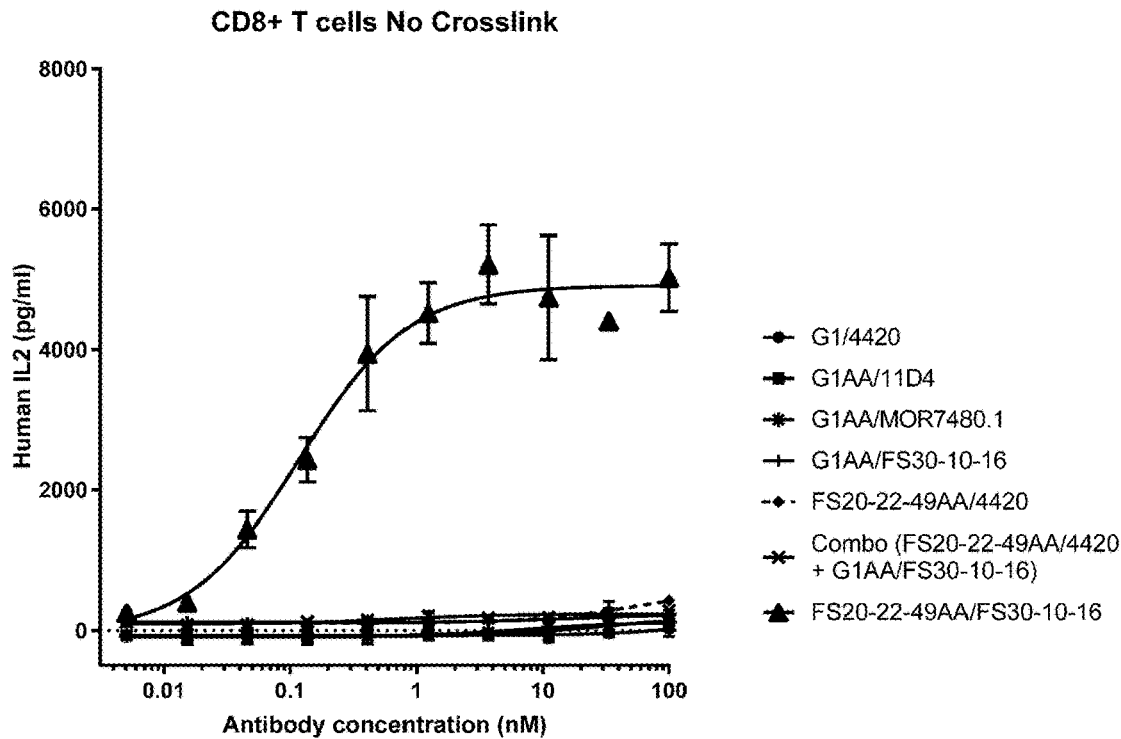
Figure 5:
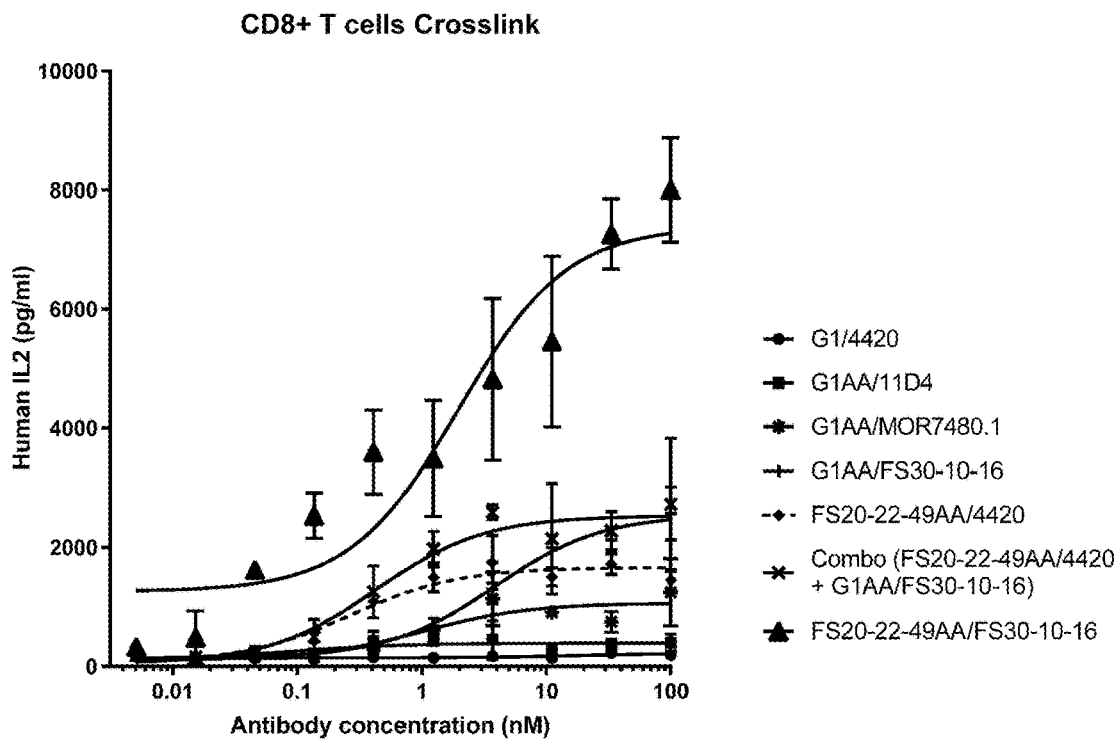
Figure 5:
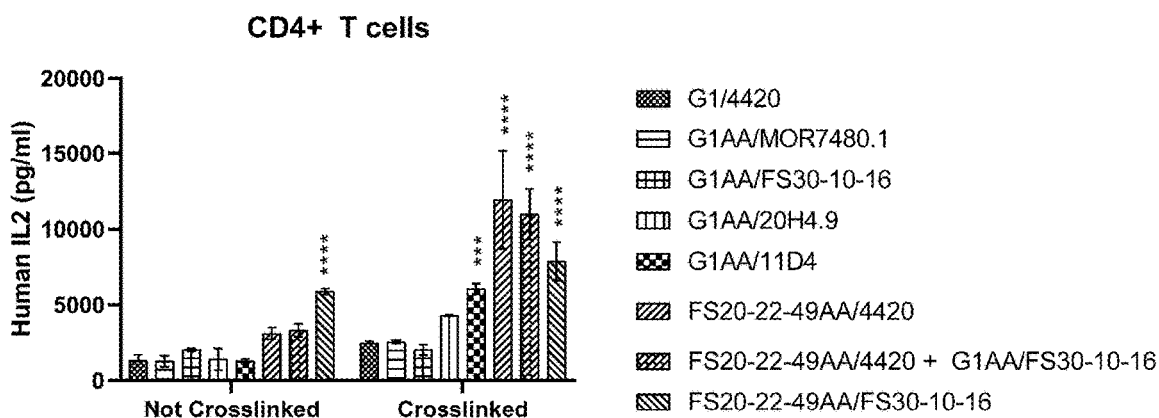
Figure 5:
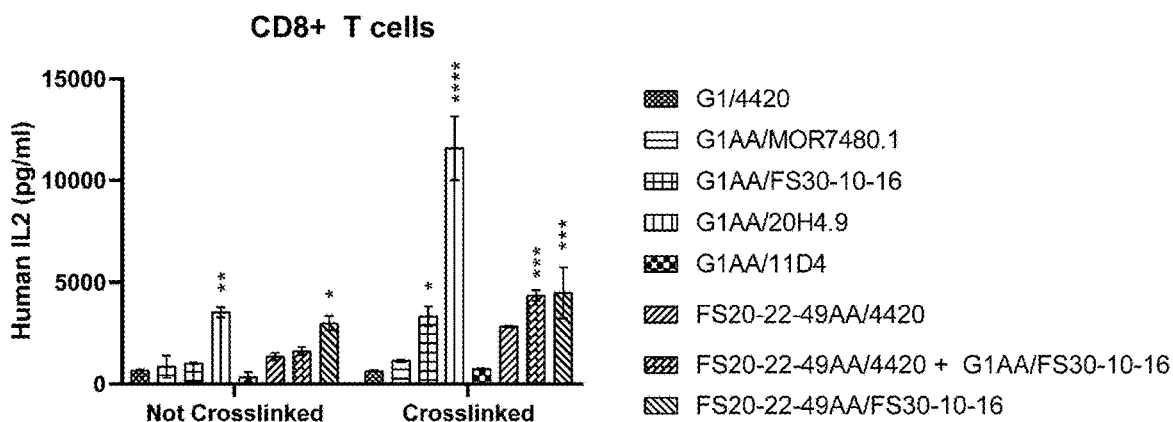

T cells were incubated at 37° C., 5% $CO_2$ for 72 hours. Supernatants were collected, IL-2 release measured and the data was prepared as described in Example 12.1. Table 25 shows the $EC_{50}$ values and maximum response of the IL-2 release observed in the separate T cell activation assays in the presence or absence of crosslinking with crosslinking agents. FIGS. 5A to C show plots of IL-2 release for the CD4+ or CD8+ T cell activation assay, respectively.

Figure 6:
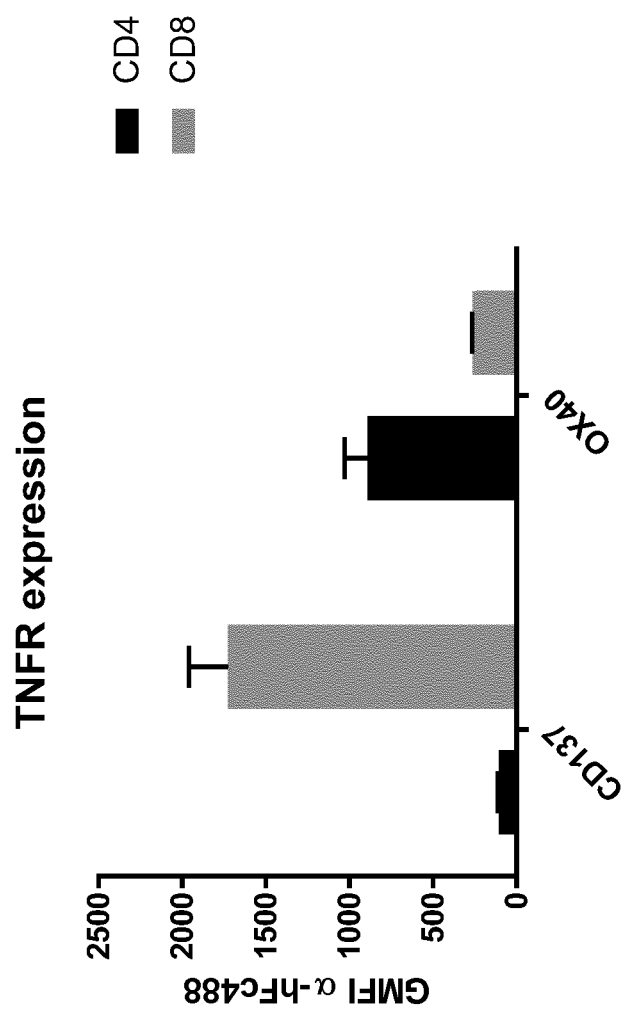
FIG. 6 shows that CD4+ T cells express lower levels of CD137 and higher levels of OX40 than CD8+ T cells. The graph shows geometric mean fluorescence intensity (GMFI) of CD4+ or CD8+ T cells treated with G1AA/MOR7480.1 or G1AA/11D4. The binding of G1AA/MOR7480.1 to CD137 is a measure of CD137 expression and the binding of G1AA/11 D4 to OX40 is a measure of OX40 expression.

After supernatants were collected, T cells were washed in PBS and stained with an Alexa Fluor 488-labelled anti-human Fc secondary antibody (Jackson Immunoresearch. cat. no. 109-546-098) diluted 1 In 1000 In PBS for 1 hour at 4° C. The cells were then washed once with PBS and resuspended in 100 µl/well PBS with DAPI (Biotium, cat. no. 89139-054) at 1 µg/ml. The cells were then analysed on a BD FACSCanto II flow cytometer (BD Biosciences). FIG. 6 shows the geometric mean fluorescence intensity in the 488 channel of either CD4+ or CD8+ T cells treated with G1 AA/MOR7480.1 or G1AA/11 D4.

TABLE 25

CD4+ and CD8+ T cell activation assay with mAb² targeting co-expressed receptors

| | No Crosslinking | | | | Crosslinking | | | |
|---|---|---|---|---|---|---|---|---|
| | $EC_{50}$ (nM) | | Max response | | $EC_{50}$ (nM) | | Max response | |
| mAbs/mAb² | (nM) | 95% Conf. Int. | (hIL-2 pg/ml) | 95% Conf. Int. | (nM) | 95% Conf. Int. | (hIL-2 pg/ml) | 95% Conf. Int. |
| | | | | CD4+ T cells | | | | |
| G1/4420 | NAD | NAD | NAD | NAD | NAD | NAD | NAD | NAD |
| G1AA/11D4 | NAD | NAD | NAD | NAD | 0.0813 | 0.01883 to 0.2796 | 8817 | 7129 to 10561 |
| G1AA/MOR7480.1 | NAD | NAD | NAD | NAD | NAD | NAD | NAD | NAD |
| G1AA/FS30-10-16 | NAD | NAD | NAD | NAD | NAD | NAD | NAD | NAD |
| FS20-22-49AA/4420 | 0.5641 | 0.06536 to ND | 2242 | 1578 to +infinity | 0.1553 | 0.06145 to 0.3765 | 18872 | 16200 to 21634 |
| FS20-22-49AA/4420 + G1AA/FS30-10-16 | 22.54 | 1.881 to 162.8 | 3820 | 2403 to 8413 | 0.181 | 0.08648 to 0.3728 | 18895 | 16953 to 20903 |
| FS20-22-49AA/FS30-10-16 | 0.1131 | 0.04802 to 0.2529 | 16232 | 14326 to 18191 | 0.08334 | 0.03012 to 0.2113 | 16232 | 14031 to 18494 |

TABLE 25-continued

CD4+ and CD8+ T cell activation assay with mAb² targeting co-expressed receptors

| | No Crosslinking | | | | Crosslinking | | | |
|---|---|---|---|---|---|---|---|---|
| | EC$_{50}$ (nM) | | Max response | | EC$_{50}$ (nM) | | Max response | |
| mAbs/mAb² | (nM) | 95% Conf. Int. | (hIL-2 pg/ml) | 95% Conf. Int. | (nM) | 95% Conf. Int. | (hIL-2 pg/ml) | 95% Conf. Int. |
| | CD8+T cells | | | | | | | |
| G1/4420 | NAD | NAD | NAD | NAD | NAD | NAD | NAD | NAD |
| G1AA/11D4 | NAD | NAD | NAD | NAD | 0.09964 | 0.004042 to 1.04 | 387.6 | 306.3 to 474.2 |
| G1AA/MOR7480.1 | NAD | NAD | NAD | NAD | 1.011 | 0.2837 to 3.658 | 1066 | 849.8 to 1308 |
| G1AA/FS30-10-16 | NAD | NAD | NAD | NAD | 3.875 | 2.547 to 5.943 | 2560 | 2344 to 2796 |
| FS20-22-49AA/4420 | NAD | NAD | NAD | NAD | 0.268 | 0.1418 to 0.5024 | 1663 | 1510 to 1821 |
| FS20-22-49AA/4420 +30 G1AA/FS30-10-16 | NAD | NAD | NAD | NAD | 0.4312 | 0.1721 to 1.081 | 2534 | 2185 to 2905 |
| FS20-22-49AA/FS30-10-16 | 0.1183 | 0.06831 to 0.2032 | 4915 | 4592 to 5246 | 1.98 | 0.3441 to 8.779 | 7397 | 6071 to 9139 |

NAD—no activity detected
ND—not determined

Table 25 and FIG. 5B show that CD4+ T cells can be activated by the crosslinked anti-OX40 controls G1 AA/11 D4 and FS20-22-49AA/4420 (both alone and in combination with G1AA/FS30-10-16) but not by the single-agent anti-CD137 controls G1AA/MOR7480.1 and G1AA/FS30-10-16. FIG. 5C shows that CD8+ T cells, on the other hand, were activated by both anti-CD137 controls G1AA/MOR7480.1 and G1AA/FS30-10-16 when crosslinked, as well as by the crosslinked anti-OX40 controls G1AA/11D4 and FS20-22-49AA/4420, although the level of response to the single-agent anti-CD137 control G1AA/FS30-10-16 was greater than to both single-agent anti-OX40 controls. As was observed in the SEA assay (Example 12.2) and the human pan-T cell activation assay (Example 13.3), the OX40 Fcab in mock mAb² format (FS20-22-49AA/4420) showed some activity in the absence of crosslinking in the presence of CD4+ T cells and this activity was increased when the antibody was crosslinked. The OX40/CD137 mAb² (FS20-22-49AA/FS30-10-16) showed activity in the presence of both CD4+ and CD8+ T cells in the absence of crosslinking, as was expected from previous results (see Examples 12 and 13).

FIG. 6 shows that CD4+ T cells express lower levels of CD137 and higher levels of OX40 than CD8+ T cells. The binding of G1AA/MOR7480.1 to CD137 is a measure of CD137 expression and the binding of G1AA/1 I D4 to OX40 Is a measure of OX40 expression.

This T cell assay with isolated CD4+ and CD8+ T cells was repeated following the same protocol as described above but with T cells Isolated from a different PBMC donor and with the addition of the anti-CD137 antibody G1 AA/20H4.9 (see Table 24). In agreement with the results shown in FIGS. 5A to D, FIGS. 5E and 5F show that CD8+ T cells respond more to CD137 agonism and CD4+ T cells respond more to OX40 agonism. The anti-OX40 antibodies (G1AA/11 D4 and the anti-OX40 Fcab in mock mAb² format FS20-22-49AA/4420) when crosslinked activated CD4+ T cells but not CDB+ T cells, and the CD137 antibodies (G1AA/20H4.9 and G1AA/FS30-10-16) when crosslinked activated CD8+ T cells but not CD4+ T cells. The G1 AA/20H4.9 antibody also activated CD8+ T cells in the absence of crosslinking antibody, similar to the results obtained in the DO11.10-hCD137 cell assay described in Example 7.1. In this repeat experiment the G1AA/MOR7480.1 antibody did not activate CD8+ T cells when crosslinked. Some PBMC donors can be more susceptible to CD137 co-stimulation than others and the different results obtained in this experiment can be the result of this natural variation.

These data indicate that CD4+ T cells are more sensitive to activation via OX40 agonism than CD8+ T cells, and conversely, that CD8+ T cells are more sensitive to activation via CD137 agonism than CD4+ T cells. This correlates with the reported differences in expression levels of OX40 and CD137 receptors on CD4+ T cells and CD8+ T cells, the former expressing higher levels of OX40 than CD137, and the latter expressing higher levels of CD137 than OX40. The activity in the presence of CD8+ T cells of the crosslinked anti-CD137 control antibody G1AA/FS30-10-16, the Fab arms of which are present in the OX40/CD137 mAb² FS20-22-9AA/FS30-10-16, demonstrates that the mAb² has the ability to activate the CD137 receptor when crosslinked by binding of its Fcabs to OX40. Furthermore, the activity in the presence of CD4+ T cells of the crosslinked anti-OX40 Fcab in mock mAb² format (FS20-22-49AA/4420), which is also present in the OX40/CDI 37 mAb² FS20-22-49AA/FS30-10-16, shows that the mAb² has the ability to activate the OX40 receptor when crosslinked by binding of its Fab arms to CD137. It can thus be concluded that the FS20-22-49AA/FS30-10-16 mAb² has the potential to function as a dual agonist by activating CD4+ T cells via agonism of OX40 and CD8+ T cells via agonism of CD137 and to a lesser extent OX40. The activation of OX40 by the mAb² occurs via its Fcabs and is Increased by crosslinking of the mAb² when bound to CD137 via Its Fab arms, while the activation of CD137 occurs via binding of its Fab arms to CD137 and crosslinking of the mAb² when bound to OX40 via its Fcabs.

Example 15- Activity of Mouse OX40/CD137 mAb² and Anti-Mouse CD137 Antibodies in T Cell Activation Assays As the anti-human OX40/CD137 mAb² do not bind to mouse proteins, in order to test the potential of an OX40/CD137 mAb² to illicit a T-cell mediated anti-tumour response a parallel reagent was made targeting mouse OX40 and mouse CD137 (see Example 8.2).

15.1 Activity of Mouse OX40/CD137 mAb² in a Pan-T Cell Activation Assay

In order to test if the mouse OX40/CD137 mAb² (FS20m-232-91AA/Lob12.3) targeting these two co-expressed receptors could induce the production of inflammatory cytokines by pre-activated T cells, a mouse T cell activation assay was established. Antibodies G1/4420 (anti-FITC), G1AA/OX86 (anti-mOX40), G1AA/Lob12.30 (anti-mCD137), G1AA/OX86 and G1AA/Lob12.3 in combination, and FS20m-232-91AA/4420 (mOX40/FITC mock mAb²) were used as controls (see Table 26 for details) and IL-2 production was used as a measure of T cell stimulation.

TABLE 26

Details of antibodies and mAb² tested

| mAb/mAb² | Fab binding to | Fcab binding to | Isotype | LALA mutation | Crosslinker | Heavy chain SEQ ID | Light chain SEQ ID |
|---|---|---|---|---|---|---|---|
| G1/4420 | FITC | None | hIgG1 | no | FITC dextran | 115 | 116 |
| G1AA/OX86 | mOX40 | None | hIgG1 | Yes | a-hCH2 | 155 | 156 |
| G1AA/Lob12.3 | mCD137 | None | hIgG1 | Yes | a-hCH2 | University of Southampton | |
| FS20m-232-91AA/4420 | FITC | mOX40 | hIgG1 | Yes | FITC dextran | 157 | 116 |
| FS20m-232-91AA/Lob12.3 | mCD137 | m0X40 | hIgG1 | Yes | a-hCH2 | Creation described above in Example 9.2 | |

To isolate T cells, spleens were collected from 4-8 week old female Balb/C mice (Charles River). Mice were humanely euthanized and spleens were isolated by dissection. Splenocytes were isolated by pushing the spleens through a 70 µm cell strainer (Corning) using the inside of a 5 ml plastic syringe. The cell strainer was washed 10 times with 1 ml Dulbecco's phosphate-buffered saline (DPBS) (Gibco) and the eluant collected in a 50 ml tube. Red blood cells present in the eluant were lysed through the addition of 10 ml red blood cell lysis buffer (eBioscience) according to the manufacturer's Instructions. T cells were isolated from the splenocytes present in the eluant using a Pan T cell Isolation Kit II (mouse) (Miltenyi Biotec Ltd) according to the manufacturer's instructions and were then activated and used in a protocol essentially the same as the human T cell activation assay described in Example 13.1 but instead using Mouse T-Activator CD3/CD28 Dynabeads (Life Technologies) for activation of T cells, anti-mouse CD3 antibody (Biolegend clone 145 2C11) for coating of plates, and a mouse IL-2 ELISA kit (eBioscience or R&D systems) for measurement of IL-2 release.

Figure 7:
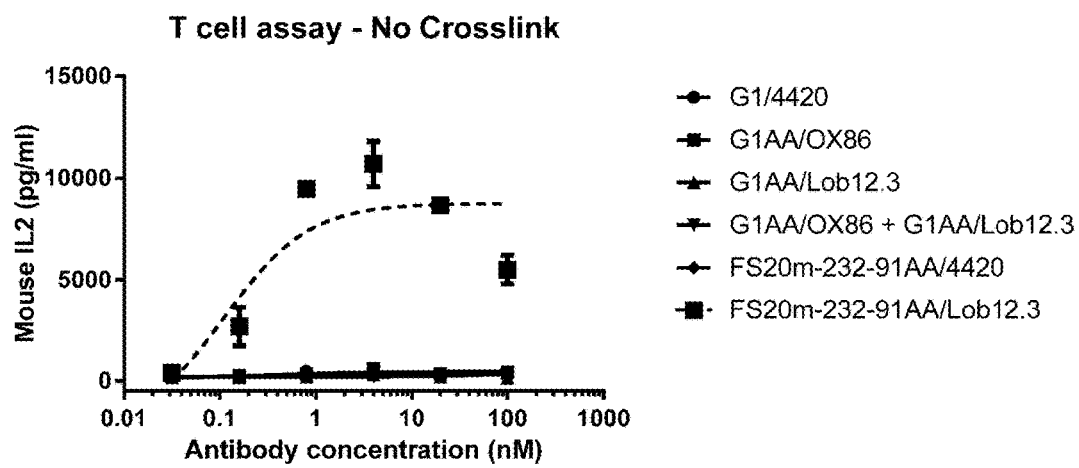
FIG. 7 shows the activity of anti-mouse CD137 mAb and mAb$^2$ In a T cell activation assay.
Figure 7:
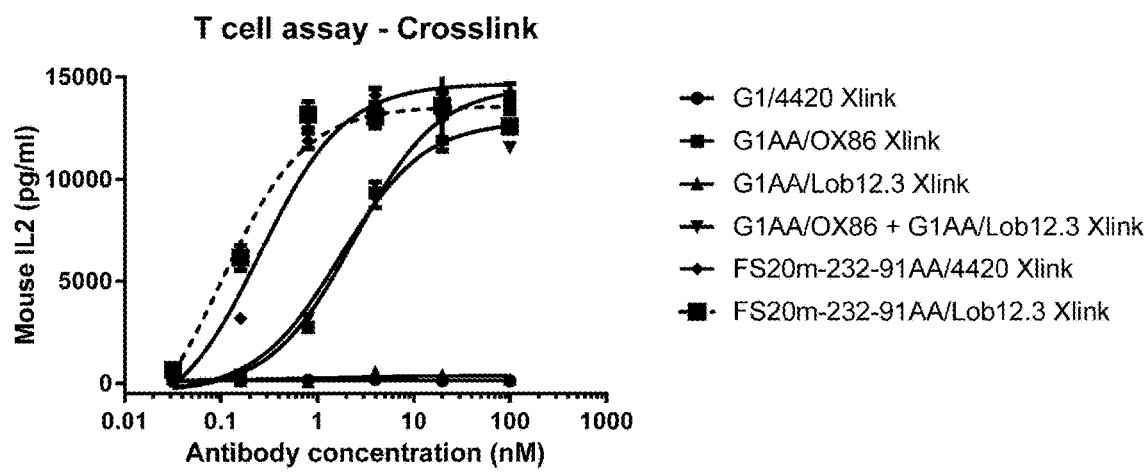
Figure 7:
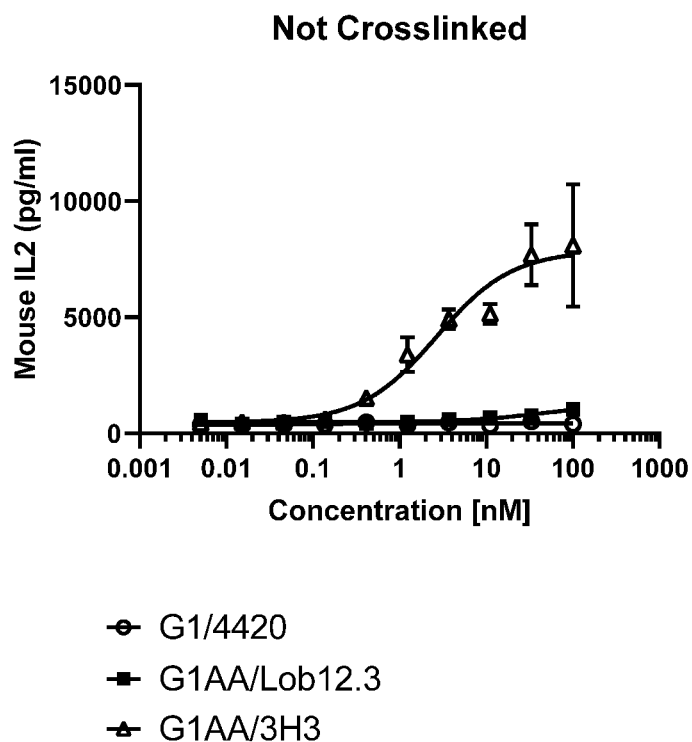
Figure 7:
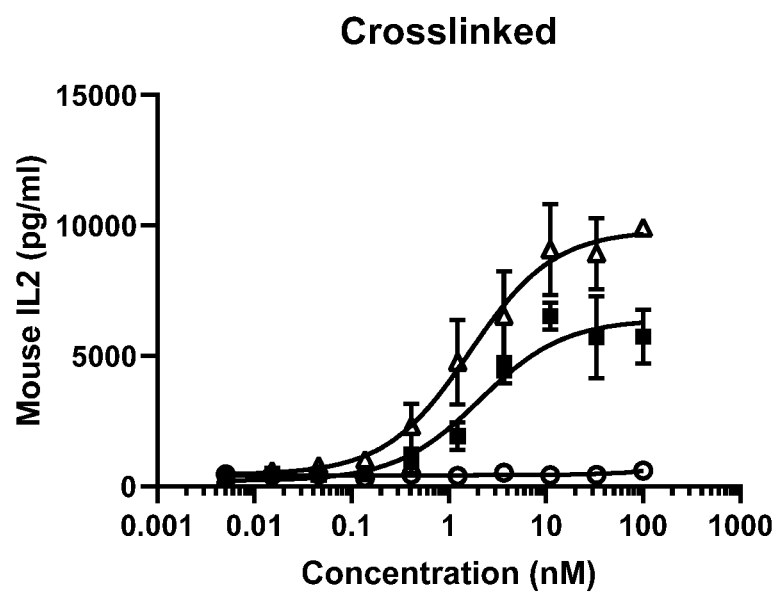

Table 27 shows the $EC_{50}$ values and maximum response of the IL-2 release observed in the T cell activation assay in the presence of the mAb² and mAbs tested. FIGS. 7A and B show representative plots of IL-2 release for the T cell activation assay.

TABLE 27

T cell activation assay with mAb² targeting co-expressed receptors

| | No Crosslink | | | | Crosslink | | | |
|---|---|---|---|---|---|---|---|---|
| | $EC_{50}$ (nM) | | Max response | | $EC_{50}$ (nM) | | Max response | |
| mAbs/mAb² | (nM) | 95% Conf. Int. | (mIL-2 pg/ml) | 95% Conf. Int. | (nM) | 95% Conf. Int. | (mIL-2 pg/ml) | 95% Conf. Int. |
| G1/4420 | NAD | NAD | NAD | NAD | NAD | NAD | NAD | NAD |
| G1AA/OX86 | NAD | NAD | NAD | NAD | 2.413 | 1.730 to 3.365 | 14544 | 13647 to 15441 |

TABLE 27-continued

T cell activation assay with mAb$^2$ targeting co-expressed receptors

| | No Crosslink | | | | Crosslink | | | |
|---|---|---|---|---|---|---|---|---|
| | EC$_{50}$ (nM) | | Max response | | EC$_{50}$ (nM) | | Max response | |
| mAbs/mAb$^2$ | (nM) | 95% Conf. Int. | (mIL-2 pg/ml) | 95% Conf. Int. | (nM) | 95% Conf. Int. | (mIL-2 pg/ml) | 95% Conf. Int. |
| G1AA/Lob12.3 | NAD | NAD | NAD | NAD | 1.179 | 0.001061 to 1309 | 373.6 | 139.3 to 607.8 |
| G1AA/OX86 + G1AA/Lob12.3 | NAD | NAD | NAD | NAD | 1.722 | 0.9596 to 3.090 | 12834 | 11531 to 14138 |
| FS20m-232-91AA/4420 | NAD | NAD | NAD | NAD | 0.2568 | 0.1181 to 0.5585 | 14672 | 13279 to 16065 |
| FS20m-232-91AA/Lob12.3 | 0.1141 | 0.01023 to 1.273 | 8750 | 6614 to 10885 | 0.1011 | 0.04358 to 0.2346 | 13563 | 12485 to 14640 |

NAD—no activity detected

Table 27 and FIG. 7B show that there is an increase in the activation of T cells when the OX40 receptor is targeted and the anti-OX40 antibodies are crosslinked. No T cell activation was observed with the crosslinked or non-crosslinked anti-FITC antibody G1/4420 as expected or with the non-crosslinked anti-OX40 antibody (G1AA/OX86 alone or In combination with G1AA/Lob12.3). IL-2 was produced by T cells when the OX40 receptor was targeted by the anti-OX40 antibody G1AA/OX86 in the presence of crosslinking agent (EC$_{50}$ of 2.41 nM for G1AA/OX86 alone, and EC$_{50}$ of 1.72 nM when in combination with G1AA/Lob12.3).

The OX40-targeting Fcab in mock mAb$^2$ format (FS20m-232-91 AA/4420) had no agonistic activity in the absence of crosslinking but when crosslinked by binding of the Fab arms to FITC-dextran showed potent T cell activation. When the OX40-targeting Fcab was paired with anti-CD137 Fab (Lob12.3), the mAb$^2$ showed T cell activity in the absence of any additional crosslinking agents. This indicates that the mAb$^2$ is crosslinked by binding to the co-expressed receptors on the same cell surface.

Marginal activity was observed with the crosslinked CD137-targeting antibody G1AA/Lob12.3 alone, and the activity of the combination of the OX40-targeting antibody G1AA/OX86 and CD137-targeting antibody G1AA/Lob12.3 when crosslinked was comparable to that of the crosslinked OX40-targeting antibody G1AA/OX86 alone, Indicating that the assay has low sensitivity for detection of agonism of CD137 by Lob12.3. This is in contrast to the human T cell assay described in Example 13.3 in which a stronger CD137-specific signal (maximum response of IL-2 release) was observed for the crosslinked anti-CD137 control G2/MOR7480.1. This difference in functional activity seen for the anti-mouse CD137 and anti-human CD137 control antibodies may be related to their having different affinities for their respective CD137 targets. This may also reflect the source of the cells (human PBMCs versus mouse splenocytes) or subtle differences between the target biology in mouse versus human systems.

This data shows that the FS20m-232-91AA/Lob12.3 OX40/CD137 mAb$^2$ can Induce T cell activation without any additional crosslinking agents, by engaging both receptors at the same time.

As the anti-human OX40/CD137 mAb$^2$ molecules are not mouse cross-reactive, and the anti-mouse OX40/CD137 mAb$^2$ are functionally comparable to the human leads in parallel in vitro experimental systems, the anti-mouse molecules are considered suitable surrogates to Infer the potential for an OX40/CD137 mAb$^2$ to Induce anti-tumour Immunity in vivo.

15.2 Activity of Anti-Mouse CD137 Antibodies in a Mouse CD137 T Cell Activation Assay Since little or no activity of the anti-CD137 Fab clone (Lob12.3) of the mouse OX40/CD137 mAb$^2$ was detected in the pan-T cell assay of Example 15.1, to understand the activity of different anti-CD137 agonist antibodies, a T cell activation assay using DO11.10-mCD137 cells was performed. The anti-CD137 agonist antibodies G1AA/Lob12.3 (see Table 26) and G1AA/3H3 (SEQ ID NOs: 166 and 167) were tested, as well as the anti-FITC antibody 4420 in IgG1 format (G1I4420; SEQ ID NOs 115 and 116) as an isotype negative control. The mAb molecules were tested both in the presence and absence of the crosslinking anti-human CH2 antibody, MK1A6 (see Example 2.1). Mouse IL-2 production was used as a measure of T cell activation.

The assay was performed as described in Example 6.2 but using DO11.10-mCD137 cells instead of DO11.10-hCD137 cells. Plates were read at 450 nm using the plate reader with Gen5 Software (BioTek). Absorbance values of 630 nm were subtracted from those of 450 nm (Correction). The standard curve for calculation of cytokine concentration was based on a four parameter logistic curve fit (Gen5 Software. BioTek). The concentration of mouse IL-2 (mIL-2) was plotted vs the log concentration of antibody and the resulting curves were fitted using the log (agonist) vs response equation in GraphPad Prism.

The results are shown in FIGS. 7C and D. The anti-CD137 antibodies differed in their requirement for the crosslinking antibody to Induce activity. Whereas G1AA/Lob12.3 was observed to require the addition of the crosslinking antibody for activity, i.e. was crosslink-dependent for its activity, G1AA/3H3 showed activity both in the presence and absence of the crosslinking antibody and so had crosslink-independent activity.

Example 16- Dual Engagement of OX40 and CD137 is Required for the Activity of the OX40/CD137 mAb²

16.1 Human OX40/CD137 mAb²

The OX40/CD137-targeting mAb² showed activity in the absence of additional crosslinking agents in the SEA (Example 12), human pan-T cell (Example 13) and human CD4+ and CD8+ T cell (Example 14) assays in which T cells co-express OX40 and CD137. In order to test if this activity requires the OX40/CD137 mAb² to bind simultaneously to the two receptors, a T cell competition assay was performed to assess the ability of the mAb² FS20-22-49AA/FS30-10-16 to activate isolated T cells in the presence of a 100-fold excess of either the OX40-targeting FS20-22-49AA/4420 mock mAb², the anti-CD137 mAb G1AA/FS30-10-16, a combination of the FS20-22-49AA/4420 mock mAb² plus the G1AA/FS30-10-16 mAb, or the isotype control mAb G1/4420. IL-2 production was used as a measure of T cell activation.

T cells were isolated as described in Example 13. The isolated T cells were then activated and plates were coated with anti-CD3 antibody as described in Example 13. Activated T cells were supplemented with 2 nM OX40/CD137 mAb² (FS20-22-49AA/FS30-10-16) and added to the plates at $2 \times 10^5$ cells/well in 100 µl. The final concentration of OX40/CD137 mAb² was therefore 1 nM.

2 µM dilutions of each test antibody were prepared in DPBS (Gibco) and further diluted 1:10 in T cell medium (30 µl+270 µl) to obtain 200 nM dilutions and 100 µl of each diluted antibody was added to the activated T cells on the plate.

T cells were incubated, supernatants were collected and IL-2 release was measured as described in Example 13. The standard curve for calculation of cytokine concentration was based on a four-parameter logistic curve fit (Gen5 Software, BioTek). Statistical analysis was performed using a one-way ANOVA test and Dunnett's multiple comparisons test using the GraphPad Prism software package.

Figure 8:
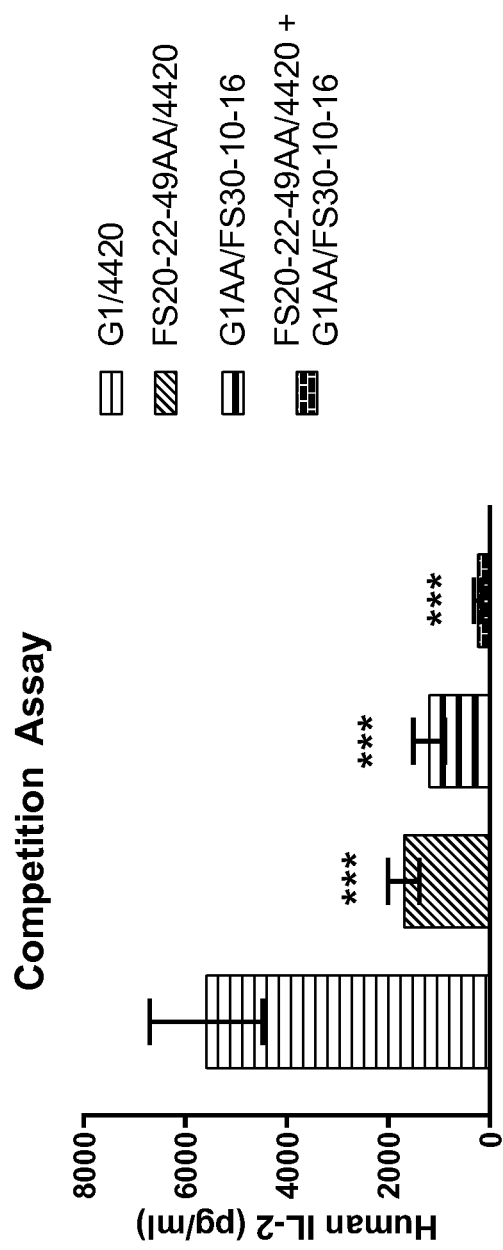
FIG. 8 shows a competition assay to test the activity of human OX40/CD137 mAb$^2$ clone FS20-22-49AA/FS30-10-16 in the presence of a 100-fold excess of a human OX40-targeting mock mAb$^2$ (FS20-22-49AA/4420), an anti-human CD137 antibody (G1AA/FS30-10-16) or their combination. Data from duplicates is shown as mean plus or minus standard deviation (SD). Statistical testing was done by one-way ANOVA and Dunnett's multiple comparisons test. Asterisks above error bars represent the significant difference compared to isotype control (G1/4420)-treated samples (*p<0.0002). The results show that the activity of the OX40/CD137 mAb$^2$ was greatly reduced when outcompeted by both the FS20-22-49AA/4420 mock mAb$^2$ for binding to OX40 and the G1 AA/FS30-10-16 mAb for binding to CD137, as compared to when the OX40/CD137 mAb$^2$ was able to bind to both receptors in the absence of the anti-OX40 and anti-CD137 antibodies. The combination of the OX40-targeting mock mAb$^2$ FS20-22-49AA/4420 and the anti-CD137 mAb G1AA/FS30-10-16 further decreased the activity of the OX40/CD137 mAb$^2$. These results indicate that in order for the OX40/CD137 mAb to induce T cell activation via clustering and agonism of OX40 and CD137, dual binding of the mAb$^2$ to both receptors is required.

FIG. 8 shows IL-2 release for the competition assay. The activity of the mAb² was greatly reduced when outcompeted by both the FS20-22-49AA/4420 mock mAb² for binding to OX40 and the G1AA/FS30-10-16 mAb for binding to CD137, as compared to when the mAb² was able to bind to both receptors in the absence of the anti-OX40 and anti-CD137 antibodies. The combination of the OX40-targeting mock mAb² FS20-22-49AA/4420 and the anti-CD137 mAb G1AA/FS30-10-16 further decreased the activity of the OX40/CD137 mAb². These results indicate that in order for the mAb² to induce T cell activation via clustering and agonism of OX40 and CD137, dual binding of the mAb² to both receptors is required.

16.2 Mouse OX40/CD137 mAb²

The mouse OX40/CD137-targeting mAb² shows activity in the absence of additional crosslinking agents in the T cell assay where T cells co-express the two receptors. In order to test if this activity requires the OX40/CD137 mAb² to bind simultaneously to the two receptors, a competition assay was performed to assess the ability of the FS20m-232-91AA/Lob12.3 mAb² to activate isolated T cells in the presence of a 100-fold excess of either the OX40-targeting mock mAb² FS20m-232-91AA/4420, the anti-CD137 mAb G1/Lob12.3 or the negative control mAb G1AA/4420 (FITC). T cells were Isolated as described in Example 15.1. The isolated T cells were then activated and plates were coated with anti-CD3 antibody as described in Example 13.1 (human pan-T cell activation assay) but instead using Mouse T-Activator CD3/CD28 Dynabeads (Life Technologies) for activation of T cells and anti-mouse CD3 antibody (Biolegend clone 145-2C11) for coating of plates. Activated T cells were supplemented with 2 nM OX40/CD137 mAb² (FS20m-232-91AA/Lob12.3) and added to the plates at 2×10 cells/well.

2 µM dilutions of each test antibody were prepared in DPBS (Gibco) and further diluted 1:10 in T cell medium (30 µl+270 µl) to obtain 200 nM dilutions and 100 µl of each diluted antibody was added to the activated T cells on the plate.

Figure 9:
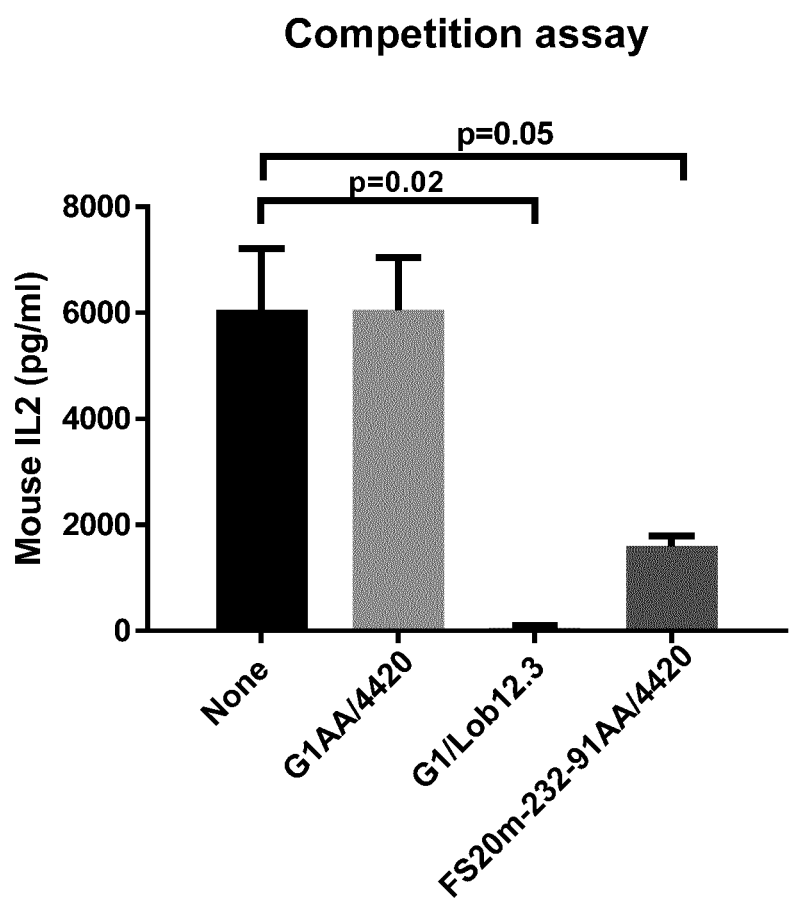
FIG. 9 shows a competition assay to test the activity of mouse OX40/CD137 mAb$^2$ FS20m-232-91AA/Lob12.3 In the presence of a 100-fold excess of either the OX40-targeting mock mAb$^2$ FS20m-232-91AA/4420, the anti-CD137 mAb G1/Lob12.3 or the negative control mAb G1AA/4420 (anti-FITC). The results show that the activity of the mAb$^2$ was greatly reduced when outcompeted by the G1/Lob12.3 mAb for binding to CD137 and was also reduced to a low level when outcompeted by the FS20m-232-91AA/4420 mock mAb$^2$ for binding to OX40, as compared to when the mAb$^2$ was able to bind to both receptors in the absence of the anti-OX40 and anti-CD137 antibodies. As expected, a similar level of activity was observed for the mAb$^2$ when in the presence of an excess of the negative control mAb as when in the absence of this and the anti-OX40 and anti-CD137 antibodies. These results indicate that in order for the mAb$^2$ to induce T cell activation via clustering and agonism of OX40 and CD137, dual binding of the mAb$^2$ to both receptors is required.

T cells were incubated, supernatants were collected and IL-2 release was measured as described in Example 12.1 but instead using a mouse IL-2 ELISA kit (eBioscience or R&D systems) for measurement of IL-2 release. The standard curve for calculation of cytokine concentration was based on a four parameter logistic curve fit (Gen5 Software, BioTek). Statistical analysis was performed using a one-way ANOVA test and Dunnett's multiple comparisons test using the GraphPad Prism software package. FIG. 9 shows a representative plot of IL-2 release for the competition assay.

FIG. 9 shows that there is a decrease in the amount of IL-2 production induced by the OX40/CD137 mAb² when antibodies competing for OX40 or CD137 binding are introduced in excess. The competing antibodies used were the mAb² component parts (the Fcab in mock (4420) mAb² format and the Fab without the Fcab) in order to ensure the same epitope is targeted. The addition of these competing antibodies reduced the amount of IL-2 release induced by the OX40/CD137 mAb² indicating this molecule requires dual binding for its activity. This shows that the OX40/CD137 mAb² activity is dependent on engaging both OX40 and CD137 at the same time, thereby clustering and agonising both receptors.

Example 17-Activity of OX40/CD137 mAb² in a CT26 Syngeneic Tumour Model

17.1 Comparison of Anti-Tumour Activity of OX40/CD137 mAb² with or without LALA Mutation A CT26 Balb/c syngeneic mouse colorectal tumour model was used to test the anti-tumour activity of the anti-mouse OX40/CD137 mAb² in vivo. The CT26 tumour model has previously been shown to be sensitive to both OX40 and CD137 agonist antibodies (Sadun et at, 2008), and tumour infiltrating lymphocytes (TILs) isolated from CT26 tumours are anticipated to express both OX40 and CD137. The antibodies tested are detailed in Table 28.

TABLE 28

Details of antibodies and mAb² tested

| mAb/mAb² | Fab binding to | Fcab binding to | Isotype | LALA mutation | Heavy chain SEQ ID | Light chain SEQ ID |
|---|---|---|---|---|---|---|
| G1/4420 | FITC | none | hIgG1 | No | 115 | 116 |
| G1/OX86 | mOX40 | none | hIgG1 | No | 159 | 156 |
| G1AA/OX86 | mOX40 | none | hIgG1 | Yes | 155 | 156 |
| G1/Lob12.3 | mCD137 | none | hIgG1 | No | University of Southampton |
| G1AA/Lob12.3 | mCD137 | none | hIgG1 | Yes | University of Southampton |

TABLE 28-continued

Details of antibodies and mAb² tested

| mAb/mAb² | Fab binding to | Fcab binding to | Isotype | LALA mutation | Heavy chain SEQ ID | Light chain SEQ ID |
|---|---|---|---|---|---|---|
| FS20m-232-91/Lob12.3 | mCD137 | mOX40 | hIgG1 | No | Creation described above in Example 9.2 | |
| FS20m-232-91AA/Lob12.3 | mCD137 | mOX40 | hIgG1 | Yes | | |

The ability of the mAb², with or without the LALA mutation (FS20m-232-91AA/Lob12.3 and FS20m-232-91/Lob12.3, respectively), to inhibit tumour growth was compared to isotype control mAb G1/4420 (anti-FITC), single-agent mAb G1/OX86 (anti-OX40 control without the LALA mutation) or G1/Lob12.3 (anti-CD137 control without the LALA mutation), a combination of G1/OX86 plus G1/Lob12.3, or a combination of G1AA/OX86 (anti-OX40 mAb with the LALA mutation) plus G1AA/Lob12.3 (anti-CD137 mAb with the LALA mutation).

BALB/c female mice (Charles River) aged 8-10 weeks and weighing approximately 20 g each were acclimatised for one week prior to the study start. All animals were microchipped and given a unique identifier. Each cohort had 12 mice. The CT26 colon carcinoma cell line (ATCC, CRL-2638) was expanded, banked, and then pre-screened by IDEXX Bioresearch for pathogens using the IMPACT I protocol and shown to be pathogen free. CT26 cells (approximately $3-5 \times 10^6$) were thawed from $-150°$ C., storage and added to 20 ml D MEM (Gibco, 61965-026) with 10% FCS (Gibco, 10270-106) in a T175 tissue culture flask. Mice were anaesthetised using isoflurane (Abbott Laboratories) and each animal received $1 \times 10^0$ cells injected subcutaneously in the left flank to generate tumours. On day 10 following tumour cell inoculation, tumours were measured and mice were randomised into study cohorts based on tumour volume. Any mice which did not have turnouts at this point were removed from the study.

Within 24 hours prior to injection, the antibodies were analysed by SEC-HPLC profiling and checked for impurities. Antibodies were diluted to a final concentration of 0.1 mg/ml in PBS, and 200 μl/mouse was injected intraperitoneally (IP), giving a final dose of 1 mg/kg for a 20 g mouse. Injections were performed on days 13, 15 and 17 (three doses every two days) following tumour inoculation. Animals were health screened under anaesthesia three times a week, during which time accurate measurements of tumours were taken. Tumour volume measurements were taken with callipers to determine the longest axis and the shortest axis of the tumour. The following formula was used to calculate the tumour volume:

$$L \times (S^2)/2$$

(Where L=longest axis: S=shortest axis)

The trial was halted at day 27 when tumour volume reached the humane endpoint in accordance with the United Kingdom Animal (Scientific Procedures) Act and EU Directive EU86/609.

For statistical testing the tumour volumes are analysed on the log scale using a mixed model. A separate model was fitted to each pair of treatments of interest. The model is: $\log_{10}(\text{volume}) = A + B \times (\text{day} - \text{start day}) + F$ A and B are the intercept and slope respectively; they are different for each mouse, and include a fixed effect for the group and a random effect for the animal:

$$A = A_0 + A_1 T + \varepsilon_A$$

$$B = B_0 + B_1 T + \varepsilon_e$$

T is a dummy variable representing the treatment group with value 0 in one group and 1 in the other. The random effects are distributed with a normal distribution:

$$\varepsilon_A \sim N(0 \cdot \sigma_A), \varepsilon_B \sim N(0, \sigma_B)$$

where $\sigma_A$ and $\sigma_B$ are the standard deviations of the inter-animal variability in the intercept and slope respectively. The intra-animal variability is also normally distributed with standard deviation σ:

$$\varepsilon \sim N(0, \sigma_B)$$

For each pair of treatments, the model above was fitted to the data. For A, and $B_1$, the (two-sided) p-value for a difference from zero was calculated: a p-value below 0.05 is statistically significant evidence for a difference between the treatment groups.

Figure 10:
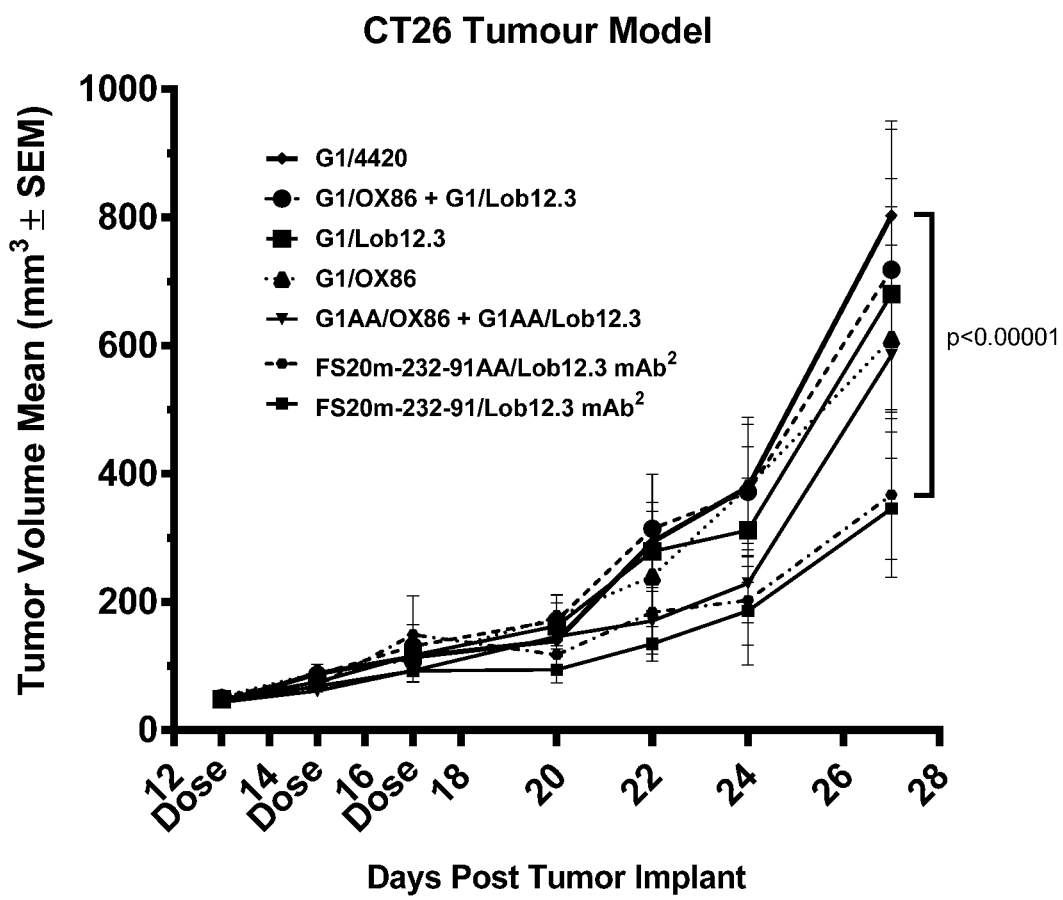
FIG. 10 shows the anti-tumour activity of anti-mouse OX40/CD137 mAb$^2$ in a CT26 syngeneic tumour model.
Figure 10:
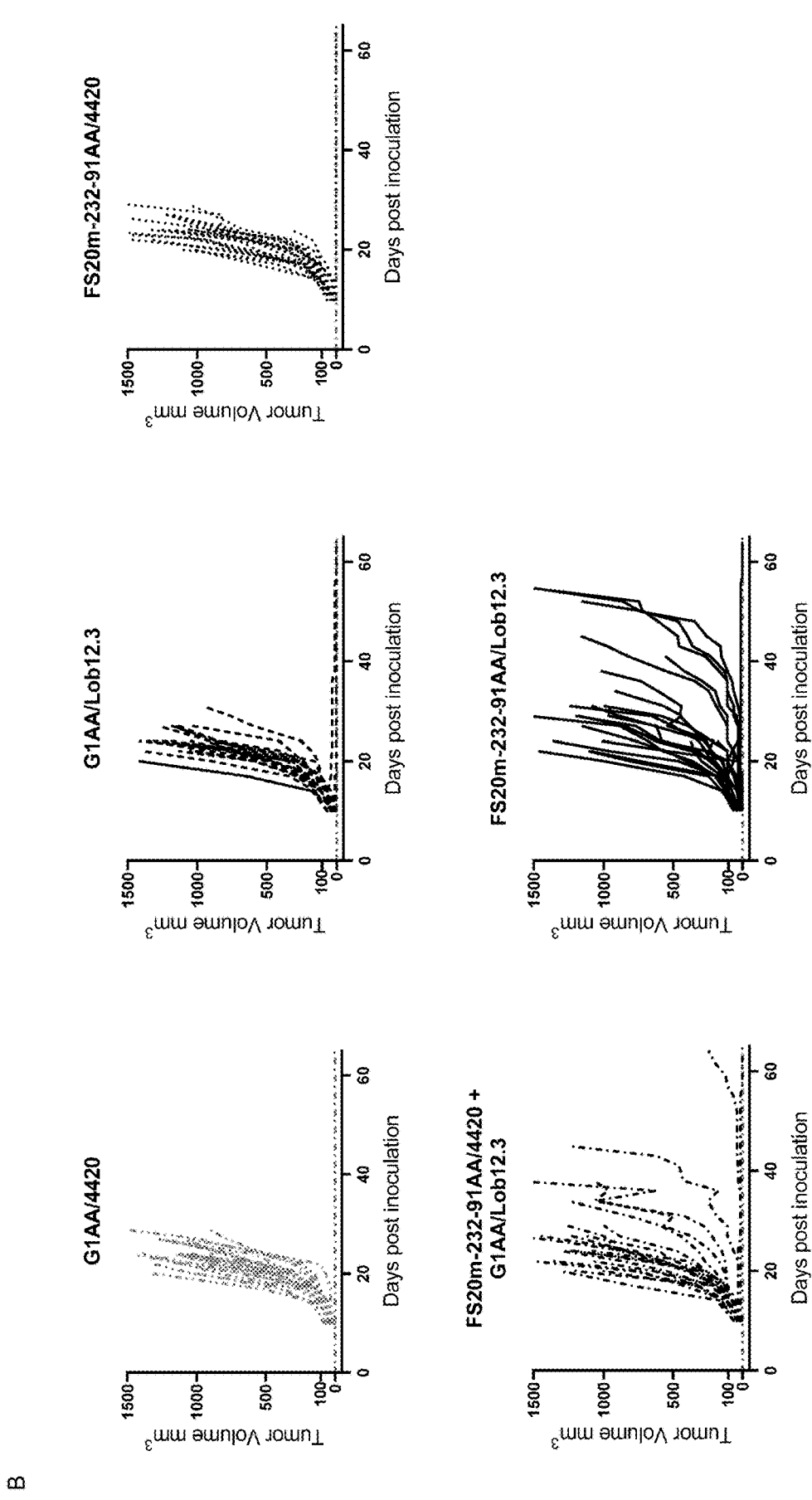
Figure 10:
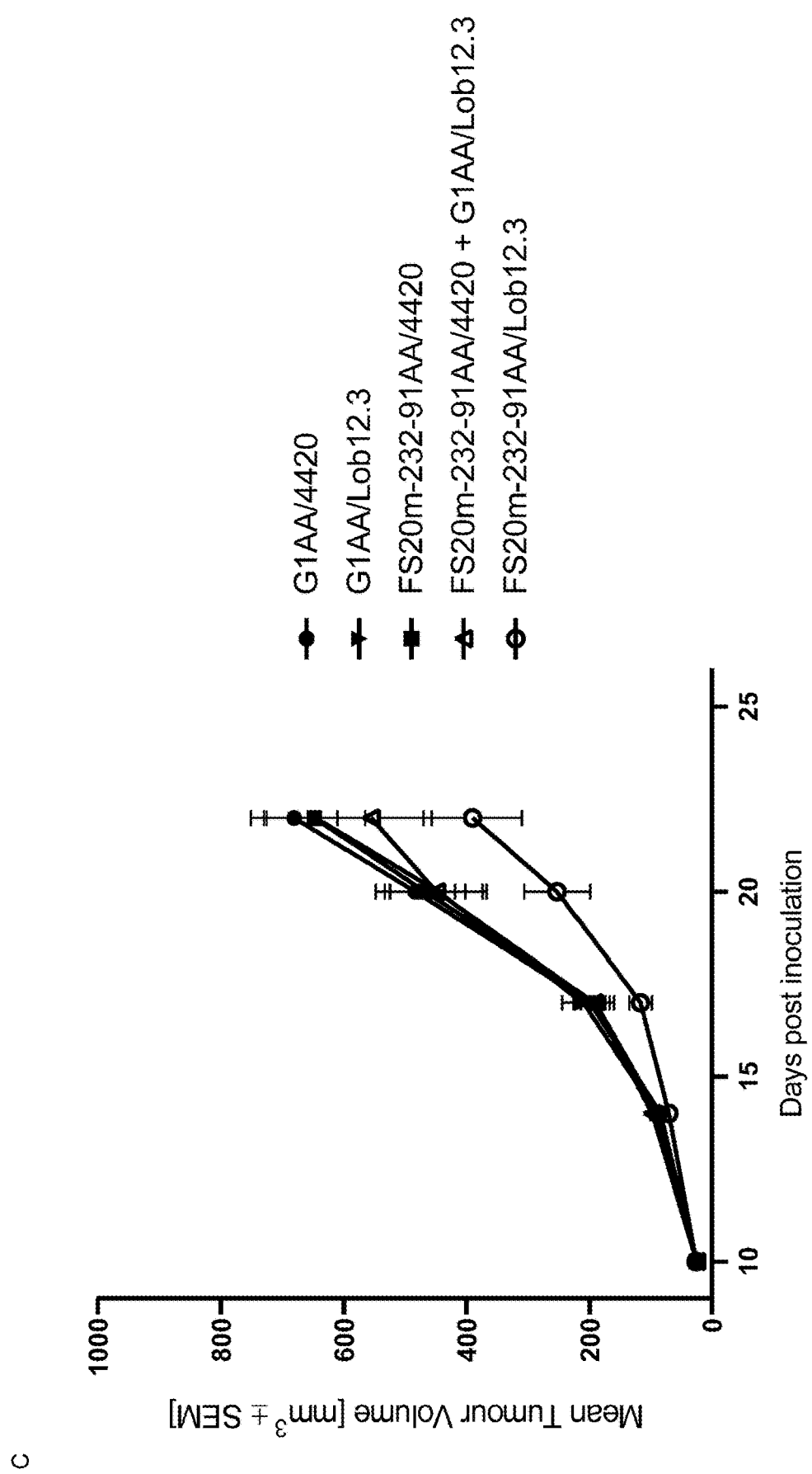
Figure 10:
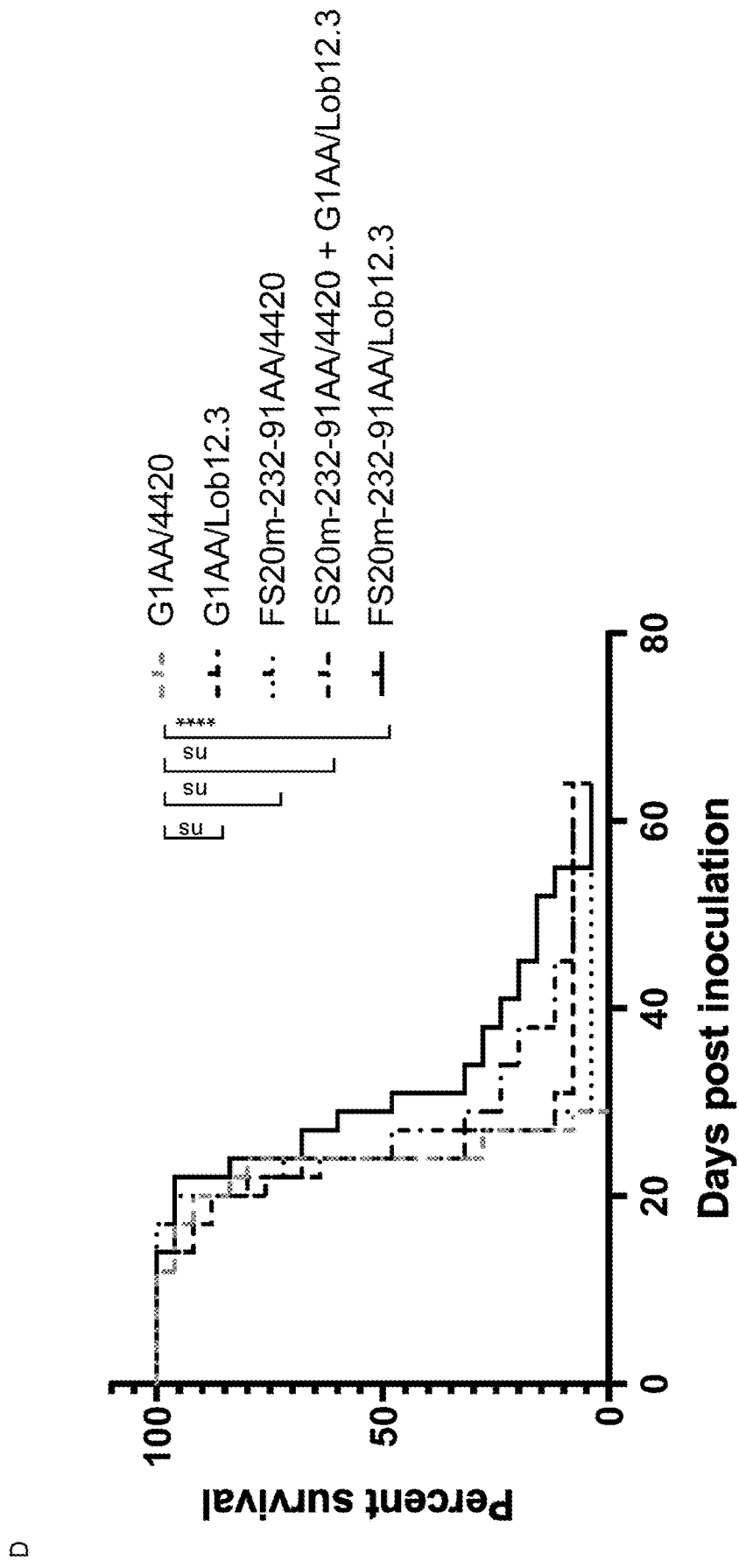

The results are shown in FIG. 10A. The mean CT26 tumour volumes plus or minus the standard error mean are plotted. The results show that treatment with the OX40/CD137 mAb² both with and without the LALA mutation (FS20m-232-91AA/Lob12.3 and FS20m-232-91/Lob12.3, respectively) resulted in a reduction in tumour growth compared to treatment with the anti-OX40 control (G1/OX86), the anti-CD137 control (G1/Lob12.3), the combination of these two antibodies (G1/OX86+G1/Lob12.3), or the combination of the LALA-containing anti-OX40 and anti-CD137 antibodies (G1AA/OX86+G1AA/Lob12.3).

The results show that there is a statistically significant anti-tumour effect of the OX40/CD137 mAb² (FS20m-232-91AA/Lob12.3 and FS20-232-91/Lob12.3) as compared to the control antibody (G114420). The activity of the combination of the OX40- and CD137-targeting antibodies (G1/OX86 plus G1/Lob12.3, or G1AA/OX86 plus G1AA/Lob12.3) did not significantly suppress tumour growth and neither did the single-agent controls (G1/OX86 or G1/Lob12.3).

The introduction of the LALA mutation in the Fc region of the human IgG1 backbone of OX40/CD137 mAb² is expected to prevent ADCC and ADCP of OX40- or CD137-expressing cells and also Fcγf receptor-mediated crosslinking of the mAb² when bound to either OX40 or CD137 on cells expressing these receptors. Hence, the activity of the FS20m-232-91AA/Lob12.3 mAb² is believed to be driven via the co-engagement of OX40 and CD137 resulting in signalling via either or both receptors, rather than via Fc-mediated effector function or Fcγ receptor-mediated crosslinking. Subsequently, this is expected to lead to the activation of OX40- and CD137-expressing T cells, ultimately resulting in T-cell mediated anti-tumour activity.

These results demonstrate that the OX40/CD137 mAb² antibody has anti-tumour efficacy in vivo against a tumour expected to comprise OX40 and CD137 expressing TILs, Indicating that the in vivo activation of OX40 and CD137 mediated by the bispecific engagement of OX40 and CD137 by the OX40/CD137 mAb² is effective in controlling tumour growth.

As described in the background section above, liver toxicity has been observed in the clinic with a CD137 agonist antibody (Segal et al., 2017). The mechanism for this toxic effect has not been fully determined but studies in preclinical models have highlighted the role of CD137-expressing myeloid cells that produce IL-27 in response to CD137 agonist antibodies (Bartkowiak el al., 2018). The role of Fcγ receptors in this liver toxicity mechanism has not been studied but a possible explanation for the toxicity observed is that the co-expression of CD137 and Fcγ receptors in myeloid cells could result in crosslinking of the CD137 agonist antibodies on these cells to trigger the production of inflammatory cytokines. It was therefore considered desirable to include the LALA mutation in the OX40/CD137 dual agonist antibody molecule of the invention in case Fcγ receptor-crosslinking of the molecule could lead to any activation of cells expressing CD137 in the absence of OX40 at locations away from the tumour microenvironment or periphery. Thus, by engineering a dual agonist antibody molecule which stimulates T cells expressing both OX40 and CD137 by simultaneously engaging both targets, but which does not activate CD137-expressing cells via Fcγ receptor-mediated crosslinking in the absence of OX40 due to the presence of the LALA mutation in the molecule, it is thought likely that the antibody molecule of the invention has a reduced potential for toxicity in the clinic.

A further reason for including the LALA mutation in the antibody molecule of the invention is that it serves to avoid Fcγ receptor-mediated killing of the OX40- and CD137-expressing cells the molecule is intended to activate to suppress tumour growth. The mechanism of action of OX40 agonist antibodies in certain preclinical tumour models has been described to be via Fcγ receptor-mediated depletion of Tregs in the tumour microenvironment, and the introduction of Fcγ receptor function-disabling mutations in these molecules has impaired their anti-tumour activity (Bulliard et al., 2014). While the effect of the LALA mutation may be the preservation of beneficial immune cells intended to be activated by the antibody molecule of the invention accompanied by a lack of depletion of Treg cells, it is noted that OX40-targeting human IgG1 antibodies designed to elicit the same mechanism of tumour Treg depletion as seen in preclinical tumour models have not shown the same ability to control tumour growth (Glisson et al., 2016). Other molecules designed to deplete Tregs have also not shown high levels of clinical activity (Powell et al., 2007; Tran et al., 2017). This lack of clinical translatability of the effects of Treg depletion seen in syngeneic mouse tumour models may be due to lower levels of Fcγ receptor-expressing cells in the tumour microenvironment (Milas et al., 1987), to differences in Treg biology between humans and mice (Liu et al., 2016). or to other unknown factors (Stewart et al., 2014).

Surprisingly, the inclusion of the LALA mutation in the FS20m-232-91AA/Lob12.3 mAb² did not impair its anti-tumour activity in the CT26 model, indicating that it has an Fcγ receptor-independent mechanism of action which is not reliant on interaction with Fcγ receptor-expressing cells. The lack of observable depletion of tumour Tregs and the induction of strong T cell proliferation in the blood by this LALA mutation-containing mAb² in the "mechanism of action" study described in Example 19 provide further support for an Fcγ receptor-independent mechanism of action of the OX40/CD137 dual agonist mAb² as described herein. Given the poor clinical activity seen with antibodies which rely on Fcγreceptor-interaction for their activity, the Fcγ receptor-independent mechanism of action of the antibody molecule of the invention is expected to result in greater efficacy in the clinic.

17.2 Comparison of Anti-Tumour Activity of OX40/CD137 mAb² and its Component Fcab and Fab parts In the mouse pan-T cell activation assay (Example 15), the mouse OX40/CD137 mAb² (FS20m-232-91AA/Lob12.3) showed in vitro activity in the absence of additional crosslinking agents, in contrast to the monospecific control antibodies G1AA/Lob12.3 (anti-mCD137 mAb) and FS20m-232-91AA/4420 (mOX40/FITC mock mAb²), by engaging both CD137 and OX40 receptors concurrently (Example 16.2). Following on from the pan-T cell activation assay, the anti-tumour activity of FS20m-232-91AA/Lob12.3 was compared to that of its component parts, i.e. the FS20m-232-91AA Fcab in mock (anti-FITC) mAb² format (FS20m-232-91AA/4420) and the monospecific anti-mouse CD137 mAb without the Fcab (G1AA/Lob12.3) as single agents or in combination, or of isotype control (G1AA/4420) in the CT26 tumour model.

Following the same method as described in Example 17.1. CT26 tumours were established subcutaneously in BALB/c female mice. On day 10 following CT26 cell-inoculation, tumour-bearing mice were randomised Into study cohorts of 25 mice per group and received antibody treatment.

Antibodies were diluted to a final concentration of 0.3 mg/mL in PBS, and a 200 µL volume was injected intraperitoneally into each mouse to give a final dose of 3 mg/kg for a 20 g mouse (fixed dose of 60 µg of each antibody). Injections were performed once every two days (Q2D) for a total of three doses starting on day 10 following tumour inoculation. Tumour volumes were determined by calliper measurements as described previously. The study was terminated at 64 days after cell inoculation, with animals taken off study when humane endpoints were reached based on tumour volume and condition.

Tumour volume data over time for individual animals are shown in FIG. 10B, and average results shown in FIG. 10C suggest that the FS20m-232-91AA/Lob12.3 mAb² inhibited early CT26 tumour growth rate (between days 10 and 22) compared to the isotype control antibody (G1AA/4420). No apparent tumour growth inhibition was observed in the cohorts treated with the anti-mouse CD137 mAb, mouse OX40/FITC mock mAb² or combination thereof.

Following the same mixed model method described previously, analysis of tumour volume data up to day 22 (following cell inoculation, Table 29) showed that FS20m-232-91AA/Lob12.3 resulted in statistically significant (p=0.003) reduction in mean tumour growth rate compared to isotype control. In comparison, treatment with the anti-mouse CD137 mAb, mouse OX40/FITC mock mAb²ᵒr combination thereof did not result in significantly different tumour growth rates compared to isotype control. Comparison of tumour growth rates over the entire study duration (64 days), using the mixed model method, showed statistically significant reductions in tumour growth rates in all treatment groups, compared to isotype control (analysis not shown).

TABLE 29

Pairwise comparison of mean OT26 tumour growth rates using Mixed Effects Model analysis

| A vs. B pairwise comparison | | Mean Log (TGR) [Lower, Upper 95% CI] | | P-value | Summary |
|---|---|---|---|---|---|
| A | B | A | B | | |
| Isotype control | FS20m-232-91AA/4420 | 0.310 [0.279, 0.340] | 0.291 [0.244, 0.339] | >0.05 | ns |
| Isotype control | G1AA/Lob12.3 | 0.310 [0.279, 0.340] | 0.281 [0.235, 0.327] | >0.05 | no |
| Isotype control | FS20m-232-91AA/4420 + G1AA/Lob12.3 | 0.310 [0.279, 0.340] | 0.277 [0.237, 0.316] | >0.05 | ns |
| Isotype control | FS20m-232-91AA/Lob12.3 | 0.310 [0.279, 0.340] | 0.205 [0.164, 0.247] | 0.003 | *** | ns = not statistically significant;
TGR = tumour growth rate;
CI = confidence interval
NOTE:
To compare early tumour growth rates, tumour volume data for the first 22 days post inoculation were used in the Mixed Effects Model. For each pairwise comparison, at least one of the groups involved in calculating p-values contains more than 50% significantly non-log normally distributed tumour growth rates.

Survival analysis showed that FS20m-232-91AA/Lob12.3 led to statistically significant improvement in survival compared to isotype control using log-rank (Mantel-Cox) test (p≤0.0001) (FIG. 10D). Tumour-bearing mice receiving either the anti-mouse CD137 mAb, mouse OX40/FITC mock mAb$^2$ or combination thereof showed no statistically significant differences in survival compared to isotype control.

In conclusion, the results demonstrate that the FS20m-232-91AA/Lob12.3 mAb$^2$ had greater and non-equivalent anti-tumour activity to the combination of its component Fcab and Fab parts, or either component part alone.

Example 18—Pharmacodynamic Response of OX40/CD137 mAb$^2$ in a CT26 Syngeneic Tumour Model 18.1 Comparison of Pharmacodynamic Response of OX40/CD137 mAb$^2$ and Anti-OX40 and anti-CD137 control mAbs The pharmacodynamic response of the OX40/CD137 surrogate mAb$^2$ was assessed in mice bearing CT26 syngeneic tumours. To this end, blood samples were taken from CT26-bearing mice inoculated with the FS20m-232-91AA/Lob12.3 mAb$^2$, isotype control (G1/4420), single-agent anti-mouse OX40 control (G1/OX86), single-agent anti-mouse CD137 control (G1/Lob12.3) or a combination of these anti-OX40 and anti-CD137 controls (G1/OX86 plus G1/Lob12.3) over a timecourse and analysed by flow cytometry for T cell activation and proliferation markers.

Following the same protocol as described in Example 17, BALB/c female mice (Charles River) aged 8-10 weeks and weighing approximately 20 g each were prepared for the study start and inoculated with the CT26 colon carcinoma cell line (ATCC, CRL-2638). On day 10 following tumour cell inoculation, tumours were measured and mice were randomised into study cohorts of 10 mice per group based on tumour volume. Any mice which did not have tumours at this point were removed from the study.

Antibodies were analysed and checked for impurities as previously described, diluted to a final concentration of 0.1 mg/ml in PBS, and 200 μl/mouse were injected, giving a final dose of 1 mg/kg for a 20 g mouse. The antibodies were administered to the mice by intraperitoneal (IP) injection on days 10, 12 and 14 following tumour inoculation.

Blood was collected into EDTA-containing tubes from the tail vein 1 hour before dosing on day 10, on day 11 (24 hours after the first dose), on day 15 (24 hours after the third dose), and by cardiac puncture on day 17 and day 24. Red blood cells of the uncoagulated blood were lysed twice in red blood cell lysis buffer (eBioscience cat no 00-4300-54) according to manufacturer's instruction. The cells were stained for flow cytometry using either stain 1 (CD4-E450 (clone GK1.5), Ki67-FITC (clone bSolA15), Foxp3-PE (clone FJK-16s), CD69-PECy5 (clone H1.2F3), CD3-PECy7 (clone 145-2C11), CD8-APC (done 53-6.7), fixable viability die 780, all supplied by eBioscience; and CD45-V500 (done 30-F11), supplied by BD Bioscience) or stain 2 (CD49b-E450 (clone DX5), F4/80-PE (clone 6F12), CD69-PECy5 (clone H1.2F3), CD19-PECy7 (clone 1D3), CD3-APC (done 145-2C11), and fixable viability die 780, all supplied by eBioscience; CD45-V500 (clone 30-F11), supplied by BD Bioscience; and anti-hFc-488 (polyclonal), supplied by Jackson ImmunoResearch) in the presence of Fc block (eBioscience cat no 14-0161-86 at 1:100). Cells were then washed once with PBS and samples stained with stain 2 were resuspended in 200 μl PBS and run on the FACS Canto II. For samples stained with stain 1, the cells were initially stained with 100 μl of antibody mix 1 (all but Ki67 and FoxP3 antibodies) for 30 minutes at 4° C. The cells were then fixed and permeabilized with the eBioscience Foxp3 staining kit (eBioscience cat no 00-5523-00) according to manufacturer's instructions. Briefly, 200 μl fixing solution was added to each well and left overnight in the dark at 4° C. Cells were then washed in 200 μl permeabilization buffer. Cells were then spun again and resuspended in 100 μl permeabilization buffer with Ki67 and Foxp3 antibodies in the presence of Fc block (all in 1:100 dilution) and incubated 30 minutes in the dark at 4° C. Cells were then washed once with permeabilization buffer and resuspended in 200 μl PBS. The cells were then analysed in a BD FACS Cantoll cytometer. Data was analysed with FlowJoX. Excell and GraphPad Prism. T cell activation and proliferation observed over time for total T cells, as well as CD4+ and CD8+ subpopulations, were determined.

This experiment showed that the OX40/CD137 mAb$^2$ had an effect on circulating T cells, increasing the frequency of activated T cells (CD45+CD3+CD69+) and CD4+ T cells (CD45+CD3+CD4+CD69+) and proliferating T cells (CD45+CD3+Ki67+), CD4+ T cells (CD45+CD3+CD4+Ki67+) and CD8+ T cells (CD45+CD3+CD8+Ki67+) compared to all control-treated groups, and also increasing the frequency of activated CD8+ T cells (CD45+CD3+CD8+CD69+) compared to treatment with either the anti-OX40 control or the anti-CD137 control alone, or the isotype control. A similar increase in the frequency of activated CD8+ T cells (CD45+CD3+CD8+CD69+) was observed for the control group treated with the combination of the anti-OX40 and anti-CD137 control mAbs. These results are in agreement with the observed in vitro results where the OX40/CD137 mAb$^2$ also showed an increase in the activation of T cells as measured by the production of IL-2, which is also known to be a cytokine involved in the proliferation of T cells.

18.2 Comparison of Pharmacodynamic Response of OX40/CD137 mAb² and its Component Fcab and Fab Parts The peripheral pharmacodynamic response of the mouse OX40/CD137 mAb² (FS20m-232-91AA/Lob12.3) was compared to that of its component parts, specifically the FS20m-232-91AA Fcab in mock (4420) mAb² format (FS20m-232-91AA/4420) and the monospecific anti-mouse CD137 mAb without the Fcab (G1AA/Lob12.3) as single agents or in combination, or of isotype control (G1AA/4420) in the CT26 tumour model.

In the same study described in Example 17.2, on day 16 following CT26 cell- inoculation, blood samples were taken from the tail veins of 10 mice per group and collected in EDTA-containing tubes. Following the same methods described in Example 18.1, red blood cells were lysed, the remaining cells were then stained with viability dye, followed by surface staining with the reagents listed in Example 22.2.2 (with the exception that anti-mouse CD4 clone GK1.5 (BD Bioscience, catalogue no. 563790) was used for this study instead of anti-CD4 done RM4-5), except for anti-Ki67 and anti-Foxp3 antibodies, in the presence of Fc block. The cells were then fixed and permeabilised overnight with the eBioscience Foxp3 staining kit (eBioscience) according to manufacturer's instructions. Cells were then intracellularly stained with anti-Ki67 and anti-Foxp3 antibodies. Following washing, the cells were then analysed using a BD Fortessa flow cytometer. Data analysis was performed using FlowJo, Excel and GraphPad Prism 7 software.

FS20m-232-91AA/Lob12.3 was observed to significantly increase the proportions of Ki67t CD4⁺ effector (as % of total CD4⁺Foxp3⁻ cells) and Ki67⁺CD8⁺ peripheral T-cells (as % of total CD8⁺ cells) in the blood compared to isotype control treatment. The anti-mouse CD137 mAb and FS20m-232-91AA/4420 mock mAb², either as single agents or in combination, were also able to induce significant increases in levels of proliferating Ki67⁺CD4⁺ effector and Ki67⁺ CD8⁺ T-cells relative to isotype control-treated mice. However, increases in levels of Ki67⁺CD8⁺ proliferating T-cells following dosing with FS20m-232-91AA/Lob12.3 were significantly greater than those observed for either the anti-mouse CD137 mAb alone, the FS20m-232-91AA/4420 mock mAb² alone or their combination.

In conclusion, these findings demonstrate that the FS20m-232-91AA/Lob12.3 mAb² was able to induce an enhanced peripheral pharmacodynamic response, with respect to increases in frequency of Ki67⁺CD8⁺ proliferating T-cells, compared to the combination of its component Fcab and Fab parts, or either component part alone.

Example 19- Mechanism of Action of OX40/CD137 mAb² in a CT26 Syngeneic Tumour Model The CT26 syngeneic tumour model was used to determine the mechanism of action (MOA) of the anti-tumour activity of the anti-mouse OX40/CD137 mAb² in vivo. The CT26 syngeneic tumour model has previously been shown to be sensitive to both OX40 and CD137 agonist antibodies (Sadun et al., 2008), and tumour infiltrating lymphocytes (TILs) isolated from CT26 tumours are expected express both OX40 and CD137. The antibodies tested are detailed in Table 30.

TABLE 30

Details of antibodies and mAb² tested

| mAb/mAb² | Fab binding to | Fcab binding to | Isotype | LALA mutation | Heavy chain SEQ ID | Light chain SEQ ID |
|---|---|---|---|---|---|---|
| G1/4420 | FITC | none | hIgG1 | No | 115 | 116 |
| G1/OX86 | mOX40 | none | hIgG1 | No | 159 | 156 |
| G1/Lob12.3 | mCD137 | none | hIgG1 | No | University of Southampton | |
| G1AA/OX86 | mOX40 | none | hIgG1 | Yes | 155 | 156 |
| G1AA/Lob12.3 | mCD137 | none | hIgG1 | Yes | Creation described above in Example 9.2 | |
| FS20m-232-91/Lob12.3 | mCD137 | mOX40 | hIgG1 | No | | |
| FS20m-232-91AA/Lob12.3 | mCD137 | mOX40 | hIgG1 | Yes | | |

The ability of the mAb², with or without the LALA mutation (FS20m-232-91AA/Lob12.3 and FS20m-232-91/Lob12.3, respectively), to activate and induce the proliferation of T cells in the blood and tumour was compared to isotype control mAb G1/4420 (anti-FITC), single-agent mAb G1/OX86 (anti-OX40 control without the LALA mutation) or G1/Lob12.3 (anti-CD137 control without the LALA mutation), a combination of G1/OX86 plus G1/Lob12.3, or a combination of G1AA/OX86 (anti-OX40 mAb with the LALA mutation) plus G1AA/Lob12.3 (anti-CD137 mAb with the LALA mutation).

BALB/c female mice (Charles River) aged 8-10 weeks and weighing approximately 20 g each were rested for one week prior to the study start. All animals were microchipped and given a unique identifier. Each cohort had 5 mice. The CT26 colon carcinoma cell line (ATCC, CRL-2638) was initially expanded, stored, and then pre-screened by IDEXX Bioresearch for pathogens using the IMPACT I protocol and shown to be pathogen free. CT26 cells (approximately $3-5 \times 10^6$) were thawed from $-150°$ C., storage and added to 20 ml D MEM (Gibco, 61965-026) with 10% FCS (Gibco, 10270-106) in a T175 tissue culture flask. Mice were anaesthetised using isoflurane (Abbott Laboratories) and each animal received $1 \times 10^8$ cells injected subcutaneously in the left flank. On day 10 following tumour cell inoculation, mice were monitored for health, tumours were measured using callipers and mice were randomised into study cohorts based on tumour volume. Any mice which did not have tumours at this point were removed from the study.

The injected antibodies were analysed within 24 hours of injection by SEC-HPLC profiling and checked for impurities. Antibodies were diluted to final concentration of 0.1 mg/ml in PBS and 200 μl/mouse were injected, giving a final dose of 1 mg/kg for a 20 g mouse. The antibodies were administered to the mice by intraperitoneal (IP) injection on days 10, 12 and 14 following tumour inoculation. Tumour volume measurements were taken three times per week with callipers to determine the longest axis and the shortest axis of the tumour. Seven days after the third dose (day 21 post tumour inoculation) mice were euthanized, tumours were Isolated by dissection and blood was collected by cardiac puncture.

Tumours were dissociated using the Tumour dissociation kit, mouse (Miltenyi 130-096-730) according to manufacturer's instructions. Briefly, enzyme mix was prepared by adding 2.35 ml RPMI 1640, 100 µl enzyme D, 50 µl enzyme R and 12.5 µl enzyme A per tumours and each tumour was placed in a gentle MACS C tube and that tube was placed on the Gentle MACS dissociator and run on the m_TDK_1 program and then incubated for 1 h at 37° C. with shaking (200 rpm). The resulting cell suspension was strained using a 70 µM cell strainer (Corning cat no 352350), centrifuged (10 minutes at @ 1500 rpm), washed once in PBS and resuspended in 5 ml PBS.

Blood was collected by cardiac puncture into EDTA containing tubes. Red blood cells of the uncoagulated blood were lysed twice in red blood cell lysis buffer (eBioscience cat no 00-4300-54) according to manufacturer's instruction.

The cells isolated from tumours and blood were stained for flow cytometry using the following antibody panel and reagents (Stain 1): CD4-E450 (clone GK1.1). Ki67-FITC (clone SolA15), Foxp3-PE (FJK-16s), CD69-PECy5 (clone H1.2F3), CD3-PECy7 (clone 145-2C11), CD8-APC (clone 53-6.7), fixable viability die 780, and Fc block (clone 93), all supplied by eBioscience; and CD45-V500 (done 30-F11), supplied by BD Bioscience. Cells were washed in PBS and then incubated with 100 µl of antibody mix 1 (all but Ki67 and FoxP3 antibodies) for 30 minutes at 4° C. The cells were then washed with PBS and then fixed and permeabilized with the eBioscience Foxp3 staining kit (eBioscience cat no 00-5523-00) according to manufacturer's instructions. Briefly, 200 µl fixing solution was added to each well and left overnight in the dark at 4° C. Cells were then washed in 200 µl permeabilization buffer. Cells were then spun again and resuspended in 100 µl permeabilization buffer with Ki67 and Foxp3 antibodies in the presence of Fc block (all in 1:100 dilution) and incubated 30 minutes in the dark at 4° C. Cells were then washed once with permeabilization buffer and resuspended in 200 µl PBS. The cells were then analysed in a BD FACS Cantoll cytometer.

Data was analysed with FlowJoX, Excell and GraphPad Prism. Statistical analysis to compare groups was performed using one-way ANOVA followed by Tukey's multiple comparison test of every pair using the GraphPad Prism software package. The frequency of T cells (CD45+CD3+), proliferating T cells (CD45+CD3+Ki67+) and T regulatory cells (CD45+CD3+CD4+ FoxP3+) in the blood or tumours of mice that were inoculated with CT26 cells following treatment with the OX40/CD137 mAb$^2$ or controls was determined. FS20m-232-91AA/Lob12.3 mAb$^2$ showed a statistically significant Increase in proliferating T cells as well as an increase in Tregs in the blood as compared to the isotype control (G1l4420). In the tumour there was a trend for the FS20m-232-91AA/Lob12.3 mAb$^2$ to increase the frequency of T cells.

There was a statistically significant decrease in the levels of Tregs in the tumour in mice treated with the anti-CD137 antibody G1/Lob12.3 and the combination of this anti-CD137 antibody with the anti-OX40 antibody G1/OX86, as compared to treatment with the isotype control. However, when the LALA-mutation was introduced into the anti-OX40 and anti-CD137 antibodies, treatment with the combination of these antibodies (G1AA/OX86 plus G1AA/Lob12.3) no longer reduced the levels of Tregs in tumours. The OX40/CD137 mAb$^2$ containing the LALA mutation (FS20m-232-91AA/Lob12.3) did not reduce the levels of Tregs but a wild-type human IgG1 version of the OX40/CD137 mAb$^2$ without the LALA mutation (FS20m-232-91/Lob12.3) did show a statistically significant decrease in the levels of Tregs in the tumour.

These data demonstrate that the introduction of the LALA mutation Into human IgG1 abrogates the ability of an OX40/CD137 mAb$^2$ to deplete Tregs and, therefore, that the anti-tumour activity observed with the human IgG1 LALA variant of OX40/CD137 mAb$^2$ (FS20m-232-91 AA/Lob12.3) is independent of Treg depletion. Furthermore, the FS20m-232-91AA/Lob12.3 mAb$^2$ was observed to induce T cell proliferation in the periphery at the timepoint assessed which is anticipated to expand the pool of T cells eliciting the anti-tumour immune response. These data suggest that human IgG1 LALA-containing OX40/CD137 mAb$^2$ have the potential for anti-tumour activity in cancers in the absence of engagement of the mAb$^2$ with Fcγ receptors, which may or may not be prevalent in the tumour.

Example 20—Activity of Anti-Mouse OX40/CD137 mAb$^2$ in a B16-F10 Syngeneic Tumour Model The B16-F10 syngeneic tumour model was used to test the anti-tumour activity of the anti-mouse OX40/CD137 mAb$^2$ (FS20m-232-91AA/Lob12.3) in vivo. Antibody G1/4420 was used as a control in the study. The B16-F10 syngeneic tumour model has not been previously shown to be sensitive to OX40 or CD137 agonist antibodies (Hirschhom-Cymerman et al., 2009; Wilcox el al., 2002). However, tumour infiltrating lymphocytes (TILs) isolated from B16-F10 tumours are expected to express both OX40 and CD137.

C57BL/6 female mice (Charles River) aged 8-10 weeks and weighing approximately 20 g each were acclimatised for one week prior to the study start. All animals were microchipped and given a unique identifier. Each cohort had 10 mice. The B16-F10 colon carcinoma cell line (ATCC cat. no. CRL-6475) was initially expanded, stored, and then pre-screened by IDEXX Bioresearch for pathogens using the IMPACT I protocol and shown to be pathogen free.

B16-F10 cells were thawed from −150° C., storage and added to 20 ml D MEM (Gibco, 61965-026) with 10% FCS (Gibco, 10270-106) in a T175 tissue culture flask. Each animal received 1×10$^6$ cells injected subcutaneously in the left flank. 7-8 days following tumour cell inoculation, mice which did not have tumours at this point were removed from the study.

Antibodies were analysed and checked for impurities as previously described before being injected at a final concentration of 0.1 mg/ml in PBS, in a volume of 200 µl/mouse, to give a final dose of 1 mg/kg for a 20 g mouse. Each mouse received the antibodies by intraperitoneal (IP) injection on days 8, 10, and 12 following tumour inoculation. Tumour volumes were determined by measuring using callipers (as described in Example 17) and any drug dosing due on the day in question was performed.

Figure 11:
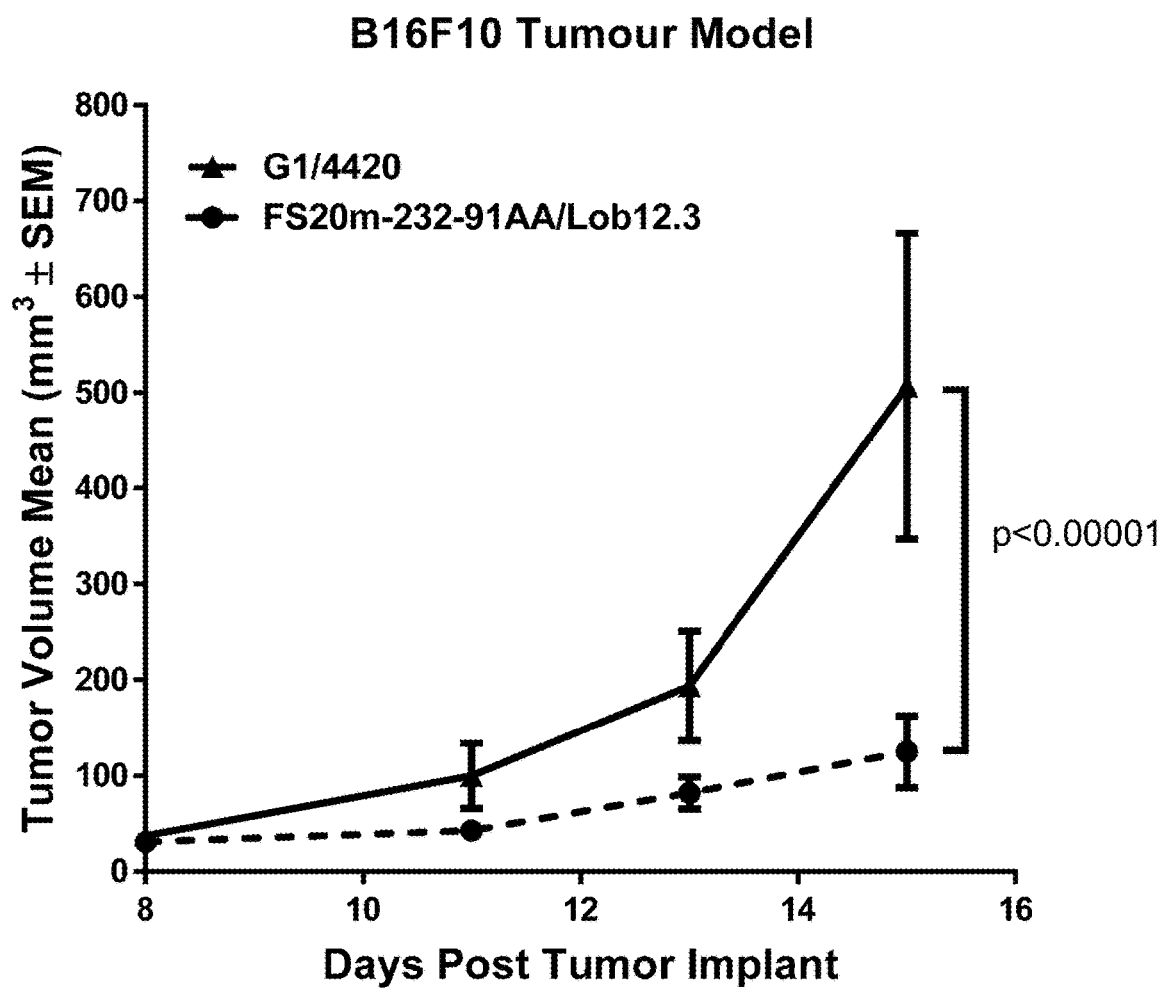
FIG. 11 shows the anti-tumour activity of an anti-mouse OX40/CD137 mAb$^2$ in a B16-F10 syngeneic tumour model. Mice were treated with FS20m-232-91AA/Lob12.3 (OX40/CD137 mAb$^2$) or G1/4420 (IgG control). The mean tumour volume plus or minus the standard error mean is plotted. The results show that the OX40/CD137 mAb$^2$ was able to significantly reduce tumour growth in a B16-F10 syngeneic model compared to mice treated with the G1/4420 control antibody.

Mice were sacrificed when humane endpoints were reached, based on tumour volume and condition. Statistical analysis of the tumour growth was performed using the mixed model statistical analysis described in Example 17. The results of the study are shown in FIG. 11.

The OX40/CD137 mAb$^2$ (FS20m-232-91AA/Lob12.3) showed significant anti-tumour activity. as compared to the control animals injected with the control antibody (G1/4420). This is surprising as this model has previously been shown to be insensitive to OX40 or CD137 stimulation (Hirschhorn-Cymerman et al., 2009; Wilcox et al., 2002). Importantly, the activity observed for the OX40/CD137 mAb$^2$ was in the presence of the LALA mutation and therefore was not dependent on tumour Treg depletion. This indicates that the MOA of the OX40/CD137 mAb$^2$ results in anti-tumour activity in a variety of syngeneic tumour models, even those with lower levels of immune infiltrate such as B16-F10.

Example 21—Analytical Characterisation and Preliminary Stability Assessment of OX40/CD137 mAb$^2$ 21.1 Expression, Purification and Analytical Characterisation of mAb$^2$ The mAb$^2$ FS20-22-49AA/FS30-5-37, FS20-22-49AA/FS30-10-3, FS20-22-9AA/FS30-10-12, FS20-22-49AA/FS30-10-16 and FS20-22-49AA/FS30-35-14 were produced at lab-scale, and characterised by standard analytical methods using SE-HPLC and SDS-PAGE.

DNA sequences encoding the mAb$^2$ were expressed transiently in HEK293-6E (National Research Council Canada). After 5 days, cell culture fluids were harvested, and purified on MabSelect Protein-A pre-packed columns using an AKTAxpress Instrument (both GE Healthcare). Equilibration of the columns was carried out in 50 mM Tris-HCl. 250 mM NaCl pH 7.0 followed by loading with harvested cell culture fluid. The resin was then subjected to a wash using 50 mM Tris-HCl, 250 mM NaCl at pH 7.0 and this was followed by eluting the mAb$^2$ using buffer at pH of 3.5. The mAb$^2$ were buffer exchanged to a pre-formulation buffer using PD-10 desalting columns (GE Healthcare, product no. 17085101).

SE-HPLC was performed on and Agilent 1100 Series HPLC System (Agilent), fitted with a TSK-GEL SUPERSW3000 4.6 mm ID×30.0 cm column (Tosoh Bioscience) using 20 mM sodium phosphate, 200 mM sodium chloride, pH 6.8 as a mobile phase. Quantification of the percentage of monomer was performed using Chemstation software (Agilent). The results of the SE-HPLC analysis are summarised in Table 31.

TABLE 31

Analytical characterisation by SE-HPLC

| mAb$^2$ | % monomer by SE-HPLC |
|---|---|
| FS20-22-49AA/FS30-5-37 | 98.4% |
| FS20-22-49AA/FS30-10-3 | 97.4% |
| FS20-22-49AA/FS30-10-12 | 95.9% |
| FS20-22-49AA/FS30-10-16 | 97.5% |
| FS20-22-49AA/FS30-35-14 | 97.3% |

SDS-PAGE analysis was performed using NuPAGE® Novex® 4-12% Bis-Tris Protein Gels and 1×MOPS separation buffer (Thermo Fisher Scientific), essentially following the manufacturer's instructions. For non-reducing SDS-PAGE, samples were exposed to alkylation reagent, N-ethylmaleimide (Sigma-Aldrich) prior to a denaturation step, and 2-mercaptoethanol was omitted from the denaturation mix. Protein bands were visualised by Coomassie InstantBlue (Expedeon).

All five mAb$^2$ showed favourable analytical characterisation parameters following protein A purification with monomer purity higher than 95% when determined by SE-HPLC. The SDS-PAGE analysis revealed protein band patterns typical for recombinant IgG1. Thus, under the non-reducing conditions, a single band migrated to the region corresponding to the expected molecular weight, and under the reducing conditions, two bands migrated close to the 51 kDa and 28 kDa molecular weight markers, corresponding to the heavy chain and light chain, respectively. No fragmentation was observed (data not shown).

21.2 Preliminary Stability Assessment of OX40/CD137 mAb$^2$

A preliminary assessment of the stability of mAb$^2$ FS20-22-49AA/FS30-5-37, FS20-22-49AA/FS30-10-3, FS20-22-49AA/FS30-10-12, FS20-22.49AA/FS30-10-16 and FS20-22-49AA/FS30-35-14 was performed. Before entering preliminary stability assessment, the mAb$^2$ were further purified by size exclusion chromatography (SEC) using a Superdex HiLoad 26/600 200 pg column (GE Healthcare) equilibrated with a pre-formulation buffer. The stability samples were stored at 5° C. and analysed after 2 and 4 weeks by standard analytical methods using SE-HPLC and Capillary Electrophoresis Sodium Dodecyl Sulphate (CE-SDS).

SE-HPLC was performed on an Agilent 1100 series HPLC System (Agilent), fitted with a TSK-GEL SUPERSW3000 4.6 mm ID×30.0 cm column (Tosoh Bioscience) using 20 mM sodium phosphate, 200 mM sodium chloride, pH 6.8 as a mobile phase. The data acquisition and quantification of monomer content was performed using Chemstation software (Agilent). The results are summarised in Table 32.

After storage at 5° C. for 4 weeks, the monomer content as determined by SE-HPLC for all mAb$^2$ tested remained comparable (within ±0.9%) to the starting material (T=0). Therefore, all mAb$^2$ tested displayed a favourable stability profile.

TABLE 32

Stability analysis by SE-HPLC

| mAb$^2$ | % monomer T = 0 | % monomer T = 2 weeks at 5° C. | % monomer T = 4 weeks at 5° C. |
|---|---|---|---|
| FS20-22-49AA/FS30-5-37 | 100.0 | 99.2 | 99.1 |
| FS20-22-49AA/FS30-10-3 | 100.0 | 100.0 | 99.9 |
| FS20-22-49AA/FS30-10-12 | 100.0 | 100.0 | 100.0 |
| FS20-22-49AA/FS30-10-16 | 100.0 | 100.0 | 100.0 |
| FS20-22-49AA/FS30-35-14 | 99.5 | 99.2 | 99.3 |

CE-SOS analysis was performed on a 2100 Bioanalyzer Capillary Electrophoresis System (Agilent), following the manufacturer's recommendations. For reducing CE-SOS, OTT was added and samples were denatured at 70° C. for 5 minutes. The data acquisition and percentage quantification of heavy chain and light chain material was performed using 2100 Expert software (Agilent). The percentage purity was calculated as the sum of the percentage of heavy chain material and the percentage of light chain material. The results of the analysis are summarised in Table 33.

The purity of all of the mAb$^2$ tested, determined as the sum of the percentage of heavy chain material and light chain material by CE-SDS under reducing conditions, also remained comparable (within ±1.0%) to the starting material. Therefore, again, all mAb$^2$ tested showed favourable stability.

TABLE 33

Stability analysis by CE-SDS

| mAb² | % purity T = 0 | % purity T = 2 weeks at 5° C. | % purity T = 4 weeks at 5° C. |
|---|---|---|---|
| FS20-22-49AA/FS30-5-37 | 99.6 | 99.7 | 99.1 |
| FS20-22-49AA/FS30-10-3 | 99.5 | 99.6 | 99.5 |
| FS20-22-49AA/FS30-10-12 | 98.8 | 99.2 | 99.5 |
| FS20-22-49AA/FS30-10-16 | 99.5 | 99.1 | 98.5 |
| FS20-22-49AA/FS30-35-14 | 99.6 | 99.0 | 100.0 |

Example 22-Activity of OX40/CD137 mAb² in Combination with an Anti-PD-1 or Anti-PD-L1

PD-L1 expression on antigen-presenting cells (e.g. dendritic cells, macrophages, B-cells). tumour cells, and on cells in the tumour microenvironment is known to inhibit the activation, proliferation, and effector and cytotoxic functions of T cells through PD-1 interaction. Blocking this interaction using monoclonal antibodies against either PD-1 or PD-L1 has been shown to result in increased survival rates in patients with several types of cancer.

However, in some tumours, anti-PD-L1 and anti-PD-1 antibodies have little or no effect. The present inventors have tested the combination of an OX40/CD137 mAb² with an anti-PD-L1 or anti-PD-1 antibody in in vitro and in vivo studies to understand whether use of the combination could result in an improved effect compared with the use of the OX40/CD137 mAb², anti-PD-L1 antibody or anti-PD-1 antibody alone.

22.1 Activity of OX40/CD137 mAb² in Combination with PD-1 or PD-L1 Blockade in a Staphylococcal Enterotoxin a (SEA) Assay The activity of the OX40/CD137 mAb² was tested in a T cell activation assay using staphylococcal enterotoxin A (SEA) superantigen as the first signal as described in Example 12 above. To test the effect of the OX40/CD137 mAb² on T cell stimulation activity in combination with blocking of the interaction between PD-1 and PD-L1, PD-1 or PD-L1 blocking antibodies were combined with the OX40/CD137 mAb² in the SEA assay.

The antibodies and mAb² used in the SEA assay are listed in Table 34 below. G1/4420 (anti-FITC) in combination with FS20-22-49AA/FS30-10-16 mAb², G1AA/S1 (anti-PD-L1), G1AA/5C4 (anti-PD-1) alone or in combination with FS20-22-49AA/FS30-10-16 mAb² were tested. Interleukin-2 (IL-2) production was used as a measure of T cell activation.

TABLE 34

Details of antibodies and mAb² tested

| mAb/mAb² | Fab binding to | Fcab binding to | Isotype | LALA mutation | Heavy chain SEQ ID NO | Light chain SEQ ID NO |
|---|---|---|---|---|---|---|
| G1/4420 | FITC | none | hIgG1 | No | 115 | 116 |
| FS20-22-49AA/FS30-10-16 | hCD137 | hOX40 | hIgG1 | Yes | 95 | 14 |
| G1AA/S1 | PD-L1 | none | hIgG1 | Yes | 162 | 163 |
| G1AA/5C4 | PD-1 | none | hIgG1 | Yes | 160 | 161 |

The variable domain sequences of the 5C4 and YW243.55.S1 (S1) antibodies are also disclosed in U.S. Pat. No. 8,008,449 B2 and US 2013/0045202 A1, respectively.

PBMCs were isolated and the SEA assay was performed essentially as described in Example 12.1 above. G1/4420 was used as an isotype control and no crosslinking agents were used in the assays.

Figure 12:
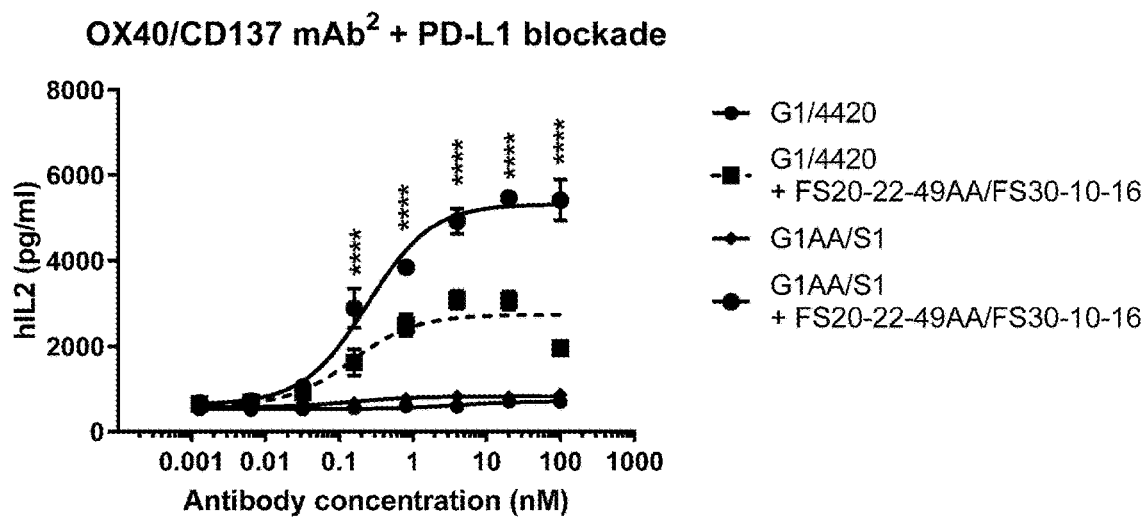
FIG. 12 shows the activity of an OX40/CD137 mAb$^2$ in combination with an anti-PD-1 or anti-PD-L1 antibody in a SEA assay. The mAb$^2$ tested was FS20-22-49AA/FS30-10-16. Controls were G114420 (anti-FITC), G1AA/S1 (anti-PD-L1.
Figure 12:
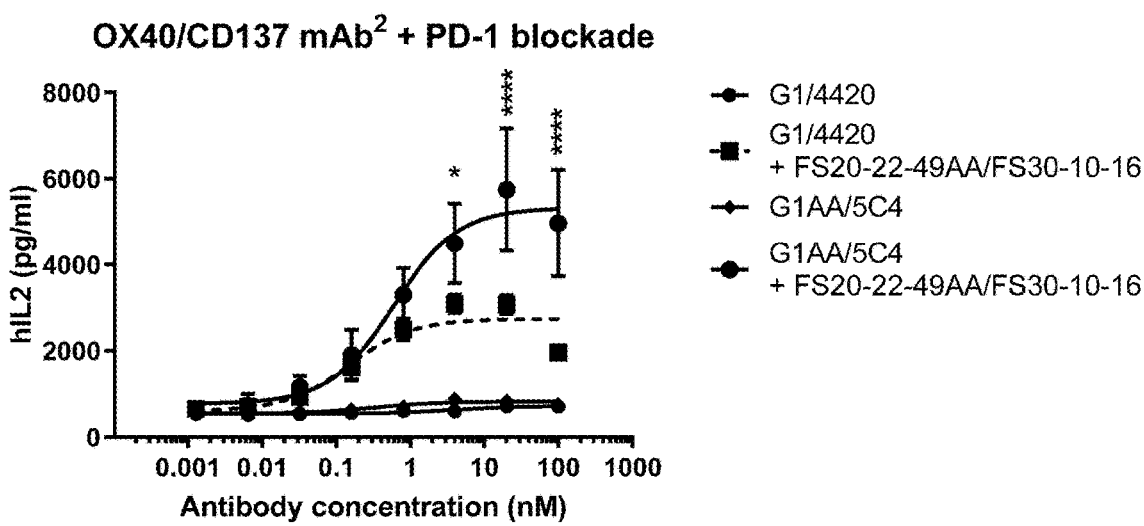

The activity of the OX40/CD137 mAb² (FS20-22-49AA/FS30-10-16) in combination with either an anti-PD-L1 (G1AA/S1) or anti-PD-1 antibody (G1AA/5C4) was compared to the activity of FS20-22-49AA/FS30-10-16 mAb² plus isotype control (G1/4420) or to the activity of the PD-L1 antibody (G1AA/S1), or PD-1 antibody (G1AA/5C4), or isotype control (G1/4420) alone. The EC$_{50}$ values and maximum response of the IL-2 release observed in the SEA assay are shown in Table 35. FIGS. 12A and B show plots of IL-2 release for the SEA assay.

TABLE 35

SEA assay with mAb² targeting OX40 and CD137 in combination with antibodies blocking the interaction between PD-1 or PD-L1

| mAbs/mAb² | EC$_{50}$ (nM) | 95% Conf. Int. | Max response (hIL-2 pg/ml) | 95% Conf. Int. |
|---|---|---|---|---|
| G1/4420 | NAD | NAD | NAD | NAD |
| FS20-22-49AA/FS30-10-16 + G1/4420 | 0.1483 | 0.04556 to 0.4517 | 2741 | 2394 to 3103 |
| G1AA/504 | NAD | NAD | NAD | NAD |
| G1AA/S1 | NAD | NAD | NAD | NAD |
| FS20-22-49AA/FS30-10-16 + G1AA/5C4 | 0.5939 | 0.1964 to 1.732 | 5326 | 4599 to 6116 |
| FS20-22-49AA/FS30-10-16 + G1AA/S1 | 0.2399 | 0.1478 to 0.3970 | 5325 | 5022 to 5640 |

NAD = no activity detected

As expected, no activity was observed with the isotype control (G1/4420). Likewise, blocking the interaction between PD-1 and PD-L1 alone had no activity in this assay. However, combining stimulation of OX40 and CD137 receptors (by the OX40/CD137 mAb²) with blockade of the interaction between PD-1 and PD-L1 (by either an anti-PD-L1 or anti-PD-1 antibody) resulted in an increase in the maximal activity of T cells, as measured by max IL-2 production, above that seen with the OX40/CD137 mAb² alone. The increase in the maximal activity of T cells seen when the OX40/CD137 mAb² was combined with an anti-PD-L1 or anti-PD-1 antibody was similar.

22.2 Anti-Tumour Activity and Pharmacodynamic Response of Administration of an Anti-Mouse OX40/CD137 mAb$^2$ and a PD-1 Antagonist in a CT26 Mouse Tumour Model The CT26 mouse tumour model was used to establish the anti-tumour activity and pharmacodynamic response of the combination of FS20m-232-91AA/Lob12.3 and a PD-1 antagonist antibody (clone RMP1-14 mouse IgG1) compared to either single agent.

22.2.1 Evaluation of Anti-Tumour Activity

Following the same protocol as described in Example 17, BALB/c female mice (Charles River) aged 8-10 weeks and weighing approximately 20 g were prepared for the study start and inoculated with the CT26 colon carcinoma cell line. 10 days following tumour cell inoculation, tumours were measured, any mice which did not have tumours were removed from the study and remaining mice were randomised into 4 treatment groups (Table 36) with 15 animals per group. Animals were injected intraperitoneally with: (1) a combination of 1 mg/kg of G1AA/4420 and 10 mg/kg of mIgG1/4420 isotype (Absolute Antibodies, Clone 4420, Catalogue number Ab00102-1.1) control antibodies, (2) 10 mg/kg of an anti-mouse PD-1 antibody (Absolute Antibodies, done RMP1-14 mouse IgG1,Catalogue number Ab00813-1.1), (3) 1 mg/kg of FS20m-232-9 I AA/Lob12.3 mAb$^2$, or (4) 10 mg/kg anti-mouse PD-1 antibody and 1 mg/kg FS20m-232-91AA/Lob12.3 mAb$^2$ in PBS. Animals received intraperitoneal (IP) injections of G1AA/4420 or FS20m-232-91AA/Lob12.3 once every 2 days for a total of 3 doses starting on day 10 following tumour inoculation. mIgG1/4420 or anti-mouse PD-1 antibody were dosed IP once every 4 days for a total of 4 doses starting on day 10 following tumour inoculation. Tumour volumes were determined by calliper measurements (as described in Example 17). The study was terminated 60 days after tumour cell inoculation, animals were taken off study when humane endpoints were reached based on tumour volume and condition. The treatment groups, molecules tested, doses, and dosing schedule are summarised in Table 36.

TABLE 36

Summary of treatment groups and molecules tested

| Group | Group name | mAb and/or mAb$^2$ administered | Dose (mg/kg) | Dosing Schedule |
|---|---|---|---|---|
| 1 | Isotype controls | G1AA/4420, mIgG1/4420 | 1, 10 | Q2D, Q4D |
| 2 | Anti-PD-1 | Anti-mouse PD-1 mIgG1 (RMP1-14) | 10 | Q4D |
| 3 | FS20m-232-91AA/Lob12.3 | FS20m-232-91AA/Lob12.3 | 1 | Q2D |
| 4 | FS20m-232-91AA/Lob12.3 + anti-PD-1 | FS20m-232-91AA/Lob12.3, Anti-mouse PD-1 mIgG1 | 1, 10 | Q2D, Q4D |

Figure 13:
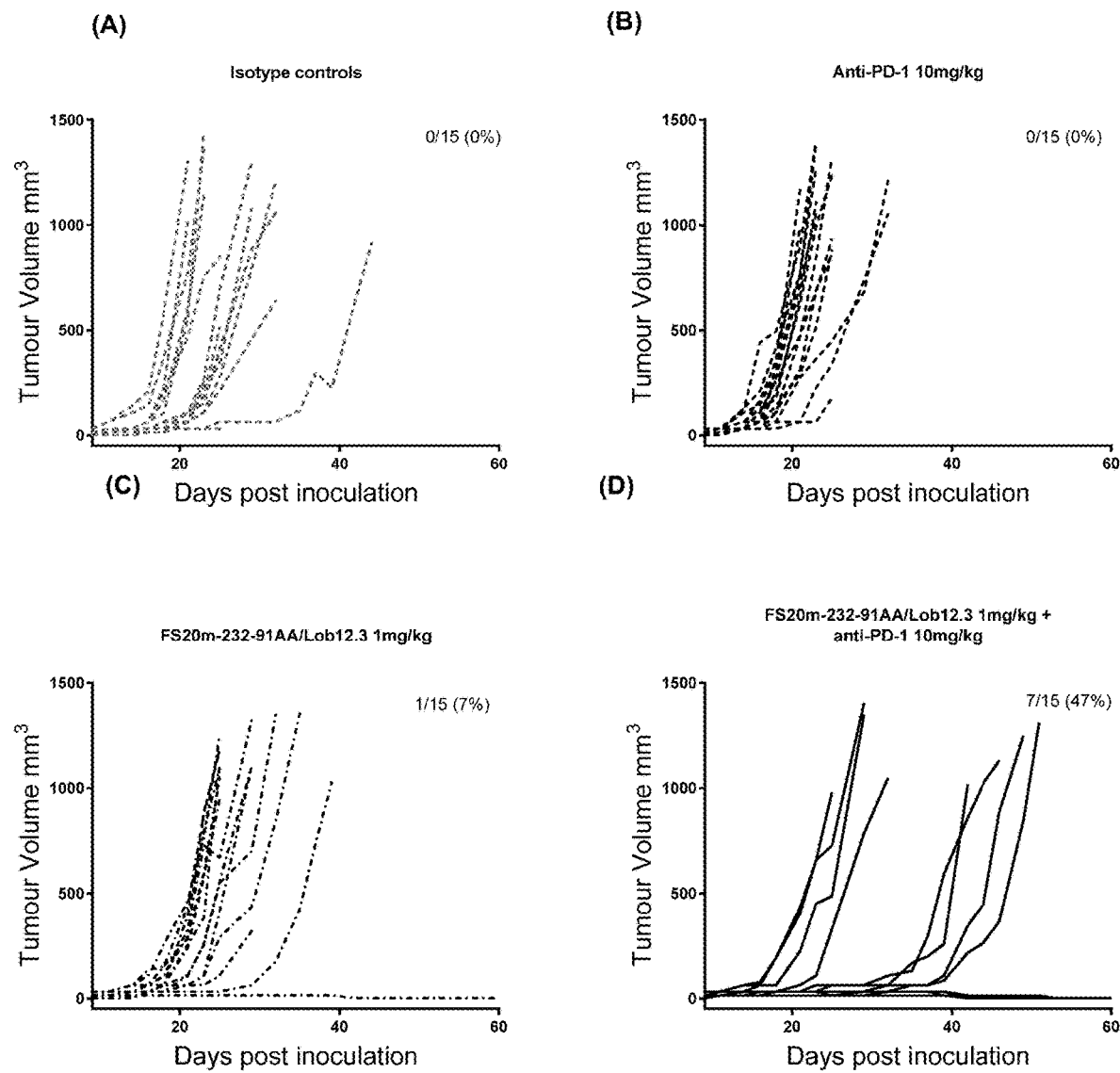
FIG. 13 shows the anti-tumour activity of an anti-mouse OX40/CD137 mAb$^2$ and a PD-1 antagonist in a CT26 mouse tumour model, tested singly and in combination. The tumour volumes in CT26-tumour bearing mice treated with (FIG. 13A) a combination of isotype control antibodies (G1AA/4420 and mIgG1/4420).
Figure 13:
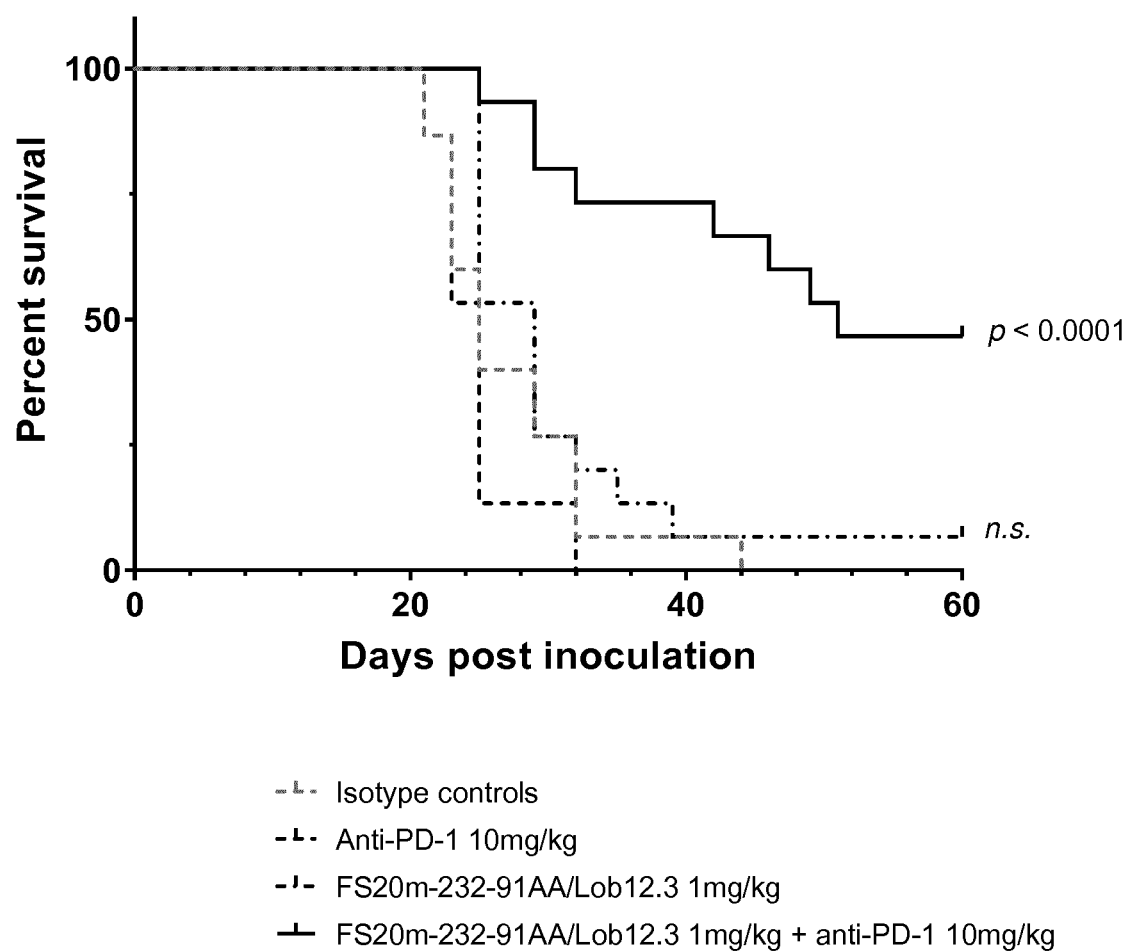

As shown in FIG. 13A-D. the combination of an anti-PD-1 antagonist antibody and 1 mg/kg of FS20m-232-91AA/Lob12.3 led to the highest proportion of animals, 7 out of 15 (47%), with complete tumour regression response (defined as a tumour volume of ≤62.5 mm$^3$) at the termination of the study (FIG. 13D). Isotype control antibodies (FIG. 13A), single agent anti-PD-1 antibody (FIG. 13B), and 1 mg/kg FS20m-232-91AA/Lob12.3 (FIGS. 13C) showed 0%, 0% and 7% tumour regression at the end of the study, respectively.

Survival analysis showed that the combination of FS20m-232-91AA/Lob12.3 with an anti-PD-1 antibody resulted in a statistically significant survival benefit compared to isotype control antibodies (log-rank (Mantel Cox) test, p<0.0001) (FIG. 13E). No significant survival differences were observed between either single agent treatments compared to isotype control antibodies. These results demonstrate that in this model, blockade of the PD-1/PD-L1 Inhibitory pathway with an antagonist and dual agonism of OX40 and CD137 with an anti-OX40/CD137 mAb$^2$ was able to increase the anti-tumour activity and provide a survival benefit compared to single agents.

22.2.2 Evaluation of Peripheral Pharmacodynamic Response

In the study described in Example 22.2.1, the ability of an anti-PD-1 antagonist to modulate the pharmacodynamic response to FS20m-232-91AA/Lob12.3 was also examined and compared to single-agent treatment. 6 days following initiation of dosing (16 days following tumour cell inoculation), blood was collected into EDTA-containing tubes from tail veins of 6 randomly selected CT26 tumour-bearing mice from treatment groups 1, 2, 3 and 5 (Table 36). Red blood cells of the uncoagulated blood were lysed twice in red blood cell lysis buffer (Miltenyi Biotech, #130-094-183) according to the manufacturer's Instructions. The cells were stained for flow cytometric analysis with reagents CD4-BUV395 (clone RM4-5), CD8-BUV737 (clone 53-6.7), CD44-BV510 (clone IM7), and CD3e-BV786 (clone 145-2C11), all supplied by BD Bioscience; CD69-FITC (done H1.2F3), NKp46-PE (done 29A1.4), PD-1-APC (done J43), CD45-Alexa700 (clone 30-F11), and fixable viability die 780, all supplied by eBioscience; and CD62L-BV421 (done MEL-14), supplied by Biolegend, in the presence of Fc block (eBioscience, catalogue no. 14-0161-86 at 1:50) for 30 minutes at 4° C. The cells were then fixed and permeabilized overnight with the eBioscience Foxp3 staining kit (eBioscience cat no 00-5523-00) according to the manufacturer's instructions. Cells were resuspended in 100 μL permeabilization buffer with Ki67 and Foxp3 antibodies (Ki67-PE-Cy7 (clone SolA15) and Foxp3-PerCP-Cy5.5 (clone FJK-16s), both supplied by eBioscience) and incubated for 30 minutes at room temperature in the dark. Cells were then washed twice with permeabilization buffer and resuspended in PBS+ 0.5% BSA. The cells were then analysed in a BD Fortessa flow cytometer. Data analysis was performed in FlowJo, Excel and GraphPad Prism 7 software.

Frequencies of proliferating Ki67+CD4+ T-cells (of total CD45+CD3+CD4+), Ki67+CD8+ T-cells (of total CD45+CD3+CD8+) and Ki67+ NKp46+NK cells (of total CD45+CD3-NKp46+) were determined by flow cytometry analysis, as described above. Compared to the isotype controls, FS20m-232-91AA/Lob12.3 induced statistically significant increases in proliferating Ki67+CD4+ and 1067+CD8+ T-cells confirming previous results (Example 18), and proliferating Ki67+NK cells (pairwise comparison Mann-Whitney nonparametric test; p≤0.005 for all three immune cell populations). Single agent anti-PD-1 antagonist antibody had no notable effect on the three immune cell populations compared to the isotype controls. The combination of 1 mg/kg FS20m-232-91AA/Lob12.3 and anti-PD-1 antibody resulted in statistically significant higher levels of proliferating Ki67+CD4+ T-cells. Ki167+CD8+ T-cells and Ki67+ NKp46+NK cells compared to either single agent or isotype controls (p≤0.005 for all statistically significant comparisons, except for the effect of the combination on levels of proliferating Ki67+CD4+ T-cells compared to FS20m-232-91AA/Lob12.3 alone, for which p≤0.05).

The effects of single agent anti-PD-1 antibody, mAb$^2$ FS20m-232-91AA/Lob12.3, and the combination of the anti-PD-1 antibody and FS20m-232-91AA/Lob12.3 on peripheral blood PD-1 expressing T-cells (CD4+ and CDB+ T cells) and NK cells were also determined by flow cytometry analysis, as described above. Single agent anti-PD-1 antibody and FS20m-232-91AA/Lob12.3 increased the proportion of PD-1-expressing CD4+ and CD8+ T-cells compared to isotype control, with higher median frequency of PD-1+ cells following FS20m-232-91AA/Lob12.3 treatment compared to anti-PD-1 alone. FS20m-232-91AA/Lob12.3 alone increased the frequency of PD-1+NK cells compared to isotype controls. The combination resulted in statistically significant higher levels of PD-1-expressing CD4+ and CD8+ T-cells (but not NK cells) compared to either single agent or isotype controls (pairwise comparison Mann-Whitney nonparametric test p≤0.005 for all statistically significant comparisons, except for the effect of the combination on frequency of PD-1-expressing CD4+ T cells compared to FS20m-232-91AA/Lob12.3 alone, for which p≤0.05).

Consistent with the findings from evaluation of anti-tumour activity, concurrent blockade of the PD-1/PD-L1 inhibitory pathway with an antagonist and dual agonism of OX40 and CD137 with an anti-OX40/CD137 mAb$^2$ resulted in enhanced pharmacodynamic modulation of proliferating T-cells and NK cells which supports utilizing the combination approach to drive anti-tumour immunity.

In conclusion, blocking the PD-1/PD-L1 axis while also agonising OX40 and CD137 results in an increased effect over blocking PD-1/PD-L1 alone. In particular, the combination of an anti-PD-1 or anti-PD-L1 antibody with an anti-OX40/CD137 mAb$^2$ resulted in an improved effect over use over the response of one of the antibodies alone. In the SEA assay described in Example 22.1, neither of the anti-PD-1 or PD-L1 antibodies tested had any activity, compared to the anti-OX40/CD137 mAb$^2$ which had an EC$_{50}$ of 0.1474 nM. However, when the anti-OX40/CD137 mAb$^2$ was tested in combination with either an anti PD-1 or an anti-PD-L1 antibody, the EC$_{50}$ values were 0.2373 nM and 0.5961 nM respectively. Furthermore, the maximal response of IL-2 produced by either combination was more than double that of the anti-OX40/CD137 mAb$^2$ alone. This in vitro data demonstrates that in a system where no activity is observed with an anti-PD-L1 or anti-PD-1 antibody, combining either of these antibodies with an anti-OX40/CD137 mAb$^2$ results in a significant improvement in activity.

This in vitro activity was further supported by in vivo testing of an anti-mouse OX40/CD137 mAb$^2$, alone or in combination with an anti-PD-1 antibody, in a CT26 tumour model, as described in Example 22.2. The results from this study showed that a larger number of animals were tumour free at the end of the study from the group treated with the combination of the anti-PD-1 antibody with an OX40/CD137 mAb$^2$, compared to the OX40/CD137 mAb$^2$ or the anti-PD-1 antibody alone (where no animals were tumour free). Further, statistically significant survival benefits were also observed (FIG. 13E) and pharmacodynamic modulation of proliferating T cells and NK cells was enhanced by treatment with the combination compared to either the mAb$^2$ or anti-PD-1 antibody alone.

Since no activity was observed in either the in vitro or In vivo studies for the anti-PD-1 or anti-PD-L1 antibodies, but significant improvements were observed when either was dosed with OX40/CD137 mAb$^2$, this may indicate that a OX40/CD137 mAb$^2$ in combination with such an antibody will result in enhanced anti-tumour efficacy, as well as that such a combination may be suitable for the treatment of tumours which are not responsive, for example are refractory or resistant or have relapsed following anti-PD-1 or anti-PD-L1 antibody monotherapy.

Example 23—Dose-Dependent, Anti-Tumour Activity of Anti-Mouse OX40/CD137 mAb$^2$ in a CT26 Syngeneic Tumour Model and Establishment of Protective Immunological Memory Against Re-Challenge with CT26 Tumour Cells To evaluate the relationship between dose and anti-tumour activity of the OX40/CD137 surrogate mAb$^2$ in the CT26 syngeneic mouse colorectal tumour model, five different dose levels from 0.1 to 10 mg/kg were assessed.

Following the same protocol as described in Example 17, BALB/c female mice (Charles River) aged 8-10 weeks and weighing approximately 20 g each were injected subcutaneously with CT26 colon carcinoma cells into the left flank of each animal. 10 days following tumour cell inoculation, tumours were measured and animals without an established tumour were removed from the study. Remaining mice were randomised into six treatment groups with 25 animals per group.

Isotype control antibody (G1AA/4420) and OX40/CD137 surrogate mAb$^2$ (FS20m-232-91AA/Lob12.3) were filtered and diluted in PBS prior to injection. Each animal was intraperitoneally administered a 200 µl volume of diluted antibody per administration, giving a final dose of 10 mg/kg of G1AA/4420 or 0.1, 0.3, 1, 3 or 10 mg/kg of FS20m-232-91AA/Lob12.3 per administration for a 20 g mouse. Injections were performed once every two days (Q2D) for a total of three doses starting on day 10 following tumour Inoculation. Tumour volumes were determined by calliper measurements as described in Example 17. The study was terminated 67 days after tumour cell inoculation, with animals taken off study when humane endpoints were reached based on tumour volume and condition.

Figure 14:
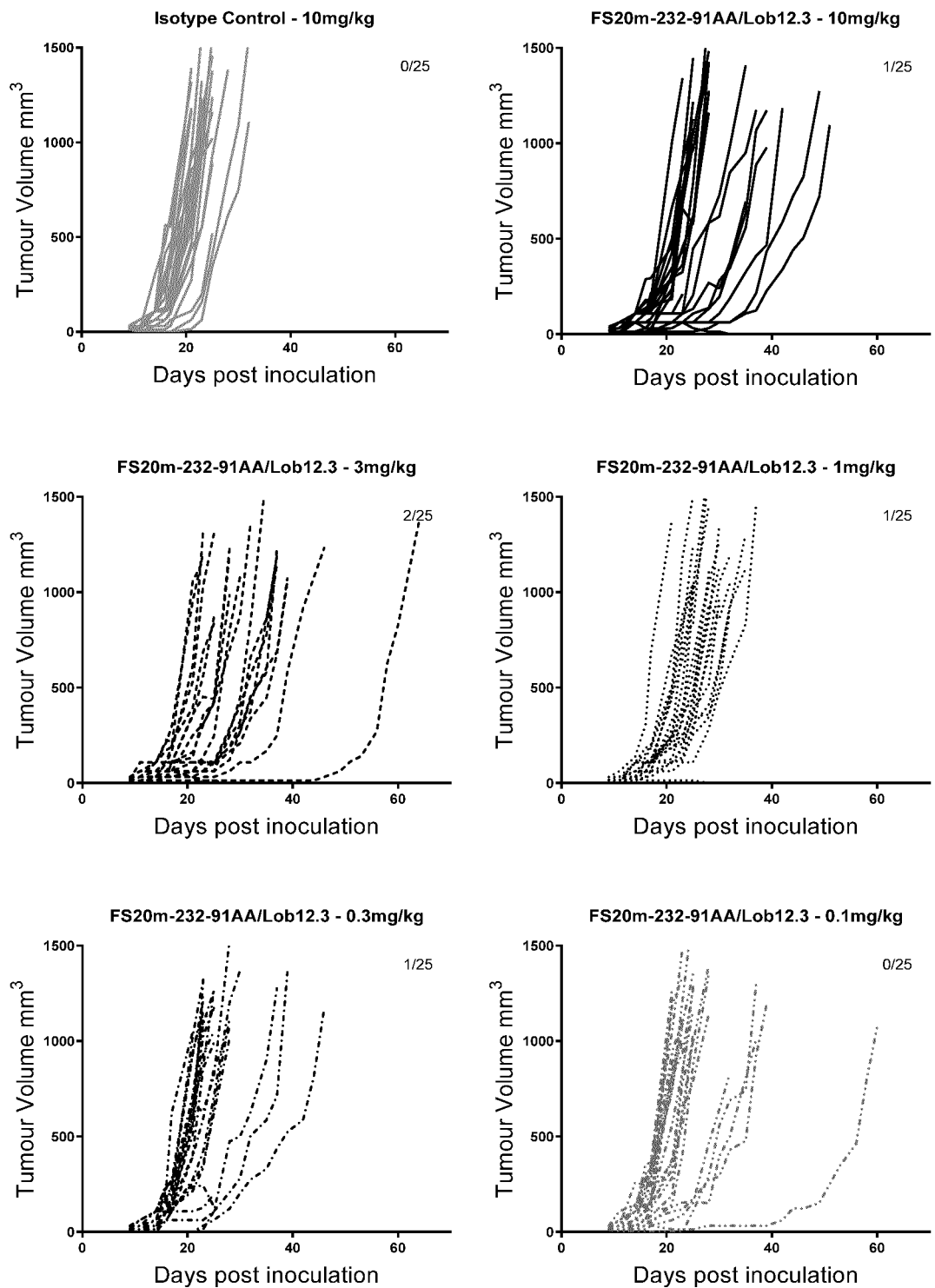
FIG. 14 shows dose-dependent, anti-tumour activity of an anti-mouse OX40/CD137 mAb² In a CT26 syngeneic tumour model.
Figure 14:
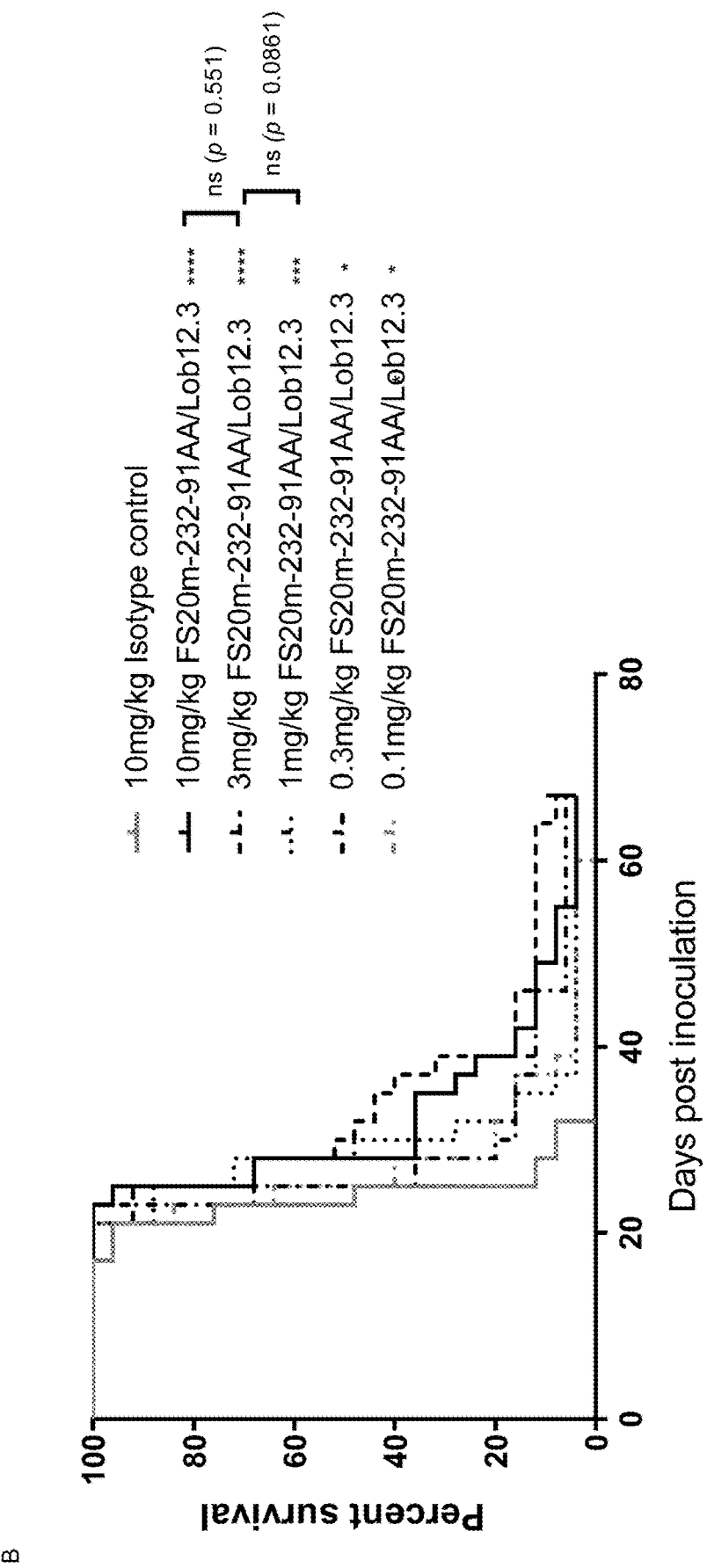

Tumour volumes over time for individual animals treated with either G1AA/4420 or FS20m-232-91AA/Lob12.3 at different dose levels are shown in FIG. 14A. Dose levels of 0.3, 1, 3 or 10 mg/kg of FS20m-232-91AA/Lob12.3 led to complete tumour regression (defined as ≤62.5 mm$^3$ on day 60) in 4% (1/25), 4% (1/25), 8% (2/25) and 4% (1/25) of animals per group, respectively. None of the animals in the isotype control and 0.1 mg/kg surrogate mAb$^2$ groups experienced complete tumour regression.

Pairwise comparisons of mean tumour growth rates between FS20m-232-91AA/Lob12.3- and G1AA/4420- treated groups were performed using mixed model statistical analysis as described in Example 17, and statistically significant differences (p<0.01) were observed across all dose levels tested (0.1, 0.3, 1, 3 and 10 mg/kg) when compared to isotype control (Table 37). FS20m-232-91AA/Lob12.3 decreased mean tumour growth rate (TGR) in a dose-dependent manner when dosed at 0.1 to 3 mg/kg (mean Log (TGR) of 0.255529 to 0.156767, respectively). Mean TGR for 3 mg/kg FS20m-232-91AA/Lob12.3 was not statistically different to that for 1 mg/kg dose level (p=0.18). However, Increasing the dose level to 10 mg/kg resulted in a faster TGR compared to the 3 mg/kg dose group (p<0.001).

TABLE 37

Pairwise comparison of mean CT26 tumour growth rates using mixed model statistical analysis

| A vs. B pairwise comparison | | Mean Log (TGR) [Lower, Upper CI] | | P-value | Summary | A > or ≈ or < B (Mean Log(TGR)) |
|---|---|---|---|---|---|---|
| A | B | A | B | | | |
| Isotype control | FS20m-232-91AA/Lob12.3 0.1 mg/kg | 0.314856 [0.288207, 0.339504] | 0.255529 [0.227356, 0.283703] | 3.63E−04 | **** | A > B |
| Isotype control | FS20m-232-91AA/Lob12.3 0.3 mg/kg | 0.313856 [0.288207, 0.339504] | 0.252407 [0.215534, 0.289281] | 2.24E−07 | **** | A > B |
| Isotype control | FS20m-232-91AA/Lob12.3 1 mg/kg | 0.313856 [0.288207, 0.339504] | 0.219461 [0.186503, 0.252419] | 1.94E−07 | **** | A > B |
| Isotype control | FS20m-232-91AA/Lob12.3 3 mg/kg | 0.313856 [0.288207, 0.339504] | 0.156767 [0.120418, 0.193116] | 2.23E−14 | **** | A > B |
| Isotype control | FS20m-232-91AA/Lob12.3 10 mg/kg | 0.313856 [0.288207, 0.339504]] | 0.197003 [0.155898, 0.238107] | 7.50E−21 | **** | A > B |
| FS20m-232-91AA/Lob12.3 1 mg/kg | FS20m-232-91AA/Lob12.3 3 mg/kg | 0.219461 [0.186503, 0.252419] | 0.156767 [0.120418, 0.193116] | 1.83E−01 | ns | A ≈ B |
| FS20m-232-91AA/Lob12.3 3 mg/kg | FS20m-232-91AA/Lob12.3 10 mg/kg | 0.156767 [0.120418, 0.193116] | 0.197003 [0.155898, 0.238107] | 4.72E−07 | **** | A < B |

Abbreviations:
ns—not statistically significant;
TGR—tumour growth rate
Note: For each pairwise comparison, at least one of the groups involved in calculating p-values contains more than 50% significantly non-lognormally distributed tumour growth rates Survival analysis showed that FS20m-232-91AA/Lob12.3 at all dose levels tested resulted in statistically significant survival benefit compared to isotype control using log-rank (Mantel-Cox) test (FIG. 148). Comparison of 1 mg/kg and 3 mg/kg groups showed no statistical difference in survival.

In conclusion, the tumour volume and survival data shown in FIGS. 14A and B and Table 37 supports the finding of Example 17 that the OX40/CD137 surrogate mAb$^2$ can elicit anti-tumour activity in vivo in the CT26 mouse tumour model. Furthermore, the observed anti-tumour activity increased dose-dependently from 0.1 mg/kg to 1 mg/kg and was maintained at the higher dose levels tested (3 mg/kg and 10 mg/kg).

To test whether the OX40/CD137 surrogate mAb$^2$ can induce protective immunological memory against CT26 tumour cells, animals that had experienced complete tumour regression (complete responders) from the dose-ranging study of the present example described above were re-inoculated subcutaneously with 1×10$^5$ CT26 cells on day 84 following the first cell Inoculation. Treatment-naïve non-tumour bearing BALB/c mice were also inoculated with CT26 cells as a control group. Tumour volumes were monitored as described above. The study was terminated on day 137 following the first cell inoculation, with animals taken off study when humane endpoints were reached based on tumour volume and condition. At end of the study, 0% (0/4) of the mice in the control group survived, while in contrast, 100% (4/4) of complete responder animals survived. These results show that in a subset of mice, the OX40/CD137 surrogate mAb$^2$ can induce complete tumour regression and establishment of protective immunological memory against re-challenge with CT26 cells.

Example 24—Dose-Dependent, Pharmacodynamic Response of Anti-Mouse OX40/CD137 mAb$^2$ in a CT26 Mouse Tumour Model The relationship between dose levels, frequency of dosing and peripheral pharmacodynamic response of the OX40/CD137 surrogate mAb$^2$ (FS20m-232-91AA/Lob12.3) was evaluated using the CT26 syngeneic mouse colorectal tumour model. Single intraperitoneal (i.p.) injections of FS20m-232-91AA/Lob12.3 at differing dose levels of 1, 3, 10 or 30 mg/kg, or three i.p. injections of FS20m-232-91AA/Lob12.3 at 1 mg/kg given once every 2 days (Q2D), were compared. Pharmacodynamic response of FS20m-232-91AA/Lob12.3, specifically the effect of the surrogate mAb$^2$ on circulating T cells, was assessed by flow cytometry analysis of immune cell subsets in the blood as described in Example 18.

Following the same protocol as described in Example 17, BALB/c female mice (Charles River) aged 8-10 weeks and weighing approximately 20 g each were injected subcutaneously with CT26 colon carcinoma cells into the left flank of each animal. 10 days following tumour cell inoculation, tumours were measured and animals without an established tumour were removed from the study. Remaining mice were randomised Into six treatment groups with six animals per group.

Isotype control antibody (G1AA/4420) and FS20m-232-91AA/Lob12.3 were filtered and diluted in PBS prior to injection. Each animal was intraperitoneally administered a 200 μl volume of diluted antibody per administration, giving a final dose of 30 mg/kg of G1AA/4420 or 1, 3, 10 or 30 mg/kg of FS20m-232-91AA/Lob12.3 per administration for a 20 g mouse. Animals received either a single i.p. injection of G1AA/4420 (at 30 mg/kg) or FS20m-232-91AA/Lob12.3 (at 1, 3, 10 or 30 mg/kg) or a total of 3 doses of FS20m-232-91AA/Lob12.3 (at 1 mg/kg per dose) given once every two days (Q2D) starting on day 10 following tumour inoculation. Tumour volumes were determined by calliper measurements as described in Example 17. Animals were taken off study after six days from dosing start (16 days post-cell inoculation).

Blood was collected into EDTA-containing tubes by cardiac puncture. Red blood cells of the uncoagulated blood were lysed twice in red blood cell lysis buffer (Miltenyi Biotech, #130 094-183) according to manufacturer's instructions. The cells were stained for flow cytometric analysis with the reagents CD4-BUV395 (clone RM4-5), CD8-BUV737 (clone 53-6.7), CD44-BV510 (done IM7), and CD3e-BV786 (clone 145-2C11), all supplied by BD Bioscience); CD69-FITC (clone H1.2F3), NKp46-PE (clone 29A1.4), CD45-Alexa700, and fixable viability die 780, all supplied by eBioscience; and CD62L-BV421 (done MEL-14), supplied by Biolegend, in the presence of Fc block (eBioscience, cat. no. 14-0161-86). The cells were then fixed and permeabilised overnight with the eBioscience Foxp3 staining kit (eBioscience, cat no 00-5523-00) according to manufacturer's instructions. Cells were resuspended in 100 μl permeabilisation buffer with anti-Gzmb, anti-Ki67 and anti-Foxp3 antibodies (Gzmb-AF647 (clone GB11), supplied by Biolegend. and Ki67-PE-Cy7 (clone SolA15) and Foxp3-PerCP-Cy5.5 (clone FJK-16s), both supplied by eBioscience) and incubated for 30 minutes in the dark at room temperature. Cells were then washed twice with permeabilisation buffer and resuspended in PBS plus 0.5% BSA. The cells were then analysed in a BD Fortessa flow cytometer. Data analysis was performed using FlowJo, Excel and GraphPad Prism 7 software.

Frequencies of Ki167+CD8+(of total CD8+) and Ki67+CD4+(of total CD4+) proliferating T cells in peripheral blood, six days following administration of the first dose, were determined by flow cytometric analysis. Statistically significant increases in the frequencies of Ki67+CD4+ proliferating T cells were observed at the 1 and 10 mg/kg single doses of FS20m-232-91AA/Lob12.3 compared to isotype control. Statistically significant increases in the frequencies of Ki67+CD8+ proliferating T cells were observed at the 1, 3 and 10 mg/kg single doses of FS20m-232-91AA/Lob12.3 compared to isotype control.

Ki67+CD8+ proliferating T cells trended the highest at the 1 mg/kg single-dose level, while Ki67+CD4+ proliferating T cells trended the highest at the 1 and 10 mg/kg dose levels. Increasing the dose level to 30 mg/kg did not result in a significant effect on Ki67+CD8+ and Ki67+CD4+ T cells, relative to isotype control. Of note, no overt clinical observations or weight loss were observed at any of the dose levels.

Comparison of the multiple-dosing group (FS20m-232-91AA/Lob12.3 at 1 mg/kg Q2D three doses), and the 1 mg/kg single-dose group showed no statistical significance in Ki67+CD8+ and Ki67+CD4+ T-cell levels (unpaired Mann-Whitney test, p=0.4848 and p=0.0931, respectively). This data suggests that multiple dosing, at least within the six-day period evaluated in this study, did not provide additional effect on peripheral Ki67+ pharmacodynamic modulation.

Consistent with the results of Example 18, this experiment shows that the OX40/CD137 surrogate mAb² has an effect on circulating T cells, significantly increasing the frequency of proliferating (Ki67+) CD8+ T cells at dose levels from 1 mg/kg to 10 mg/kg, and of proliferating (Ki67+) CD4+ T cells at dose levels of 1 mg/kg and 10 mg/kg.

Example 25—Effect of CD4 T-Cell Depletion on Pharmacodynamic Response of Anti-Mouse OX40/CD137 mAb² in a CT26 Mouse Tumour Model Combination of CD137- and OX40-targeting costimulatory antibodies has previously been shown to synergistically enhance specific CD8+ T-cell clonal expansion, compared to either agent alone, following staphylococcal enterotoxin A administration in mice (Lee et al., 2004). Mechanistically, Lee et al. demonstrated that CD4 T cells plays a role in driving the enhanced specific CD8+ T-cell response. A CT26 mouse tumour model and mouse CD4 T cell-depleting antibody were used to test whether host CD4 T cells are required for, or contribute towards, activation and proliferation of peripheral CD8+ T cells in response to treatment with the OX40/CD137 surrogate mAb².

Following the same protocol as described in Example 17, BALB/c female mice (Charles River) aged 8-10 weeks and weighing approximately 20 g were Injected subcutaneously into the left flank of each animal with CT26 colon carcinoma cells. Animals were randomised into treatment groups on day seven, with five animals per group per timepoint.

Antibodies were analysed and checked for impurities as previously described. Isotype control antibody (G1/4420) and OX40/CD137 surrogate mAb² (FS20m-232-91AA/Lob12.3) were diluted to a final concentration of 0.1 mg/ml in PBS. Anti-mouse CD4 antibody (GK1.5: BioXCell, cat. no. BE0003-1) was diluted to a final concentration of 1 mg/ml in PBS. Each animal received a 200 μl volume of diluted antibody per administration, giving a final dose of either 1 mg/kg (G1/4420 or FS20m-232-91AA/Lob12.3) or 10 mg/kg (GK1.5) for a 20 g mouse. G1/4420 and FS20m-232-91AA/Lob12.3 were administered to animals via intraperitoneal (i.p.) injections on days 10, 12 and 14 following cell inoculation. I.p. injections of GK1.5 were given on days 8, 9, 11, 13 and 15.

Animals were taken off study on day 16 following cell inoculation and tissues were collected for flow cytometric analysis. Blood was collected into EDTA-containing tubes by cardiac puncture. Following the same protocol as described in Example 19, red blood cells of the uncoagulated blood were lysed twice in red blood cell lysis buffer (Miltenyi Biotech, #130-094-183) according to manufacturer's instructions, and tumours were dissociated using the Tumour dissociation kit, mouse (Miltenyi Biotech, 130-096-730) and the gentleMACS Dissociator (Miltenyi Biotech) according to manufacturer's instructions. The resulting tumour cell suspension was strained using a 70 μm cell strainer (Corning, cat. no. 352350), washed and resuspended in PBS. Cell suspension from spleens was prepared by pushing the spleens through a 70 μm cell strainer (Corning), lysing red blood cells by incubation in red blood cell lysis buffer (Milteny Biotech), washing remaining splenocytes and resuspending them in PBS.

Cells were first stained with the reagents CD4-E450 (clone GK1.5), CD69-PE-Cy5 (done H1.2F3), CD3-PE-Cy7 (clone 145-2C11), CD8-APC (clone 53-6.7), and fixable viability die 780, all supplied by eBioscience; and CD45-V500 (done 30-F11), supplied by BD Bioscience, in the presence of Fc block (eBioscience, cat. no. 14-0161-86). The cells were then fixed and permeabilised with the eBioscience Foxp3 staining kit (eBioscience, cat. no. 00-5523-00) according to manufacturer's instructions. Cells were resuspended in 100 μl permeabilisation buffer with anti-Ki67 and anti-Foxp3 antibodies (Ki67-FITC (done SolA15) and Foxp3-PE (clone FJK-16s), both supplied by eBioscience) in the presence of Fc block (all 1:100) and Incubated for 30 minutes in the dark at 4° C. Cells were then washed once with permeabilisation buffer and resuspended in 200 ul PBS. Cells were analysed on a BD FACSCanto II cytometer. Data analysis was performed using FlowJo, Excel and GraphPad Prism software. Pairwise comparison between treatment groups was performed using two-tailed Mann-Whitney test within the GraphPad Prism software.

Treatment with FS20m-232-91AA/Lob12.3 alone Induced statistically significant increases in the proportion of activated CD69+ and proliferating Ki67+CD8+ T cells in the blood and spleen, and of proliferating Ki67+CD8+ T cells in the tumour, compared to isotype control-treated animals.

Combining FS20m-232-91AA/Lob12.3 with CD4+ T cell-depleting antibody GK1.5 also led to a statistically significant increase in proliferating Ki67+CD8+ T cells in the blood, compared to isotype control, but this increase was significantly lower than that observed in the FS20m-232-91AA/Lob12.3 single agent-treated animals. No statistically significant differences in levels of proliferating CD8+ T cells were observed in the spleen and tumour tissues following treatment with FS20m-232-91AA/Lob12.3 alone compared to treatment with FS20m-232-91AA/Lob12.3 plus CD4+ T cell-depleting antibody GK1.5.

FS20m-232-91AA/Lob12.3-Induced increases in activated CD69+CD8+ T cells in the blood were inhibited by the GK1.5 antibody, as there were no statistically significant differences observed between the isotype control group and the FS20m-232-91AA/Lob12.3 plus CD4-depletion group (median 1.6% and 2.33% of total CD8 T cells, respectively). Comparison of the FS20m-232-91AA/Lob12.3 single agent group and the FS20m-232-91AA/Lob12.3 plus CD4-depletion group showed that the frequency of activated CD8+ T cells was significantly reduced in the spleen (29.3% versus 6.45% median frequency, without and with depletion, respectively), and in the tumour (86.4% versus 66.5% median frequency, without and with depletion, respectively).

Consistent with previous findings as described in Example 18. the OX40/CD137 surrogate mAb$^2$ increased the frequency of activated (CD69+) and proliferating (Ki67+) CD8 T cells, and the results of the present study show that CD4+ T-cell depletion had a detrimental effect on this OX40/CD137 mAb$^2$-mediated peripheral pharmacodynamic response. Moreover, the data suggests a potential interaction of CD4+ and CD8+ T cells in mediating anti-OX40/CD137 mAb$^2$ activity in vivo, and that CD4+ T cells may be required for optimal co-stimulation of CD8+ T-cell immunity in vivo with an anti-OX40/CD137 mAb$^2$.

Example 26—Functional Activity of OX40/CD137 mAb$^2$ in Cynomolgus Monkey Cell-Based Assay and Pharmacodynamic Response to and Tolerability of OX40/CD137 mAb$^2$ in Cynomolgus Monkeys 26.1 Functional Activity of OX40/CD137 mAb$^2$ in Cynomolgus Monkey Cell-Based Assay A primary PBMC assay, similar to the primary T cell assay described in Example 13 but using PBMCs instead of isolated, activated T cells, was performed to establish the relative potency of the anti-human FS20-22-49AA/FS30-10-16 mAb$^2$ on endogenously expressed human and cynomolgus monkey receptors. Briefly, cynomolgus monkey or human PBMCs were Isolated and stimulated with a coated anti-CD3 antibody in the presence of increasing concentrations of FS20-22-49AA/FS30-10-16 mAb$^2$ or an isotype control for three (cynomolgus monkey) or four (human) days, with IL-2 release serving as a measure of T-cell activation.

The functional activity of the mAb$^2$ on cynomolgus monkey PBMCs (mean $EC_{50}$=0.28±0.15 nM) was observed to be similar to activity observed in an equivalent human assay (mean $EC_{50}$=0.26±0.1 nM; IL-2). Cynomolgus monkeys are therefore considered to be a pharmacologically relevant species for toxicity studies for the mAb$^2$.

26.2 Tolerability of and Pharmacodynamic Response to OX40/CD137 mAb$^2$ in Cynomolgus Monkeys A preliminary dose range finding study was conducted to evaluate the tolerability of the anti-human OX40/CD137 mAb$^2$ FS20-22-49AA/FS30-10-16 and to assess potential pharmacodynamic changes in proportions of the major leukocyte populations as well as induction of proliferation and activation of specific T-cell subsets in response to FS20-22-49AA/FS30-10-16 in cynomolgus monkeys.

Briefly, the FS20-22-49AA/FS30-10-16 mAb$^2$ was administered to cynomolgus monkeys via intravenous infusion as a single dose or as repeat dose administrations. Standard toxicology parameters such as body weight, food consumption, clinical observations, haematology and blood chemistry were assessed for the evaluation of tolerability over the duration of the study.

The FS20-22-49AA/FS30-10-16 mAb$^2$ was well tolerated up to 30 mg/kg dosed weekly as determined by clinical chemistry and histopathology results.

Consistent with the findings of the study to assess the effect of the anti-mouse OX40/CD137 mAb$^2$ on circulating T cells in a CT26 syngeneic mouse tumour model (Example 18). a drug-related increase in cell proliferation and activation was observed in central memory and effector memory CD4+ and CD8+ T cells, and also in NK cells, which was measured by an increased expression of Ki67 and, to some extent, CD69.

Taken together these results strongly indicate that the anti-human FS20-22-49AA/FS30-10-16 mAb$^2$ has potent in vivo pharmacological activity in cynomolgus monkeys and is well tolerated up to 30 mg/kg. Furthermore, the pharmacodynamic data generated in this study is in line with the data observed for the OX40/CD137 surrogate mAb$^2$ in the mouse pharmacodynamic study described in Example 18, and provides further evidence for the expected anti-tumour efficacy and tolerability of mAb$^2$ binding OX40 and CD137, such as the FS20-22-49AA/FS30-10-16 mAb$^2$, in human cancer patients.

Example 27—Liver Pharmacology of OX40/CD137 mAb$^2$ in BALB/c Mice

CD137 agonist antibodies have been shown to induce increased liver T cell infiltration in mouse pre-clinical models and one CD137 agonist antibody Induced liver toxicity at doses above 1 mg/kg in the clinic (Dubrot et al., 2010; Segal et at, 2017). The effects of the anti-mouse OX40/CD137 mAb$^2$ in BALB/c mice were therefore studied to determine if there is increased liver T cell infiltration as compared to CD137 agonist antibodies. Blood and spleen tissues were used as controls and T cell levels as well as T cell proliferation and activation were studied. Details of the antibodies tested are set out in Table 38.

TABLE 38

Details of antibodies and mAb² tested

| mAb/mAb² | Fab binding to | Fcab binding to | Isotype | LALA mutation | Heavy chain SEQ ID NO | Light chain SEQ ID NO |
|---|---|---|---|---|---|---|
| G1/4420 | FITC | none | hIgG1 | No | 115 | 116 |
| G1/OX86 | mOX40 | none | hIgG1 | No | 159 | 156 |
| G1/Lob12.3 | mCD137 | none | hIgG1 | No | University of Southampton | |
| G1/3H3 | mCD137 | none | hIgG1 | No | 168 | 167 |
| FS20m-232-91AA/Lob12.3 | mCD137 | mOX40 | hIgG1 | Yes | Creation described above in Example 9.2 | |

The ability of the mAb² (FS20m-232-91AA/Lob12.3) to increase, activate and induce the proliferation of T cells in the blood, spleen and liver was compared to single-agent mAb (G1/OX86, G1/Lob12.3, G1/3H3 and G114420) and combination (G1/OX86 and G1/Lob12.3) controls. BALB/c female mice (Charles River) aged 8-10 weeks and weighing approximately 20 g each were rested for one week prior to the study start. All animals were micro-chipped and given a unique identifier. Each cohort had 6 mice.

Within 24 hours prior to injection, the antibodies were analysed by SEC-HPLC profiling and checked for impurities. Antibodies were diluted to a final concentration of 1 mg/ml in PBS, and 200 μl/mouse were injected intraperitoneally (IP), giving a final dose of 10 mg/kg for a 20 g mouse. Injections were performed on days 0, 2 and 4 (one dose every two days) of the study. Seven and fourteen days after the third dose, 3 mice per group were euthanised, spleens and liver were isolated by dissection and blood was collected by cardiac puncture.

Livers and spleens were dissociated using the Miltenyl dissociation kits, (Liver - Miltenyi, 130-105-807; Spleen - Miltenyi, 130-095-926) according to manufacturer's instructions. The resulting cell suspension was strained using a 70 μM cell strainer (Corning, cat no 352350), centrifuged (10 minutes at 1500 rpm), washed once in PBS and resuspended in 5 ml PBS.

Blood was collected by cardiac puncture into EDTA-containing tubes. Red blood cells of the uncoagulated blood were lysed twice in red blood cell lysis buffer (eBioscience, catalogue no. 00-4300-54) according to manufacturers instructions.

The cells isolated from tumours and blood were stained for flow cytometry using the antibody panel and reagents detailed in Example 19 (Stain 1). Cells were washed in PBS and then incubated with 100 μl of antibody mix 1 (all but Ki67 and FoxP3 antibodies) for 30 minutes at 4° C. The cells were then washed with PBS and then fixed and permeabilised with the eBioscience Foxp3 staining kit (eBioscience, catalogue no. 00-5523-00) according to manufacturer's instructions. Briefly, 200 μl fixing solution was added to each well and left overnight in the dark at 4° C. Cells were then washed in 200 μl permeabilisation buffer. Cells were then spun again and resuspended in 100 μl permeabilisation buffer with Ki67 and Foxp3 antibodies in the presence of Fc block (all in 1:100 dilution) and incubated for 30 minutes in the dark at 4° C. Cells were then washed once with permeabilization buffer and resuspended in 200 μl PBS. The cells were then analysed in a BD FACSCanto II flow cytometer.

Data was analysed with FlowJoX, Excel and GraphPad Prism software. Statistical analysis to compare groups was performed using one-way ANOVA followed by Tukey's multiple comparison test of every pair using the Graph Pad Prism software package. The data was expressed as the percentage of the parental population The results showed that the crosslink-independent CD137 agonist antibody (G1/3H3) induced increased T cell levels in the liver, spleen and blood at both 7 and 14 days, and that those T cells showed increased levels of proliferation and activation, as compared to the isotype control antibody (G1/4420). The crosslink-dependent CD137 agonist antibody (G1/Lob12.3) did not show significant increases in either T cell levels, proliferation or activation in liver, spleen or blood. The OX40 agonist antibody (G1/OX86) did not Induce increased T cell levels in any of the tissues but showed increased T cell proliferation levels in the liver, spleen and blood on day 7 of the study, which returned to isotype control levels by day 14. The combination of OX40 and crosslink-dependent CD137 agonist antibodies (G1/OX86 and G1/Lob12.3) showed an increase in liver T cell infiltration levels on day 7, increased T cell proliferation in the liver at day 7 and in the spleen (not significant) and blood on days 7 and 14, and increased T cell activation in the liver and blood at day 14 and in the spleen at days 7 and 14. The OX40/CD137 mAb² showed an increase in liver T cell infiltration levels (not significant) and blood T cell levels on day 7, which returned to isotype control levels by day 14, and Increased T cell proliferation In the liver (not significant), spleen and blood on day 7, which also returned to isotype control levels by day 14. These results indicate that only the crosslink-independent CD137 agonist (G1/3H3) induced elevated and sustained T cell infiltration, proliferation and activation in the liver, and also in the spleen and blood, and suggest that the OX40/CD137-targeting antibody molecules of the invention may have a lower hepatotoxicity risk than crosslink-independent CD137 agonist antibodies. These results raise the possibility of an association between the crosslink-independent CD137 agonism induced by clone 3H3 and the increased liver T cell inflammation observed for this crosslink-independent clone in this study.

Example 28—Comparison of OX40/CD137 mAb² Antibodies Containing Different Anti-CD137 Fab Clones in a CT26 Syngeneic Tumour Model In Example 27, the crosslink-independent CD137 agonist antibody (G1/3H3) was observed to Induce elevated and sustained T cell infiltration, proliferation and activation levels in BALB/c mice. To test whether this increased activity has a beneficial anti-tumour activity in the context of an OX40/CD137 mAb², the CT26 syngeneic tumour model was used to compare the activity of two different anti-mouse OX40/CD137 mAb² in vivo, one in which the CD137 agonist is the crosslink-dependent clone Lob1.23 and the other in which the CD137 agonist is the crosslink-independent clone 3H3. The CT26 syngeneic tumour model has previously been shown to be sensitive to both OX40 and CD137 agonist antibodies, and tumour infiltrating lymphocytes (TILs) isolated from CT26 tumours express both OX40 and CD137.

28.1 Anti-Tumour Activity of OX40/CD137 mAb$^2$ Antibodies Containing Different Anti-CD137 Fab Clones in a CT26 Syngeneic Tumour Model The anti-tumour activity of two different OX40/CD137 mAb$^2$, FS20m-232-91AA/3H3 (SEQ ID NOs: 169 and 167) and FS20m-232-91AA/Lob12.3 (see Table 38), was determined in vivo in a CT26 syngeneic mouse tumour model and compared to the activity of an isotype control antibody (G1/4420; see Table 38). Additionally, the levels of T cell proliferation and activation induced in the blood by the two OX40/CD137 mAb$^2$ were analysed and compared to those induced by the isotype control antibody. BALB/c female mice (Charles River) aged 8-10 weeks and weighing approximately 20 g each were rested for one week prior to the study start. All animals were micro-chipped and given a unique identifier. Each cohort had 10 mice. The CT26 colon carcinoma cell line (ATCC, CRL-2638) was initially expanded, stored. and then pre-screened by IDEXX Bioresearch for pathogens using the IMPACT I protocol and shown to be pathogen free. CT26 cells (approximately 3-5×10$^6$) were thawed from 150° C., storage and added to 20 ml D MEM (Gibco, 61965-026) with 10% FCS (Gibco, 10270 106) in a T175 tissue culture flask. Mice were anaesthetised using isoflurane (Abbott Laboratories) and each animal received 1×10$^6$ cells injected subcutaneously in the left flank. On day 10 following tumour cell inoculation, mice were monitored for health and tumour growth and were sorted and randomised into study cohorts. Any mice which did not have tumours at this point were removed from the study.

Within 24 hours prior to injection, the antibodies were analysed by SEC-HPLC profiling and checked for impurities. Antibodies were diluted to a final concentration of 0.1 mg/ml in PBS and 200 µl/mouse were injected intraperitoneally (IP), giving a final dose of 1 mg/kg for a 20 g mouse. Injections were performed on days 10, 12 and 14 (one dose every two days) following tumour inoculation. Animals were health screened under anaesthesia three times a week in a blinded fashion, during which time accurate measurements of tumours were taken. Tumour volumes were determined by calliper measurements (as described in Example 17).

The study was terminated 35 days after tumour cell inoculation and animals were taken off study when humane endpoints were reached based on tumour volume and condition. The treatment groups, molecules tested, doses, and dosing schedule are summarised in Table 39. The tumour volumes on day 21 were statistically tested by two-way ANOVA and Tukey's multiple comparison test using GraphPad Prism software. Statistical testing of survival was performed by log rank test (Mantel-Cox) using GraphPad Prism software.

TABLE 39

Summary of treatment groups and molecules tested

| Group | Group name | mAb and/or mAb$^2$ administered | Dose (mg/kg) | Dosing Schedule |
|---|---|---|---|---|
| 1 | Isotype control | G1/4420 | 1 | Q2D |
| 3 | FS20m-232-91AA/Lob12.3 | FS20m-232-91AA/Lob12.3 | 1 | Q2D |

TABLE 39-continued

Summary of treatment groups and molecules tested

| Group | Group name | mAb and/or mAb$^2$ administered | Dose (mg/kg) | Dosing Schedule |
|---|---|---|---|---|
| 4 | FS20m-232-91AA/3H3 | FS20m-232-91AA/3H3 | 1 | Q2D |

Figure 15:
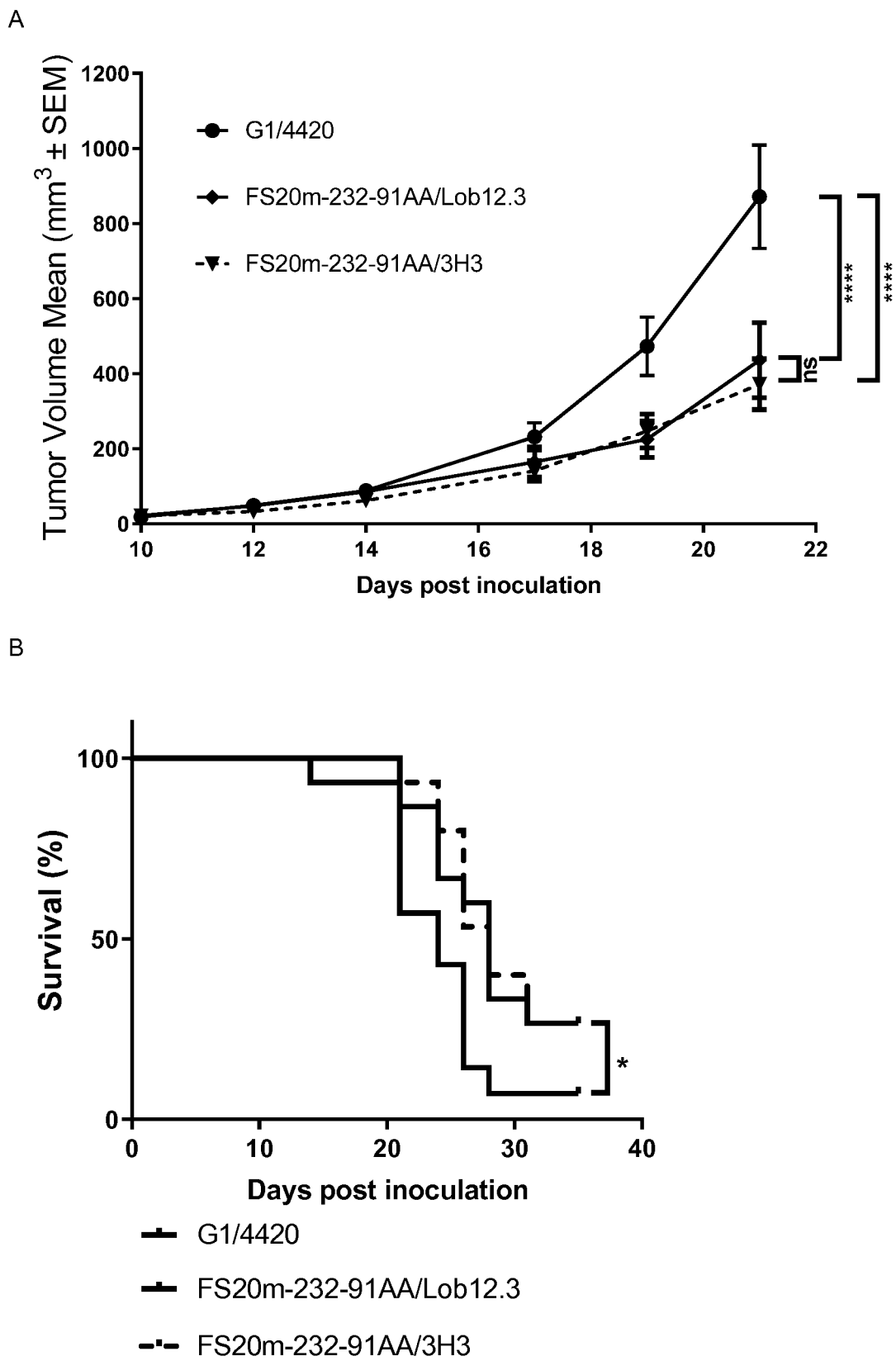
FIG. 15 shows a comparison of the anti-tumour efficacy of OX40/CD137 mAb² antibodies containing different anti-CD137 Fab clones in a CT26 syngeneic tumour model.

As shown in FIGS. 15A and 15B, treatment with either of the two OX40/CD137 mAb$^2$ antibodies delayed tumour growth and increased survival as compared to treatment with the isotype control antibody. No differences in tumour growth or survival were observed between the mice treated with the FS20m-232-91AA/3H3 mAb$^2$ and the FS20m-232-91AA/Lob12.3 mAb$^2$, respectively. This data suggests that despite the increased T cell activation and proliferation observed for the crosslink-independent CD137 agonist (G1/3H3) as described in Example 27, there is no increased anti-tumour activity of an OX40/CD137 mAb$^2$ in which the anti-CD137 Fab clone is crosslink-independent clone 3H3 (FS20m-232-91AA/3H3) as compared to an OX40/CD137 mAb$^2$ in which the anti-CD137 Fab clone is crosslink-dependent clone Lob12.3 (FS20m-232-91AA/Lob12.3).

28.2 Evaluation of Peripheral Pharmacodynamic Response of OX40/CD137 mAb$^2$ Containing Different Anti-CD137 Fab Clones in a CT26 Syngeneic Tumour Model In an extension of the study described above in Example 28.1. five days after administration of the third dose (i.e. day 19 post tumour inoculation) blood was collected from the tail vein of five mice into EDTA containing tubes. Red blood cells of the uncoagulated blood were lysed twice in red blood cell lysis buffer (eBioscience, catalogue no. 00-4300-54) according to manufacturer's instructions.

The cells isolated from blood were stained for flow cytometry using the antibody panel and reagents detailed In Example 19 (Stain 1). Cells were washed in PBS and then Incubated with 100 µl of antibody mix 1 (all but Ki67 and FoxP3 antibodies) for 30 minutes at 4° C. The cells were then washed with PBS and then fixed and permeabilised with a Foxp3 staining kit (eBioscience, cat no 00-5523-00) according to manufacturer's instructions. Briefly, 200 µl fixing solution was added to each well and left overnight in the dark at 4° C. Cells were then washed in 200 µl permeabilisation buffer. Cells were then spun again and resuspended in 100 µl permeabilisation buffer with Ki67 and Foxp3 antibodies in the presence of Fc block (all In 1:100 dilution) and incubated for 30 minutes In the dark at 4° C. Cells were then washed once with permeabilisation buffer and resuspended in 200 µl PBS. The cells were then analysed in a BD FACSCanto II flow cytometer.

Data was analysed with FlowJoX, Excel and GraphPad Prism software. Statistical analysis to compare groups was performed using one-way ANOVA followed by Tukey's multiple comparison test of every pair using the Graph Pad Prism software package.

FS20m-232-91AA/3H3 induced statistically significant increases in blood T cell levels as compared to both the isotype control antibody (G114420) and FS20m-232-91AA/Lob12.3. These increased T cell levels induced by FS20m-232-91AA/3H3 were accompanied by a statistically significant decrease in the relative percentage of CD4+ T cells and a statistically significant increase in the relative percentage of CD8+ T cells compared to the relative percentages of these cell types observed for the G1/4420 isotype control and FS20m-232-91AA/Lob12.3 mAb$^2$. Both OX40/CD137 mAb$^2$ antibodies also induced the proliferation of CD4+ and CD8+ T cells but the levels induced by the FS20m-232-91AA/3H3 were significantly higher than those induced by the FS20m-232-91AA/Lob12.3 mAb². The FS20m-232-91AA/3H3 mAb² Induced Increased levels of activated CD4+ T cells as compared to the isotype control. Changes in the levels of activated T cells and activated CD8+ T cells in mice treated with FS20m-232-91AA/Lob12.3 or FS20m-232-91AA/3H3, as compared to the isotype control-treated cohort, were modest and not statistically significant, as were changes in the levels of activated CD4+ T cells in mice treated with FS20m-232-91 AA/Lob12.3.These results indicate that the crosslink-independent CD137 agonist clone 3H3 is active in the context of an OX40/CD137 mAb² and is able to induce increased T cell levels and proliferation as compared to the crosslink-dependent CD137 agonist clone Lob12.3 in the context of an OX40/CD137 mAb², and are therefore consistent with the increased T cell levels and proliferation induced by clone 3H3 as a monoclonal antibody (mAb) as were observed In the BALB/c mice study described in Example 27.

Together with the anti-tumour activity data, these results suggest that there Is no additional benefit in terms of anti-tumour response of the increased T cell levels and proliferation induced by the crosslink-independent CD137 agonist in the context of an OX40/CD137 mAb². These results, taken together with the results of Example 27 in which increased liver T cell inflammation was observed for crosslink-independent CD137 agonism induced by clone 3H3, suggest that using an OX40/CD137 mAb², the CD137 agonism of which is dependent on binding to OX40, may provide a safe and effective way to stimulate the immune system to fight cancer.

---

Sequence Listing

```
CDR amino acid sequences of FS30-10-16 mAb (IMGT)
VH CDR1-GFTFSSYD (SEQ ID NO: 1)

VH CDR2-IDPTGSKT (SEQ ID NO: 2)

VH CDR3-ARDLLVYGFDY (SEQ ID NO: 3)

VL CDR1-QSVSSSY (SEQ ID NO: 4)

VL CDR2-GAS (SEQ ID NO: 5)

VL CDR3-QQSYSYPVT (SEQ ID NO: 6)

CDR amino acid sequences of FS30-10-16 mAb (Kabat)
VH CDR1-SYDMS (SEQ ID NO: 7)

VH CDR2-DIDPTGSKTDYADSVKG (SEQ ID NO: 8)

VH CDR3-DLLVYGFDY (SEQ ID NO: 9)

VL CDR1-RASQSVSSSYLA (SEQ ID NO: 10)

VL CDR2-GASSRAT (SEQ ID NO: 11)

VL CDR3-QQSYSYPVT (SEQ ID NO: 6)

Amino acid sequence of the heavy chain variable domain of FS30-10-16 mAb (SEQ ID NO: 12)
CDRs IMGT numbering (bold italics), CDRs Kabat numbering (underlined italics)
EVQLLESGGGLVQPGGSLRLSCAAS GFTFSSYDMMSWVRQAPGKGLEWVSD DIDPTGSKTDYADSVK
GRFTISRDNSKNTLYLQMNSLRAEDTAVYYC ARDLLVYGFDYWGQGTLVTVSS Nucleic acid sequence of the heavy chain variable domain of FS30-10-16 mAb (SEQ ID NO: 13)
GAAGTTCAGCTGCTGGAATCTGGCGGCGGATTGGTTCAACCTGGCGGCTCTCTGAGACTGTCTT
GTGCCGCTTCCGGCTTCACCTTCTCCAGCTACGACATGTCCTGGGTCCGACAGGCTCCTGGCAA
AGGACTGGAATGGGTGTCCGACATCGACCCCACCGGCTCTAAGACCGACTACGCCGATTCTGTG
AAGGGCAGATTCACCATCAGCCGGGACAACTCCAAGAACACCCTGTACCTGCAGATGAACTCCC
TGAGAGCCGAGGACACCGCCGTGTACTACTGTGCCAGAGATCTGCTGGTGTACGGCTTCGACTA
TTGGGGCCAGGGCACACTGGTCACCGTGTCCTCT Amino acid sequence of the light chain variable domain of FS30-10-16 mAb (SEQ ID NO: 14)
CDRs IMGT numbering (bold italics), CDRs Kabat numbering (underlined italics)
EIVLTQSPGTLSLSPGERATLSCRAS QSVSSSY LAWYQQKPGQAPRLLIY GASSRATGIPDRFSGSG
SGTDFTLTISRLEPEDFAVYYC QQSYSYPVTFGQGTKVEIK Nucleic acid sequence of the light chain variable domain of FS30-10-16 mAb (SEQ ID NO: 15)
GAGATCGTGCTGACCCAGTCTCCTGGCACACTGTCACTGTCTCCAGGCGAGAGAGCTACCCTGT
CCTGTAGAGCCTCTCAGTCCGTGTCCTCCTCTTACCTGGCCTGGTATCAGCAGAAGGCTGGACA
GGCTCCCCGGCTGTTGATCTACGGCGCTTCTTCTAGAGCCACAGGCATCCCTGACCGGTTCTCC
GGATCTGGCTCTGGCACCGATTTCACCCTGACCATCTCTCGGCTGGAACCCGAGGATTTCGCCG
TGTACTACTGCCAGCAGTCCTACAGCTACCCCGTGACCTTTGGCCAGGGCACCAAGGTGGAAAT
CAAG CDR amino acid sequences of FS30-10-3 mAb (IMGT)
VH CDR1-GFTFSSYD (SEQ ID NO: 1)

VH CDR2-IDPTGSKT (SEQ ID NO: 2)

VH CDR3-ARDLNVYGFDY (SEQ ID NO: 16)
```

Sequence Listing

VL CDR1-QSVSSSY (SEQ ID NO: 4)

VL CDR2-GAS (SEQ ID NO: 5)

VL CDR3-QQSYSYPVT (SEQ ID NO: 6)

CDR amino acid sequences of FS30-10-3 mAb (Kabat)
VH CDR1-SYDMS (SEQ ID NO: 7)

VH CDR2-DIDPTGSKTDYADSVKG (SEQ ID NO: 8)

VH CDR3-DLNVYGFDY (SEQ ID NO: 17)

VL CDR1-RASQSVSSSYLA (SEQ ID NO: 10)

VL CDR2-GASSRAT (SEQ ID NO: 11)

VL CDR3-QQSYSYPVT (SEQ ID NO: 6)

Amino acid sequence of the heavy chain variable domain of FS30-10-3 mAb (SEQ ID NO: 18)
CDRs IMGT numbering (bold italics), CDRs Kabat numbering (underlined italics)
EVQLLESGGGLVQPGGSLRLSCAAS **GFTFS*SYD*MSWVRQAPGKGLEWVSD *IDPTGSKT*DYADSVK
GRFTISRDNSKNTLYLQMNSLRAEDTAVYYC AR*DLNVYGFDY*WGQGTLVTVSS Nucleic acid sequence of the heavy chain variable domain of FS30-10-3 mAb (SEQ ID NO: 19)
GAAGTGCAACTGCTGGAGTCCGGTGGTGGTCTGGTACAGCCGGGTGGTTCTCTGCGTCTGAGT
TGCGCGGCCAGTGGCTTTACCTTCAGTAGTTACGATATGAGCTGGGTGCGTCAGGCTCCGGGCA
AAGGTCTGGAATGGGTTAGCGATATTGATCCGACTGGTAGCAAGACCGACTATGCGGATAGCGT
GAAAGGCCGTTTTACCATTTCTCGCGACAACAGCAAGAACACGCTGTACCTGCAGATGAACTCAC
TGCGTGCCGAAGATACGGCCGTGTATTACTGTGCGAGAGACCTCAATGTGTACGGGTTCGACTA
CTGGGGCCAGGGAACCCTGGTCACCGTCTCGAGT Amino acid sequence of the light chain variable domain of FS30-10-3 mAb (SEQ ID NO: 14)
CDRs IMGT numbering (bold italics), CDRs Kabat numbering (underlined italics)
EIVLTQSPGTLSLSPGERATLSCRAS QSVSSSYLAWYQQKPGQAPRLLIY GASSRATGIPDRFSGSG
SGTDFTLTISRLEPEDFAVYYC QQSYSYPVTFGQGTKVEIK Nucleic acid sequence of the light chain variable domain of FS30-10-3 mAb (SEQ ID NO: 20)
GAAATTGTGCTGACCCAGTCTCCGGGCACGTTATCTCTGAGCCCTGGTGAGCGCGCCACTCTGT
CATGCCGGGCTTCTCAAAGTGTTAGCAGTAGCTACCTGGCGTGGTATCAGCAAAAACCGGGCCA
GGCCCCGCGTCTGCTGATTTACGGTGCATCCAGCCGTGCCACCGGCATTCCAGATCGTTTTTCC
GGTAGTGGTTCTGGGACGGACTTCACTCTGACAATCTCACGCCTGGAACCGGAGGATTTTGCGG
TGTATTACTGCCAGCAATCTTATTCTTATCCTGTCACGTTCGGCCAAGGGACCAAGGTGGAAATC
AAA CDR amino acid sequences of FS30-10-12 mAb (IMGT)
VH CDR1-GFTFSSYD (SEQ ID NO: 1)

VH CDR2-IDPTGSKT (SEQ ID NO: 2)

VH CDR3-ARDLTVYGFDY (SEQ ID NO: 21)

VL CDR1-QSVSSSY (SEQ ID NO: 4)

VL CDR2-GAS (SEQ ID NO: 5)

VL CDR3-QQSYSYPVT (SEQ ID NO: 6)

CDR amino acid sequences of FS30-10-12 mAb (Kabat)
VH CDR1-SYDMS (SEQ ID NO: 7)

VH CDR2-DIDPTGSKTDYADSVKG (SEQ ID NO: 8)

VH CDR3-DLTVYGFDY (SEQ ID NO: 22)

VL CDR1-RASQSVSSSYLA (SEQ ID NO: 10)

VL CDR2-GASSRAT (SEQ ID NO: 11)

VL CDR3-QQSYSYPVT (SEQ ID NO: 6)

Amino acid sequence of the heavy chain variable domain of FS30-10-12 mAb (SEQ ID NO: 23)
CDRs IMGT numbering (bold italics), CDRs Kabat numbering (underlined italics)
EVQLLESGGGLVQPGGSLRLSCAAS **GFTFS*SYD*MSWVRQAPGKGLEWVSD *IDPTGSK*DYADSVK
GRFTISRDNSKNTLYLQMNSLRAEDTAVYYC AR*DLTVYGFDY*WGQGTLVTVSS -continued Sequence Listing Nucleic acid sequence of the heavy chain variable domain of FS30-10-12 mAb (SEQ ID NO: 24)
GAAGTGCAACTGCTGGAGTCCGGTGGTGGTCTGGTACAGCCGGGTGGTTCTCTGCGTCTGAGT
TGCGCGGCCAGTGGCTTTACCTTCAGTAGTTACGATATGCATTGGGTGCGTCAGGCTCCGGGCA
AAGGTCTGGAATGGGTTAGCGATATTGATCCGACTGGTAGCAAGACCGACTATGCGGATAGCGT
GAAAGGCCGTTTTACCATTTCTCGCGACAACAGCAAGAACACGCTGTACCTGCAGATGAACTCAC
TGCGTGCCGAAGATACGGCCGTGTATTACTGTGCGAGAGACCTCACGGTGTAGGGGTTCGACTA
CTGGGGCCAGGGAACCCTGGTCACCGTCTCGAGT Amino acid sequence of the light chain variable domain of FS30-10-12 mAb (SEQ ID NO: 14)
CDRs IMGT numbering (bold italics), CDRs Kabat numbering (underlined italics)
EIVLTQSPGTLSLSPGERATLSCRAS *QSVSSSY*LAWYQQKPGQAPRLLIY *GAS*SRATGIPDRFSGSG
SGTDFTLTISRLEPEDFAVYYC *QQSYSYPVT*FGQGTKVEIK Nucleic acid sequence of the light chain variable domain of FS30-10-12 mAb (SEQ ID NO: 20)
GAAATTGTGCTGACCCAGTCTCCGGGCACGTTATCTCTGAGCCCTGTGAGCGCGCCACTCTGT
CATGCCGGGCTTCTCAAAGTGTTAGCAGTAGCTACCTGGCGTGGTATCAGCAAAAACCGGGCA
GGCCCCGCGTCTGCTGATTTACGGTGCATCCAGCCGTGCCACCGGCATTCCAGATCGTTTTTCC
GGTAGTGGTTCTGGGACGGACTTCACTCTGACAATCTCACGCCTGGAACCGGAGGATTTTGCGG
TGTATTACTGCCAGCAATCTTATTCTTATCCTGTCACGTTCGGCCAAGGGACCAAGGTGGAAATC
AAA CDR amino acid sequences of FS30-35-14 mAb (IMGT)
VH CDR1-GFTFSAYN (SEQ ID NO: 25)

VH CDR2-ISPYGGAT (SEQ ID NO: 26)

VH CDR3-ARNLYELSAYSYGADY (SEQ ID NO: 27)

VL CDR1-QSVSSSY (SEQ ID NO: 4)

VL CDR2-GAS (SEQ ID NO: 5)

VL CDR3-QQYYSSPIT (SEQ ID NO: 28)

CDR amino acid sequences of FS30-35-14 mAb (Kabat)
VH CDR1-AYNIH (SEQ ID NO: 29)

VH CDR2-DISPYGGATNYADSVKG (SEQ ID NO: 30)

VH CDR3-NLYELSAYSYGADY (SEQ ID NO: 31)

VL CDR1-RASQSVSSSYLA (SEQ ID NO: 10)

VL CDR2-GASSRAT (SEQ ID NO: 11)

VL CDR3-QQYYSSPIT (SEQ ID NO: 28)

Amino acid sequence of the heavy chain variable domain of FS30-35-14 mAb (SEQ ID NO: 170)
CDRs IMGT numbering (bold italics), CDRs Kabat numbering (underlined italics)
EVQLLESGGGLVQPGGSLRLSCAAS *GFTFSAYN*IHWVRQAPGKGLEWVSD *ISPYGGAT*NYADSVKG
RFTISRDNSKNTLYLQMNSLRAEDTAVYYC *ARNLYELSAYSYGADY*WGQGTLVTVSS Nucleic acid sequence of the heavy chain variable domain of FS30-35-14 mAb (SEQ ID NO: 171)
GAAGTGCAACTGCTGGAGTCCGGTGGTGGTCTGGTACAGCCGGGTGGTTCTCTGCGTCTGAGT
TGCGCGGCCAGTGGCTTTACCTTCAGTGCCTATAATATCCATTGGGTGCGTCAGGCTCCGGGCA
AAGGTCTGGAATGGGTTAGCGATATTTCTCCGTATGGTGGCGCGACCAACTATGCGGATAGCGT
GAAAGGCCGTTTTACCATTTCTCGCGACAACAGCAAGAACACGCTGTACCTGCAGATGAACTCAC
TGCGTGCCGAAGATACGGCCGTGTATTACTGTGCGAGAAACCTCTACGAGTTGAGCGCTTACTC
TTACGGGGCGGACTACTGGGGCCAGGGAACCCTGGTCACCGTCTCGTCG Amino acid sequence of the light chain variable domain of FS30-35-14 mAb (SEQ ID NO: 172)
CDRs IMGT numbering (bold italics), CDRs Kabat numbering (underlined italics)
EIVLTQSPGTLSLSPGERATLSCRAS *QSVSSSY*LAWYQQKPGQAPRLLIY *GAS*SRATGIPDRFSGSG
SGTDFTLTISRLEPEDFAVYYC *QQYYSSPIT*FGQGTKVEIK Nucleic acid sequence of the light chain variable domain of FS30-35-14 mAb (SEQ ID NO: 32)
GAAATTGTGCTGACCCAGTCTCCGGGCACGTTATCTCTGAGCCCTGTGAGCGCGCCACTCTGT
CATGCCGGGCTTCTCAAAGTGTTAGCAGTAGCTACCTGGCGTGGTATCAGCAAAAACCGGGCCA
GGCCCCGCGTCTGCTGATTTACGGTGCATCCAGCCGTGCCACCGGCATTCCAGATCGTTTTTCC
GGTAGTGGTTCTGGGACGGACTTCACTCTGACAATCTCACGCCTGGAACCGGAGGATTTTGCGG
TGTATTACTGCCAGCAATATTATTATTCTTCCTATCACGTTCGGCCAAGGGACCAAGGTGGAA
ATCAAA CDR amino acid sequences of FS30-5-37 mAb (IMGT)
VH CDR1-GFTFSSYA (SEQ ID NO: 33)

VH CDR2-ISGSGGST (SEQ ID NO: 34)

Sequence Listing

VH CDR3-ARSYDKYWGSSIYSGLDY (SEQ ID NO: 35)

VL CDR1-QSVSSSY (SEQ ID NO: 4)

VL CDR2-GAS (SEQ ID NO: 5)

VL CDR3-QQYYSYYPVT (SEQ ID NO: 36)

CDR amino acid sequences of FS30-5-37 mAb (Kabat)
VH CDR1-SYAMS (SEQ ID NO: 37)

VH CDR2-AISGSGGSTYYADSVKG (SEQ ID NO: 38)

VH CDR3-SYDKYWGSSIYSGLDY (SEQ ID NO: 39)

VL CDR1-RASQSVSSSYLA (SEQ ID NO: 10)

VL CDR2-GASSRAT (SEQ ID NO: 11)

VL CDR3-QQYYSYYPVT (SEQ ID NO: 36)

Amino acid sequence of the heavy chain variable domain of FS30-5-37 mAb (SEQ ID NO: 40)
CDRs IMGT numbering (bold italics), CDRs Kabat numbering (underlined italics)
EVQLLESGGGLVQPGGSLRLNCAAS **GFTFS*SYA* WVRQAPGKGLEWVSA *ISGSGGST*** YYADSVK
GRFTISRDNSKNTLYLQMNSLRAEDTAVYYC A**R*SYDKYWGSSIYSGLDY*** WGQGTLVTVSS Nucleic acid sequence of the heavy chain variable domain of FS30-5-37 mAb (SEQ ID NO: 41)
GAAGTGCAACTGCTGGAGTCCGGTGGTGGTCTGGTACAGCCGGGTGGTTCTCTGCGTCTGAATT
GCGCGGCCAGTGGCTTTACCTTCAGTAGCTATGCCATGAGCTGGGTGCGTCAGGCGCCGGGCA
AAGGTCTGGAATGGGTTAGCGCGATTAGCGGTAGTGGCGGTAGCACGTACTATGCGGATAGCG
TGAAAGGCCGTTTTACCATTTCTCGCGACAACAGCAAGAACACGCTGTACCTGCAGATGAACTCA
CTGCGTGCCGAAGATACGGCCGTGTATTACTGTGCGAGATCTTACGACAAATACTGGGGTTCTT
CTATTTACTCTGGCTTGGACTACTGGGGCCAGGGAACCCTGGTCACCGTCTCGAGT Amino acid sequence of the light chain variable domain of FS30-5-37 mAb (SEQ ID NO: 42)
CDRs IMGT numbering (bold italics), CDRs Kabat numbering (underlined italics)
EIVLTQSPGTLSLSPGERATLSCRAS *QSVSSSYLA* LAWYQQKPGQAPRLLIY *GAS* SRATGIPDRFSGSG
SGTDFTLTISRLEPEDFAVYYC *QQYYSYYPVT* FGQGTKVEIK Nucleic acid sequence of the light chain variable domain of FS30-5-37 mAb (SEQ ID NO: 43)
GAAATTGTGCTGACCCAGTCTCCGGGCACGTTATCTCTGAGCCCTGGTGAGCGCGCCACTCTGT
CATGCCGGGCTTCTCAAAGTGTTAGCAGTAGCTACCTGGCGTGGTATCAGCAAAAACCGGGCCA
GGCCCCGCGTCTGCTGATTTACGGTGCATCCAGCCGTGCCACCGGCATTCCAGATCGTTTTTCC
GGTAGTGGTTCTGGGACGGACTTCACTCTGACAATCTCACGCCTGGAACCGGAGGATTTTGCGG
TGTATTACTGCCAGCAATATTATTCTTATTATCCTGTCACGTTCGGCCAAGGGACCAAGGTGGAA
ATCAAA Amino acid sequences of WT CH3 domain structural loops
WT AB loop-RDELTKNQ (SEQ ID NO: 44)

WT CD loop-SNGQPENNY (SEQ ID NO: 45)

WT EF loop-DKSRWQQGNV (SEQ ID NO: 46)

Amino acid sequence of WT CH3 domain (SEQ ID NO: 47)
AB, CD and EF loops underlined
GQPREPQVYTLPPSR<u>DELTKNQ</u>VSLTCLVKGFYPSDIAVEWE<u>SNGQPENNY</u>KTTPPVLDSDGSFFLY
SKLTV<u>DKSRWQQGNV</u>FSCSVMHEALHNHYTQKSLSLSPG Amino acid sequence of the CH2 domain (SEQ ID NO: 48)
APELLGGPSVFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAK Amino acid sequence of the CH2 domain with LALA mutation (SEQ ID NO: 49)
LALA mutation underlined
APE<u>AA</u>GGPSVFLFPPKPKDTLMISRTPEVTCVVVDVSHEDPEVKFNWYVDGVEVHNAKTKPREEQY
NST<u>Y</u>RVVSVLTVLHQDWLNGKEYKCKVSNKALPAPIEKTISKAK Amino acid sequence of the CH2 domain with LALA mutation and P114A mutation (SEQ ID NO: 50)
LALA mutation underlined; P114A mutation bold and underlined
APE<u>AA</u>GGPSVFLFPPKPKDTLMISRTPEVTCVVVDVSHEDPEVKFNWYVDGVEVHNAKTKPREEQY
NST<u>Y</u>RVVSVLTVLHQDWLNGKEYKCKVSNKAL<u>A</u>APIEKTISKAK Amino acid sequences of Fcab FS20-22-49 CH3 domain structural loop sequences
FS20-22-49 first sequence-YWDQE (SEQ ID NO: 51)

-continued

Sequence Listing

FS20-22-49 second sequence-DEQFA (SEQ ID NO: 52)

FS20-22-49 third sequence-QYRWNPADY (SEQ ID NO: 53)

Amino acid sequence of Fcab FS20-22-49 CH3 domain (SEQ ID NO: 54)
First, second and third sequences underlined
GQPREPQVYTLPPSRDEYWDQEVSLTCLVKGFYPSDIAVEWESNGDEQFAYKTTPPVLDSDGSFFL
YSKLTVDQYRWNPADYFSCSVMHEALHNHYTQKSLSLSPG Nucleic acid sequence of Fcab FS20-22-49 CH3 domain (SEQ ID NO: 55)
GGCCAGCCTAGGGAACCCCAGGTTTACACCTTGCCTCCAAGCCGGGACGAGTACTGGGATCAA
GAGGTGTCCCTGACCTGCCTCGTGAAGGGCTTCTACCCTTCCGATATCGCCGTGGAATGGGAGA
GCAATGGCGACGAGCAGTTCGCCTACAAGACAACCCCTCCTGTGCTGGACTCCGACGGCTCATT
CTTTCTGTACTCCAAGCTGACAGTGGACCAGTACAGATGGAACCCCGCCGACTACTTCTCTTGCT
CCGTGATGCACGAGGCCCTGCACAACCACTACACACAGAAGTCCCTGTCTCTGTCCCCTGGC Amino acid sequences of Fcab FS20-22-49 CH3 domain AB, CD and EF loop sequences
FS20-22-49 AB loop-RDEYWDQE (SEQ ID NO: 56)

FS20-22-49 CD loop-SNGDEQFAY (SEQ ID NO: 57)

FS20-22-49 EF loop-DQYRWNPADY (SEQ ID NO: 58)

Amino acid sequences of Fcab FS20-22-38 CH3 domain structural loop sequences
FS20-22-38 first sequence-YWDQE (SEQ ID NO: 51)

FS20-22-38 second sequence-AEKYQ (SEQ ID NO: 59)

FS20-22-38 third sequence-QYRWNPGDY (SEQ ID NO: 60)

Amino acid sequence of Fcab FS20-22-38 CH3 domain (SEQ ID NO: 61)
First, second and third sequences underlined
GQPREPQVYTLPPSRDEYWDQEVSLTCLVKGFYPSDIAVEWESNGAEKYQYKTTPPVLDSDGSFFL
YSKLTVDQYRWNPGDYFSCSVMHEALHNHYTQKSLSLSPG Nucleic acid sequence of Fcab FS20-22-38 CH3 domain (SEQ ID NO: 62)
GGACAGCCTCGAGAACCACAGGTGTACACCCTGCCCCCATCCCGGGATGAGTACTGGGACCAG
GAAGTCAGCCTGACCTGCCTGGTCAAAGGCTTCTATCCCAGCGACATCGCCGTGGAGTGGGAG
AGCAATGGGGCAGAAAAATACCAGTACAAGACCACGCCTCCCGTGCTGGACTCCGACGGCTCCT
TCTTCCTCTACAGCAAGCTCACCGTGGATCAGTATAGGTGGAACCCAGGCGACTATTTCTCATGC
TCCGTGATGCATGAGGCTCTGCACAACCACTACACACAGAAGAGCCTCTCCCTGTCTCCGGGT Amino acid sequences of Fcab FS20-22-41 CH3 domain structural loop sequences
FS20-22-41 first sequence-YWDQE (SEQ ID NO: 51)

FS20-22-41 second sequence-DEQFA (SEQ ID NO: 52)

FS20-22-41 third sequence-QYRWNPGDY (SEQ ID NO: 60)

Amino acid sequence of Fcab FS20-22-41 CH3 domain (SEQ ID NO: 63)
First, second and third sequences underlined
GQPREPQVYTLPPSRDEYWDQEVSLTCLVKGFYPSDIAVEWESNGDEQFAYKTTPPVLDSDGSFFL
YSKLTVDQYRWNPGDYFSCSVMHEALHNHYTQKSLSLSPG Nucleic acid sequence of Fcab FS20-22-41 CH3 domain (SEQ ID NO: 64)
GGACAGCCTCGAGAACCACAGGTGTACACCCTGCCCCCATCCCGGGATGAGTACTGGGACCAG
GAAGTCAGCCTGACCTGCCTGGTCAAAGGCTTCTATCCCAGCGACATCGCCGTGGAGTGGGAG
AGCAATGGGGATGAACAGTTCGCATACAAGACCACGCCTCCCGTGCTGGACTCCGACGGCTCCT
TCTTCCTCTACAGCAAGCTCACCGTGGATCAGTATAGGTGGAACCCAGGCGACTATTTCTCATGC
TCCGTGATGCATGAGGCTCTGCACAACCACTACACACAGAAGAGCCTCTCCCTGTCTCCGGGA Amino acid sequences of Fcab FS20-22-47 CH3 domain structural loop sequences
FS20-22-47 first sequence-YWDQE (SEQ ID NO: 51)

FS20-22-47 second sequence-DEQFA (SEQ ID NO: 52)

FS20-22-47 third sequence-QYRWSPGDY (SEQ ID NO: 65)

Amino acid sequence of Fcab FS20-22-47 CH3 domain (SEQ ID NO: 66)
First, second and third sequences underlined
GQPREPQVYTLPPSRDEYWDQEVSLTCLVKGFYPSDIAVEWESNGDEQFAYKTTPPVLDSDGSFFL
YSKLTVDQYRWSPGDYFSCSVMHEALHNHYTQKSLSLSPG Nucleic acid sequence of Fcab FS20-22-47 CH3 domain (SEQ ID NO: 67)
GGACAGCCTCGAGAACCACAGGTGTACACCCTGCCCCCATCCCGGGATGAGTACTGGGACCAG
GAAGTCAGCCTGACCTGCCTGGTCAAAGGCTTCTATCCCAGCGACATCGCCGTGGAGTGGGAG
AGCAATGGGGATGAACAGTTCGCATACAAGACCACGCCTCCCGTGCTGGACTCCGACGGCTCCT TCTTCCTCTACAGCAAGCTCACCGTGGATCAGTATAGGTGGAGTCCGGGTGATTATTTCTCATGC
TCCGTGATGCATGAGGCTCTGCACAACCACTACACTCAGAAGAGCTTGTCCCTGTCGCCCGGA Amino acid sequences of Fcab FS20-22-85 CH3 domain structural loop sequences
FS20-22-85 first sequence-YWDQE (SEQ ID NO: 51)

FS20-22-85 second sequence-DEQFA (SEQ ID NO: 52)

FS20-22-85 third sequence-QYRWNPFDD (SEQ ID NO: 68)

Amino acid sequence of Fcab FS20-22-85 CH3 domain (SEQ ID NO: 69)
First, second and third sequences underlined
GQPREPQVYTLPPSRDEYWDQEVSLTCLVKGFYPSDIAVEWESNGDEQFAYKTTPPVLDSDGSFFL
YSKLTLDQYRWNPFDDFSCSVMHEALHNHYTQKSLSLSPG Nucleic acid sequence of Fcab FS20-22-85 CH3 domain (SEQ ID NO: 70)
GGACAGCCTCGAGAACCACAGGTGTACACCCTGCCCCCATCCCGGGATGAGTACTGGGACCAG
GAAGTCAGCCTGACCTGCCTGGTCAAAGGCTTCTATCCCAGCGACATCGCCGTGGAGTGGGAG
AGCAATGGGGATGAACAGTTCGCATACAAGACCACGCCTCCCGTGCTGGACTCCGACGGCTCCT
TCTTCCTCTACAGCAAGCTCACCTTGGATCAGTATAGGTGGAATCCGTTTGATGATTTCTCATGCT
CCGTGATGCATGAGGCTCTGCACAACCACTACACTCAGAAGAGCTTGTCCCTGTCGCCCGGA Amino acid sequences of Fcab FS20-31-58 CH3 domain structural loop sequences
FS20-31-58 first sequence-YYSGE (SEQ ID NO: 71)

FS20-31-58 second sequence-QPEND (SEQ ID NO: 72)

FS20-31-58 third sequence-PYWRWGSPRT (SEQ ID NO: 73)

Amino acid sequence of Fcab FS20-31-58 CH3 domain (SEQ ID NO: 74)
First, second and third sequences underlined
GQPREPQVYTLPPSRDEYYSGEVSLTCLVKGFYPSDIAVEWESNGQPENDYKTTPPVLDSDGSFFLY
SKLTVPYWRWGSPRTFSCSVMHEALHN HYTQKSLSLSPG Nucleic acid sequence of Fcab FS20-31-58 CH3 domain (SEQ ID NO: 75)
GGACAGCCTCGAGAACCACAGGTGTACACCCTGCCCCCATCCCGGGATGAGTACTACTCTGGT
GAAGTCAGCCTGACCTGCCTGGTCAAAGGCTTCTATCCCAGCGACATCGCCGTGGAGTGGGAG
AGCAATGGGCAGCCGGAGAACGACTACAAGACCACGCCTCCCGTGCTGGACTCCGACGGCTCC
TTCTTCCTCTACAGCAAGCTCACCGTGCCTTATTGGAGGTGGGGTAGTCCGCGTACTTTCTCATG
CTCCGTGATGCATGAGGCTCTGCACAACCACTACACACAGAAGAGCCTCTCCCTGTCTCCGGGT Amino acid sequences of Fcab FS20-31-66 CH3 domain structural loop sequences
FS20-31-66 first sequence-YYSGE (SEQ ID NO: 71)

FS20-31-66 second sequence-QPEND (SEQ ID NO: 72)

FS20-31-66 third sequence-PYWRWGVPRT (SEQ ID NO: 76)

Amino acid sequence of Fcab FS20-31-66 CH3 domain (SEQ ID NO: 77)
First, second and third sequences underlined
GQPREPQVYTLPPSRDEYYSGEVSLTCLVKGFYPSDIAVEWESNGQPENDYKTTPPVLDSDGSFFLY
SKLTVPYWRWGVPRTFSCSVMHEALHNHYTQKSLSLSPG Nucleic acid sequence of Fcab FS20-31-66 CH3 domain (SEQ ID NO: 78)
GGACAGCCTCGAGAACCACAGGTGTACACCCTGCCCCCATCCCGGGATGAGTACTACTCTGGT
GAAGTCAGCCTGACCTGCCTGGTCAAAGGCTTCTATCCCAGCGACATCGCCGTGGAGTGGGAG
AGCAATGGGCAGCCGGAGAACGACTACAAGACCACGCCTCCCGTGCTGGACTCCGACGGCTCC
TTCTTCCTCTACAGCAAGCTCACCGTGCCGTATTGGAGGTGGGGTGTTCCGCGTACTTTCTCATG
CTCCGTGATGCATGAGGCTCTGCACAACCACTACACACAGAAGAGCCTCTCCCTGTCTCCGGGT Amino acid sequences of Fcab FS20-31-94 Fcab CH3 domain structural loop sequences
FS20-31-94 first sequence-WEHGE (SEQ ID NO: 79)

FS20-31-94 second sequence-IREHD (SEQ ID NO: 80)

FS20-31-94 third sequence-PYWRWGGPGT (SEQ ID NO: 81)

Amino acid sequence of Fcab FS20-31-94 Fcab CH3 domain (SEQ ID NO: 82)
First, second and third sequences underlined
GQPREPQVYTLPPSRDEWEHGEVSLTCLVKGFYPSDIAVEWESNGIREHDYKTTPPVLDSDGSFFLY
SKLTVPYWRWGGPGTFSCSVMHEALHNHYTQKSLSLSPG Nucleic acid sequence of Fcab FS20-31-94 Fcab CH3 domain (SEQ ID NO: 83)
GGACAGCCTCGAGAACCACAGGTGTACACCCTGCCCCCATCCCGGGATGAGTGGGAACATGGT
GAAGTCAGCCTGACCTGCCTGGTCAAAGGCTTCTATCCCAGCGACATCGCCGTGGAGTGGGAG
AGCAATGGGATCAGAGAACATGATTACAAGACCACGCCTCCCGTGCTGGACTCCGACGGCTCCT

```
TCTTCCTCTACAGCAAGCTCACCGTGCCATATTGGAGGTGGGGCGGCCCAGGCACCTTCTCATG
CTCCGTGATGCATGAGGCTCTGCACAACCACTACACTCAGAAGAGCTTGTCCCTGTCGCCCGGA
```

Amino acid sequences of Fcab FS20-31-102 CH3 domain structural loop sequences
FS20-31-102 first sequence-WASGE (SEQ ID NO: 84)

FS20-31-102 second sequence-QPEVD (SEQ ID NO: 85)

FS20-31-102 third sequence-PYWRWGVPRT (SEQ ID NO: 76)

Amino acid sequence of Fcab FS20-31-102 CH3 domain (SEQ ID NO: 86)
First, second and third sequences underlined
```
GQPREPQVYTLPPSRDEWASGEVSLTCLVKGFYPSDIAVEWESNGQPEVDYKTTPPVLDSDGSFFL
YSKLTVPYWRWGVPRTFSCSVMHEALHNHYTQKSLSLSPG
```

Nucleic acid sequence of Fcab FS20-31-102 CH3 domain (SEQ ID NO: 87)
```
GGCCAGCCTCGAGAACCACAGGTGTACACCCTGCCCCCATCCCGGGATGAGTGGGCATCTGGT
GAAGTCAGCCTGACCTGCCTGGTCAAAGGCTTCTATCCCAGCGACATCGCCGTGGAGTGGGAG
AGCAATGGGCAGCCAGAAGTTGATTACAAGACCACGCCTCCCGTGCTGGACTCCGACGGCTCCT
TCTTCCTCTACAGCAAGCTCACCGTGCCGTATTGGAGGTGGGGTGTTCCGCGTACTTTCTCATG
CTCCGTGATGCATGAGGCTCTGCACAACCACTACACACAGAAGAGCCTCTCCCTGTCTCCGGGT
```

Amino acid sequences of Fcab FS20-31-108 CH3 domain structural loop sequences
FS20-31-108 first sequence-WASGE (SEQ ID NO: 84)

FS20-31-108 second sequence-EKEID (SEQ ID NO: 88)

FS20-31-108 third sequence-PYWRWGAKRT (SEQ ID NO: 89)

Amino acid sequence of Fcab FS20-31-108 CH3 domain (SEQ ID NO: 90)
First, second and third sequences underlined
```
GQPREPQVYTLPPSRDEWASGEVSLTCLVKGFYPSDIAVEWESNGEKEIDYKTTPPVLDSDGSFFLY
SKLTVPYWRWGAKRTFSCSVMHEALHNHYTQKSLSLSPG
```

Nucleic acid sequence of Fcab FS20-31-108 CH3 domain (SEQ ID NO: 91)
```
GGCCAGCCTCGAGAACCACAGGTGTACACCCTGCCCCCATCCCGGGATGAGTGGGCATCTGGT
GAAGTCAGCCTGACCTGCCTGGTCAAAGGCTTCTATCCCAGCGACATCGCCGTGGAGTGGGAG
AGCAATGGGAAAAAGAAATCGATTACAAGACCACGCCTCCCGTGCTGGACTCCGACGGCTCCT
TCTTCCTCTACAGCAAGCTCACCGTGCCGTATTGGAGGTGGGGTGCTAAGCGTACTTTCTCATG
CTCCGTGATGCATGAGGCTCTGCACAACCACTACACACAGAAGAGCCTCTCCCTGTCTCCGGGT
```

Amino acid sequences of Fcab FS20-31-115 CH3 domain structural loop sequences
FS20-31-115 first sequence-WASGE (SEQ ID NO: 84)

FS20-31-115 second sequence-EQEFD (SEQ ID NO: 92)

FS20-31-115 third sequence-PYWRWGAKRT (SEQ ID NO: 89)

Amino acid sequence of Fcab FS20-31-1 15 CH3 domain (SEQ ID NO: 93)
First, second and third sequences underlined
```
GQPREPQVYTLPPSRDEWASGEVSLTCLVKGFYPSDIAVEWESNGEQEFDYKTTPPVLDSDGSFFL
YSKLTVPYWRWGAKRTFSCSVMHEALHNHYTQKSLSLSPG
```

Nucleic acid sequence of Fcab FS20-31-115 CH3 domain (SEQ ID NO: 94)
```
GGACAGCCTCGAGAACCACAGGTGTACACCCTGCCCCCATCCCGGGATGAGTGGGCATCTGGT
GAAGTCAGCCTGACCTGCCTGGTCAAAGGCTTCTATCCCAGCGACATCGCCGTGGAGTGGGAG
AGCAATGGGAACAGGAATTCGATTACAAGACCACGCCTCCCGTGCTGGACTCCGACGGCTCCT
TCTTCCTCTACAGCAAGCTCACCGTGCCGTATTGGAGGTGGGGTGCTAAGCGTACTTTCTCATG
CTCCGTGATGCATGAGGCTCTGCACAACCACTACACTCAGAAGAGCTTGTCCCTGTCGCCCGGA
```

Amino acid sequence of the heavy chain of FS20-22-49AA/FS30-10-16 with LALA mutation
(SEQ ID NO: 95)
Variable domain (italics), LALA mutation (underlined bold)
*EVQLLESGGGLVQPGGSLRLSCAASGFTFSSYDMSWVRQAPGKGLEWVSDIDPTGSKTDYADSVK*
*GRFTISRDNSKNTLYLQMNSLRAEDTAVYYCARDLLVYGFDYWGQGTLVTVSS*ASTKGPSVFPLAPS
SKSTSGGTAALGCLVKDYFPEPVTVSWNSGALTSGVHTFPAVLQSSGLYSLSSVVTVPSSSLGTQTYI
CNVNHKPSNTKVDKKVEPKSCDKTHTCPPCPAPEAAGGPSVFLFPPKPKDTLMISRTPEVTCVVVDV
SHEDPEVKFNWYVDGVEVHNAKTKPREEQYNSTYRVVSVLTVLHQDWLNGKEYKCKVSNKALPAPI
EKTISKAKGQPREPQVYTLPPSRDEYWDQEVSLTCLVKGFYPSDIAVEWESNGDEQFAYKTTPPVLD
SDGSFFLYSKLTVDQYRWNPADYFSCSVMHEALHNHYTQKSLSLSPG Nucleic acid sequence of the heavy chain of FS20-22-49AA/FS30-10-16 with LALA mutation
(SEQ ID NO: 96)
```
GAAGTTCAGCTGCTGGAATCTGGCGGCGGATTGGTTCAACCTGGCGGCTCTCTGAGACTGTCTT
GTGCCGCTTCCGGCTTCACCTTCTCCAGCTACGACATGTCCTGGGTCCGACAGGCTCCTGGCAA
AGGACTGGAATGGGTGTCCGACATCGACCCCACCGGCTCTAAGACCGACTACGCCGATTCTGTG
AAGGGCAGATTCACCATCAGCCGGGACAACTCCAAGAACACCCTGTACCTGCAGATGAACTCCC
```

TGAGAGCCGAGGACACCGCCGTGTACTACTGTGCCAGAGATCTGCTGGTGTACGGCTTCGACTA
TTGGGGCCAGGGCACACTGGTCACCGTGTCCTCTGCTTCTACCAAGGGACCCAGCGTGTTCCCT
CTGGCTCCTTCCAGCAAGTCTACCTCTGGCGGAACAGCTGCTCTGGGCTGCCTGGTCAAGGACT
ACTTTCCTGAGCCTGTGACCGTGTCTTGGAACTCTGGCGCTCTGACATCTGGCGTGCACACCTTT
CCAGCAGTGCTGCAGTCCTCCGGCCTGTACTCTCTGTCCTCTGTCGTGACCGTGCCTTCCAGCT
CTCTGGGAACCCAGACCTACATCTGCAATGTGAACCACAAGCCTTCCAACACCAAGGTGGACAA
GAAGGTGGAACCCAAGTCCTGCGACAAGACCCACACCTGTCCTCCATGTCCTGCTCCAGAAGCT
GCTGGCGGCCCTTCCGTGTTTCTGTTCCCTCCAAAGCCTAAGGACACCCTGATGATCTCTCGGA
CCCCTGAAGTGACCTGCGTGGTGGTGGATGTGTCTCACGAGGACCCAGAAGTGAAGTTCAATTG
GTACGTGGACGGCGTGGAAGTGCACAACGCCAAGACCAAGCCTAGAGAGGAACAGTACAACTC
CACCTACAGAGTGGTGTCCGTGCTGACCGTGCTGCACCAGGATTGGCTGAACGGCAAAGAGTA
CAAGTGCAAGGTGTCCAACAAGGCCCTGCCTGCTCCTATCGAAAAGACCATCTCCAAGGCCAAG
GGCCAGCCTAGGGAACCCCAGGTTTACACCTTGCCTCCAAGCCGGGACGAGTACTGGGATCAA
GAGGTGTCCCTGACCTGCCTCGTGAAGGGCTTCTACCCTTCCGATATCGCCGTGGAATGGGAGA
GCAATGGCGACGAGCAGTTCGCCTACAAGACAACCCCTCCTGTGCTGGACTCCGACGGCTCATT
CTTTCTGTACTCCAAGCTGACAGTGGACCAGTACAGATGGAACCCCGCCGACTACTTCTCTTGCT
CCGTGATGCACGAGGCCCTGCACAACCACTACACACAGAAGTCCCTGTCTCTGTCCCCTGGC

Amino acid sequence of the light chain of FS30-10-16 (SEQ ID NO: 97)
Variable domain (italics)
*EIVLTQSPGTLSLSPGERATLSCRASQSVSSSYLAWYQQKPGQAPRLLIYGASSRATGIPDRFSGSGS*
*GTDFTLTISRLEPEDFAVYYCQQSYSYPVTFGQGTKVEIK*RTVAAPSVFIFPPSDEQLKSGTASVVCLL
NNFYPREAKVQWKVDNALQSGNSQESVTEQDSKDSTYSLSSTLTLSKADYEKHKVYACEVTHQGLS
SPVTKSFNRGEC Nucleic acid sequence of the light chain of FS30-10-16 (SEQ ID NO: 98)
GAGATCGTGCTGACCCAGTCTCCTGGCACACTGTCACTGTCTCCAGGCGAGAGAGCTACCCTGT
CCTGTAGAGCCTCTCAGTCCGTGTCCTCCTCTTACCTGGCCTGGTATCAGCAGAAGCCTGGACA
GGCTCCCCGGCTGTTGATCTACGGCGCTTCTTCTAGAGCCACAGGCATCCCTGACCGGTTCTCC
GGATCTGGCTCTGGCACCGATTTCACCCTGACCATCTCTCGGCTGGAACCCGAGGATTTCGCCG
TGTACTACTGCCAGCAGTCCTACAGCTACCCCGTGACCTTTGGCCAGGGCACCAAGGTGGAAAT
CAAGCGTACGGTGGCCGCTCCCAGCGTGTTCATCTTCCCCCCAAGCGACGAGCAGCTGAAGAG
CGGCACCGCCAGCGTGGTGTGTCTGCTGAACAACTTCTACCCCAGGGAGGCCAAGGTGCAGTG
GAAGGTGGACAACGCCCTGCAGAGCGGCAACAGCCAGGAGAGCGTCACCGAGCAGGACAGCA
AGGACTCCACCTACAGCCTGAGCAGCACCCTGACCCTGAGCAAGGCCGACTACGAGAAGCACA
AGGTGTACGCCTGTGAGGTGACCCACCAGGGCCTGTCCAGCCCCGTGACCAAGAGCTTCAACA
GGGGCGAGTGC Amino acid sequence of the heavy chain of FS20-22-49AA/FS30-10-3 with LALA mutation
(SEQ ID NO: 99)
Variable domain (italics), LALA mutation (underlined bold)
*EVQLLESGGGLVQPGGSLRLSCAASGFTFSSYDMSWVRQAPGKGLEWVSDIDPTGSKTDYADSVK*
*GRFTISRDNSKNTLYLQMNSLRAEDTAVYYCARDLNVYGFDYWGQGTLVTVSS*ASTKGPSVFPLAPS
SKSTSGGTAALGCLVKDYFPEPVTVSWNSGALTSGVHTFPAVLQSSGLYSLSSVVTVPSSSLGTQTYI
CNVNHKPSNTKVDKKVEPKSCDKTHTCPPCPAPEAAGGPSVFLFPPKPKDTLMISRTPEVTCVVVDV
SHEDPEVKFNWYVDGVEVHNAKTKPREEQYNSTYRVVSVLTVLHQDWLNGKEYKCKVSNKALPAPI
EKTISKAKGQPREPQVYTLPPSRDEYWDQEVSLTCLVKGFYPSDIAVEWESNGDEQFAYKTTPPVLD
SDGSFFLYSKLTVDQYRWNPADYFSCSVMHEALHNHYTQKSLSLSPG Nucleic acid sequence of the heavy chain of FS20-22-49AA/FS30-10-3 with LALA mutation
(SEQ ID NO: 100)
GAAGTGCAACTGCTGGAGTCCGGTGGTGGTCTGGTACAGCCGGGTGGTTCTCTGCGTCTGAGT
TGCGCGGCCAGTGGCTTTACCTTCAGTAGTTACGATATGAGCTGGGTGCGTCAGGCTCCGGGCA
AAGGTCTGGAATGGGTTAGCGATATTGATCCGACTGGTAGCAAGACCGACTATGCGGATAGCGT
GAAAGGCCGTTTTACCATTTCTCGCGACAACAGCAAGAACACGCTGTACCTGCAGATGAACTCAC
TGCGTGCCGAAGATACGGCCGTGTATTACTGTGCGAGAGACCTCAATGTGTACGGGTTCGACTA
CTGGGGCCAGGGAACCCTGGTCACCGTCTCGAGTGCTAGCACTAAGGGCCCGTCGGTGTTCCC
GCTGGCCCCATCGTCCAAGAGCACATCAGGGGGTACCGCCGCCCTGGGCTGCCTTGTGAAGGA
TTACTTTCCCGAGCCCGTCACAGTGTCCTGGAACAGCGGAGCCCTGACCTCCGGAGTGCATACT
TTCCCGGCTGTGCTTCAGTCCTCTGGCCTGTACTCATTGTCCTCCGTGGTCACCGTCCCTTCGTC
CTCCCTGGGCACCCAGACCTATATCTGTAATGTCAACCATAAGCCCTCGAACACCAAGGTCGAC
AAGAAGGTCGAGCCGAAGTCGTGCGACAAGACTCACACTTGCCCGCCTTGCCCAGCCCCGGAA
GCTGCCGGTGGTCCTTCGGTGTTCCTCTTCCCGCCCAAGCCGAAGGATACCCTGATGATCTCAC
GGACCCCCGAAGTGACCTGTGTGGTGGTGGACGTGTCCCACGAGGACCCGGAAGTGAAATTCA
ATTGGTACGTGGATGGAGTGGAAGTGCACAACGCCAAGACCAAGCCACGGGAAGAACAGTACA
ACTCTACCTACCGCGTGGTGTCCGTGCTCACTGTGCTGCACCAAGACTGGCTGAACGGGAAGGA
GTACAAGTGCAAAGTGTCCAACAAGGCGCTGCCTGCCCCAATTGAGAAAACTATCTCAAAGCC
AAGGGACAGCCTCGAGAACCACAGGTGTACACCCTGCCCCCATCCCGGGATGAGTACTGGGAC
CAGGAAGTCAGCCTGACCTGCCTGGTCAAAGGCTTCTATCCCAGCGACATCGCCGTGGAGTGG
GAGAGCAATGGGGATGAACAGTTCGCATACAAGACCACGCCTCCCGTGCTGGACTCCGACGGC
TCCTTCTTCCTCTACAGCAAGCTCACCGTGGATCAGTATAGGTGGAATCCTGCTGATTATTTCTCA
TGCTCCGTGATGCATGAGGCTCTGCACAACCACTACACTCAGAAGAGCTTGTCCCTGTCGCCCG
GA -continued Sequence Listing Amino acid sequence of the light chain of FS30-10-3 (SEQ ID NO: 97)
Variable domain (italics)
*EIVLTQSPGTLSLSPGERATLSCRASQSVSSSYLAWYQQKPGQAPRLLIYGASSRATGIPDRFSGSGS*
*GTDFTLTISRLEPEDFAVYYGQQSYSYPVTFGQGTKVEIK*RTVAAPSVFIFPPSDEQLKSGTASVVCLL
NNFYPREAKVQWKVDNALQSGNSQESVTEQDSKDSTYSLSSTLTLSKADYEKHKVYACEVTHQGLS
SPVTKSFNRGEC Nucleic acid sequence of the light chain of FS30-10-3 (SEQ ID NO: 102)
GAAATTGTGCTGACCCAGTCTCCGGGCACGTTATCTCTGAGCCCTGGTGAGCGCGCCACTCTGT
CATGCCGGGCTTCTCAAAGTGTTAGCAGTAGCTACCTGGCGTGGTATCAGCAAAAACCGGGCCA
GGCCCCGCGTCTGCTGATTTACGGTGCATCCAGCCGTGCCACCGGCATTCCAGATCGTTTTTCC
GGTAGTGGTTCTGGGACGGACTTCACTCTGACAATCTCACGCCTGGAACCGGAGGATTTTGCGG
TGTATTACTGCCAGCAATCTTATTCTTATCCTGTCACGTTCGGCCAAGGGACCAAGGTGGAAATC
AAACGTACTGTGGCCGCTCCTAGCGTGTTCATTTTTCCGCCATCCGACGAGCAGCTCAAGTCCG
GCACCGCCTCCGTGGTCTGCCTGCTCAACAACTTCTACCCTCGCGAAGCTAAGGTCCAGTGGAA
GGTCGACAATGCCCTGCAGTCCGGAAACTCGCAGGAAAGCGTGACTGAACAGGACTCCAAGGA
CTCCACCTATTCACTGTCCTCGACTCTGACCCTGAGCAAGGCGGATTACGAAAAGCACAAAGTGT
ACGCATGCGAAGTGACCCACCAGGGTCTTTCGTCCCCCGTGACCAAGAGCTTCAACAGAGGAGA
GTGT Amino acid sequence of the heavy chain of FS20-22-49AA/FS30-10-12 with LALA mutation
(SEQ ID NO: 103)
Variable domain (italics), LALA mutation (underlined bold)
*EVQLLESGGGLVQPGGSLRLSCAASGFTFSSYDMSWVRQAPGKGLEWVSDIDPTGSKTDYADSVK*
*GRFTISRDNSKNTLYLQMNSLRAEDTAVYYCARDLTVYGFDYWGQGTLVTVSS*ASTKGPSVFPLAPS
SKSTSGGTAALGCLVKDYFPEPVTVSWNSGALTSGVHTFPAVLQSSGLYSLSSVVTVPSSSLGTQTYI
CNVNHKPSNTKVDKKVEPKSCDKTHTCPPCPAPEAAGGPSVFLFPPKPKDTLMISRTPEVTCVVVVDV
SHEDPEVKFNWYVDGVEVHNAKTKPREEQYNSTYRVVSVLTVLHQDWLNGKEYKCKVSNKALPAPI
EKTISKAKGQPREPQVYTLPPSRDEYWDQEVSLTCLVKGFYPSDIAVEWESNGDEQFAYKTTPPVLD
SDGSFFLYSKLTVDQYRWNPADYFSCSVMHEALHNHYTQKSLSLSPG Nucleic acid sequence of the heavy chain of FS20-22-49AA/FS30-10-12 with LALA mutation
(SEQ ID NO: 104)
GAAGTGCAACTGCTGGAGTCCGGTGGTGGTCTGGTACAGCCGGGTGGTTCTCTGCGTCTGAGT
TGCGCGGCCAGTGGCTTTACCTTCAGTAGTTACGATATGAGCTGGGTGCGTCAGGCTCCGGGCA
AAGGTCTGGAATGGGTTAGCGATATTGATCCGACTGGTAGCAAGACCGACTATGCGGATAGCGT
GAAAGGCCGTTTTACCATTTCTCGCGACAACAGCAAGAACACGCTGTACCTGCAGATGAACTCAC
TGCGTGCCGAAGATACGGCCGTGTATTACTGTGCGAGAGACCTCACGGTGTACGGGTTCGACTA
CTGGGGCCAGGGAACCCTGGTCACCGTCTCGAGTGCTAGCACTAAGGGCCCGTCGGTGTTCCC
GCTGGCCCATCGTCCAAGAGCACATCAGGGGGTACCGCCGCCCTGGGCTGCCTTGTGAAGGA
TTACTTTCCCGAGCCCGTCACAGTGTCCTGGAACAGCGGAGCCCTGACCTCCGGAGTGCATACT
TTCCCGGCTGTGCTTCAGTCCTCTGGCCTGTACTCATTGTCCTCCGTGGTCACCGTCCCTTCGTC
CTCCCTGGGCACCCAGACCTATATCTGTAATGTCAACCATAAGCCCTCGAACACCAAGGTCGAC
AAGAAGGTCGAGCCGAAGTCGTGCGACAAGACTCACACTTGCCCGCCTTGCCCAGCCCCGGAA
GCTGCCGGTGGTCCTTCGGTGTTCCTCTTCCCGCCCAAGCCGAAGGATACCCTGATGATCTCAC
GGACCCCCGAAGTGACCTGTGTGGTGGTGGACGTGTCCCACGAGGACCCGGAAGTGAAATTCA
ATTGGTACGTGGATGGAGTGGAAGTGCACAACGCCAAGACCAAGCCACGGGAAGAACAGTACA
ACTCTACCTACCGCGTGGTGTCCGTGCTCACTGTGCTGCACCAAGACTGGCTGAACGGGAAGGA
GTACAAGTGCAAAGTGTCCAACAAGGCGCTGCCTGCCCCAATTGAGAAAACTATCTCGAAAGCC
AAGGGACAGCCTCGAGAACCACAGGTGTACACCCTGCCCCATCCCGGGATGAGTACTGGGAC
CAGGAAGTCAGCCTGACCTGCCTGGTCAAAGGCTTCTATCCCAGCGACATCGCCGTGGAGTGG
GAGAGCAATGGGATGAACAGTTCGCATACAAGACCACGCCTCCCGTGCTGGACTCCGACGGC
TCCTTCTTCCTCTACAGCAAGCTCACCGTGGATCAGTATAGGTGGAATCCTGCTGATTATTTCTCA
TGCTCCGTGATGCATGAGGCTCTGCACAACCACTACACTCAGAAGAGCTTGTCCCTGTCGCCCG
GA Amino acid sequence of the light chain of FS30-10-12 (SEQ ID NO: 97)
Variable domain (italics)
*EIVLTQSPGTLSLSPGERATLSCRASQSVSSSYLAWYQQKPGQAPRLLIYGASSRATGIPDRFSGSGS*
*GTDFTLTISRLEPEDFAVYYCQQSYSYPVTFGQGTKVEIK*RTVAAPSVFIFPPSDEQLKSGTASVVCLL
NNFYPREAKVQWKVDNALQSGNSQESVTEQDSKDSTYSLSSTLTLSKADYEKHKVYACEVTHQGLS
SPVTKSFNRGEC Nucleic acid sequence of the light chain of FS30-10-12 (SEQ ID NO: 102)
GAAATTGTGCTGACCCAGTCTCCGGGCACGTTATCTCTGAGCCCTGGTGAGCGCGCCACTCTGT
CATGCCGGGCTTCTCAAAGTGTTAGCAGTAGCTACCTGGCGTGGTATCAGCAAAAACCGGGCCA
GGCCCCGCGTCTGCTGATTTACGGTGCATCCAGCCGTGCCACCGGCATTCCAGATCGTTTTTCC
GGTAGTGGTTCTGGGACGGACTTCACTCTGACAATCTCACGCCTGGAACCGGAGGATTTTGCGG
TGTATTACTGCCAGCAATCTTATTCTTATCCTGTCACGTTCGGCCAAGGGACCAAGGTGGAAATC
AAACGTACTGTGGCCGCTCCTAGCGTGTTCATTTTTCCGCCATCCGACGAGCAGCTCAAGTCCG
GCACCGCCTCCGTGGTCTGCCTGCTCAACAACTTCTACCCTCGCGAAGCTAAGGTCCAGTGGAA
GGTCGACAATGCCCTGCAGTCCGGAAACTCGCAGGAAAGCGTGACTGAACAGGACTCCAAGGA
CTCCACCTATTCACTGTCCTCGACTCTGACCCTGAGCAAGGCGGATTACGAAAAGCACAAAGTGT
ACGCATGCGAAGTGACCCACCAGGGTCTTTCGTCCCCCGTGACCAAGAGCTTCAACAGAGGAGA
GTGT

Sequence Listing

Amino acid sequence of the heavy chain of FS20-22-49AA/FS30-35-14 with LALA mutation
(SEQ ID NO: 105)
Variable domain (italics), LALA mutation (underlined bold)
*EVQLLESGGGLVQPGGSLRLSCAASGFTFSAYNIHWVRQAPGKGLEWVSDISPYGGATNYADSVKG*
*RFTISRDNSKNTLYLQMNSLRAEDTAVYYCARNLYELSAYSYGADYWGQGTLVTVSS*ASTKGPSVFP
LAPSSKSTSGGTAALGCLVKDYFPEPVTVSWNSGALTSGVHTFPAVLQSSGLYSLSSVVTVPSSSLG
TQTYICNVNHKPSNTKVDKKVEPKSCDKTHTCPPCPAPEAAGGPSVFLFPPKPKDTLMISRTPEVTC
VVVDVSHEDPEVKFNWYVDGVEVHNAKTKPREEQYNSTY<u>R</u>VVSVLTVLHQDWLNGKEYKCKVSNK
ALPAPIEKTISKAKGQPREPQVYTLPPSRDEYWDQEVSLTCLVKGFYPSDIAVEWESNGDEQFAYKTT
PPVLDSDGSFFLYSKLTVDQYRWNPADYFSCSVMHEALHNHYTQKSLSLSPG Nucleic acid sequence of the heavy chain of FS20-22-49AA/FS30-35-14 with LALA mutation
(SEQ ID NO: 106)
GAAGTGCAACTGCTGGAGTCCGGTGGTGGTCTGGTACAGCCGGGTGGTTCTCTGCGTCTGAGT
TGCGCGGCCAGTGGCTTTACCTTCAGTGCCTATAATATCCATTGGGTGCGTCAGGCTCCGGGCA
AAGGTCTGGAATGGGTTAGCGATATTTCTCCGTATGGTGGCGGCGACCAACTATGCGGATAGCGT
GAAAGGCCGTTTTACCATTTCTCGCGACAACAGCAAGAACACGCTGTACCTGCAGATGAACTCAC
TGCGTGCCGAAGATACGGCCGTGTATTACTGTGCGAGAAACCTCTACGAGTTGAGCGCTTACTC
TTACGGGGCGGACTACTGGGGCCAGGGAACCCTGGTCACCGTCTCGTCGGCTAGCACTAAGGG
CCCGTCGGTGTTCCCGCTGGCCCCATCGTCCAAGAGCACATCAGGGGGTACCGCCGCCCTGGG
CTGCCTTGTGAAGGATTACTTTCCCGAGCCCGTCACAGTGTCCTGGAACAGCGGAGCCCTGACC
TCCGGAGTGCATACTTTCCCGGCTGTGCTTCAGTCCTCTGGCCTGTACTCATTGTCCTCCGTGGT
CACCGTCCCTTCGTCCTCCCTGGGCACCCAGACCTATATCTGTAATGTCAACCATAAGCCCTCGA
ACACCAAGGTCGACAAGAAGGTCGAGCCGAAGTCGTGCGACAGACTCACACTTGCCCGCCTT
GCCCAGCCCCGGAAGCTGCCGGTGGTCCTTCGGTGTTCCTCTTCCCGCCCAAGCCGAAGGATA
CCCTGATGATCTCTACGGACCCCCGAAGTGACCTGTGTGGTGGTGGACGTGTCCCACGAGGACC
CGGAAGTGAAATTCAATTGGTACGTGGATGGAGTGGAAGTGCACAACGCCAAGACCAAGCCACG
GGAAGAACAGTACAACTCTACCTACCGCGTGGTGTCCGTCCACTGTGCTGCACCAAGACTGG
CTGAAGGGGAAGGAGTACAAGTGCAAAGTGTCCAACAAGGCGCTGCCTGCCCCAATTGAGAAAA
CTATCTCGAAAGCCAAGGGACAGCCTCGAGAACCACAGGTGTACACCCTGCCCCCATCCCGGG
ATGAGTACTGGGACCAGGAAGTCAGCCTGACCTGCCTGGTCAAAGGCTTCTATCCCAGCGACAT
CGCCGTGGAGTGGGAGAGCAATGGGGATGAACAGTTCGCATACAAGACCACGCCTCCCGTGCT
GGACTCCGACGGCTCCTTCTTCCTCTACAGCAAGCTCACCGTGGATCAGTATAGGTGGAATCCT
GCTGATTATTTCTCATGCTCCGTGATGCATGAGGCTCTGCACAACCACTACACTCAGAAGAGCTT
GTCCCTGTCGCCCGGA Amino acid sequence of the light chain of FS30-35-14 (SEQ ID NO: 107)
Variable domain (italics)
*EIVLTQSPGTLSLSPGERATLSCRASQSVSSSYLAWYQQKPGQAPRLLIYGASSRATGIPDRFSGSGS*
*GTDFTLTISRLEPEDFAVYYCQQYYYSSPITFGQGTKVEIK*RTVAAPSVFIFPPSDEQLKSGTASVVCL
LNNFYPREAKVQWKVDNALQSGNSQESVTEQDSKDSTYSLSSTLTLSKADYEKHKVYACEVTHQGL
SSPVTKSFNRGEC Nucleic acid sequence of the light chain of FS30-35-14 (SEQ ID NO: 108)
GAAATTGTGCTGACCCAGTCTCCGGGCACGTTATCTCTGAGCCCTGGTGAGCGCGCCACTCTGT
CATGCCGGGCTTCTCAAAGTGTTAGCAGTAGCTACCTGGCGTGGTATCAGCAAAAACCGGGCCA
GGCCCCGCGTCTGCTGATTTACGGTGCATCCAGCCGTGCCACCGGCATTCCAGATCGTTTTTCC
GGTAGTGGTTCTGGGACGGACTTCACTCTGACAATCTCACGCCTGGAACCGGAGGATTTTGCGG
TGTATTACTGCCAGCAATATTATTATTCTTCTCCTATCACGTTCGGCCAAGGGACCAAGGTGGAA
ATCAAACGTACTGTGGCCGCTCCTAGCGTGTTCATTTTTCCGCCATCCGACGAGCAGCTCAAGTC
CGGCACCGCCTCCGTGGTCTGCCTGCTCAACAACTTCTACCCTCGCGAAGCTAAGGTCCAGTGG
AAGGTCGACAATGCCCTGCAGTCCGGAAACTCGCAGGAAAGCGTGACTGAACAGGACTCCAAG
GACTCCACCTATTCACTGTCCTCGACTCTGACCCTGAGCAAGGCGGATTACGAAAAGCACAAAG
TGTACGCATGCGAAGTGACCCACCAGGGTCTTTCGTCCCCGTGACCAAGAGCTTCAACAGAGG
AGAGTGT Amino acid sequence of the heavy chain of FS20-22-49AA/FS30-5-37 with LALA mutation (SEQ ID
NO: 109)
Variable domain (italics), LALA mutation (underlined bold)
*EVQLLESGGGLVQPGGSLRLNCAASGFTFSSYAMSWVRQAPGKGLEWVSAISGSGGSTYYADSVK*
*GRFTISRDNSKNTLYLQMNSLRAEDTAVYYCARSYDKYWGSSIYSGLDYWGQGTLVTVSS*ASTKGP
SVFPLAPSSKSTSGGTAALGCLVKDYFPEPVTVSWNSGALTSGVHTFPAVLQSSGLYSLSSVVTVPS
SSLGTQTYICNVNHKPSNTKVDKKVEPKSCDKTHTCPPCPAPEAAGGPSVFLFPPKPKDTLMISRTP
EVTCVVVDVSHEDPEVKFNWYVDGVEVHNAKTKPREEQYNSTY<u>R</u>VVSVLTVLHQDWLNGKEYKCK
VSNKALPAPIEKTISKAKGQPREPQVYTLPPSRDEYWDQEVSLTCLVKGFYPSDIAVEWESNGDEQF
AYKTTPPVLDSDGSFFLYSKLTVDQYRWNPADYFSCSVMHEALHNHYTQKSLSLSPG Nucleic acid sequence of the heavy chain of FS20-22-49AA/FS30-5-37 with LALA mutation (SEQ ID
NO: 110)
GAAGTGCAACTGCTGGAGTCCGGTGGTGGTCTGGTACAGCCGGGTGGTTCTCTGCGTCTGAATT
GCGCGGCCAGTGGCTTTACCTTCAGTAGCTATGCCATGAGCTGGGTGCGTCAGGCGCCGGGCA
AAGGTCTGGAATGGGTTAGCGCGATTAGCGGTAGTGGCGGTAGCACGTACTATGCGGATAGCG
TGAAAGGCCGTTTTACCATTTCTCGCGACAACAGCAAGAACACGCTGTACCTGCAGATGAACTCA
CTGCGTGCCGAAGATACGGCCGTGTATTACTGTGCGAGATCTTACGACAAATACTGGGGTTCTT
CTATTTACTCTGGCTTGGACTACTGGGGCCAGGGAACCCTGGTCACCGTCTCGAGTGCTAGCAC
TAAGGGCCCGTCGGTGTTCCCGCTGGCCCCATCGTCCAAGAGCACATCAGGGGGTACCGCCGC
CCTGGGCTGCCTTGTGAAGGATTACTTTCCCGAGCCCGTCACAGTGTCCTGGAACAGCGGAGCC

```
CTGACCTCCGGAGTGCATACTTTCCCGGCTGTGCTTCAGTCCTCTGGCCTGTACTCATTGTCCTC
CGTGGTCACCGTCCCTTCGTCCTCCCTGGGCACCCAGACCTATATCTGTAATGTCAACCATAAGC
CCTCGAACACCAAGGTCGACAAGAAGGTCGAGCCGAAGTCGTGCGACAAGACTCACACTTGCC
CGCCTTGCCCAGCCCCGGAAGCTGCCGGTGGTCCTTCGGTGTTCCTCTTCCCGCCCAAGCCGA
AGGATACCCTGATGATCTCACGGACCCCCGAAGTGACCTGTGTGGTGGTGGACGTGTCCCACG
AGGACCCGGAAGTGAAATTCAATTGGTACGTGGATGGAGTGGAAGTGCACAACGCCAAGACCAA
GCCACGGGAAGAACAGTACAACTCTACCTACCGCGTGGTGTCCGTGCTCACTGTGCTGCACCAA
GACTGGCTGAACGGGAAGGAGTACAAGTGCAAAGTGTCCAACAAGGCGCTGCCTGCCCCAATT
GAGAAAACTATCTCGAAAGCCAAGGGACAGCCTCGAGAACCACAGGTGTACACCCTGCCCCCAT
CCCGGGATGAGTACTGGGACCAGGAAGTCAGCCTGACCTGCCTGGTCAAAGGCTTCTATCCCA
GCGACATCGCCGTGGAGTGGGAGAGCAATGGGGATGAACAGTTCGCATACAAGACCACGCCTC
CCGTGCTGGACTCCGACGGCTCCTTCTTCCTCTACAGCAAGCTCACCGTGGATCAGTATAGGTG
GAATCCTGCTGATTATTTCTCATGCTCCGTGATGCATGAGGCTCTGCACAACCACTACACTCAGA
AGAGCTTGTCCCTGTCGCCCGGA

Amino acid sequence of the light chain of FS30-5-37 (SEQ ID NO: 111)
Variable domain (italics)
*EIVLTQSPGTLSLSPGERATLSCRASQSVSSSYLAWYQQKPGQAPRLLIYGASSRATGIPDRFSGSGS*
*GTDFTLTISRLEPEDFAVYYCQQYYSYYPVTFGQGTKVEIK*RTVAAPSVFIFPPSDEQLKSGTASVVCL
LNNFYPREAKVQWKVDNALQSGNSQESVTEQDSKDSTYSLSSTLTLSKADYEKHKVYACEVTHQGL
SSPVTKSFNRGEC Nucleic acid sequence of the light chain of FS30-5-37 (SEQ ID NO: 112)
GAAATTGTGCTGACCCAGTCTCCGGGCACGTTATCTCTGAGCCCTGGTGAGCGCGCCACTCTGT
CATGCCGGGCTTCTCAAAGTGTTAGCAGTAGCTACCTGGCGTGGTATCAGCAAAAACCGGGCCA
GGCCCCGCGTCTGCTGATTTACGGTGCATCCAGCCGTGCCACCGGCATTCCAGATCGTTTTTCC
GGTAGTGGTTCTGGGACGGACTTCACTCTGACAATCTCACGCCTGGAACCGGAGGATTTTGCGG
TGTATTACTGCCAGCAATATTATTCTTATTATCCTGTCACGTTCGGCCAAGGGACCAAGGTGGAA
ATCAAACGTACTGTGGCCGCTCCTAGCGTGTTCATTTTTCCGCCATCCGACGAGCAGCTCAAGTC
CGGCACCGCCTCCGTGGTCTGCCTGCTCAACAACTTCTACCCTCGCGAAGCTAAGGTCCAGTGG
AAGGTCGACAATGCCCTGCAGTCCGGAAACTCGCAGGAAAGCGTGACTGAACAGGACTCCAAG
GACTCCACCTATTCACTGTCCTCGACTCTGACCCTGAGCAAGGCGGATTACGAAAAGCACAAAG
TGTACGCATGCGAAGTGACCCACCAGGGTCTTTCGTCCCCGTGACCAAGAGCTTCAACAGAGG
AGAGTGT Alternative nucleic acid sequence of Fcab FS20-22-49 CH3 domain (SEQ ID NO: 113)
GGACAGCCTCGAGAACCACAGGTGTACACCCTGCCCCCATCCCGGGATGAGTACTGGGACCAG
GAAGTCAGCCTGACCTGCCTGGTCAAAGGCTTCTATCCCAGCGACATCGCCGTGGAGTGGGAG
AGCAATGGGGATGAACAGTTCGCATACAAGACCACGCCTCCCGTGCTGGACTCCGACGGCTCCT
TCTTCCTCTACAGCAAGCTCACCGTGGATCAGTATAGGTGGAATCCTGCTGATTATTTCTCATGC
TCCGTGATGCATGAGGCTCTGCACAACCACTACACTCAGAAGAGCTTGTCCCTGTCGCCCGGA Amino acid sequence of the heavy chain of anti-FITC mAb G1AA/4420 comprising LALA mutation
(SEQ ID NO: 114)
Position of the CDRs are underlined. Position of LALA mutation is in bold.
EVKLDETGGGLVQPGRPMKLSCVAS<u>GFTFSDYWMN</u>WVRQSPEKGLEWVA<u>QIRNKPYNYETYYSDS</u>
VKGRFTISRDDSKSSVYLQMNNLRV<u>EDMGIYYCTGSYYGMDY</u>WGQGTSVTVSSASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPEAAGGPSVFLFPPKPKDTLMISRTPEVTCVVV
DVSHEDPEVKFNWYVDGVEVHNAKTKPREEQYNSTYRVVSVLTVLHQDWLNGKEYKCKVSNKALP
APIEKTISKAKGQPREPQVYTLPPSRDELTKNQVSLTCLVKGFYPSDIAVEWESNGQPENNYKTTPPV
LDSDGSFFLYSKLTVDKSRWQQGNVFSCSVMHEALHNHYTQKSLSLSPG Amino acid sequence of the heavy chain of anti-FITC mAb G1/4420 without LALA mutation (SEQ ID
NO: 115)
Position of the CDRs are underlined.
EVKLDETGGGLVQPGRPMKLSCVAS<u>GFTFSDYWMN</u>WVRQSPEKGLEWVA<u>QIRNKPYNYETYYSDS</u>
VKGRFTISRDDSKSSVYLQMNNLRV<u>EDMGIYYCTGSYYGMDY</u>WGQGTSVTVSSASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLNGKEYKCKVSNKALPAP
IEKTISKAKGQPREPQVYTLPPSRDELTKNQVSLTCLVKGFYPSDIAVEWESNGQPENNYKTTPPVLD
SDGSFFLYSKLTVDKSRWQQGNVFSCSVMHEALHNHYTQKSLSLSPG Amino acid sequence of the light chain of 4420 mAb (SEQ ID NO: 116)
VL domain (italics)
*DVVMMTPLSLPVSLGDQASISCRSSQSLVHSNGNTYLRWYLQKPGQSPKVLIYKVSNRFSGVPDRF*
*SGSGSGTDFTLKISRVEAEDLGVYFCSQSTHVPWTFGGGTKLEIK*RTVAAPSVFIFPPSDEQLKSGTA
SVVCLLNNFYPREAKVQWKVDNALQSGNSQESVTEQDSKDSTYSLSSTLTLSKADYEKHKVYACEV
THQGLSSPVTKSFNRGEC Amino acid sequence of the heavy chain of the G1AA/HelD1.3 antibody with LALA mutation (SEQ ID
NO: 117)
QVQLQESGPGLVRPSQTLSLTCTVSGSTFSGYGVNWVRQPPGRGLEWIGMIWGDGNTDYNSALKS
RVTMLVDTSKNQFSLRLSSVTAADTAVYYCARERDYRLDYWGQGSLVTVSSASTKGPSVFPLAPSS
KSTSGGTAALGCLVKDYFPEPVTVSWNSGALTSGVHTFPAVLQSSGLYSLSSVVTVPSSSLGTQTYI
CNVNHKPSNTKVDKKVEPKSCDKTHTCPPCPAPEAAGGPSVFLFPPKPKDTLMISRTPEVTCVVVD
```

Sequence Listing

SHEDPEVKFNWYVDGVEVHNAKTKPREEQYNSTYRVVSVLTVLHQDWLNGKEYKCKVSNKALPAPI
EKTISKAKGQPREPQVYTLPPSRDELTKNQVSLTCLVKGFYPSDIAVEWESNGQPENNYKTTPPVLD
SDGSFFLYSKLTVDKSRWQQGNVFSCSVMHEALHNHYTQKSLSLSPGK

Amino acid sequence of the light chain of HelD1.3 mAb (SEQ ID NO: 118)
VL domain (italics)
*DIQMTQSPASLSASVGETVTITCRASGNIHNYLAWYQQKQGKSPQLLVYNAKTLADGVPSRFSGSGS*
*GTQYSLKINSLQPEDFGSYYCQHFWSTPRTFGGGTKLEIK*RTVAAPSVFIFPPSDEQLKSGTASVVCL
LNNFYPREAKVQWKVDNALQSGNSQESVTEQDSKDSTYSLSSTLTLSKADYEKHKVYACEVTHQGL
SSPVTKSFNRGEC Amino acid sequence of the heavy chain of the G1/MOR7480.1 (SEQ ID NO: 119)
VH domain (italics)
*EVQLVQSGAEVKKPGESLRISCKGSGYSFSTYWISWVRQMPGKGLEWMGKIYPGDSYTNYSPSFQ*
*GQVTISADKSISTAYLQWSSLKASDTAMYYCARGYGIFDYWGQGTLVTVSS*ASTKGPSVFPLAPSSK
STSGGTAALGCLVKDYFPEPVTVSWNSGALTSGVHTFPAVLQSSGLYSLSSVVTVPSSSLGTQTYIC
NVNHKPSNTKVDKKVEPKSCDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLNGKEYKCKVSNKALPAPIE
KTISKAKGQPREPQVYTLPPSRDELTKNQVSLTCLVKGFYPSDIAVEWESNGQPENNYKTTPPVLDS
DGSFFLYSKLTVDKSRWQQGNVFSCSVMHEALHNHYTQKSLSLSPG Amino acid sequence of the light chain of G1/MOR7480.1, G1AA/MOR7480.1 and G2/MOR7480.1
mAbs (SEQ ID NO: 120)
VL domain (italics)
*SYELTQPPSVSVSPGQTASITCSGDNIGDQYAHWYQQPGQSPVLVIYQDKNRPSGIPERFSGSNSG*
*NTATLTISGTQAMDEADYYCATYTGFGSLAVFGGGTKLTVL*GQPKAAPSVTLFPPSSEELQANKATLV
CLISDFYPGAVTVAWKADSSPVKAGVETTTPSKQSNNKYAASSYLSLTPEQWKSHRSYSCQVTHEG
STVEKTVAPTECS Amino acid sequence of the heavy chain of the G1/20H4.9 (SEQ ID NO: 121)
VH domain (italics)
*QVQLQQWGAGLLKPSETLSLTCAVYGGSFSGYYWSWIRQSPEKGLEWIGEINHGGYVTYNPSLESR*
*VTISVDTSKNQFSLKLSSVTAADTAVYYCARDYGPGNYDWYFDLWGRGTLVTVSS*ASTKGPSVFPLA
PSSKSTSGGTAALGCLVKDYFPEPVTVSWNSGALTSGVHTFPAVLQSSGLYSLSSVVTVPSSSLGTQ
TYICNVNHKPSNTKVDKKVEPKSCDKTHTCPPCPAPELLGGPSVFLFPPKPKDTLMISRTPEVTCVVV
DVSHEDPEVKFNWYVDGVEVHNAKTKPREEQYNSTYRVVSVLTVLHQDWLNGKEYKCKVSNKALP
APIEKTISKAKGQPREPQVYTLPPSRDELTKNQVSLTCLVKGFYPSDIAVEWESNGQPENNYKTTPPV
LDSDGSFFLYSKLTVDKSRWQQGNVFSCSVMHEALHNHYTQKSLSLSPG Amino acid sequence of the light chain of G1/20H4.9 and G1AA/20H4.9 mAbs (SEQ ID NO: 122)
VL domain (italics)
*EIVLTQSPATLSLSPGERATLSCRASQSVSSYLAWYQQKPGQAPRLLIYDASNRATGIPARFSGSGSG*
*TDFTLTISSLEPEDFAVYYCQQRSNWPPALTFGGGTKVEIK*RTVAAPSVFIFPPSDEQLKSGTASVVCL
LNNFYPREAKVQWKVDNALQSGNSQESVTEQDSKDSTYSLSSTLTLSKADYEKHKVYACEVTHQGL
SSPVTKSFNRGEC Amino acid sequence of the heavy chain of FS20-22-49AA/4420 (with LALA mutation) (SEQ ID NO: 123)
VH domain (italics); LALA mutation (bold and underlined)
*EVKLDETGGGLVQPGRPMKLSCVASGFTFSDYWMNWVRQSPEKGLEWVAQIRNKPYNYETYYSDS*
*VKGRFTISRDDSKSSVYLQMNNLRVEDMGIYYCTGSYYGMDYWGQGTSVTVSS*ASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPEAAGGPSVFLFPPKPKDTLMISRTPEVTCVVV
DVSHEDPEVKFNWYVDGVEVHNAKTKPREEQYNSTYRVVSVLTVLHQDWLNGKEYKCKVSNKALP
APIEKTISKAKGQPREPQVYTLPPSRDEYWDQEVSLTCLVKGFYPSDIAVEWESNGDEQFAYKTTPP
VLDSDGSFFLYSKLTVDQYRWNPADYFSCSVMHEALHNHYTQKSLSLSPG Amino acid sequence of the heavy chain of the G2/MOR7480.1 (SEQ ID NO: 124)
VH domain (italics)
*EVQLVQSGAEVKKPGESLRISCKGSGYSFSTYWISWVRQMPGKGLEWMGKIYPGDSYTNYSPSFQ*
*GCVTISADKSISTAYLCWSSLKASDTAMYYCARGYGIFDYWGQGTLVTVSS*ASTKGPSVFPLAPCSR
STSESTAALGCLVKDYFPEPVTVSWNSGALTSGVHTFPAVLQSSGLYSLSSVVTVPSSNFGTQTYTC
NVDHKPSNTKVDKTVERKCCVECPPCPAPPVAGPSVFLFPPKPKDTLMISRTPEVTCVVVDVSHEDP
EVQFNWYVDGVEVHNAKTKPREEQFNSTFRVVSVLTVVHQDWLNGKEYKCKVSNKGLPAPIEKTISK
TKGQPREPQVYTLPPSREEMTKNQVSLTCLVKGFYPSDIAVEWESNGQPENNYKTTPPMLDSDGSF
FLYSKLTVDKSRWQQGNVFSCSVMHEALHNHYTQKSLSLSPG Amino acid sequence of the heavy chain of the G1AA/MOR7480.1 (SEQ ID NO: 125)
VH domain (italics) LALA (bold and underlined)
*EVQLVQSGAEVKKPGESLRISCKGSGYSFSTYWISWVRQMPGKGLEWMGKIYPGDSYTNYSPSFQ*
*GQVTISADKSISTAYLCWSSLKASDTAMYYCARGYGIFDYWGQGTLVTVSS*ASTKGPSVFPLAPSSK
STSGGTAALGCLVKDYFPEPVTVSWNSGALTSGVHTFPAVLQSSGLYSLSSVVTVPSSSLGTQTYIC
NVNHKPSNTKVDKKVEPKSCDKTHTCPPCPAPEAAGGPSVFLFPPKPKDTLMISRTPEVTCVVVDVS
HEDPEVKFNWYVDGVEVHNAKTKPREEQYNSTYRVVSVLTVLHCDWLNGKEYKCKVSNKALPAPIE
KTISKAKGQPREPQVYTLPPSRDELTKNQVSLTCLVKGFYPSDIAVEWESNGQPENNYKTTPPVLDS
DGSFFLYSKLTVDKSRWQQGNVFSCSVMHEALHNHYTQKSLSLSPG

Sequence Listing

Amino acid sequence of human CD137 (SEQ ID NO: 126)
Extracellular domain (italics); transmembrane and intracellular domains (bold)
*LQDPCSNCPAGTFCDNNRNQICSPCPPNSFSSAGGQRTCDICRCCKGVFRTRKECSSTSNAECDCT*
*PGFHCLGAGCSMCEQDCKQGQELTKKGCKDCCFGTFNDCKRGICRPWTNCSLDGKSVLVNGTKER*
*DVVCGPSPADLSPGASSVTPPAPAREPGHSPQ*IISFFLALTSTALLFLLFFLTLRFSVVKRGRKKLLYI
FKQPFMRPVQTTQEEDGCSCRFPEEEEGGCEL

Amino acid sequence of human CD137 extracellular domain (SEQ ID NO: 127)
LQDPCSNCPAGTFCDNNRNQICSPCPPNSFSSAGGQRTCDICRQCKGVFRTRKECSSTSNAECDCT
PGFHCLGAGCSMCECDCKQGQELTKKGCKDCCFGTFNDQKRGICRPWTNCSLDGKSVLVNGTKER
DVVCGPSPADLSPGASSVTPPAPAREPGHSPQ Amino acid sequence of cynomolqus CD137 (SEQ ID NO: 128)
Extracellular domain (italics); transmembrane and intracellular domains (bold)
*LCDLCSNCPAGTFCDNNRSCICSPCPPNSFSSAGGCRTCDICRCCKGVFKTRKECSSTSNAECDCIS*
*GYHCLGAECSMCEQDCKQGQELTKKGCKDCCFGTFNDCKRGICRPWTNCSLDGKSVLVNGTKERD*
*VVCGPSPADLSPGASSATPPAPAREPGHSPQ*IIFFLALTSTVVLFLLFFLVLRFSVVKRSRKKLLYIFK
QPFMRPVQTTQEEDGCSCRFPEEEEGGCEL

Amino acid sequence of cynomolqus CD137 extracellular domain (SEQ ID NO: 129)
LQDLCSNCPAGTFCDNNRSQICSPCPPNSFSSAGGQRTCDICRQCKGVFKTRKECSSTSNAECDCIS
GYHCLGAECSMCEQDCKQGQELTKKGCKDCCFGTFNDQKRGICRPVVTNCSLDGKSVLVNGTKERD
VVCGPSPADLSPGASSATPPAPAREPGHSPQ Amino acid sequence of human OX40 extracellular domain (SEQ ID NO: 130)
LHCVGDTYPSNDRCCHECRPGNGMVSRCSRSQNTVCRPCGPGFYNDVVSSKPCKPCTWCNLRSG
SERKQLCTATQDTVCRCRAGTQPLDSYKPGVDCAPCPPGHFSPGDNQACKPWTNCTLAGKHTLQP
ASNSSDAICEDRDPPATQPQETQGPPARPITVQPTEAWPRTSQGPSTRPVEVPGGRA Amino acid sequence of cynomolqus OX40 extracellular domain (SEQ ID NO: 131)
LHCVGDTYPSNDRCCQECRPGNGMVSRCNRSQNTVCRPCGPGFYNDVVSAKPCKACTVVCNLRSG
SERKQPCTATQDTVCRCRAGTQPLDSYKPGVDCAPCPPGHFSPGDNQACKPWTNCTLAGKHTLQP
ASNSSDAICEDRDPPPTQPQETQGPPARPTTVQPTEAWPRTSQRPSTRPVEVPRGPA Amino acid sequence of DO11.10-hOX40 and human OX40 receptor (SEQ ID NO: 132)
LHCVGDTYPSNDRCCHECRPGNGMVSRCSRSQNTVCRPCGPGFYNDVVSSKPCKPCTWCNLRSG
SERKQLCTATQDTVCRCRAGTQPLDSYKPGVDCAPCPPGHFSPGDNQACKPWTNCTLAGKHTLQP
ASNSSDAICEDRDPPATQPQETQGPPARPITVQPTEAWPRTSQGPSTRPVEVPGGRAVAAILGLGLV
LGLLGPLAILLALYLLRRDQRLPPDAHKPPGGGSFRTPIQEEQADAHSTLAKI Amino acid sequence of DO11.10-mOX40 and mouse OX40 receptor (SEQ ID NO: 133)
VTARRLNCVKHTYPSGHKCCRECQPGHGMVSRCDHTRDTLCHPCETGFYNEAVNYDTCKQCTQCN
HRSGSELKCNCTPTQDTVCRCRPGTQPRQDSGYKLGVDCVPCPPGHFSPGNNQACKPVVTNCTLS
GKQTRHPASDSLDAVCEDRSLLATLLWETQRPTFRPTTVQSTTVWPRTSELPSPPTLVTPEGPAFAV
LLGLGLGLLAPLTVLLALYLLRKAWRLPNTPKPCWGNSFRTPIQEEHTDAHFTLAKI Amino acid sequence of DO11.10-cOX40 and cynomolqus monkey OX40 receptor (SEQ ID NO: 134)
KLHCVGDTYPSNDRCCQECRPGNGMVSRCNRSQNTVCRPCGPGFYNDVVSAKPCKACTWCNLRS
GSERKQPCTATQDTVCRCRAGTQPLDSYKPGVDCAPCPPGHFSPGDNQACKPVVTNCTLAGKHTLQ
PASNSSDAICEDRDPPPTQPQETQGPPARPTTVQPTEAWPRTSQRPSTRPVEVPRGPAVAAILGLGL
ALGLLGPLAMLLALLLLRRDQRLPPDAPKAPGGGSFRTPIQEEQADAHSALAKI Amino acid sequence of human OX40-mFc (SEQ ID NO: 135)
IL-2 leader sequence (underlined), OX40 extracellular domain (italics), Mouse IgG2a Fc domain (bold)
<u>MYRMQLLSCIALSLALVINS</u>*LHCVGDTYPSNDRCCHECRPGNGMVSRCSRSCNTVCRPCGPGFYN*
*DVVSSKPCKPCTWCNLRSGSERKCLCTATCDTVCRCRAGTCPLDSYKPGVDCAPCPPGHFSPGDN*
*QACKPWTNCTLAGKHTLCPASNSSDAICEDRDPPATCPQETQGPPARPITVQPTEAWPRTSQGPST*
*RPVEVPGGRAVA*GSPRGPTIKPCPPCKCPAPNLLGGPSVFIFPPKIKDVLMISLSPIVTCVVVDVSED
DPDVQISWFVNNVEVHTAQTQTHREDYNSTLRVVSALPIQHQDWMSGKEFKCKVNNKDLPAPIERT
ISKPKGSVRAPQVYVLPPPEEEMTKKQVTLTCMVTDFMPEDIYVEWTNNGKTELNYKNTEPVLDSD
GSYFMYSKLRVEKKNWVERNSYSCSVVHEGLHNHHTTKSFSRTPGK

Amino acid sequence of mouse OX40-mFc (SEQ ID NO: 136)
IL-2 leader sequence (underlined), OX40 extracellular domain (italics), Mouse IgG2a Fc domain (bold)
<u>MYRMQLLSCIALSLALVTNS</u>*VTARRLNCVKHTYPSGHKCCRECQPGHGMVSRCDHTRDTLCHPCET*
*GFYNEAVNYDTCKQCTQCNHRSGSELKQNCTPTQDTVCRCRPGTQPRQDSGYKLGVDCVPCPPG*
*HFSPGNNQACKPWTNCTLSGKQTRHPASDSLDAVCEDRSLLATLLWETQRPTFRPTTVQSTTVWPR*
*TSELPSPPTLVTPEGPA*GSPRGPTIKPCPPCKCPAPNLLGGPSVFIFPPKIKDVLMISLSPIVTCVVVD
VSEDDPDVQISWFVNNVEVHTAQTQTHREDYNSTLRVVSALPIQHQDWMSGKEFKCKVNNKDLPA
PIERTISKPKGSVRAPQVYVLPPPEEEMTKKQVTLTCMVTDFMPEDIYVEWTNNGKTELNYKNTEPV
LDSDGSYFMYSKLRVEKKNWVERNSYSCSVVHEGLHNHHTTKSFSRTPGK

-continued

Sequence Listing

Amino acid sequence of cyno OX40-mFc (SEQ ID NO: 137)
IL-2 leader sequence (underlined), OX40 extracellular domain (italics), Mouse IgG2a Fc domain
(bold)
MYRMQLLSCIALSLALVTNSLHCVGDTYPSNDRCCQECRPGNGMVSRCNRSQNTVCRPCGPGFYN
DVVSAKPCKACTWCNLRSGSERKQPCTATQDTVCRCRAGTQPLDSYKPGVDCAPCPPGHFSPGDN
QACKPWTNCTLAGKHTLQPASNSSDAICEDRDPPPTQPQETQGPPARPTTVQPTEAWPRTSQRPST
RPVEVPRGPAVAAI GSPRGPTIKPCPPCKCPAPNLLGGPSVFIFPPKIKDVLMISLSPIVTCVVVDVSE
DDPDVQISWFVNNVEVHTAQTQTHREDYNSTLRVVSALPIQHQDWMSGKEFKCKVNNKDLPAPIER
TISKPKGSVRAPQVYVLPPPEEEMTKKQVTLTCMVTDFMPEDIYVEWTNNGKTELNYKNTEPVLDS
DGSYFMYSKLRVEKKNWVERNSYSCSVVHEGLHNHHTTKSFSRTPGK Amino acid sequence of human CD137 sequence for use with CD137-mFc-Avi recombinant antigen
(SEQ ID NO: 138)
SLQDPCSNCPAGTFCDNNRNQICSPCPPNSFSSAGGQRTCDICRQCKGVFRTRKECSSTSNAECDC
TPGFHCLGAGCSMCEQDCKQGQELTKKGCKDCCFGTFNDQKRGICRPWINCSLDGKSVLVNGTKE
RDVVCGPSPADLSPGASSVTPPAPAREPGHSPQ Amino acid sequence of cynomolgus CD137 sequence for use with CD137-mFc-Avi and CD137-Avi-
His recombinant antigens (SEQ ID NO: 139)
SLQDLCSNCPAGTFCDNNRSQICSPCPPNSFSSAGGQRTCDICRQCKGVFKTRKECSSTSNAECDCI
SGYHCLGAECSMCEQDCKQGQELTKKGCKDCCFGTFNDQKRGICRPWTNCSLDGKSVLVNGTKER
DVVCGPSPADLSPGASSATPPAPAREPGHSPQ Amino acid sequence of mouse CD137 sequence for use with CD137-mFc-Avi recombinant antigen
(SEQ ID NO: 140)
AVQNSCDNCQPGTFCRKYNPVCKSCPPSTFSSIGGQPNCNICRVCAGYFRFKKFCSSTHNAECECIE
GPHCLGPQCTRCEKDCRPGQELTKQGCKTCSLGTFNDQNGTGVCRPWTNCSLDGRSVLKTGTTEK
DVVCGPPVVSFSPSTTISVTPEGGPGGHSLQVL Amino acid sequence of mFc-Avi for use with CD137-mFc-Avi recombinant antigens (SEQ ID NO:
141)
Mouse Fc domain (italics) Avi tag (bold)
PRGPTIKPCPPCKCPAPNLEGGPSVFIFPPKIKDVLMISLSPIVTCVVVDVSEDDPDVQISWFVNNVEV
HTAQTQTHREDYNSTLRVVSALPIQHQDWMSGKAFACAVNNKDLPAPIERTISKPKGSVRAPQVYVL
PPPEEEMTKKQVTLTCMVTDFMPEDIYVEWTNNGKTELNYKNTEPVLDSDGSYFMYSKLRVEKKNW
VERNSYSCSVVHEGLHNHHTTKSFSRTPGKGGGLNDIFEAQKIEWHE

Amino acid sequence of the truncated Fcab hinge region (SEQ ID NO: 101)
TCPPCP

Alternative nucleic acid sequence of Fcab FS20-22-49 CH3 domain (SEQ ID NO: 143)
GGACAGCCTCGAGAACCACAGGTGTACACCCTGCCCCCATCCCGGGATGAGTACTGGGACCAG
GAAGTCAGCCTGACCTGCCTGGTCAAAGGCTTCTATCCCAGCGACATCGCCGTGGAGTGGGAG
AGCAATGGGGATGAACAGTTCGCATACAAGACCACGCCTCCCGTGCTGGACTCCGACGGCTCCT
TCTTCCTCTACAGCAAGCTCACCGTGGATCAGTATAGGTGGAATCCTGCTGATTATTTCTCATGC
TCCGTGATGCATGAGGCTCTGCACAACCACTACACTCAGAAGAGCTTGTCCCTGTCGCCCGGA FS20-22-49/FS30-5-37 Heavy chain AA (without LALA) (SEQ ID NO: 144)
EVQLLESGGGLVQPGGSLRLNCAASGFTFSSYAMSWVRQAPGKGLEWVSAISGSGGSTYYADSVK
GRFTISRDNSKNTLYLQMNSLRAEDTAVYYCARSYDKYWGSSIYSGLDYWGQGTLVTVSSASTKGP
SVFPLAPSSKSTSGGTAALGCLVKDYFPEPVTVSWNSGALTSGVHTFPAVLQSSGLYSLSSVVTVPS
SSLGTQTYICNVNHKPSNTKVDKKVEPKSCDKTHTCPPCPAPELLGGPSVFLFPPKPKDTLMISRTPE
VTCVVVDVSHEDPEVKFNWYVDGVEVHNAKTKPREEQYNSTYRVVSVLTVLHQDWLNGKEYKCKV
SNKALPAPIEKTISKAKGQPREPQVYTLPPSRDEYWDQEVSLTCLVKGFYPSDIAVEWESNGDEQFA
YKTTPPVLDSDGSFFLYSKLTVDQYRWNPADYFSCSVMHEALHNHYTQKSLSLSPG FS20-22-49/FS30-5-37 Heavy chain DNA (without LALA) (SEQ ID NO: 145)
GAAGTGCAACTGCTGGAGTCCGTGGTGGTCTGGTACAGCCGGGTGGITCTCTGCGTCTGAATT
GCGCGGCCAGTGGCTTTACCTTCAGTAGCTATGCCATGAGCTGGGTGCGTCAGGCGCCGGGCA
AAGGTCTGGAATGGGTTAGCGCGATTAGCGGTAGTGGCGGTGACACGTACTATGCGGATAGCG
TGAAAGGCCGTTTTACCATTTCTCGCGACAACAGCAAGAACACGCTGTACCTGCAGATGAACTCA
CTGCGTGCCGAAGATACGGCCGTGTATTACTGTGCGAGATCTTACGACAAATACTGGGGTTCTT
CTATTTACTCTGGCTTGGACTACTGGGGCCAGGGAACCCTGGTCACCGTCTCGAGTGCTAGCAC
TAAGGGCCCGTCGGTGTTCCCGCTGGCCCCATCGTCCAAGAGCACATCAGGGGGTACCGCCGC
CCTGGGCTGCCTTGTGAAGGATTACTTTCCCGAGCCCGTCACAGTGTCCTGGAACAGCGGAGCC
CTGACCTCCGGAGTGCATACTTTCCCGGCTGTGCTTCAGTCCTCTGGCCTGTACTCATTGTCCTC
CGTGGTCACCGTCCCTTCGTCCTCCCTGGGCACCCAGACCTATATCTGTAATGTCAACCATAAGC
CCTCGAACACCAAGGTCGACAAGAAGGTCGAGCCGAAGTCGTGCGACAAGACTCACACTTGCC
CGCCTTGCCCAGCCCCGGAACTGCTGGGTGGTCCTTCGGTGTTCCTCTTCCCGCCCAAGCCGA
AGGATACCCTGATGATCTCACGGACCCCCGAAGTGACCTGTGTGGTGGTGGACGTGTCCCACG
AGGACCCGGAAGTGAAATTCAATTGGTACGTGGATGGAGTGGAAGTGCACAACGCCAAGACCAA
GCCACGGGAAGAACAGTACAACTCTACCTACCGCGTGGTGTCCGTGCTCACTGTGCTGCACCAA
GACTGGCTGAACGGGAAGGAGTACAAGTGCAAAGTGTCCAACAAGGCGCTGCCTGCCCCAATT
GAGAAAACTATCTCGAAAGCCAAGGGACAGCCTCGAGAACCACAGGTGTACACCCTGCCCCCAT
CCCGGGATGAGTACTGGGACCAGGAAGTCAGCCTGACCTGCCTGGTCAAAGGCTTCTATCCCA
GCGACATCGCCGTGGAGTGGGAGAGCAATGGGGATGAACAGTTCGCATACAAGACCACGCCTC

| Sequence Listing |
|---|
| CCGTGCTGGACTCCGACGGCTCCTTCTTCCTCTACAGCAAGCTCACCGTGGATCAGTATAGGTG<br>GAATCCTGCTGATTATTTCTCATGCTCCGTGATGCATGAGGCTCTGCACAACCACTACACTCAGA<br>AGAGCTTGTCCCTGTCGCCCGGA<br><br>FS20-22-49/FS30-10-3 Heavy chain AA (without LALA) (SEQ ID NO: 146)<br>EVQLLESGGGLVQPGGSLRLSCAASGFTFSSYDMSWVRQAPGKGLEWVSDIDPTGSKTDYADSVK<br>GRFTISRDNSKNTLYLQMNSLRAEDTAVYYCARDLNVYGFDYWGQGTLVTVSSASTKGPSVFPLAPS<br>SKSTSGGTAALGCLVKDYFPEPVTVSWNSGALTSGVHTFPAVLQSSGLYSLSSVVTVPSSSLGTQTYI<br>CNVNHKPSNTKVDKKVEPKSCDKTHTCPPCPAPELLGGPSVFLFPPKPKDTLMISRTPEVTCVVVDV<br>SHEDPEVKFNWYVDGVEVHNAKTKPREEQYNSTYRVVSVLTVLHQDWLNGKEYKCKVSNKALPAPI<br>EKTISKAKGQPREPQVYTLPPSRDEYWDQEVSLTCLVKGFYPSDIAVEWESNGDEQFAYKTTPPVLD<br>SDGSFFLYSKLTVDQYRWNPADYFSCSVMHEALHNHYTQKSLSLSPG<br><br>FS20-22-49/FS30-10-3 Heavy chain DNA (without LALA) (SEQ ID NO: 147)<br>GAAGTGCAACTGCTGGAGTCCGGTGGTGGTCTGGTACAGCCGGGTGGTTCTCTGCGTCTGAGT<br>TGCGCGGCCAGTGGCTTTACCTTCAGTAGTTACGATATGAGCTGGGTGCGTCAGGCTCCGGGCA<br>AAGGTCTGGAATGGGTTAGCGATATTGATCCGACTGGTAGCAAGACCGACTATGCGGATAGCGT<br>GAAAGGCCGTTTTACCATTTCTCGCGACAACAGCAAGAACACGCTGTACCTGCAGATGAACTCAC<br>TGCGTGCCGAAGATACGGCCGTGTATTACTGTGCGAGAGACCTCAATGTGTACGGGTTCGACTA<br>CTGGGGCCAGGGAACCCTGGTCACCGTCTCGAGTGCTAGCACTAAGGGCCCGTCGGTGTTCCC<br>GCTGGCCCCATCGTCCAAGAGCACATCAGGGGGTACCGCCGCCCTGGGCTGCCTTGTGAAGGA<br>TTACTTTCCCGAGCCCGTCACAGTGTCCTGGAACAGCGGAGCCCTGACCTCCGGAGTGCATACT<br>TTCCCGGCTGTGCTTCAGTCCTCTGGCCTGTACTCATTGTCCTCCGTGGTCACCGTCCCTTCGTC<br>CTCCCTGGGCACCCAGACCTATATCTGTAATGTCAACCATAAGCCCTCGAACACCAAGGTCGAC<br>AAGAAGGTCGAGCCGAAGTCGTGCGACAAGACTCACACTTGCCCGCCTTGCCCAGCCCCGGAA<br>CTGCTGGGTGGTCCTTCGGTGTTCCTCTTCCCGCCCAAGCCGAAGGATACCCTGATGATCTCAC<br>GGACCCCCGAAGTGACCTGTGTGGTGGTGGACGTGTCCCACGAGGACCCGGAAGTGAAATTCA<br>ATTGGTACGTGGATGGAGTGGAAGTGCACAACGCCAAGACCAAGCCACGGGAAGAACAGTACA<br>ACTCTACCTACCGCGTGGTGTCCGTGCTCACTGTGCTGCACCAAGACTGGCTGAACGGGAAGGA<br>GTACAAGTGCAAAGTGTCCAACAAGGCGCTGCCTGCCCCAATTGAGAAACTATCTCGAAAGCC<br>AAGGGACAGCCTCGAGAACCACAGGTGTACACCCTGCCCCCATCCCGGGATGAGTACTGGGAC<br>CAGGAAGTCAGCCTGACCTGCCTGGTCAAAGGCTTCTATCCCAGCGACATCGCCGTGGAGTGG<br>GAGAGCAATGGGGATGAACAGTTCGCATACAAGACCACGCCTCCCGTGCTGGACTCCGACGGC<br>TCCTTCTTCCTCTACAGCAAGCTCACCGTGGATCAGTATAGGTGGAATCCTGCTGATTATTTCTCA<br>TGCTCCGTGATGCATGAGGCTCTGCACAACCACTACACTCAGAAGAGCTTGTCCCTGTCGCCCG<br>GA<br><br>FS20-22-49/FS30-10-12 Heavy chain AA (without LALA) (SEQ ID NO: 148)<br>EVQLLESGGGLVQPGGSLRLSCAASGFTFSSYDMSWVRQAPGKGLEWVSDIDPTGSKTDYADSVK<br>GRFTISRDNSKNTLYLQMNSLRAEDTAVYYCARDLTVYGFDYWGQGTLVTVSSASTKGPSVFPLAPS<br>SKSTSGGTAALGCLVKDYFPEPVTVSWNSGALTSGVHTFPAVLQSSGLYSLSSVVTVPSSSLGTQTYI<br>CNVNHKPSNTKVDKKVEPKSCDKTHTCPPCPAPELLGGPSVFLFPPKPKDTLMISRTPEVTCVVVDV<br>SHEDPEVKFNWYVDGVEVHNAKTKPREEQYNSTYRVVSVLTVLHQDWLNGKEYKCKVSNKALPAPI<br>EKTISKAKGQPREPQVYTLPPSRDEYWDQEVSLTCLVKGFYPSDIAVEWESNGDEQFAYKTTPPVLD<br>SDGSFFLYSKLTVDQYRWNPADYFSCSVMHEALHNHYTQKSLSLSPG<br><br>FS20-22-49/FS30-10-12 Heavy chain DNA (without LALA) (SEQ ID NO: 149)<br>GAAGTGCAACTGCTGGAGTCCGGTGGTGGTCTGGTACAGCCGGGTGGTTCTCTGCGTCTGAGT<br>TGCGCGGCCAGTGGCTTTACCTTCAGTAGTTACGATATGAGCTGGGTGCGTCAGGCTCCGGGCA<br>AAGGTCTGGAATGGGTTAGCGATATTGATCCGACTGGTAGCAAGACCGACTATGCGGATAGCGT<br>GAAAGGCCGTTTTACCATTTCTCGCGACAACAGCAAGAACACGCTGTACCTGCAGATGAACTCAC<br>TGCGTGCCGAAGATACGGCCGTGTATTACTGTGCGAGAGACCTCACGGTGTACGGGTTCGACTA<br>CTGGGGCCAGGGAACCCTGGTCACCGTCTCGAGTGCTAGCACTAAGGGCCCGTCGGTGTTCCC<br>GCTGGCCCCATCGTCCAAGAGCACATCAGGGGGTACCGCCGCCCTGGGCTGCCTTGTGAAGGA<br>TTACTTTCCCGAGCCCGTCACAGTGTCCTGGAACAGCGGAGCCCTGACCTCCGGAGTGCATACT<br>TTCCCGGCTGTGCTTCAGTCCTCTGGCCTGTACTCATTGTCCTCCGTGGTCACCGTCCCTTCGTC<br>CTCCCTGGGCACCCAGACCTATATCTGTAATGTCAACCATAAGCCCTCGAACACCAAGGTCGAC<br>AAGAAGGTCGAGCCGAAGTCGTGCGACAAGACTCACACTTGCCCGCCTTGCCCAGCCCCGGAA<br>CTGCTGGGTGGTCCTTCGGTGTTCCTCTTCCCGCCCAAGCCGAAGGATACCCTGATGATCTCAC<br>GGACCCCCGAAGTGACCTGTGTGGTGGTGGACGTGTCCCACGAGGACCCGGAAGTGAAATTCA<br>ATTGGTACGTGGATGGAGTGGAAGTGCACAACGCCAAGACCAAGCCACGGGAAGAACAGTACA<br>ACTCTACCTACCGCGTGGTGTCCGTGCTCACTGTGCTGCACCAAGACTGGCTGAACGGGAAGGA<br>GTACAAGTGCAAAGTGTCCAACAAGGCGCTGCCTGCCCCAATTGAGAAACTATCTCGAAAGCC<br>AAGGGACAGCCTCGAGAACCACAGGTGTACACCCTGCCCCCATCCCGGGATGAGTACTGGGAC<br>CAGGAAGTCAGCCTGACCTGCCTGGTCAAAGGCTTCTATCCCAGCGACATCGCCGTGGAGTGG<br>GAGAGCAATGGGGATGAACAGTTCGCATACAAGACCACGCCTCCCGTGCTGGACTCCGACGGC<br>TCCTTCTTCCTCTACAGCAAGCTCACCGTGGATCAGTATAGGTGGAATCCTGCTGATTATTTCTCA<br>TGCTCCGTGATGCATGAGGCTCTGCACAACCACTACACTCAGAAGAGCTTGTCCCTGTCGCCCG<br>GA<br><br>FS20-22-49/FS30-10-16 Heavy chain AA (without LALA) (SEQ ID NO: 150)<br>EVQLLESGGGLVQPGGSLRLSCAASGFTFSSYDMSWVRQAPGKGLEWVSDIDPTGSKTDYADSVK<br>GRFTISRDNSKNTLYLQMNSLRAEDTAVYYCARDLLVYGFDYWGQGTLVTVSSASTKGPSVFPLAPS<br>SKSTSGGTAALGCLVKDYFPEPVTVSWNSGALTSGVHTFPAVLQSSGLYSLSSVVTVPSSSLGTQTYI<br>CNVNHKPSNTKVDKKVEPKSCDKTHTCPPCPAPELLGGPSVFLFPPKPKDTLMISRTPEVTCVVVDV<br>SHEDPEVKFNWYVDGVEVHNAKTKPREEQYNSTYRVVSVLTVLHQDWLNGKEYKCKVSNKALPAPI |

Sequence Listing

EKTISKAKGQPREPQVYTLPPSRDEYWDQEVSLTCLVKGFYPSDIAVEWESNGDEQFAYKTTPPVLD
SDGSFFLYSKLTVDQYRWNPADYFSCSVMHEALHNHYTQKSLSLSPG

FS20-22-49/FS30-10-16 Heavy chain DNA (without LALA) (SEQ ID NO: 151)
GAAGTGCAACTGCTGGAGTCCGGTGGTGGTCTGGTACAGCCGGGTGGTTCTCTGCGTCTGAGT
TGCGCGGCCAGTGGCTTTACCTTCAGTAGTTACGATATGAGCTGGGTGCGTCAGGCTCCGGGCA
AAGGTCTGGAATGGGTTAGCGATATTGATCCGACTGGTAGCAAGACCGACTATGCGGATAGCGT
GAAAGGCCGTTTTACCATTTCTCGCGACAACAGCAAGAACACGCTGTACCTGCAGATGAACTCAC
TGCGTGCCGAAGATACGGCCGTGTATTACTGTGCGAGAGACCTCTTGGTGTACGGGTTCGACTA
CTGGGGCCAGGGAACCCTGGTCACCGTCTCGAGTGCTAGCACTAAGGGCCCGTCGGTGTTCCC
GCTGGCCCCATCGTCCAAGAGCACATCAGGGGGTACCGCCGCCCTGGGCTGCCTTGTGAAGGA
TTACTTTCCCGAGCCCGTCACAGTGTCCTGGAACAGCGGAGCCCTGACCTCCGGAGTGCATACT
TTCCCGGCTGTGCTTCAGTCCTCTGGCCTGTACTCATTGTCCTCCGTGGTCACCGTCCCTTCGTC
CTCCCTGGGCACCCAGACCTATATCTGTAATGTCAACCATAAGCCCTCGAACACCAAGGTCGAC
AAGAAGGTCGAGCCGAAGTCGTGCGACAAGACTCACACTTGCCCGCCTTGCCCAGCCCCGGAA
CTGCTGGGTGGTCCTTCGGTGTTCCTCTTCCCGCCCAAGCCGAAGGATACCCTGATGATCTCAC
GGACCCCCGAAGTGACCTGTGTGGTGGTGGACGTGTCCCACGAGGACCCGGAAGTGAAATTCA
ATTGGTACGTGGATGGAGTGGAAGTGCACAACGCCAAGACCAAGCCACGGGAAGAACAGTACA
ACTCTACCTACCGCGTGGTGTCCGTGCTCACTGTGCTGCACCAAGACTGGCTGAACGGGAAGGA
GTACAAGTGCAAAGTGTCCAACAAGGCGCTGCCTGCCCCAATTGAGAAAACTATCTCGAAAGCC
AAGGGACAGCCTCGAGAACCACAGGTGTACACCCTGCCCCCATCCCGGGATGAGTACTGGGAC
CAGGAAGTCAGCCTGACCTGCCTGGTCAAAGGCTTCTATCCCAGCGACATCGCCGTGGAGTGG
GAGAGCAATGGGGATGAACAGTTCGCATACAAGACCACGCCTCCCGTGCTGGACTCCGACGGC
TCCTTCTTCCTCTACAGCAAGCTCACCGTGGATCAGTATAGGTGGAATCCTGCTGATTATTTCTCA
TGCTCCGTGATGCATGAGGCTCTGCACAACCACTACACTCAGAAGAGCTTGTCCCTGTCGCCCG
GA FS20-22-49/FS30-35-14 Heavy chain AA (without LALA) (SEQ ID NO: 152)
EVQLLESGGGLVQPGGSLRLSCAASGFTFSAYNIHWVRQAPGKGLEWVSDISPYGGATNYADSVKG
RFTISRDNSKNTLYLQMNSLRAEDTAVYYCARNLYELSAYSYGADYWGQGTLVTVSSASTKGPSVFP
LAPSSKSTSGGTAALGCLVKDYFPEPVTVSWNSGALTSGVHTFPAVLQSSGLYSLSSVVTVPSSSLG
TQTYICNVNHKPSNTKVDKKVEPKSCDKTHTCPPCPAPELLGGPSVFLFPPKPKDTLMISRTPEVTCV
VVDVSHEDPEVKFNWYVDGVEVHNAKTKPREEQYNSTYRVVSVLTVLHQDWLNGKEYKCKVSNKA
LPAPIEKTISKAKGQPREPQVYTLPPSRDEYWDQEVSLTCLVKGFYPSDIAVEWESNGDEQFAYKTTP
PVLDSDGSFFLYSKLTVDQYRWNPADYFSCSVMHEALHNHYTQKSLSLSPG FS20-22-49/FS30-35-14 Heavy chain DNA (without LALA) (SEQ ID NO: 153)
GAAGTGCAACTGCTGGAGTCCGGTGGTGGTCTGGTACAGCCGGGTGGTTCTCTGCGTCTGAGT
TGCGCGGCCAGTGGCTTTACCTTCAGTGCCTATAATATCCATTGGGTGCGTCAGGCTCCGGGCA
AAGGTCTGGAATGGGTTAGCGATATTTCTCCGTATGGTGGCGCGACCAACTATGCGGATAGCGT
GAAAGGCCGTTTTACCATTTCTCGCGACAACAGCAAGAACACGCTGTACCTGCAGATGAACTCAC
TGCGTGCCGAAGATACGGCCGTGTATTACTGTGCGAGAAACCTCTACGAGTTGAGCGCTTACTC
TTACGGGGCGGACTACTGGGGCCAGGGAACCCTGGTCACCGTCTCGAGTGCTAGCACTAAGGG
CCCGTCGGTGTTCCCGCTGGCCCCATCGTCCAAGAGCACATCAGGGGGTACCGCCGCCCTGGG
CTGCCTTGTGAAGGATTACTTTCCCGAGCCCGTCACAGTGTCCTGGAACAGCGGAGCCCTGACC
TCCGGAGTGCATACTTTCCCGGCTGTGCTTCAGTCCTCTGGCCTGTACTCATTGTCCTCCGTGGT
CACCGTCCCTTCGTCCTCCCTGGGCACCCAGACCTATATCTGTAATGTCAACCATAAGCCCTCGA
ACACCAAGGTCGACAAGAAGGTCGAGCCGAAGTCGTGCGACAAGACTCACACTTGCCCGCCTT
GCCCAGCCCCGGAACTGCTGGGTGGTCCTTCGGTGTTCCTCTTCCCGCCCAAGCCGAAGGATA
CCCTGATGATCTCACGGACCCCCGAAGTGACCTGTGTGGTGGTGGACGTGTCCCACGAGGACC
CGGAAGTGAAATTCAATTGGTACGTGGATGGAGTGGAAGTGCACAACGCCAAGACCAAGCCACG
GGAAGAACAGTACAACTCTACCTACCGCGTGGTGTCCGTGCTCACTGTGCTGCACCAAGACTGG
CTGAACGGGAAGGAGTACAAGTGCAAAGTGTCCAACAAGGCGCTGCCTGCCCCAATTGAGAAAA
CTATCTCGAAAGCCAAGGGACAGCCTCGAGAACCACAGGTGTACACCCTGCCCCCATCCCGGG
ATGAGTACTGGGACCAGGAAGTCAGCCTGACCTGCCTGGTCAAAGGCTTCTATCCCAGCGACAT
CGCCGTGGAGTGGGAGAGCAATGGGGATGAACAGTTCGCATACAAGACCACGCCTCCCGTGCT
GGACTCCGACGGCTCCTTCTTCCTCTACAGCAAGCTCACCGTGGATCAGTATAGGTGGAATCCT
GCTGATTATTTCTCATGCTCCGTGATGCATGAGGCTCTGCACAACCACTACACTCAGAAGAGCTT
GTCCCTGTCGCCCGGA Amino acid sequence of heavy chain of G1AA/FS30-10-16 mAb (with LALA) (SEQ ID NO: 154)
EVQLLESGGGLVQPGGSLRLSCAASGFTFSSYDMSWVRQAPGKGLEWVSDIDPTGSKTDYADSVK
GRFTISRDNSKNTLYLQMNSLRAEDTAVYYCARDLLVYGFDYWGQGTLVTVSSASTKGPSVFPLAPS
SKSTSGGTAALGCLVKDYFPEPVTVSWNSGALTSGVHTFPAVLQSSGLYSLSSVVTVPSSSLGTQTYI
CNVNHKPSNTKVDKKVEPKSCDKTHTCPPCPAPEAAGGPSVFLFPPKPKDTLMISRTPEVTCVVVDV
SHEDPEVKFNWYVDGVEVHNAKTKPREEQYNSTYRVVSVLTVLHQDWLNGKEYKCKVSNKALPAPI
EKTISKAKGQPREPQVYTLPPSRDELTKNQVSLTCLVKGFYPSDIAVEWESNGQPENNYKTTPPVLD
SDGSFFLYSKLTVDKSRWQQGNVFSCSVMHEALHNHYTQKSLSLSPG Amino acid sequence of light chain of G1AA/FS30-10-16 mAb (SEQ ID NO: 97)
EIVLTQSPGTLSLSPGERATLSCRASQSVSSSYLAWYQQKPGQAPRLLIYGASSRATGIPDRFSGSGS
GTDFTLTISRLEPEDFAVYYCQQSYSYPVTFGQGTKVEIKRTVAAPSVFIFPPSDEQLKSGTASVVCLL
NNFYPREAKVQWKVDNALQSGNSQESVTEQDSKDSTYSLSSTLTLSKADYEKHKVYACEVTHQGLS
SPVTKSFNRGEC

Sequence Listing

Amino acid sequence of heavy chain of G1AA/OX86 mAb (with LALA) (SEQ ID NO: 155)
QVQLKESGPGLVQPSQTLSLTCTVSGFSLTGYNLHWVRQPPGKGLEWMGRMRYDGDTYYNSVLKS
RLSISRDTSKNQVFLKMNSLQTDDTAIYYCTRDGRGDSFDYWGQGVMVTVSSASTKGPSVFPLAPS
SKSTSGGTAALGCLVKDYFPEPVTVSWNSGALTSGVHTFPAVLQSSGLYSLSSVVTVPSSSLGTQTYI
CNVNHKPSNTKVDKKVEPKSCDKTHTCPPCPAPEAAGGPSVFLFPPKPKDTLMISRTPEVTCVVVDV
SHEDPEVKFNWYVDGVEVHNAKTKPREEQYNSTYRVVSVLTVLHQDWLNGKEYKCKVSNKALPAPI
EKTISKAKGQPREPQVYTLPPSRDELTKNQVSLTCLVKGFYPSDIAVEWESNGQPENNYKTTPPVLD
SDGSFFLYSKLTVDKSRWQQGNVFSCSVMHEALHNHYTQKSLSLSPG Amino acid sequence of light chain of G1/OX86 and G1AA/OX86 mAb (SEQ ID NO: 156)
DIVMTQGALPNPVPSGESASITCRSSQSLVYKDGQTYLNWFLQRPGQSPQLLTYWMSTRASGVSDR
FSGSGSGTYFTLKISRVRAEDAGVYYCQQVREYPFTFGSGTKLEIKRTVAAPSVFIFPPSDEQLKSGT
ASVVCLLNNFYPREAKVQWKVDNALQSGNSQESVTEQDSKDSTYSLSSTLTLSKADYEKHKVYACE
VTHQGLSSPVTKSFNRGEC Amino acid sequence of heavy chain of FS20m-232-91AA/4420 (with LALA) (SEQ ID NO: 157)
EVKLDETGGGLVQPGRPMKLSCVASGFTFSDYWMNWVRQSPEKGLEWVAQIRNKPYNYETYYSDS
VKGRFTISRDDSKSSVYLQMNNLRVEDMGIYYCTGSYYGMDYWGQGTSVTVSSASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPEAAGGPSVFLFPPKPKDTLMISRTPEVTCVVVD
VSHEDPEVKFNWYVDGVEVHNAKTKPREEQYNSTYRVVSVLTVLHQDWLNGKEYKCKVSNKALPAP
IEKTISKAKGQPREPQVYTLPPSRDELFDPMYYYNQVSLTCLVKGFYPSDIAVEWESNGEPLWDYKTT
PPVLDSDGSFFLYSKLTVWRDRWEDGNVFSCSVMHEALHNHYTQKSLSLSPGK Amino acid sequence of light chain of FS20m-232-91AA/4420 (SEQ ID NO: 116)
DVVMTQTPLSLPVSLGDQASISCRSSQSLVHSNGNTYLRWYLQKPGQSPKVLIYKVSNRFSGVPDRF
SGSGSGTDFTLKISRVEAEDLGVYFCSQSTHVPVVTFGGGTKLEIKRTVAAPSVFIFPPSDEQLKSGTA
SVVCLLNNFYPREAKVQWKVDNALQSGNSQESVTEQDSKDSTYSLSSTLTLSKADYEKHKVYACEV
THQGLSSPVTKSFNRGEC Amino acid sequence of Human CD137-Avi-His (SEQ ID NO: 158)
Extracellular domain CD137 (bold); Avi tag (italics); His tag (underlined)
**SLQDPCSNCPAGTFCDNNRNQICSPCPPNSFSSAGGQRTCDICRQCKGVFRTRKECSSTSNAECD
CTPGFHCLGAGCSMCEQDCKQGQELTKKGCKDCCFGTFNDQKRGICRPWTNCSLDGKSVLVNGT
KERDVVCGPSPADLSPGASSVTPPAPAREPGHSPQGS***GGGLNDIFEAQKIEWHE*<u>HHHHHH</u>

Amino acid sequence of heavy chain of G1/OX86 mAb (without LALA) (SEQ ID NO: 159)
QVQLKESGPGLVQPSQTLSLTCTVSGFSLTGYNLHWVRQPPGKGLEWMGRMRYDGDIYYNSVLKS
RLSISRDTSKNQVFLKMNSLQTDDTAIYYCTRDGRGDSFDYWGQGVMVTVSSASTKGPSVFPLAPS
SKSTSGGTAALGCLVKDYFPEPVTVSWNSGALTSGVHTFPAVLQSSGLYSLSSVVTVPSSSLGTQTYI
CNVNHKPSNTKVDKKVEPKSCDKTHTCPPCPAPELLGGPSVFLFPPKPKDTLMISRTPEVTCVVVDV
SHEDPEVKFNWYVDGVEVHNAKTKPREEQYNSTYRVVSVLTVLHQDWLNGKEYKCKVSNKALPAPI
EKTISKAKGQPREPQVYTLPPSRDELTKNQVSLTCLVKGFYPSDIAVEWESNGQPENNYKTTPPVLD
SDGSFFLYSKLTVDKSRWQQGNVFSCSVMHEALHNHYTQKSLSLSPG Amino acid sequence of the heavy chain of anti-PD-1 mAb G1AA/5C4 (SEQ ID NO: 160)
Variable domain (bold)
**QVQLVESGGGVVQPGRSLRLDCKASGITFSNSGMHWVRQAPGKGLEWVAVIWYDGSKRYYADSV
KGRFTISRDNSKNTLFLQMNSLRAEDTAVYYCATNDDYWGQGTLVTVSS**ASTKGPSVFPLAPSSKS
TSGGTAALGCLVKDYFPEPVTVSWNSGALTSGVHTFPAVLQSSGLYSLSSVVTVPSSSLGTQTYICN
VNHKPSNTKVDKKVEPKSCDKTHTCPPCPAPEAAGGPSVFLFPPKPKDTLMISRTPEVTCVVVDVSH
EDPEVKFNWYVDGVEVHNAKTKPREEQYNSTYRVVSVLTVLHQDWLNGKEYKCKVSNKALPAPIEK
TISKAKGQPREPQVYTLPPSRDELTKNQVSLTCLVKGFYPSDIAVEWESNGQPENNYKTTPPVLDSD
GSFFLYSKLTVDKSRWQQGNVFSCSVMHEALHNHYTQKSLSLSPGK Amino acid sequence of the light chain of anti-PD-1 mAb G1AA/5C4 (SEQ ID NO: 161)
Variable domain (bold)
**EIVLTQSPATLSLSPGERATLSCRASQSVSSYLAWYQQKPGQAPRLLIYDASNRATGIPARFSGSG
SGTDFTLTISSLEPEDFAVYYCQQSSNWPRTFGQGTKVEIK**RTVAAPSVFIFPPSDEQLKSGTASVVC
LLNNFYPREAKVQWKVDNALQSGNSQESVTEQDSKDSTYSLSSTLTLSKADYEKHKVYACEVTHQG
LSSPVTKSFNRGEC Amino acid sequence of the heavy chain of anti-PD-L1 mAb G1AA/S1 (SEQ ID NO: 162)
Variable domain (bold)
**EVQLVESGGGLVQPGGSLRLSCAASGFTFSDSWIHWVRQAPGKGLEWVAWISPYGGSTYYADSV
KGRFTISADTSKNTAYLQMNSLRAEDTAVYYCARRHWPGGFDYWGQGTLVTVSA**ASTKGPSVFPL
APSSKSTSGGTAALGCLVKDYFPEPVTVSWNSGALTSGVHTFPAVLQSSGLYSLSSVVTVPSSSLGT
QTYICNVNHKPSNTKVDKKVEPKSCDKTHTCPPCPAPEAAGGPSVFLFPPKPKDTLMISRTPEVTCVV
VDVSHEDPEVKFNWYVDGVEVHNAKTKPREEQYNSTYRVVSVLTVLHQDWLNGKEYKCKVSNKAL
PAPIEKTISKAKGQPREPQVYTLPPSRDELTKNQVSLTCLVKGFYPSDIAVEWESNGQPENNYKTTPP
VLDSDGSFFLYSKLTVDKSRWQQGNVFSCSVMHEALHNHYTQKSLSLSPGK Amino acid sequence of the light chain of anti-PD-L1 mAb G1AA/S1 (SEQ ID NO: 163)
Variable domain (bold)
**DIQMTQSPSSLSASVGDRVTITCRASQDVSTAVAVVYQQKPGKAPKLLIYSASFLYSGVPSRFSGSG
SGTDFTLTISSLQPEDFATYYCQQYLFTPPTFGQGTKVEIK**RTVAAPSVFIFPPSDEQLKSGTASVVCL

```
LNNFYPREAKVQWKVDNALQSGNSQESVTEQDSKDSTYSLSSTLTLSKADYEKHKVYACEVTHQGL
SSPVTKSFNRGEC

Amino acid sequence of mouse CD137 (SEQ ID NO: 164)
Extracellular domain (italics); transmembrane and intracellular domains (bold)
VQNSCDNCQPGTFCRKYNPVCKSCPPSTFSSIGGQPNCNICRVCAGYFRFKKFCSSTHNAECECIE
GFHCLGIDQCTRCEKDCRPGQELTKQGCKTCSLGTFNDQNGTGVCRPWTNCSLDGRSVLKTGTTEK
DVVCGPPVVSFSPSTTISVTPEGGPGGHSLQVL**TLFLALTSALLLALIFITLLFSVLKWIRKKFPHIFKQ
PFKKTTGAAQEEDACSCRCPQEEEGGGGYEL**

Amino acid sequence of the heavy chain of G1AA/20H4.9 mAb (SEQ ID NO: 165)
VH domain (italics)
QVQLQQWGAGLLKPSETLSLTCAVYGGSFSGYYWSWIRQSPEKGLEWIGEINHGGYVTYNPSLESR
VTISVDTSKNQFSLKLSSVTAADTAVYYCARDYGPGNYDWYFDLWGRGTLVTVSSASTKGPSVFPLA
PSSKSTSGGTAALGCLVKDYFPEPVTVSWNSGALTSGVHTFPAVLQSSGLYSLSSVVTVPSSSLGTQ
TYICNVNHKPSNTKVDKKVEPKSCDKTHTCPPCPAPEAAGGPSVFLFPPKPKDTLMISRTPEVTCVVV
DVSHEDPEVKFNWYVDGVEVHNAKTKPREEQYNSTYRVVSVLTVLHQDWLNGKEYKCKVSNKALP
APIEKTISKAKGQPREPQVYTLPPSRDELTKNQVSLTCLVKGFYPSDIAVEWESNGQPENNYKTTPPV
LDSDGSFFLYSKLTVDKSRWQQGNVFSCSVMHEALHNHYTQKSLSLSPG Amino acid sequence of the heavy chain of G1AA/3H3 mAb (SEQ ID NO: 166)
VH domain (italics)
EMQLVESGGGLVQPGRSMKLSCAGSGFTLSDYGVAWVRQAPKKGLEWVAYISYAGGTTYYRESVK
GRFTISRDNAKSTLYLQMDSLRSEDTATYYCTIDGYGGYSGSHWYFDFWGPGTMVTVSSASTKGPS
VFPPLAPSSKSTSGGTAALGCLVKDYFPEPVTVSWNSGALTSGVHTFPAVLQSSGLYSLSSVVTVPSS
SLGTQTYICNVNHKPSNTKVDKKVEPKSCDKTHTCPPCPAPEAAGGPSVFLFPPKPKDTLMISRTPEV
TCVVVDVSHEDPEVKFNWYVDGVEVHNAKTKPREEQYNSTYRVVSVLTVLHQDWLNGKEYKCKVS
NKALPAPIEKTISKAKGQPREPQVYTLPPSRDELTKNQVSLTCLVKGFYPSDIAVEWESNGQPENNYK
TTPPVLDSDGSFFLYSKLTVDKSRWQQGNVFSCSVMHEALHNHYTQKSLSLSPGK Amino acid sequence of the light chain of G1AA/3H3 and G1/3H3 mAbs and FS20m-232-91AA/3H3
mAb² (SEQ ID NO: 167)
VL domain (italics)
DIQMTQSPSLLSASVGDRVTLNCRTSQNVYKNLAWYQQQLGEAPKLLIYNANSLQAGIPSRFSGSGS
GTDFTLTISSLQPEDVATYFCQQYYSGNTFGAGTNLELKRTVAAPSVFIFPPSDEQLKSGTASVVCLL
NNFYPREAKVQWKVDNALQSGNSQESVTEQDSKDSTYSLSSTLTLSKADYEKHKVYACEVTHQGLS
SPVTKSFNRGEC Amino acid sequence of the heavy chain of G1/3H3 mAb (SEQ ID NO: 168)
VH domain (italics)
EMQLVESGGGLVQPGRSMKLSCAGSGFTLSDYGVAWVRQAPKKGLEWVAYISYAGGTTYYRESVK
GRFTISRDNAKSTLYLQMDSLRSEDTATYYCTIDGYGGYSGSHWYFDFWGPGTMVTVSSASTKGPS
VFPPLAPSSKSTSGGTAALGCLVKDYFPEPVTVSWNSGALTSGVHTFPAVLQSSGLYSLSSVVTVPSS
SLGTQTYICNVNHKPSNTKVDKKVEPKSCDKTHTCPPCPAPELLGGPSVFLFPPKPKDTLMISRTPEV
TCVVVDVSHEDPEVKFNWYVDGVEVHNAKTKPREEQYNSTYRVVSVLTVLHQDWLNGKEYKCKVS
NKALPAPIEKTISKAKGQPREPQVYTLPPSRDELTKNQVSLTCLVKGFYPSDIAVEWESNGQPENNYK
TTPPVLDSDGSFFLYSKLTVDKSRWQQGNVFSCSVMHEALHNHYTQKSLSLSPGK Amino acid sequence of the heavy chain FS20m-232-91AA/3H3 (with LALA) (SEQ ID NO: 169)
VH domain (italics)
EMQLVESGGGLVQPGRSMKLSCAGSGFTLSDYGVAWVRQAPKKGLEWVAYISYAGGTTYYRESVK
GRFTISRDNAKSTLYLQMDSLRSEDTATYYCTIDGYGGYSGSHWYFDFWGPGTMVTVSSASTKGPS
VFPPLAPSSKSTSGGTAALGCLVKDYFPEPVTVSWNSGALTSGVHTFPAVLQSSGLYSLSSVVTVPSS
SLGTQTYICNVNHKPSNTKVDKKVEPKSCDKTHTCPPCPAPEAAGGPSVFLFPPKPKDTLMISRTPEV
TCVVVDVSHEDPEVKFNWYVDGVEVHNAKTKPREEQYNSTYRVVSVLTVLHQDWLNGKEYKCKVS
NKALPAPIEKTISKAKGQPREPQVYTLPPSRDELFDPMYYYNQVSLTCLVKGFYPSDIAVEWESNGEP
LWDYKTTPPVLDSDGSFFLYSKLTVWRDRWEDGNVFSCSVMHEALHNHYTQKSLSLSPGK Amino acid sequence of the heavy chain of anti-OX40 mAb G1AA/11D4 (SEQ ID NO: 173)
VH domain (italics)
EVQLVESGGGLVQPGGSLRLSCAASGFTFSSYSMNWVRQAPGKGLEWVSYISSSSSTIDYADSVKG
RFTISRDNAKNSLYLQMNSLRDEDTAVYYCARESGWYLFDYWGQGTLVTVSSASTKGPSVFPLAPS
SKSTSGGTAALGCLVKDYFPEPVTVSWNSGALTSGVHTFPAVLQSSGLYSLSSVVTVPSSSLGTQTYI
CNVNHKPSNTKVDKKVEPKSCDKTHTCPPCPAPEAAGGPSVFLFPPKPKDTLMISRTPEVTCVVVD
SHEDPEVKFNWYVDGVEVHNAKTKPREEQYNSTYRVVSVLTVLHQDWLNGKEYKCKVSNKALPAPI
EKTISKAKGQPREPQVYTLPPSRDELRFYQVSLTCLVKGFYPSDIAVEWESNGQPDIFPNGLNYKTTP
PVLDSDGSFFLYSKLTVPYPSWLMGTRFSCSVMHEALHNHYTQKSLSLSPG Amino acid sequence of the heavy chain of anti-OX40 mAb G1/11D4 (SEQ ID NO: 174)
VH domain (italics)
EVQLVESGGGLVQPGGSLRLSCAASGFTFSSYSMNWVRQAPGKGLEWVSYISSSSSTIDYADSVKG
RFTISRDNAKNSLYLQMNSLRDEDTAVYYCARESGWYLFDYWGQGTLVTVSSASTKGPSVFPLAPS
SKSTSGGTAALGCLVKDYFPEPVTVSWNSGALTSGVHTFPAVLQSSGLYSLSSVVTVPSSSLGTQTYI
CNVNHKPSNTKVDKKVEPKSCDKTHTCPPCPAPELLGGPSVFLFPPKPKDTLMISRTPEVTCVVVDV
SHEDPEVKFNWYVDGVEVHNAKTKPREEQYNSTYRVVSVLTVLHQDWLNGKEYKCKVSNKALPAPI
```

Sequence Listing

```
EKTISKAKGQPREPQVYTLPPSRDELRFYQVSLTCLVKGFYPSDIAVEWESNGQPDIFPNGLNYKTTP
PVLDSDGSFFLYSKLTVPYPSWLMGTRFSCSVMHEALHNHYTQKSLSLSPG
```

Amino acid sequence of the light chain of anti-OX40 mAbs G1AA/11D4 and G1/1104 (SEQ ID NO: 175)
VL domain (italics)

```
DIQMTQSPSSLSASVGDRVTITCRASQGISSWLAWYQQKPEKAPKSLIYAASSLQSGVPSRFSGSGS
GTDFTLTISSLQPEDFATYYMQYNSYPPTFGGGTKVEIKRTVAAPSVFIFPPSDEQLKSGTASVVCLL
NNFYPREAKVQWKVDNALQSGNSQESVTEQDSKDSTYSLSSTLTLSKADYEKHKVYACEVTHQGLS
SPVTKSFNRGEC
```

References

All documents mentioned in this specification are incorporated herein by reference in their entirety.

Altschul SF, Gish W, Miller W, Myers EW, Lipman DJ. Basic local alignment search tool. J. Mol. Biol. 215(3). 403-10 (1990).

Altschul SF, Madden TL. Schaffer AA, Zhang J, Zhang Z, Miller W, Lipman DJ. Gapped BLAST and PSI-BLAST: a new generation of protein database search programs. Nucleic Acids Res. 25(17), 3389-402 (1997).

Aspeslagh S, Postel-Vinay S. Rusakiewicz S, Soria J C, Zitvogel L, Marabelle A. Rationale for anti-OX40 cancer immunotherapy. Eur. J. Cancer 52, 50-66 (2016).

Bagshawe K D, Sharma SK, Springer C J, Antoniw P, Rogers G T, Burke P J, Melton R, Antibody-enzyme conjugates can generate cytotoxic drugs from inactive precursors at tumor sites. Antibody, Immunoconjugates and Radiopharmaceuticals 4, 915-22 (1991).

Bartkowiak T. Curran MA. 4-1 BB agonists: multi-potent potentiators of tumor immunity. Front. Oncol. 5.117 (2015).

Bartkowiak T. Jaiswal A R, Ager CR, Chin R, Chen C-H, Budhani P, Al M, Reilley M J. Sebastian M M, Hong D S, Curran M A. Activation of 4-1 BB on liver myeloid cells triggers hepatitis via an interleukin-27 dependent pathway. Clin. Cancer Res. 24(5), 1138-51 (2018).

Bedzyk W D, Johnson L S, Riordan GS, Voss EW Jr. Comparison of variable region primary structures within an anti-fluorescein idiotype family. J. Biol. Chem. 264(3), 1565-69 (1989).

Bedzyk W D, Weidner KM, Denzin L K, Johnson L S, Hardman K D, Pantoliano M W, Asel ED, Voss EW Jr. Immunological and structural characterization of a high affinity anti-fluorescein single-chain antibody. J. Biol. Chem. 265(30), 18615-20 (1990).

Braden BC, Fields BA, Ysern X, Goldbaum FA, Dall'Acqua W, Schwarz FP, Poljak RJ. Mariuzza RA.

Crystal structure of the complex of the variable domain of antibody D1.3 and turkey egg white lysozyme: a novel conformational change in antibody CD3-L3 selects for antigen. J. Mol. Biol. 257(5), 889-94 (1996).

Bremer E. Targeting of the Tumor Necrosis Factor Receptor Superfamily for Cancer Immunotherapy. ISRN Oncol. 2013, 1-25 (2013).

Bruhns P. Iannascoli B, England P, Mancardi D A, Fernandez N, Jorieux S, Daëron M. Specificity and affinity of human Fcγ receptors and their polymorphic variants for human IgG subclasses. Blood 113(16), 3716-25 (2009).

Bulliard Y, Jolicoeur R, Windman M, Rue S M, Ettenberg S. Knee D A, Wilson D S, Dranoff G, Brogdon J L. Activating Fc γ receptors contribute to the antitumor activities of immunoregulatory receptor-targeting antibodies. J. Exp. Med. 210(9), 1685-93 (2013)

Bulliard Y, Jollcoeur R. Zhang J, Dranoff G, Wilson N S, Brogdon J L. OX40 engagement depletes intratumoral Tregs via activating FcγRs, leading to antitumor efficacy. Immunol. Cell Biol. 92(6). 475-80 (2014).

Chan R C, Ong E Z, Mok D Z, Ooi E E. Fc receptors and their influence on efficacy of therapeutic antibodies for treatment of viral diseases. Expert Rev. Anti-infect. Ther. 13(11), 1351-60 (2015).

Croft M, So T, Duan W, Soroosh P. The significance of OX40 and OX40L to T-cell biology and immune disease. Immunol. Rev. 229(1), 173-91 (2009).

Croft M. The TNF family in T cell differentiation and function - unanswered questions and future directions. Semin. Immunol. 26(3). 183-90 (2014).

Curti BD, Kovacsovics-Bankowski M, Morris N, Walker E. Chisholm L, Floyd K, Walker J, Gonzalez I, Meeuwsen T, Fox BA, Moudgil T, Miller W, Haley D, Coffey T, Fisher B, Delanty-Miller L, Rymarchyk N, Kelly T, Crocenzi T, Bernstein E, Sanborn R, Urba W J, Weinberg AD. OX40 is a potent immune-stimulating target in late-stage cancer patients. Cancer Res. 73(24), 7189-98 (2013).

Dubrot J, Milheiro F, Atfaro C, Palazbn A, Martinez-Forero I, Perez-Gracia J L, Morales-Kastresana A, Romero-Trevejo J L, Ochoa M C, Hervds-Stubbs S, Prieto J, Jure-Kunkel M, Chen L, Melero I. Treatment with anti-CD137 mAbs cause intense accumulations of liver T cells without selective antitumor immunotherapeutic effects in this organ. Cancer Immunol. Immunother. 59(8), 1223-33 (2010).

Glisson BS, Leidner R, Ferris R L, Powderly J, Rizvi N, Norton J D, Burton J, Lanasa M C, Patel S P. Phase 1 study of MEDI0562, a humanized OX40 agonist monoclonal antibody (mAb), in adult patients (pts) with advanced solid tumours. Ann. Oncol. 27(suppl 6), 1052PD (2016).

Gopal A, Levy R, Houot, R, Patel S, Hatake K, Popplewen L, Chen V, Davis C, Huang, B, Cesare R, Thall A, WoolFson A, Bartlett N, A phase I study of utomilumab (PF-05082566), a 4-1 BB/CD137 agonist, in combination with ritixumab in patients with CD20+ non-Hodgkin's lymphoma. Hernatol. Oncol. 35, 260 (2017).

Jefferis R, Reimer C B, Skvaril F, de Lange G, Ling N R, Lowe J, Walker M R, Phillips D J, Aloisio C H, Wells T W. Evaluation of monoclonal antibodies having specificity for human IgG sub-classes: results of an IUIS/WHO collaborative study. Immunol. Lett.1, 223-52(1985).

Jefferis R, Reimer C B, Skvaril F, de Lange G G, Goodall D M, Bentley T L, Phillips D J, Vlug A, Harada S, Radl J. Evaluation of monoclonal antibodies having specificity for human IgG subclasses: results of the 2nd IUIS/WHO collaborative study. Immunol. Lett. 31(2), 143-68 (1992).

Hezareh M, Hassell A J, Jensen R C, van de Winkel J G, Parren P W. Effector function activities of a panel of mutants of a broadly neutralizing antibody against human immunodeficiency virus type 1. J. Virol. 75(24), 12161-8 (2001).

Hirschhorn-Cymerman D, Rizzuto G A, Merghoub T, Cohen A D, Avogadn F, Lesokhin A M, Weinberg A D, Woichok J D, Houghton A N. OX40 engagement and chemotherapy combination provides potent antitumor immunity with concomitant regulatory T cell apoptosis. J. Exp. Med. 206(5), 1103-16(2009).

Holliger P, Hudson P J, Engineered antibody fragments and the rise of single domains. Nat. Biotechnol. 23(9), 1126-36 (2005).

Hu S, Shively L, Raubitschek A, Sherman M, Williams L E, Wong J Y, Shively J E, Wu A M. Minibody: A novel engineered anti-carcinoembryonic antigen antibody fragment (single-chain Fv-CH3) which exhibits rapid, high-level targeting of xenografts. Cancer Res. 56(13), 3055-61 (1996).

Idusogie E E, Presta L G, Gazzano-Santoro H, Totpal K, Wong P Y, Ultsch M, Meng Y G, Mulkerrin M G. Mapping of the C1q binding site on rituxan, a chimeric antibody with a human IgG1 Fc. J. Immunol. 164(8). 4178-84 (2000).

Kabat E A, Wu T T, Perry H M, Gottesman K S, Foeler C. Sequences of Proteins of Immunological Interest, 5th ed. NIH Publication No. 91-3242. Washington, D.C.: U.S. Department of Health and Human Services (1991).

Kjaergaard J, Tanaka J, Kim J A, Rothchild K, Weinberg A, Shu S. Therapeutic efficacy of OX-40 receptor antibody depends on tumor immunogenicity and anatomic site of tumor growth. Cancer Res. 60(19), 5514-21 (2000).

Klein C, Schaefer W. Regula J T. The use of CrossMAb technology for the generation of bi- and muitispecitic antibodies. MAbs 8(6), 1010-20 (2016).

Ledermann J A, Begent R H, Massof C, Kelly A M, Adam T, Bagshawe K D. A phase-I study of repeated therapy with radiolabelled antibody to carcinoembryonic antigen using Intermittent or continuous administration of cyclosporin A to supress the immune response. Int. J. Cancer 47(5), 659-64 (1991).

Lee S J, Myers L, Muralimohan G, Dan J, Qiao V, Li Z, Mittler R S, Vella A T. 4-1 B B and OX40 dual costimuiation synergistically stimulate primary specific CD8 T cells for robust effector function. J. Immunol. 173(5), 3002-12 (2004).

Lefranc M P, Pommiê C, Kaas Q, Duprat E, Bosc N, Guiraudou D, Jean C, Ruiz M, Da Piêdade I, Rouard M, Foulquier E, Thouvenin V, Lefranc G, IMGT unique numbering for immunoglobulin and T cell receptor constant domains and Ig superfamily C-like domains. Dev. Comp. Immunol. 29(3), 185 203 (2005).

Lefranc M P, Giudicelli V. Duroux P, Jabado-Michakwd J, Folch G, Aouinti S, Carillon E, Duvergey H, Houses A, Paysan-Lafosse T, Hadi-Saljoqi S, Sasorith S, Lefranc G, Kossida S. IMGT®, the international ImMunoGeneTics information system® 25 years on. Nucleic Acids Res. 43(Database issue), D413-22 (2015).

Liu C, Workman C J, Vignab D A. Targeting regulatory T cells in tumors. FEBS J. 283(14), 2731-48 (2016).

Ma B Y, Mikolajczak S A, Danesh A, Hosiawa K A, Cameron C M, Takaori-Kondo A, Uchiyama T, Kelvin D J, Ochi A. The expression and the regulatory role of OX40 and 4-1BB heterodimer in activated human T cells. Blood 106(6), 2002-10 (2005).

Mayes P A, Hance K W, Hoos A. The promise and challenges of immune agonist antibody development in cancer. Nat. Rev. Drug Discov. 17, 509-27 (2018).

Melero I, Hirschhom-Cymerman D, Morales-Kastresana A. Sanmamed M F, Wolchok J D. Agonist antibodies to TNFR molecules that costimulate T and NK cells. Clin. Cancer Res. 19(5), 1044-53 (2013).

Miles L, Wike J, Hunter N, Volpe J, Basic I. Macrophage content of murine sarcomas and carcinomas: associations with tumor growth parameters and tumor radiocurability. Cancer Res. 47(4), 1069-75 (1987).

Miller L, Rymarchyk N, Kelly T, Crocenzi T, Bernstein E, Sanborn R, Urba W J, Weinberg A D. OX40 is a potent immune-stimulating target in late-stage cancer patients. Cancer Res. 73(24), 7189-98 (2013).

Moran A E, Kovacsovics-Bankowski M, Weinberg A D. The TNFRs OX40, 4-1BB, and CD40 as targets for cancer immunotherapy. Curr. Opin. Immunol. 25(2), 230-7 (2013).

Müller N, Wyzgol A, Minkel S, Pfizenmaier K, Wajant H, Activity of soluble OX40 ligand is enhanced by oligomerization and cell surface immobilization. FEBS J. 275(9), 2296-304 (2008).

Nizar S. Copier J, Meyer B, Bodman-Smith M, Galustian C, Kumar D, Dalgleish A. T-regulatory cell modulation: the future of cancer immunotherapy?Br. J. Cancer 100(11), 1697-703 (2009).

Pardoll D M. The blockade of immune checkpoints in cancer immunotherapy. Nat. Rev. Cancer 12(4), 252-264 (2012).

Pearson W R, Upman D J. Improved tools for biological sequence comparison. Proc. Natl. Aced. Sci. U.S.A. 85(8), 2444-8 (1988).

Petty J K, He K, Corless C L, Vetto J T, Weinberg A D. Survival in human colorectal cancer correlates with expression of the T-cell costimulatory molecule OX-40 (CD134). Am. J. Surg. 183(5), 512-8 (2002).

Powell D J Jr, de Vries C R, Allen T, Ahmadzadeh M, Rosenberg S A. Inability to mediate prolonged reduction of regulatory T cells after transfer of autologous CD25-depleted PBMC and interleukin-2 after lymphodepleting chemotherapy. J. Immunother. 30(4), 438-47 (2007).

Qui H Z, Hagymasi A T, Bandyopadhyay S, St Rose M-C, Ramanarasimhaiah R, Menoret A, Mittler R S, Gordon S M, Reiner S L, Vella A T, Adler A J. CD134 plus CD137 dual costimulation induces Eomesodermin in CD4 T cells to program cytotoxic Th1 differentiation. J. Immunol. 187(7), 3555-64 (2011).

Rosenberg S. Development of Cancer Vaccines. ASCO Educational Book Spring: 60-62 (2000).

Ryan J M, Mittel P, Menoret A, Svedova J, Wasser J S, Adler A J, Vella A T. A novel biologic platform elicits profound T cell costimulatory activity and antitumor immunity in mice. Cancer Immunol. Immunother. 67(4), 605-13 (2018).

Sadun R E, Hsu W E, Zhang N, Nien Y C, Bergfeld S A, Sabzevari H, Lutsiak M E, Khawli L, Hu P, Epstein A L. Fc-mOX40L fusion protein produces complete remission and enhanced survival in 2 murine tumour models. J. Immunother. 31(3), 235-45(2008).

Sanchez-Paulete A R, Labiano S, Rodriguez-Ruiz M E, Azpilikueta A, Etxeberria I, BolaPos E, Lang V, Rodriguez M. Aznar M A, Jure-Kunkel M, Melero I. Deciphering C D137 (4-1BB) signaling In T-cell costimulation for translation into successful cancer immunotherapy. Eur. J. Immunol. 46(3), 513-22 (2016).

Scheer D A, Hirschhorn-Cymerman D, Woichok J D. Targeting tumor-necrosis factor receptor pathways for tumor immunotherapy. J. Immunother. Cancer 2, 7 (2014).

Segal N H, Logan T F, Hodi F S, McDermott D, Melero I, Hamid O, Schmidt H, Robert C, Chiarion-Sileni V, Ascierto P A, Maio M, Urba W J, Gangadhar T C, Suryawanshi S, Neely J, Jure-Kunkel M, Krishnan S, Kohrt H, Sznol M, Levy R. Results from an integrated safety analysis of urelumab, an agonist anti-CD137 monocbnal antibody. Clin. Cancer Res. 23(8). 1929-36 (2017).

Simpson T R., Li F, Montalvo-Ortiz W, Sepulveda MA, Bergerhoff K, Arce F, Roddie C, Henry J Y, Yagita H, Wokhok J D, Peggs K S, Ravetch J V, Allison J P, Quezada S A. Fc-dependent depletion of tumor-infiltrating regulatory T cells co-defines the efficacy of anti-CTLA-4 therapy against melanoma. J. Exp. Med. 210(9), 1695-710 (2013).

Smith T F, Waterman MS. Identification of common molecular subsequences. J. Mol. Biol. 147(1), 195-7 (1981).

Stewart R, Hammond S A, Oberst M, Wilkinson R W. The role of Fc gamma receptors in the activity of immunomodulatory antibodies for cancer. J. Immunother. Cancer 2(29) (2014).

Takeda I, Ine S, Killeen N, Ndhlovu LC, Murata K, Satomi S, Sugamura K, Ishii N. Distinct roles for the OX40-OX40 ligand interaction in regulatory and nonregulatory T cells. J. Immunol. 172(6), 3580-9 (2004).

Taraban VY, Rowley T F, O'Brien L, Chan H T. Haswell L E, Green MH, Tutt AL, Glennie MJ, Al-Shamkhani A. Expression and costimulatory effects of the TNF receptor superfamily members CD134 OX40) and CD137 (4-1 BB), and their role in the generation of anti-tumor immune responses. Eur. J. Immunol. 32(12). 3617-27 (2002).

Tolcher AW, Sznol M, Hu-Lieskovan S, Papadopoulos K P, Patnalk A, Rasco D W, Di Gravlo D, Huang B, Gambhire D, Chen Y, Thall AD, Pathan N, Schmidt EV, Chow LQM. Phase Ib study of utomilumab (PF-05082566), a 4-1BB/CD137 agonist, in combination with pembrolizumab (MK-3475) in patients with advanced solid tumors. Clin. Cancer Res. 23(18), 5349-57 (2017).

Tran B, Carvajal RD, Marabelle A, Patel SP, LoRusso P, Ramussen E, Juan G, Upreti W, Ngarmchamnanrlth G, Schöffski P. Dose escalation results from a first-in-human, phase 1 study of the glucocorticoid-induced TNF receptor-related protein (GITR) agonist AMG 228 in patients (Pts) with advanced solid tumours. J. Clin. Oncol. 35(15 suppl), 2521 (2017).

Vanarnee E S, Faustman DL, Structural principles of tumor necrosis factor superfamily signaling. Sci. Signal. 11(511), 1-12 (2018).

Vetto JT, Lum S, Morris A, Sicotte M, Davis J, Lemon M, Weinberg A. Presence of the T-cell activation marker OX-40 on tumor infiltrating lymphocytes and draining lymph node cells from patients with melanoma and head and neck cancers. Am. J. Surg. 174(3), 258-65(1997).

Vignali D A, Collison L W, Workman CJ. How regulatory T cells work. Nat. Rev. Immunol. 8(7), 523-32 (2008).

Wajant H. Principles of antibody-mediated TNF receptor activation. Cell Death Differ. 22(11), 1727-41 (2015).

Wang X, Mathieu M, Brezski RJ. IgG Fc engineering to modulate antibody effector functions. Protein Cell 9(1), 63-73 (2018).

Weigelin B, Bolanos E, Rodriguez-Ruiz M E, Martinez-Forero I, Friedl P, Melero I. Anti-CD137 monoclonal antibodies and adoptive T cell therapy: a perfect marriage? Cancer Immunol. Immunother. 65(5), 493-7 (2016).

Wen T, Bukczynski J, Watts TH. 4-1 BB ligand-mediated costimulation of human T cells induces CD4 and CD8 T cell expansion, cytokine production, and the development of cytolytic effector function. J. Immunol. 168(10), 4897-906 (2002).

Wesche-Soldato DE, Chung CS, Gregory SH, Salazar-Mather TP, Ayala CA, Ayala A. CD8+ T cells promote inflammation and apoptosis in the liver after sepsis: role of Fas-FasL. Am. J. Pathol. 171(1), 87-96 (2007).

Wilcox RA, Flies DB, Zhu G, Johnson A J, Tornado K, Chapoval Al, Strome SE, Pease L R, Chen L. Provision of antigen and CD137 signaling breaks Immunological Ignorance, promoting regression of poorly immunogenic tumors. J. Clin. Invest. 109(5), 651-9 (2002).

Wozniak-Knopp G, Bard S, Bauer A, Mostageer M, Woisetschlager M, Antes B, Ettl K, Kainer M, Weberhofer G, Wiederkum S, Himmler G, Mudde G C, Ruker F. Introducing antigen-binding sites in structural loops of immunoglobulin constant domains: Fc fragments with engineered HER2/neu-binding sites and antibody properties. Protein Eng. Des. Sol. 23(4), 289-97 (2010).

The invention claimed is:

1. An antibody that binds to CD137 and OX40, comprising (a) a complementarity determining region (CDR)-based antigen-binding site for CD137 wherein the CDR-based antigen-binding site for CD137 comprises the VH CDR1, VH CDR2, VH CDR3, VL CDR1, VL CDR2 and VL CDR3, defined according to the ImMunoGeneTics (IMGT) numbering scheme, comprising:
   (i) SEQ ID NOs: 1, 2, 3, 4, 5 and 6, respectively;
   (ii) SEQ ID NOs: 1, 2, 16, 4, 5 and 6, respectively;
   (iii) SEQ ID NOs: 1, 2, 21, 4, 5 and 6, respectively;
   (iv) SEQ ID NOs: 25, 26, 27, 4, 5 and 28, respectively;
   or (v) SEQ ID NOs: 33, 34, 35, 4, 5 and 36, respectively; and/or
   wherein the CDR-based antigen-binding site for CD137 comprises the VH CDR1, VH CDR2, VH CDR3, VL CDR1, VL CDR2 and VL CDR3, defined according to the Kabat numbering scheme, comprising:
   (vi) SEQ ID NOs: 7, 8, 9, 10, 11 and 6, respectively;
   (vii) SEQ ID NOs: 7, 8, 17, 10, 11 and 6, respectively;
   (viii) SEQ ID NOs: 7, 8, 22, 10, 11 and 6, respectively;
   (ix) SEQ ID NOs: 29, 30, 31, 10, 11 and 28, respectively; or
   (x) SEQ ID NOs: 37, 38, 39, 10, 11 and 36, respectively; and
   (b) an OX40 antigen-binding site located in a CH3 domain of the antibody, wherein the OX40 antigen-binding site comprises a first sequence comprising SEQ ID NO: 51 in the AB loop, a second sequence comprising SEQ ID NO: 52 in the CD loop, and a third sequence comprising SEQ ID NO: 53 in the EF loop of the CH3 domain according to the IMGT numbering scheme.

2. The antibody of claim 1, wherein:
   (i) the first sequence is located at positions 14 to 18 of the CH3 domain of the antibody molecule;
   (ii) the second sequence is located at positions 45.1 to 77 of the CH3 domain of the antibody molecule; and/or
   (iii) the third sequence is located at positions 93 to 101 of the CH3 domain of the antibody molecule; and
   wherein the amino acid residue numbering is according to the IMGT numbering scheme.

3. The antibody of claim 1, wherein the antibody comprises the CH3 domain sequence of SEQ ID NO: 54.

4. The antibody of claim 1, wherein the antibody comprises the VH domain and VL domain comprising:
   (i) SEQ ID NOs: 12 and 14, respectively;
   ii) SEQ ID NOs: 18 and 14, respectively;
   (iii) SEQ ID NOs: 23 and 14, respectively;
   (iv) SEQ ID NOs: 170 and 172, respectively; or
   (v) SEQ ID NOs: 40 and 42, respectively.

5. The antibody of claim 1, wherein the antibody comprises the heavy chain and light chain comprising:
   (i) SEQ ID NOs: 95 and 97, respectively;
   (ii) SEQ ID NOs: 99 and 97, respectively;
   (iii) SEQ ID NOs: 103 and 97, respectively;
   (iv) SEQ ID NOs: 105 and 107, respectively; or
   (v) SEQ ID NOs: 109 and 111, respectively.

6. The antibody of claim 1, wherein the antibody comprises:
   (i) the VH CDR1, VH CDR2, VH CDR3, VL CDR1, VL CDR2 and VL CDR3, defined according to the IMGT numbering scheme, comprising SEQ ID NOs: 1, 2, 3, 4, 5 and 6, respectively;
   (ii) the VH CDR1, VH CDR2, VH CDR3, VL CDR1, VL CDR2 and VL CDR3, defined according to the Kabat numbering scheme, comprising SEQ ID NOs: 7, 8, 9, 10, 11 and 6, respectively;
   (iii) the VH domain and VL domain comprising SEQ ID NOs: 12 and 14, respectively; and/or (iv) the heavy chain and light chain comprising SEQ ID NOs: 95 and 97, respectively.

7. The antibody of claim 1, wherein the antibody binds human CD137 and human OX40.

8. The antibody of claim 7, wherein the antibody binds to human CD137 and human OX40 concurrently.

9. The antibody of claim 1, wherein the antibody activates the OX40 on an immune cell in the presence of cell-surface expressed CD137, and/or the antibody activates CD137 on an immune cell in the presence of cell surface expressed OX40.

10. The antibody of claim 1, wherein binding of the antibody to OX40 on an immune cell and to CD137 causes clustering of OX40 on the immune cell, and/or wherein binding of the antibody to CD137 on the immune cell and to OX40 causes clustering of CD137 on the immune cell.

11. The antibody of claim 1, wherein the antibody has been modified to reduce or abrogate binding of the CH2 domain of the antibody to one or more Fcγ receptors.

12. A nucleic acid encoding the antibody of claim 1.

13. A vector comprising the nucleic acid of claim 12.

14. A recombinant host cell comprising the nucleic acid of claim 12, or a vector comprising the nucleic acid of claim 12.

15. A method of producing the antibody comprising culturing the recombinant host cell of claim 14 under conditions for production of the antibody.

16. The method of claim 15 further comprising isolating and/or purifying the antibody.

17. A pharmaceutical composition comprising the antibody of claim 1 and a pharmaceutically acceptable excipient.

18. A method of treating cancer or an infectious disease in an individual comprising administering to the individual a therapeutically effective amount of the antibody of claim 1.

19. The method of treating cancer of claim 18, wherein the method comprises administering the antibody to the individual in combination with a second therapeutic.

20. The method of claim 19, wherein the second therapeutic is an antibody that binds PD-1 or PD-L 1.

21. The antibody of claim 3, wherein the antibody further comprises a lysine residue (K) adjoined at the C-terminus of the CH3 domain sequence of SEQ ID NO:54.

22. The antibody of claim 5, wherein the antibody further comprises a lysine residue (K) adjoined at the C-terminus of the heavy chain sequence of SEQ ID NO: 95, 99, 103, 105, or 109.

* * * * *

UNITED STATES PATENT AND TRADEMARK OFFICE
CERTIFICATE OF CORRECTION

| | |
|---|---|
| PATENT NO. | : 12,252,537 B2 |
| APPLICATION NO. | : 17/259796 |
| DATED | : March 18, 2025 |
| INVENTOR(S) | : Mihriban Tuna et al. |

It is certified that error appears in the above-identified patent and that said Letters Patent is hereby corrected as shown below:

In the Claims

At Column 354, Claim 4, Line 44:
"ii) SEQ ID Nos: 18 and 14, respectively;"
Should read:
--(ii) SEQ ID Nos. 18 and 14, respectively;--

Page 1 of 1

Signed and Sealed this
Eighth Day of July, 2025

Coke Morgan Stewart
*Acting Director of the United States Patent and Trademark Office*

SEQUENCE LISTING

```
<160> NUMBER OF SEQ ID NOS: 175

<210> SEQ ID NO 1
<211> LENGTH: 8
<212> TYPE: PRT
<213> ORGANISM: Artificial Sequence
<220> FEATURE:
<223> OTHER INFORMATION: FS30-10-16 mAb (IMGT) VH CDR1

<400> SEQUENCE: 1

Gly Phe Thr Phe Ser Ser Tyr Asp
1               5

<210> SEQ ID NO 2
<211> LENGTH: 8
<212> TYPE: PRT
<213> ORGANISM: Artificial Sequence
<220> FEATURE:
```

```
<223> OTHER INFORMATION: FS30-10-16 mAb (IMGT) VH CDR2

<400> SEQUENCE: 2

Ile Asp Pro Thr Gly Ser Lys Thr
1               5

<210> SEQ ID NO 3
<211> LENGTH: 11
<212> TYPE: PRT
<213> ORGANISM: Artificial Sequence
<220> FEATURE:
<223> OTHER INFORMATION: FS30-10-16 mAb (IMGT) VH CDR3

<400> SEQUENCE: 3

Ala Arg Asp Leu Leu Val Tyr Gly Phe Asp Tyr
1               5                   10

<210> SEQ ID NO 4
<211> LENGTH: 7
<212> TYPE: PRT
<213> ORGANISM: Artificial Sequence
<220> FEATURE:
<223> OTHER INFORMATION: FS30-10-16 mAb (IMGT) VL CDR1

<400> SEQUENCE: 4

Gln Ser Val Ser Ser Ser Tyr
1               5

<210> SEQ ID NO 5
<211> LENGTH: 3
<212> TYPE: PRT
<213> ORGANISM: Artificial Sequence
<220> FEATURE:
<223> OTHER INFORMATION: FS30-10-16 mAb (IMGT) VL CDR2

<400> SEQUENCE: 5

Gly Ala Ser
1

<210> SEQ ID NO 6
<211> LENGTH: 9
<212> TYPE: PRT
<213> ORGANISM: Artificial Sequence
<220> FEATURE:
<223> OTHER INFORMATION: FS30-10-16 mAb (IMGT) VL CDR3

<400> SEQUENCE: 6

Gln Gln Ser Tyr Ser Tyr Pro Val Thr
1               5

<210> SEQ ID NO 7
<211> LENGTH: 5
<212> TYPE: PRT
<213> ORGANISM: Artificial Sequence
<220> FEATURE:
<223> OTHER INFORMATION: FS30-10-16 mAb (Kabat) VH CDR1

<400> SEQUENCE: 7

Ser Tyr Asp Met Ser
1               5

<210> SEQ ID NO 8
<211> LENGTH: 17
<212> TYPE: PRT
<213> ORGANISM: Artificial Sequence
<220> FEATURE:
<223> OTHER INFORMATION: FS30-10-16 mAb (Kabat) VH CDR2
```

-continued

```
<400> SEQUENCE: 8

Asp Ile Asp Pro Thr Gly Ser Lys Thr Asp Tyr Ala Asp Ser Val Lys
1               5                   10                  15

Gly

<210> SEQ ID NO 9
<211> LENGTH: 9
<212> TYPE: PRT
<213> ORGANISM: Artificial Sequence
<220> FEATURE:
<223> OTHER INFORMATION: FS30-10-16 mAb (Kabat) VH CDR3

<400> SEQUENCE: 9

Asp Leu Leu Val Tyr Gly Phe Asp Tyr
1               5

<210> SEQ ID NO 10
<211> LENGTH: 7
<212> TYPE: PRT
<213> ORGANISM: Artificial Sequence
<220> FEATURE:
<223> OTHER INFORMATION: FS30-10-16 mAb (Kabat) VL CDR1

<400> SEQUENCE: 10

Gly Ala Ser Ser Arg Ala Thr
1               5

<210> SEQ ID NO 11
<211> LENGTH: 9
<212> TYPE: PRT
<213> ORGANISM: Artificial Sequence
<220> FEATURE:
<223> OTHER INFORMATION: FS30-10-16 mAb (Kabat) VL CDR2

<400> SEQUENCE: 11

Gln Gln Ser Tyr Ser Tyr Pro Val Thr
1               5

<210> SEQ ID NO 12
<211> LENGTH: 118
<212> TYPE: PRT
<213> ORGANISM: Artificial Sequence
<220> FEATURE:
<223> OTHER INFORMATION: heavy chain variable domain of FS30-10-16 mAb

<400> SEQUENCE: 12

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Asp Ile Asp Pro Thr Gly Ser Lys Thr Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Leu Val Tyr Gly Phe Asp Tyr Trp Gly Gln Gly Thr
            100                 105                 110
```

```
<210> SEQ ID NO 13
<211> LENGTH: 354
<212> TYPE: DNA
<213> ORGANISM: Artificial Sequence
<220> FEATURE:
<223> OTHER INFORMATION: heavy chain variable domain of FS30-10-16 mAb

<400> SEQUENCE: 13
gaagttcagc tgctggaatc tggcggcgga ttggttcaac ctggcggctc tctgagactg      60
tcttgtgccg cttccggctt caccttctcc agctacgaca tgtcctgggt ccgacaggct     120
cctggcaaag gactgaatg gtgtccgac atcgaccca ccggctctaa gaccgactac        180
gccgattctg tgaagggcag attcaccatc agccgggaca actccaagaa caccctgtac     240
ctgcagatga actccctgag agccgaggac accgccgtgt actactgtgc cagagatctg     300
ctggtgtacg gcttcgacta ttggggccag ggcacactgg tcaccgtgtc ctct            354

<210> SEQ ID NO 14
<211> LENGTH: 108
<212> TYPE: PRT
<213> ORGANISM: Artificial Sequence
<220> FEATURE:
<223> OTHER INFORMATION: light chain variable domain of FS30-10-16 mAb

<400> SEQUENCE: 14

Glu Ile Val Leu Thr Gln Ser Pro Gly Thr Leu Ser Leu Ser Pro Gly
1               5                  10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ser Tyr Ser Tyr Pro
                85                  90                  95

Val Thr Phe Gly Gln Gly Thr Lys Val Glu Ile Lys
            100                 105

<210> SEQ ID NO 15
<211> LENGTH: 324
<212> TYPE: DNA
<213> ORGANISM: Artificial Sequence
<220> FEATURE:
<223> OTHER INFORMATION: light chain variable domain of FS30-10-16 mAb

<400> SEQUENCE: 15
gagatcgtgc tgacccagtc tcctggcaca ctgtcactgt ctccaggcga gagagctacc      60
ctgtcctgta gagcctctca gtccgtgtcc tcctcttacc tggcctggta tcagcagaag     120
cctggacagg ctccccggct gttgatctac ggcgcttctt ctagagccac aggcatccct     180
gaccggttct ccggatctgg ctctggcacc gatttcaccc tgaccatctc tcggctggaa     240
cccgaggatt tcgccgtgta ctactgccag cagtcctaca gctaccccgt gacctttggc     300
cagggcacca aggtggaaat caag                                            324
```

<210> SEQ ID NO 16
<211> LENGTH: 11
<212> TYPE: PRT
<213> ORGANISM: Artificial Sequence
<220> FEATURE:
<223> OTHER INFORMATION: FS30-10-3 mAb (IMGT) VH CDR3

<400> SEQUENCE: 16

Ala Arg Asp Leu Asn Val Tyr Gly Phe Asp Tyr
1               5                   10

<210> SEQ ID NO 17
<211> LENGTH: 9
<212> TYPE: PRT
<213> ORGANISM: Artificial Sequence
<220> FEATURE:
<223> OTHER INFORMATION: FS30-10-3 mAb (Kabat) VH CDR3

<400> SEQUENCE: 17

Asp Leu Asn Val Tyr Gly Phe Asp Tyr
1               5

<210> SEQ ID NO 18
<211> LENGTH: 118
<212> TYPE: PRT
<213> ORGANISM: Artificial Sequence
<220> FEATURE:
<223> OTHER INFORMATION: heavy chain variable domain of FS30-10-3 mAb

<400> SEQUENCE: 18

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Asp Ile Asp Pro Thr Gly Ser Lys Thr Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Asn Val Tyr Gly Phe Asp Tyr Trp Gly Gln Gly Thr
            100                 105                 110

Leu Val Thr Val Ser Ser
        115

<210> SEQ ID NO 19
<211> LENGTH: 354
<212> TYPE: DNA
<213> ORGANISM: Artificial Sequence
<220> FEATURE:
<223> OTHER INFORMATION: heavy chain variable domain of FS30-10-3 mAb

<400> SEQUENCE: 19
gaagtgcaac tgctggagtc cggtggtggt ctggtacagc cgggtggttc tctgcgtctg     60
agttgcgcgg ccagtggctt taccttcagt agttacgata tgagctgggt gcgtcaggct    120
ccgggcaaag gtctgaatg ggttagcgat attgatccga ctggtagcaa gaccgactat     180
gcggatagcg tgaaaggccg ttttaccatt tctcgcgaca acagcaagaa cacgctgtac    240

-continued

```
ctgcagatga actcactgcg tgccgaagat acggccgtgt attactgtgc gagagacctc      300
aatgtgtacg ggttcgacta ctggggccag ggaaccctgg tcaccgtctc gagt            354
```

<210> SEQ ID NO 20
<211> LENGTH: 324
<212> TYPE: DNA
<213> ORGANISM: Artificial Sequence
<220> FEATURE:
<223> OTHER INFORMATION: light chain variable domain of FS30-10-3 mAb

<400> SEQUENCE: 20

```
gaaattgtgc tgacccagtc tccgggcacg ttatctctga gccctggtga gcgcgccact      60
ctgtcatgcc gggcttctca aagtgttagc agtagctacc tggcgtggta tcagcaaaaa     120
ccgggccagg ccccgcgtct gctgatttac ggtgcatcca gccgtgccac cggcattcca     180
gatcgttttt ccggtagtgg ttctgggacg gacttcactc tgacaatctc acgcctggaa     240
ccggaggatt ttgcggtgta ttactgccag caatcttatt cttatcctgt cacgttcggc     300
caagggacca aggtggaaat caaa                                             324
```

<210> SEQ ID NO 21
<211> LENGTH: 11
<212> TYPE: PRT
<213> ORGANISM: Artificial Sequence
<220> FEATURE:
<223> OTHER INFORMATION: FS30-10-12 mAb (IMGT) VH CDR3

<400> SEQUENCE: 21

Ala Arg Asp Leu Thr Val Tyr Gly Phe Asp Tyr
1               5                   10

<210> SEQ ID NO 22
<211> LENGTH: 9
<212> TYPE: PRT
<213> ORGANISM: Artificial Sequence
<220> FEATURE:
<223> OTHER INFORMATION: FS30-10-12 mAb (Kabat) VH CDR3

<400> SEQUENCE: 22

Asp Leu Thr Val Tyr Gly Phe Asp Tyr
1               5

<210> SEQ ID NO 23
<211> LENGTH: 118
<212> TYPE: PRT
<213> ORGANISM: Artificial Sequence
<220> FEATURE:
<223> OTHER INFORMATION: heavy chain variable domain of FS30-10-12 mAb

<400> SEQUENCE: 23

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Asp Ile Asp Pro Thr Gly Ser Lys Thr Ala Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Asp Leu Thr Val Tyr Gly Phe Asp Tyr Trp Gly Gln Gly Thr
            100                 105                 110

Leu Val Thr Val Ser Ser
        115

<210> SEQ ID NO 24
<211> LENGTH: 354
<212> TYPE: DNA
<213> ORGANISM: Artificial Sequence
<220> FEATURE:
<223> OTHER INFORMATION: heavy chain variable domain of FS30-10-12 mAb

<400> SEQUENCE: 24
gaagtgcaac tgctggagtc cggtggtggt ctggtacagc cgggtggttc tctgcgtctg      60
agttgcgcgg ccagtggctt taccttcagt agttacgata tgagctgggt gcgtcaggct     120
ccgggcaaag gtctggaatg ggttagcgat attgatccga ctggtagcaa gaccgactat     180
gcggatagcg tgaaaggccg ttttaccatt tctcgcgaca acagcaagaa cacgctgtac     240
ctgcagatga actcactgcg tgccgaagat acggccgtgt attactgtgc gagagaccta     300
acggtgtacg ggttcgacta ctggggccag ggaaccctgg tcaccgtctc gagt           354

<210> SEQ ID NO 25
<211> LENGTH: 8
<212> TYPE: PRT
<213> ORGANISM: Artificial Sequence
<220> FEATURE:
<223> OTHER INFORMATION: FS30-35-14 mAb (IMGT) VH CDR1

<400> SEQUENCE: 25

Gly Phe Thr Phe Ser Ala Tyr Asn
1               5

<210> SEQ ID NO 26
<211> LENGTH: 8
<212> TYPE: PRT
<213> ORGANISM: Artificial Sequence
<220> FEATURE:
<223> OTHER INFORMATION: FS30-35-14 mAb (IMGT) VH CDR2

<400> SEQUENCE: 26

Ile Ser Pro Tyr Gly Gly Ala Thr
1               5

<210> SEQ ID NO 27
<211> LENGTH: 16
<212> TYPE: PRT
<213> ORGANISM: Artificial Sequence
<220> FEATURE:
<223> OTHER INFORMATION: FS30-35-14 mAb (IMGT) VH CDR3

<400> SEQUENCE: 27

Ala Arg Asn Leu Tyr Glu Leu Ser Ala Tyr Ser Tyr Gly Ala Asp Tyr
1               5                   10                  15

<210> SEQ ID NO 28
<211> LENGTH: 10
<212> TYPE: PRT
<213> ORGANISM: Artificial Sequence
<220> FEATURE:
<223> OTHER INFORMATION: FS30-35-14 mAb (IMGT) VL CDR3

<400> SEQUENCE: 28

Gln Gln Tyr Tyr Tyr Ser Ser Pro Ile Thr
1               5                   10

<210> SEQ ID NO 29
<211> LENGTH: 5
<212> TYPE: PRT
<213> ORGANISM: Artificial Sequence
<220> FEATURE:
<223> OTHER INFORMATION: FS30-35-14 mAb (Kabat) VH CDR1

<400> SEQUENCE: 29

Ala Tyr Asn Ile His
1               5

<210> SEQ ID NO 30
<211> LENGTH: 17
<212> TYPE: PRT
<213> ORGANISM: Artificial Sequence
<220> FEATURE:
<223> OTHER INFORMATION: FS30-35-14 mAb (Kabat) VH CDR2

<400> SEQUENCE: 30

Asp Ile Ser Pro Tyr Gly Gly Ala Thr Asn Tyr Ala Asp Ser Val Lys
1               5                   10                  15

Gly

<210> SEQ ID NO 31
<211> LENGTH: 14
<212> TYPE: PRT
<213> ORGANISM: Artificial Sequence
<220> FEATURE:
<223> OTHER INFORMATION: FS30-35-14 mAb (Kabat) VH CDR3

<400> SEQUENCE: 31

Asn Leu Tyr Glu Leu Ser Ala Tyr Ser Tyr Gly Ala Asp Tyr
1               5                   10

<210> SEQ ID NO 32
<211> LENGTH: 327
<212> TYPE: DNA
<213> ORGANISM: Artificial Sequence
<220> FEATURE:
<223> OTHER INFORMATION: light chain variable domain of FS30-35-14 mAb

<400> SEQUENCE: 32
gaaattgtgc tgacccagtc tccgggcacg ttatctctga gccctggtga gcgcgccact      60
ctgtcatgcc gggcttctca aagtgttagc agtagctacc tggcgtggta tcagcaaaaa     120
ccgggccagg ccccgcgtct gctgatttac ggtgcatcca gccgtgccac cggcattcca     180
gatcgttttt ccggtagtgg ttctgggacg gacttcactc tgacaatctc acgcctggaa     240
ccggaggatt ttgcggtgta ttactgccag caatattatt attcttctcc tatcacgttc     300
ggccaaggga ccaaggtgga aatcaaa                                         327

<210> SEQ ID NO 33
<211> LENGTH: 8
<212> TYPE: PRT
<213> ORGANISM: Artificial Sequence
<220> FEATURE:
<223> OTHER INFORMATION: FS30-5-37 mAb (IMGT) VH CDR1

<400> SEQUENCE: 33

Gly Phe Thr Phe Ser Ser Tyr Ala
1               5

<210> SEQ ID NO 34
<211> LENGTH: 8
<212> TYPE: PRT
<213> ORGANISM: Artificial Sequence
<220> FEATURE:
<223> OTHER INFORMATION: FS30-5-37 mAb (IMGT) VH CDR2

<400> SEQUENCE: 34

Ile Ser Gly Ser Gly Gly Ser Thr
1               5

<210> SEQ ID NO 35
<211> LENGTH: 18
<212> TYPE: PRT
<213> ORGANISM: Artificial Sequence
<220> FEATURE:
<223> OTHER INFORMATION: FS30-5-37 mAb (IMGT) VH CDR3

<400> SEQUENCE: 35

Ala Arg Ser Tyr Asp Lys Tyr Trp Gly Ser Ser Ile Tyr Ser Gly Leu
1               5                   10                  15

Asp Tyr

<210> SEQ ID NO 36
<211> LENGTH: 10
<212> TYPE: PRT
<213> ORGANISM: Artificial Sequence
<220> FEATURE:
<223> OTHER INFORMATION: FS30-5-37 mAb (IMGT) VL CDR3

<400> SEQUENCE: 36

Gln Gln Tyr Tyr Ser Tyr Tyr Pro Val Thr
1               5                   10

<210> SEQ ID NO 37
<211> LENGTH: 5
<212> TYPE: PRT
<213> ORGANISM: Artificial Sequence
<220> FEATURE:
<223> OTHER INFORMATION: FS30-5-37 mAb (Kabat) VH CDR1

<400> SEQUENCE: 37

Ser Tyr Ala Met Ser
1               5

<210> SEQ ID NO 38
<211> LENGTH: 17
<212> TYPE: PRT
<213> ORGANISM: Artificial Sequence
<220> FEATURE:
<223> OTHER INFORMATION: FS30-5-37 mAb (Kabat) VH CDR2

<400> SEQUENCE: 38

Ala Ile Ser Gly Ser Gly Gly Ser Thr Tyr Tyr Ala Asp Ser Val Lys
1               5                   10                  15

Gly

<210> SEQ ID NO 39
<211> LENGTH: 16
<212> TYPE: PRT

<213> ORGANISM: Artificial Sequence
<220> FEATURE:
<223> OTHER INFORMATION: FS30-5-37 mAb (Kabat) VH CDR3

<400> SEQUENCE: 39

Ser Tyr Asp Lys Tyr Trp Gly Ser Ser Ile Tyr Ser Gly Leu Asp Tyr
1               5                   10                  15

<210> SEQ ID NO 40
<211> LENGTH: 125
<212> TYPE: PRT
<213> ORGANISM: Artificial Sequence
<220> FEATURE:
<223> OTHER INFORMATION: heavy chain variable domain of FS30-5-37 mAb

<400> SEQUENCE: 40

Glu Val Gln Leu Leu Glu Ser Gly Gly Gly Leu Val Gln Pro Gly Gly
1               5                   10                  15

Ser Leu Arg Leu Asn Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Tyr Asp Lys Tyr Trp Gly Ser Ser Ile Tyr Ser Gly Leu
            100                 105                 110

Asp Tyr Trp Gly Gln Gly Thr Leu Val Thr Val Ser Ser
        115                 120                 125

<210> SEQ ID NO 41
<211> LENGTH: 375
<212> TYPE: DNA
<213> ORGANISM: Artificial Sequence
<220> FEATURE:
<223> OTHER INFORMATION: heavy chain variable domain of FS30-5-37 mAb

<400> SEQUENCE: 41
gaagtgcaac tgctggagtc cggtggtggt ctggtacagc cgggtggttc tctgcgtctg      60
aattgcgcgg ccagtggctt taccttcagt agctatgcca tgagctgggt gcgtcaggcg     120
ccgggcaaag gtctggaatg ggttagcgcg attagcggta gtggcggtag cacgtactat     180
gcggatagcg tgaaaggccg ttttaccatt tctcgcgaca acagcaagaa cacgctgtac     240
ctgcagatga actcactgcg tgccgaagat acggccgtgt attactgtgc gagatcttac     300
gacaaatact ggggttcttc tatttactct ggcttggact actggggcca gggaaccctg     360
gtcaccgtct cgagt                                                      375

<210> SEQ ID NO 42
<211> LENGTH: 109
<212> TYPE: PRT
<213> ORGANISM: Artificial Sequence
<220> FEATURE:
<223> OTHER INFORMATION: light chain variable domain of FS30-5-37 mAb

<400> SEQUENCE: 42

Glu Ile Val Leu Thr Gln Ser Pro Gly Thr Leu Ser Leu Ser Pro Gly
1               5                   10                  15

```
Glu Arg Ala Thr Leu Ser Cys Arg Ala Ser Gln Ser Val Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Tyr Ser Tyr Tyr
                85                  90                  95

Pro Val Thr Phe Gly Gln Gly Thr Lys Val Glu Ile Lys
            100                 105

<210> SEQ ID NO 43
<211> LENGTH: 327
<212> TYPE: DNA
<213> ORGANISM: Artificial Sequence
<220> FEATURE:
<223> OTHER INFORMATION: light chain variable domain of FS30-5-37 mAb

<400> SEQUENCE: 43
gaaattgtgc tgacccagtc tccgggcacg ttatctctga gccctggtga gcgcgccact     60
ctgtcatgcc gggcttctca aagtgttagc agtagctacc tggcgtggta tcagcaaaaa    120
ccgggccagg ccccgcgtct gctgatttac ggtgcatcca gccgtgccac cggcattcca    180
gatcgttttt ccggtagtgg ttctgggacg gacttcactc tgacaatctc acgcctggaa    240
ccggaggatt ttgcggtgta ttactgccag caatattatt cttattatcc tgtcacgttc    300
ggccaaggga ccaaggtgga aatcaaa                                         327

<210> SEQ ID NO 44
<211> LENGTH: 8
<212> TYPE: PRT
<213> ORGANISM: Artificial Sequence
<220> FEATURE:
<223> OTHER INFORMATION: WT CH3 domain AB loop

<400> SEQUENCE: 44

Arg Asp Glu Leu Thr Lys Asn Gln
1               5

<210> SEQ ID NO 45
<211> LENGTH: 9
<212> TYPE: PRT
<213> ORGANISM: Artificial Sequence
<220> FEATURE:
<223> OTHER INFORMATION: WT CH3 domain CD loop

<400> SEQUENCE: 45

Ser Asn Gly Gln Pro Glu Asn Asn Tyr
1               5

<210> SEQ ID NO 46
<211> LENGTH: 10
<212> TYPE: PRT
<213> ORGANISM: Artificial Sequence
<220> FEATURE:
<223> OTHER INFORMATION: WT CH3 domain EF loop

<400> SEQUENCE: 46

Asp Lys Ser Arg Trp Gln Gln Gly Asn Val
1               5                   10
```

<210> SEQ ID NO 47
<211> LENGTH: 106
<212> TYPE: PRT
<213> ORGANISM: Artificial Sequence
<220> FEATURE:
<223> OTHER INFORMATION: WT CH3 domain

<400> SEQUENCE: 47

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly
            100                 105

<210> SEQ ID NO 48
<211> LENGTH: 110
<212> TYPE: PRT
<213> ORGANISM: Artificial Sequence
<220> FEATURE:
<223> OTHER INFORMATION: CH2 domain

<400> SEQUENCE: 48

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

<210> SEQ ID NO 49
<211> LENGTH: 110
<212> TYPE: PRT
<213> ORGANISM: Artificial Sequence
<220> FEATURE:
<223> OTHER INFORMATION: CH2 domain with LALA mutation

<400> SEQUENCE: 49

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

```
Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
 50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys
            100                 105                 110

<210> SEQ ID NO 50
<211> LENGTH: 110
<212> TYPE: PRT
<213> ORGANISM: Artificial Sequence
<220> FEATURE:
<223> OTHER INFORMATION: CH2 domain with LALA mutation and P114A
      mutation

<400> SEQUENCE: 50

Ala Pro Glu Ala Ala Gly Gly Pro Ser Val Phe Leu Phe Pro Pro Lys
 1               5                  10                  15

Pro Lys Asp Thr Leu Met Ile Ser Arg Thr Pro Glu Val Thr Cys Val
             20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
 50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Ala Ala Pro Ile Glu Lys Thr Ile Ser Lys Ala Lys
            100                 105                 110

<210> SEQ ID NO 51
<211> LENGTH: 5
<212> TYPE: PRT
<213> ORGANISM: Artificial Sequence
<220> FEATURE:
<223> OTHER INFORMATION: Fcab FS20-22-49 CH3 domain structural loop
      sequence

<400> SEQUENCE: 51

Tyr Trp Asp Gln Glu
 1               5

<210> SEQ ID NO 52
<211> LENGTH: 5
<212> TYPE: PRT
<213> ORGANISM: Artificial Sequence
<220> FEATURE:
<223> OTHER INFORMATION: Fcab FS20-22-49 CH3 domain structural loop
      sequence

<400> SEQUENCE: 52

Asp Glu Gln Phe Ala
 1               5

<210> SEQ ID NO 53
<211> LENGTH: 9
<212> TYPE: PRT
```

<213> ORGANISM: Artificial Sequence
<220> FEATURE:
<223> OTHER INFORMATION: Fcab FS20-22-49 CH3 domain structural loop sequence

<400> SEQUENCE: 53

Gln Tyr Arg Trp Asn Pro Ala Asp Tyr
1               5

<210> SEQ ID NO 54
<211> LENGTH: 106
<212> TYPE: PRT
<213> ORGANISM: Artificial Sequence
<220> FEATURE:
<223> OTHER INFORMATION: Fcab FS20-22-49 CH3 domain

<400> SEQUENCE: 54

Gly Gln Pro Arg Glu Pro Gln Val Tyr Thr Leu Pro Pro Ser Arg Asp
1               5                   10                  15

Glu Tyr Trp Asp Gln Glu Val Ser Leu Thr Cys Leu Val Lys Gly Phe
                20                  25                  30

Tyr Pro Ser Asp Ile Ala Val Glu Trp Glu Ser Asn Gly Asp Glu Gln
            35                  40                  45

Phe Ala Tyr Lys Thr Thr Pro Pro Val Leu Asp Ser Asp Gly Ser Phe
    50                  55                  60

Phe Leu Tyr Ser Lys Leu Thr Val Asp Gln Tyr Arg Trp Asn Pro Ala
65                  70                  75                  80

Asp Tyr Phe Ser Cys Ser Val Met His Glu Ala Leu His Asn His Tyr
                85                  90                  95

Thr Gln Lys Ser Leu Ser Leu Ser Pro Gly
                100                 105

<210> SEQ ID NO 55
<211> LENGTH: 318
<212> TYPE: DNA
<213> ORGANISM: Artificial Sequence
<220> FEATURE:
<223> OTHER INFORMATION: Fcab FS20-22-49 CH3 domain

<400> SEQUENCE: 55

```
ggccagccta gggaacccca ggtttacacc ttgcctccaa gccgggacga gtactgggat      60
caagaggtgt ccctgacctg cctcgtgaag ggcttctacc cttccgatat cgccgtggaa     120
tgggagagca atggcgacga gcagttcgcc tacaagacaa cccctcctgt gctggactcc     180
gacggctcat tctttctgta ctccaagctg acagtggacc agtacagatg gaaccccgcc     240
gactacttct cttgctccgt gatgcacgag gccctgcaca accactacac acagaagtcc     300
ctgtctctgt cccctggc                                                  318
```

<210> SEQ ID NO 56
<211> LENGTH: 8
<212> TYPE: PRT
<213> ORGANISM: Artificial Sequence
<220> FEATURE:
<223> OTHER INFORMATION: Fcab FS20-22-49 CH3 domain AB loop

<400> SEQUENCE: 56

Arg Asp Glu Tyr Trp Asp Gln Glu
1               5

<210> SEQ ID NO 57
<211> LENGTH: 9

```
<212> TYPE: PRT
<213> ORGANISM: Artificial Sequence
<220> FEATURE:
<223> OTHER INFORMATION: Fcab FS20-22-49 CH3 domain CD loop

<400> SEQUENCE: 57

Ser Asn Gly Asp Glu Gln Phe Ala Tyr
1               5

<210> SEQ ID NO 58
<211> LENGTH: 10
<212> TYPE: PRT
<213> ORGANISM: Artificial Sequence
<220> FEATURE:
<223> OTHER INFORMATION: Fcab FS20-22-49 CH3 domain EF loop

<400> SEQUENCE: 58

Asp Gln Tyr Arg Trp Asn Pro Ala Asp Tyr
1               5                   10

<210> SEQ ID NO 59
<211> LENGTH: 5
<212> TYPE: PRT
<213> ORGANISM: Artificial Sequence
<220> FEATURE:
<223> OTHER INFORMATION: Fcab FS20-22-38 CH3 domain structural loop
      sequence

<400> SEQUENCE: 59

Ala Glu Lys Tyr Gln
1               5

<210> SEQ ID NO 60
<211> LENGTH: 9
<212> TYPE: PRT
<213> ORGANISM: Artificial Sequence
<220> FEATURE:
<223> OTHER INFORMATION: Fcab FS20-22-38 CH3 domain structural loop
      sequence

<400> SEQUENCE: 60

Gln Tyr Arg Trp Asn Pro Gly Asp Tyr
1               5

<210> SEQ ID NO 61
<211> LENGTH: 106
<212> TYPE: PRT
<213> ORGANISM: Artificial Sequence
<220> FEATURE:
<223> OTHER INFORMATION: Fcab FS20-22-38 CH3 domain

<400> SEQUENCE: 61

Gly Gln Pro Arg Glu Pro Gln Val Tyr Thr Leu Pro Pro Ser Arg Asp
1               5                   10                  15

Glu Tyr Trp Asp Gln Glu Val Ser Leu Thr Cys Leu Val Lys Gly Phe
            20                  25                  30

Tyr Pro Ser Asp Ile Ala Val Glu Trp Glu Ser Asn Gly Ala Glu Lys
        35                  40                  45

Tyr Gln Tyr Lys Thr Thr Pro Pro Val Leu Asp Ser Asp Gly Ser Phe
    50                  55                  60

Phe Leu Tyr Ser Lys Leu Thr Val Asp Gln Tyr Arg Trp Asn Pro Gly
65                  70                  75                  80

Asp Tyr Phe Ser Cys Ser Val Met His Glu Ala Leu His Asn His Tyr
                85                  90                  95
```

Thr Gln Lys Ser Leu Ser Leu Ser Pro Gly
            100                 105

<210> SEQ ID NO 62
<211> LENGTH: 318
<212> TYPE: DNA
<213> ORGANISM: Artificial Sequence
<220> FEATURE:
<223> OTHER INFORMATION: Fcab FS20-22-38 CH3 domain

<400> SEQUENCE: 62

```
ggacagcctc gagaaccaca ggtgtacacc ctgcccccat cccgggatga gtactgggac    60
caggaagtca gcctgacctg cctggtcaaa ggcttctatc ccagcgacat cgccgtggag   120
tgggagagca atgggcaga aaaataccag tacaagacca cgcctcccgt gctggactcc    180
gacggctcct tcttcctcta cagcaagctc accgtggatc agtataggtg aacccaggc    240
gactatttct catgctccgt gatgcatgag gctctgcaca accactacac acagaagagc   300
ctctcccctgt ctccgggt                                                 318
```

<210> SEQ ID NO 63
<211> LENGTH: 106
<212> TYPE: PRT
<213> ORGANISM: Artificial Sequence
<220> FEATURE:
<223> OTHER INFORMATION: Fcab FS20-22-41 CH3 domain

<400> SEQUENCE: 63

Gly Gln Pro Arg Glu Pro Gln Val Tyr Thr Leu Pro Pro Ser Arg Asp
1               5                   10                  15

Glu Tyr Trp Asp Gln Glu Val Ser Leu Thr Cys Leu Val Lys Gly Phe
            20                  25                  30

Tyr Pro Ser Asp Ile Ala Val Glu Trp Glu Ser Asn Gly Asp Glu Gln
        35                  40                  45

Phe Ala Tyr Lys Thr Thr Pro Pro Val Leu Asp Ser Asp Gly Ser Phe
    50                  55                  60

Phe Leu Tyr Ser Lys Leu Thr Val Asp Gln Tyr Arg Trp Asn Pro Gly
65                  70                  75                  80

Asp Tyr Phe Ser Cys Ser Val Met His Glu Ala Leu His Asn His Tyr
                85                  90                  95

Thr Gln Lys Ser Leu Ser Leu Ser Pro Gly
            100                 105

<210> SEQ ID NO 64
<211> LENGTH: 318
<212> TYPE: DNA
<213> ORGANISM: Artificial Sequence
<220> FEATURE:
<223> OTHER INFORMATION: Fcab FS20-22-41 CH3 domain

<400> SEQUENCE: 64

```
ggacagcctc gagaaccaca ggtgtacacc ctgcccccat cccgggatga gtactgggac    60
caggaagtca gcctgacctg cctggtcaaa ggcttctatc ccagcgacat cgccgtggag   120
tgggagagca atggggatga acagttcgca tacaagacca cgcctcccgt gctggactcc   180
gacggctcct tcttcctcta cagcaagctc accgtggatc agtataggtg aacccaggc    240
gactatttct catgctccgt gatgcatgag gctctgcaca accactacac acagaagagc   300
ctctcccctgt ctccggga                                                 318
```

```
<210> SEQ ID NO 65
<211> LENGTH: 9
<212> TYPE: PRT
<213> ORGANISM: Artificial Sequence
<220> FEATURE:
<223> OTHER INFORMATION: Fcab FS20-22-47 CH3 domain structural loop
      sequence

<400> SEQUENCE: 65

Gln Tyr Arg Trp Ser Pro Gly Asp Tyr
1               5

<210> SEQ ID NO 66
<211> LENGTH: 106
<212> TYPE: PRT
<213> ORGANISM: Artificial Sequence
<220> FEATURE:
<223> OTHER INFORMATION: Fcab FS20-22-47 CH3 domain

<400> SEQUENCE: 66

Gly Gln Pro Arg Glu Pro Gln Val Tyr Thr Leu Pro Pro Ser Arg Asp
1               5                   10                  15

Glu Tyr Trp Asp Gln Glu Val Ser Leu Thr Cys Leu Val Lys Gly Phe
            20                  25                  30

Tyr Pro Ser Asp Ile Ala Val Glu Trp Glu Ser Asn Gly Asp Glu Gln
        35                  40                  45

Phe Ala Tyr Lys Thr Thr Pro Pro Val Leu Asp Ser Asp Gly Ser Phe
    50                  55                  60

Phe Leu Tyr Ser Lys Leu Thr Val Asp Gln Tyr Arg Trp Ser Pro Gly
65                  70                  75                  80

Asp Tyr Phe Ser Cys Ser Val Met His Glu Ala Leu His Asn His Tyr
                85                  90                  95

Thr Gln Lys Ser Leu Ser Leu Ser Pro Gly
            100                 105

<210> SEQ ID NO 67
<211> LENGTH: 318
<212> TYPE: DNA
<213> ORGANISM: Artificial Sequence
<220> FEATURE:
<223> OTHER INFORMATION: Fcab FS20-22-47 CH3 domain

<400> SEQUENCE: 67
ggacagcctc gagaaccaca ggtgtacacc ctgcccccat cccgggatga gtactgggac    60
caggaagtca gcctgacctg cctggtcaaa ggcttctatc ccagcgacat cgccgtggag   120
tgggagagca atggggatga acagttcgca tacaagacca cgcctcccgt gctggactcc   180
gacggctcct tcttcctcta cagcaagctc accgtggatc agtataggtg gagtccgggt   240
gattatttct catgctccgt gatgcatgag gctctgcaca accactacac tcagaagagc   300
ttgtccctgt cgcccgga                                                 318

<210> SEQ ID NO 68
<211> LENGTH: 9
<212> TYPE: PRT
<213> ORGANISM: Artificial Sequence
<220> FEATURE:
<223> OTHER INFORMATION: Fcab FS20-22-85 CH3 domain structural loop
      sequence

<400> SEQUENCE: 68

Gln Tyr Arg Trp Asn Pro Phe Asp Asp
1               5
```

<210> SEQ ID NO 69
<211> LENGTH: 106
<212> TYPE: PRT
<213> ORGANISM: Artificial Sequence
<220> FEATURE:
<223> OTHER INFORMATION: Fcab FS20-22-85 CH3 domain

<400> SEQUENCE: 69

Gly Gln Pro Arg Glu Pro Gln Val Tyr Thr Leu Pro Pro Ser Arg Asp
1               5                   10                  15

Glu Tyr Trp Asp Gln Glu Val Ser Leu Thr Cys Leu Val Lys Gly Phe
            20                  25                  30

Tyr Pro Ser Asp Ile Ala Val Glu Trp Glu Ser Asn Gly Asp Glu Gln
        35                  40                  45

Phe Ala Tyr Lys Thr Thr Pro Pro Val Leu Asp Ser Asp Gly Ser Phe
    50                  55                  60

Phe Leu Tyr Ser Lys Leu Thr Leu Asp Gln Tyr Arg Trp Asn Pro Phe
65                  70                  75                  80

Asp Asp Phe Ser Cys Ser Val Met His Glu Ala Leu His Asn His Tyr
                85                  90                  95

Thr Gln Lys Ser Leu Ser Leu Ser Pro Gly
            100                 105

<210> SEQ ID NO 70
<211> LENGTH: 318
<212> TYPE: DNA
<213> ORGANISM: Artificial Sequence
<220> FEATURE:
<223> OTHER INFORMATION: Fcab FS20-22-85 CH3 domain

<400> SEQUENCE: 70
ggacagcctc gagaaccaca ggtgtacacc ctgcccccat cccgggatga gtactgggac     60
caggaagtca gcctgacctg cctggtcaaa ggcttctatc ccagcgacat cgccgtggag    120
tgggagagca atggggatga acagttcgca tacaagacca cgcctcccgt gctggactcc    180
gacggctcct tcttcctcta cagcaagctc accttggatc agtataggtg gaatccgttt    240
gatgatttct catgctccgt gatgcatgag gctctgcaca accactacac tcagaagagc    300
ttgtccctgt cgcccgga                                                   318

<210> SEQ ID NO 71
<211> LENGTH: 5
<212> TYPE: PRT
<213> ORGANISM: Artificial Sequence
<220> FEATURE:
<223> OTHER INFORMATION: Fcab FS20-31-58 CH3 domain structural loop
      sequence

<400> SEQUENCE: 71

Tyr Tyr Ser Gly Glu
1               5

<210> SEQ ID NO 72
<211> LENGTH: 5
<212> TYPE: PRT
<213> ORGANISM: Artificial Sequence
<220> FEATURE:
<223> OTHER INFORMATION: Fcab FS20-31-58 CH3 domain structural loop
      sequence

<400> SEQUENCE: 72

Gln Pro Glu Asn Asp
1               5

<210> SEQ ID NO 73
<211> LENGTH: 10
<212> TYPE: PRT
<213> ORGANISM: Artificial Sequence
<220> FEATURE:
<223> OTHER INFORMATION: Fcab FS20-31-58 CH3 domain structural loop
      sequence

<400> SEQUENCE: 73

Pro Tyr Trp Arg Trp Gly Ser Pro Arg Thr
1               5                   10

<210> SEQ ID NO 74
<211> LENGTH: 106
<212> TYPE: PRT
<213> ORGANISM: Artificial Sequence
<220> FEATURE:
<223> OTHER INFORMATION: Fcab FS20-31-58 CH3 domain

<400> SEQUENCE: 74

Gly Gln Pro Arg Glu Pro Gln Val Tyr Thr Leu Pro Pro Ser Arg Asp
1               5                   10                  15

Glu Tyr Tyr Ser Gly Glu Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asp Tyr Lys Thr Thr Pro Pro Val Leu Asp Ser Asp Gly Ser Phe
    50                  55                  60

Phe Leu Tyr Ser Lys Leu Thr Val Pro Tyr Trp Arg Trp Gly Ser Pro
65                  70                  75                  80

Arg Thr Phe Ser Cys Ser Val Met His Glu Ala Leu His Asn His Tyr
                85                  90                  95

Thr Gln Lys Ser Leu Ser Leu Ser Pro Gly
            100                 105

<210> SEQ ID NO 75
<211> LENGTH: 318
<212> TYPE: DNA
<213> ORGANISM: Artificial Sequence
<220> FEATURE:
<223> OTHER INFORMATION: Fcab FS20-31-58 CH3 domain

<400> SEQUENCE: 75
ggacagcctc gagaaccaca ggtgtacacc ctgcccccat cccgggatga gtactactct     60
ggtgaagtca gcctgacctg cctggtcaaa ggcttctatc ccagcgacat cgccgtggag    120
tgggagagca atgggcagcc ggagaacgac tacaagacca cgcctcccgt gctggactcc    180
gacggctcct tcttcctcta cagcaagctc accgtgcctt attggaggtg gggtagtccg    240
cgtactttct catgctccgt gatgcatgag gctctgcaca accactacac acagaagagc    300 ctctcccctgt ctccgggt                                                 318

<210> SEQ ID NO 76
<211> LENGTH: 10
<212> TYPE: PRT
<213> ORGANISM: Artificial Sequence
<220> FEATURE:

<223> OTHER INFORMATION: Fcab FS20-31-66 CH3 domain structural loop
      sequence

<400> SEQUENCE: 76

Pro Tyr Trp Arg Trp Gly Val Pro Arg Thr
1               5                   10

<210> SEQ ID NO 77
<211> LENGTH: 106
<212> TYPE: PRT
<213> ORGANISM: Artificial Sequence
<220> FEATURE:
<223> OTHER INFORMATION: Fcab FS20-31-66 CH3 domain

<400> SEQUENCE: 77

Gly Gln Pro Arg Glu Pro Gln Val Tyr Thr Leu Pro Pro Ser Arg Asp
1               5                   10                  15

Glu Tyr Tyr Ser Gly Glu Val Ser Leu Thr Cys Leu Val Lys Gly Phe
                20                  25                  30

Tyr Pro Ser Asp Ile Ala Val Glu Trp Glu Ser Asn Gly Gln Pro Glu
            35                  40                  45

Asn Asp Tyr Lys Thr Thr Pro Pro Val Leu Asp Ser Asp Gly Ser Phe
50                  55                  60

Phe Leu Tyr Ser Lys Leu Thr Val Pro Tyr Trp Arg Trp Gly Val Pro
65                  70                  75                  80

Arg Thr Phe Ser Cys Ser Val Met His Glu Ala Leu His Asn His Tyr
                85                  90                  95

Thr Gln Lys Ser Leu Ser Leu Ser Pro Gly
            100                 105

<210> SEQ ID NO 78
<211> LENGTH: 318
<212> TYPE: DNA
<213> ORGANISM: Artificial Sequence
<220> FEATURE:
<223> OTHER INFORMATION: Fcab FS20-31-66 CH3 domain

<400> SEQUENCE: 78
ggacagcctc gagaaccaca ggtgtacacc ctgcccccat cccgggatga gtactactct     60
ggtgaagtca gcctgacctg cctggtcaaa ggcttctatc ccagcgacat cgccgtggag    120
tgggagagca atgggcagcc ggagaacgac tacaagacca cgcctcccgt gctggactcc    180
gacggctcct tcttcctcta cagcaagctc accgtgccgt attggaggtg ggtgttccg     240 cgtactttct catgctccgt gatgcatgag gctctgcaca accactacac acagaagagc    300 ctctcccctgt ctccgggt                                                  318

<210> SEQ ID NO 79
<211> LENGTH: 5
<212> TYPE: PRT
<213> ORGANISM: Artificial Sequence
<220> FEATURE:
<223> OTHER INFORMATION: Fcab FS20-31-94 Fcab CH3 domain structural loop
      sequence

<400> SEQUENCE: 79

Trp Glu His Gly Glu
1               5

<210> SEQ ID NO 80
<211> LENGTH: 5
<212> TYPE: PRT

-continued

<213> ORGANISM: Artificial Sequence
<220> FEATURE:
<223> OTHER INFORMATION: Fcab FS20-31-94 Fcab CH3 domain structural loop
      sequence

<400> SEQUENCE: 80

Ile Arg Glu His Asp
1               5

<210> SEQ ID NO 81
<211> LENGTH: 10
<212> TYPE: PRT
<213> ORGANISM: Artificial Sequence
<220> FEATURE:
<223> OTHER INFORMATION: Fcab FS20-31-94 Fcab CH3 domain structural loop
      sequence

<400> SEQUENCE: 81

Pro Tyr Trp Arg Trp Gly Gly Pro Gly Thr
1               5                   10

<210> SEQ ID NO 82
<211> LENGTH: 106
<212> TYPE: PRT
<213> ORGANISM: Artificial Sequence
<220> FEATURE:
<223> OTHER INFORMATION: Fcab FS20-31-94 Fcab CH3 domain

<400> SEQUENCE: 82

Gly Gln Pro Arg Glu Pro Gln Val Tyr Thr Leu Pro Pro Ser Arg Asp
1               5                   10                  15

Glu Trp Glu His Gly Glu Val Ser Leu Thr Cys Leu Val Lys Gly Phe
            20                  25                  30

Tyr Pro Ser Asp Ile Ala Val Glu Trp Glu Ser Asn Gly Ile Arg Glu
        35                  40                  45

His Asp Tyr Lys Thr Thr Pro Pro Val Leu Asp Ser Asp Gly Ser Phe
    50                  55                  60

Phe Leu Tyr Ser Lys Leu Thr Val Pro Tyr Trp Arg Trp Gly Gly Pro
65                  70                  75                  80

Gly Thr Phe Ser Cys Ser Val Met His Glu Ala Leu His Asn His Tyr
                85                  90                  95

Thr Gln Lys Ser Leu Ser Leu Ser Pro Gly
            100                 105

<210> SEQ ID NO 83
<211> LENGTH: 318
<212> TYPE: DNA
<213> ORGANISM: Artificial Sequence
<220> FEATURE:
<223> OTHER INFORMATION: Fcab FS20-31-94 Fcab CH3 domain

<400> SEQUENCE: 83
ggacagcctc gagaaccaca ggtgtacacc ctgcccccat cccgggatga gtgggaacat      60
ggtgaagtca gcctgacctg cctggtcaaa ggcttctatc cagcgacat cgccgtggag     120 tgggagagca atgggatcag agaacatgat tacaagacca cgcctcccgt gctggactcc    180
gacggctcct tcttcctcta cagcaagctc accgtgccta attggaggtg gggcggccca    240
ggcaccttct catgctccgt gatgcatgag gctctgcaca accactacac tcagaagagc    300
ttgtccctgt cgcccgga                                                  318

<210> SEQ ID NO 84

```
<211> LENGTH: 5
<212> TYPE: PRT
<213> ORGANISM: Artificial Sequence
<220> FEATURE:
<223> OTHER INFORMATION: Fcab FS20-31-102 CH3 domain structural loop
      sequence

<400> SEQUENCE: 84

Trp Ala Ser Gly Glu
1               5

<210> SEQ ID NO 85
<211> LENGTH: 5
<212> TYPE: PRT
<213> ORGANISM: Artificial Sequence
<220> FEATURE:
<223> OTHER INFORMATION: Fcab FS20-31-102 CH3 domain structural loop
      sequence

<400> SEQUENCE: 85

Gln Pro Glu Val Asp
1               5

<210> SEQ ID NO 86
<211> LENGTH: 106
<212> TYPE: PRT
<213> ORGANISM: Artificial Sequence
<220> FEATURE:
<223> OTHER INFORMATION: Fcab FS20-31-102 CH3 domain

<400> SEQUENCE: 86

Gly Gln Pro Arg Glu Pro Gln Val Tyr Thr Leu Pro Pro Ser Arg Asp
1               5                   10                  15

Glu Trp Ala Ser Gly Glu Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Val Asp Tyr Lys Thr Thr Pro Pro Val Leu Asp Ser Asp Gly Ser Phe
    50                  55                  60

Phe Leu Tyr Ser Lys Leu Thr Val Pro Tyr Trp Arg Trp Gly Val Pro
65                  70                  75                  80

Arg Thr Phe Ser Cys Ser Val Met His Glu Ala Leu His Asn His Tyr
                85                  90                  95

Thr Gln Lys Ser Leu Ser Leu Ser Pro Gly
            100                 105

<210> SEQ ID NO 87
<211> LENGTH: 318
<212> TYPE: DNA
<213> ORGANISM: Artificial Sequence
<220> FEATURE:
<223> OTHER INFORMATION: Fcab FS20-31-102 CH3 domain

<400> SEQUENCE: 87
ggccagcctc gagaaccaca ggtgtacacc ctgcccccat cccgggatga gtgggcatct    60
ggtgaagtca gcctgacctg cctggtcaaa ggcttctatc ccagcgacat cgccgtggag   120
tgggagagca atgggcagcc agaagttgat tacaagacca cgcctcccgt gctggactcc   180
gacggctcct tcttcctcta cagcaagctc accgtgccgt attggaggtg ggtgttccg    240 cgtactttct catgctccgt gatgcatgag gctctgcaca accactacac acagaagagc   300 ctctcccctgt ctccgggt                                                318
```

-continued

```
<210> SEQ ID NO 88
<211> LENGTH: 5
<212> TYPE: PRT
<213> ORGANISM: Artificial Sequence
<220> FEATURE:
<223> OTHER INFORMATION: Fcab FS20-31-108 CH3 domain structural loop
      sequence

<400> SEQUENCE: 88

Glu Lys Glu Ile Asp
1               5

<210> SEQ ID NO 89
<211> LENGTH: 10
<212> TYPE: PRT
<213> ORGANISM: Artificial Sequence
<220> FEATURE:
<223> OTHER INFORMATION: Fcab FS20-31-108 CH3 domain structural loop
      sequence

<400> SEQUENCE: 89

Pro Tyr Trp Arg Trp Gly Ala Lys Arg Thr
1               5                   10

<210> SEQ ID NO 90
<211> LENGTH: 106
<212> TYPE: PRT
<213> ORGANISM: Artificial Sequence
<220> FEATURE:
<223> OTHER INFORMATION: Fcab FS20-31-108 CH3 domain

<400> SEQUENCE: 90

Gly Gln Pro Arg Glu Pro Gln Val Tyr Thr Leu Pro Pro Ser Arg Asp
1               5                   10                  15

Glu Trp Ala Ser Gly Glu Val Ser Leu Thr Cys Leu Val Lys Gly Phe
            20                  25                  30

Tyr Pro Ser Asp Ile Ala Val Glu Trp Glu Ser Asn Gly Glu Lys Glu
        35                  40                  45

Ile Asp Tyr Lys Thr Thr Pro Pro Val Leu Asp Ser Asp Gly Ser Phe
    50                  55                  60

Phe Leu Tyr Ser Lys Leu Thr Val Pro Tyr Trp Arg Trp Gly Ala Lys
65                  70                  75                  80

Arg Thr Phe Ser Cys Ser Val Met His Glu Ala Leu His Asn His Tyr
                85                  90                  95

Thr Gln Lys Ser Leu Ser Leu Ser Pro Gly
            100                 105

<210> SEQ ID NO 91
<211> LENGTH: 318
<212> TYPE: DNA
<213> ORGANISM: Artificial Sequence
<220> FEATURE:
<223> OTHER INFORMATION: Fcab FS20-31-108 CH3 domain

<400> SEQUENCE: 91
ggccagcctc gagaaccaca ggtgtacacc ctgcccccat cccgggatga gtgggcatct     60
ggtgaagtca gcctgacctg cctggtcaaa ggcttctatc ccagcgacat cgccgtggag    120
tgggagagca atggggaaaa agaaatcgat tacaagacca cgcctcccgt gctggactcc    180
gacggctcct tcttcctcta cagcaagctc accgtgccgt attggaggtg ggtgctaag     240
```

```
cgtactttct catgctccgt gatgcatgag gctctgcaca accactacac acagaagagc    300
ctctccctgt ctccgggt                                                  318
```

<210> SEQ ID NO 92
<211> LENGTH: 5
<212> TYPE: PRT
<213> ORGANISM: Artificial Sequence
<220> FEATURE:
<223> OTHER INFORMATION: Fcab FS20-31-115 CH3 domain structural loop
      sequence

<400> SEQUENCE: 92

Glu Gln Glu Phe Asp
1               5

<210> SEQ ID NO 93
<211> LENGTH: 106
<212> TYPE: PRT
<213> ORGANISM: Artificial Sequence
<220> FEATURE:
<223> OTHER INFORMATION: Fcab FS20-31-115 CH3 domain

<400> SEQUENCE: 93

Gly Gln Pro Arg Glu Pro Gln Val Tyr Thr Leu Pro Pro Ser Arg Asp
1               5                   10                  15

Glu Trp Ala Ser Gly Glu Val Ser Leu Thr Cys Leu Val Lys Gly Phe
            20                  25                  30

Tyr Pro Ser Asp Ile Ala Val Glu Trp Glu Ser Asn Gly Glu Gln Glu
        35                  40                  45

Phe Asp Tyr Lys Thr Thr Pro Pro Val Leu Asp Ser Asp Gly Ser Phe
    50                  55                  60

Phe Leu Tyr Ser Lys Leu Thr Val Pro Tyr Trp Arg Trp Gly Ala Lys
65                  70                  75                  80

Arg Thr Phe Ser Cys Ser Val Met His Glu Ala Leu His Asn His Tyr
                85                  90                  95

Thr Gln Lys Ser Leu Ser Leu Ser Pro Gly
            100                 105

<210> SEQ ID NO 94
<211> LENGTH: 318
<212> TYPE: DNA
<213> ORGANISM: Artificial Sequence
<220> FEATURE:
<223> OTHER INFORMATION: Fcab FS20-31-115 CH3 domain

<400> SEQUENCE: 94

```
ggacagcctc gagaaccaca ggtgtacacc ctgcccccat cccgggatga gtgggcatct    60
ggtgaagtca gcctgacctg cctggtcaaa gcttctatc ccagcgacat cgccgtggag    120
tgggagagca atggggaaca ggaattcgat tacaagacca cgcctccgt gctgactcc     180 gacggctcct tcttcctcta cagcaagctc accgtgccgt attggaggtg gggtgctaag    240
cgtactttct catgctccgt gatgcatgag gctctgcaca accactacac tcagaagagc    300
ttgtccctgt cgcccgga                                                  318
```

<210> SEQ ID NO 95
<211> LENGTH: 447
<212> TYPE: PRT
<213> ORGANISM: Artificial Sequence
<220> FEATURE:
<223> OTHER INFORMATION: heavy chain of FS20-22-49AA/FS30-10-16 with LALA mutation

<400> SEQUENCE: 95

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Asp Ile Asp Pro Thr Gly Ser Lys Thr Asp Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Leu Val Tyr Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Tyr Trp Asp Gln Glu Val Ser Leu Thr Cys
        355                 360                 365

Leu Val Lys Gly Phe Tyr Pro Ser Asp Ile Ala Val Glu Trp Glu Ser
370                 375                 380
```

Asn Gly Asp Glu Gln Phe Ala Tyr Lys Thr Thr Pro Pro Val Leu Asp
385                 390                 395                 400

Ser Asp Gly Ser Phe Phe Leu Tyr Ser Lys Leu Thr Val Asp Gln Tyr
                405                 410                 415

Arg Trp Asn Pro Ala Asp Tyr Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 96
<211> LENGTH: 1341
<212> TYPE: DNA
<213> ORGANISM: Artificial Sequence
<220> FEATURE:
<223> OTHER INFORMATION: heavy chain of FS20-22-49AA/FS30-10-16 with
      LALA mutation

<400> SEQUENCE: 96

| | | | | |
|---|---|---|---|---|
| gaagttcagc | tgctggaatc | tggcggcgga | ttggttcaac | ctggcggctc | tctgagactg | 60 |
| tcttgtgccg | cttccggctt | caccttctcc | agctacgaca | tgtcctgggt | ccgacaggct | 120 |
| cctggcaaag | gactggaatg | ggtgtccgac | atcgacccca | ccggctctaa | gaccgactac | 180 |
| gccgattctg | tgaagggcag | attcaccatc | agccgggaca | actccaagaa | caccctgtac | 240 |
| ctgcagatga | actccctgag | agccgaggac | accgccgtgt | actactgtgc | cagagatctg | 300 |
| ctggtgtacg | gcttcgacta | ttggggccag | ggcacactgg | tcaccgtgtc | ctctgcttct | 360 |
| accaagggac | ccagcgtgtt | ccctctggct | ccttccagca | agtctacctc | tggcggaaca | 420 |
| gctgctctgg | gctgcctggt | caaggactac | tttcctgagc | ctgtgaccgt | gtcttggaac | 480 |
| tctggcgctc | tgacatctgg | cgtgcacacc | tttccagcag | tgctgcagtc | ctccggcctg | 540 |
| tactctctgt | cctctgtcgt | gaccgtgcct | tccagctctc | tgggaaccca | gacctacatc | 600 |
| tgcaatgtga | accacaagcc | ttccaacacc | aaggtggaca | agaaggtgga | acccaagtcc | 660 |
| tgcgacaaga | cccacacctg | tcctccatgt | cctgctccag | aagctgctgg | cggcccttcc | 720 |
| gtgtttctgt | tccctccaaa | gcctaaggac | accctgatga | tctctcggac | ccctgaagtg | 780 |
| acctgcgtgg | tggtggatgt | gtctcacgag | gacccagaag | tgaagttcaa | ttggtacgtg | 840 |
| gacggcgtgg | aagtgcacaa | cgccaagacc | aagcctagag | aggaacagta | caactccacc | 900 |
| tacagagtgg | tgtccgtgct | gaccgtgctg | caccaggatt | ggctgaacgg | caaagagtac | 960 |
| aagtgcaagg | tgtccaacaa | ggcccctgcct | gctcctatcg | aaaagaccat | ctccaaggcc | 1020 |
| aagggccagc | ctagggaacc | ccaggtttac | accttgcctc | caagccggga | cgagtactgg | 1080 |
| gatcaagagg | tgtccctgac | ctgcctcgtg | aagggcttct | accttccga | tatcgccgtg | 1140 |
| gaatgggaga | gcaatggcga | cgagcagttc | gcctacaaga | caacccctcc | tgtgctggac | 1200 |
| tccgacggct | cattctttct | gtactccaag | ctgacagtgg | accagtacag | atggaacccc | 1260 |
| gccgactact | tctcttgctc | cgtgatgcac | gaggccctgc | acaaccacta | cacacagaag | 1320 |
| tccctgtctc | tgtcccctgg | c | | | | 1341 |

<210> SEQ ID NO 97
<211> LENGTH: 215
<212> TYPE: PRT
<213> ORGANISM: Artificial Sequence
<220> FEATURE:
<223> OTHER INFORMATION: light chain of FS30-10-16

<400> SEQUENCE: 97

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65              70                  75                  80

Pro Glu Asp Phe Ala Val Tyr Tyr Cys Gln Gln Ser Tyr Ser Tyr Pro
                85                  90                  95

Val Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 98
<211> LENGTH: 645
<212> TYPE: DNA
<213> ORGANISM: Artificial Sequence
<220> FEATURE:
<223> OTHER INFORMATION: light chain of FS30-10-16 (

<400> SEQUENCE: 98

```
gagatcgtgc tgacccagtc tcctggcaca ctgtcactgt ctccaggcga gagagctacc      60
ctgtcctgta gagcctctca gtccgtgtcc tctcttacc tggcctggta tcagcagaag      120
cctggacagg ctccccggct gttgatctac ggcgcttctt ctagagccac aggcatccct     180
gaccggttct ccgatctggg ctctggcacc gatttcaccc tgaccatctc tcggctggaa     240
cccgaggatt tcgccgtgta ctactgccag cagtcctaca gctacccgt gacctttggc      300
cagggcacca aggtggaaat caagcgtacg gtggccgctc ccagcgtgtt catcttcccc     360
ccaagcgacg agcagctgaa gagcggcacc gccagcgtgg tgtgtctgct gaacaacttc     420
taccccaggg aggccaaggt gcagtggaag gtggacaacg ccctgcagag cggcaacagc     480
caggagagcg tcaccgagca ggacagcaag gactccacct acagcctgag cagcaccctg     540
accctgagca aggccgacta cgagaagcac aaggtgtacg cctgtgaggt gacccaccag     600
ggcctgtcca gccccgtgac caagagcttc aacaggggcg agtgc                     645
```

<210> SEQ ID NO 99

```
<211> LENGTH: 447
<212> TYPE: PRT
<213> ORGANISM: Artificial Sequence
<220> FEATURE:
<223> OTHER INFORMATION: heavy chain of FS20-22-49AA/FS30-10-3 with LALA
      mutation

<400> SEQUENCE: 99
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Asp Ile Asp Pro Thr Gly Ser Lys Thr Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Asn Val Tyr Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Tyr Trp Asp Gln Glu Val Ser Leu Thr Cys
        355                 360                 365

Leu Val Lys Gly Phe Tyr Pro Ser Asp Ile Ala Val Glu Trp Glu Ser
    370                 375                 380

Asn Gly Asp Glu Gln Phe Ala Tyr Lys Thr Thr Pro Pro Val Leu Asp
385                 390                 395                 400

Ser Asp Gly Ser Phe Phe Leu Tyr Ser Lys Leu Thr Val Asp Gln Tyr
                405                 410                 415

Arg Trp Asn Pro Ala Asp Tyr Phe Ser Cys Ser Val Met His Glu Ala
            420                 425                 430

Leu His Asn His Tyr Thr Gln Lys Ser Leu Ser Leu Ser Pro Gly
            435                 440                 445

<210> SEQ ID NO 100
<211> LENGTH: 1341
<212> TYPE: DNA
<213> ORGANISM: Artificial Sequence
<220> FEATURE:
<223> OTHER INFORMATION: heavy chain of FS20-22-49AA/FS30-10-3 with LALA
      mutation

<400> SEQUENCE: 100
gaagtgcaac tgctggagtc cggtggtggt ctggtacagc cgggtggttc tctgcgtctg      60
agttgcgcgg ccagtggctt taccttcagt agttacgata tgagctgggt gcgtcaggct     120
ccgggcaaag gtctgaatg ggttagcgat attgatccga ctggtagcaa gaccgactat      180
gcggatagcg tgaaaggccg ttttaccatt tctcgcgaca cagcaagaa cacgctgtac      240 ctgcagatga actcactgcg tgccgaagat acggccgtgt attactgtgc gagagacctc     300
aatgtgtacg ggttcgacta ctggggccag ggaaccctgg tcaccgtctc gagtgctagc     360
actaagggcc cgtcggtgtt cccgctggcc ccatcgtcca agagcacatc aggggggtacc   420 gccgccctgg gctgccttgt gaaggattac tttcccgagc ccgtcacagt gtcctggaac     480
agcggagccc tgacctccgg agtgcatact tcccggctg tgcttcagtc ctctggcctg      540
tactcattgt cctccgtggt caccgtccct tcgtcctccc tgggcaccca gacctatatc     600
tgtaatgtca accataagcc ctcgaacacc aaggtcgaca gaaaggtcga gccgaagtcg     660
tgcgacaaga ctcacacttg cccgccttgc ccagccccgg aagctgccgg tgtccttcg      720 gtgttcctct ccccgcccaa gccgaaggat accctgatga tctcacggac cccgaagtg    780 acctgtgtgg tggtggacgt gtcccacgag gacccgaag tgaaattcaa ttggtacgtg     840
gatggagtgg aagtgcacaa cgccaagacc aagccacggg aagaacagta caactctacc    900
taccgcgtgg tgtccgtgct cactgtgctg caccaagact ggctgaacgg aaggagtac     960 aagtgcaaag tgtccaacaa ggcgctgcct gccccaattg agaaaactat ctcgaaagcc   1020
aagggacagc ctcgagaacc acaggtgtac accctgcccc catcccggga tgagtactgg   1080
gaccaggaag tcagcctgac ctgcctggtc aaaggcttct atccagcga catcgccgtg    1140 gagtgggaga gcaatgggga tgaacagttc gcatacaaga ccacgcctcc cgtgctggac   1200
tccgacggct ccttcttcct ctacagcaag ctcaccgtgg atcagtatag gtggaatcct   1260
gctgattatt tctcatgctc cgtgatgcat gaggctctgc acaaccacta cactcagaag   1320
agcttgtccc tgtcgcccgg a                                              1341

<210> SEQ ID NO 101
<211> LENGTH: 6
<212> TYPE: PRT
<213> ORGANISM: Artificial Sequence
<220> FEATURE:

<223> OTHER INFORMATION: truncated Fcab hinge region

<400> SEQUENCE: 101

Thr Cys Pro Pro Cys Pro
1               5

<210> SEQ ID NO 102
<211> LENGTH: 645
<212> TYPE: DNA
<213> ORGANISM: Artificial Sequence
<220> FEATURE:
<223> OTHER INFORMATION: light chain of FS30-10-3

<400> SEQUENCE: 102

```
gaaattgtgc tgacccagtc tccgggcacg ttatctctga gccctggtga gcgcgccact      60
ctgtcatgcc gggcttctca aagtgttagc agtagctacc tggcgtggta tcagcaaaaa     120
ccgggccagg ccccgcgtct gctgatttac ggtgcatcca gccgtgccac cggcattcca     180
gatcgttttt ccggtagtgg ttctgggacg gacttcactc tgacaatctc acgcctggaa     240
ccggaggatt ttgcggtgta ttactgccag caatcttatt cttatcctgt cacgttcggc     300
caagggacca aggtggaaat caaacgtact gtggccgctc ctagcgtgtt cattttccg      360
ccatccgacg agcagctcaa gtccggcacc gcctccgtgg tctgcctgct caacaacttc     420
taccctcgcg aagctaaggt ccagtggaag gtcgacaatg ccctgcagtc cggaaactcg     480
caggaaagcg tgactgaaca ggactccaag gactccacct attcactgtc ctcgactctg     540
accctgagca aggcggatta cgaaaagcac aaagtgtacg catgcgaagt gacccaccag     600
ggtctttcgt cccccgtgac caagagcttc aacagaggag agtgt              645
```

<210> SEQ ID NO 103
<211> LENGTH: 447
<212> TYPE: PRT
<213> ORGANISM: Artificial Sequence
<220> FEATURE:
<223> OTHER INFORMATION: heavy chain of FS20-22-49AA/FS30-10-12 with
      LALA mutation

<400> SEQUENCE: 103

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Asp Ile Asp Pro Thr Gly Ser Lys Thr Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Asp Leu Thr Val Tyr Gly Phe Asp Tyr Trp Gly Gln Gly Thr
        100                 105                 110

Leu Val Thr Val Ser Ser Ala Ser Thr Lys Gly Pro Ser Val Phe Pro
    115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

| | | | | | | | | | | | |
|---|---|---|---|---|---|---|---|---|---|---|---|
|Ser|Gly|Ala|Leu|Thr|Ser|Gly|Val|His|Thr|Phe|Pro|Ala|Val|Leu|Gln|
| | | |165| | | |170| | | |175| | | | |

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Arg Asp Glu Tyr Trp Asp Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Asp Glu Gln Phe Ala Tyr Lys Thr Thr Pro Pro Val Leu Asp
385                 390                 395                 400

Ser Asp Gly Ser Phe Phe Leu Tyr Ser Lys Leu Thr Val Asp Gln Tyr
            405                 410                 415

Arg Trp Asn Pro Ala Asp Tyr Phe Ser Cys Ser Val Met His Glu Ala
            420                 425                 430

Leu His Asn His Tyr Thr Gln Lys Ser Leu Ser Leu Ser Pro Gly
            435                 440                 445

<210> SEQ ID NO 104
<211> LENGTH: 1341
<212> TYPE: DNA
<213> ORGANISM: Artificial Sequence
<220> FEATURE:
<223> OTHER INFORMATION: heavy chain of FS20-22-49AA/FS30-10-12 with
      LALA mutation

<400> SEQUENCE: 104
gaagtgcaac tgctggagtc cggtggtggt ctggtacagc cgggtggttc tctgcgtctg      60
agttgcgcgg ccagtggctt taccttcagt agttacgata tgagctgggt gcgtcaggct     120
ccgggcaaag gtctgaatg ggttagcgat attgatccga ctggtagcaa gaccgactat     180
gcggatagcg tgaaaggccg ttttaccatt tctcgcgaca acagcaagaa cacgctgtac     240
ctgcagatga actcactgcg tgccgaagat acggccgtgt attactgtgc gagagacctc     300
acggtgtacg ggttcgacta ctggggccag ggaaccctgg tcaccgtctc gagtgctagc     360
actaagggcc cgtcggtgtt cccgctggcc ccatcgtcca agagcacatc aggggtacc     420

-continued

```
gccgccctgg gctgccttgt gaaggattac tttcccgagc ccgtcacagt gtcctggaac    480
agcggagccc tgacctccgg agtgcatact ttcccggctg tgcttcagtc ctctggcctg    540
tactcattgt cctccgtggt caccgtccct tcgtcctccc tgggcaccca gacctatatc    600
tgtaatgtca accataagcc ctcgaacacc aaggtcgaca agaaggtcga gccgaagtcg    660
tgcgacaaga ctcacacttg cccgccttgc ccagccccgg aagctgccgg tggtccttcg    720
gtgttcctct tccgcccaa gccgaaggat accctgatga tctcacggac ccccgaagtg    780
acctgtgtgg tggtggacgt gtcccacgag gacccggaag tgaaattcaa ttggtacgtg    840
gatggagtgg aagtgcacaa cgccaagacc aagccacggg aagaacagta caactctacc    900
taccgcgtgg tgtccgtgct cactgtgctg caccaagact ggctgaacgg aaggagtac    960 aagtgcaaag tgtccaacaa ggcgctgcct gccccaattg agaaaactat ctcgaaagcc   1020
aagggacagc ctcgagaacc acaggtgtac accctgcccc catcccggga tgagtactgg   1080
gaccaggaag tcagcctgac ctgcctggtc aaaggcttct atcccagcga catcgccgtg   1140
gagtgggaga gcaatgggga tgaacagttc gcatacaaga ccacgcctcc cgtgctggac   1200
tccgacggct ccttcttcct ctacagcaag ctcaccgtgg atcagtatag gtggaatcct   1260
gctgattatt tctcatgctc cgtgatgcat gaggctctgc acaaccacta cactcagaag   1320
agcttgtccc tgtcgcccgg a                                             1341
```

<210> SEQ ID NO 105
<211> LENGTH: 452
<212> TYPE: PRT
<213> ORGANISM: Artificial Sequence
<220> FEATURE:
<223> OTHER INFORMATION: heavy chain of FS20-22-49AA/FS30-35-14 with LALA mutation

<400> SEQUENCE: 105

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Asn Ile His Trp Val Arg Gln Ala Pro Gly Lys Gly Leu Glu Trp Val
        35                  40                  45

Ser Asp Ile Ser Pro Tyr Gly Gly Ala Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Tyr Glu Leu Ser Ala Tyr Ser Tyr Gly Ala Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190
```

```
Thr Val Pro Ser Ser Leu Gly Thr Gln Thr Tyr Ile Cys Asn Val
        195                 200                 205

Asn His Lys Pro Ser Asn Thr Lys Val Asp Lys Val Glu Pro Lys
    210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Tyr Trp Asp Gln Glu
    355                 360                 365

Val Ser Leu Thr Cys Leu Val Lys Gly Phe Tyr Pro Ser Asp Ile Ala
370                 375                 380

Val Glu Trp Glu Ser Asn Gly Asp Glu Gln Phe Ala Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Gln Tyr Arg Trp Asn Pro Ala Asp Tyr Phe Ser Cys Ser
            420                 425                 430

Val Met His Glu Ala Leu His Asn His Tyr Thr Gln Lys Ser Leu Ser
    435                 440                 445

Leu Ser Pro Gly
    450

<210> SEQ ID NO 106
<211> LENGTH: 1356
<212> TYPE: DNA
<213> ORGANISM: Artificial Sequence
<220> FEATURE:
<223> OTHER INFORMATION: heavy chain of FS20-22-49AA/FS30-35-14 with
      LALA mutation

<400> SEQUENCE: 106
gaagtgcaac tgctggagtc cggtggtggt ctggtacagc cgggtggttc tctgcgtctg      60
agttgcgcgg ccagtggctt taccttcagt gcctataata tccattgggt gcgtcaggct     120
ccgggcaaag gtctggaatg ggttagcgat atttctccgt atggtggcgc gaccaactat     180
gcggatagcg tgaaaggccg ttttaccatt tctcgcgaca acagcaagaa cacgctgtac     240
ctgcagatga actcactgcg tgccgaagat acggccgtgt attactgtgc gagaaacctc     300
tacgagttga gcgcttactc ttacggggcg gactactggg gccaggggac cctggtcacc     360
gtctcgtcgg ctagcactaa gggcccgtcg gtgttcccgc tggccccatc gtccaagagc     420
acatcagggg gtaccgccgc cctgggctgc cttgtgaagg attacttttc cgagcccgtc     480
```

```
acagtgtcct ggaacagcgg agccctgacc tccggagtgc atactttccc ggctgtgctt    540
cagtcctctg gcctgtactc attgtcctcc gtggtcaccg tcccttcgtc ctccctgggc    600
acccagacct atatctgtaa tgtcaaccat aagccctcga acaccaaggt cgacaagaag    660
gtcgagccga agtcgtgcga caagactcac acttgcccgc cttgcccagc ccggaagct    720 gccggtggtc cttcggtgtt cctcttcccg cccaagccga aggatacccct gatgatctca    780 cggacccccg aagtgacctg tgtggtggtg gacgtgtccc acgaggaccc ggaagtgaaa    840
ttcaattggt acgtggatgg agtggaagtg cacaacgcca agaccaagcc acgggaagaa    900
cagtacaact ctacctaccg cgtggtgtcc gtgctcactg tgctgcacca agactggctg    960
aacgggaagg agtacaagtg caaagtgtcc aacaaggcgc tgcctgcccc aattgagaaa   1020
actatctcga aagccaaggg acagcctcga gaaccacagg tgtacacccct gcccccatcc   1080 cgggatgagt actgggacca ggaagtcagc ctgacctgcc tggtcaaagg cttctatccc   1140
agcgacatcg ccgtggagtg ggagagcaat gggcagccg gaggagca caagaccacg   1200 cctcccgtgc tggactccga cggctccttc ttcctctaca gcaagctcac cgtggatcag   1260
tataggtgga atcctgctga ttatttctca tgctccgtga tgcatgaggc tctgcacaac   1320
cactacactc agaagagctt gtccctgtcg cccgga                             1356
```

<210> SEQ ID NO 107
<211> LENGTH: 216
<212> TYPE: PRT
<213> ORGANISM: Artificial Sequence
<220> FEATURE:
<223> OTHER INFORMATION: light chain of FS30-35-14

<400> SEQUENCE: 107

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Tyr Ser Ser
                85                  90                  95

Pro Ile Thr Phe Gly Gln Gly Thr Lys Val Glu Ile Lys Arg Thr Val
                100                 105                 110

Ala Ala Pro Ser Val Phe Ile Phe Pro Pro Ser Asp Glu Gln Leu Lys
            115                 120                 125

Ser Gly Thr Ala Ser Val Val Cys Leu Leu Asn Asn Phe Tyr Pro Arg
        130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205
```

Lys Ser Phe Asn Arg Gly Glu Cys
    210                 215

<210> SEQ ID NO 108
<211> LENGTH: 648
<212> TYPE: DNA
<213> ORGANISM: Artificial Sequence
<220> FEATURE:
<223> OTHER INFORMATION: light chain of FS30-35-14

<400> SEQUENCE: 108

```
gaaattgtgc tgacccagtc tccgggcacg ttatctctga gccctggtga gcgcgccact    60
ctgtcatgcc gggcttctca aagtgttagc agtagctacc tggcgtggta tcagcaaaaa   120
ccgggccagg ccccgcgtct gctgatttac ggtgcatcca gccgtgccac cggcattcca   180
gatcgttttt ccggtagtgg ttctgggacg gacttcactc tgacaatctc acgcctggaa   240
ccggaggatt ttgcggtgta ttactgccag caatattatt attcttctcc tatcacgttc   300
ggccaaggga ccaaggtgga aatcaaacgt actgtggccg ctcctagcgt gttcattttt   360
ccgccatccg acgagcagct caagtccggc accgcctccg tggtctgcct gctcaacaac   420
ttctaccctc gcgaagctaa ggtccagtgg aaggtcgaca tgccctgca  gtccggaaac   480
tcgcaggaaa gcgtgactga acaggactcc aaggactcca cctattcact gtcctcgact   540
ctgaccctga gcaaggcgga ttacgaaaag cacaaagtgt acgcatgcga agtgacccac   600
cagggtcttt cgtcccccgt gaccaagagc ttcaacagag gagagtgt              648
```

<210> SEQ ID NO 109
<211> LENGTH: 454
<212> TYPE: PRT
<213> ORGANISM: Artificial Sequence
<220> FEATURE:
<223> OTHER INFORMATION: heavy chain of FS20-22-49AA/FS30-5-37 with LALA
      mutation

<400> SEQUENCE: 109

Glu Val Gln Leu Leu Glu Ser Gly Gly Gly Leu Val Gln Pro Gly Gly
1               5                   10                  15

Ser Leu Arg Leu Asn Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Tyr Asp Lys Tyr Trp Gly Ser Ser Ile Tyr Ser Gly Leu
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

```
Thr Phe Pro Ala Val Leu Gln Ser Ser Gly Leu Tyr Ser Leu Ser Ser
                180                 185                 190
Val Val Thr Val Pro Ser Ser Leu Gly Thr Gln Thr Tyr Ile Cys
            195                 200                 205
Asn Val Asn His Lys Pro Ser Asn Thr Lys Val Asp Lys Lys Val Glu
        210                 215                 220
Pro Lys Ser Cys Asp Lys Thr His Thr Cys Pro Pro Cys Pro Ala Pro
225                 230                 235                 240
Glu Ala Ala Gly Gly Pro Ser Val Phe Leu Phe Pro Pro Lys Pro Lys
                245                 250                 255
Asp Thr Leu Met Ile Ser Arg Thr Pro Glu Val Thr Cys Val Val Val
            260                 265                 270
Asp Val Ser His Glu Asp Pro Glu Val Lys Phe Asn Trp Tyr Val Asp
        275                 280                 285
Gly Val Glu Val His Asn Ala Lys Thr Lys Pro Arg Glu Glu Gln Tyr
        290                 295                 300
Asn Ser Thr Tyr Arg Val Val Ser Val Leu Thr Val Leu His Gln Asp
305                 310                 315                 320
Trp Leu Asn Gly Lys Glu Tyr Lys Cys Lys Val Ser Asn Lys Ala Leu
                325                 330                 335
Pro Ala Pro Ile Glu Lys Thr Ile Ser Lys Ala Lys Gly Gln Pro Arg
            340                 345                 350
Glu Pro Gln Val Tyr Thr Leu Pro Pro Ser Arg Asp Glu Leu Thr Lys
        355                 360                 365
Asn Gln Val Ser Leu Thr Cys Leu Val Lys Gly Phe Tyr Pro Ser Asp
        370                 375                 380
Ile Ala Val Glu Trp Glu Ser Asn Gly Asp Glu Gln Phe Ala Tyr Lys
385                 390                 395                 400
Thr Thr Pro Pro Val Leu Asp Ser Asp Gly Ser Phe Phe Leu Tyr Ser
                405                 410                 415
Lys Leu Thr Val Asp Gln Tyr Arg Trp Asn Pro Ala Asp Tyr Phe Ser
            420                 425                 430
Cys Ser Val Met His Glu Ala Leu His Asn His Tyr Thr Gln Lys Ser
        435                 440                 445
Leu Ser Leu Ser Pro Gly
    450
```

<210> SEQ ID NO 110
<211> LENGTH: 1362
<212> TYPE: DNA
<213> ORGANISM: Artificial Sequence
<220> FEATURE:
<223> OTHER INFORMATION: heavy chain of FS20-22-49AA/FS30-5-37 with LALA mutation

<400> SEQUENCE: 110

```
gaagtgcaac tgctggagtc cggtggtggt ctggtacagc cgggtggttc tctgcgtctg      60
aattgcgcgg ccagtggctt taccttcagt agctatgcca tgagctgggt gcgtcaggcg     120
ccgggcaaag gtctggaatg ggttagcgcg attagcggta gtggcggtag cacgtactat     180
gcggatagcg tgaaaggccg ttttaccatt tctcgcgaca cagcaagaa cacgctgtac      240 ctgcagatga actcactgcg tgccgaagat acggccgtgt attactgtgc gagatcttac     300
gacaaatact gggggttctt catttactct ggcttggact actggggcca gggaaccctg     360
gtcaccgtct cgagtgctag cactaagggc ccgtcggtgt tcccgctggc ccatcgtcc     420
```

```
aagagcacat cagggggtac cgccgccctg gctgccttg tgaaggatta ctttcccgag    480
cccgtcacag tgtcctggaa cagcggagcc ctgacctccg gagtgcatac tttcccggct    540
gtgcttcagt cctctggcct gtactcattg tcctccgtgg tcaccgtccc ttcgtcctcc    600
ctgggcaccc agacctatat ctgtaatgtc aaccataagc cctcgaacac caaggtcgac    660
aagaaggtcg agccgaagtc gtgcgacaag actcacactt gcccgccttg cccagccccg    720
gaagctgccg gtggtccttc ggtgttcctc ttcccgccca gccaaggga taccctgatg    780
atctcacgga cccccgaagt gacctgtgtg gtggtggacg tgtcccacga ggacccggaa    840
gtgaaattca attggtacgt ggatggagtg aagtgcaca acgccaagac caagccacgg    900
gaagaacagt acaactctac ctaccgcgtg gtgtccgtgc tcactgtgct gcaccaagac    960
tggctgaacg gaaggagta caagtgcaaa gtgtccaaca aggcgctgcc tgccccaatt   1020
gagaaaacta tctcgaaagc caagggacag cctcgagaac acaggtgta caccctgccc   1080
ccatcccggg atgagtactg ggaccaggaa gtcagcctga cctgcctggt caaaggcttc   1140
tatcccagcg acatcgccgt ggagtgggag agcaatgggg atgaacagtt cgcatacaag   1200
accacgcctc ccgtgctgga ctccgacggc tccttcttcc tctacagcaa gctcaccgtg   1260
gatcagtata ggtggaatcc tgctgattat ttctcatgct ccgtgatgca tgaggctctg   1320
cacaaccact acactcagaa gagcttgtcc ctgtcgcccg ga                      1362
```

<210> SEQ ID NO 111
<211> LENGTH: 216
<212> TYPE: PRT
<213> ORGANISM: Artificial Sequence
<220> FEATURE:
<223> OTHER INFORMATION: light chain of FS30-5-37

<400> SEQUENCE: 111

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Tyr Ser Tyr Tyr
                85                  90                  95

Pro Val Thr Phe Gly Gln Gly Thr Lys Val Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 112
<211> LENGTH: 648
<212> TYPE: DNA
<213> ORGANISM: Artificial Sequence
<220> FEATURE:
<223> OTHER INFORMATION: light chain of FS30-5-37

<400> SEQUENCE: 112

```
gaaattgtgc tgacccagtc tccgggcacg ttatctctga gccctggtga gcgcgccact    60
ctgtcatgcc gggcttctca aagtgttagc agtagctacc tggcgtggta tcagcaaaaa   120
ccgggccagg ccccgcgtct gctgatttac ggtgcatcca gccgtgccac cggcattcca   180
gatcgttttt ccggtagtgg ttctgggacg gacttcactc tgacaatctc acgcctggaa   240
ccggaggatt ttgcggtgta ttactgccag caatattatt cttattatcc tgtcacgttc   300
ggccaaggga ccaaggtgga aatcaaacgt actgtggccg ctcctagcgt gttcattttt   360
ccgccatccg acgagcagct caagtccggc accgcctccg tggtctgcct gctcaacaac   420
ttctacccta gcgaagctaa ggtccagtgg aaggtcgaca tgccctgca gtccggaaac   480
tcgcaggaaa gcgtgactga acaggactcc aaggactcca cctattcact gtcctcgact   540
ctgaccctga gcaaggcgga ttacgaaaag cacaaagtgt acgcatgcga agtgacccac   600
cagggtcttt cgtcccccgt gaccaagagc ttcaacagag agagtgt                648
```

<210> SEQ ID NO 113
<211> LENGTH: 318
<212> TYPE: DNA
<213> ORGANISM: Artificial Sequence
<220> FEATURE:
<223> OTHER INFORMATION: Alternative Fcab FS20-22-49 CH3 domain

<400> SEQUENCE: 113

```
ggacagcctc gagaaccaca ggtgtacacc ctgcccccat cccgggatga gtactgggac    60
caggaagtca gcctgacctg cctggtcaaa ggcttctatc ccagcgacat cgccgtggag   120
tgggagagca tggggatga acagttcgca tacaagacca cgcctcccgt gctggactcc   180
gacggctcct tcttcctcta cagcaagctc accgtggatc agtataggtg gaatcctgct   240
gattatttct catgctccgt gatgcatgag gctctgcaca accactacac tcagaagagc   300
ttgtccctgt cgcccgga                                                  318
```

<210> SEQ ID NO 114
<211> LENGTH: 447
<212> TYPE: PRT
<213> ORGANISM: Artificial Sequence
<220> FEATURE:
<223> OTHER INFORMATION: heavy chain of anti-FITC mAb G1AA/4420
      comprising LALA mutation

<400> SEQUENCE: 114

Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Tyr
            20                  25                  30

```
Trp Met Asn Trp Val Arg Gln Ser Pro Glu Lys Gly Leu Glu Trp Val
            35                  40                  45
Ala Gln Ile Arg Asn Lys Pro Tyr Asn Tyr Glu Thr Tyr Tyr Ser Asp
 50                  55                  60
Ser Val Lys Gly Arg Phe Thr Ile Ser Arg Asp Asp Ser Lys Ser Ser
 65                  70                  75                  80
Val Tyr Leu Gln Met Asn Asn Leu Arg Val Glu Asp Met Gly Ile Tyr
                 85                  90                  95
Tyr Cys Thr Gly Ser Tyr Tyr Gly Met Asp Tyr Trp Gly Gln Gly Thr
                100                 105                 110
Ser Val Thr Val Ser Ser Ala Ser Thr Lys Gly Pro Ser Val Phe Pro
            115                 120                 125
Leu Ala Pro Ser Ser Lys Ser Thr Ser Gly Gly Thr Ala Ala Leu Gly
        130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
            180                 185                 190
Ser Leu Gly Thr Gln Thr Tyr Ile Cys Asn Val Asn His Lys Pro Ser
        195                 200                 205
Asn Thr Lys Val Asp Lys Lys Val Glu Pro Lys Ser Cys Asp Lys Thr
    210                 215                 220
His Thr Cys Pro Pro Cys Pro Ala Pro Glu Ala Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
            260                 265                 270
Glu Val Lys Phe Asn Trp Tyr Val Asp Gly Val Glu Val His Asn Ala
        275                 280                 285
Lys Thr Lys Pro Arg Glu Glu Gln Tyr Asn Ser Thr Tyr Arg Val Val
    290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Arg Asp Glu Leu Thr Lys Asn Gln Val Ser Leu Thr Cys
        355                 360                 365
Leu Val Lys Gly Phe Tyr Pro Ser Asp Ile Ala Val Glu Trp Glu Ser
    370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro Gly
        435                 440                 445
```

<210> SEQ ID NO 115
<211> LENGTH: 447
<212> TYPE: PRT
<213> ORGANISM: Artificial Sequence
<220> FEATURE:
<223> OTHER INFORMATION: heavy chain of anti-FITC mAb G1/4420 without LALA mutation

<400> SEQUENCE: 115

```
Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Tyr
            20                  25                  30

Trp Met Asn Trp Val Arg Gln Ser Pro Glu Lys Gly Leu Glu Trp Val
        35                  40                  45

Ala Gln Ile Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Met Gly Ile Tyr
                85                  90                  95

Tyr Cys Thr Gly Ser Tyr Tyr Gly Met Asp Tyr Trp Gly Gln Gly Thr
            100                 105                 110

Ser Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365
```

```
Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 116
<211> LENGTH: 219
<212> TYPE: PRT
<213> ORGANISM: Artificial Sequence
<220> FEATURE:
<223> OTHER INFORMATION: light chain of 4420 mAb

<400> SEQUENCE: 116

Asp Val Val Met Thr Gln Thr Pro Leu Ser Leu Pro Val Ser Leu Gly
1               5                   10                  15

Asp Gln Ala Ser Ile Ser Cys Arg Ser Gln Ser Leu Val His Ser
            20                  25                  30

Asn Gly Asn Thr Tyr Leu Arg Trp Tyr Leu Gln Lys Pro Gly Gln Ser
        35                  40                  45

Pro Lys Val Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 117
<211> LENGTH: 446
<212> TYPE: PRT
<213> ORGANISM: Artificial Sequence
<220> FEATURE:
<223> OTHER INFORMATION: heavy chain of the G1AA/HelD1.3 antibody with
      LALA mutation
```

<400> SEQUENCE: 117

```
Gln Val Gln Leu Gln Glu Ser Gly Pro Gly Leu Val Arg Pro Ser Gln
1               5                   10                  15

Thr Leu Ser Leu Thr Cys Thr Val Ser Gly Ser Thr Phe Ser Gly Tyr
            20                  25                  30

Gly Val Asn Trp Val Arg Gln Pro Pro Gly Arg Gly Leu Glu Trp Ile
        35                  40                  45

Gly Met Ile Trp Gly Asp Gly Asn Thr Asp Tyr Asn Ser Ala Leu Lys
    50                  55                  60

Ser Arg Val Thr Met Leu Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Glu Arg Asp Tyr Arg Leu Asp Tyr Trp Gly Gln Gly Ser Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400
```

```
Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445
```

<210> SEQ ID NO 118
<211> LENGTH: 214
<212> TYPE: PRT
<213> ORGANISM: Artificial Sequence
<220> FEATURE:
<223> OTHER INFORMATION: light chain of HelD1.3 mAb

<400> SEQUENCE: 118

```
Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Asn Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Asp Gly Val Pro Ser Arg Phe Ser Gly
    50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln His Phe Trp Ser Thr Pro Arg
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 119
<211> LENGTH: 445
<212> TYPE: PRT
<213> ORGANISM: Artificial Sequence
<220> FEATURE:
<223> OTHER INFORMATION: heavy chain of the G1/MOR7480.1

<400> SEQUENCE: 119

```
Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Tyr
            20                  25                  30
```

```
Trp Ile Ser Trp Val Arg Gln Met Pro Gly Lys Gly Leu Glu Trp Met
         35                  40                  45

Gly Lys Ile Tyr Pro Gly Asp Ser Tyr Thr Asn Tyr Ser Pro Ser Phe
 50                  55                  60

Gln Gly Gln Val Thr Ile Ser Ala Asp Lys Ser Ile Ser Thr Ala Tyr
 65              70                  75                  80

Leu Gln Trp Ser Ser Leu Lys Ala Ser Asp Thr Ala Met Tyr Tyr Cys
             85                  90                  95

Ala Arg Gly Tyr Gly Ile Phe Asp Tyr Trp Gly Gln Gly Thr Leu Val
             100                 105                 110

Thr Val Ser Ser Ala Ser Thr Lys Gly Pro Ser Val Phe Pro Leu Ala
         115                 120                 125

Pro Ser Ser Lys Ser Thr Ser Gly Gly Thr Ala Ala Leu Gly Cys Leu
         130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                 165                 170                 175

Gly Leu Tyr Ser Leu Ser Ser Val Val Thr Val Pro Ser Ser Ser Leu
             180                 185                 190

Gly Thr Gln Thr Tyr Ile Cys Asn Val Asn His Lys Pro Ser Asn Thr
         195                 200                 205

Lys Val Asp Lys Lys Val Glu Pro Lys Ser Cys Asp Lys Thr His Thr
         210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                 245                 250                 255

Glu Val Thr Cys Val Val Val Asp Val Ser His Glu Asp Pro Glu Val
             260                 265                 270

Lys Phe Asn Trp Tyr Val Asp Gly Val Glu Val His Asn Ala Lys Thr
         275                 280                 285

Lys Pro Arg Glu Glu Gln Tyr Asn Ser Thr Tyr Arg Val Val Ser Val
         290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                 325                 330                 335

Lys Ala Lys Gly Gln Pro Arg Glu Pro Gln Val Tyr Thr Leu Pro Pro
             340                 345                 350

Ser Arg Asp Glu Leu Thr Lys Asn Gln Val Ser Leu Thr Cys Leu Val
         355                 360                 365

Lys Gly Phe Tyr Pro Ser Asp Ile Ala Val Glu Trp Glu Ser Asn Gly
         370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                 405                 410                 415

Gln Gln Gly Asn Val Phe Ser Cys Ser Val Met His Glu Ala Leu His
             420                 425                 430

Asn His Tyr Thr Gln Lys Ser Leu Ser Leu Ser Pro Gly
         435                 440                 445
```

```
<210> SEQ ID NO 120
<211> LENGTH: 214
<212> TYPE: PRT
<213> ORGANISM: Artificial Sequence
<220> FEATURE:
<223> OTHER INFORMATION: light chain of G1/MOR7480.1, G1AA/MOR7480.1 and
      G2/MOR7480.1 mAbs

<400> SEQUENCE: 120

Ser Tyr Glu Leu Thr Gln Pro Pro Ser Val Ser Val Ser Pro Gly Gln
1               5                   10                  15

Thr Ala Ser Ile Thr Cys Ser Gly Asp Asn Ile Gly Asp Gln Tyr Ala
            20                  25                  30

His Trp Tyr Gln Gln Lys Pro Gly Gln Ser Pro Val Leu Val Ile Tyr
        35                  40                  45

Gln Asp Lys Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Ala Thr Tyr Thr Gly Phe Gly Ser Leu
                85                  90                  95

Ala Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 121
<211> LENGTH: 450
<212> TYPE: PRT
<213> ORGANISM: Artificial Sequence
<220> FEATURE:
<223> OTHER INFORMATION: heavy chain of the G1/20H4.9

<400> SEQUENCE: 121

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Ser Pro Glu Lys Gly Leu Glu Trp Ile
        35                  40                  45

Gly Glu Ile Asn His Gly Gly Tyr Val Thr Tyr Asn Pro Ser Leu Glu
    50                  55                  60

Ser Arg Val Thr Ile Ser Val Asp Thr Ser Lys Asn Gln Phe Ser Leu
65                  70                  75                  80
```

Lys Leu Ser Ser Val Thr Ala Ala Asp Thr Ala Val Tyr Tyr Cys Ala
                85                  90                  95

Arg Asp Tyr Gly Pro Gly Asn Tyr Asp Trp Tyr Phe Asp Leu Trp Gly
            100                 105                 110

Arg Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450

<210> SEQ ID NO 122
<211> LENGTH: 216
<212> TYPE: PRT
<213> ORGANISM: Artificial Sequence
<220> FEATURE:

<223> OTHER INFORMATION: the light chain of G1/20H4.9 and G1AA/20H4.9 mAbs

<400> SEQUENCE: 122

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Ala Leu Thr Phe Gly Gly Gly Thr Lys Val Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
210                 215

<210> SEQ ID NO 123
<211> LENGTH: 447
<212> TYPE: PRT
<213> ORGANISM: Artificial Sequence
<220> FEATURE:
<223> OTHER INFORMATION: heavy chain of FS20-22-49AA/4420 (with LALA mutation)

<400> SEQUENCE: 123

Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Tyr
            20                  25                  30

Trp Met Asn Trp Val Arg Gln Ser Pro Glu Lys Gly Leu Glu Trp Val
        35                  40                  45

Ala Gln Ile Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Met Gly Ile Tyr
                85                  90                  95

Tyr Cys Thr Gly Ser Tyr Tyr Gly Met Asp Tyr Trp Gly Gln Gly Thr
            100                 105                 110

```
Ser Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Tyr Trp Asp Gln Glu Val Ser Leu Thr Cys
        355                 360                 365

Leu Val Lys Gly Phe Tyr Pro Ser Asp Ile Ala Val Glu Trp Glu Ser
370                 375                 380

Asn Gly Asp Glu Gln Phe Ala Tyr Lys Thr Thr Pro Pro Val Leu Asp
385                 390                 395                 400

Ser Asp Gly Ser Phe Phe Leu Tyr Ser Lys Leu Thr Val Asp Gln Tyr
                405                 410                 415

Arg Trp Asn Pro Ala Asp Tyr Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 124
<211> LENGTH: 441
<212> TYPE: PRT
<213> ORGANISM: Artificial Sequence
<220> FEATURE:
<223> OTHER INFORMATION: heavy chain of the G2/MOR7480.1

<400> SEQUENCE: 124

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Tyr
            20                  25                  30
```

Trp Ile Ser Trp Val Arg Gln Met Pro Gly Lys Gly Leu Glu Trp Met
 35                  40                  45
Gly Lys Ile Tyr Pro Gly Asp Ser Tyr Thr Asn Tyr Ser Pro Ser Phe
 50                  55                  60
Gln Gly Gln Val Thr Ile Ser Ala Asp Lys Ser Ile Ser Thr Ala Tyr
 65                  70                  75                  80
Leu Gln Trp Ser Ser Leu Lys Ala Ser Asp Thr Ala Met Tyr Tyr Cys
             85                  90                  95
Ala Arg Gly Tyr Gly Ile Phe Asp Tyr Trp Gly Gln Gly Thr Leu Val
            100                 105                 110
Thr Val Ser Ser Ala Ser Thr Lys Gly Pro Ser Val Phe Pro Leu Ala
            115                 120                 125
Pro Cys Ser Arg Ser Thr Ser Glu Ser Thr Ala Ala Leu Gly Cys Leu
130                 135                 140
Val Lys Asp Tyr Phe Pro Glu Pro Val Thr Val Ser Trp Asn Ser Gly
145                 150                 155                 160
Ala Leu Thr Ser Gly Val His Thr Phe Pro Ala Val Leu Gln Ser Ser
                165                 170                 175
Gly Leu Tyr Ser Leu Ser Ser Val Val Thr Val Pro Ser Ser Asn Phe
            180                 185                 190
Gly Thr Gln Thr Tyr Thr Cys Asn Val Asp His Lys Pro Ser Asn Thr
            195                 200                 205
Lys Val Asp Lys Thr Val Glu Arg Lys Cys Cys Val Glu Cys Pro Pro
210                 215                 220
Cys Pro Ala Pro Pro Val Ala Gly Pro Ser Val Phe Leu Phe Pro Pro
225                 230                 235                 240
Lys Pro Lys Asp Thr Leu Met Ile Ser Arg Thr Pro Glu Val Thr Cys
                245                 250                 255
Val Val Val Asp Val Ser His Glu Asp Pro Glu Val Gln Phe Asn Trp
            260                 265                 270
Tyr Val Asp Gly Val Glu Val His Asn Ala Lys Thr Lys Pro Arg Glu
            275                 280                 285
Glu Gln Phe Asn Ser Thr Phe Arg Val Val Ser Val Leu Thr Val Val
290                 295                 300
His Gln Asp Trp Leu Asn Gly Lys Glu Tyr Lys Cys Lys Val Ser Asn
305                 310                 315                 320
Lys Gly Leu Pro Ala Pro Ile Glu Lys Thr Ile Ser Lys Thr Lys Gly
                325                 330                 335
Gln Pro Arg Glu Pro Gln Val Tyr Thr Leu Pro Pro Ser Arg Glu Glu
            340                 345                 350
Met Thr Lys Asn Gln Val Ser Leu Thr Cys Leu Val Lys Gly Phe Tyr
            355                 360                 365
Pro Ser Asp Ile Ala Val Glu Trp Glu Ser Asn Gly Gln Pro Glu Asn
370                 375                 380
Asn Tyr Lys Thr Thr Pro Pro Met Leu Asp Ser Asp Gly Ser Phe Phe
385                 390                 395                 400
Leu Tyr Ser Lys Leu Thr Val Asp Lys Ser Arg Trp Gln Gln Gly Asn
                405                 410                 415
Val Phe Ser Cys Ser Val Met His Glu Ala Leu His Asn His Tyr Thr
            420                 425                 430
Gln Lys Ser Leu Ser Leu Ser Pro Gly
            435                 440

```
<210> SEQ ID NO 125
<211> LENGTH: 445
<212> TYPE: PRT
<213> ORGANISM: Artificial Sequence
<220> FEATURE:
<223> OTHER INFORMATION: heavy chain of the G1AA/MOR7480.1

<400> SEQUENCE: 125
```

| | | | | | | | | | | | | | | | |
|---|---|---|---|---|---|---|---|---|---|---|---|---|---|---|---|
| Glu | Val | Gln | Leu | Val | Gln | Ser | Gly | Ala | Glu | Val | Lys | Pro | Gly | Glu | |
| 1 | | | | 5 | | | | | 10 | | | | | 15 | |

| | | | | | | | | | | | | | |
|---|---|---|---|---|---|---|---|---|---|---|---|---|---|
| Ser | Leu | Arg | Ile | Ser | Cys | Lys | Gly | Ser | Gly | Tyr | Ser | Phe | Ser | Thr | Tyr |
| | | | 20 | | | | | 25 | | | | | 30 | | |

| Trp | Ile | Ser | Trp | Val | Arg | Gln | Met | Pro | Gly | Lys | Gly | Leu | Glu | Trp | Met |
|---|---|---|---|---|---|---|---|---|---|---|---|---|---|---|---|
| | | | 35 | | | | | 40 | | | | | 45 | | |

| Gly | Lys | Ile | Tyr | Pro | Gly | Asp | Ser | Tyr | Thr | Asn | Tyr | Ser | Pro | Ser | Phe |
|---|---|---|---|---|---|---|---|---|---|---|---|---|---|---|---|
| | 50 | | | | | 55 | | | | | 60 | | | | |

| Gln | Gly | Gln | Val | Thr | Ile | Ser | Ala | Asp | Lys | Ser | Ile | Ser | Thr | Ala | Tyr |
|---|---|---|---|---|---|---|---|---|---|---|---|---|---|---|---|
| 65 | | | | | 70 | | | | | 75 | | | | | 80 |

| Leu | Gln | Trp | Ser | Ser | Leu | Lys | Ala | Ser | Asp | Thr | Ala | Met | Tyr | Tyr | Cys |
|---|---|---|---|---|---|---|---|---|---|---|---|---|---|---|---|
| | | | | 85 | | | | | 90 | | | | | 95 | |

| Ala | Arg | Gly | Tyr | Gly | Ile | Phe | Asp | Tyr | Trp | Gly | Gln | Gly | Thr | Leu | Val |
|---|---|---|---|---|---|---|---|---|---|---|---|---|---|---|---|
| | | | 100 | | | | | 105 | | | | | 110 | | |

| Thr | Val | Ser | Ser | Ala | Ser | Thr | Lys | Gly | Pro | Ser | Val | Phe | Pro | Leu | Ala |
|---|---|---|---|---|---|---|---|---|---|---|---|---|---|---|---|
| | 115 | | | | | 120 | | | | | 125 | | | | |

| Pro | Ser | Ser | Lys | Ser | Thr | Ser | Gly | Gly | Thr | Ala | Ala | Leu | Gly | Cys | Leu |
|---|---|---|---|---|---|---|---|---|---|---|---|---|---|---|---|
| | 130 | | | | | 135 | | | | | 140 | | | | |

| Val | Lys | Asp | Tyr | Phe | Pro | Glu | Pro | Val | Thr | Val | Ser | Trp | Asn | Ser | Gly |
|---|---|---|---|---|---|---|---|---|---|---|---|---|---|---|---|
| 145 | | | | | 150 | | | | | 155 | | | | | 160 |

| Ala | Leu | Thr | Ser | Gly | Val | His | Thr | Phe | Pro | Ala | Val | Leu | Gln | Ser | Ser |
|---|---|---|---|---|---|---|---|---|---|---|---|---|---|---|---|
| | | | | 165 | | | | | 170 | | | | | 175 | |

| Gly | Leu | Tyr | Ser | Leu | Ser | Ser | Val | Val | Thr | Val | Pro | Ser | Ser | Ser | Leu |
|---|---|---|---|---|---|---|---|---|---|---|---|---|---|---|---|
| | | | 180 | | | | | 185 | | | | | 190 | | |

| Gly | Thr | Gln | Thr | Tyr | Ile | Cys | Asn | Val | Asn | His | Lys | Pro | Ser | Asn | Thr |
|---|---|---|---|---|---|---|---|---|---|---|---|---|---|---|---|
| | | 195 | | | | | 200 | | | | | 205 | | | |

| Lys | Val | Asp | Lys | Lys | Val | Glu | Pro | Lys | Ser | Cys | Asp | Lys | Thr | His | Thr |
|---|---|---|---|---|---|---|---|---|---|---|---|---|---|---|---|
| | 210 | | | | | 215 | | | | | 220 | | | | |

| Cys | Pro | Pro | Cys | Pro | Ala | Pro | Glu | Ala | Ala | Gly | Gly | Pro | Ser | Val | Phe |
|---|---|---|---|---|---|---|---|---|---|---|---|---|---|---|---|
| 225 | | | | | 230 | | | | | 235 | | | | | 240 |

| Leu | Phe | Pro | Pro | Lys | Pro | Lys | Asp | Thr | Leu | Met | Ile | Ser | Arg | Thr | Pro |
|---|---|---|---|---|---|---|---|---|---|---|---|---|---|---|---|
| | | | | 245 | | | | | 250 | | | | | 255 | |

| Glu | Val | Thr | Cys | Val | Val | Val | Asp | Val | Ser | His | Glu | Asp | Pro | Glu | Val |
|---|---|---|---|---|---|---|---|---|---|---|---|---|---|---|---|
| | | | 260 | | | | | 265 | | | | | 270 | | |

| Lys | Phe | Asn | Trp | Tyr | Val | Asp | Gly | Val | Glu | Val | His | Asn | Ala | Lys | Thr |
|---|---|---|---|---|---|---|---|---|---|---|---|---|---|---|---|
| | | 275 | | | | | 280 | | | | | 285 | | | |

| Lys | Pro | Arg | Glu | Glu | Gln | Tyr | Asn | Ser | Thr | Tyr | Arg | Val | Val | Ser | Val |
|---|---|---|---|---|---|---|---|---|---|---|---|---|---|---|---|
| | 290 | | | | | 295 | | | | | 300 | | | | |

| Leu | Thr | Val | Leu | His | Gln | Asp | Trp | Leu | Asn | Gly | Lys | Glu | Tyr | Lys | Cys |
|---|---|---|---|---|---|---|---|---|---|---|---|---|---|---|---|
| 305 | | | | | 310 | | | | | 315 | | | | | 320 |

| Lys | Val | Ser | Asn | Lys | Ala | Leu | Pro | Ala | Pro | Ile | Glu | Lys | Thr | Ile | Ser |
|---|---|---|---|---|---|---|---|---|---|---|---|---|---|---|---|
| | | | | 325 | | | | | 330 | | | | | 335 | |

| Lys | Ala | Lys | Gly | Gln | Pro | Arg | Glu | Pro | Gln | Val | Tyr | Thr | Leu | Pro | Pro |
|---|---|---|---|---|---|---|---|---|---|---|---|---|---|---|---|
| | | | 340 | | | | | 345 | | | | | 350 | | |

| Ser | Arg | Asp | Glu | Leu | Thr | Lys | Asn | Gln | Val | Ser | Leu | Thr | Cys | Leu | Val |
|---|---|---|---|---|---|---|---|---|---|---|---|---|---|---|---|
| | | 355 | | | | | 360 | | | | | 365 | | | |

```
Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly
                435                 440                 445

<210> SEQ ID NO 126
<211> LENGTH: 232
<212> TYPE: PRT
<213> ORGANISM: Homo sapiens

<400> SEQUENCE: 126

Leu Gln Asp Pro Cys Ser Asn Cys Pro Ala Gly Thr Phe Cys Asp Asn
1               5                   10                  15

Asn Arg Asn Gln Ile Cys Ser Pro Cys Pro Pro Asn Ser Phe Ser Ser
                20                  25                  30

Ala Gly Gly Gln Arg Thr Cys Asp Ile Cys Arg Gln Cys Lys Gly Val
            35                  40                  45

Phe Arg Thr Arg Lys Glu Cys Ser Ser Thr Ser Asn Ala Glu Cys Asp
    50                  55                  60

Cys Thr Pro Gly Phe His Cys Leu Gly Ala Gly Cys Ser Met Cys Glu
65                  70                  75                  80

Gln Asp Cys Lys Gln Gly Gln Glu Leu Thr Lys Lys Gly Cys Lys Asp
                85                  90                  95

Cys Cys Phe Gly Thr Phe Asn Asp Gln Lys Arg Gly Ile Cys Arg Pro
                100                 105                 110

Trp Thr Asn Cys Ser Leu Asp Gly Lys Ser Val Leu Val Asn Gly Thr
            115                 120                 125

Lys Glu Arg Asp Val Val Cys Gly Pro Ser Pro Ala Asp Leu Ser Pro
130                 135                 140

Gly Ala Ser Ser Val Thr Pro Pro Ala Pro Ala Arg Glu Pro Gly His
145                 150                 155                 160

Ser Pro Gln Ile Ile Ser Phe Phe Leu Ala Leu Thr Ser Thr Ala Leu
                165                 170                 175

Leu Phe Leu Leu Phe Phe Leu Thr Leu Arg Phe Ser Val Val Lys Arg
                180                 185                 190

Gly Arg Lys Lys Leu Leu Tyr Ile Phe Lys Gln Pro Phe Met Arg Pro
            195                 200                 205

Val Gln Thr Thr Gln Glu Glu Asp Gly Cys Ser Cys Arg Phe Pro Glu
210                 215                 220

Glu Glu Glu Gly Gly Cys Glu Leu
225                 230

<210> SEQ ID NO 127
<211> LENGTH: 163
<212> TYPE: PRT
<213> ORGANISM: Homo sapiens

<400> SEQUENCE: 127

Leu Gln Asp Pro Cys Ser Asn Cys Pro Ala Gly Thr Phe Cys Asp Asn
1               5                   10                  15
```

```
Asn Arg Asn Gln Ile Cys Ser Pro Cys Pro Asn Ser Phe Ser Ser
             20                  25                  30

Ala Gly Gly Gln Arg Thr Cys Asp Ile Cys Arg Gln Cys Lys Gly Val
         35                  40                  45

Phe Arg Thr Arg Lys Glu Cys Ser Ser Thr Ser Asn Ala Glu Cys Asp
 50                  55                  60

Cys Thr Pro Gly Phe His Cys Leu Gly Ala Gly Cys Ser Met Cys Glu
 65                  70                  75                  80

Gln Asp Cys Lys Gln Gly Gln Glu Leu Thr Lys Lys Gly Cys Lys Asp
             85                  90                  95

Cys Cys Phe Gly Thr Phe Asn Asp Gln Lys Arg Gly Ile Cys Arg Pro
             100                 105                 110

Trp Thr Asn Cys Ser Leu Asp Gly Lys Ser Val Leu Val Asn Gly Thr
             115                 120                 125

Lys Glu Arg Asp Val Val Cys Gly Pro Ser Pro Ala Asp Leu Ser Pro
 130                 135                 140

Gly Ala Ser Ser Val Thr Pro Pro Ala Pro Ala Arg Glu Pro Gly His
 145                 150                 155                 160

Ser Pro Gln

<210> SEQ ID NO 128
<211> LENGTH: 231
<212> TYPE: PRT
<213> ORGANISM: Macaca fascicularis

<400> SEQUENCE: 128

Leu Gln Asp Leu Cys Ser Asn Cys Pro Ala Gly Thr Phe Cys Asp Asn
 1               5                  10                  15

Asn Arg Ser Gln Ile Cys Ser Pro Cys Pro Pro Asn Ser Phe Ser Ser
             20                  25                  30

Ala Gly Gly Gln Arg Thr Cys Asp Ile Cys Arg Gln Cys Lys Gly Val
         35                  40                  45

Phe Lys Thr Arg Lys Glu Cys Ser Ser Thr Ser Asn Ala Glu Cys Asp
 50                  55                  60

Cys Ile Ser Gly Tyr His Cys Leu Gly Ala Glu Cys Ser Met Cys Glu
 65                  70                  75                  80

Gln Asp Cys Lys Gln Gly Gln Glu Leu Thr Lys Lys Gly Cys Lys Asp
             85                  90                  95

Cys Cys Phe Gly Thr Phe Asn Asp Gln Lys Arg Gly Ile Cys Arg Pro
             100                 105                 110

Trp Thr Asn Cys Ser Leu Asp Gly Lys Ser Val Leu Val Asn Gly Thr
             115                 120                 125

Lys Glu Arg Asp Val Val Cys Gly Pro Ser Pro Ala Asp Leu Ser Pro
 130                 135                 140

Gly Ala Ser Ser Ala Thr Pro Pro Ala Pro Ala Arg Glu Pro Gly His
 145                 150                 155                 160

Ser Pro Gln Ile Ile Phe Phe Leu Ala Leu Thr Ser Thr Val Val Leu
             165                 170                 175

Phe Leu Leu Phe Phe Leu Val Leu Arg Phe Ser Val Val Lys Arg Ser
             180                 185                 190

Arg Lys Lys Leu Leu Tyr Ile Phe Lys Gln Pro Phe Met Arg Pro Val
             195                 200                 205

Gln Thr Thr Gln Glu Glu Asp Gly Cys Ser Cys Arg Phe Pro Glu Glu
 210                 215                 220
```

```
Glu Glu Gly Gly Cys Glu Leu
225                 230

<210> SEQ ID NO 129
<211> LENGTH: 163
<212> TYPE: PRT
<213> ORGANISM: Macaca fascicularis

<400> SEQUENCE: 129

Leu Gln Asp Leu Cys Ser Asn Cys Pro Ala Gly Thr Phe Cys Asp Asn
1               5                   10                  15

Asn Arg Ser Gln Ile Cys Ser Pro Cys Pro Pro Asn Ser Phe Ser Ser
            20                  25                  30

Ala Gly Gly Gln Arg Thr Cys Asp Ile Cys Arg Gln Cys Lys Gly Val
        35                  40                  45

Phe Lys Thr Arg Lys Glu Cys Ser Ser Thr Ser Asn Ala Glu Cys Asp
    50                  55                  60

Cys Ile Ser Gly Tyr His Cys Leu Gly Ala Glu Cys Ser Met Cys Glu
65                  70                  75                  80

Gln Asp Cys Lys Gln Gly Gln Glu Leu Thr Lys Lys Gly Cys Lys Asp
                85                  90                  95

Cys Cys Phe Gly Thr Phe Asn Asp Gln Lys Arg Gly Ile Cys Arg Pro
            100                 105                 110

Trp Thr Asn Cys Ser Leu Asp Gly Lys Ser Val Leu Val Asn Gly Thr
        115                 120                 125

Lys Glu Arg Asp Val Val Cys Gly Pro Ser Pro Ala Asp Leu Ser Pro
    130                 135                 140

Gly Ala Ser Ser Ala Thr Pro Pro Ala Pro Ala Arg Glu Pro Gly His
145                 150                 155                 160

Ser Pro Gln

<210> SEQ ID NO 130
<211> LENGTH: 186
<212> TYPE: PRT
<213> ORGANISM: Homo sapiens

<400> SEQUENCE: 130

Leu His Cys Val Gly Asp Thr Tyr Pro Ser Asn Asp Arg Cys Cys His
1               5                   10                  15

Glu Cys Arg Pro Gly Asn Gly Met Val Ser Arg Cys Ser Arg Ser Gln
            20                  25                  30

Asn Thr Val Cys Arg Pro Cys Gly Pro Gly Phe Tyr Asn Asp Val Val
        35                  40                  45

Ser Ser Lys Pro Cys Lys Pro Cys Thr Trp Cys Asn Leu Arg Ser Gly
    50                  55                  60

Ser Glu Arg Lys Gln Leu Cys Thr Ala Thr Gln Asp Thr Val Cys Arg
65                  70                  75                  80

Cys Arg Ala Gly Thr Gln Pro Leu Asp Ser Tyr Lys Pro Gly Val Asp
                85                  90                  95

Cys Ala Pro Cys Pro Pro Gly His Phe Ser Pro Gly Asp Asn Gln Ala
            100                 105                 110

Cys Lys Pro Trp Thr Asn Cys Thr Leu Ala Gly Lys His Thr Leu Gln
        115                 120                 125

Pro Ala Ser Asn Ser Ser Asp Ala Ile Cys Glu Asp Arg Asp Pro Pro
    130                 135                 140
```

```
Ala Thr Gln Pro Gln Glu Thr Gln Gly Pro Pro Ala Arg Pro Ile Thr
145                 150                 155                 160

Val Gln Pro Thr Glu Ala Trp Pro Arg Thr Ser Gln Gly Pro Ser Thr
                165                 170                 175

Arg Pro Val Glu Val Pro Gly Gly Arg Ala
            180                 185

<210> SEQ ID NO 131
<211> LENGTH: 186
<212> TYPE: PRT
<213> ORGANISM: Macaca fascicularis

<400> SEQUENCE: 131

Leu His Cys Val Gly Asp Thr Tyr Pro Ser Asn Asp Arg Cys Cys Gln
1               5                   10                  15

Glu Cys Arg Pro Gly Asn Gly Met Val Ser Arg Cys Asn Arg Ser Gln
                20                  25                  30

Asn Thr Val Cys Arg Pro Cys Gly Pro Gly Phe Tyr Asn Asp Val Val
            35                  40                  45

Ser Ala Lys Pro Cys Lys Ala Cys Thr Trp Cys Asn Leu Arg Ser Gly
50                  55                  60

Ser Glu Arg Lys Gln Pro Cys Thr Ala Thr Gln Asp Thr Val Cys Arg
65                  70                  75                  80

Cys Arg Ala Gly Thr Gln Pro Leu Asp Ser Tyr Lys Pro Gly Val Asp
                85                  90                  95

Cys Ala Pro Cys Pro Pro Gly His Phe Ser Pro Gly Asp Asn Gln Ala
            100                 105                 110

Cys Lys Pro Trp Thr Asn Cys Thr Leu Ala Gly Lys His Thr Leu Gln
        115                 120                 125

Pro Ala Ser Asn Ser Ser Asp Ala Ile Cys Glu Asp Arg Asp Pro Pro
130                 135                 140

Pro Thr Gln Pro Gln Glu Thr Gln Gly Pro Pro Ala Arg Pro Thr Thr
145                 150                 155                 160

Val Gln Pro Thr Glu Ala Trp Pro Arg Thr Ser Gln Arg Pro Ser Thr
                165                 170                 175

Arg Pro Val Glu Val Pro Arg Gly Pro Ala
            180                 185

<210> SEQ ID NO 132
<211> LENGTH: 249
<212> TYPE: PRT
<213> ORGANISM: Artificial Sequence
<220> FEATURE:
<223> OTHER INFORMATION: DO11.10-hOX40 and human OX40 receptor

<400> SEQUENCE: 132

Leu His Cys Val Gly Asp Thr Tyr Pro Ser Asn Asp Arg Cys Cys His
1               5                   10                  15

Glu Cys Arg Pro Gly Asn Gly Met Val Ser Arg Cys Ser Arg Ser Gln
                20                  25                  30

Asn Thr Val Cys Arg Pro Cys Gly Pro Gly Phe Tyr Asn Asp Val Val
            35                  40                  45

Ser Ser Lys Pro Cys Lys Pro Cys Thr Trp Cys Asn Leu Arg Ser Gly
50                  55                  60

Ser Glu Arg Lys Gln Leu Cys Thr Ala Thr Gln Asp Thr Val Cys Arg
65                  70                  75                  80
```

```
Cys Arg Ala Gly Thr Gln Pro Leu Asp Ser Tyr Lys Pro Gly Val Asp
                85                  90                  95

Cys Ala Pro Cys Pro Pro Gly His Phe Ser Pro Gly Asp Asn Gln Ala
            100                 105                 110

Cys Lys Pro Trp Thr Asn Cys Thr Leu Ala Gly Lys His Thr Leu Gln
        115                 120                 125

Pro Ala Ser Asn Ser Ser Asp Ala Ile Cys Glu Asp Arg Asp Pro Pro
    130                 135                 140

Ala Thr Gln Pro Gln Glu Thr Gln Gly Pro Pro Ala Arg Pro Ile Thr
145                 150                 155                 160

Val Gln Pro Thr Glu Ala Trp Pro Arg Thr Ser Gln Gly Pro Ser Thr
                165                 170                 175

Arg Pro Val Glu Val Pro Gly Gly Arg Ala Val Ala Ala Ile Leu Gly
            180                 185                 190

Leu Gly Leu Val Leu Gly Leu Leu Gly Pro Leu Ala Ile Leu Leu Ala
        195                 200                 205

Leu Tyr Leu Leu Arg Arg Asp Gln Arg Leu Pro Pro Asp Ala His Lys
    210                 215                 220

Pro Pro Gly Gly Gly Ser Phe Arg Thr Pro Ile Gln Glu Glu Gln Ala
225                 230                 235                 240

Asp Ala His Ser Thr Leu Ala Lys Ile
                245

<210> SEQ ID NO 133
<211> LENGTH: 253
<212> TYPE: PRT
<213> ORGANISM: Artificial Sequence
<220> FEATURE:
<223> OTHER INFORMATION: DO11.10-mOX40 and mouse OX40 receptor

<400> SEQUENCE: 133

Val Thr Ala Arg Arg Leu Asn Cys Val Lys His Thr Tyr Pro Ser Gly
1               5                   10                  15

His Lys Cys Cys Arg Glu Cys Gln Pro Gly His Gly Met Val Ser Arg
                20                  25                  30

Cys Asp His Thr Arg Asp Thr Leu Cys His Pro Cys Glu Thr Gly Phe
            35                  40                  45

Tyr Asn Glu Ala Val Asn Tyr Asp Thr Cys Lys Gln Cys Thr Gln Cys
    50                  55                  60

Asn His Arg Ser Gly Ser Glu Leu Lys Gln Asn Cys Thr Pro Thr Gln
65                  70                  75                  80

Asp Thr Val Cys Arg Cys Arg Pro Gly Thr Gln Pro Arg Gln Asp Ser
                85                  90                  95

Gly Tyr Lys Leu Gly Val Asp Cys Val Pro Cys Pro Pro Gly His Phe
            100                 105                 110

Ser Pro Gly Asn Asn Gln Ala Cys Lys Pro Trp Thr Asn Cys Thr Leu
        115                 120                 125

Ser Gly Lys Gln Thr Arg His Pro Ala Ser Asp Ser Leu Asp Ala Val
    130                 135                 140

Cys Glu Asp Arg Ser Leu Leu Ala Thr Leu Leu Trp Glu Thr Gln Arg
145                 150                 155                 160

Pro Thr Phe Arg Pro Thr Thr Val Gln Ser Thr Thr Val Trp Pro Arg
                165                 170                 175

Thr Ser Glu Leu Pro Ser Pro Pro Thr Leu Val Thr Pro Glu Gly Pro
            180                 185                 190
```

Ala Phe Ala Val Leu Leu Gly Leu Gly Leu Leu Ala Pro Leu
            195                 200                 205

Thr Val Leu Leu Ala Leu Tyr Leu Leu Arg Lys Ala Trp Arg Leu Pro
    210                 215                 220

Asn Thr Pro Lys Pro Cys Trp Gly Asn Ser Phe Arg Thr Pro Ile Gln
225                 230                 235                 240

Glu Glu His Thr Asp Ala His Phe Thr Leu Ala Lys Ile
            245                 250

<210> SEQ ID NO 134
<211> LENGTH: 250
<212> TYPE: PRT
<213> ORGANISM: Artificial Sequence
<220> FEATURE:
<223> OTHER INFORMATION: DO11.10-cOX40 and cynomolgus monkey OX40
      receptor

<400> SEQUENCE: 134

Lys Leu His Cys Val Gly Asp Thr Tyr Pro Ser Asn Asp Arg Cys Cys
1               5                   10                  15

Gln Glu Cys Arg Pro Gly Asn Gly Met Val Ser Arg Cys Asn Arg Ser
            20                  25                  30

Gln Asn Thr Val Cys Arg Pro Cys Gly Pro Gly Phe Tyr Asn Asp Val
        35                  40                  45

Val Ser Ala Lys Pro Cys Lys Ala Cys Thr Trp Cys Asn Leu Arg Ser
50                  55                  60

Gly Ser Glu Arg Lys Gln Pro Cys Thr Ala Thr Gln Asp Thr Val Cys
65                  70                  75                  80

Arg Cys Arg Ala Gly Thr Gln Pro Leu Asp Ser Tyr Lys Pro Gly Val
                85                  90                  95

Asp Cys Ala Pro Cys Pro Pro Gly His Phe Ser Pro Gly Asp Asn Gln
            100                 105                 110

Ala Cys Lys Pro Trp Thr Asn Cys Thr Leu Ala Gly Lys His Thr Leu
        115                 120                 125

Gln Pro Ala Ser Asn Ser Ser Asp Ala Ile Cys Glu Asp Arg Asp Pro
    130                 135                 140

Pro Pro Thr Gln Pro Gln Glu Thr Gln Gly Pro Pro Ala Arg Pro Thr
145                 150                 155                 160

Thr Val Gln Pro Thr Glu Ala Trp Pro Arg Thr Ser Gln Arg Pro Ser
                165                 170                 175

Thr Arg Pro Val Glu Val Pro Arg Gly Pro Ala Val Ala Ala Ile Leu
            180                 185                 190

Gly Leu Gly Leu Ala Leu Gly Leu Leu Gly Pro Leu Ala Met Leu Leu
        195                 200                 205

Ala Leu Leu Leu Leu Arg Arg Asp Gln Arg Leu Pro Pro Asp Ala Pro
    210                 215                 220

Lys Ala Pro Gly Gly Gly Ser Phe Arg Thr Pro Ile Gln Glu Glu Gln
225                 230                 235                 240

Ala Asp Ala His Ser Ala Leu Ala Lys Ile
                245                 250

<210> SEQ ID NO 135
<211> LENGTH: 442
<212> TYPE: PRT
<213> ORGANISM: Homo sapiens

<400> SEQUENCE: 135

```
Met Tyr Arg Met Gln Leu Leu Ser Cys Ile Ala Leu Ser Leu Ala Leu
1               5                   10                  15

Val Thr Asn Ser Leu His Cys Val Gly Asp Thr Tyr Pro Ser Asn Asp
            20                  25                  30

Arg Cys Cys His Glu Cys Arg Pro Gly Asn Gly Met Val Ser Arg Cys
        35                  40                  45

Ser Arg Ser Gln Asn Thr Val Cys Arg Pro Cys Gly Pro Gly Phe Tyr
    50                  55                  60

Asn Asp Val Val Ser Ser Lys Pro Cys Lys Pro Cys Thr Trp Cys Asn
65                  70                  75                  80

Leu Arg Ser Gly Ser Glu Arg Lys Gln Leu Cys Thr Ala Thr Gln Asp
                85                  90                  95

Thr Val Cys Arg Cys Arg Ala Gly Thr Gln Pro Leu Asp Ser Tyr Lys
            100                 105                 110

Pro Gly Val Asp Cys Ala Pro Cys Pro Pro Gly His Phe Ser Pro Gly
        115                 120                 125

Asp Asn Gln Ala Cys Lys Pro Trp Thr Asn Cys Thr Leu Ala Gly Lys
130                 135                 140

His Thr Leu Gln Pro Ala Ser Asn Ser Ser Asp Ala Ile Cys Glu Asp
145                 150                 155                 160

Arg Asp Pro Pro Ala Thr Gln Pro Gln Glu Thr Gln Gly Pro Pro Ala
                165                 170                 175

Arg Pro Ile Thr Val Gln Pro Thr Glu Ala Trp Pro Arg Thr Ser Gln
            180                 185                 190

Gly Pro Ser Thr Arg Pro Val Glu Val Pro Gly Gly Arg Ala Val Ala
        195                 200                 205

Gly Ser Pro Arg Gly Pro Thr Ile Lys Pro Cys Pro Pro Cys Lys Cys
    210                 215                 220

Pro Ala Pro Asn Leu Leu Gly Gly Pro Ser Val Phe Ile Phe Pro Pro
225                 230                 235                 240

Lys Ile Lys Asp Val Leu Met Ile Ser Leu Ser Pro Ile Val Thr Cys
                245                 250                 255

Val Val Val Asp Val Ser Glu Asp Asp Pro Asp Val Gln Ile Ser Trp
            260                 265                 270

Phe Val Asn Asn Val Glu Val His Thr Ala Gln Thr Gln Thr His Arg
        275                 280                 285

Glu Asp Tyr Asn Ser Thr Leu Arg Val Val Ser Ala Leu Pro Ile Gln
    290                 295                 300

His Gln Asp Trp Met Ser Gly Lys Glu Phe Lys Cys Lys Val Asn Asn
305                 310                 315                 320

Lys Asp Leu Pro Ala Pro Ile Glu Arg Thr Ile Ser Lys Pro Lys Gly
                325                 330                 335

Ser Val Arg Ala Pro Gln Val Tyr Val Leu Pro Pro Pro Glu Glu Glu
            340                 345                 350

Met Thr Lys Lys Gln Val Thr Leu Thr Cys Met Val Thr Asp Phe Met
        355                 360                 365

Pro Glu Asp Ile Tyr Val Glu Trp Thr Asn Asn Gly Lys Thr Glu Leu
    370                 375                 380

Asn Tyr Lys Asn Thr Glu Pro Val Leu Asp Ser Asp Gly Ser Tyr Phe
385                 390                 395                 400
```

```
Met Tyr Ser Lys Leu Arg Val Glu Lys Lys Asn Trp Val Glu Arg Asn
            405                 410                 415

Ser Tyr Ser Cys Ser Val Val His Glu Gly Leu His Asn His His Thr
            420                 425                 430

Thr Lys Ser Phe Ser Arg Thr Pro Gly Lys
            435                 440

<210> SEQ ID NO 136
<211> LENGTH: 447
<212> TYPE: PRT
<213> ORGANISM: Mus musculus

<400> SEQUENCE: 136

Met Tyr Arg Met Gln Leu Leu Ser Cys Ile Ala Leu Ser Leu Ala Leu
1               5                   10                  15

Val Thr Asn Ser Val Thr Ala Arg Arg Leu Asn Cys Val Lys His Thr
            20                  25                  30

Tyr Pro Ser Gly His Lys Cys Cys Arg Glu Cys Gln Pro Gly His Gly
        35                  40                  45

Met Val Ser Arg Cys Asp His Thr Arg Asp Thr Leu Cys His Pro Cys
    50                  55                  60

Glu Thr Gly Phe Tyr Asn Glu Ala Val Asn Tyr Asp Thr Cys Lys Gln
65                  70                  75                  80

Cys Thr Gln Cys Asn His Arg Ser Gly Ser Glu Leu Lys Gln Asn Cys
                85                  90                  95

Thr Pro Thr Gln Asp Thr Val Cys Arg Cys Arg Pro Gly Thr Gln Pro
            100                 105                 110

Arg Gln Asp Ser Gly Tyr Lys Leu Gly Val Asp Cys Val Pro Cys Pro
            115                 120                 125

Pro Gly His Phe Ser Pro Gly Asn Asn Gln Ala Cys Lys Pro Trp Thr
        130                 135                 140

Asn Cys Thr Leu Ser Gly Lys Gln Thr Arg His Pro Ala Ser Asp Ser
145                 150                 155                 160

Leu Asp Ala Val Cys Glu Asp Arg Ser Leu Leu Ala Thr Leu Leu Trp
                165                 170                 175

Glu Thr Gln Arg Pro Thr Phe Arg Pro Thr Thr Val Gln Ser Thr Thr
            180                 185                 190

Val Trp Pro Arg Thr Ser Glu Leu Pro Ser Pro Pro Thr Leu Val Thr
            195                 200                 205

Pro Glu Gly Pro Ala Gly Ser Pro Arg Gly Pro Thr Ile Lys Pro Cys
        210                 215                 220

Pro Pro Cys Lys Cys Pro Ala Pro Asn Leu Leu Gly Gly Pro Ser Val
225                 230                 235                 240

Phe Ile Phe Pro Pro Lys Ile Lys Asp Val Leu Met Ile Ser Leu Ser
                245                 250                 255

Pro Ile Val Thr Cys Val Val Val Asp Val Ser Glu Asp Asp Pro Asp
            260                 265                 270

Val Gln Ile Ser Trp Phe Val Asn Asn Val Glu Val His Thr Ala Gln
        275                 280                 285

Thr Gln Thr His Arg Glu Asp Tyr Asn Ser Thr Leu Arg Val Val Ser
    290                 295                 300

Ala Leu Pro Ile Gln His Gln Asp Trp Met Ser Gly Lys Glu Phe Lys
305                 310                 315                 320
```

```
Cys Lys Val Asn Asn Lys Asp Leu Pro Ala Pro Ile Glu Arg Thr Ile
            325                 330                 335

Ser Lys Pro Lys Gly Ser Val Arg Ala Pro Gln Val Tyr Val Leu Pro
            340                 345                 350

Pro Pro Glu Glu Glu Met Thr Lys Lys Gln Val Thr Leu Thr Cys Met
            355                 360                 365

Val Thr Asp Phe Met Pro Glu Asp Ile Tyr Val Glu Trp Thr Asn Asn
    370                 375                 380

Gly Lys Thr Glu Leu Asn Tyr Lys Asn Thr Glu Pro Val Leu Asp Ser
385                 390                 395                 400

Asp Gly Ser Tyr Phe Met Tyr Ser Lys Leu Arg Val Glu Lys Lys Asn
                405                 410                 415

Trp Val Glu Arg Asn Ser Tyr Ser Cys Ser Val Val His Glu Gly Leu
                420                 425                 430

His Asn His His Thr Thr Lys Ser Phe Ser Arg Thr Pro Gly Lys
            435                 440                 445

<210> SEQ ID NO 137
<211> LENGTH: 444
<212> TYPE: PRT
<213> ORGANISM: Macaca fascicularis

<400> SEQUENCE: 137

Met Tyr Arg Met Gln Leu Leu Ser Cys Ile Ala Leu Ser Leu Ala Leu
1               5                   10                  15

Val Thr Asn Ser Leu His Cys Val Gly Asp Thr Tyr Pro Ser Asn Asp
            20                  25                  30

Arg Cys Cys Gln Glu Cys Arg Pro Gly Asn Gly Met Val Ser Arg Cys
        35                  40                  45

Asn Arg Ser Gln Asn Thr Val Cys Arg Pro Cys Gly Pro Gly Phe Tyr
    50                  55                  60

Asn Asp Val Val Ser Ala Lys Pro Cys Lys Ala Cys Thr Trp Cys Asn
65                  70                  75                  80

Leu Arg Ser Gly Ser Glu Arg Lys Gln Pro Cys Thr Ala Thr Gln Asp
                85                  90                  95

Thr Val Cys Arg Cys Arg Ala Gly Thr Gln Pro Leu Asp Ser Tyr Lys
                100                 105                 110

Pro Gly Val Asp Cys Ala Pro Cys Pro Pro Gly His Phe Ser Pro Gly
            115                 120                 125

Asp Asn Gln Ala Cys Lys Pro Trp Thr Asn Cys Thr Leu Ala Gly Lys
    130                 135                 140

His Thr Leu Gln Pro Ala Ser Asn Ser Ser Asp Ala Ile Cys Glu Asp
145                 150                 155                 160

Arg Asp Pro Pro Thr Gln Pro Gln Glu Thr Gln Gly Pro Pro Ala
                165                 170                 175

Arg Pro Thr Thr Val Gln Pro Thr Glu Ala Trp Pro Arg Thr Ser Gln
            180                 185                 190

Arg Pro Ser Thr Arg Pro Val Glu Val Pro Arg Gly Pro Ala Val Ala
        195                 200                 205

Ala Ile Gly Ser Pro Arg Gly Pro Thr Ile Lys Pro Cys Pro Pro Cys
    210                 215                 220

Lys Cys Pro Ala Pro Asn Leu Leu Gly Gly Pro Ser Val Phe Ile Phe
225                 230                 235                 240
```

```
Pro Pro Lys Ile Lys Asp Val Leu Met Ile Ser Leu Ser Pro Ile Val
                245                 250                 255

Thr Cys Val Val Val Asp Val Ser Glu Asp Pro Val Gln Ile
    260                 265                 270

Ser Trp Phe Val Asn Asn Val Glu Val His Thr Ala Gln Thr Gln Thr
        275                 280                 285

His Arg Glu Asp Tyr Asn Ser Thr Leu Arg Val Val Ser Ala Leu Pro
    290                 295                 300

Ile Gln His Gln Asp Trp Met Ser Gly Lys Glu Phe Lys Cys Lys Val
305                 310                 315                 320

Asn Asn Lys Asp Leu Pro Ala Pro Ile Glu Arg Thr Ile Ser Lys Pro
                325                 330                 335

Lys Gly Ser Val Arg Ala Pro Gln Val Tyr Val Leu Pro Pro Pro Glu
            340                 345                 350

Glu Glu Met Thr Lys Lys Gln Val Thr Leu Thr Cys Met Val Thr Asp
                355                 360                 365

Phe Met Pro Glu Asp Ile Tyr Val Glu Trp Thr Asn Asn Gly Lys Thr
    370                 375                 380

Glu Leu Asn Tyr Lys Asn Thr Glu Pro Val Leu Asp Ser Asp Gly Ser
385                 390                 395                 400

Tyr Phe Met Tyr Ser Lys Leu Arg Val Glu Lys Lys Asn Trp Val Glu
                405                 410                 415

Arg Asn Ser Tyr Ser Cys Ser Val Val His Glu Gly Leu His Asn His
            420                 425                 430

His Thr Thr Lys Ser Phe Ser Arg Thr Pro Gly Lys
            435                 440

<210> SEQ ID NO 138
<211> LENGTH: 164
<212> TYPE: PRT
<213> ORGANISM: Homo sapiens

<400> SEQUENCE: 138

Ser Leu Gln Asp Pro Cys Ser Asn Cys Pro Ala Gly Thr Phe Cys Asp
1               5                   10                  15

Asn Asn Arg Asn Gln Ile Cys Ser Pro Cys Pro Pro Asn Ser Phe Ser
                20                  25                  30

Ser Ala Gly Gly Gln Arg Thr Cys Asp Ile Cys Arg Gln Cys Lys Gly
            35                  40                  45

Val Phe Arg Thr Arg Lys Glu Cys Ser Ser Thr Ser Asn Ala Glu Cys
        50                  55                  60

Asp Cys Thr Pro Gly Phe His Cys Leu Gly Ala Gly Cys Ser Met Cys
65                  70                  75                  80

Glu Gln Asp Cys Lys Gln Gly Gln Glu Leu Thr Lys Lys Gly Cys Lys
                85                  90                  95

Asp Cys Cys Phe Gly Thr Phe Asn Asp Gln Lys Arg Gly Ile Cys Arg
                100                 105                 110

Pro Trp Thr Asn Cys Ser Leu Asp Gly Lys Ser Val Leu Val Asn Gly
            115                 120                 125

Thr Lys Glu Arg Asp Val Val Cys Gly Pro Ser Pro Ala Asp Leu Ser
130                 135                 140
```

Pro Gly Ala Ser Ser Val Thr Pro Pro Ala Pro Ala Arg Glu Pro Gly
145                 150                 155                 160

His Ser Pro Gln

<210> SEQ ID NO 139
<211> LENGTH: 164
<212> TYPE: PRT
<213> ORGANISM: Macaca fascicularis

<400> SEQUENCE: 139

Ser Leu Gln Asp Leu Cys Ser Asn Cys Pro Ala Gly Thr Phe Cys Asp
1               5                   10                  15

Asn Asn Arg Ser Gln Ile Cys Ser Pro Cys Pro Asn Ser Phe Ser
            20                  25                  30

Ser Ala Gly Gly Gln Arg Thr Cys Asp Ile Cys Arg Gln Cys Lys Gly
            35                  40                  45

Val Phe Lys Thr Arg Lys Glu Cys Ser Ser Thr Ser Asn Ala Glu Cys
    50                  55                  60

Asp Cys Ile Ser Gly Tyr His Cys Leu Gly Ala Glu Cys Ser Met Cys
65                  70                  75                  80

Glu Gln Asp Cys Lys Gln Gly Gln Glu Leu Thr Lys Lys Gly Cys Lys
                85                  90                  95

Asp Cys Cys Phe Gly Thr Phe Asn Asp Gln Lys Arg Gly Ile Cys Arg
            100                 105                 110

Pro Trp Thr Asn Cys Ser Leu Asp Gly Lys Ser Val Leu Val Asn Gly
            115                 120                 125

Thr Lys Glu Arg Asp Val Val Cys Gly Pro Ser Pro Ala Asp Leu Ser
    130                 135                 140

Pro Gly Ala Ser Ser Ala Thr Pro Pro Ala Pro Ala Arg Glu Pro Gly
145                 150                 155                 160

His Ser Pro Gln

<210> SEQ ID NO 140
<211> LENGTH: 165
<212> TYPE: PRT
<213> ORGANISM: Mus musculus

<400> SEQUENCE: 140

Ala Val Gln Asn Ser Cys Asp Asn Cys Gln Pro Gly Thr Phe Cys Arg
1               5                   10                  15

Lys Tyr Asn Pro Val Cys Lys Ser Cys Pro Pro Ser Thr Phe Ser Ser
            20                  25                  30

Ile Gly Gly Gln Pro Asn Cys Asn Ile Cys Arg Val Cys Ala Gly Tyr
            35                  40                  45

Phe Arg Phe Lys Lys Phe Cys Ser Ser His Asn Ala Glu Cys Glu
    50                  55                  60

Cys Ile Glu Gly Phe His Cys Leu Gly Pro Gln Cys Thr Arg Cys Glu
65                  70                  75                  80

Lys Asp Cys Arg Pro Gly Gln Glu Leu Thr Lys Gln Gly Cys Lys Thr
                85                  90                  95

Cys Ser Leu Gly Thr Phe Asn Asp Gln Asn Gly Thr Gly Val Cys Arg
            100                 105                 110

Pro Trp Thr Asn Cys Ser Leu Asp Gly Arg Ser Val Leu Lys Thr Gly
            115                 120                 125

```
Thr Thr Glu Lys Asp Val Val Cys Gly Pro Pro Val Ser Phe Ser
    130                 135                 140
Pro Ser Thr Thr Ile Ser Val Thr Pro Glu Gly Pro Gly Gly His
145                 150                 155                 160
Ser Leu Gln Val Leu
            165

<210> SEQ ID NO 141
<211> LENGTH: 249
<212> TYPE: PRT
<213> ORGANISM: Artificial Sequence
<220> FEATURE:
<223> OTHER INFORMATION: mFc-Avi for use with CD137-mFc-Avi recombinant
      antigens

<400> SEQUENCE: 141

Pro Arg Gly Pro Thr Ile Lys Pro Cys Pro Pro Cys Lys Cys Pro Ala
1               5                   10                  15
Pro Asn Leu Glu Gly Gly Pro Ser Val Phe Ile Phe Pro Pro Lys Ile
            20                  25                  30
Lys Asp Val Leu Met Ile Ser Leu Ser Pro Ile Val Thr Cys Val Val
        35                  40                  45
Val Asp Val Ser Glu Asp Asp Pro Asp Val Gln Ile Ser Trp Phe Val
    50                  55                  60
Asn Asn Val Glu Val His Thr Ala Gln Thr Gln Thr His Arg Glu Asp
65                  70                  75                  80
Tyr Asn Ser Thr Leu Arg Val Val Ser Ala Leu Pro Ile Gln His Gln
                85                  90                  95
Asp Trp Met Ser Gly Lys Ala Phe Ala Cys Ala Val Asn Asn Lys Asp
            100                 105                 110
Leu Pro Ala Pro Ile Glu Arg Thr Ile Ser Lys Pro Lys Gly Ser Val
        115                 120                 125
Arg Ala Pro Gln Val Tyr Val Leu Pro Pro Glu Glu Glu Met Thr
    130                 135                 140
Lys Lys Gln Val Thr Leu Thr Cys Met Val Thr Asp Phe Met Pro Glu
145                 150                 155                 160
Asp Ile Tyr Val Glu Trp Thr Asn Asn Gly Lys Thr Glu Leu Asn Tyr
                165                 170                 175
Lys Asn Thr Glu Pro Val Leu Asp Ser Asp Gly Ser Tyr Phe Met Tyr
            180                 185                 190
Ser Lys Leu Arg Val Glu Lys Lys Asn Trp Val Glu Arg Asn Ser Tyr
        195                 200                 205
Ser Cys Ser Val Val His Glu Gly Leu His Asn His Thr Thr Lys
    210                 215                 220
Ser Phe Ser Arg Thr Pro Gly Lys Gly Gly Gly Leu Asn Asp Ile Phe
225                 230                 235                 240
Glu Ala Gln Lys Ile Glu Trp His Glu
                245

<210> SEQ ID NO 142

<400> SEQUENCE: 142

000

<210> SEQ ID NO 143
<211> LENGTH: 318
```

```
<212> TYPE: DNA
<213> ORGANISM: Artificial Sequence
<220> FEATURE:
<223> OTHER INFORMATION: Fcab FS20-22-49 CH3 domain

<400> SEQUENCE: 143
ggacagcctc gagaaccaca ggtgtacacc ctgcccccat cccgggatga gtactgggac    60
caggaagtca gcctgacctg cctggtcaaa ggcttctatc ccagcgacat cgccgtggag   120
tgggagagca atgggatga acagttcgca tacaagacca cgcctcccgt gctggactcc   180
gacggctcct tcttcctcta cagcaagctc accgtggatc agtataggtg gaatcctgct   240
gattatttct catgctccgt gatgcatgag gctctgcaca accactacac tcagaagagc   300
ttgtccctgt cgcccgga                                                 318

<210> SEQ ID NO 144
<211> LENGTH: 454
<212> TYPE: PRT
<213> ORGANISM: Artificial Sequence
<220> FEATURE:
<223> OTHER INFORMATION: FS20-22-49/FS30-5-37 Heavy chain AA (without
      LALA)

<400> SEQUENCE: 144
```

Glu Val Gln Leu Leu Glu Ser Gly Gly Gly Leu Val Gln Pro Gly Gly
1               5                   10                  15

Ser Leu Arg Leu Asn Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Tyr Asp Lys Tyr Trp Gly Ser Ser Ile Tyr Ser Gly Leu
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

```
Asp Thr Leu Met Ile Ser Arg Thr Pro Glu Val Thr Cys Val Val Val
                260                 265                 270

Asp Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln Tyr
        290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Tyr Trp Asp
        355                 360                 365

Gln Glu Val Ser Leu Thr Cys Leu Val Lys Gly Phe Tyr Pro Ser Asp
    370                 375                 380

Ile Ala Val Glu Trp Glu Ser Asn Gly Asp Glu Gln Phe Ala Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Gln Tyr Arg Trp Asn Pro Ala Asp Tyr Phe Ser
            420                 425                 430

Cys Ser Val Met His Glu Ala Leu His Asn His Tyr Thr Gln Lys Ser
        435                 440                 445

Leu Ser Leu Ser Pro Gly
    450

<210> SEQ ID NO 145
<211> LENGTH: 1362
<212> TYPE: DNA
<213> ORGANISM: Artificial Sequence
<220> FEATURE:
<223> OTHER INFORMATION: FS20-22-49/FS30-5-37 Heavy chain AA (without
      LALA)

<400> SEQUENCE: 145
gaagtgcaac tgctggagtc cggtggtggt ctggtacagc cgggtggttc tctgcgtctg        60
aattgcgcgg ccagtggctt taccttcagt agctatgcca tgagctgggt gcgtcaggcg       120
ccgggcaaag gtctggaatg ggttagcgcg attagcggta gtggcggtag cacgtactat       180
gcggatagcg tgaaaggccg ttttaccatt tctcgcgaca acagcaagaa cacgctgtac       240
ctgcagatga actcactgcg tgccgaagat acggccgtgt attactgtgc gagatcttac       300
gacaaatact ggggttcttc tatttactct ggcttggact actggggcca gggaaccctg       360
gtcaccgtct cgagtgctag cactaagggc ccgtcggtgt tcccgctggc cccatcgtcc       420
aagagcacat caggggggtac cgccgccctg gctgccttg tgaaggatta ctttcccgag       480
cccgtcacag tgtcctggaa cagcggagcc ctgacctccg gagtgcatac tttcccggct       540
gtgcttcagt cctctggcct gtactcattg tcctccgtgg tcaccgtccc ttcgtcctcc       600
ctgggcaccc agacctatat ctgtaatgtc aaccataagc cctcgaacac caaggtcgac       660
aagaaggtcg agccgaagtc gtgcgacaag actcacactt gcccgccttg cccagccccg       720
gaactgctgg gtggtccttc ggtgttcctc ttcccgccca gccgaagga tacccctgatg       780 atctcacgga cccccgaagt gacctgtgtg gtggtggacg tgtcccacga ggacccggaa       840
```

```
gtgaaattca attggtacgt ggatggagtg gaagtgcaca acgccaagac caagccacgg    900
gaagaacagt acaactctac ctaccgcgtg gtgtccgtgc tcactgtgct gcaccaagac    960
tggctgaacg ggaaggagta caagtgcaaa gtgtccaaca aggcgctgcc tgccccaatt   1020
gagaaaacta tctcgaaagc caagggacag cctcgagaac cacaggtgta caccctgccc   1080
ccatcccggg atgagtactg ggaccaggaa gtcagcctga cctgcctggt caaaggcttc   1140
tatcccagcg acatcgccgt ggagtgggag agcaatgggg atgaacagtt cgcatacaag   1200
accacgcctc ccgtgctgga ctccgacggc tccttcttcc tctacagcaa gctcaccgtg   1260
gatcagtata ggtggaatcc tgctgattat ttctcatgct ccgtgatgca tgaggctctg   1320
cacaaccact acactcagaa gagcttgtcc ctgtcgcccg ga                      1362
```

<210> SEQ ID NO 146
<211> LENGTH: 447
<212> TYPE: PRT
<213> ORGANISM: Artificial Sequence
<220> FEATURE:
<223> OTHER INFORMATION: FS20-22-49/FS30-10-3 Heavy chain AA (without LALA)

<400> SEQUENCE: 146

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Asp Ile Asp Pro Thr Gly Ser Lys Thr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Asn Val Tyr Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270
```

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Tyr Trp Asp Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Asp Glu Gln Phe Ala Tyr Lys Thr Thr Pro Pro Val Leu Asp
385                 390                 395                 400

Ser Asp Gly Ser Phe Phe Leu Tyr Ser Lys Leu Thr Val Asp Gln Tyr
                405                 410                 415

Arg Trp Asn Pro Ala Asp Tyr Phe Ser Cys Ser Val Met His Glu Ala
            420                 425                 430

Leu His Asn His Tyr Thr Gln Lys Ser Leu Ser Leu Ser Pro Gly
            435                 440                 445

<210> SEQ ID NO 147
<211> LENGTH: 1341
<212> TYPE: DNA
<213> ORGANISM: Artificial Sequence
<220> FEATURE:
<223> OTHER INFORMATION: FS20-22-49/FS30-10-3 Heavy chain AA (without
      LALA)

<400> SEQUENCE: 147

```
gaagtgcaac tgctggagtc cggtggtggt ctggtacagc cgggtggttc tctgcgtctg      60
agttgcgcgg ccagtggctt taccttcagt agttacgata tgagctgggt gcgtcaggct     120
ccgggcaaag gtctggaatg ggttagcgat attgatccga ctggtagcaa gaccgactat     180
gcggatagcg tgaaaggccg tttttaccatt tctcgcgaca acagcaagaa cacgctgtac     240
ctgcagatga actcactgcg tgccgaagat acggccgtgt attactgtgc gagagacctc     300
aatgtgtacg ggttcgacta ctggggccag ggaaccctgg tcaccgtctc gagtgctagc     360
actaagggcc cgtcggtgtt cccgctggcc ccatcgtcca agagcacatc agggggtacc     420
gccgccctgg gctgccttgt gaaggattac tttcccgagc cggtcacagt gtcctggaac     480
agcggagccc tgacctccgg agtgcatact tcccggctg tgcttcagtc ctctggcctg     540
tactcattgt cctccgtggt caccgtccct tcgtcctccc tgggcaccca gacctatatc     600
tgtaatgtca accataagcc ctcgaacacc aaggtcgaca gaaggtcga ccgaagtcg      660 tgcgacaaga ctcacacttg cccgccttgc ccagccccgg aactgctggg tggtccttcg     720
gtgttcctct tcccgcccaa gccgaaggat accctgatga tctcacggac ccccgaagtg     780
acctgtgtgt ggtggacgt gtcccacgag acccggaag tgaaattcaa ttggtacgtg     840
gatggagtgg aagtgcacaa cgccaagacc aagccacggg aagaacagta caactctacc     900
taccgcgtgg tgtccgtgct cactgtgctg caccaagact ggctgaacgg gaaggagtac     960
aagtgcaaag tgtccaacaa ggcgctgcct gccccaattg agaaaactat ctcgaaagcc    1020
```

```
aagggacagc ctcgagaacc acaggtgtac accctgcccc catcccggga tgagtactgg    1080
gaccaggaag tcagcctgac ctgcctggtc aaaggcttct atcccagcga catcgccgtg    1140
gagtgggaga gcaatgggga tgaacagttc gcatacaaga ccacgcctcc cgtgctggac    1200
tccgacggct ccttcttcct ctacagcaag ctcaccgtgg atcagtatag gtggaatcct    1260
gctgattatt tctcatgctc cgtgatgcat gaggctctgc acaaccacta cactcagaag    1320
agcttgtccc tgtcgcccgg a                                              1341
```

```
<210> SEQ ID NO 148
<211> LENGTH: 447
<212> TYPE: PRT
<213> ORGANISM: Artificial Sequence
<220> FEATURE:
<223> OTHER INFORMATION: FS20-22-49/FS30-10-12 Heavy chain AA (without
      LALA)

<400> SEQUENCE: 148
```

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Asp Ile Asp Pro Thr Gly Ser Lys Thr Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Thr Val Tyr Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300
```

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Tyr Trp Asp Gln Glu Val Ser Leu Thr Cys
        355                 360                 365

Leu Val Lys Gly Phe Tyr Pro Ser Asp Ile Ala Val Glu Trp Glu Ser
    370                 375                 380

Asn Gly Asp Glu Gln Phe Ala Tyr Lys Thr Thr Pro Pro Val Leu Asp
385                 390                 395                 400

Ser Asp Gly Ser Phe Phe Leu Tyr Ser Lys Leu Thr Val Asp Gln Tyr
                405                 410                 415

Arg Trp Asn Pro Ala Asp Tyr Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 149
<211> LENGTH: 1341
<212> TYPE: DNA
<213> ORGANISM: Artificial Sequence
<220> FEATURE:
<223> OTHER INFORMATION: FS20-22-49/FS30-10-12 Heavy chain AA (without LALA)

<400> SEQUENCE: 149

```
gaagtgcaac tgctggagtc cggtggtggt ctggtacagc cgggtggttc tctgcgtctg      60
agttgcgcgg ccagtggctt taccttcagt agttacgata tgagctgggt gcgtcaggct     120
ccgggcaaag gtctgaatg ggttagcgat attgatccga ctggtagcaa gaccgactat     180
gcggatagcg tgaaaggccg ttttaccatt tctcgcgaca cagcaagaa cacgctgtac     240
ctgcagatga actcactgcg tgccgaagat acggccgtgt attactgtgc gagagacctc     300
acggtgtacg ggttcgacta ctggggccag ggaaccctgg tcaccgtctc gagtgctagc     360
actaagggcc cgtcggtgtt cccgctggcc catcgtcca gagcacatc agggggtacc     420
gccgccctgg gctgccttgt gaaggattac tttcccgagc cgtcacagt gtcctggaac     480
agcggagccc tgacctccgg agtgcatact ttccggctg tgcttcagtc ctctggcctg     540
tactcattgt cctccgtggt caccgtccct tcgtcctccc tgggcaccca gacctatatc     600
tgtaatgtca accataagcc ctcgaacacc aaggtcgaca agaaggtcga gccgaagtcg     660
tgcgacaaga ctcacacttg cccgccttgc ccagccccgg aactgctggg tggtccttcg     720
gtgttcctct ccccgcccaa gccgaaggat accctgatga tctcacggac ccccgaagtg     780
acctgtgtgg tggtggacgt gtcccacgag acccggaag tgaaattcaa ttggtacgtg     840
gatggagtgg aagtgcacaa cgccaagacc aagccacggg aagaacagta caactctacc     900
taccgcgtgg tgtccgtgct cactgtgctg caccaagact ggctgaacgg aaggagtac     960
aagtgcaaag tgtccaacaa ggcgctgcct gccccaattg agaaaactat ctcgaaagcc    1020
aagggacagc ctcgagaacc acaggtgtac accctgcccc catcccggga tgagtactgg    1080
gaccaggaag tcagcctgac ctgcctggtc aaaggcttct atcccagcga catcgccgtg    1140
gagtgggaga gcaatgggga tgaacagttc gcatacaaga ccacgcctcc cgtgctggac    1200
```

-continued

```
tccgacggct ccttcttcct ctacagcaag ctcaccgtgg atcagtatag gtggaatcct    1260
gctgattatt tctcatgctc cgtgatgcat gaggctctgc acaaccacta cactcagaag    1320
agcttgtccc tgtcgcccgg a                                              1341
```

<210> SEQ ID NO 150
<211> LENGTH: 447
<212> TYPE: PRT
<213> ORGANISM: Artificial Sequence
<220> FEATURE:
<223> OTHER INFORMATION: FS20-22-49/FS30-10-16 Heavy chain AA (without LALA)

<400> SEQUENCE: 150

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Asp Ile Asp Pro Thr Gly Ser Lys Thr Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Leu Val Tyr Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335
```

```
Ile Ser Lys Ala Lys Gly Gln Pro Arg Glu Pro Gln Val Tyr Thr Leu
            340                 345                 350

Pro Pro Ser Arg Asp Glu Tyr Trp Asp Gln Glu Val Ser Leu Thr Cys
            355                 360                 365

Leu Val Lys Gly Phe Tyr Pro Ser Asp Ile Ala Val Glu Trp Glu Ser
370                 375                 380

Asn Gly Asp Glu Gln Phe Ala Tyr Lys Thr Thr Pro Pro Val Leu Asp
385                 390                 395                 400

Ser Asp Gly Ser Phe Phe Leu Tyr Ser Lys Leu Thr Val Asp Gln Tyr
            405                 410                 415

Arg Trp Asn Pro Ala Asp Tyr Phe Ser Cys Ser Val Met His Glu Ala
            420                 425                 430

Leu His Asn His Tyr Thr Gln Lys Ser Leu Ser Leu Ser Pro Gly
            435                 440                 445

<210> SEQ ID NO 151
<211> LENGTH: 1341
<212> TYPE: DNA
<213> ORGANISM: Artificial Sequence
<220> FEATURE:
<223> OTHER INFORMATION: FS20-22-49/FS30-10-16 Heavy chain AA (without
      LALA)

<400> SEQUENCE: 151
gaagtgcaac tgctggagtc cggtggtggt ctggtacagc cgggtggttc tctgcgtctg      60
agttgcgcgg ccagtggctt taccttcagt agttacgata tgagctgggt gcgtcaggct     120
ccgggcaaag gtctggaatg ggttagcgat attgatccga ctggtagcaa gaccgactat     180
gcggatagcg tgaaaggccg ttttaccatt tctcgcgaca acagcaagaa cacgctgtac     240
ctgcagatga actcactgcg tgccgaagat acggccgtgt attactgtgc gagagacctc     300
ttggtgtacg ggttcgacta ctggggccag ggaaccctgg tcaccgtctc gagtgctagc     360
actaagggcc cgtcggtgtt cccgctggcc ccatcgtcca agagcacatc aggggggtacc     420 gccgccctgg gctgccttgt gaaggattac tttcccgagc ccgtcacagt gtcctggaac     480
agcggagccc tgacctccgg agtgcatact tccggctgt gcttcagtc ctctggcctg      540 tactcattgt cctccgtggt caccgtccct tcgtcctccc tgggcaccca gacctatatc     600
tgtaatgtca accataagcc ctcgaacacc aaggtcgaca gaaggtcga gccgaagtcg     660 tgcgacaaga ctcacacttg cccgccttgc ccagccccgg aactgctggg tggtccttcg     720
gtgttcctct tccgcccaa gccgaaggat accctgatga tctcacggac ccccgaagtg     780
acctgtgtgg tggtggacgt gtcccacgag gacccggaag tgaaattcaa ttggtacgtg     840
gatggagtgg aagtgcacaa cgccaagacc aagccacggg aagaacagta caactctacc     900
taccgcgtgg tgtccgtgct cactgtgctg caccaagact ggctgaacgg aaggagtac     960 aagtgcaaag tgtccaacaa ggcgctgcct gccccaattg agaaaactat ctcgaaagcc    1020
aagggacagc ctcgagaacc acaggtgtac accctgcccc catcccggga tgagtactgg    1080
gaccaggaag tcagcctgac ctgcctggtc aaaggcttct atcccagcga catcgccgtg    1140
gagtgggaga gcaatgggga tgaacagttc gcatacaaga ccacgcctcc cgtgctggac    1200
tccgacggct ccttcttcct ctacagcaag ctcaccgtgg atcagtatag gtggaatcct    1260
gctgattatt tctcatgctc cgtgatgcat gaggctctgc acaaccacta cactcagaag    1320
agcttgtccc tgtcgcccgg a                                              1341
```

<210> SEQ ID NO 152
<211> LENGTH: 452
<212> TYPE: PRT
<213> ORGANISM: Artificial Sequence
<220> FEATURE:
<223> OTHER INFORMATION: FS20-22-49/FS30-35-14 Heavy chain AA (without LALA)

<400> SEQUENCE: 152

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Asn Ile His Trp Val Arg Gln Ala Pro Gly Lys Gly Leu Glu Trp Val
        35                  40                  45

Ser Asp Ile Ser Pro Tyr Gly Gly Ala Thr Asn Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Tyr Glu Leu Ser Ala Tyr Ser Tyr Gly Ala Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Tyr Trp Asp Gln Glu
        355                 360                 365

Val Ser Leu Thr Cys Leu Val Lys Gly Phe Tyr Pro Ser Asp Ile Ala
    370                 375                 380

Val Glu Trp Glu Ser Asn Gly Asp Glu Gln Phe Ala Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Gln Tyr Arg Trp Asn Pro Ala Asp Tyr Phe Ser Cys Ser
            420                 425                 430

Val Met His Glu Ala Leu His Asn His Tyr Thr Gln Lys Ser Leu Ser
        435                 440                 445

Leu Ser Pro Gly
    450

<210> SEQ ID NO 153
<211> LENGTH: 1356
<212> TYPE: DNA
<213> ORGANISM: Artificial Sequence
<220> FEATURE:
<223> OTHER INFORMATION: FS20-22-49/FS30-35-14 Heavy chain AA (without LALA)

<400> SEQUENCE: 153

```
gaagtgcaac tgctggagtc cggtggtggt ctggtacagc cgggtggttc tctgcgtctg    60
agttgcgcgg ccagtggctt taccttcagt gcctataata tccattgggt cgtcaggct   120
ccgggcaaag gtctggaatg ggttagcgat atttctccgt atggtggcgc gaccaactat   180
gcggatagcg tgaaaggccg ttttaccatt tctcgcgaca cagcaagaa cacgctgtac   240
ctgcagatga actcactgcg tgccgaagat acggccgtgt attactgtgc gagaaacctc   300
tacgagttga gcgcttactc ttacggggcg gactactggg gccagggaac cctggtcacc   360
gtctcgtcgg ctagcactaa gggcccgtcg gtgttcccgc tggccccatc gtccaagagc   420
acatcagggg gtaccgccgc cctgggctgc cttgtgaagg attactttcc cgagcccgtc   480
acagtgtcct ggaacagcgg agccctgacc tccggagtgc atactttccc ggctgtgctt   540
cagtcctctg gcctgtactc attgtcctcc gtggtcaccg tcccttcgtc ctccctgggc   600
acccagacct atatctgtaa tgtcaaccat aagccctcga acaccaaggt cgacaagaag   660
gtcgagccga gtcgtgcga caagactcac acttgcccgc cttgcccagc ccggaactg   720
ctgggtggtc cttcggtgtt cctcttcccg cccaagccga aggataccct gatgatctca   780
cggaccccg aagtgacctg tgtggtggtg gacgtgtccc acgaggaccc ggaagtgaaa   840
ttcaattggt acgtggatgg agtggaagtg cacaacgcca agaccaagcc acgggaagaa   900
cagtacaact ctacctaccg cgtggtgtcc gtgctcactg tgctgcacca agactggctg   960
aacgggaagg agtacaagtg caaagtgtcc aacaaggcgc tgcctgcccc aattgagaaa  1020
actatctcga aagccaaggg acagcctcga gaaccacagg tgtacaccct gccccatcc  1080
cgggatgagt actgggacca ggaagtcagc ctgacctgcc tggtcaaagg cttctatccc  1140
agcgacatcg ccgtggagtg ggagagcaat gggcagccgg agaacaacta caagaccacg  1200
cctcccgtgc tggactccga cggctccttc ttcctctaca gcaagctcac cgtggatcag  1260
tataggtgga atcctgctga ttatttctca tgctccgtga tgcatgaggc tctgcacaac  1320
cactacactc agaagagctt gtccctgtcg cccgga                            1356
```

<210> SEQ ID NO 154
<211> LENGTH: 447

<212> TYPE: PRT
<213> ORGANISM: Artificial Sequence
<220> FEATURE:
<223> OTHER INFORMATION: heavy chain of G1AA/FS30-10-16 mAb (with LALA)

<400> SEQUENCE: 154

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Asp Ile Asp Pro Thr Gly Ser Lys Thr Asp Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Leu Val Tyr Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

```
Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
            435                 440                 445
```

<210> SEQ ID NO 155
<211> LENGTH: 446
<212> TYPE: PRT
<213> ORGANISM: Artificial Sequence
<220> FEATURE:
<223> OTHER INFORMATION: heavy chain of G1AA/OX86 mAb (with LALA)

<400> SEQUENCE: 155

```
Gln Val Gln Leu Lys Glu Ser Gly Pro Gly Leu Val Gln Pro Ser Gln
1               5                   10                  15

Thr Leu Ser Leu Thr Cys Thr Val Ser Gly Phe Ser Leu Thr Gly Tyr
            20                  25                  30

Asn Leu His Trp Val Arg Gln Pro Pro Gly Lys Gly Leu Glu Trp Met
            35                  40                  45

Gly Arg Met Arg Tyr Asp Gly Asp Thr Tyr Tyr Asn Ser Val Leu Lys
    50                  55                  60

Ser Arg Leu Ser Ile Ser Arg Asp Thr Ser Lys Asn Gln Val Phe Leu
65                  70                  75                  80

Lys Met Asn Ser Leu Gln Thr Asp Thr Ala Ile Tyr Tyr Cys Thr
                85                  90                  95

Arg Asp Gly Arg Gly Asp Ser Phe Asp Tyr Trp Gly Gln Gly Val Met
            100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
    290                 295                 300
```

```
Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
            325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
            435                 440                 445

<210> SEQ ID NO 156
<211> LENGTH: 219
<212> TYPE: PRT
<213> ORGANISM: Artificial Sequence
<220> FEATURE:
<223> OTHER INFORMATION: light chain of G1/OX86 and G1AA/OX86 mAb

<400> SEQUENCE: 156

Asp Ile Val Met Thr Gln Gly Ala Leu Pro Asn Pro Val Pro Ser Gly
1               5                   10                  15

Glu Ser Ala Ser Ile Thr Cys Arg Ser Ser Gln Ser Leu Val Tyr Lys
            20                  25                  30

Asp Gly Gln Thr Tyr Leu Asn Trp Phe Leu Gln Arg Pro Gly Gln Ser
            35                  40                  45

Pro Gln Leu Leu Thr Tyr Trp Met Ser Thr Arg Ala Ser Gly Val Ser
50                  55                  60

Asp Arg Phe Ser Gly Ser Gly Ser Gly Thr Tyr Phe Thr Leu Lys Ile
65                  70                  75                  80

Ser Arg Val Arg Ala Glu Asp Ala Gly Val Tyr Tyr Cys Gln Gln Val
            85                  90                  95

Arg Glu Tyr Pro Phe Thr Phe Gly Ser Gly Thr Lys Leu Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
            130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
            165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
            210                 215
```

```
<210> SEQ ID NO 157
<211> LENGTH: 453
<212> TYPE: PRT
<213> ORGANISM: Artificial Sequence
<220> FEATURE:
<223> OTHER INFORMATION: heavy chain of FS20m-232-91AA/4420 (with LALA)

<400> SEQUENCE: 157
```

Glu Val Lys Leu Asp Glu Thr Gly Gly Leu Val Gln Pro Gly Arg
1               5                   10                  15

Pro Met Lys Leu Ser Cys Val Ala Ser Gly Phe Thr Phe Ser Asp Tyr
            20                  25                  30

Trp Met Asn Trp Val Arg Gln Ser Pro Glu Lys Gly Leu Glu Trp Val
        35                  40                  45

Ala Gln Ile Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Met Gly Ile Tyr
                85                  90                  95

Tyr Cys Thr Gly Ser Tyr Tyr Gly Met Asp Tyr Trp Gly Gln Gly Thr
            100                 105                 110

Ser Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Phe Asp Pro Met Tyr Tyr Tyr Asn Gln
        355                 360                 365

-continued

Val Ser Leu Thr Cys Leu Val Lys Gly Phe Tyr Pro Ser Asp Ile Ala
            370                 375                 380

Val Glu Trp Glu Ser Asn Gly Glu Pro Leu Trp Asp Tyr Lys Thr Thr
385                 390                 395                 400

Pro Pro Val Leu Asp Ser Asp Gly Ser Phe Phe Leu Tyr Ser Lys Leu
                405                 410                 415

Thr Val Trp Arg Asp Arg Trp Glu Asp Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 158
<211> LENGTH: 189
<212> TYPE: PRT
<213> ORGANISM: Homo sapiens

<400> SEQUENCE: 158

Ser Leu Gln Asp Pro Cys Ser Asn Cys Pro Ala Gly Thr Phe Cys Asp
1               5                   10                  15

Asn Asn Arg Asn Gln Ile Cys Ser Pro Cys Pro Pro Asn Ser Phe Ser
            20                  25                  30

Ser Ala Gly Gly Gln Arg Thr Cys Asp Ile Cys Arg Gln Cys Lys Gly
        35                  40                  45

Val Phe Arg Thr Arg Lys Glu Cys Ser Ser Thr Ser Asn Ala Glu Cys
    50                  55                  60

Asp Cys Thr Pro Gly Phe His Cys Leu Gly Ala Gly Cys Ser Met Cys
65                  70                  75                  80

Glu Gln Asp Cys Lys Gln Gly Gln Glu Leu Thr Lys Lys Gly Cys Lys
                85                  90                  95

Asp Cys Cys Phe Gly Thr Phe Asn Asp Gln Lys Arg Gly Ile Cys Arg
            100                 105                 110

Pro Trp Thr Asn Cys Ser Leu Asp Gly Lys Ser Val Leu Val Asn Gly
        115                 120                 125

Thr Lys Glu Arg Asp Val Val Cys Gly Pro Ser Pro Ala Asp Leu Ser
    130                 135                 140

Pro Gly Ala Ser Ser Val Thr Pro Pro Ala Pro Ala Arg Glu Pro Gly
145                 150                 155                 160

His Ser Pro Gln Gly Ser Gly Gly Leu Asn Asp Ile Phe Glu Ala
                165                 170                 175

Gln Lys Ile Glu Trp His Glu His His His His His
            180                 185

<210> SEQ ID NO 159
<211> LENGTH: 446
<212> TYPE: PRT
<213> ORGANISM: Artificial Sequence
<220> FEATURE:
<223> OTHER INFORMATION: heavy chain of G1/OX86 mAb (without LALA)

<400> SEQUENCE: 159

Gln Val Gln Leu Lys Glu Ser Gly Pro Gly Leu Val Gln Pro Ser Gln
1               5                   10                  15

Thr Leu Ser Leu Thr Cys Thr Val Ser Gly Phe Ser Leu Thr Gly Tyr
            20                  25                  30

```
Asn Leu His Trp Val Arg Gln Pro Gly Lys Gly Leu Glu Trp Met
         35                  40                  45
Gly Arg Met Arg Tyr Asp Gly Asp Ile Tyr Tyr Asn Ser Val Leu Lys
 50                  55                  60
Ser Arg Leu Ser Ile Ser Arg Asp Thr Ser Lys Asn Gln Val Phe Leu
 65                  70                  75                  80
Lys Met Asn Ser Leu Gln Thr Asp Asp Thr Ala Ile Tyr Tyr Cys Thr
                 85                  90                  95
Arg Asp Gly Arg Gly Asp Ser Phe Asp Tyr Trp Gly Gln Gly Val Met
                100                 105                 110
Val Thr Val Ser Ser Ala Ser Thr Lys Gly Pro Ser Val Phe Pro Leu
            115                 120                 125
Ala Pro Ser Ser Lys Ser Thr Ser Gly Gly Thr Ala Ala Leu Gly Cys
130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
            180                 185                 190
Leu Gly Thr Gln Thr Tyr Ile Cys Asn Val Asn His Lys Pro Ser Asn
        195                 200                 205
Thr Lys Val Asp Lys Lys Val Glu Pro Lys Ser Cys Asp Lys Thr His
    210                 215                 220
Thr Cys Pro Pro Cys Pro Ala Pro Glu Leu Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser His Glu Asp Pro Glu
            260                 265                 270
Val Lys Phe Asn Trp Tyr Val Asp Gly Val Glu Val His Asn Ala Lys
        275                 280                 285
Thr Lys Pro Arg Glu Glu Gln Tyr Asn Ser Thr Tyr Arg Val Val Ser
    290                 295                 300
Val Leu Thr Val Leu His Gln Asp Trp Leu Asn Gly Lys Glu Tyr Lys
305                 310                 315                 320
Cys Lys Val Ser Asn Lys Ala Leu Pro Ala Pro Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Arg Asp Glu Leu Thr Lys Asn Gln Val Ser Leu Thr Cys Leu
        355                 360                 365
Val Lys Gly Phe Tyr Pro Ser Asp Ile Ala Val Glu Trp Glu Ser Asn
    370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
            420                 425                 430
His Asn His Tyr Thr Gln Lys Ser Leu Ser Leu Ser Pro Gly
        435                 440                 445
```

```
<210> SEQ ID NO 160
<211> LENGTH: 443
<212> TYPE: PRT
<213> ORGANISM: Artificial Sequence
<220> FEATURE:
<223> OTHER INFORMATION: heavy chain of anti-PD-1 mAb G1AA/5C4

<400> SEQUENCE: 160
```

Gln Val Gln Leu Val Glu Ser Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Lys Val Glu Pro Lys Ser Cys Asp Lys Thr His Thr Cys Pro Pro
    210                 215                 220

Cys Pro Ala Pro Glu Ala Ala Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
        275                 280                 285

Glu Glu Gln Tyr Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Asp
            340                 345                 350

Glu Leu Thr Lys Asn Gln Val Ser Leu Thr Cys Leu Val Lys Gly Phe
        355                 360                 365

```
Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
                420                 425                 430

Thr Gln Lys Ser Leu Ser Leu Ser Pro Gly Lys
            435                 440

<210> SEQ ID NO 161
<211> LENGTH: 214
<212> TYPE: PRT
<213> ORGANISM: Artificial Sequence
<220> FEATURE:
<223> OTHER INFORMATION: light chain of anti-PD-1 mAb G1AA/5C4

<400> SEQUENCE: 161

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 162
<211> LENGTH: 448
<212> TYPE: PRT
<213> ORGANISM: Artificial Sequence
<220> FEATURE:
<223> OTHER INFORMATION: heavy chain of anti-PD-L1 mAb G1AA/S1

<400> SEQUENCE: 162

Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Asp Ser
         20                  25                  30

Trp Ile His Trp Val Arg Gln Ala Pro Gly Lys Gly Leu Glu Trp Val
         35                  40                  45

Ala Trp Ile Ser Pro Tyr Gly Gly Ser Thr Tyr Tyr Ala Asp Ser Val
     50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Arg His Trp Pro Gly Gly Phe Asp Tyr Trp Gly Gln Gly Thr
             100                 105                 110

Leu Val Thr Val Ser Ala Ala Ser Thr Lys Gly Pro Ser Val Phe Pro
         115                 120                 125

Leu Ala Pro Ser Ser Lys Ser Thr Ser Gly Gly Thr Ala Ala Leu Gly
     130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                 165                 170                 175

Ser Ser Gly Leu Tyr Ser Leu Ser Ser Val Val Thr Val Pro Ser Ser
             180                 185                 190

Ser Leu Gly Thr Gln Thr Tyr Ile Cys Asn Val Asn His Lys Pro Ser
         195                 200                 205

Asn Thr Lys Val Asp Lys Lys Val Glu Pro Lys Ser Cys Asp Lys Thr
     210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                 245                 250                 255

Thr Pro Glu Val Thr Cys Val Val Asp Val Ser His Glu Asp Pro
             260                 265                 270

Glu Val Lys Phe Asn Trp Tyr Val Asp Gly Val Glu Val His Asn Ala
         275                 280                 285

Lys Thr Lys Pro Arg Glu Glu Gln Tyr Asn Ser Thr Tyr Arg Val Val
     290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                 325                 330                 335

Ile Ser Lys Ala Lys Gly Gln Pro Arg Glu Pro Gln Val Tyr Thr Leu
             340                 345                 350

Pro Pro Ser Arg Asp Glu Leu Thr Lys Asn Gln Val Ser Leu Thr Cys
         355                 360                 365

Leu Val Lys Gly Phe Tyr Pro Ser Asp Ile Ala Val Glu Trp Glu Ser
     370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                 405                 410                 415

Arg Trp Gln Gln Gly Asn Val Phe Ser Cys Ser Val Met His Glu Ala
             420                 425                 430
```

```
Leu His Asn His Tyr Thr Gln Lys Ser Leu Ser Leu Ser Pro Gly Lys
            435                 440                 445
```

```
<210> SEQ ID NO 163
<211> LENGTH: 214
<212> TYPE: PRT
<213> ORGANISM: Artificial Sequence
<220> FEATURE:
<223> OTHER INFORMATION: light chain of anti-PD-L1 mAb G1AA/S1

<400> SEQUENCE: 163

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Phe Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

```
<210> SEQ ID NO 164
<211> LENGTH: 233
<212> TYPE: PRT
<213> ORGANISM: Mus musculus

<400> SEQUENCE: 164

Val Gln Asn Ser Cys Asp Asn Cys Gln Pro Gly Thr Phe Cys Arg Lys
1               5                   10                  15

Tyr Asn Pro Val Cys Lys Ser Cys Pro Pro Ser Thr Phe Ser Ser Ile
            20                  25                  30

Gly Gly Gln Pro Asn Cys Asn Ile Cys Arg Val Cys Ala Gly Tyr Phe
        35                  40                  45

Arg Phe Lys Lys Phe Cys Ser Ser Thr His Asn Ala Glu Cys Glu Cys
    50                  55                  60

Ile Glu Gly Phe His Cys Leu Gly Pro Gln Cys Thr Arg Cys Glu Lys
65                  70                  75                  80
```

```
Asp Cys Arg Pro Gly Gln Glu Leu Thr Lys Gln Gly Cys Lys Thr Cys
                85                  90                  95

Ser Leu Gly Thr Phe Asn Asp Gln Asn Gly Thr Gly Val Cys Arg Pro
            100                 105                 110

Trp Thr Asn Cys Ser Leu Asp Gly Arg Ser Val Leu Lys Thr Gly Thr
        115                 120                 125

Thr Glu Lys Asp Val Val Cys Gly Pro Pro Val Ser Phe Ser Pro
130                 135                 140

Ser Thr Thr Ile Ser Val Thr Pro Glu Gly Pro Gly Gly His Ser
145                 150                 155                 160

Leu Gln Val Leu Thr Leu Phe Leu Ala Leu Thr Ser Ala Leu Leu Leu
                165                 170                 175

Ala Leu Ile Phe Ile Thr Leu Leu Phe Ser Val Leu Lys Trp Ile Arg
            180                 185                 190

Lys Lys Phe Pro His Ile Phe Lys Gln Pro Phe Lys Lys Thr Thr Gly
        195                 200                 205

Ala Ala Gln Glu Glu Asp Ala Cys Ser Cys Arg Cys Pro Gln Glu Glu
    210                 215                 220

Glu Gly Gly Gly Gly Gly Tyr Glu Leu
225                 230

<210> SEQ ID NO 165
<211> LENGTH: 450
<212> TYPE: PRT
<213> ORGANISM: Artificial Sequence
<220> FEATURE:
<223> OTHER INFORMATION: heavy chain of G1AA/20H4.9 mAb

<400> SEQUENCE: 165

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Ser Pro Glu Lys Gly Leu Glu Trp Ile
        35                  40                  45

Gly Glu Ile Asn His Gly Gly Tyr Val Thr Tyr Asn Pro Ser Leu Glu
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Tyr Gly Pro Gly Asn Tyr Asp Trp Tyr Phe Asp Leu Trp Gly
            100                 105                 110

Arg Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205
```

-continued

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450

<210> SEQ ID NO 166
<211> LENGTH: 454
<212> TYPE: PRT
<213> ORGANISM: Artificial Sequence
<220> FEATURE:
<223> OTHER INFORMATION: heavy chain of G1AA/3H3 mAb

<400> SEQUENCE: 166

Glu Met Gln Leu Val Glu Ser Gly Gly Gly Leu Val Gln Pro Gly Arg
1               5                   10                  15

Ser Met Lys Leu Ser Cys Ala Gly Ser Gly Phe Thr Leu Ser Asp Tyr
            20                  25                  30

Gly Val Ala Trp Val Arg Gln Ala Pro Lys Lys Gly Leu Glu Trp Val
        35                  40                  45

Ala Tyr Ile Ser Tyr Ala Gly Gly Thr Thr Tyr Tyr Arg Glu Ser Val
    50                  55                  60

Lys Gly Arg Phe Thr Ile Ser Arg Asp Asn Ala Lys Thr Leu Tyr
65                  70                  75                  80

Leu Gln Met Asp Ser Leu Arg Ser Glu Asp Thr Ala Thr Tyr Tyr Cys
                85                  90                  95

Thr Ile Asp Gly Tyr Gly Gly Tyr Ser Gly Ser His Trp Tyr Phe Asp
                100                 105                 110

Phe Trp Gly Pro Gly Thr Met Val Thr Val Ser Ser Ala Ser Thr Lys
            115                 120                 125

Gly Pro Ser Val Phe Pro Leu Ala Pro Ser Ser Lys Ser Thr Ser Gly
130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Ala Ala Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450

<210> SEQ ID NO 167
<211> LENGTH: 213
<212> TYPE: PRT
<213> ORGANISM: Artificial Sequence
<220> FEATURE:
<223> OTHER INFORMATION: light chain of G1AA/3H3 and G1/3H3 mAbs and
      FS20m-232-91AA/3H3 mAb2

<400> SEQUENCE: 167

```
Asp Ile Gln Met Thr Gln Ser Pro Ser Leu Leu Ser Ala Ser Val Gly
1               5                   10                  15

Asp Arg Val Thr Leu Asn Cys Arg Thr Ser Gln Asn Val Tyr Lys Asn
            20                  25                  30

Leu Ala Trp Tyr Gln Gln Leu Gly Glu Ala Pro Lys Leu Leu Ile
        35                  40                  45

Tyr Asn Ala Asn Ser Leu Gln Ala Gly Ile Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Phe Cys Gln Gln Tyr Tyr Ser Gly Asn Thr
                85                  90                  95

Phe Gly Ala Gly Thr Asn Leu Glu Leu Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
210
```

<210> SEQ ID NO 168
<211> LENGTH: 454
<212> TYPE: PRT
<213> ORGANISM: Artificial Sequence
<220> FEATURE:
<223> OTHER INFORMATION: heavy chain of G1/3H3 mAb

<400> SEQUENCE: 168

```
Glu Met Gln Leu Val Glu Ser Gly Gly Gly Leu Val Gln Pro Gly Arg
1               5                   10                  15

Ser Met Lys Leu Ser Cys Ala Gly Ser Gly Phe Thr Leu Ser Asp Tyr
            20                  25                  30

Gly Val Ala Trp Val Arg Gln Ala Pro Lys Lys Gly Leu Glu Trp Val
        35                  40                  45

Ala Tyr Ile Ser Tyr Ala Gly Gly Thr Thr Tyr Tyr Arg Glu Ser Val
    50                  55                  60

Lys Gly Arg Phe Thr Ile Ser Arg Asp Asn Ala Lys Ser Thr Leu Tyr
65                  70                  75                  80

Leu Gln Met Asp Ser Leu Arg Ser Glu Asp Thr Ala Thr Tyr Tyr Cys
                85                  90                  95

Thr Ile Asp Gly Tyr Gly Gly Tyr Ser Gly Ser His Trp Tyr Phe Asp
            100                 105                 110

Phe Trp Gly Pro Gly Thr Met Val Thr Val Ser Ser Ala Ser Thr Lys
        115                 120                 125
```

Gly Pro Ser Val Phe Pro Leu Ala Pro Ser Ser Lys Ser Thr Ser Gly
130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450

<210> SEQ ID NO 169
<211> LENGTH: 459
<212> TYPE: PRT
<213> ORGANISM: Artificial Sequence
<220> FEATURE:
<223> OTHER INFORMATION: heavy chain FS20m-232-91AA/3H3 (with LALA)

<400> SEQUENCE: 169

Glu Met Gln Leu Val Glu Ser Gly Gly Gly Leu Val Gln Pro Gly Arg
1               5                   10                  15

Ser Met Lys Leu Ser Cys Ala Gly Ser Gly Phe Thr Leu Ser Asp Tyr
            20                  25                  30

-continued

```
Gly Val Ala Trp Val Arg Gln Ala Pro Lys Lys Gly Leu Glu Trp Val
         35                  40                  45

Ala Tyr Ile Ser Tyr Ala Gly Thr Thr Tyr Tyr Arg Glu Ser Val
 50                  55                  60

Lys Gly Arg Phe Thr Ile Ser Arg Asp Asn Ala Lys Ser Thr Leu Tyr
 65                  70                  75                  80

Leu Gln Met Asp Ser Leu Arg Ser Glu Asp Thr Ala Thr Tyr Tyr Cys
                 85                  90                  95

Thr Ile Asp Gly Tyr Gly Gly Tyr Ser Gly Ser His Trp Tyr Phe Asp
                100                 105                 110

Phe Trp Gly Pro Gly Thr Met Val Thr Val Ser Ser Ala Ser Thr Lys
        115                 120                 125

Gly Pro Ser Val Phe Pro Leu Ala Pro Ser Ser Lys Ser Thr Ser Gly
130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
                180                 185                 190

Val Thr Val Pro Ser Ser Ser Leu Gly Thr Gln Thr Tyr Ile Cys Asn
            195                 200                 205

Val Asn His Lys Pro Ser Asn Thr Lys Val Asp Lys Lys Val Glu Pro
210                 215                 220

Lys Ser Cys Asp Lys Thr His Thr Cys Pro Pro Cys Pro Ala Pro Glu
225                 230                 235                 240

Ala Ala Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
                260                 265                 270

Val Ser His Glu Asp Pro Glu Val Lys Phe Asn Trp Tyr Val Asp Gly
            275                 280                 285

Val Glu Val His Asn Ala Lys Thr Lys Pro Arg Glu Glu Gln Tyr Asn
290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
                340                 345                 350

Pro Gln Val Tyr Thr Leu Pro Pro Ser Arg Asp Glu Leu Phe Asp Pro
            355                 360                 365

Met Tyr Tyr Tyr Asn Gln Val Ser Leu Thr Cys Leu Val Lys Gly Phe
370                 375                 380

Tyr Pro Ser Asp Ile Ala Val Glu Trp Glu Ser Asn Gly Glu Pro Leu
385                 390                 395                 400

Trp Asp Tyr Lys Thr Thr Pro Pro Val Leu Asp Ser Asp Gly Ser Phe
                405                 410                 415

Phe Leu Tyr Ser Lys Leu Thr Val Trp Arg Asp Arg Trp Glu Asp Gly
                420                 425                 430

Asn Val Phe Ser Cys Ser Val Met His Glu Ala Leu His Asn His Tyr
            435                 440                 445
```

```
Thr Gln Lys Ser Leu Ser Leu Ser Pro Gly Lys
    450                 455

<210> SEQ ID NO 170
<211> LENGTH: 123
<212> TYPE: PRT
<213> ORGANISM: Artificial Sequence
<220> FEATURE:
<223> OTHER INFORMATION: heavy chain variable domain of FS30-35-14 mAb

<400> SEQUENCE: 170

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Asn Ile His Trp Val Arg Gln Ala Pro Gly Lys Gly Leu Glu Trp Val
        35                  40                  45

Ser Asp Ile Ser Pro Tyr Gly Gly Ala Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Tyr Glu Leu Ser Ala Tyr Ser Tyr Gly Ala Asp Tyr
            100                 105                 110

Trp Gly Gln Gly Thr Leu Val Thr Val Ser Ser
        115                 120

<210> SEQ ID NO 171
<211> LENGTH: 369
<212> TYPE: DNA
<213> ORGANISM: Artificial Sequence
<220> FEATURE:
<223> OTHER INFORMATION: heavy chain variable domain of FS30-35-14 mAb

<400> SEQUENCE: 171
gaagtgcaac tgctggagtc cggtggtggt ctggtacagc cgggtggttc tctgcgtctg     60
agttgcgcgg ccagtggctt taccttcagt gcctataata tccattgggt gcgtcaggct    120
ccgggcaaag gtctggaatg ggttagcgat atttctccgt atggtggcgc gaccaactat    180
gcggatagcg tgaaaggccg ttttaccatt tctcgcgaca acagcaagaa cacgctgtac    240
ctgcagatga actcactgcg tgccgaagat acggccgtgt attactgtgc gagaaacctc    300
tacgagttga gcgcttactc ttacggggcg gactactggg gccagggaac cctggtcacc    360
gtctcgtcg                                                            369

<210> SEQ ID NO 172
<211> LENGTH: 109
<212> TYPE: PRT
<213> ORGANISM: Artificial Sequence
<220> FEATURE:
<223> OTHER INFORMATION: light chain variable domain of FS30-35-14 mAb

<400> SEQUENCE: 172

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30
```

```
Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Tyr Ser Ser
                85                  90                  95

Pro Ile Thr Phe Gly Gln Gly Thr Lys Val Glu Ile Lys
            100                 105

<210> SEQ ID NO 173
<211> LENGTH: 327
<212> TYPE: DNA
<213> ORGANISM: Artificial Sequence
<220> FEATURE:
<223> OTHER INFORMATION: light chain variable domain of FS30-35-14 mAb

<400> SEQUENCE: 173
gaaattgtgc tgacccagtc tccgggcacg ttatctctga gccctggtga gcgcgccact     60
ctgtcatgcc gggcttctca aagtgttagc agtagctacc tggcgtggta tcagcaaaaa    120
ccgggccagg ccccgcgtct gctgatttac ggtgcatcca gccgtgccac cggcattcca    180
gatcgttttt ccggtagtgg ttctgggacg gacttcactc tgacaatctc acgcctggaa    240
ccggaggatt ttgcggtgta ttactgccag caatattatt attcttctcc tatcacgttc    300
ggccaaggga ccaaggtgga aatcaaa                                        327

<210> SEQ ID NO 174
<211> LENGTH: 452
<212> TYPE: PRT
<213> ORGANISM: Artificial Sequence
<220> FEATURE:
<223> OTHER INFORMATION: heavy chain of anti-OX40 mAb G1/11D4

<400> SEQUENCE: 174

Glu Val Gln Leu Val Glu Ser Gly Gly Gly Leu Val Gln Pro Gly Gly
 1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
         35                  40                  45

Ser Tyr Ile Ser Ser Ser Ser Thr Ile Asp Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Asp Glu Asp Thr Ala Val Tyr Tyr Cys
                85                  90                  95

Ala Arg Glu Ser Gly Trp Tyr Leu Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160
```

```
Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
        210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
                275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Asp Glu Leu Arg Phe Tyr Gln Val Ser Leu Thr Cys
                355                 360                 365

Leu Val Lys Gly Phe Tyr Pro Ser Asp Ile Ala Val Glu Trp Glu Ser
        370                 375                 380

Asn Gly Gln Pro Asp Ile Phe Pro Asn Gly Leu Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Pro Tyr Pro Ser Trp Leu Met Gly Thr Arg Phe Ser Cys Ser
                420                 425                 430

Val Met His Glu Ala Leu His Asn His Tyr Thr Gln Lys Ser Leu Ser
                435                 440                 445

Leu Ser Pro Gly
            450

<210> SEQ ID NO 175
<211> LENGTH: 214
<212> TYPE: PRT
<213> ORGANISM: Artificial Sequence
<220> FEATURE:
<223> OTHER INFORMATION: light chain of anti-OX40 mAbs G1AA/11D4 and
      G1/11D4

<400> SEQUENCE: 175

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45
```

```
Tyr Ala Ala Ser Ser Leu Gln Ser Gly Val Pro Ser Arg Phe Ser Gly
    50              55              60

Ser Gly Ser Gly Thr Asp Phe Thr Leu Thr Ile Ser Ser Leu Gln Pro
65              70              75              80

Glu Asp Phe Ala Thr Tyr Tyr Cys Gln Gln Tyr Asn Ser Tyr Pro Pro
                85              90              95

Thr Phe Gly Gly Gly Thr Lys Val Glu Ile Lys Arg Thr Val Ala Ala
            100             105             110

Pro Ser Val Phe Ile Phe Pro Pro Ser Asp Glu Gln Leu Lys Ser Gly
        115             120             125

Thr Ala Ser Val Val Cys Leu Leu Asn Asn Phe Tyr Pro Arg Glu Ala
    130             135             140

Lys Val Gln Trp Lys Val Asp Asn Ala Leu Gln Ser Gly Asn Ser Gln
145             150             155             160

Glu Ser Val Thr Glu Gln Asp Ser Lys Asp Ser Thr Tyr Ser Leu Ser
            165             170             175

Ser Thr Leu Thr Leu Ser Lys Ala Asp Tyr Glu Lys His Lys Val Tyr
            180             185             190

Ala Cys Glu Val Thr His Gln Gly Leu Ser Ser Pro Val Thr Lys Ser
        195             200             205

Phe Asn Arg Gly Glu Cys
    210
```